(12) United States Patent
Burnette et al.

(10) Patent No.: US 12,233,054 B2
(45) Date of Patent: Feb. 25, 2025

(54) DIMERIC IMMUNO-MODULATORY COMPOUNDS AGAINST CEREBLON-BASED MECHANISMS

(71) Applicant: H. LEE MOFFITT CANCER CENTER AND RESEARCH INSTITUTE, INC., Tampa, FL (US)

(72) Inventors: Pearlie Burnette, Tampa, FL (US); Nicholas J. Lawrence, Tampa, FL (US); Harshani Lawrence, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 18/235,987

(22) Filed: Aug. 21, 2023

(65) Prior Publication Data
US 2024/0165095 A1 May 23, 2024

Related U.S. Application Data

(63) Continuation of application No. 17/259,005, filed as application No. PCT/US2019/041413 on Jul. 11, 2019, now Pat. No. 11,730,726.

(60) Provisional application No. 62/696,508, filed on Jul. 11, 2018.

(51) Int. Cl.
| | | |
|---|---|---|
| A61K 31/454 | (2006.01) | |
| A61K 31/4015 | (2006.01) | |
| A61K 31/427 | (2006.01) | |
| A61K 31/45 | (2006.01) | |
| A61K 31/517 | (2006.01) | |
| A61K 31/551 | (2006.01) | |
| A61K 47/54 | (2017.01) | |
| A61K 47/55 | (2017.01) | |

(52) U.S. Cl.
CPC ........ *A61K 31/454* (2013.01); *A61K 31/4015* (2013.01); *A61K 31/427* (2013.01); *A61K 31/45* (2013.01); *A61K 31/517* (2013.01); *A61K 31/551* (2013.01); *A61K 47/54* (2017.08); *A61K 47/545* (2017.08); *A61K 47/55* (2017.08)

(58) Field of Classification Search
CPC .................................................. A61K 31/454
See application file for complete search history.

(56) References Cited

U.S. PATENT DOCUMENTS

| | | |
|---|---|---|
| 3,012,997 A | 12/1961 | Kocay et al. |
| 3,126,395 A | 3/1964 | Kitahonoki |
| 3,185,708 A | 5/1965 | Mims |
| 3,232,295 A | 2/1966 | Mims |
| 3,314,953 A | 4/1967 | Vazakas et al. |
| 3,565,794 A | 2/1971 | Elie |
| 3,705,162 A | 12/1972 | Ivars et al. |
| 3,975,388 A | 8/1976 | Hakim et al. |
| 4,217,130 A | 8/1980 | Masanobu et al. |
| 4,397,854 A | 8/1983 | Sircar |
| 4,404,203 A | 9/1983 | Sircar |
| 4,559,157 A | 12/1985 | Smith et al. |
| 4,608,392 A | 8/1986 | Jacquet et al. |
| 4,619,916 A | 10/1986 | Di Stazio et al. |
| 4,748,155 A | 5/1988 | Sisto et al. |
| 4,816,454 A | 3/1989 | Zoller et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 5,238,947 A | 8/1993 | Hendry et al. |
| 5,741,793 A | 4/1998 | Young et al. |
| 5,859,008 A | 1/1999 | Jonas et al. |
| 6,054,579 A | 4/2000 | Harriman |
| 6,399,611 B1 | 6/2002 | Jonas et al. |
| 6,455,472 B1 | 9/2002 | Fischer et al. |
| 6,531,473 B2 | 3/2003 | Jonas et al. |
| 6,656,937 B2 | 12/2003 | Germann et al. |
| 6,960,648 B2 | 11/2005 | Bonny |
| 7,238,711 B1 | 7/2007 | Grainger et al. |
| 7,541,474 B2 | 6/2009 | Bunel et al. |
| 7,790,723 B2 | 9/2010 | Eggenweiler et al. |
| 7,850,955 B2 | 12/2010 | Saito et al. |
| 7,989,466 B2 | 8/2011 | Grainger et al. |
| 8,012,997 B2 | 9/2011 | Robarge et al. |
| 8,481,558 B2 | 7/2013 | Grainger et al. |
| 8,629,157 B2 | 1/2014 | Berry et al. |
| 8,785,357 B2 | 7/2014 | Mosier et al. |
| 8,906,932 B2 | 12/2014 | Muller et al. |
| 11,730,726 B2 * | 8/2023 | Burnette .............. C07D 417/14 514/220 |

(Continued)

FOREIGN PATENT DOCUMENTS

| | | |
|---|---|---|
| CL | 2021000046 A1 | 6/2021 |
| CL | 2021000073 A1 | 7/2021 |

(Continued)

OTHER PUBLICATIONS

Steinebach et al. ACS Chem. Biol., 2018, vol. 13, p. 2771-2782 (Year: 2018).*

(Continued)

*Primary Examiner* — James D. Anderson
(74) *Attorney, Agent, or Firm* — Meunier Carlin & Curfman LLC

(57) ABSTRACT

Disclosed are small molecules against cereblon to enhance effector T cell function. Methods of making these molecules and methods of using them to treat various disease states are also disclosed.

13 Claims, 25 Drawing Sheets

(56) References Cited

U.S. PATENT DOCUMENTS

| | | | |
|---|---|---|---|
| 2002/0035243 A1 | 3/2002 | Imfeld et al. | |
| 2002/0072601 A1 | 6/2002 | Mathias et al. | |
| 2002/0111356 A1 | 8/2002 | Jonas et al. | |
| 2002/0120100 A1 | 8/2002 | Bonny | |
| 2003/0032594 A1 | 2/2003 | Bonny | |
| 2003/0064987 A1 | 4/2003 | Germann et al. | |
| 2004/0048859 A1 | 3/2004 | Germann et al. | |
| 2005/0222160 A1 | 10/2005 | Eggenweiler et al. | |
| 2008/0045557 A1 | 2/2008 | Grainger et al. | |
| 2008/0311164 A1 | 12/2008 | Saito et al. | |
| 2012/0065401 A1 | 3/2012 | Grainger et al. | |
| 2014/0073801 A1 | 3/2014 | Storer et al. | |
| 2015/0291562 A1* | 10/2015 | Crew | A61P 7/04 435/375 |
| 2016/0016913 A1 | 1/2016 | Lewis et al. | |
| 2016/0039788 A1 | 2/2016 | Ladner et al. | |
| 2016/0058872 A1 | 3/2016 | Crew et al. | |
| 2017/0121321 A1 | 5/2017 | Crew et al. | |

FOREIGN PATENT DOCUMENTS

| | | |
|---|---|---|
| CN | 103497175 A | 1/2014 |
| CN | 105037721 A | 11/2015 |
| DE | 3434680 A1 | 4/1986 |
| DE | 19604388 A1 | 8/1997 |
| EP | 0498268 A2 | 8/1992 |
| EP | 0738715 A2 | 10/1996 |
| EP | 1964842 A1 | 9/2008 |
| EP | 2386565 A2 | 11/2011 |
| EP | 3932922 A1 | 1/2022 |
| GB | 962857 A | 7/1964 |
| GB | 1002856 A | 9/1965 |
| JP | S5479269 A | 6/1979 |
| JP | S6014610 A | 1/1985 |
| JP | S6016624 A | 1/1985 |
| JP | H09315946 A | 12/1997 |
| JP | H1149755 A | 2/1999 |
| JP | 2003145933 A | 5/2003 |
| JP | 2012123292 A | 6/2012 |
| WO | 1995001348 A2 | 1/1995 |
| WO | 1999001103 A2 | 1/1999 |
| WO | 2000035871 A1 | 6/2000 |
| WO | 2000042071 A2 | 7/2000 |
| WO | 2001053261 A1 | 7/2001 |
| WO | 2005016326 A1 | 2/2005 |
| WO | 2005028436 A1 | 3/2005 |
| WO | 2007062817 A1 | 6/2007 |
| WO | 2007078013 A1 | 7/2007 |
| WO | 2009092764 A1 | 7/2009 |
| WO | 2013021363 A1 | 2/2013 |
| WO | 2014164704 A1 | 10/2014 |
| WO | 2015137846 A1 | 9/2015 |
| WO | 2016105518 A1 | 6/2016 |
| WO | 2016210141 A1 | 12/2016 |
| WO | 2017007612 A1 | 1/2017 |
| WO | 2017197051 A1 | 11/2017 |
| WO | 2018071606 A1 | 4/2018 |
| WO | 2018098275 A1 | 5/2018 |
| WO | 2018189554 A1 | 10/2018 |
| WO | 2019078522 A1 | 4/2019 |
| WO | 2019078588 A1 | 4/2019 |
| WO | 2020014440 A1 | 1/2020 |
| WO | 2020014460 A1 | 1/2020 |

OTHER PUBLICATIONS

Alvarez-Gutierrez, et al., Solid phase synthesis of 1-substituted pyroglutamates, Tetrahedron Lett. 2000, 41(6), 851-4.
Arora, et al., A comprehensive review of lenalidomide in B-cell non-Hodgkin lymphoma. Ther Adv Hematol. 2016, 7, 209-21.
Balaev, et al., Alternative synthesis of lenalidomide, Pharm. Chem. J. 2013, 46, 676-8.
Barta, et al., Synthesis of Novel Chiral Phosphorous Triamides Based on (S)-N-(Pyrrolidin-2-ylmethyl)aniline and Their Application in Asymmetric Catalysis, Eur. J. Org. Chem. 2009, 24, 4102-16.
Basavaiah, et al., Chiral diamides as efficient catalytic precursors for the borane-mediated asymmetric reduction of prochiral ketones, Tetrahedron: Asymmetry 2007, 18(8), 968-74.
Battersby, et al., Specific chemical fission of peptide links. III. Fission of peptides containing one glutamic acid residue, J. Chem. Soc. 1961, 524-30.
Behr, et al., Chiral N-dienyl-L-pyroglutamic esters in asymmetric hetero-Diels-Alder reactions with acylnitroso dienophiles, Tetrahedron 1996, 52(9), 3283-302.
Belzile, et al., HIV-1 Vpr-mediated G2 arrest involves the DDB1-CUL4AVPRBP E3 ubiquitin ligase. PLoS Pathog. 2007, 3, e85.
Benoiton, et al., N-9-fluorenylmethoxycarbonylpyroglutamate: preparation of the acid, chloride and succinimidyl ester, Intl. J. Peptide & Protein Res. 1994, 43(4), 321-4.
Bjorklund, et al., Rate of CRL4(CRBN) substrate Ikaros and Aiolos degradation underlies differential activity of lenalidomide and pomalidomide in multiple myeloma cells by regulation of c-Myc and IRF4. Blood Cancer J. 2015, 5, e354.
Bjorkman, et al., Peptides related to melanostatin (Pro-Leu-Gly-amide) as inhibitors of oxotremorine-induced tremor, Acta Pharmaceutica Suecica 1976, 13(4), 289-98.
Boichenko, I et al., "A FRET-based assay for the identification and characterization of cereblon ligands", Journal of Medicinal Chemistry, Jan. 5, 2016, vol. 59, No. 2, pp. 770-774, See abstract; p. 771; and figure 1.
Brana, M. F., et al., "Discovering a new analogue of thalidomide which may be used as a potent modulator of TNF-α production," European Journal of Medicinal Chemistry, vol. 44, No. 9, 2009, pp. 3533-3542.
Briere, et al., Regioselective reductions of various 3-aminosuccinimides; application to the synthesis of two heterocyclic systems, Tetrahedron 1997, 53(6), 2075-86.
Brunel, et al., A Practical Method for the Large-Scale Synthesis of Diastereomerically Pure (2R,5S)-3-Phenyl-2-(8-quinolinoxy)-1,3-diaza-2-phosphabicyclo-[3.3.0]-octane Ligand (QU1PHOS). Synthesis and X-ray Structure of its Corresponding Chiral π-Allyl Palladium Complex, J. Org. Chem. 1999, 64(24), 8940-2.
CAS Database Registry, Accession No. 1494653-61-0 for2-cyano-N-(2,6-dioxo-3-piperidinyl)-3fluoro-benzenesulfonamide, Dec. 13, 2013, 3 pages.
Chamberlain, et al., Structure of the human Cereblon-DDB1-lenalidomide complex reveals basis for responsiveness to thalidomide analogs. Nat. Struct. Mol Biol. 2014, 21, 803-9.
Chen, et al., The modified resolution process of 1,1'-binaphthol by kinetic control crystallization, Huaxue Yu Nianhe 2007, 29(3), 157-60. English Abstract included in text.
Choi, B. G., et al., "Synthesis of Antineoplaston A10 Analogs as Potential Antitumor Agents," Archives of Pharmaca Research, vol. 21, No. 2, 1998, pp. 157-163.
Clayden, et al., Conformational arm-wrestling: battles for stereochemical control in benzamides bearing matched and mismatched chiral 2- and 6-substituents, Org. Biomol. Chem. 2006, 4(3), 444-54.
Davis, et al., Peptide synthesis from heterocyclic intermediates. I. 2-Thioxo-5-thiazolidone derivatives of valine, leucine, norleucine, methionine, L-tyrosine, glutamine, α-amino-isobutyric acid, and aminomalonamide, J. Chem. Soc. 1951 2419-25.
De, et al., "Possible antineoplastic agents II", Journal of Pharmaceuticals Sci., 66:2, 1977, 232-235.
Diggle, Geoffrey E. "Thalidomide: 40 years on." International journal of clinical practice 55.9 (2001): 627-631.
Du, et al., A new method for optical resolution of BINOL by molecular complexation with (S)-5-oxopyrrolidine-2-carboxanilide, Tetrahedron Lett. 2002, 43(30), 5273-6.
Dubinskaya, et al., Bactericidal ability of a No. of mixed nitrogen containing inhibitors of hydro sulfide corrosion, Praktika Protivokorrozionnoi Zashchity 2013, 3, 23-8. English Abstract—Machine Translation.
Edwards, et al., Synthesis and application to asymmetric allylic amination of substituted monodonor diazaphospholidine ligands, Tetrahedron 2003, 59(34), 6473-80.

(56) References Cited

OTHER PUBLICATIONS

Ellis, et al., Michael addition reactions between various nucleophilic glycine equivalents and (S,E)-1-enoyl-5-oxo-N-phenylpyrrolidine-2-carboxamide, an optimal type of chiral Michael acceptor in the asymmetric synthesis of β-phenyl pyroglutamic acid and related compounds, Tetrahedron: Asymmetry 2009, 20(22), 2629-34.
El-Zahabi, M. A. et al., Synthesis of new cyclic imides derivatives with potential hypolipidemic activity, Medicinal Chemistry Research, 2012, vol. 21, No. 1, pp. 75-84, See abstract; p. 75; and scheme 2.
Eriksson, et al., Synthesis and alkaline hydrolysis of some N-substituted phthalimides, Acta Pharmaceutica Suecica 1973, 10(1), 63-74.
Examination Report No. 1 issued for Australian Application No. 2017232906, dated Mar. 29, 2021.
Examination Report No. 2 issued for Australian Application No. 2017232906, dated Jan. 13, 2022.
Extended European Search Report issued for Application No. EP17767524.6, dated Jan. 14, 2020, 13 pages.
Extended European Search Report, dated Mar. 10, 2022, received in corresponding EP Application No. 19833126.6.
Fabro, et al., Teratogenic activity of thalidomide and related compounds, Life Sciences 1964, 3(9), 987-92.
Fang et al., A calcium- and calpain-dependent pathway determines the response to Tenalidomide in myelodysplastic syndromes. Nat. Med. 2016, 22, 727-34.
Farid et al., New insights about HERG blockade obtained from protein modeling, potential energy mapping, and docking studies. Bioorg. Med. Chem. 2006, 14, 3160-73.
Fink, et al., "The novel mechanism of lenalidomide activity", Blood 126:21, 2015, 2366-2369.
Fionda et al., The IMiDs targets IKZF-1/3 and IRF4 as novel negative regulators of NK cell-activating ligands expression in multiple myeloma. Oncotarget. 2015, 6, 23609-30.
First Examination Report, dated Jul. 15, 2022, received in corresponding IN Application No. 202117005720 (and English translation).
First Office Action issued in CN Application No. 201980050796.2 dated May 5, 2023, 16 pages.
Fischer et al., Structure of the DDB1-CRBN E3 ubiquitin ligase in complex with thalidomide. Nature. 2014, 512, 49-53.
Fox, et al., Design, Synthesis, and Preliminary Pharmacological Evaluation of N-Acyl-3-aminoglutarimides as Broad-Spectrum Chemokine Inhibitors in Vitro and Anti-inflammatory Agents in Vivo. J. Med. Chem. 2002, 45(2), 360-70.
Fox, et al., Identification of 3-(Acylamino)azepan-2-ones as Stable Broad-Spectrum Chemokine Inhibitors Resistant to Metabolism in Vivo. J. Med. Chem. 2005, 48(3), 867-74.
Frank, et al., Toxicity to protozoa of thalidomide breakdown products and counteraction by nicotinic acid and glutamine, Proc. Soc. Exp. Biol. Med. 1963, 114, 326-8.
Friesner, et al., Extra precision glide: docking and scoring incorporating a model of hydrophobic enclosure for protein-ligand complexes. J. Med. Chem. 2006, 49, 6177-96.
Gandhi, et al. Measuring cereblon as a biomarker of response or resistance to Tenalidomide and pomalidomide requires use of standardized reagents and understanding of gene complexity. Br. J. Haematol. 2014, 164, 233-44.
Gandhi, et al., Immunomodulatory agents lenalidomide and pomalidomide costimulate T cells by inducing degradation of T cell repressors Ikaros and Aiolos via modulation of the E3 ubiquitin ligase complex CRL4(CRBN.). Br. J. Haematol. 2014, 164, 811-21.
Gawron, et al., pH Effects on the kinetics of the cystine-cyanide reaction, J. Am. Chem. Soc. 1964, 86(11), 2283-6.
Gopalakrishnan, et al., Immunomodulatory drugs target IKZF1-IRF4-MYC axis in primary effusion lymphoma in a cereblon-dependent manner and display synergistic cytotoxicity with BRD4 inhibitors. Oncogene. 2016, 35, 1797-810.
Guo, et al., Probing the alpha-helical structural stability of stapled p53 peptides molecular dynamics simulations and analysis. Chem. Biol. Drug. Des. 2010, 75, 348-59.

Hagner, et al., CC-122, a pleiotropic pathway modifier, mimics an interferon response and has antitumor activity in DLBCL. Blood. 2015, 126, 779-89.
Hartmann, et al., Thalidomide mimics uridine binding to an aromatic cage in cereblon. J. Struct. Biol. 2014, 188, 225-32.
Hashem, et al., Novel pyrazolo, isoxazolo, and thiazolo steroidal systems and model analogs containing dimethoxylaryl (or dihydroxylaryl) groups and derivatives. Synthesis, spectral properties, and biological activity, J. Med. Chem. 1976, 19, 229-39.
Haslett, et al., Thalidomide costimulates primary human T lymphocytes, preferentially inducing proliferation, cytokine production, and cytotoxic responses in the CD8+ subset. J. Exp. Med. 1998, 187, 1885-92.
Huang, et al., The synthesized for chiral agent (S)-2-(anilinomethyl)pyrrolidine, Jiangxi Shifan Daxue Xuebao, Ziran Kexueban 2011, 35(4), 347-349. English Abstract included in text.
Humne, et al., Iodine-mediated facile dehydrogenation of dihydropyridazin-3(2H)one, Chinese Chem. Lett. 2011, 22(12), 1435-8.
International Preliminary Report on Patentability issued for Application No. PCT/US2017/022711, dated Sep. 27, 2018.
International Preliminary Report on Patentability issued for Application No. PCT/US2019/041413, dated Jan. 21, 2021.
International Search Report and Written Opinion in PCT/US2019/041413. Mailed Oct. 1, 2019. 8 pages.
International Search Report and Written Opinion issued for Application No. PCT/US2019/041413, dated Oct. 1, 2019, 8 pages.
Iriuchijima, et al., A convenient synthesis of (R)- and (S)-2-anilinomethylpyrrolidines. Synthesis 1978, (9), 684-5.
Ito, et al., Identification of a Primary Target of Thalidomide Teratogenicity. Science 2010, 327(5971), 1345-50.
Iwakura, Y., et al., "Syntheses and Properties of New Aromatic-Aliphatic Copolyimides," vol. 175, No. 1, Die Makromolekulare Chemie, vol. 175, 1974, pp. 137-159.
Jonasova, et al., High level of full-length cereblon mRNA in lower risk myelodysplastic syndrome with isolated 5q deletion is implicated in the efficacy of lenalidomide. Eur. J. Haematol. 2015, 95, 27-34.
Jones, et al., Outcomes and Resource Use of Sepsis-associated Stays by Presence on Admission, Severity, and Hospital Type. Med. Care 2016, 54, 303-10.
Jorgensen, et al., Development and testing of the OPLS all-atom force field on conformational energetics and properties of organic liquids. J. Am. Chem. Soc. 1996, 118, 11225-36.
Kagayama, et al., Synthesis and biological evaluation of novel phthalazinone derivatives as topically active phosphodiesterase 4 inhibitors, Bioorg. Med. Chem. 2009, 17, 6959-70.
Kaldrikyan, et al., Pyrimidines LIX. Synthesis and biological properties of N-substituted dihydrouracils and dihydrothiouracils. Pharm. Chem. J. 1983, 17, 727-30.
Kameyama, et al., Effect of N-phthalylaspartic imide on motor activity and hypnotic activity in mice, Tohoku Yakka Daigaku Kiyo 1962, 9, 51-5.
Kaminski et al., Evaluation and reparametrization of the OPLS-AA force field for proteins via comparison with accurate quantum chemical calculations on peptides. J. Phys. Chem. B. 2001, 105, 6474-87.
Karaluka, V. et al., "B(OCH2CF3)3-mediated direct amidation of pharmaceutically relevant building blocks in cyclopentyl methyl ether", Organic & Biomolecular Chemistry, 2015, vol. 13, No. 44, pp. 10888-10894 See abstract; p. 10889; scheme 2; and compound 3n.
Khan, et al., Syntheses and antiinflammatory activity of some 6-aryl-2,3,4,5-tetrahydro-3-pyridazinones, Indian J. Chem., B: Org. Chem. Med. Chem. 2000, 39B(8), 614-9.
Kim W, Lee S, Son Y, Ko C, Ryu Ws. DDB1 Stimulates Viral Transcription of Hepatitis B Virus via HBx-Independent Mechanisms. J. Virol. 2016, 90, 9644-53.
Kimura, et al., Development of New P-Chiral Phosphorodiamidite Ligands Having a Pyrrolo[1,2-c]diazaphosphol-1-one Unit and Their Application to Regio- and Enantioselective Iridium-Catalyzed Allylic Etherification, J. Org. Chem. 2007, 72(3), 707-14.

(56) References Cited

OTHER PUBLICATIONS

Kiso, Efficient solid phase peptide synthesis. Use of methanesulfonic acid α-amino deprotecting procedure and new coupling reagent, 2-(benzotriazol-1-yl)oxy-1,3-dimethylimidazolidinium hexafluorophosphate (BOI), International Journal of Peptide & Protein Research 1992, 40(3-4), 308-14.

Kodi Philip, "In Vitro Antifungal Activity Screening of Some New Glutamoyl derivatives", Research Journal of Chemical Sciences (2014), vol. 4, No. 8, pp. 17-24.

Kohn, et al., Synthesis and characterization of chiral 1,2-diamines from 5-oxo-pyrrolidine-(S)-2-carboxylic acid, Tetrahedron: Asymmetry 2007, 18(14), 1735-41.

Kronke, et al., Lenalidomide causes selective degradation of IKZF1 and IKZF3 in multiple myeloma cells. Science. 2014, 343, 301-5.

Kronke, et al., Lenalidomide induces ubiquitination and degradation of CK1alpha in del(5q) MDS. Nature. 2015, 523, 183-8.

Kupfer, et al., Stimulation by o,p'-DDD of cortisol metabolism in the guinea pig, Life Sci. 1964, 3(9), 959-64.

LeBlanc, et al., Immunomodulatory drug costimulates T cells via the B7-CD28 pathway. Blood. 2004, 103, 1787-90.

Lebraud, et al., Protein Degradation by In-Cell Self-Assembly of Proteolysis Targeting Chimeras. ACS Cent Sci. 2016, 2, 927-34.

Lee, et al., Syntheses of anilide derivatives from amino acids and their biological activities. I. Preparation of (R)-2-pyrrolidone-5-carbox-anilide derivatives and their effects on the germination of plant seeds, Taehan Hwahakhoe Chi 1981, 25(1), 38-43. English Abstract included in text.

Lepper, et al., Comparative Molecular Field Analysis and Comparative Molecular Similarity Indices Analysis of Thalidomide Analogues as Angiogenesis Inhibitors, J. Med. Chem. 2004, 47(9), 2219-27.

Li, et al., Very fast empirical prediction and rationalization of protein pKa values. Proteins. 2005, 61, 704-21.

Lindner et al. The molecular mechanism of thalidomide analogs in hematologic malignancies. J. Mol. Med. (Berl) 94:1327-1334, 2016.

Lindner, S., et al., "Chemical Inactivation of the E3 Ubiquitin Ligase Cereblon by Pomalidomide-based Homo-PROTACs," Journal of Visualized Experiments, Issue 147, 2019, 9 pages.

List, et al., Efficacy of lenalidomide in myelodysplastic syndromes. N. Engl. J. Med. 2005, 352, 549-57.

Lu, et al., Hijacking the E3 Ubiquitin Ligase Cereblon to Efficiently Target BRD4. Chem. Biol. 2015, 22, 755-63.

Lu, et al., Thalidomide metabolites in mice and patients with multiple myeloma. Clin. Cancer. Res. 2003, 9, 1680-8.

Luptakova, et al., Lenalidomide enhances anti-myeloma cellular immunity, Cancer immunology, immunotherapy: 2013, 62:39-49.

Mahon, et al., E3 ligases and their rewiring by viral factors. Biomolecules. 2014, 4, 897-930.

Maniaci, C., et al., "Homo-PROTACs: bivalent small-molecule dimerizers of the VHL E3 ubiquitin ligase to induce self-degradation," Nature Communications, vol. 8, No. 1, 2017, 14 pages.

Martin, et al., A novel approach to the discovery of small-molecule ligands of CDK2. Chembiochem. 2012, 13, 2128-36.

Martyna, et al., Explicit reversible integrators for extended systems dynamics. Mol. Physics. 1996, 87, 1117-57.

McDaniel, et al., Molecular action of lenalidomide in lymphocytes and hematologic malignancies. Adv. Hematol. 2012, 2012, 513702.

McDaniel, et al., Reversal of T-cell tolerance in myelodysplastic syndrome through lenalidomide immune modulation. Leukemia. 2012, 26, 1425-9.

Misiti, et al., Effects of 3-phthalimidoglutarimide and N-phthaloyl-DL-as-partimide on rat pregnancy, J. Med. Chem. 1963, 6, 464-5.

Mizukami, et al., Sulfonamide derivatives as analytical reagents. I. 2'-Mercaptosulfonanilide derivatives, Chem. Pharm. Bull. 1965, 13(1), 33-9.

Nunes, et al., Signalling through CD28 T-cell activation pathway involves an inositol phospholipid-specific phospholipase C activity. Biochem. J. 1993, 293 (Pt 3), 835-42.

O'Brien, et al., Ikaros imposes a barrier to CD8+ T cell differentiation by restricting autocrine IL-2 production. J Immunol. 2014, 192, 5118-29.

Office Action and Search report issued for Chinese Application No. 201780030049.3, dated Dec. 29, 2021.

Office Action and Search report issued for Chinese Application No. 201780030049.3, dated Jul. 19, 2021.

Office Action issued for Japanese Application No. 2018-548365, dated Apr. 27, 2021.

Office Action issued for Korean Application No. 10-2018-7029689, dated Jan. 18, 2022.

Office Action issued for Korean Application No. 10-2018-7029689, dated Sep. 17, 2021.

Office Action issued for Mexican Application No. MX/a/2018/011216, dated Oct. 14, 2021.

Office Action issued for Mexican Patent Application No. MX/a/2018/011216, dated Jun. 17, 2021.

Office Action issued for U.S. Appl. No. 16/084,068, dated Oct. 5, 2021.

Office Action, dated Feb. 1, 2022, received in corresponding JP Application No. 2018548365 (and English translation).

Office Action, dated Feb. 11, 2022, received in corresponding CL Application No. 202100061 (and English translation).

Office Action, dated Jun. 29, 2022, received in corresponding EA Application No. 202190248 (and English translation).

Office Action, dated Mar. 11, 2022, received in related KR Application No. 1020187029689 (and English translation).

Office Action, dated Mar. 16, 2022, received in related EP Application No. 17767524.6.

Office Action, dated Mar. 17, 2022, received in related U.S. Appl. No. 16/084,068.

Office Action, dated Mar. 28, 2022, received in related CN Application No. 201780030049.3 (and English translation).

Onat, et al., Stimulation of gap junctional intercellular communication by thalidomide and thalidomide analogs in human fetal skin fibroblasts (HFFF2) and in rat liver epithelial cells (WB-F344), Biochem. Pharmacol. 2001, 62(8), 1081-6.

Otahal, et al., Lenalidomide enhances antitumor functions of chimeric antigen receptor modified T cells. Oncoimmunology. 2016, 5, e1115940.

Ott, et al., Tetrahydroisoquino [2,1-d][1,4]benzodiazepines. Synthesis and Neuropharmacological Activity, J. Med. Chem. 1968, 11(4), 777-7.

Papaioannou, et al., Facile preparation of the 1-hydroxybenzotriazolyl ester of N-tritylpyroglutamic acid and its application to the synthesis of TRH, [D-His2]TRH and analogs incorporating cis- and trans-4-hydroxy-L-proline, Acta Chemica Scandinavica 1995, 49(2), 103-14.

Partial Supplementary European Search Report issued for Application No. 17767524.6, dated Sep. 25, 2019.

Paul, et al., Zinc binding to the HCCH motif of HIV-1 virion infectivity factor induces a conformational change that mediates protein-protein interactions. Proc Natl. Acad. Sci. USA. 2006, 103, 18475-80.

Petzold et al. Structural basis of lenalidomide-induced CK1 alpha degradation by the CRL4 CRBN ubiquitin ligase, Nature 532:127-130, 2016.

Pitarch, et al., Chemical and pharmacological study of a series of substituted pyridazones, Eur. J. Med. Chem. 1974, 9(6), 644-50.

Ponder, et al., An efficient newton-like method for molecular mechanics energy minimization of large molecules. J. Comp. Chem. 1987, 8, 1016-24.

Pourvali, A. et al., "A new method for peptide synthesis in the N->C direction: amide assembly through silver-promoted reaction of thioamides" , Chemical Communications, 2014, vol. 50, No. 100, pp. 15963-15966 See abstract; table 1; and entry 5.

Qin, et al., (S)-5-Oxo-N-phenylpyrrolidine-2-carboxamide, Acta Crystallographica, Section E: Structure Reports Online 2011, 67(10), 02763.

Raina, et al., PROT AC-induced BET protein degradation as a therapy for castration-resistant prostate cancer. Proc. Natl. Acad. Sci. USA. 2016, 113, 7124-9.

(56) References Cited

OTHER PUBLICATIONS

Rajadhyaksha, et al., Behavioral characterization of cereblon forebrain-specific conditional null mice: a model for human non-syndromic intellectual disability. Behavioural Brain Res. 2012, 226, 428-34.
Rhodes, et al., Synthesis of 2,6-dioxo-3-phthalimidopiperidine-3,4,4,5,5,-d5 and 2,5-dioxo-3-phthalimidopyrrolidine-3,4,4-d3 from L-deuterioglutamic acid and L-deuterioaspartic acid, J. Pharm. Sci. 1965, 54(10), 1440-3.
Rigo, et al., Studies on pyrrolidinones. Synthesis and reactivity of some N-protected pyroglutamic derivatives, J. Heterocyclic Chem. 1995, 32(5), 1599-604.
Robak, et al., Antibody therapy alone and in combination with targeted drugs in chronic lymphocytic leukemia. Semin. Oncol. 2016, 43, 280-90.
Rosnati, et al., Substances structurally related to 2-phthalimidoglutarimide (thalidomide), Farmaco, Edizione Scientifica 1965, 20(1), 3-24. English Summary included in text.
Ryckaert, et al., Numerical integration of the cartesian equations of motion of a system with constraints: molecular dynamics of n-alkanes. J. Comp. Physics. 1977, 23, 327-41.
Saenz, et al., Novel BET protein proteolysis targeting chimera (BET-PROTAC) exerts superior lethal activity than bromodomain inhibitor (BETi) against post-myeloproliferative neoplasm (MPN) secondary (s) AML cells. Leukemia. 2017, 31(9), 1951-61.
Saigo, et al., Optical resolution of 2-(anilinomethyl)pyrrolidine, Bull. Chem. Soc. Japan 1982, 55(7), 2299-300.
Sakamoto, et al., Development of Protacs to target cancer-promoting proteins for ubiquitination and degradation. Mol. Cell Proteomics. 2003, 2, 1350-8.
Sakamoto, et al., Protacs: chimeric molecules that target proteins to the Skp1-Cullin-F box complex for ubiquitination and degradation. Proc. Natl. Acad. Sci. USA. 2001, 98, 8554-9.
Sakamoto. Protacs for treatment of cancer. Pediatr. Res. 2010, 67, 505-8.
Sastry, et al., Protein and ligand preparation: parameters, protocols, and influence on virtual screening enrichments. J. Comp. Aided Mol. Des. 2013, 27, 221-34.
Search report and written opinion for Singapore Application 11202012464W from IPOS, dated Oct. 5, 2022.
Shannon, et al., Thalidomide increases the synthesis of IL-2 in cultures of human mononuclear cells stimulated with Concanavalin-A, Staphylococcal enterotoxin A, and purified protein derivative. Immunopharmacology. 1995, 31, 109-16.
Sherman, et al., Use of an induced fit receptor structure in virtual screening. Chem. Biol. Drug Des. 2006, 67, 83-4.
Sherman, Novel procedure for modeling ligand/receptor induced fit effects. J. Med. Chem. 2006, 49, 534-53.
Siddiqui, et al., Synthesis and antiinflammatory activity of 6-(substituted-aryl)-2,3,4,5-tetrahydro-3-thiopyridazinones, Indian J. Heterocyclic Chem. 2004, 13(3), 257-60.
Signorini, et al., Energetic fitness of histidine protonation states in PDB structures. J. Phys. Chem. B. 2004, 108, 12252-7.
Singhal, et al., Antitumor activity of thalidomide in refractory multiple myeloma. N. Engl. J. Med. 1999, 341, 1565-71.
Smith, et al., Relation between the chemical structure and embryotoxic activity of thalidomide and related compounds, Symp. Embryopathic Act. Drugs 1965, 194-209.
Steinebach, C., et al., "A MedChem toolbox for creblon-directed PROTACs," Medical Chemical Communication, vol. 10, No. 6, 2019, pp. 1037-1041.
Steinebach, C., et al., "Homo-PROTACs for the Chemical Knockdown of Cereblon," ACS Chemical Biology, vol. 13, No. 9, 2018, pp. 2771-2782.
The International Search Report and Written Opinion issued for Application No. PCT/US2017/022711, dated Jun. 29, 2017, 16 pages.
Toyama, et al., Synthesis of optically active N2-phthaloylaspartimide, Yakugaku Zasshi 1964, 84(4), 372-3.
Toyoizumi, et al., Combined therapy with chemotherapeutic agents and herpes simplex virus type IICP34.5 mutant (HSV-1716) in human non-small cell lung cancer, Human Gene Therapy, 1999, 10(18), 3013-29.
Veerman, et al., Synthesis and evaluation of analogs of the phenylpyridazinone NPD-001 as potent trypanosomal TbrPDEB1 phosphodiesterase inhibitors and in vitro trypanocidal, Bioorg. Med. Chem. 2016, 24(7), 1573-81.
Wiget, et al., Sulfur incorporation generally improves Ricin inhibition in pterin-appended glycine-phenylalanine dipeptide mimics, BOMCL, 2013, 6799-6804.
Winter, et al., Selective Target Protein Degradation via Phthalimide Conjugation. Science. 2015, 348, 1376-81.
Wuest, et al., Teratological studies in the thalidomide field, Life Sci. 1966, 5(5), 393-6.
Yuan, et al., A new and efficient asymmetric synthesis of 1-amino-1-alkylphosphonic acids, Heteroatom Chem. 2000, 11(7), 528-35.
Yuan, et al., Efficient synthesis of aryl hydroxylactams by reducing imides with activated zinc dust, Synthetic Communications 2006, 36(4), 435-44.
Yuan, et al., Facile and efficient asymmetric synthesis of a-aminoalkylphosphonic acids, Chinese J. Chem. 2005, 23(12), 1671-6.
Yuan, et al., Organophosphorus compounds. 79. A convenient asymmetric synthesis of 1-aminoalkylphosphonic acids, Chinese Chem. Lett. 1993, 4(9), 753-6.
Zengerle, et al., Selective Small Molecule Induced Degradation of the BET Bromodomain Protein BRD4. ACS Chem. Biol. 2015, 10, 1770-7.
Zhang, et al., Lenalidomide efficacy in activated B-cell-like subtype diffuse large B-cell lymphoma is dependent upon IRF4 and cereblon expression. Br. J. Haematol. 2013, 160, 487-502.
Zhou, et al., Immunotherapy in mantle cell lymphoma: Anti-CD20-based therapy and beyond, Am. J. Hematol. 2008, 83 (2), 144-9.
Zhu, et al., Cereblon expression is required for the antimyeloma activity of Tenalidomide and pomalidomide. Blood. 2011, 118, 4771-9.
Office Action issued for Chinese Application No. 201980050796.2 dated Oct. 20, 2023.
Office Action issued for Canadian Application No. 3,017,740, dated Jan. 18, 2024.

* cited by examiner

Y = O, CH₂, NH, NMe, SO₂, SO₂NH, CO, COO, CONH, NHCO, COCH₂, NHSO₂, OCH₂O, NHCONH, NHCH₂CH₂O, NH-CH₂CH₂CH₂NH, NHCH₂CF₂CH₂

R" = OH, Cl, F, Br, CN, CF₃, NO₂, n-alkyl, branched-alkyl, OMe, OEt, COOH, NH₂, NMe, NHSO₂, NHCO, heteroalkyl, aromatic, SO₂CF₃, NHSO₂-R (R = Me, Et, propyl, isopropyl), NHCONH,

DIMERIC IMMUNO-MODULATORY COMPOUNDS AGAINST CEREBLON-BASED MECHANISMS

CROSS REFERENCE TO RELATED APPLICATIONS

This application is a continuation of U.S. application Ser. No. 17/259,005, filed Jan. 8, 2021, which is a U.S. National Phase Application of International Application No. PCT/US2019/041413, filed Jul. 11, 2019, which claims the benefit of priority to U.S. Provisional Application No. 62/696,508, filed Jul. 11, 2018, which is incorporated by reference herein in its entirety.

BACKGROUND

Emerging from its beginnings as a catastrophic teratogen, analogs derived from thalidomide, known as immunomodulatory drugs, are now rapidly emerging for the treatment of cancer. One of the hallmarks of immunomodulatory therapy is its association with T-lymphocytes activation (McDaniel, J. M. et al., *Adv. Hematol.* 2012:513702, 2012)). One of the anti-cancer mechanisms posited for this drug class is an emergent immunological response against endogenous tumor-associated antigens that restores functional immuno-surveillance against tumor cells. Numerous barriers impede anti-tumor immunity with complexity that has largely evolved to keep autoimmune recognition in check. Using a zebrafish model, thalidomide was shown to modulate the function of an E3-ubiquitin ligase substrate receptor known as cereblon, which subsequently results in abnormal limb development (Ito, T. et al., *Science* 327(5971):1345, 2010). Cereblon is conserved across all vertebrate species. It has been stated that "structural differences among IMiD drug analogs will influence the potency and selectivity of substrate recognition and degradation (Chamberlain, P. P., et al., Structure of the human cereblon-DDB1-lenalidomide complex reveals the molecular basis for responsiveness to thalidomide analogs. *Nat. Struct. Mol. Biol.* 21:803-9, 2014). Cereblon's physiological role in T cell signaling and homeostasis was demonstrated using homozygous Crbn germline knockouts achieved by flp-mediated excision of exon 3 and 4 after mating with ovum promoter-Cre recombinase-expressing transgenic mice (Rajadhyaksha, A. M., et al. *Behavioural Brain Res.* 226(2):428, 2012). The knockout ablates Crbn expression in all tissues including those of hematopoietic origin. Peripheral blood and splenic lymphocytes are similar in phenotype and in number in deficient mice compared to wild-type C57BL6 littermates at 3 months of age. To explore the intrinsic threshold for activation of $Crbn^{-/-}$ T cells, in vitro studies and adoptive cell transfers have been conducted into fully mismatched allogeneic host and sub-lethally-irradiated congenic mice. These studies show cereblon's role in regulating IL-2, IFNg and T cell receptor activation. Using B16 melanoma, it has been demonstrated that the genetic ablation of cereblon leads to a significant delay in tumor growth.

New developments of targeted therapy for cereblon-based mechanisms for potentiation of immunotherapy in malignant diseases would be desirable. Many of the features associated with Crbn deficiency are notable with IMiD therapy (McDaniel, J. M., et al. Id.; Luptakova, K. J., et al., *Cancer immunology, immunotherapy: CII* 62(1):39, 2013; Zhou, Y., et al., *Am. J. Hematol.* 83 (2), 144, 2008). Lenaliomide, one of the most immunologically active immunomodulatory drugs was confirmed to bind to the CRBN-DDB1 complex using beads and quantitative mass spectrometry (MS) (Kronke, J., et al., *Science* 343(6168): 301, 2014). However, numerous barriers impede anti-tumor immunity with complexity that has largely evolved to keep autoimmune recognition in check. Improved modalities that enhance checkpoint blockade therapy will expand the use of immunotherapies in cancer patients that have limited therapeutic responses to current agents or develop drug resistance on therapy. What are thus needed are new compounds that target cereblon-based mechanisms and methods of making and using the new compounds. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific examples, discloses are dimers of immunomodulatory drugs, e.g., dimers of E3-ligase ligands. The dimers disclosed herein can be two of the same immunomodulatory drugs linked together or two different immunomodulatory drugs linked together.

In certain embodiments, the disclosed compounds can have a structure represented by Formula I:

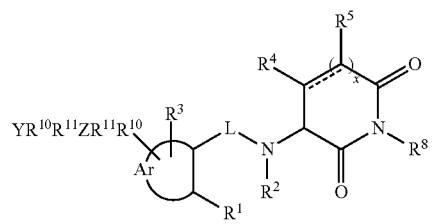

Formula I wherein,

Ar is aryl or heteroaryl;

L is absent (i.e., a bond) or a linker selected from the group consisting of $-SO_2$, $-SO_2R'$; $SO_2R'R''$, $-SO_2NR'R''$; $-SO_2NR'R''C(=O)$; $-NR'SO_2R''$; $-R'SO_2NR'''$; $-C(=O)$; $-C(=O)R'$; $-OC(=O)R'$; $-C(=O)NR'R''$; $-NR'C(=O)R''$; $-NR'C(=O)R''C(=O)$; $-OR'$; $-NR'R'$; $-SR'$; $-N_3-C(=O)OR'$; $-O(CR'R'')_rC(=O)R'$; $-O(CR'R'')_rNR''C(=O)R'$; $-O(CR'R'')_rNR''SO_2R'$; $-OC(=O)NR'R''$; $-NR'C(=O)OR''$; and substituted or unsubstituted $C_1$-$C_6$ alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, substituted or unsubstituted heterocyclyl, and combinations thereof; or $R^1$ and $R^2$ combine to form a 5-7 membered heterocyclic ring; and when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof;

each $R^{10}$ is independently selected from O, NH, $CH_2$, $OCH_2$, $NHCH_2$, $N(CH_3)$, $CH=CH$, $C\equiv C$, $SO_2$, $SO_2NH$, $C(O)$, $C(O)O$, $C(O)NH$, $C(O)CH_2$, $NHSO_2$, $OCH_2O$, $NHCONH$, $NHCH_2CH_2O$, $NH(CH_2)_3NH$, and $NHCH_2CF_2CH_2$;

each $R^{11}$ is independently selected from $(CR'R")_r$, $C(=O)NR'$, $NR'C(O)$, $C(=O)$, $-SO_2$, $-SO_2R'$; $SO_2R"$, $-SO_2NR'$; $-SO_2NR"C(=O)$; $-NR'SO_2R"$; $-R'SO_2NR'$; $-C(=O)R'$; $-OC(=O)R'$; $-C(=O)NR"$; $-NR'C(=O)R"$; $-NR'C(=O)R"C(=O)$; $-OR'$; $-NR'$; $-SR'$; where r is from 1 to 6;

Z is absent, amino, $C_1$-$C_{10}$ alkyl, $C_1$-$C_{10}$ polyalkoxide, cycloalkyl, or heterocycloalkyl;

Y is an E-3 ligase ligand; and

X is 0, 1, or 2;

wherein the bond --- is present or absent.

In a specific example of Formula I, the compounds can have a formula represented by Formula I-A:

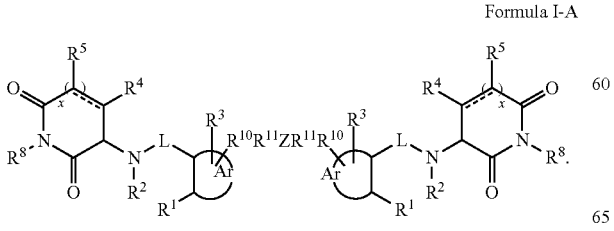

Formula I-A

The disclosed compounds can have a structure represented by Formula II:

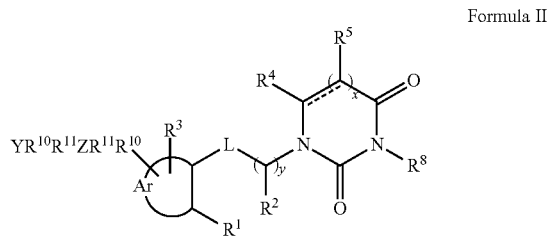

Formula II wherein,

Ar is aryl or heteroaryl;

L is absent or a linker selected from the group consisting of $-SO_2$, $-SO_2R'$; $SO_2R'R"$, $-SO_2NR'R"$; $-SO_2NR'R"C(=O)$; $-NR'SO_2R"$; $-R'SO_2NR'R"$; $-C(=O)$; $-C(=O)R'$; $-OC(=O)R'$; $-C(=O)NR'R"$; $-NR'C(=O)R"$; $-NR'C(=O)R"C(=O)$; $-OR'$; $-NR'R"'$; $-SR'$; $-N_3$-$C(=O)OR'$; $-O(CR'R")_rC(=O)R'$; $-O(CR'R")_rNR"C(=O)R'$; $-O(CR'R")_rNR"SO_2R'$; $-OC(=O)NR'R"$; $-NR'C(=O)OR"$; and substituted or unsubstituted $C_1$-$C_6$ aliphatic alkyl;

wherein R', R", and R''' are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, heterocyclyl, and combinations thereof or $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

R⁸ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof;

each $R^{10}$ is independently selected from O, NH, CH$_2$, OCH$_2$, NHCH$_2$, N(CH$_3$), CH=CH, C≡C, SO$_2$, SO$_2$NH, C(O), C(O)O, C(O)NH, C(O)CH$_2$, NHSO$_2$, OCH$_2$O, NHCONH, NHCH$_2$CH$_2$O, NH(CH$_2$)$_3$NH, and NHCH$_2$CF$_2$CH$_2$;

each $R^{11}$ is independently selected from (CR'R")$_r$, C(=O)NR', NR'C(O), C(=O), —SO$_2$, —SO$_2$R'; SO$_2$R", —SO$_2$NR'; —SO$_2$NR"C(=O); —NR'SO$_2$R"; —R'SO$_2$NR'; —C(=O)R'; —OC(=O)R'; —C(=O)NR"; —NR'C(=O)R"; —NR'C(=O)R"C(=O); —OR'; —NR'; —SR'; where r is from 1 to 6;

Z is absent, amino, C$_1$-C$_{10}$ alkyl, C$_1$-C$_{10}$ polyalkoxide, cycloalkyl, or heterocycloalkyl;

Y is an E-3 ligase ligand; and

X is 0, 1, or 2;

y is from 1 to 6; and wherein the bonder--- is present or absent.

In a specific example of Formula II, the compounds can have a formula represented by Formula II-A:

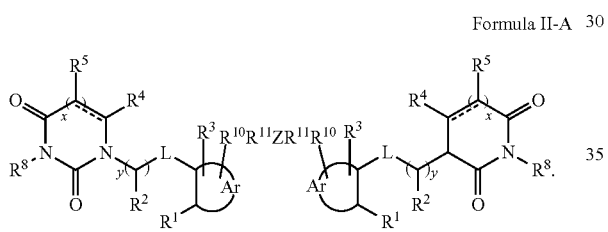

Formula II-A

The disclosed compounds can have a structure represented by Formula III:

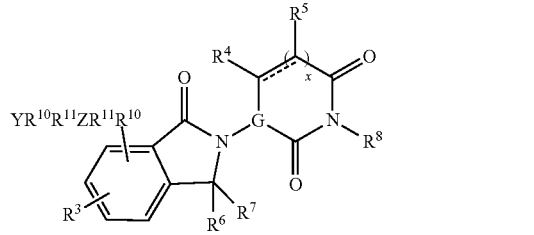

Formula III wherein,

G is C, S, N, substituted or unsubstituted C$_1$-C$_8$ alkyl, or combinations thereof;

R³ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted cycloalkyl, and combinations thereof;

R⁴, R⁵, and R⁸ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and R⁶ and R⁷ are individually hydrogen or C$_1$-C$_8$ alkyl, or R⁶ and R⁷ combine to form =O;

each $R^{10}$ is independently selected from O, NH, CH$_2$, OCH$_2$, NHCH$_2$, N(CH$_3$), CH=CH, C≡C, SO$_2$, SO$_2$NH, C(O), C(O)O, C(O)NH, C(O)CH$_2$, NHSO$_2$, OCH$_2$O, NHCONH, NHCH$_2$CH$_2$O, NH(CH$_2$)$_3$NH, and NHCH$_2$CF$_2$CH$_2$;

each $R^{11}$ is independently selected from (CR'R")$_r$, C(=O)NR', NR'C(O), C(=O), —SO$_2$, —SO$_2$R'; SO$_2$R", —SO$_2$NR'; —SO$_2$NR"C(=O); —NR'SO$_2$R"; —R'SO$_2$NR'; —C(=O)R'; —OC(=O)R'; —C(=O)NR"; —NR'C(=O)R"; —NR'C(=O)R"C(=O); —OR'; —NR'; —SR'; where r is from 1 to 6;

Z is absent, amino, C$_1$-C$_{10}$ alkyl, C$_1$-C$_{10}$ polyalkoxide, cycloalkyl, or heterocycloalkyl;

Y is an E-3 ligase ligand; and x is 0, 1, or 2; and wherein the bond --- is present or absent.

In a specific example of Formula III, the compounds can have a formula represented by Formula III-A:

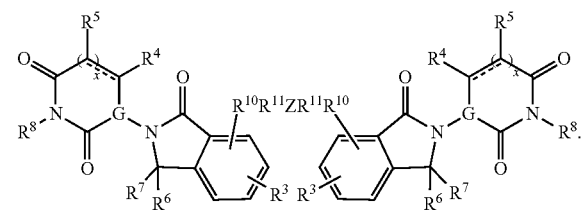

Formula III-A

The disclosed compounds can have a structure represented by Formula IV:

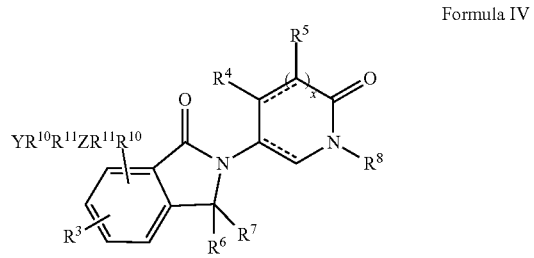

Formula IV wherein,

R³ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

R⁴, R⁵, and R⁸ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

each $R^{10}$ is independently selected from O, NH, $CH_2$, $OCH_2$, $NHCH_2$, $N(CH_3)$, CH=CH, C≡C, $SO_2$, $SO_2NH$, C(O), C(O)O, C(O)NH, $C(O)CH_2$, $NHSO_2$, $OCH_2O$, NHCONH, $NHCH_2CH_2O$, $NH(CH_2)_3NH$, and $NHCH_2CF_2CH_2$;

each $R^{11}$ is independently selected from $(CR'R'')_r$, C(=O)NR', NR'C(O), C(=O), —$SO_2$, —$SO_2R'$; $SO_2R''$, —$SO_2NR'$; —$SO_2NR''C(=O)$; —$NR'SO_2R''$; —$R'SO_2NR'$; —C(=O)R'; —OC(=O)R'; —C(=O)NR''; —NR'C(=O)R''; —NR'C(=O)R''C(=O)$; —OR'; —NR'; —SR'; where r is from 1 to 6;

Z is absent, amino, $C_1$-$C_{10}$ alkyl, $C_1$-$C_{10}$ polyalkoxide, cycloalkyl, or heterocycloalkyl;

Y is an E-3 ligase ligand; and x is 0, 1, or 2; and wherein the bond --- is present or absent.

In specific aspects, the disclosed subject matter relates to methods for reducing the risk of, preventing, or treating a subject having an autoimmune disease or disorder. In other specific aspects, the disclosed subject matter relates to methods for inducing degradation of a target protein in a cell. In other specific aspects, the disclosed subject matter relates to methods for reducing the risk of, preventing, or treating a disease state or condition in a patient wherein dysregulated protein activity is responsible for said disease state or condition. In other specific aspects, the disclosed subject matter relates to methods for inhibiting a cereblon E3 Ubiquitin Ligase binding moiety (CLM), the method comprising administering an effective amount of a compound disclosed herein. In other specific aspects, the disclosed subject matter relates to methods for reducing the risk of, preventing, or treating cancer in a subject. In other specific aspects, the disclosed subject matter relates to methods for treating a genetic disease or disorder in a subject.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

(FIG. 8C) Western blot analysis of human and mouse T cells stimulated with anti-CD3ε 5 μg/ml+1 μg/ml anti-CD28 antibody treated for 24 h with DMSO, 10 and 20 μM lenalidomide or pomalidomide. Results are representative of three independent experiments. WB shows expression of IKZF1 (also known as Ikaros), CRBN and β-actin. Statistical analysis was conducted ANOVA, followed by Dunnett's multiple comparison test. *=$p<0.05$, ***=$p<0.001$ (FIG. 9A) is a ribbon overlay of human (purple, PDB 4TZ4), chicken (blue, PDB 4CI2) X-ray crystal structures and post-MD structure of mouse (yellow, PDB 4TZ4) cereblon with residues His378, Trp380, Trp400, Tyr402 and ligands thalidomide (yellow), lenalidomide (green) and pomalidomide (blue) shown for reference. FIG. 9B is a superposition of ligand poses of lenalidomide (green) for the post-MD equilibrated systems of the CRBN thalidomide binding site after induced fit docking (IFD) for hCRBN (red), hmCRBN (green), gCRBN (orange), shown with the post-MD equilibrated protein structure of hCRBN (red) shown for reference. FIG. 9C is an overlay of human and mouse cereblon (Val380 and Ile391 for mCRBN; Glu377 and Val388 for hCRBN), are demarcated as thin tubes.

In FIG. 10A, PCR amplification of DNA from Crbn$^{+/+}$, Crbn$^{+/-}$ and Crbn$^{-/-}$ C57BL/6 mice (NT=no template control) with wild-type (WT) and knockout (KO) specific primers confirm the germline Crbn knockout (n=2). Genotype was confirmed on all mice used for experimentation. FIG. 10B shows qRT-PCR for exon 3-4 specific cereblon mRNA relative to TATA box binding protein (TBP) isolated from bone marrow (BM), lymph node (LN), peripheral blood (PB), thymus (TH), spleen (SP), splenic B cells (B), splenic T cells (T), CD4+ T and CD8+ T cells. In FIG. 10C, the expression of cereblon protein by immunoblot in unactivated Crbn$^{+/+}$, Crbn$^{+/-}$, and Crbn$^{-/-}$ splenic T cells demonstrates cereblon deficiency. Cytokine production from Crbn$^{+/+}$ and Crbn$^{-/-}$ CD3+ T cells following anti-CD3 or anti-CD3/anti-CD28 stimulation. FIG. 10D shows IL-2 following 48 hours, (FIG. 10E) interferon gamma (IFN γ) and (FIG. 10F) TNF α after 72 hours, Cytokines from Crbn$^{-/-}$ and Crbn$^{+/+}$ mouse serum (n=3). FIGS. 10G-10I show in vitro proliferation using CellTrace Violet area (CTV-A) staining of Crbn$^{+/+}$ and Crbn$^{-/-}$ T cells induced by anti-CD3ε/anti-CD28 (FIGS. 10G and 10I) or anti-CD3 alone (FIG. 10H) with total area under curve indicated. Data were analyzed by unpaired two-way t-test with significant data indicated *p≤0.05, p≤0.01, *p≤0.001, ****p≤0.0001.

In FIGS. 11A and 11B, B16 tumors were injected subcutaneously into Crbn$^{+/+}$ (n=4) or Crbn (n=5) mice and tumor volume was measured for 18 days. In FIG. 11C, tumor growth is shown after injection of 1×10$^6$ Crbn$^{+/+}$ (n=9) or Crbn$^{-/-}$ (n=9) mice with 20 IU of mouse IL-2 administered on days 3, 4, and 5 after tumor injection. In FIG. 11D, tumors were removed on day 14 and analyzed for anti-tumor reactive T cells. Flow cytometry for CD44 and Trp2 tetramer interaction by tumor infiltrating T cells. In FIG. 11E, expression of granzyme B on TIL and (FIG. 11F) cytotoxicity of Crbn$^{+/+}$ and Crbn$^{-/-}$ OT1 T cells against B16 melanoma expressing the cognate ligand ovalbumin that is reactive to the transgenic T cell receptor expressed by OT1 CD8+ T cells. FIG. 11G shows flow cytometry for expression of 2-NBDG after gating on CD8+ TIL expressing the suppressive (FIG. 11H) PD-1 marker.

FIG. 13 left shows structures of SY2-060 and SM2-048. FIG. 13 right shows Western blot analysis of anti-CD3/anti-CD28 stimulated human T cells purified from peripheral blood of a healthy donor. CRBN and vinculin expression after treatment with DMSO (0.1%), pomalidomide (Pom 10 μM), CC122 (10 μM) and after SY2-060 or SM2-048 0.1, 1, and 10 μM shows significant reduction in CRBN expression with SM2-048. Exemplary results from two bifunctional CRBN degraders are shown.

In FIG. 14C, cells treated with rapamycin to block mTORC1 signaling failed to increase cereblon. In FIG. 14D, Crbn−/− T cells have a higher proliferation index which is sensitive to rapamycin treatment. Results indicate that higher levels of cereblon are related to a negative feed-back loop downstream of mTOR.

DETAILED DESCRIPTION

Figure 1:
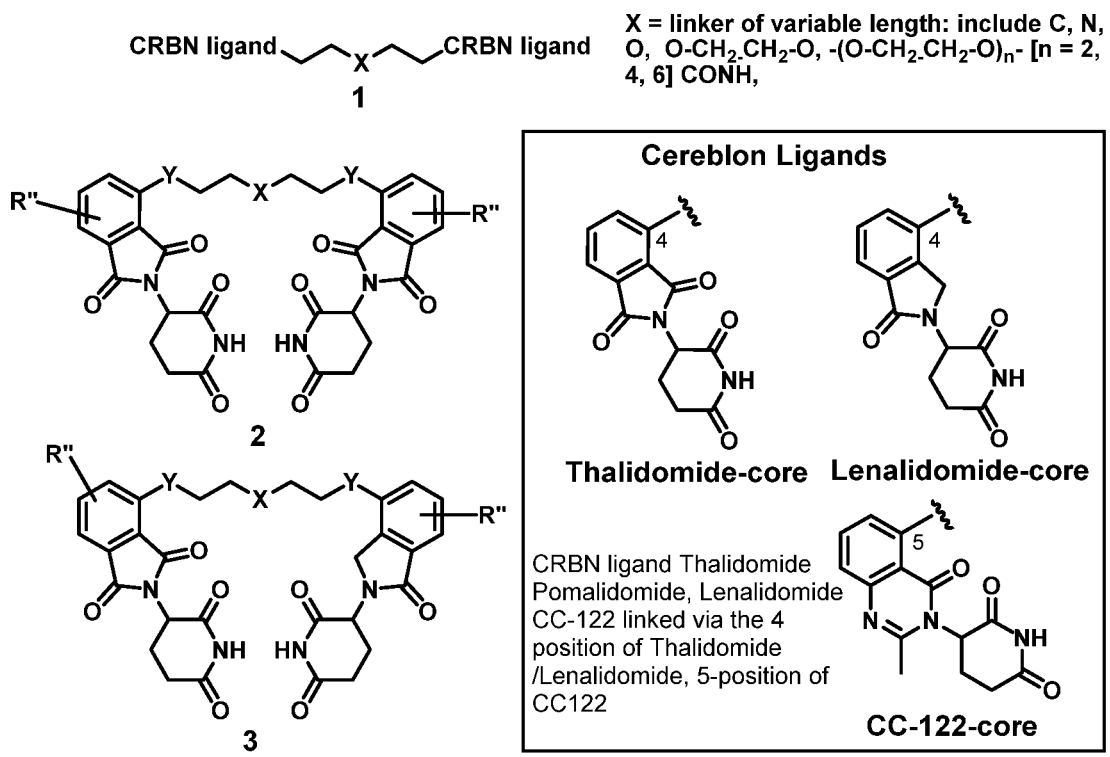
FIG. 1 shows a general class of bis-immunomodulatory drugs capable of targeting cereblon protein degradation mechanisms.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols A" is used herein as merely a generic substitutent in the definitions below.

The term "alkoxy" as used herein is an alkyl group bound through a single, terminal ether linkage; that is, an "alkoxy" group can be defined as —OA$^1$ where A$^1$ is alkyl as defined above.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

"Aryl", as used herein, refers to 5-, 6- and 7-membered aromatic rings. The ring can be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that can include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure can also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

"Alkylaryl" or "aryl-alkyl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, (C$_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, (C$_1$-C$_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula: —NA'A" or NA'A"A''', wherein A', A", and A''' each independently represent a hydrogen, an alkyl, an alkenyl, —(CH$_2$)$_m$-A"" or A" and A''' taken together with the N atom to which they are attached complete a heterocycle having from 4 to 8 atoms in the ring structure; A"" represents an aryl, a cycloalkyl, a cycloalkenyl, a heterocycle or a polycycle; and m is zero or an integer in the range of 1 to 8. In some embodiments, only one of $R_9$ or $R_{10}$ can be a carbonyl, e.g., A', A" and the nitrogen together do not form an imide. In some embodiments, the term "amine" does not encompass amides, e.g., wherein one of A' and A" represents a carbonyl. In some embodiments, A' and A" (and optionally A''') each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of A' and A" is an alkyl group.

The term "amido" is art-recognized as an amino-substituted carbonyl and includes a moiety that can be represented by the general formula —CONA'A" wherein A' and A" are as defined above.

"Halogen", as used herein, refers to fluorine, chlorine, bromine, or iodine.

The term "carboxylic acid" as used herein is represented by the formula —C(O)OH. A "carboxylate" as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "cyano" as used herein is represented by the formula —CN.

The term "azido" as used herein is represented by the formula —N$_3$.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH$_2$.

The term "thiol" as used herein is represented by the formula —SH.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aryloxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples and Figures.

Compounds

Figures 8A, 8B, 8C:
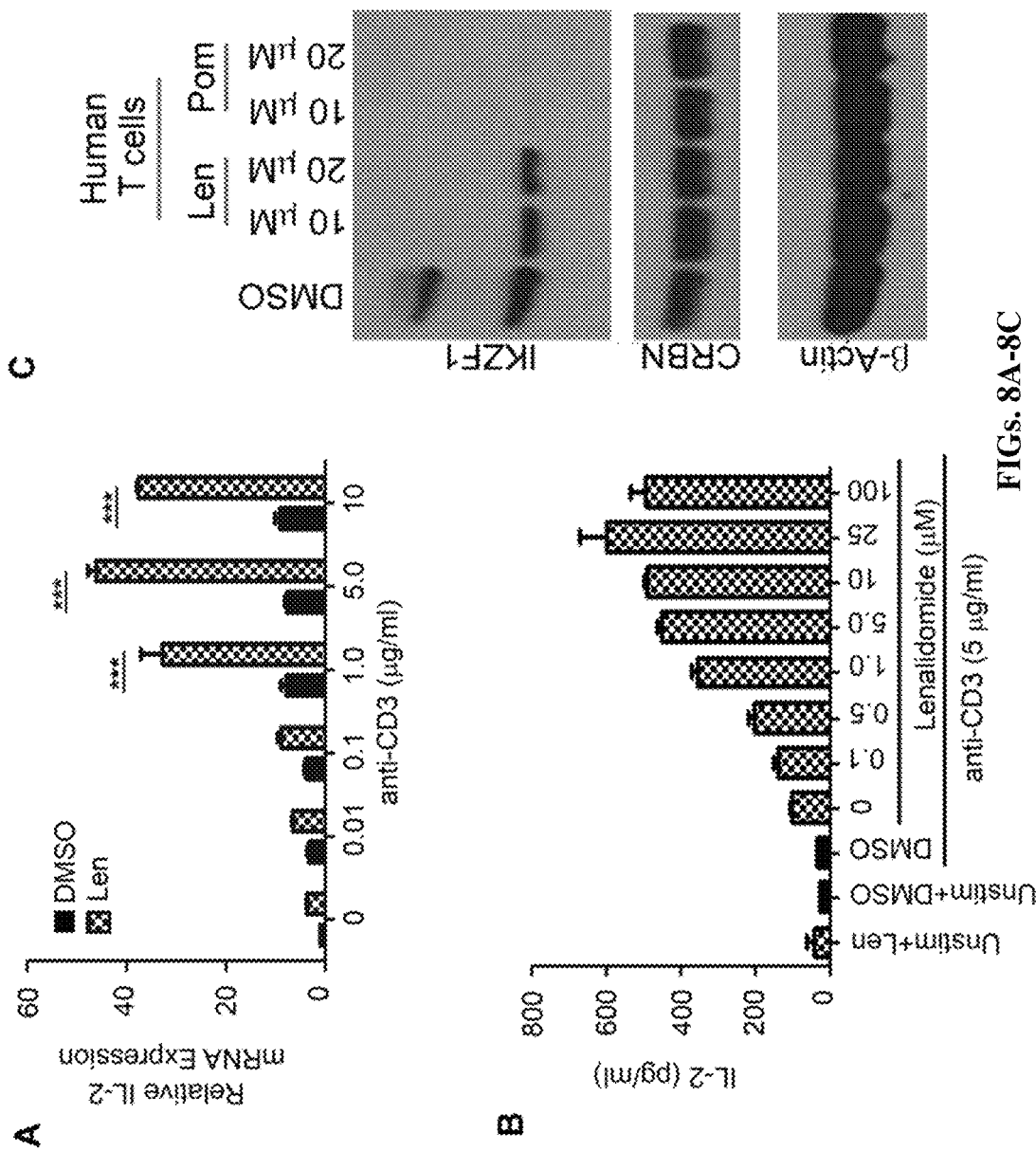
FIGS. 8A-8C show lenalidomide augments IL-2 production in the absence of CD28 co-stimulation in human but not mouse T cells. T cells purified from healthy donor peripheral blood mononuclear cells (PBMCs) were stimulated in the presence of increasing concentrations of anti-CD3ε antibody in the presence of 10 μM lenalidomide (Len) or vehicle control (DMSO). IL-2 mRNA (FIG. 8A) and protein secretion (FIG. 8B) were measured in cells and culture supernatant, respectively. T cells were stimulated with increasing concentrations of anti-CD3α alone without anti-CD28 antibody to provide co-stimulation in the presence of DMSO (vehicle control) or (A) 10 μM lenalidomide (Len) or (FIG. 8B) increasing concentrations of lenalidomide ranging from 0.1 to 100 μM. Cytokine levels were determined by ELISA.

Cereblon acts as the E3 ubiquitin ligase (UbL) substrate receptor component of the DNA damage binding protein 1 (DDB1), cullin-4 (CUL4A and B), and ROC1 complex (Anger, A. M. et al. Structures of the human and Drosophila 80S ribosome. *Nature* 497, 80-85, 2013). CRBN's thalidomide binding domain (TBD) interacts with thalidomide, and other immunomodulatory drugs of this class, including lenalidomide, pomalidomide, and CC122, and either recruits new proteins for degradation or prevents the degradation or regulation of other CRBN-bound proteins (Ito, T. et al. Identification of a primary target of thalidomide teratogenicity. *Science* 327:1345-1350, 2010; Kronke, J. et al. Lenalidomide causes selective degradation of IKZF1 and IKZF3 in multiple myeloma cells. *Science* 343:301-305, 2014; Bjorklund, C. C., et al. Rate of CRL4 (CRBN) substrate Ikaros and Aiolos degradation underlies differential activity of lenalidomide and pomalidomide in multiple myeloma cells by regulation of c-Myc and IRF4. *Blood Cancer J* 5, e354, 2015). IKZF1 (ikaros) and IKZF3 (aiolos) are recognized drug-induced target proteins (Kronke, J. et al. Lenalidomide induces ubiquitination and degradation of CK1alpha in del(5q) MDS. *Nature* 523:183-188, 2015). Based on the current data, a reduction in the expression of these proteins appears to be sufficient to augment IL-2 production by T cells (Shannon, E. J. & Sandoval, F., Thalidomide increases the synthesis of IL-2 in cultures of human mononuclear cells stimulated with Concanavalin-A, Staphylococcal enterotoxin A, and purified protein derivative. *Immunopharmacology* 31:109-116, 1995) in the absence and presence of anti-CD28 co-stimulation Otahal, P. et al. Lenalidomide enhances antitumor functions of chimeric antigen receptor modified T cells. *Oncoimmunology* 5, e1115940, 2016; Gandhi, A. K., et al. Immunomodulatory agents lenalidomide and pomalidomide co-stimulate T cells by inducing degradation of T cell repressors Ikaros and Aiolos via modulation of the E3 ubiquitin ligase complex CRL4 (CRBN). *Br. J. Haematol.* 164:811-821, 2014; McDaniel, J. M. et al. Reversal of T cell tolerance in myelodysplastic syndrome through lenalidomide immune modulation. *Leukemia* 26:1425-1429, 2012), which is the hallmark of the immunomodulatory drug class. In lenalidomide-treated human T cells stimulated with anti-CD3ε antibody to cross-link the T cell receptor (TCR) and induce intracellular signal transduction, the levels of IL2 mRNA (FIG. 8A) and protein secretion (FIG. 8B) were significantly increased relative to DMSO-(vehicle) treated cells. IKZF1 was also decreased after lenalidomide (Len) and pomolidomide (Pom) treatment in multiple myeloma cells and T cells, as shown previously (FIG. 8C) (Kronke, J. et al. Lenalidomide induces ubiquitination and degradation of CK1alpha in del(5q) MDS. *Nature* 523:183-188, 2015; Petzold, G., et al., Structural basis of lenalidomide-induced CK1alpha degradation by the CRL4 ubiquitin ligase. *Nature*, doi:10.1038/nature16979, 2016).

Figures 9A, 9B, 9C:
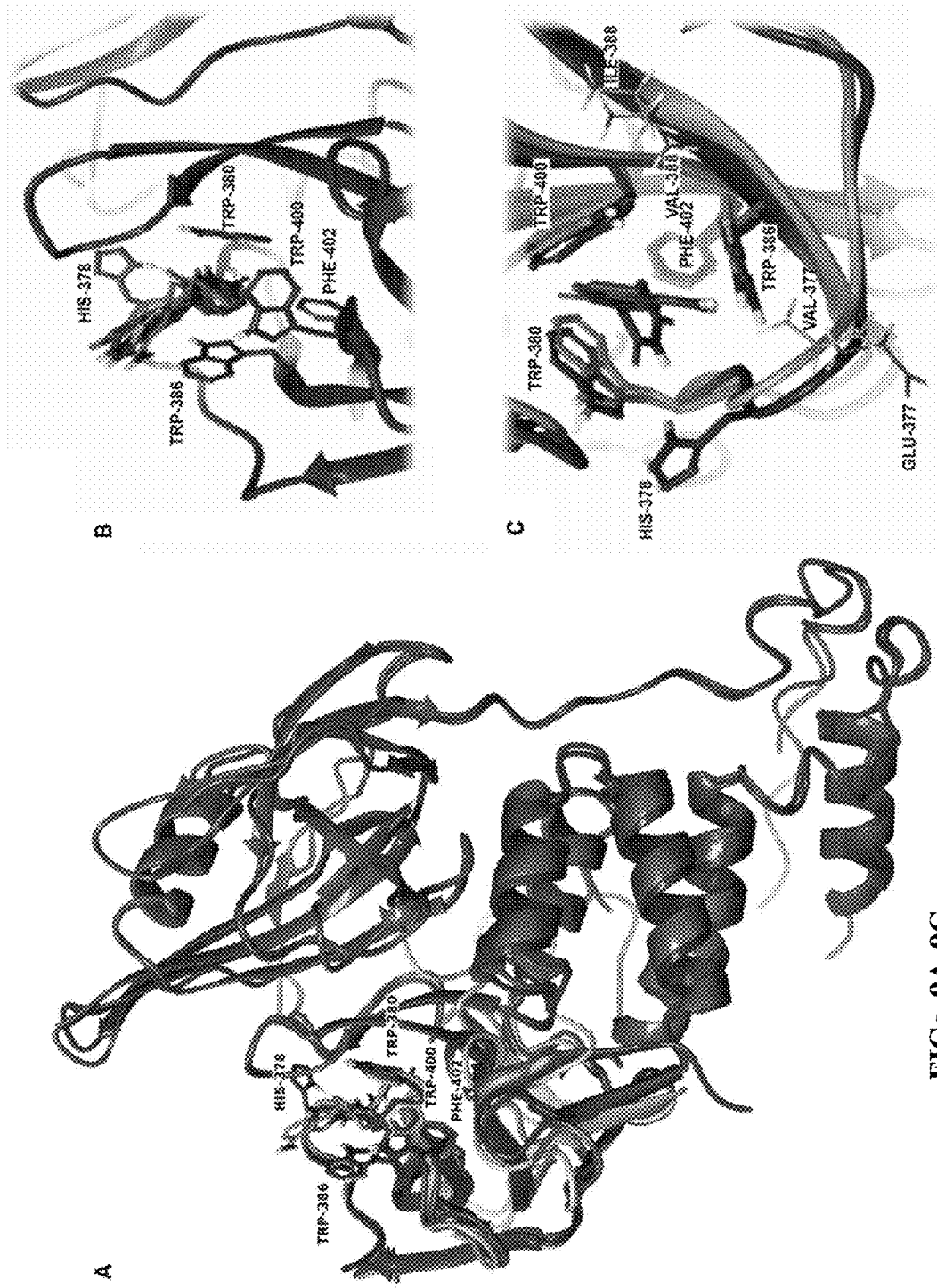
FIGS. 9A-9C show the structure of cereblon is conserved across different species.

Thalidomide binding domain (TBD) of cereblon has a conserved immunomodulatory compound binding motif. Based on crystal structures, immunomodulatory compounds bind to a conserved pocket within the thalidomide binding domain (TBD) located in the C-terminus of cereblon (FIG. 9A) (Chamberlain, P. P., et al. Structure of the human cereblon-DDB1-lenalidomide complex reveals basis for responsiveness to thalidomide analogs. *Nat. Struct. Mol. Biol.* 21:803-809, 2014; Fischer, E. S., et al. Structure of the DDB1-CRBN E3 ubiquitin ligase in complex with thalidomide. *Nature* 512:49-53, 2014). These interactions are governed by hydrogen bonding, aromatic quadrupole, and Van der Waals (VDW) interactions. Analysis of the X-ray crystal structures of cereblon [human (hCRBN), mouse (mCRBN) and chicken (gCRBN)] in complex with thalidomide, lenalidomide, and pomalidomide, respectively (FIG. 9A) shows negligible variations of root mean square deviation (RMSD) between the inhibitor poses. Thus, an in-depth theoretical investigation of the molecular binding mechanics of immunomodulatory compounds in complex with cereblon was conducted to explore possible differences in drug interactions between mouse and human cereblon caused by induced fit, protein flexibility, or crystal artifacts. These results reveal little or no difference between mouse and human cereblon protein structure across species. There are, however, minor species-specific amino acid differences in mouse CRBN-TBD at Val380 (equivalent to Glu377) and Ile391 (equivalent to Val388) (FIGS. 9B and 9C) which appear to have no relevance in the structure or corresponding immunomodulatory drug binding interaction.

Figures 10A, 10B, 10C, 10D, 10E, 10F, 10G, 10H, 10I:
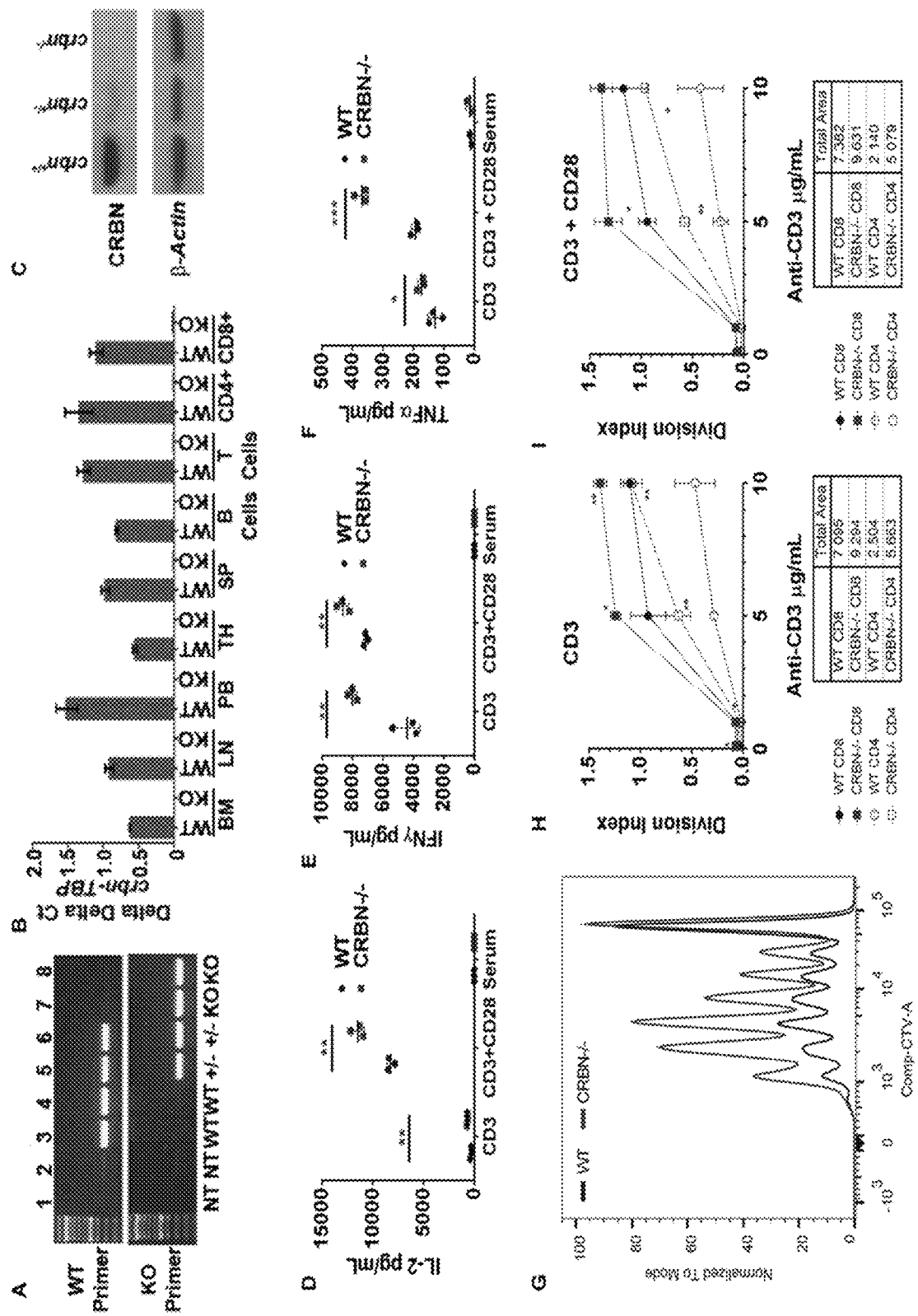
FIGS. 10A-10I show the characterization of CRBN deficient mice.

Since cereblon's roles in physiology are undefined and the protein is structurally and functionally conserved, we used genetically deficient mice to explore its involvement in immune regulation. As demonstrated previously, germline deficiency was confirmed with WT and KO-specific primers (FIG. 10A-10C) (Rajadhyaksha, A. M., et al. Behavioral characterization of cereblon forebrain-specific conditional null mice: a model for human non-syndromic intellectual disability. *Behavioural Brain Res.* 226:428-434, 2012). Quantitative RT-PCR defined Crbn expression in cells of hematopoietic origin in WT C57BL/6 mice and confirmed the deficiency of Crbn mRNA in these tissues and cells the in knockout mice. Although the basal serum levels of IL-2, IFN-γ, and TNFα are normal in Crbn$^{-/-}$ mice, purified T cells from Crbn–/– mice had higher detectable level of these $T_H$-1-type cytokines after stimulation (FIG. 10D). In proliferation assays, Crbn–/– T cells showed significantly higher likelihood of progressing past generation 0 (FIG. 10A-10D) compared to WT T cells; a difference was also noted after anti-CD3 and anti-CD3 plus anti-CD28. Our data suggests that Crbn deficiency or loss of function is responsible for immune modulation.

Figures 11A, 11B, 11C, 11D, 11E, 11F, 11G, 11H:
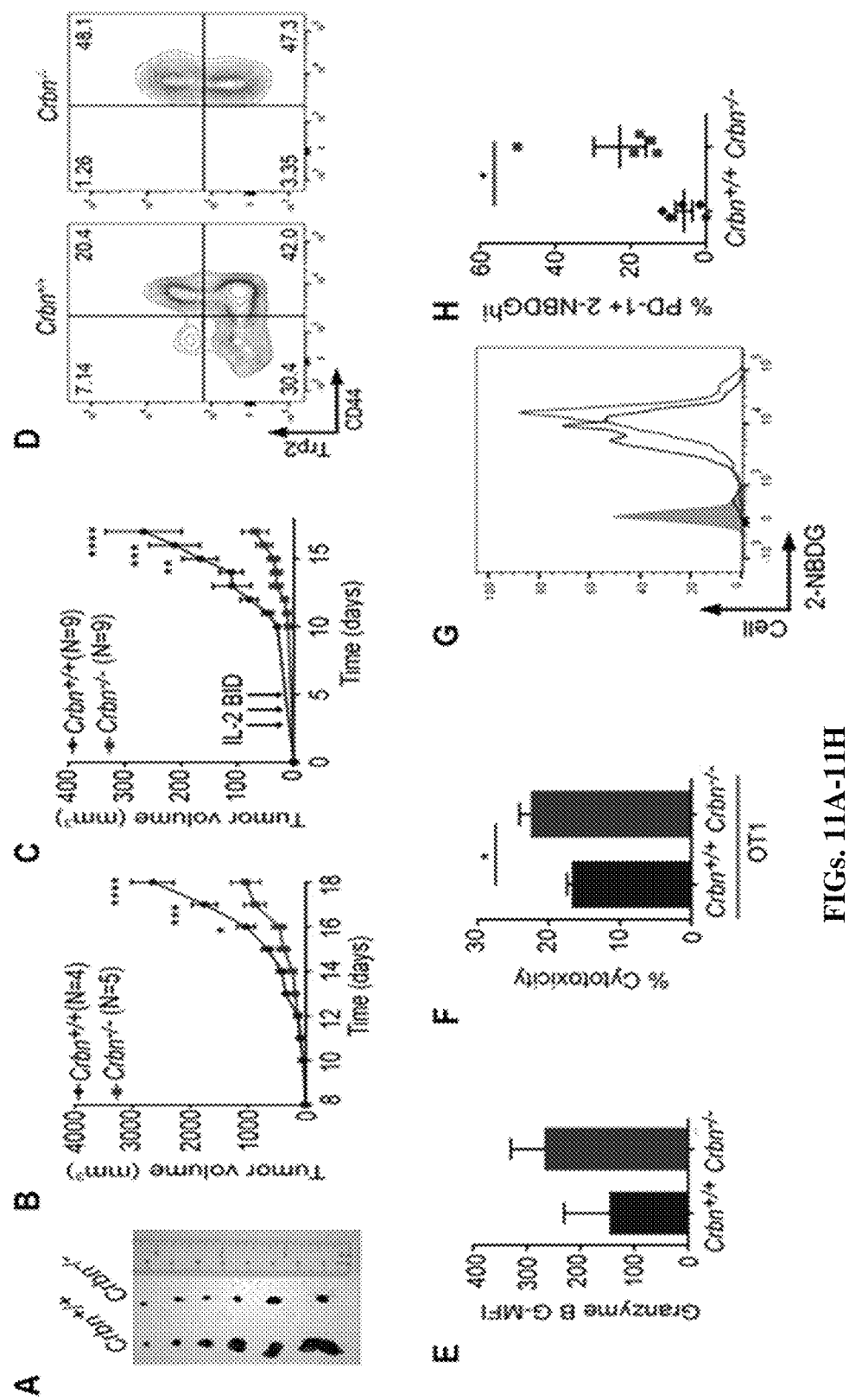
FIGS. 11A-11H show cereblon deficiency promotes anti-tumor T cell immunity.

Regulation of protein phosphorylation governs the cellular activation potential of T cells starting with the recruitment of cytosolic tyrosine kinases that phosphorylate proximal signaling intermediates. These activation events are countered by phosphatases and ubiquitin-mediated degradation. Several families of E3-Ub ligases are involved in establishing the threshold for contextual T cell stimulation. Genetic ablation of casitas B-lineage lymphoma-b (Cbl-b) (Bachmaier, K., et al. Negative regulation of lymphocyte activation and autoimmunity by the molecular adaptor Cbl-b. *Nature* 403:211-216, 2000; Chiang, Y. J., et al. Cbl-b regulates the CD28 dependence of T cell activation. *Nature* 403:216-220, 2000), its related family member C Cbl (Ota, Y., et al., The product of the proto-oncogene c-cbl: a negative regulator of the Syk tyrosine kinase. *Science* 276: 418-420, 1997), itch (Melino, G., et al. Itch: a HECT-type E3 ligase regulating immunity, skin and cancer. *Cell death and differentiation* 15:1103-1112, 2008) and gene related to anergy in lymphocytes (GRAIL) (Seroogy, C. M., et al. The gene related to anergy in lymphocytes, an E3 ubiquitin ligase, is necessary for anergy induction in CD4 T cells. *J Immunol* 173:79-85, 2004) lowers the threshold for lymphocyte activation and causes spontaneous T cell activation. Thus far, these molecules have not been successfully targeted by small molecules but result in superior anti-tumor immune responses when genetically deleted in T cells. Subcutaneous injection of B16 melanoma tumors into Crbn$^{+/+}$ versus Crbn$^{-/-}$ mice resulted in significant differences in tumor growth (FIGS. 11A-11B). Adoptive transfer of Crbn$^{-/-}$ T cells into B16 tumor bearing mice significantly slows melanoma growth compared to Crbn+/+ T cells (FIG. 11C) suggesting that the reduced tumor growth may be related to intrinsic anti-tumor T cells. In this experiment, IL-2 was added exogenously twice daily for three days to ensure T cell survival and to improve T cell expansion. Consistent with an improved response by T cells to the tumor, an activation antigen (CD44) and tumor antigenic response (tetramer staining for anti-Trp2 reactive T cells) were assessed in tumor infiltrating lymphocytes. FIG. 11D shows that Crbn$^{-/-}$ T cells have superior reactivity to the tumor mean 48.1% versus 20.4%. Cytolytic granule expression and cytotoxicity of antigen-specific T cells was enhanced in Crbn–/– T cells suggesting that the cells have superior function. In FIGS. 11G and 11H, results show that PD-1 positive T cells have increased function as indicated by an increase in uptake of a fluorescent glucose analog (2-NBDG). These results demonstrate that CRBN harnesses anti-tumor reactive T cells and suggest that pharmacological suppression or deletion would promote anti-tumor immunity. In aggregate, cereblon based mechanisms regulate four major T-cell functions that is important for anti-tumor immunity: 1) proliferation, 2) cytokine production, 3) cytotoxicity, and 4) metabolism. Many of the features associated with cereblon deficiency, but not all, are notable with immunomodulatory therapy.

Figure 12:
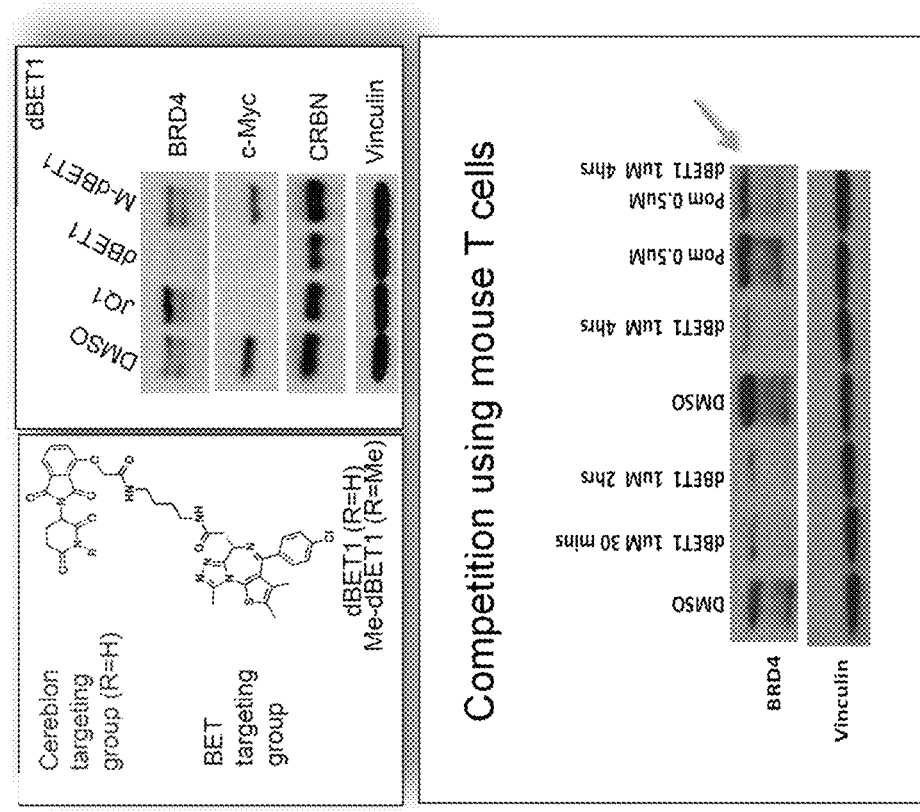
FIG. 12 shows the functional activity of dBET1 in human and mouse T cells. On the right is a schematic diagram of CRBN/DDB1/CUL4A and ubiquitin degrading function. On the left is the structure of dBET1 and N-methyl-dBET1. Human T cells purified from PBMCs and activated by anti-CD3ε/anti-CD28 and treated with DMSO (vehicle control), or treated with DMSO (0.1%), 10 μM JQ1, dBET1 or an inactive control of dBET1 (M-dBET1). Degradation of the JQ1 target BRD4 is shown in dBET1-treated cells. Suppression of c-Myc is evident with both enzymatic suppression by JQ1 and dBET1 through degradation. Mouse T cells were isolated and activated with anti-CD3ε/anti-CD28 and treated with 1 μM dBET1 for 30 minutes or 2 hours. DMSO was used in these experiments as a vehicle control. Treatment with Pomalidomide (Pom) (0.5 μM) failed to reduce BRD4 expression but reversed the degradation observed through dBET1 indicating that Pom binds CRBN and competes for interaction with dBET1. Western blot analysis for expression of BRD4, c-Myc, CRBN and β-actin in human and mouse T cells treated with vehicle (DMSO), JQ1 and dBET1 and M-dBET1 for 48 h. CRBN is shown for human T cells and vinculin loading control of human and mouse T cells are provided. Treated with vehicle (DMSO, 0.1%), JQ1, dBET1 (1 μM) shown for mouse cells. Results shown are representative of three independent experiments.
Figure 12:
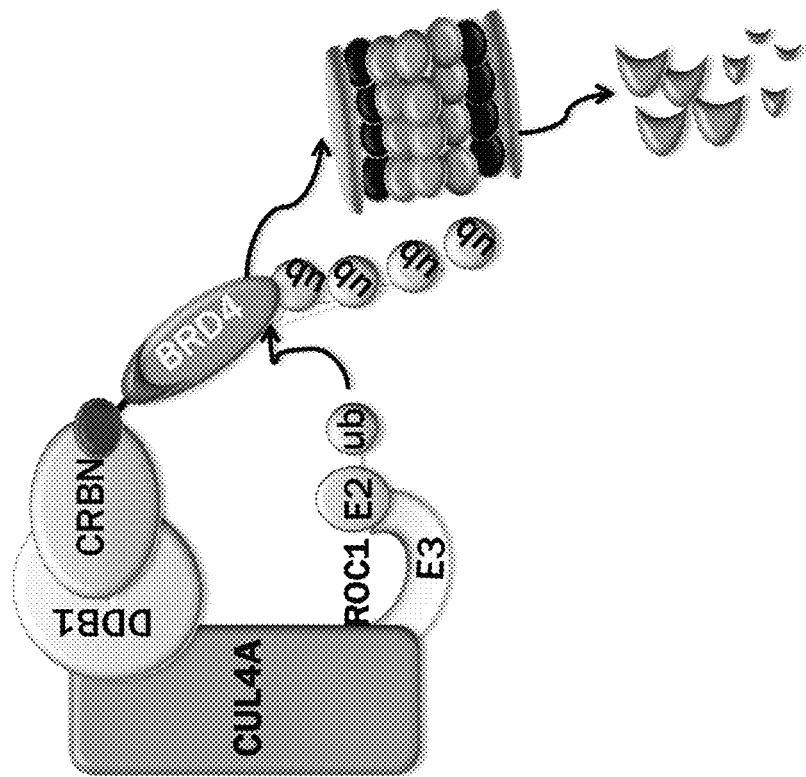

Based on cereblon's function as a substrate binding protein, a new class of intracellular protein degraders has recently been developed with complementary bifunctional components that: 1) interact with specific protein substrates; and 2) engage an E3 ligase that leads to polyubiquitination and target-specific degradation by the 26S proteasome. This technology, coined Proteolysis Targeting Chimera (PROTAC) (Sakamoto, K. M., et al. Protacs: chimeric molecules that target proteins to the Skp1-Cullin-F box complex for ubiquitination and degradation. *Proc Natl Acad Sci USA* 98, 8554-8559, 2001) has significant therapeutic potential (Sakamoto, K. M., et al. Development of Protacs to target cancer-promoting proteins for ubiquitination and degradation. *Mol Cell Proteomics* 2:1350-1358, 2003; Sakamoto, K. M. Protacs for treatment of cancer. Pediatr Res 67:505-508, 2010) where oncogenic proteins may be difficult to target with small molecules. Three research groups (Zengerle, M., et al., Selective Small Molecule Induced Degradation of the BET Bromodomain Protein BRD4. *ACS Chem. Biol.* 10:1770-1777, 2015; Winter, G. E., et al., Phthalimide conjugation as a strategy for in vivo target protein degradation. *Science* 348:1376-1381, 2015; Lu, J., et al., Hijacking the E3 Ubiquitin Ligase Cereblon to Efficiently Target BRD4. *Chem. Biol.* 22:755-763, 2015) recently selected BRD4 as a target protein for PROTAC as this epigenetic regulator plays critical roles in the transcriptional regulation of several oncogenes including c-MYC. Both the Bradner and Crews laboratories conjugated JQ1, an established inhibitor of bromodomain and extraterminal domain (BET) family members, to a thalidomide analog to promote degradation of BRD4 via a cereblon (CRBN)-dependent mechanism. FIG. 12 shows that dBET1 degrades BRD4 in a CRBN-dependent manner in both mouse and human cells.

Figure 13:
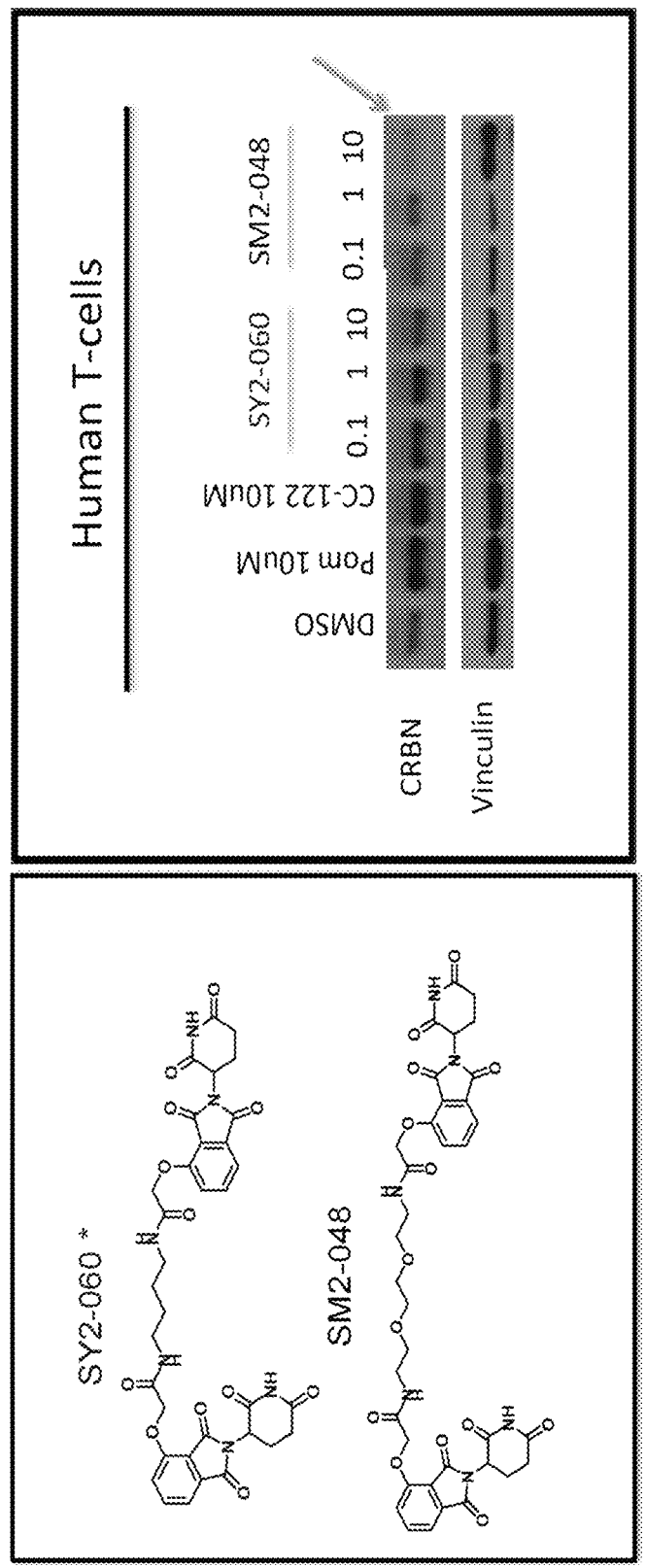
FIG. 13 illustrates targeting CRBN protein depletion through targeted degradation.
Figures 14A, 14B, 14C, 14D:
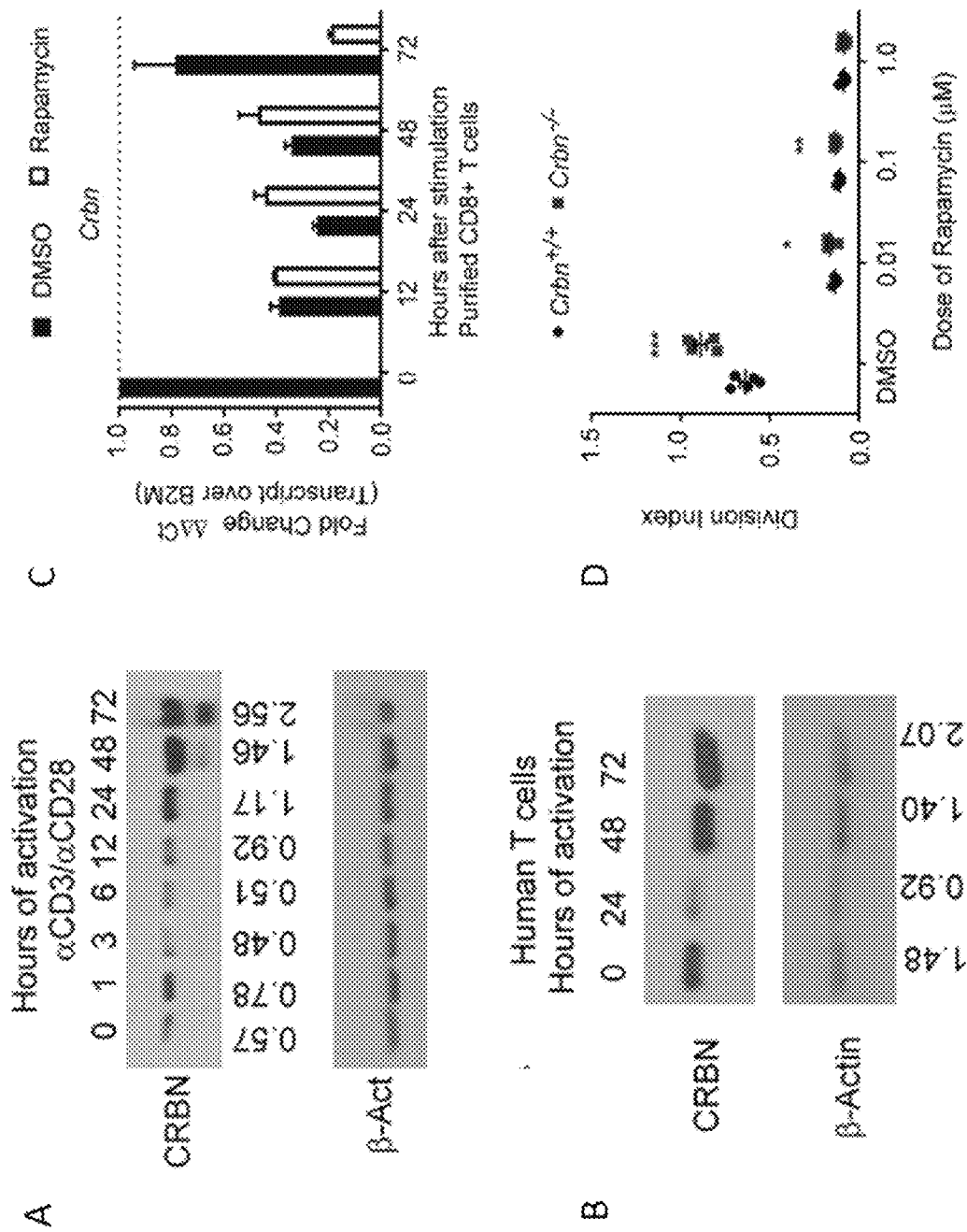
FIGS. 14A, 14C, and 14D show data from mouse
FIG. 14B shows data from human CD8+ T cells activated with anti-CD3 and anti-CD28 antibodies. Intracellular cereblon levels decreased and then increased at later time points suggesting that it may play a role in immune resolution.
Figures 15A, 15B, 15C:
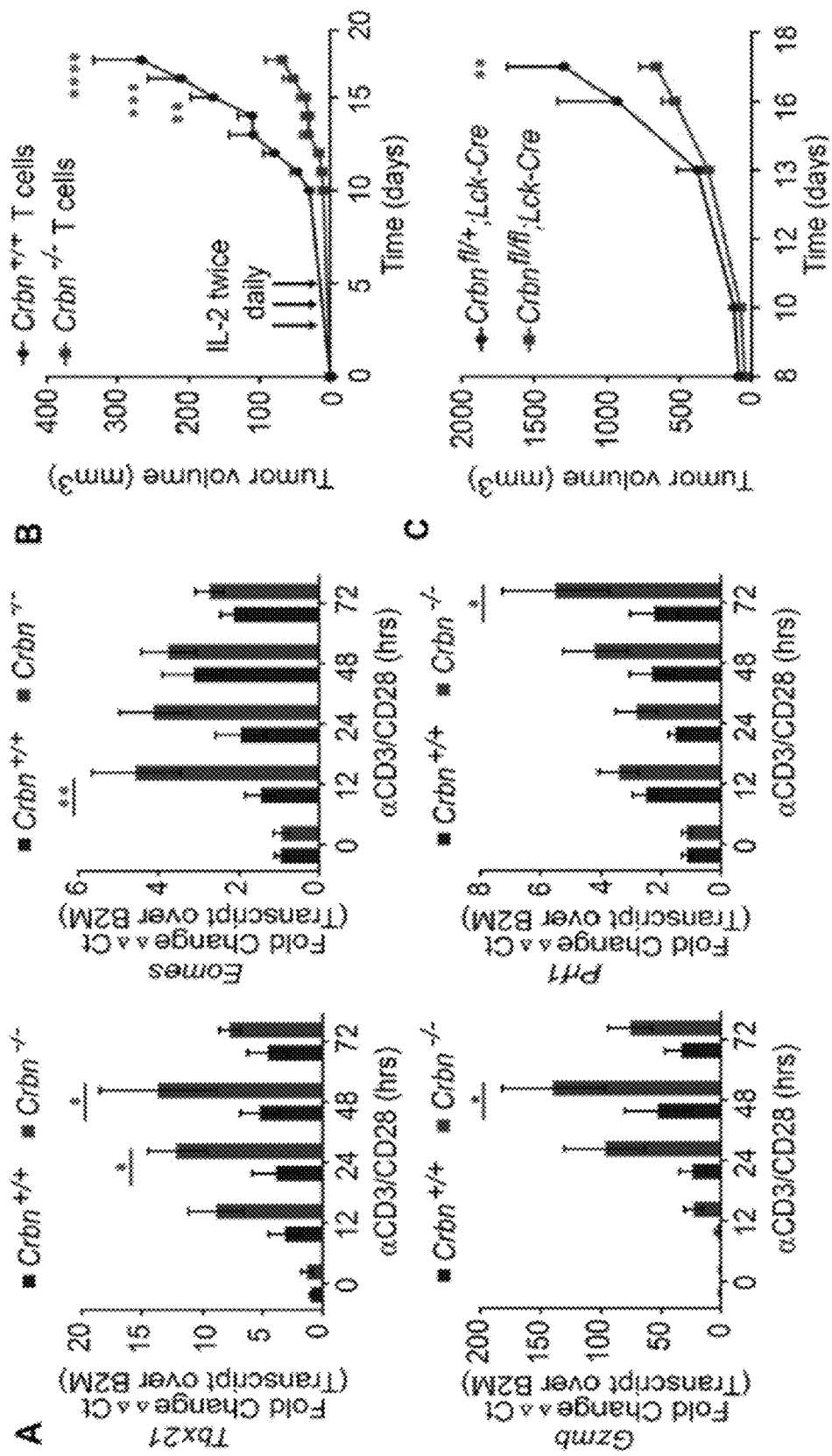
In FIG. 15A, Crbn−/− and Crbn+/+ CD8+ T cells were activated with anti-CD3 and anti-CD28 antibodies. Increased effector-related genes (Tbx21, Eomes, Gzmb, and Prf1) were all significantly increased in Crbn−/− CD8+ T cells.
In FIG. 15B, adoptive transfer of Crbn−/− T cells into mice with B16 melanoma tumors significantly delayed tumor growth which is consistent with improved effector functions in vivo.
In FIG. 15C, cell specific gene deletion of Crbn in T cells with Crbn$^{fl/fl}$; Lck-Cre also resulted in reduced tumor growth indicating that Crbn−/− T cell have improved antitumor immunity and increased effector functions leading to the therapeutic hypothesis that reducing cereblon levels in T cells may promote their anti-cancer therapeutic potential.
Figure 16:
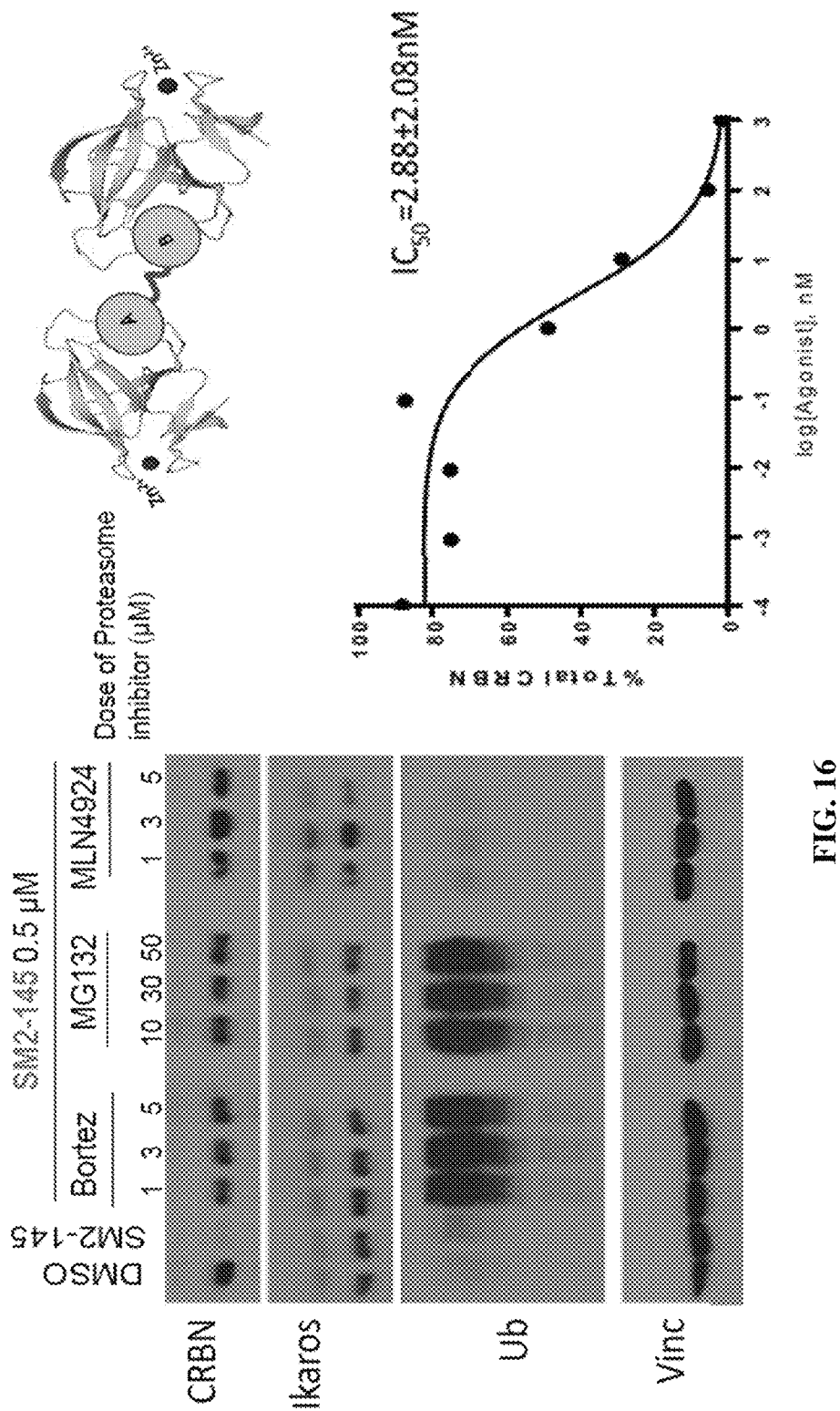
FIG. 16 contains a Western blot showing reduced intracellular cereblon levels in human T cells after 24 hours of treatment with SM2-145. Depletion of cereblon with this treatment is dependent on the ubiquitin proteasome activity as it was reversed by three different proteasome inhibitors. Specificity is shown for CRBN degradation over Ikaros (also known as IKZF1), which is the established targets of immunomodulatory drugs. SM2145 concentration leading to 50% degradation of cereblon ($DC_{50}$) is shown=2.88 nM. Bortez=bortezomib; MG132=proteasome inhibitor; MLN4924=NEDD8 inhibitor.
Figure 17:
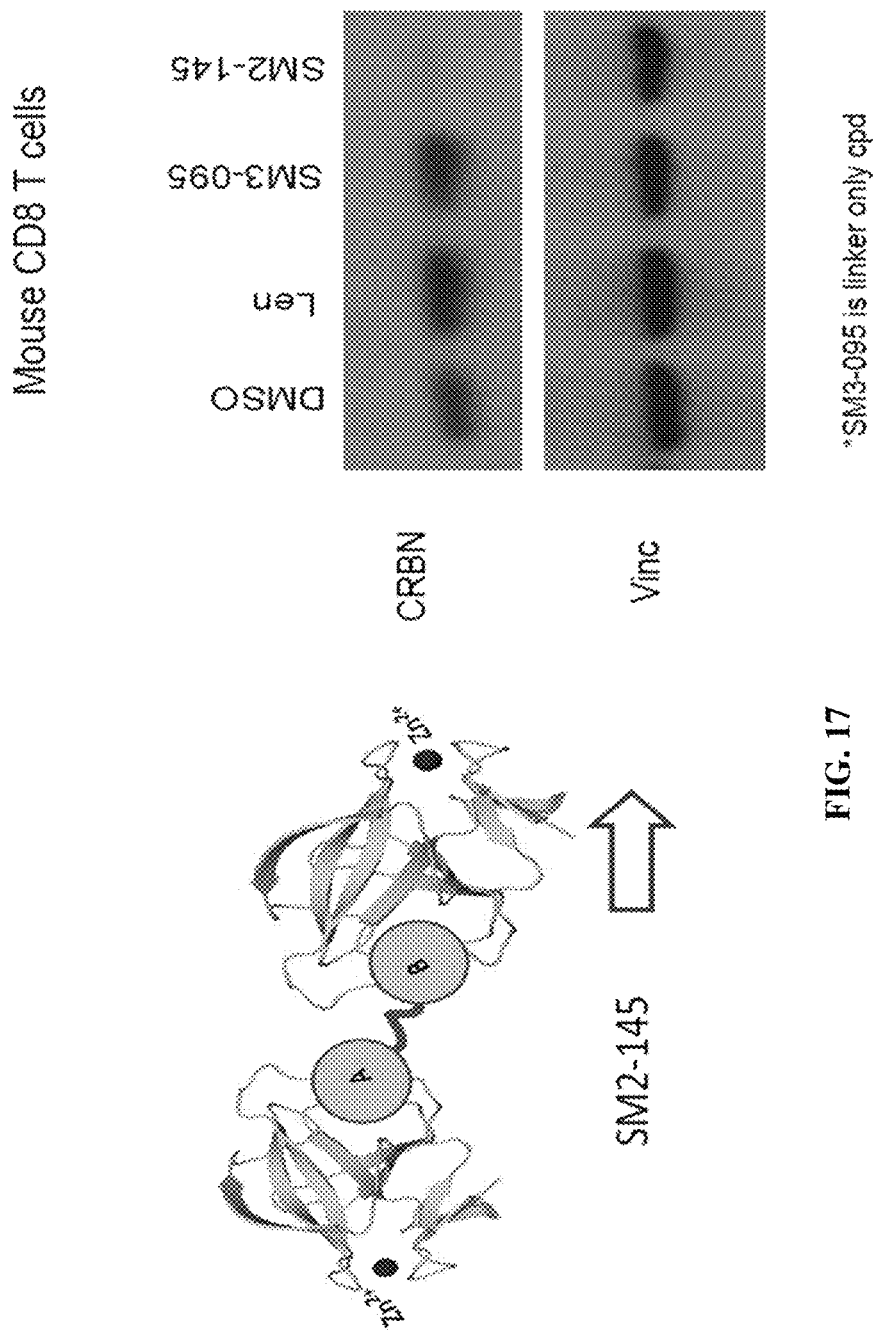
FIG. 17 contains a Western blot showing reduced cereblon (CRBN) levels in mouse CD8+ T cells after 24 hours of treatment with SM2145 (cereblon destroying molecule, CDM) but not lenalidomide (Len) or the linker-Len conjugate (SM3-095). Data indicates that mice can be used for testing of this class of compounds which requires a dimeric structure to reduce CRBN levels.
Figure 18:
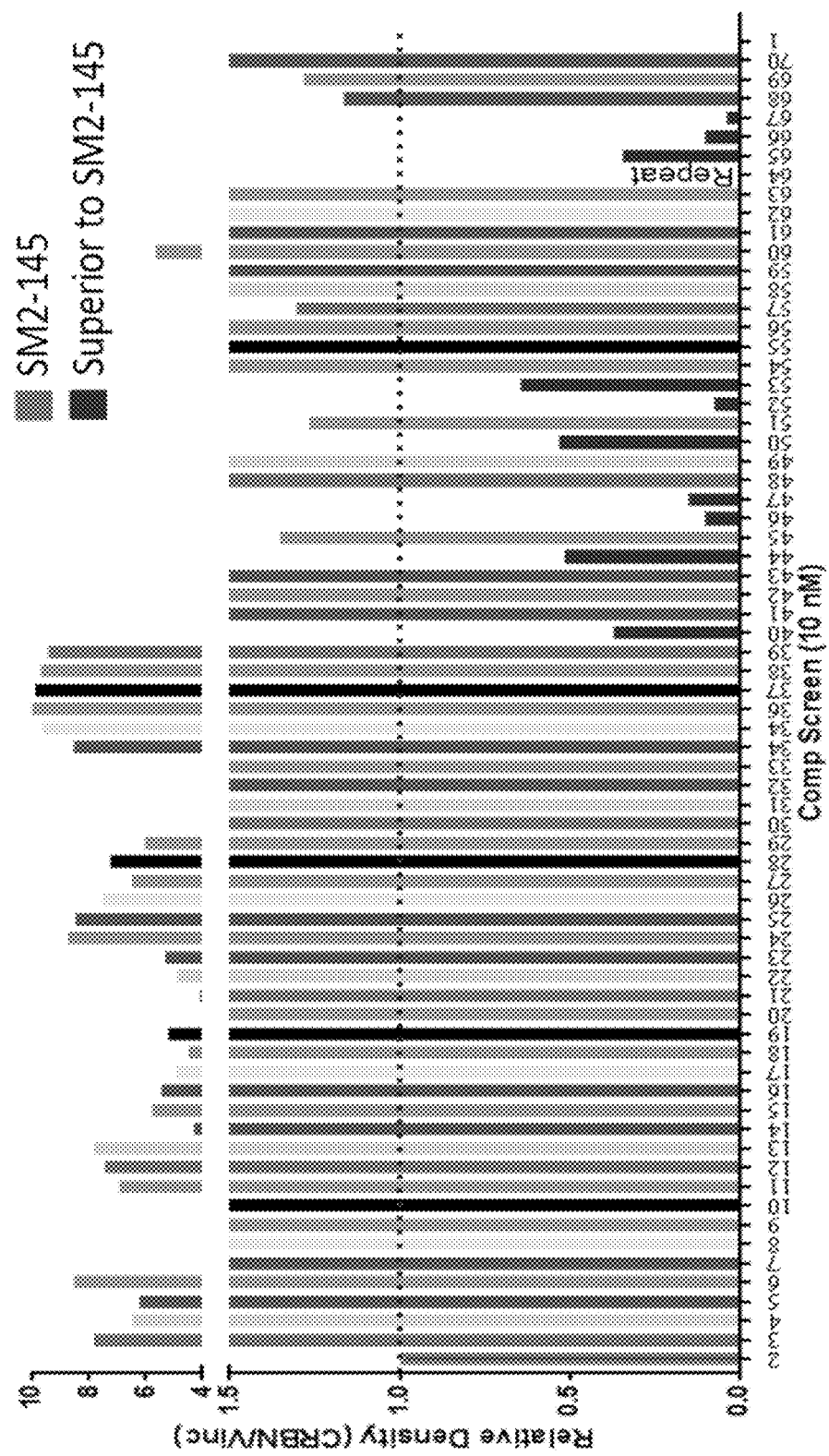
FIG. 18 is a graphic display of combined results of 70 compounds screened at 10 nM using Western blot showing reduced cereblon (CRBN) levels in human CD8+ T cells after 24 hours of drug treatment. Relative density of CRBN/vinculin was established for SM2145 and other compounds. Data indicate that several related homo or heterodimeric small molecules reduce CRBN levels to that lower than SM2-145 (bars shown at 40, 44, 46, 47, 50, 52, 53, and 65-67). This assay is a standard Western blot assay for expression of CRBN relative to vinculin. Each compound was added for 24 hours at a concentration of 10 nM to human T cells. 0.1 percent DMSO was used as a vehicle control. Results were expressed relative to SM2-145 treated cells on the same plate as a ratio of CRBN/vinculin. Each blot contained a control treated with SM2-145. Densitometry was performed and ratio of each compound expressed relative to SM2-145 run on the blot.
Figure 19:
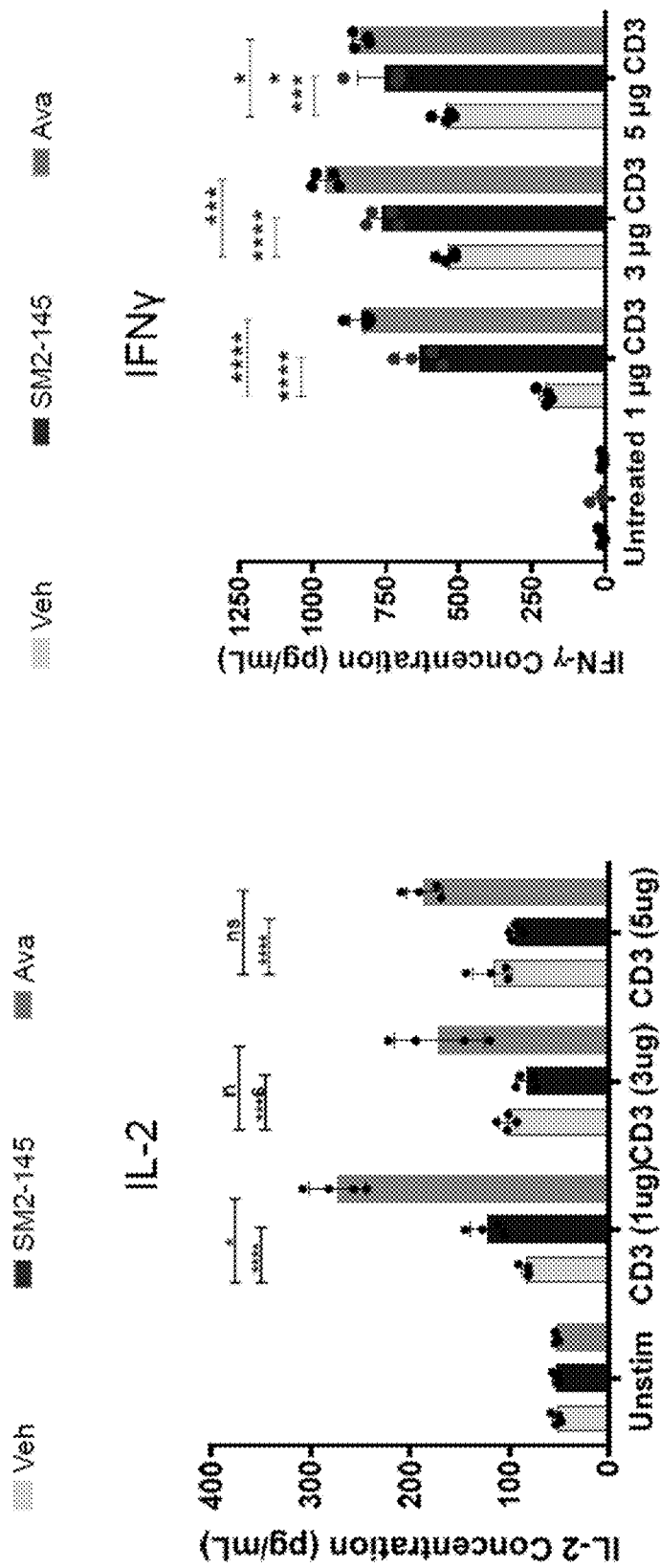
FIG. 19 shows T cells expanded from patients with melanoma subjected to activation and cytokine analysis. Cytokine assays for detection of interleukin-2 (IL-2) and interferon-γ (IFN-γ) after activation with increasing concentration of anti-CD3 (OKT3) antibody show a different profile for SM2-145 (CDM) compared to CC122 (avadomide, Ava) indicating that these small molecules are actively increasing T cell function but through distinct mechanisms. Veh=vehicle-treated cells DMSO 0.1%
Figure 20:
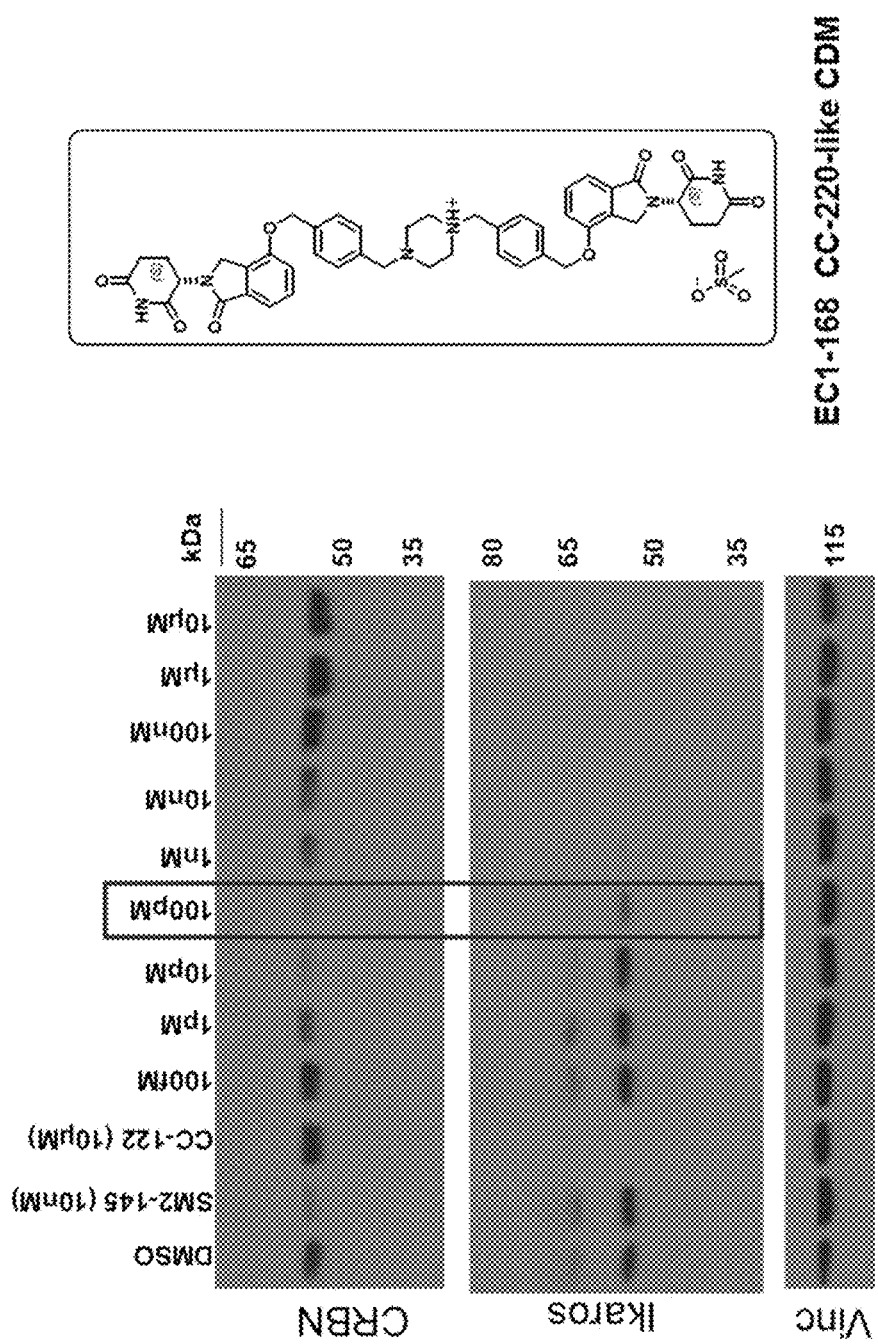
FIG. 20 shows structural properties of CDMs induce different target specificity. Isolated human CD8+ T cells were treated with increasing doses of EC1-168. This molecule has a $DC_{50}$ for Ikaros at 10 pM and for CRBN at <1 pM. Unique functional properties may be afforded to the CDM compounds via distinct protein recruitment.
Figure 21:
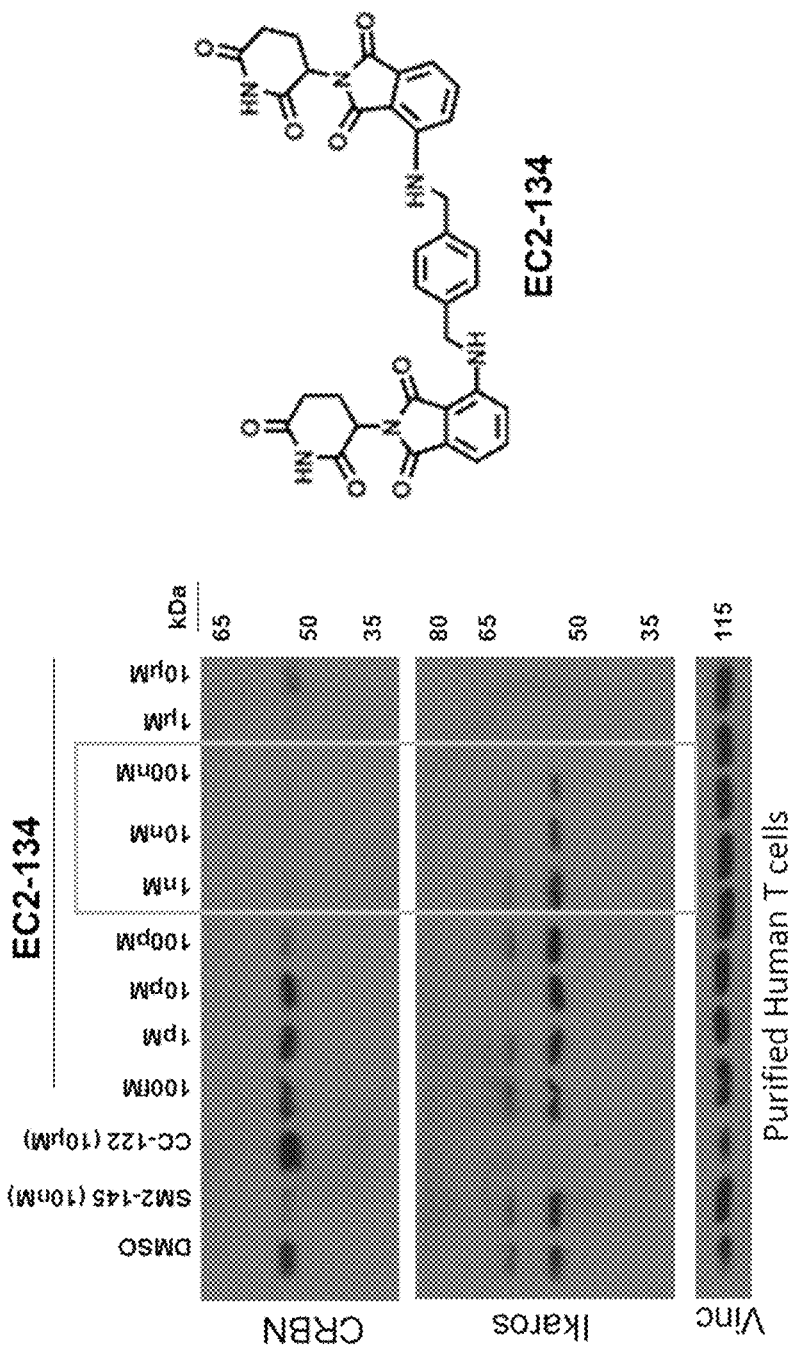
FIG. 21 shows structural properties of CDMs induce different target specificity. Isolated human CD8+ T cells were treated with increasing doses of EC2-134. This molecule has a $DC_{50}$ for Ikaros at 10 nM and for CRBN at 100 pM. Unique functional properties may be afforded to the CDM compounds via distinct protein recruitment.
Figure 22:
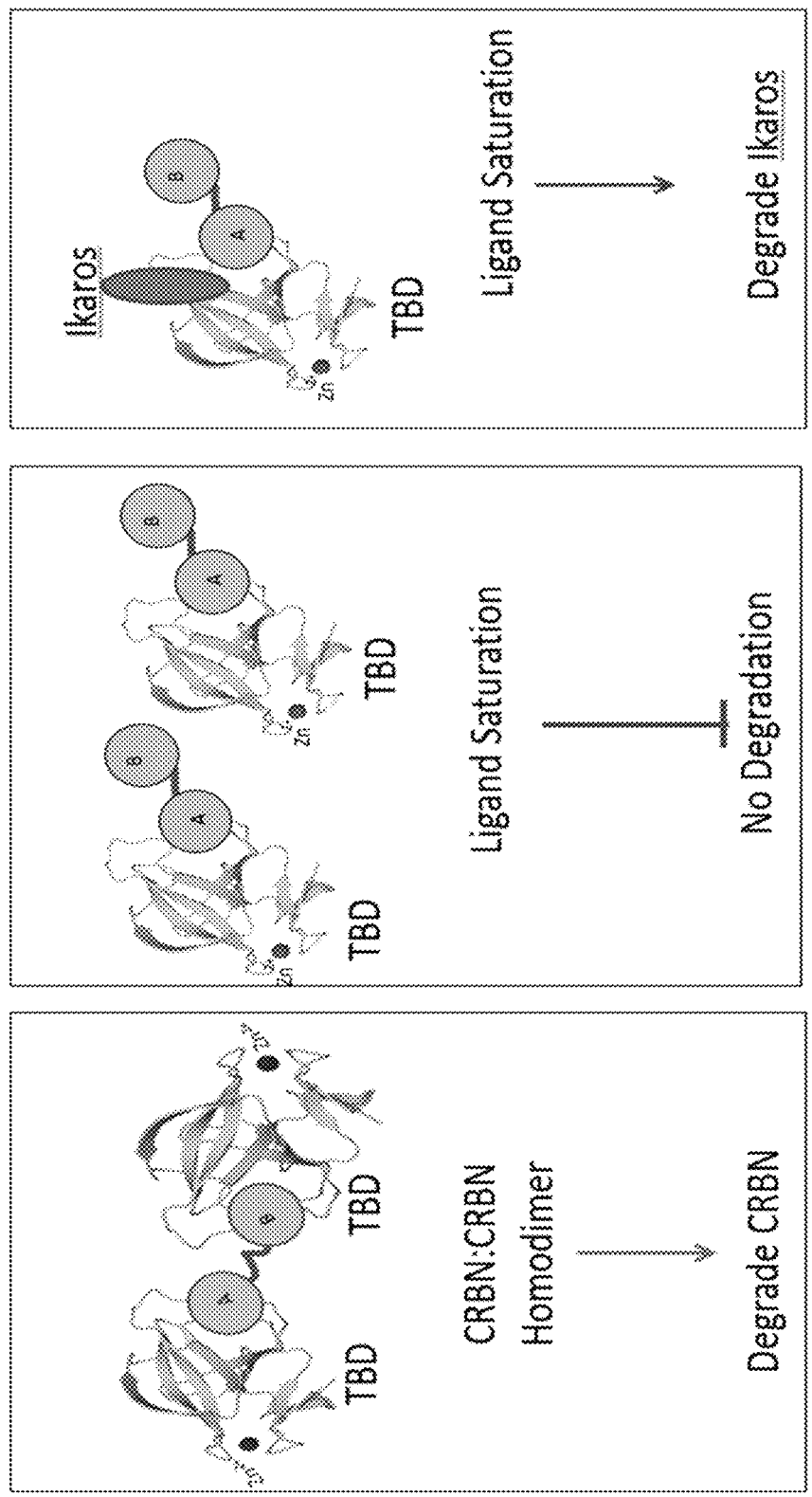
FIG. 22 is a schematic of a hypothesis for selectivity of CDMs that first induce a CRBN:CRBN homodimer at lower doses leading to proteasome-dependent degradation. Ligand saturation then blocks this complex leading to monomeric functions of immunomodulatory drug component which then degrades its target molecule (such as Ikaros). Unique functional properties may be afforded to the CDM compounds via distinct protein recruitment. These are hypothesized to show more therapeutic activity than traditional immunomodulatory drugs.
Figure 23:
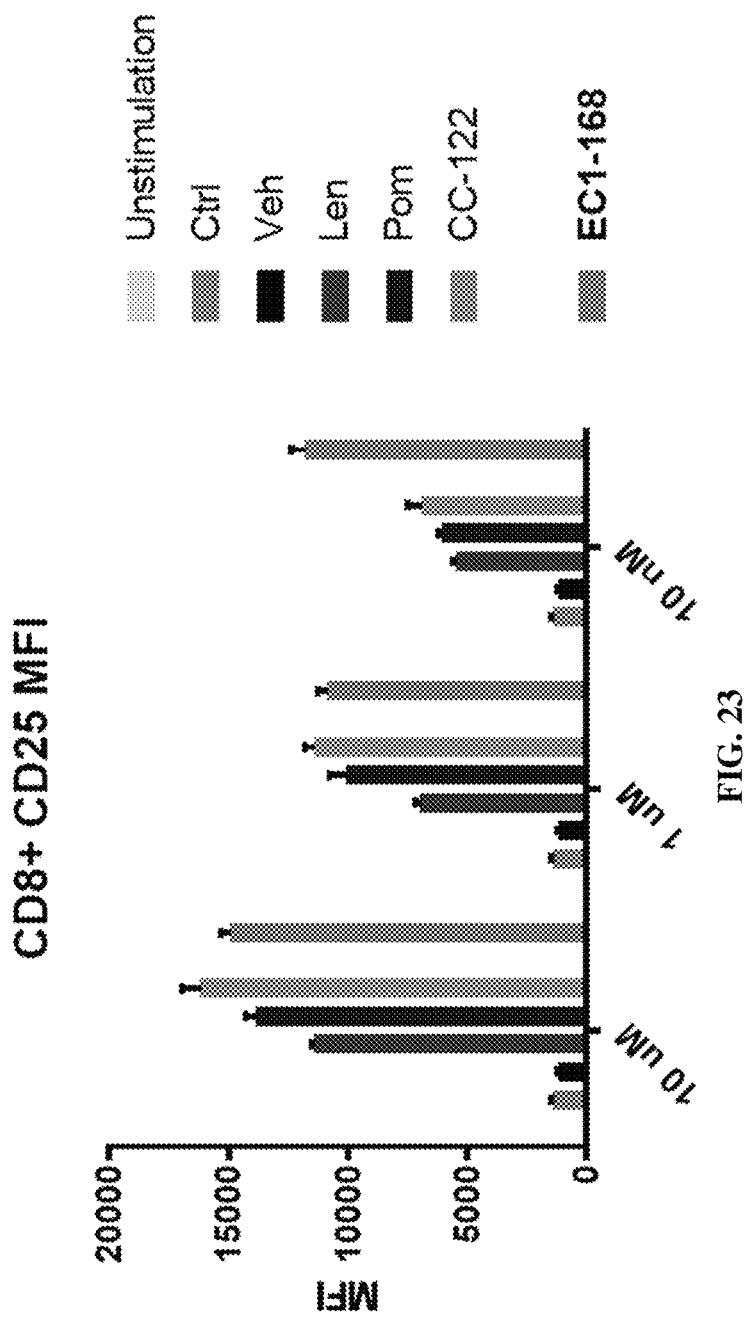
FIG. 23 is a graph showing human T cells activated with a series of immunomodulatory drugs lead to higher levels of expression of the activation marker CD25 (IL-2 receptor alpha) compared to unstimulated cells and control activated cells. CDM molecule EC1-168 induces more immune potentiation at 10 nM in this assay. Ctrl=anti-CD3/anti-CD28-stimulated cells; Veh=vehicle, DMSO 0.1%; Len=lenalidomide; Pom=pomalidomide; CC-122=avadomide.
Figure 24:
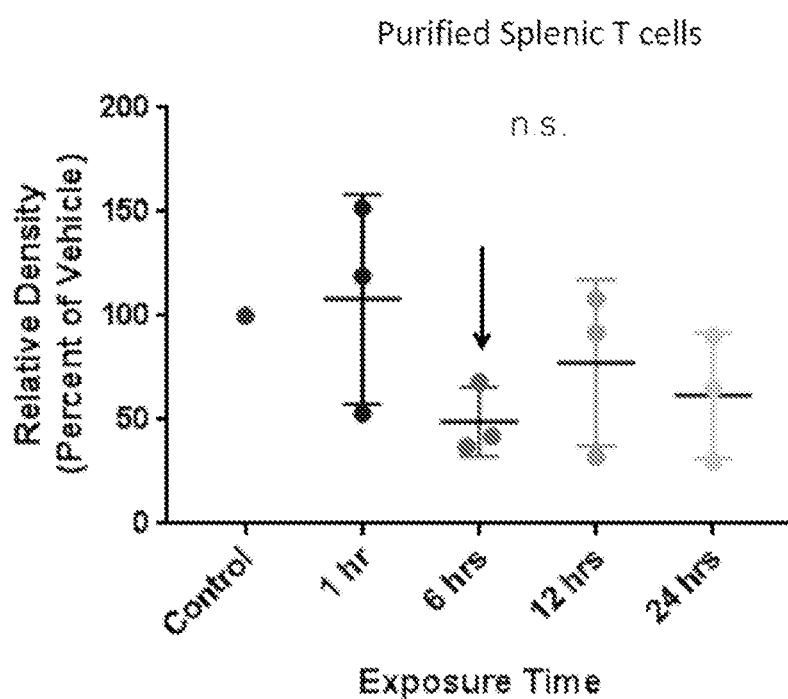
FIG. 24 is a graph of results from Western blots from purified splenic T cells of mice treated orally with a single dose of 75 mg/kg SM2-145. Three mice were obtained from each time point (1, 6, 12, and 24 hrs) after treatment. Results show a partial reduction in cereblon levels at 6 hours. Poor stability of this compound was observed in pharmacokinetic studies.
Figure 25:
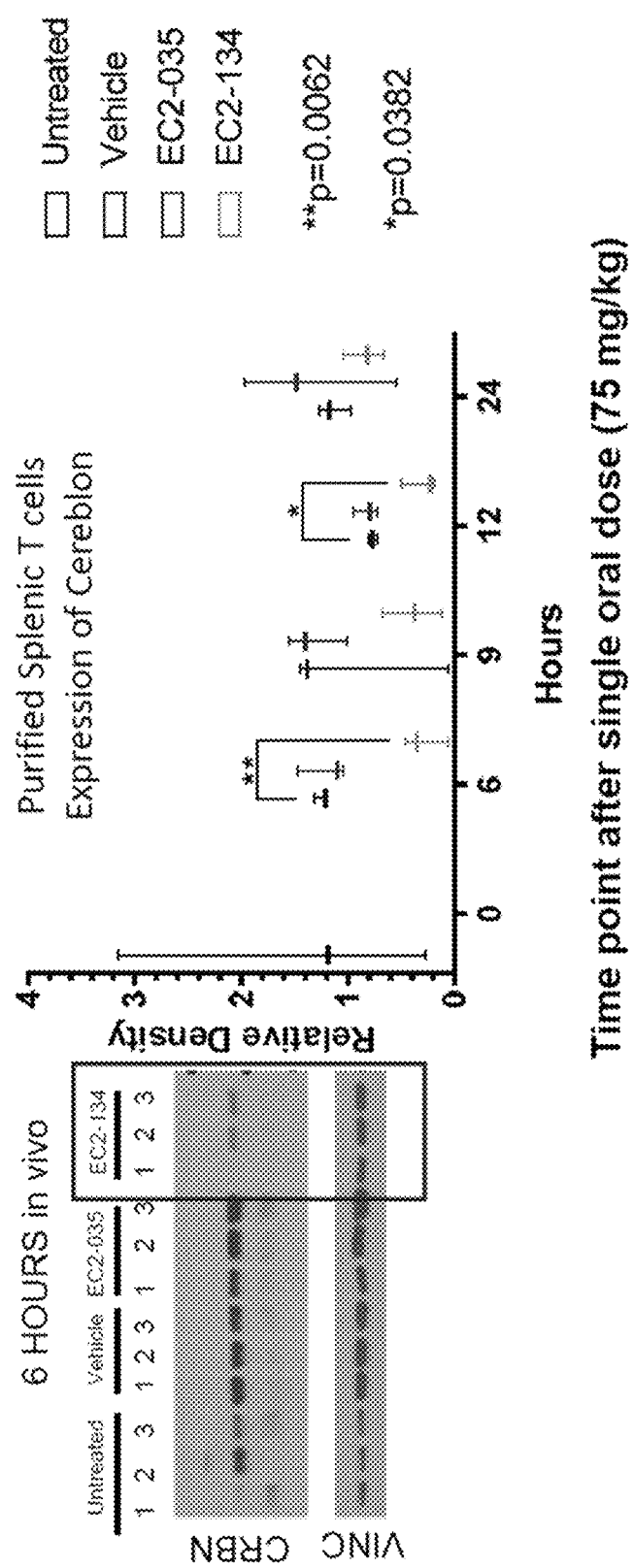
FIG. 25 contains a Western blot analysis of purified T cells from mice treated orally with a single dose of 75 mg/kg EC2-035 and EC2-134. Results show sustained reduction in cereblon levels at 6, 9 and 12 hours in purified splenic T cells.
Figure 26:
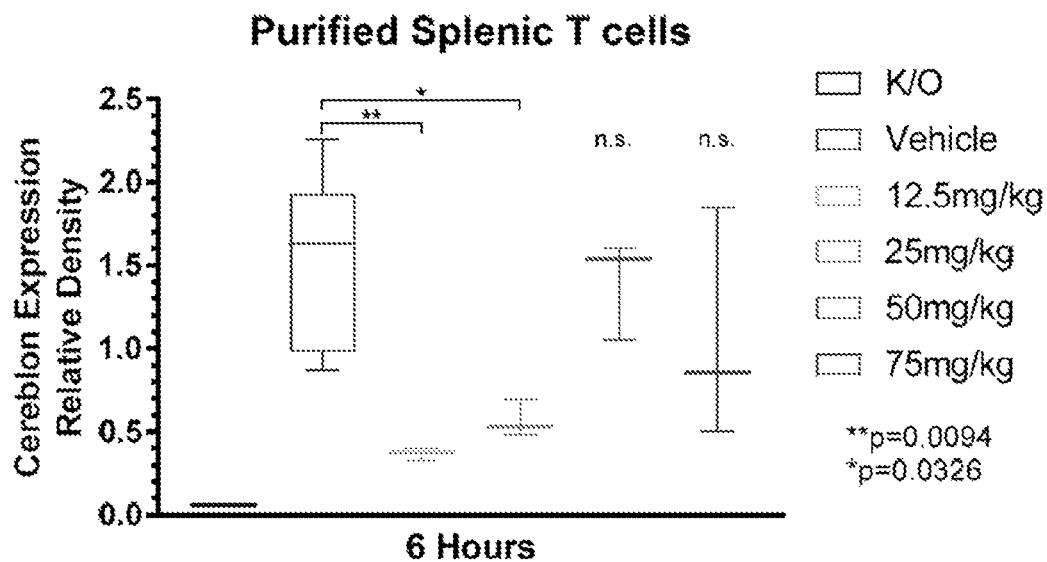
FIG. 26 is a graph of results from Western blot analysis performed and displayed graphically from purified T cells from Crbn−/− T cells (K/O), wild-type Crbn+/+ T cells, and from T cells isolated from mice treated orally with a single dose of 12.5, 25, and 75 mg/kg of EC2-134. Results show inverse dose dependent levels of cereblon indicating that there was target saturation. However, levels of cereblon are significantly reduced reaching to that of Crbn−/− T cells at the lowest dose.
Figure 27:
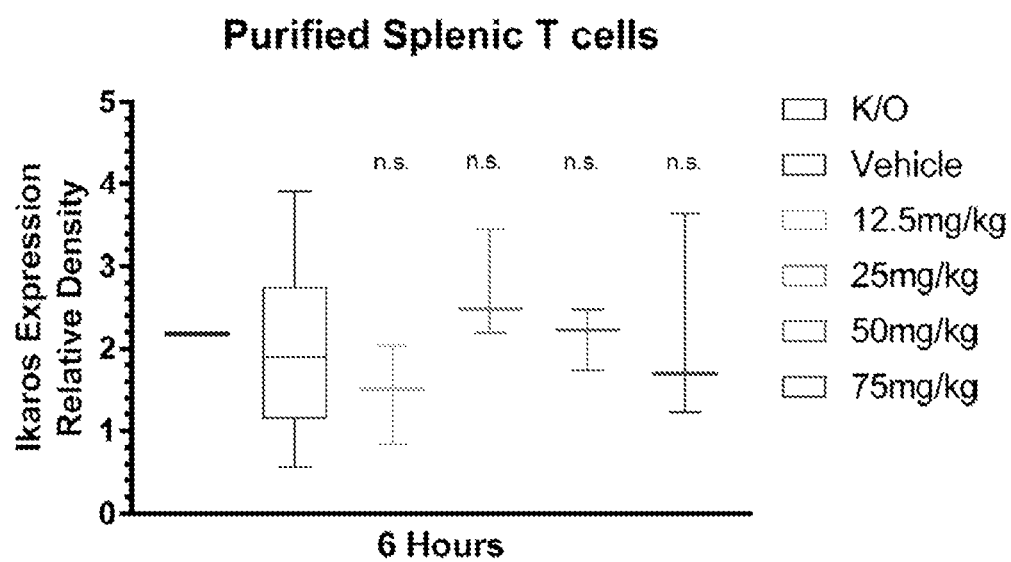
FIG. 27 is a graph of results from Western blot analysis performed from mice shown in FIG. 26 with evaluation of Ikaros. Purified T cells from Crbn−/− T cells (K/O), wild-type Crbn+/+ T cells, and from T cells isolated from mice treated orally with a single dose of 12.5, 25, and 75 mg/kg of EC2-134 have similar levels of Ikaros. Results show specific target engagement.
Figure 28:
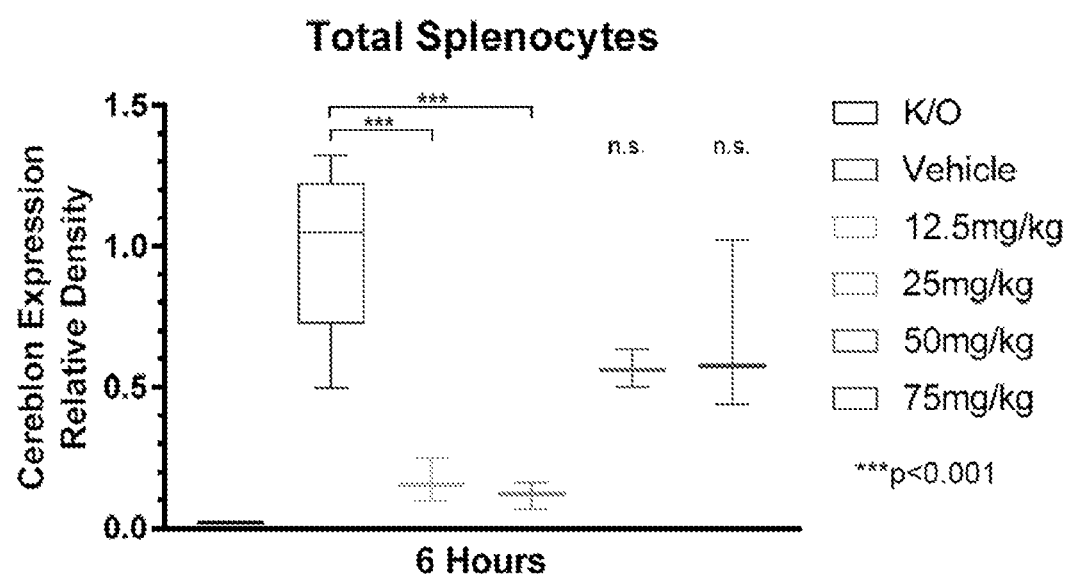
FIG. 28 is a graph of results from Western blot analysis performed and displayed graphically from total splenocytes from Crbn−/− T cells (K/O), wild-type Crbn+/+ T cells, and from T cells isolated from mice treated orally with a single dose of 12.5, 25, and 75 mg/kg of EC2-134. Results show inverse dose dependent levels of cereblon in a more complex population of cells including T cells.
Figure 29:
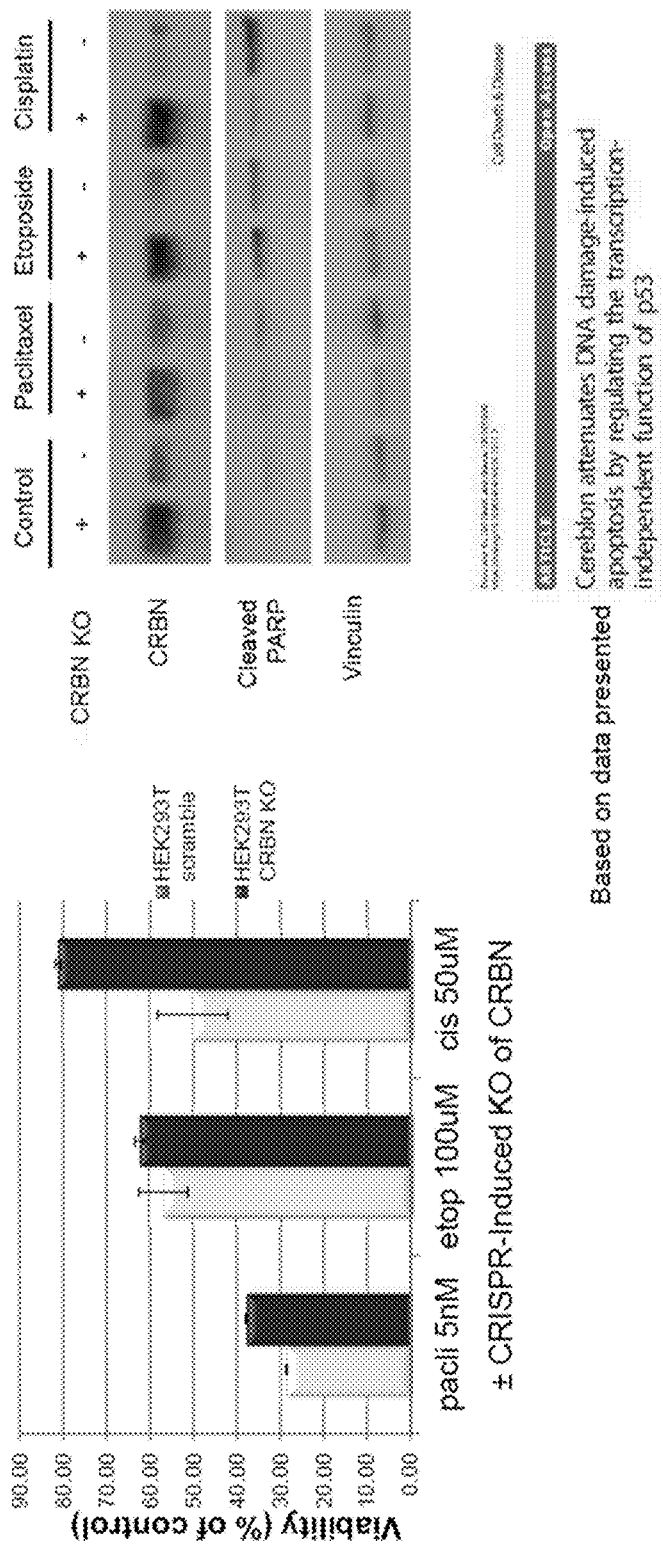
FIG. 29 shows a Western blot analysis performed on HEK cells that lack CRBN due to CRISPR-induced gene depletion. Results show increased PARP cleavage and cell death in response to DNA damaging agents paclitaxel, etoposide and cisplatin. Results support the idea presented in the associated manuscript that cereblon controls DNA damage induced apoptosis. Therapeutic hypothesis based on this result is that cereblon destroying molecules (CDMs) may increase anti-tumor activity in combination with radiation therapy and DNA damaging chemotherapy in addition to potentiation of T cell immunotherapy.

Based on the superior anti-tumor immunity of Crbn$^{-/-}$ T cells relative to immunomodulatory drug treated cells, disclosed herein is a class of bifunctional cereblon degraders. The compounds can be used for: 1) immune regulation, 2) antitumor cytotoxicity, 3) modification of anti-PD1 therapeutic responses, 4) biochemical analysis of cereblon-based mechanisms important for immunomodulatory drug response, and 5) an aide in the analysis of new regions important for CRBN metabolic regulation. Exemplary results from two bifunctional CRBN degraders are shown in FIG. 13.

Disclosed herein are compounds comprising dimers of immunomodulatory drugs (bis-immunomodulatory drugs), e.g., dimers of E3-ligase ligands. The dimers disclosed herein can be two of the same immunomodulatory drugs linked together or two different immunomodulatory drugs linked together. In specific examples, the E3 ligase ligands are cereblon binding ligands.

Figure 2:
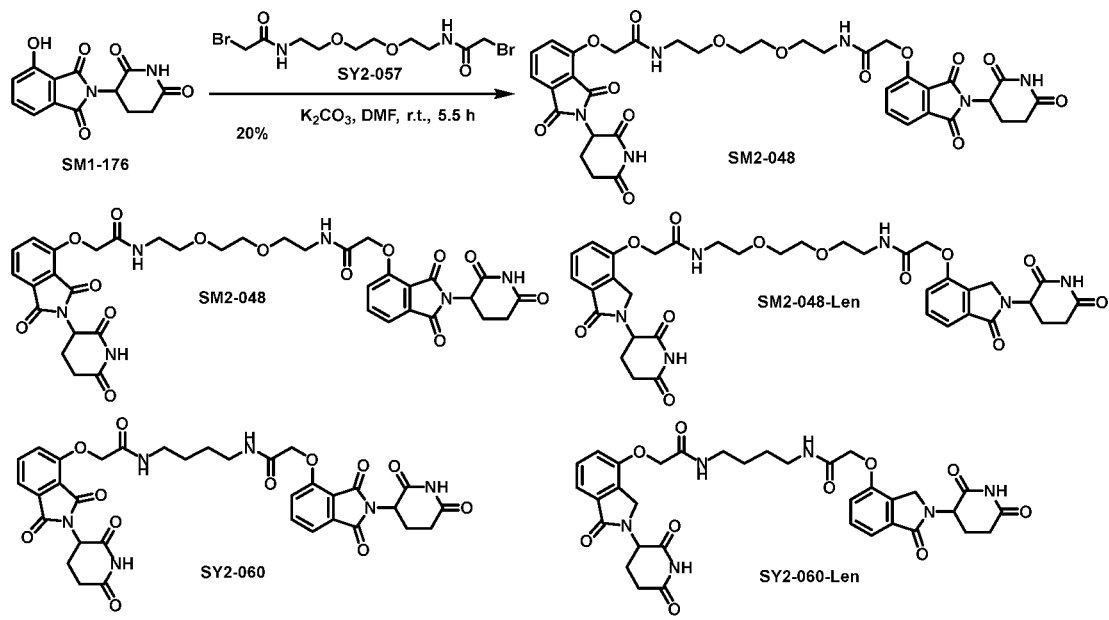
FIG. 2 shows structures of bis-immunomodulatory drugs SM2-048 and SY2-060.
Figure 3:
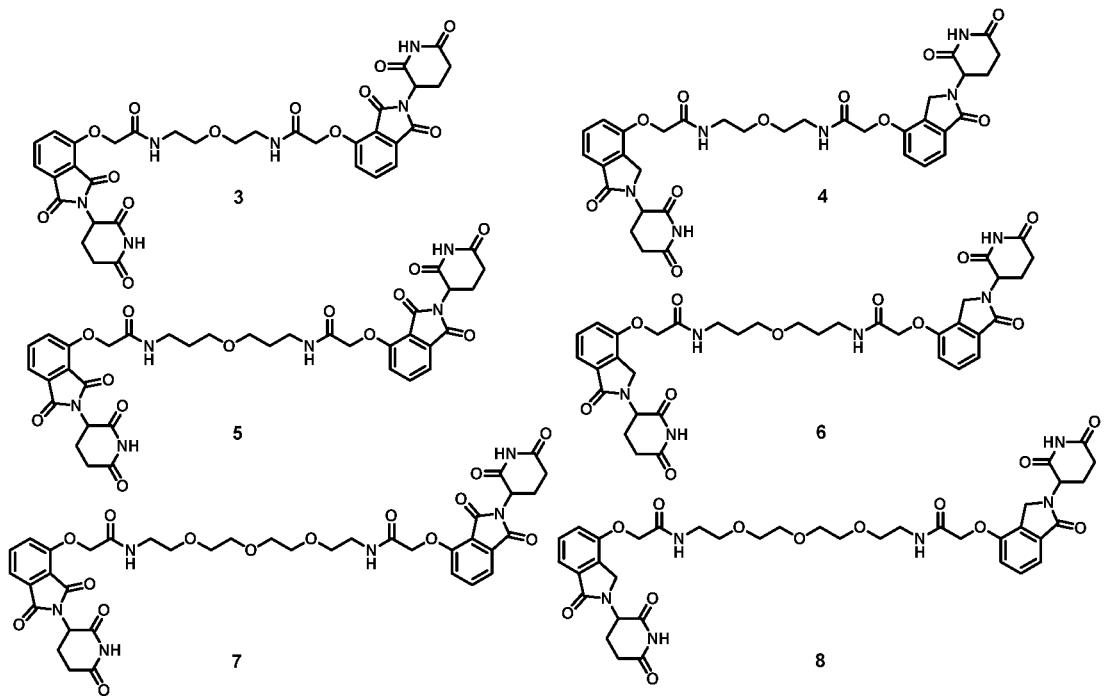
FIG. 3 shows other examples of O-linked bis-immunomodulatory drugs.

The disclosed compounds are capable of degrading cereblon by formation of a dimeric IMiD (Winter, G. E.; et al. Drug Development. Phthalimide conjugation as a strategy for in vivo target protein degradation. *Science* 348:1376-81, 2015). A cereblon binding ligand (e.g. thalidomide, lenalidomide, pomalidomide, CC-122) (Fischer, E. S.; et al. Structure of the DDB1-CRBN E3 ubiquitin ligase in complex with thalidomide. *Nature* 512:49-53, 2014; Kronke, J.; et al., Lenalidomide induces ubiquitination and degradation of CK1alpha in del(5q) MDS. *Nature* 523:183-8, 2015) is linked to another cereblon binding ligand, via a flexible linking chain of variable length and composition to provide a general compound class 1 as shown FIG. 1. The cereblon binding ligand in the bis-IMiD can be different, as shown in class 2. In the example shown in FIG. 1, compound 2 incorporates both a thalidomide and lenalidomide ligand The first two bis-IMiD derivatives SM2-048 and SY2-060 prepared are shown in FIG. 2. These were prepared by alkylation of 4-hydroxythalidomide (SM1-176) with a bis-bromoacetamide (of type SY2-057 and SY2-058, see examples section and FIG. 2). By starting from a bis-amine, a linker can be incorporated into the bis-IMiD with differing chain length and composition, which will affect affinity for and degradation of the target E3 ligase cereblon. Further examples of O-linked bis-immunomodulatory drugs 3-8 with varying linkers are shown in FIG. 3.

Figure 4:
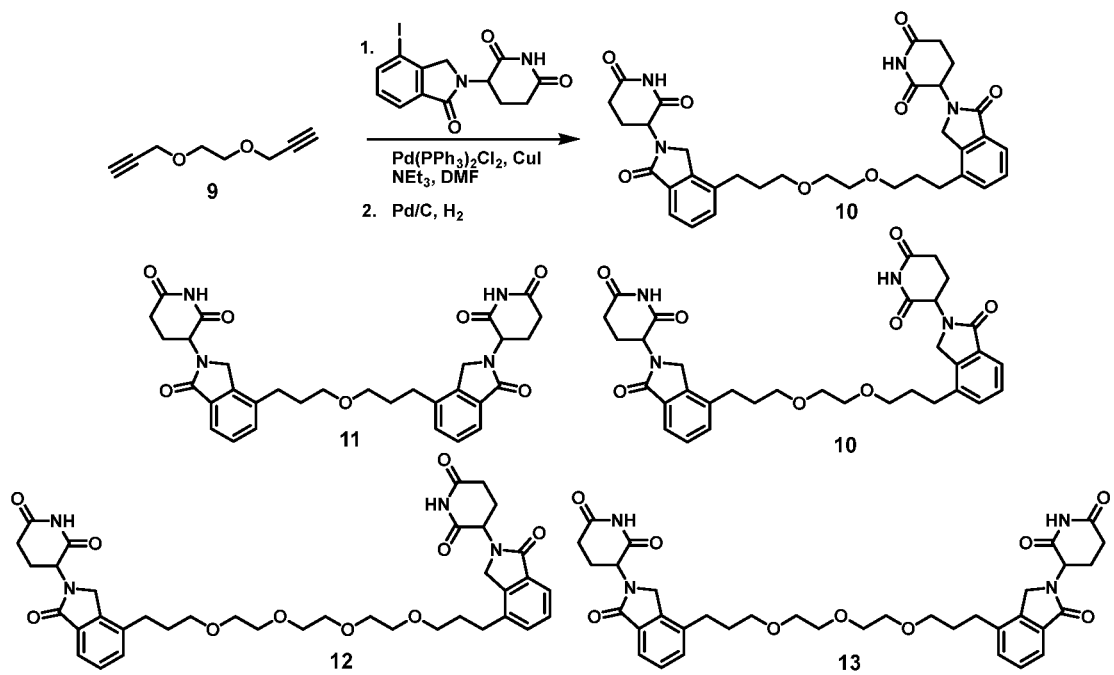
FIG. 4 shows examples of C-linked bis-immunomodulatory drugs.

Examples of bis-immunomodulatory drugs were prepared by Sonogashira coupling of a bis-alkyne of type 9 with an iodo- or bromo-immunomodulatory drugs, as shown in FIG. 4. Reduction of the bis-immunomodulatory drugs provides the C-linked bis-immunomodulatory drugs 10.

Figure 5:
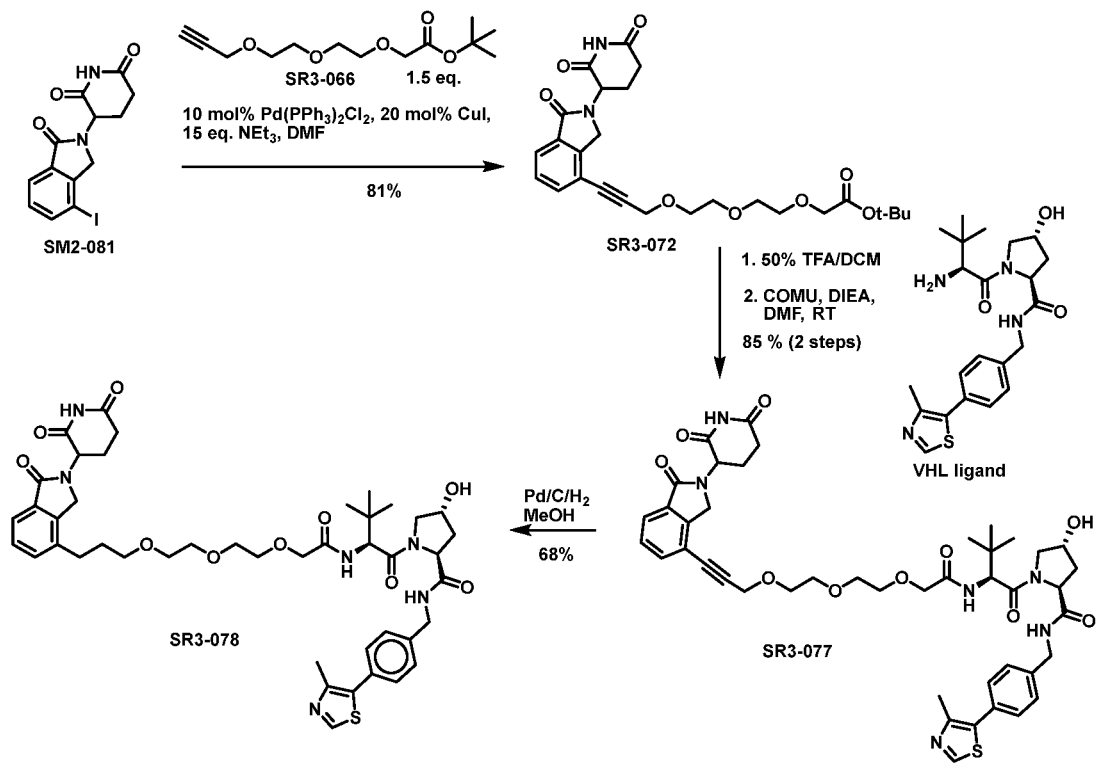
FIG. 5 shows examples of a Len-immunomodulatory drugs linked to a VHL-E3 ligase ligand.
Figure 6:
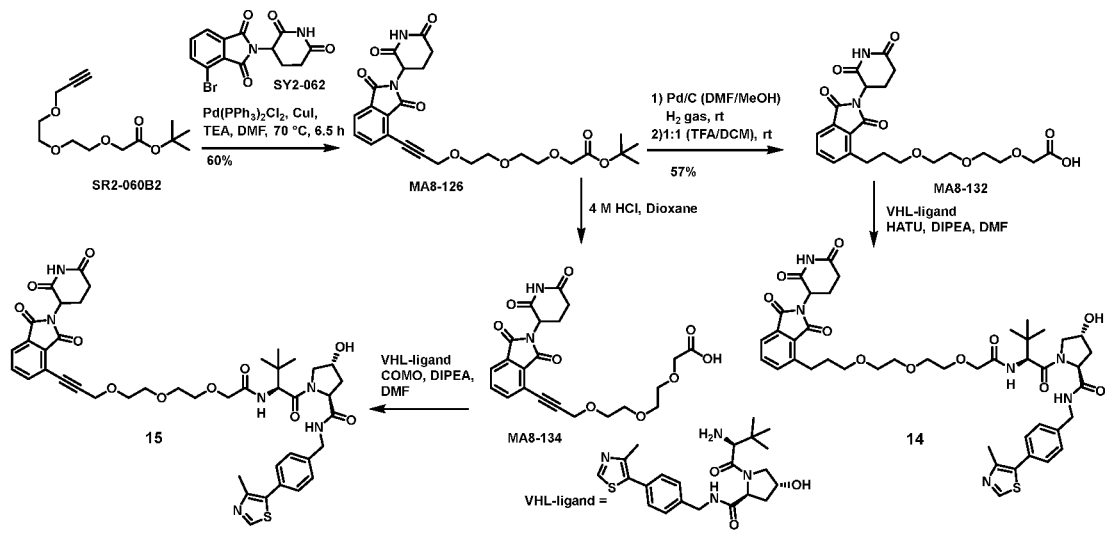
FIG. 6 shows examples of a thalidomide-immunomodulatory drugs linked to a VHL-E3 ligase ligand.

The cereblon ligand can be linked to a ligand that targets a different E3 ligase. Overall this generates a cereblon degrading agent. For example, linking a lenalidomide-like ligand to a ligand of the E3 ligase VHL (Gadd, M. S.; et al., Structural basis of PROTAC cooperative recognition for selective protein degradation. *Nat. Chem. Biol.* 13:514-521, 2017; Galdeano, C.; et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. *J. Med. Chem.* 57:8657-63, 2014), provides a potential cereblon degrader SR3-078 as shown in FIG. 5. Alternatively, the route to thalidomide-VHL ligand conjugates 14 and 15 is shown in FIG. 6.

Figure 7:
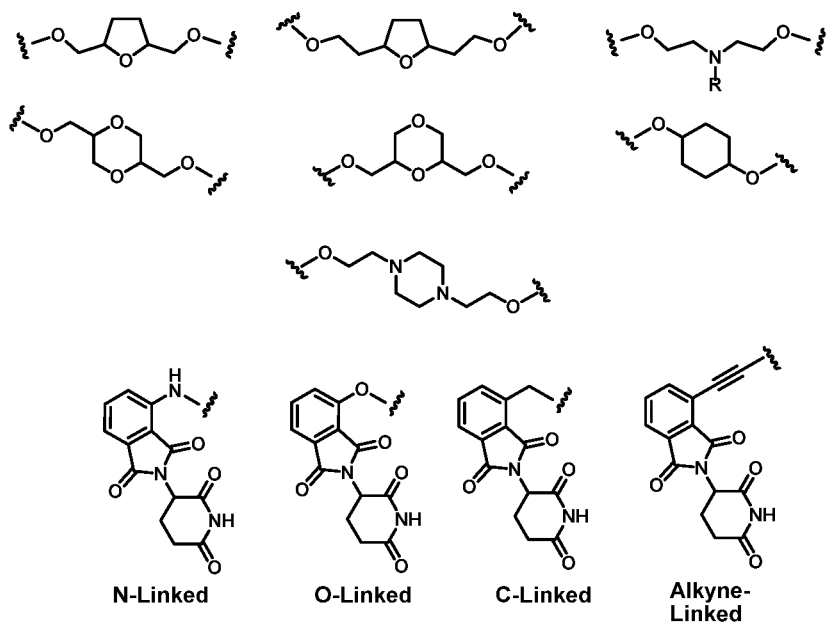
FIG. 7 shows examples of alternative linker units.

The linker used to attach the IMiD to another E3 ligase ligand can also incorporate a heterocyclic ring to conformationally constrain the overall conjugate, or contain amine substituents to modulate affinity and solubility, as shown in FIG. 7. The point of attachment to the IMiD ligand can be via NH, O, CH$_2$ or an alkyne as shown in FIG. 7.

Each of the ligands of the disclosed dimers can be grouped into various classes. For example, the ligands can belong to one of the following classes:

Class 2A
Glutarimide-amide
Glutarimide-sulfonamide

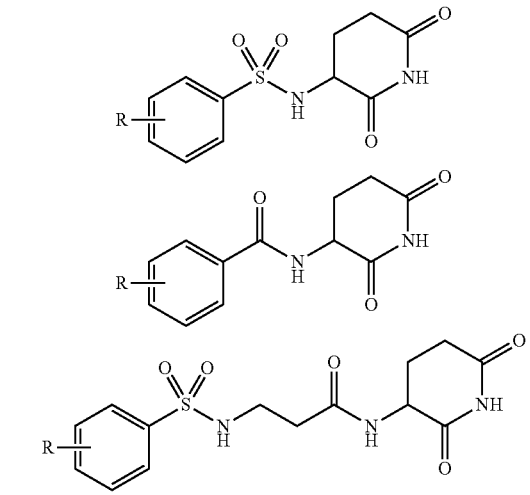

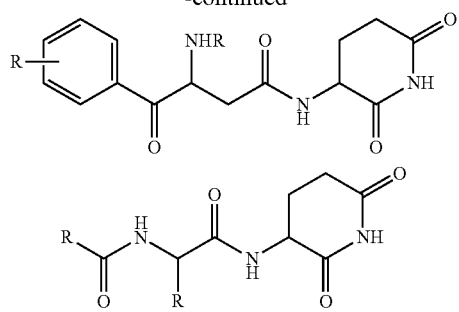
Class 2B
Glutarimide-amine
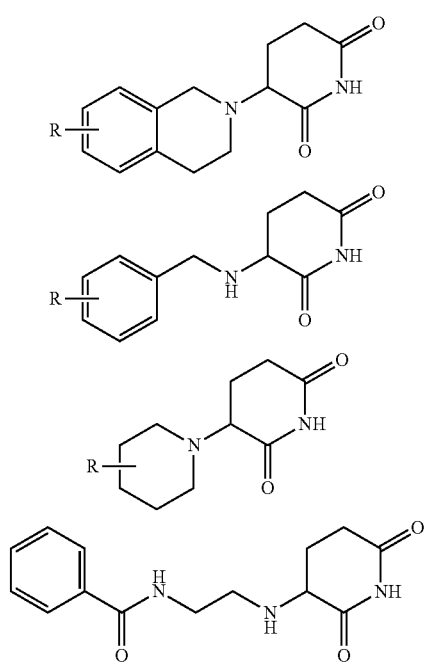
Class 3
Uracil
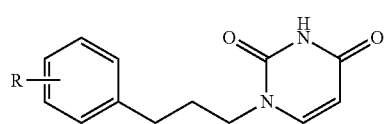
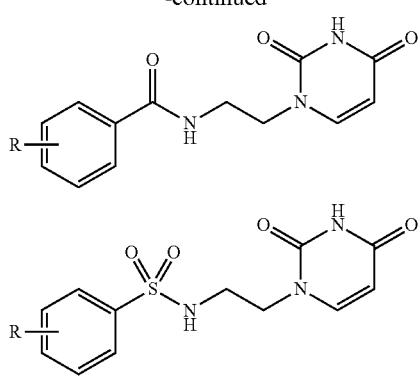
Class 4
Dihydrouracil
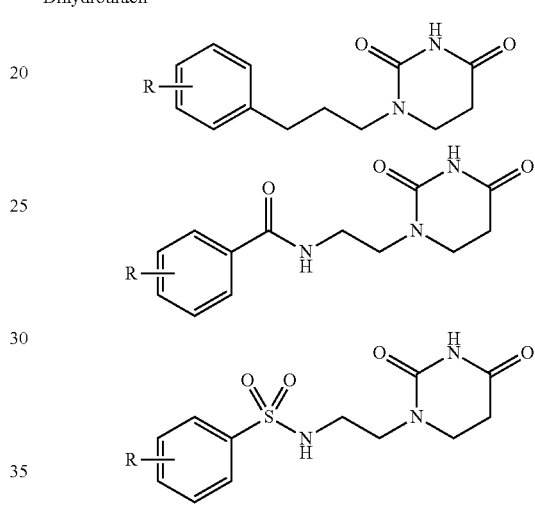
Class 5 Other
Pyroglutaramide
Pyridinone
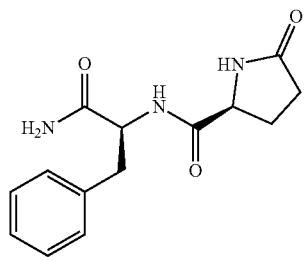
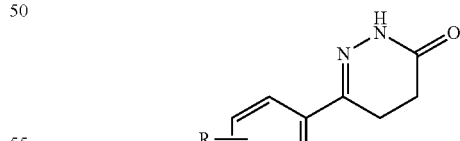
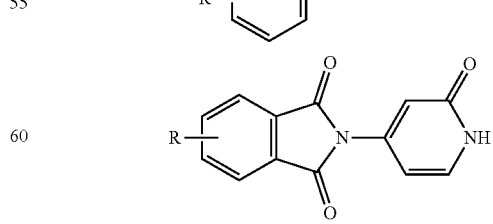
Class 6
Succinimides
Hydantoins -continued
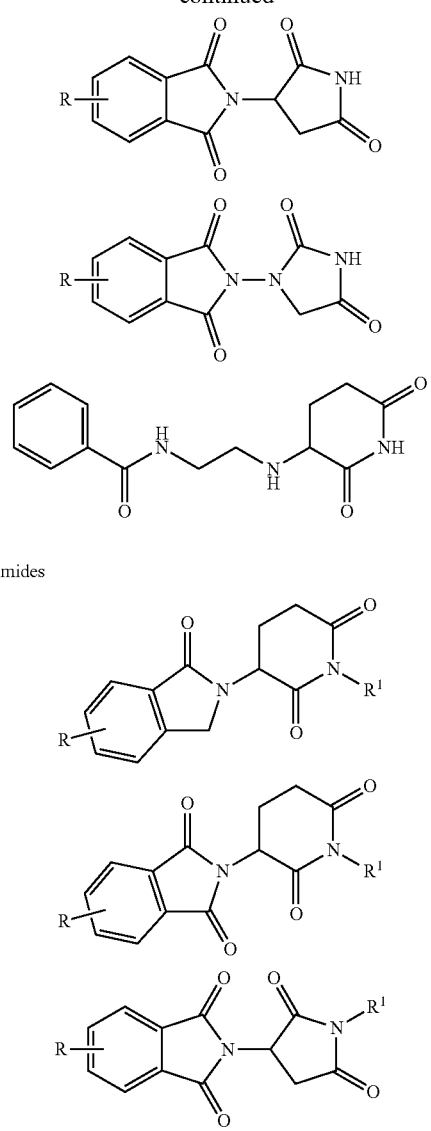
Class 7
N-alkyl imides
$R^1$ = alkyl, alkylaryl
Acyclic imides/amides
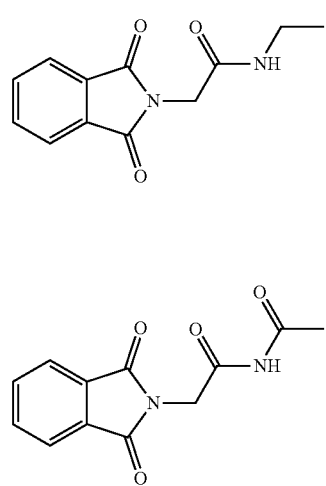
SY1-184
SY2-002
-continued
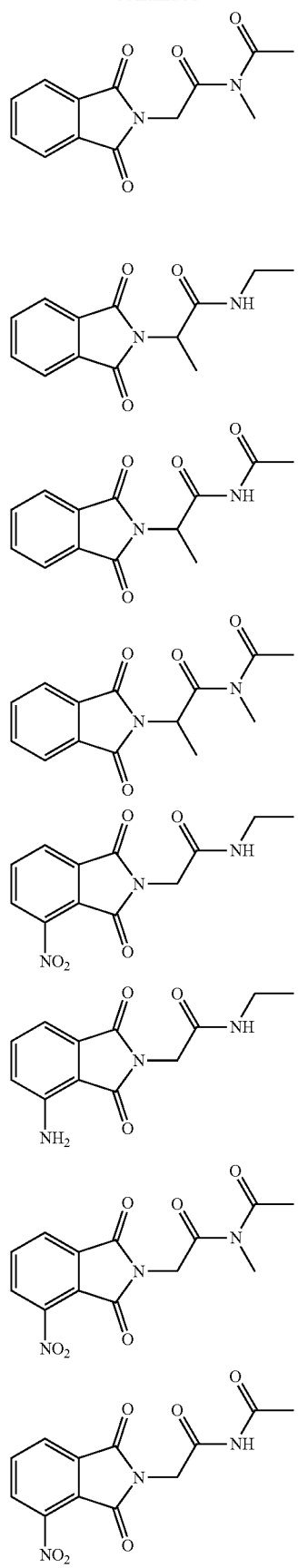

-continued

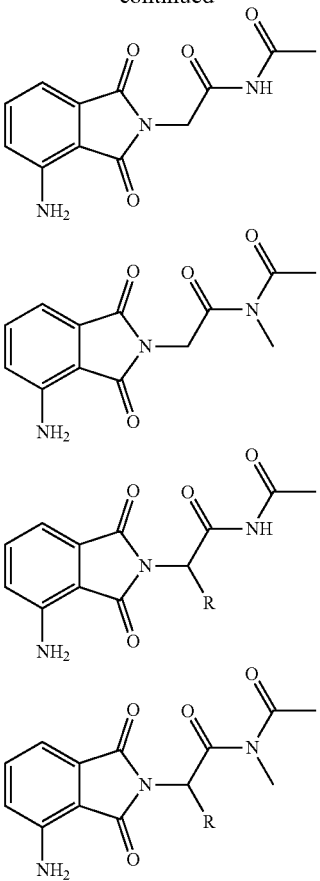

R = Me, Et, Pr, i-Pr, etc.

Any member of these classes can be coupled to any other member of these classes to form a dimer, e.g., using linker L as described herein. The linking can be accomplished by methods disclosed herein and can occur at the aryl moiety of the disclosed ligands.

In some aspects, the compounds disclosed herein can be represented by Formula I:

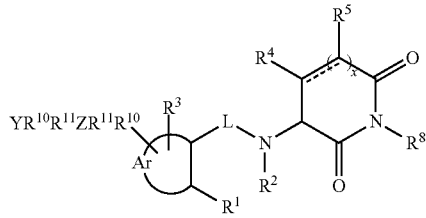

Formula I wherein,

Ar is aryl or heteroaryl;

L is absent or a linker selected from the group consisting of —SO$_2$, —SO$_2$R'; SO$_2$R'R"; —SO$_2$NR'R"; —SO$_2$NR'R"C(=O); —NR'SO$_2$R"; —R'SO$_2$NR'R"'; —C(=O); —C(=O)R'; —OC(=O)R'; —C(=O)NR'R"; —NR'C(=O)R"; —NR'C(=O)R"C(=O); —OR'; —NR'R'; —SR'; —N$_3$—C(=O)OR'; —O(CR'R")$_r$C(=O)R'; —O(CR'R")$_r$NR"C(=O)R'; —O(CR'R")$_r$NR"SO$_2$R'; —OC(=O)NR'R"; —NR'C(=O)OR"; and substituted or unsubstituted C$_1$-C$_6$ alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

R$^1$, R$^2$, and R$^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, substituted or unsubstituted heterocyclyl, and combinations thereof; or R$^1$ and R$^2$ combine to form a 5-7 membered heterocyclic ring; and when R$^1$ and R$^2$ combine to form a 5-7 membered heterocyclic ring, Ar is optionally not fused to the 5-7 membered heterocyclic ring but is a substituent of the 5-7 membered heterocyclic ring;

R$^4$ and R$^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

R$^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof;

each R$^{10}$ is independently selected from null, O, NH, CH$_2$, OCH$_2$, NHCH$_2$, CH=CH, and C≡C;

each R$^{11}$ is independently selected from null, a bond, (CR'R")$_r$, C(=O)NR', NR'C(O), C(=O), —SO$_2$, —SO$_2$R'; SO$_2$R", —SO$_2$NR'; —SO$_2$NR"C(=O); —NR'SO$_2$R"; —R'SO$_2$NR'; —C(=O)R'; —OC(=O) R'; —C(=O)NR"; —NR'C(=O)R"; —NR'C(=O) R"C(=O); —OR'; —NR'; —SR'; where r is from 1 to 6, wherein R' and R" are H or C$_1$-C$_6$ alkyl;

Z is absent, amino, C$_1$-C$_{12}$ alkyl, C$_1$-C$_{12}$ polyalkoxide, cycloalkyl, or heterocycloalkyl;

Y is an E-3 ligase ligand; and

X is 0, 1, or 2;

wherein the bond --- is present or absent.

In a specific example of Formula I, the compounds can have a formula represented by Formula I-A:

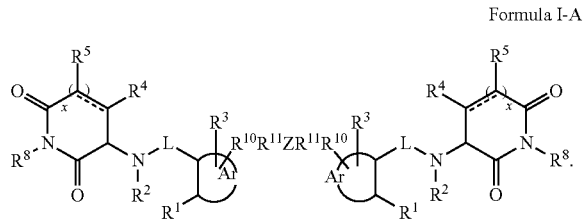

Formula I-A

In some examples of Formula I and IA, Ar can include an aromatic group such phenyl, pyrrolyl, furanyl, thiophenyl, imidazolyl, oxazolyl, thiazolyl, triazolyl, pyrazolyl, pyridinyl, pyrazinyl, pyridazinyl, pyrazolyl, oxazoyl, isoxazoyl, or pyrimidinyl, furyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide), isoquinolinyl, quinolinyl, piperidine, piperazine, pyrimidine, thiane, thiopyran, morpholine, oxazine, tetrahydropyran, pyrolidine, pyrroline, imidazoline, pyrazoline, indoline, benzofuran, indoline, or indole. In certain specific examples, Ar includes phenyl.

The Ar group can be substituted or unsubstituted. For example, the substituent on Ar can be selected from hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof. In certain embodiments, the substituent on Ar can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, Ar is substituted with $NO_2$, $NH_2$, OH, alkyl, aryl, halogen, amide, ether, or a combination thereof.

In the disclosed compounds of Formula I or IA, there can be from 1 to 5 different substituents $R^3$, e.g., 1, 2, 3, 4, or 5 $R^3$ substituents. The substituents can be the same or different. In specific examples, $R^3$ is $SO_2NH_2$, $SO_2NHR'$, or $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is NHC(O)R', wherein R' is $C_1$-$C_6$ alkyl or $C_1$-$C_6$ cycloalkyl optionally substituted with $C_1$-$C_6$ alkyl, $C_1$-$C_6$ alkoxyl, cycloalkyl, cycloheteroalkyl, hydroxyl, or halide. In other examples, $R^3$ is $C_1$-$C_6$ alkyl or $C_1$-$C_6$ cycloalkyl. In other examples, $R^3$ is $C_1$-$C_6$ alkoxyl. In other examples, $R^3$ is halide. In other examples, n is 2 and each $R^3$ is selected from the group consisting of $C_1$-$C_6$ alkyl, $C_1$-$C_6$ alkoxyl, halide, $SO_2NH_2$, $SO_2NHR'$, and $NHSO_2R'$, wherein R' is $C_1$-$C_6$ alkyl or $C_1$-$C_6$ cycloalkyl optionally substituted with $C_1$-$C_6$ alkyl, $C_1$-$C_6$ alkoxyl, hydroxyl, or halide. In other examples, $R^3$ is hydrogen, halogen, hydroxyl, substituted or unsubstituted amine, substituted or unsubstituted amide, nitro, ester, morpholino, dioxolane, substituted or unsubstituted $C_1$-$C_6$ alkyl, or combinations thereof. In preferred examples, R3 is hydrogen. In further examples, $R^3$ is OH, Cl, F, Br, CN, $CF_3$, $NO_2$, $C_{1-6}$ alkyl, $OCH_3$, OEt, C(O)OH, $NH_2$, $NCH_3$, $NHSO_2$, NHC(O), heteroalkyl, aryl, heteroaryl, $SO_2CH_3$, or $NHSO_2$—R', where R' is $C_{1-6}$ alkyl or NHC(O)NH In some examples of Formula I or IA, L is absent (i.e., a bond). In other examples of Formula I or IA, L is a linker. When L is present, L can be $SO_2$, —$SO_2R'$; —$SO_2R'R''$, —$SO_2NR'R''$; —$SO_2NR'R''C(=O)$; —$NR'SO_2R''$; $R'SO_2NR'R'''$; C(=O); C(=O)R'; —OC(=O)R'; —C(=O)NR'R''; —NR'C(=O)R''; —NR'C(=O)R''C(=O)$; substituted or unsubstituted $C_1$-$C_6$ aliphatic alkyl, wherein R', R'', and R''' are individually selected from hydrogen; substituted or unsubstituted alkyl; substituted or unsubstituted alkenyl; substituted or unsubstituted ether substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some specific examples of Formula I or IA, R', R'', and R''' can be individually selected from hydrogen; substituted or unsubstituted $C_1$-$C_8$ alkyl; substituted or unsubstituted $C_1$-$C_8$ ether; or substituted or unsubstituted amine. In specific examples R', R'', and R''' are all hydrogen.

In some embodiments of Formula I or IA, $R^1$ can be hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^1$ can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In certain specific examples, $R^1$ can be hydrogen, halogen, hydroxyl, substituted or unsubstituted amine, substituted or unsubstituted amide, nitro, ester, morpholino, dioxolane, substituted or unsubstituted $C_1$-$C_6$ alkyl, and combinations thereof.

In other specific examples, $R^1$ can be selected from the group consisting of hydrogen, substituted or unsubstituted amine, substituted or unsubstituted $C_1$-$C_6$ alkyl, and combinations thereof.

In some embodiments of Formula I or IA, $R^2$ can be hydrogen, halogen, hydroxyl, azide, alkoxyl, sulfhydryl, carbonyl, carboxyl, cyano, silyl, ether, alkylthio, sulfonyl, sulfonamido, ketone, aldehyde, substituted or unsubstituted amine, substituted or unsubstituted amide, nitro, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^2$ can be selected from H and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula I or IA, $R^1$ and $R^2$ can combine to form a 5-7 membered heterocyclic ring. When $R^1$ and $R^2$ combine to form a 5-7 membered heterocyclic ring, L can be absent or present.

In some embodiments of Formula I or IA, $R^4$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some embodiments of Formula I or IA, $R^5$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In specific embodiments of Formula I or IA, $R^4$ and $R^5$ are both hydrogen. In some embodiments of Formula I or I-A, one of $R^4$ and $R^5$ are hydrogen.

In certain specific examples, x is 0.

In certain specific examples, x is 1.

In some aspects, the compounds disclosed herein can be represented by Formula II:

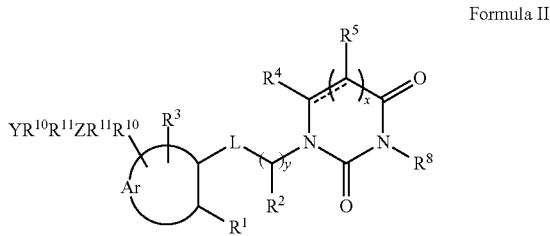

Formula II wherein,

Ar is aryl or heteroaryl;

L is absent or a linker selected from the group consisting of —SO$_2$, —SO$_2$R'; SO$_2$R'R", —SO$_2$NR'R"; —SO$_2$NR"R"C(=O); —NR'SO$_2$R"; —R'SO$_2$NR'"; —C(=O); —C(=O)R'; —OC(=O)R'; —C(=O)NR'R"; —NR'C(=O)R"; —NR'C(=O)R"C(=O); —OR'; —NR'R'; —SR'; —N$_3$—C(=O)OR'; —O(CR'R")$_r$C(=O)R'; —O(CR'R")$_r$NR"C(=O)R'; —O(CR'R")$_r$NR"SO$_2$R'; —OC(=O)NR'R"; —NR'C(=O)OR"; and substituted or unsubstituted C$_1$-C$_6$ aliphatic alkyl;

wherein R', R", and R'" are individually selected from hydrogen; substituted or unsubstituted alkyl; substituted or unsubstituted alkenyl; substituted or unsubstituted ether; substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6;

$R^1$, $R^2$, and $R^3$ are individually selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted alkenyl, substituted or unsubstituted alkynyl, substituted or unsubstituted cycloalkyl, heterocyclyl, and combinations thereof or $R^1$ and $R^2$ combine to form a 5-7 membered heterocyclic ring; and wherein when $R^1$ and $R^2$ combine to form a 5-7 membered heterocyclic ring, Ar is optionally not fused to the 5-7 membered heterocyclic ring but is a substituent of the 5-7 membered heterocyclic ring;

$R^4$ and $R^5$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof;

$R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof;

each $R^{10}$ is independently selected from null, O, NH, CH$_2$, OCH$_2$, NHCH$_2$, CH=CH, and C≡C;

each $R^{11}$ is independently selected from null, a bond, (CR'R")$_r$, C(=O)NR', NR'C(O), C(=O), —SO$_2$, —SO$_2$R'; SO$_2$R", —SO$_2$NR'; —SO$_2$NR"C(=O); —NR'SO$_2$R"; —R'SO$_2$NR'; —C(=O)R'; —OC(=O)R'; —C(=O)NR"; —NR'C(=O)R"; —NR'C(=O)R"C(=O); —OR'; —NR'; —SR'; where r is from 1 to 6; wherein R' and R" are H or C$_1$-C$_6$ alkyl;

Z is absent, amino, C$_1$-C$_{12}$ alkyl, C$_1$-C$_{12}$ polyalkoxide, cycloalkyl, or heterocycloalkyl;

Y is an E-3 ligase ligand; and

X is 0, 1, or 2;

y is from 1 to 6; and wherein the bond --- is present or absent.

In a specific example of Formula II, the compounds can have a formula represented by Formula II-A:

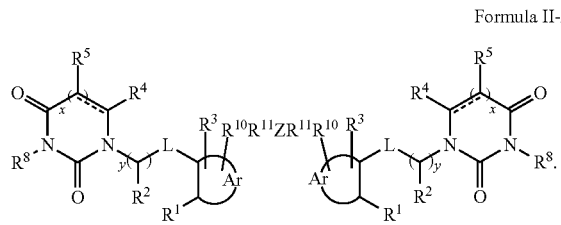

Formula II-A

In some examples of Formula II or II-A, Ar is as described herein. For example, Ar can be phenyl. The Ar group can be substituted or unsubstituted as described herein. For example, the Ar group can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol. In the disclosed compounds of Formula II or II-A, there can be from 1 to 5 different substituents $R^3$, e.g., 1, 2, 3, 4, or 5 $R^3$ substituents.

In some examples of Formula II or II-A, L is absent. In other examples of Formula II or II-A, L is a linker. When L is present, L can be $SO_2$, —$SO_2R'$; —$SO_2R'R''$, —$SO_2NR'R''$; —$SO_2NR'R''C(=O)$; —$NR'SO_2R''$; $R'SO_2NR'R'''$; $C(=O)$; $C(=O)R'$; —$OC(=O)R'$; —$C(=O)NR'R''$; —$NR'C(=O)R''$; —$NR'C(=O)R''C(=O)$; substituted or unsubstituted $C_1$-$C_6$ aliphatic alkyl, wherein R', R'', and R''' are individually selected from hydrogen; substituted or unsubstituted alkyl; substituted or unsubstituted alkenyl; substituted or unsubstituted ether substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, or substituted or unsubstituted amine; and r is an integer from 1 to 6.

In some specific examples of Formula II or II-A, R', R'', and R''' can be individually selected from hydrogen; substituted or unsubstituted $C_1$-$C_8$ alkyl; substituted or unsubstituted $C_1$-$C_8$ ether; or substituted or unsubstituted amine.

In some embodiments of Formula II or II-A, $R^1$ can be as described herein. For example, $R^1$ can be hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^1$ can be selected from H, Cl, F, Br, I, CN, $NO_2$, $NH_2$, $CF_3$, $CO_2H$, $CO_2NH_2$, $CO_2NHR^5$, $CO_2R^5$, $C(O)R^5$, $C(O)NH_2$, $C(O)NHR^5$, and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula II or II-A, $R^2$ can be hydrogen, halogen, hydroxyl, azide, alkoxyl, sulfhydryl, carbonyl, carboxyl, cyano, silyl, ether, alkylthio, sulfonyl, sulfonamido, ketone, aldehyde, substituted or unsubstituted amine, substituted or unsubstituted amide, nitro, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, and combinations thereof. For example, $R^2$ can be selected from H and $C_1$-$C_6$ alkyl optionally substituted with alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol.

In some embodiments of Formula II or II-A, $R^1$ and $R^2$ can combine to form a 5-7 membered heterocyclic ring. When $R^1$ and $R^2$ combine to form a 5-7 membered heterocyclic ring, L can be absent or present.

In some embodiments of Formula II or II-A, $R^4$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In some embodiments of Formula II or II-A, $R^5$ is selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, and combinations thereof.

In specific embodiments of Formula II or II-A, $R^4$ and $R^5$ are both hydrogen. In some embodiments of Formula II, one of $R^4$ and $R^5$ are hydrogen.

In certain specific examples of Formula II or II-A, x is 0.
In certain specific examples of Formula II or II-A, x is 1.
In some aspects, the compounds disclosed herein can be represented by Formula III:

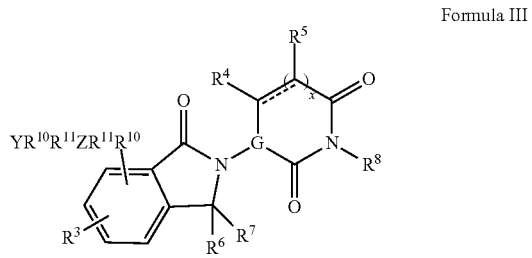

Formula III wherein,
G is C, S, N, substituted of unsubstituted $C_1$-$C_8$ alkyl, or combinations thereof;
$R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, substituted or unsubstituted cycloalkyl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

each $R^{10}$ is independently selected from null, O, NH, $CH_2$, $OCH_2$, $NHCH_2$, $N(CH_3)$, $CH=CH$, $C\equiv C$, $SO_2$, $SO_2NH$, $C(O)$, $C(O)O$, $C(O)NH$, $C(O)CH_2$, $NHSO_2$, $OCH_2O$, $NHCONH$, $NHCH_2CH_2O$, $NH(CH_2)_3NH$, and $NHCH_2CF_2CH_2$;

each $R^{11}$ is independently selected from null, a bond, $(CR'R'')_r$, $C(=O)NR'$, $NR'C(O)$, $C(=O)$, $—SO_2$, $—SO_2R'$; $SO_2R''$, $—SO_2NR'$; $—SO_2NR''C(=O)$; $—NR'SO_2R''$; $—R'SO_2NR'$; $—C(=O)R'$; $—OC(=O)R'$; $—C(=O)NR''$; $—NR'C(=O)R''$; $—NR'C(=O)R''C(=O)$; $—OR'$; $—NR'$; $—SR'$; where r is from 1 to 6; wherein R' and R'' are H or $C_1$-$C_6$ alkyl;

Z is absent, amino, $C_1$-$C_{12}$ alkyl, $C_1$-$C_{12}$ polyalkoxide, cycloalkyl, or heterocycloalkyl;

Y is an E-3 ligase ligand; and x is 0, 1, or 2; and wherein the bond --- is present or absent.

In a specific example of Formula III, the compounds can have a formula represented by Formula III-A:

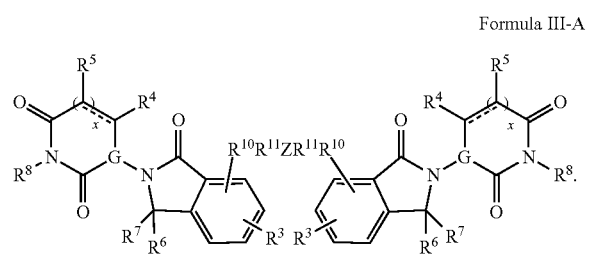

Formula III-A

In some examples of Formula III or III A, $R^3$, $R^4$, $R^5$, $R^6$, $R^7$, and $R^8$ are as described herein. In some examples of Formula III or III-A, $R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof.

In some embodiments of Formula III, the compound can have a structure as represented below

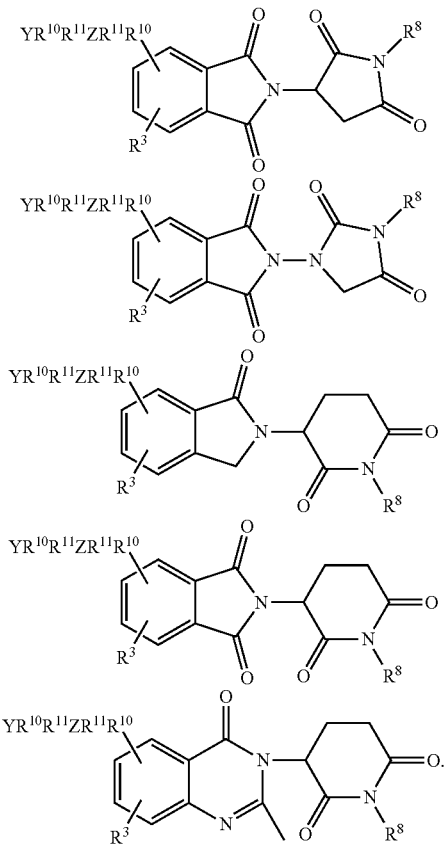

In certain examples $R^8$ is H or $C_1$-$C_6$ alkyl.

In a specific example of Formula III, the compounds can have a formula represented by Formula III-B.

Formula III-B

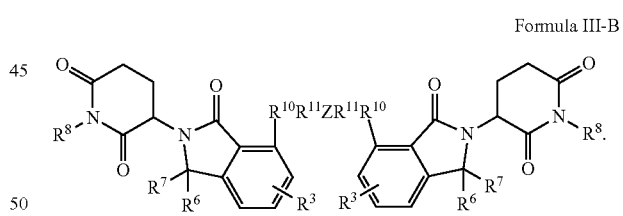

In some examples of Formula III-B, $R^3$, $R^6$, $R^7$, and $R^8$ are as described herein. In some examples of Formula III-B, $R^8$ is selected from the group consisting of hydrogen, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, heterocyclyl, substituted or unsubstituted aryl, substituted or unsubstituted alkylaryl, and combinations thereof. In specific examples, $R^8$ is H. In other examples, $R^6$ and $R^7$ are both H. In other examples, $R^6$ and $R^7$ together form =O. In specific examples, each $R^3$ is OH, Cl, F, Br, CN, $CF_3$, $NO_2$, $C_{1-6}$ alkyl, $OCH_3$, OEt, C(O)OH, $NH_2$, $NCH_3$, $NHSO_2$, NHC(O), heteroalkyl, aryl, heteroaryl, $SO_2CH_3$, or $NHSO_2$—R', where R' is $C_{1-6}$ alkyl or NHC(O)NH.

In some aspects, the compounds disclosed herein can have a structure represented by Formula IV:

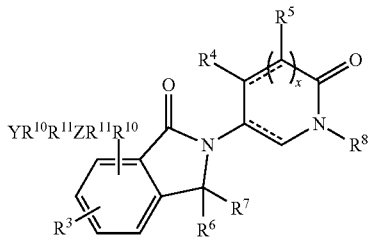

Formula IV wherein, $R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

$R^4$, $R^5$, and $R^8$ are individually selected from the group consisting of hydrogen, halogen, hydroxyl, azide, ether, alkoxyl, sulfhydryl, alkylthio, sulfonyl, sulfonamido, ketone, aldehyde, ester, substituted or unsubstituted alkyl, substituted or unsubstituted alkylhalide, substituted or unsubstituted aralkyl, substituted or unsubstituted aryl, substituted or unsubstituted alkylaryl, substituted or unsubstituted alkenyl, substituted or unsubstituted alkynyl, substituted or unsubstituted cycloalkyl, heterocyclyl, and combinations thereof; and $R^6$ and $R^7$ are individually =O, hydrogen, $C_1$-$C_8$ alkyl, or $R^6$ and $R^7$ combine to form =O;

each $R^{10}$ is independently selected from null, O, NH, $CH_2$, $OCH_2$, $NHCH_2$, $N(CH_3)$, CH=CH, C≡C, $SO_2$, $SO_2NH$, C(O), C(O)O, C(O)NH, $C(O)CH_2$, $NHSO_2$, $OCH_2O$, NHCONH, $NHCH_2CH_2O$, $NH(CH_2)_3NH$, and $NHCH_2CF_2CH_2$;

each $R^{11}$ is independently selected from null, a bond, $(CR'R'')_r$, C(=O)NR', NR'C(O), C(=O), —$SO_2$, —$SO_2R'$; $SO_2R''$, —$SO_2NR'$; —$SO_2NR''C(=O)$; —$NR'SO_2R''$; —$R'SO_2NR'$; —C(=O)R'; —OC(=O)R'; —C(=O)NR''; —NR'C(=O)R''; —NR'C(=O)R''C(=O); —OR'; —NR'; —SR'; where r is from 1 to 6; wherein R' and R'' are H or $C_1$-$C_6$ alkyl;

Z is absent, amino, $C_1$-$C_{12}$ alkyl, $C_1$-$C_{12}$ polyalkoxide, cycloalkyl, or heterocycloalkyl;

Y is an E-3 ligase ligand; and

X is 0, 1, or 2; and wherein the bond --- is present or absent.

In specific examples of Formula I through III, $R^3$ can be OH, Cl, F, Br, CN, $CF_3$, $NO_2$, $C_{1-6}$ alkyl, $OCH_3$, OEt, C(O)OH, $NH_2$, $NCH_3$, $NHSO_2$, NHC(O), heteroalkyl, aryl, heteroaryl, $SO_2CH_3$, $NHSO_2$—R', where R' is $C_{1-6}$ alkyl or NHC(O)NH.

In any of Formula IV through III, the moiety $R^{10}R^{11}ZR^{11}R^{10}$ can be a linker to the E-3 ligase ligand Y. In many cases, Z can be a $C_1$-$C_{12}$ alkyl, a $C_1$-$C_{12}$ heteroalkyl, $C_1$-$C_{12}$ heteroalkylhetercycloalkyl. In many cases, this moiety can be a polyalkyloxide. Additional examples are shown in FIG. 7. In further examples, this moiety can be represented as C(O)ZC(O), C(O)OZOC(O), C(O)ZNH, C(O)OZNH, NHZNH, or C(O)NHZNHC(O), C(S)OZOC(S); wherein Z is $C_1$-$C_{10}$ alkyl; $C_1$-$C_{10}$ heteroalkyl; $C_1$-$C_{10}$ alkylamine; $C_1$-$C_{10}$ alkoxyl; $C_1$-$C_{10}$ alkanoyloxyl; or $C_1$-$C_{10}$ alkylamido, any of which can be optionally substituted with one or more substituents including halogen, alkoxyl, alkyl, alkenyl, cycloalkyl, cycloalkenyl, heterocycloalkyl, aryl, heteroaryl, amine, cyano, nitro, hydroxyl, carbonyl, acyl, carboxylic acid (—COOH), —C(O)$R^{12}$, —C(O)$OR^{12}$, carboxylate (—COO⁻), primary amide (e.g., —$CONH_2$), secondary amide (e.g., —$CONHR^{12}$), —C(O)$NR^{12}R^{13}$, —$NR^{12}R^{13}$, —$NR^{12}S(O)_2R^{13}$, —$NR^{12}C(O)R^{13}$, —$S(O)_2R^{12}$, —$SR^{12}$, and —$S(O)_2NR^{12}R^{13}$, sulfinyl group (e.g., —$SOR^{12}$), and sulfonyl group (e.g., —$SOOR^{12}$); wherein $R^{12}$ and $R^{13}$ can each independently be hydrogen, halogen, hydroxyl, alkyl, haloalkyl, alkenyl, alkynyl, cycloalkyl, heterocycloalkyl, aryl, heteroaryl, carbonyl, cyano, amino, alkylamino, dialkylamino, alkoxyl, aryloxyl, cycloalkyl, alkoxycarbonyl, aminocarbonyl, alkylaminocarbonyl, or dialkylaminocarbonyl.

In further examples, the disclosed compounds can have formula V:

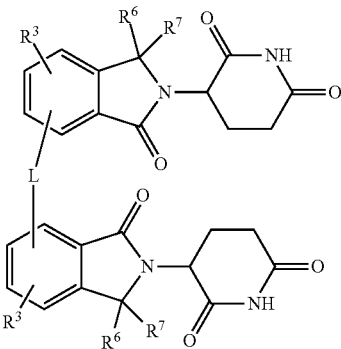

V wherein $R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;

$R^6$ and $R^7$ are individually =O, hydrogen, $C_1$-$C_8$ alkyl, or $R^6$ and $R^7$ combine to form =O; and
L is a linker of from 1 to 20 atoms in length, e.g., NH, O, S, $(CH_2O)_{1-10}$, $(CH_2CH_2O)_{1-6}$, $(CH_2)_{1-20}$, C≡C, C=C, C(O)NH, NHC(O), $SO_2NH$, $NHSO_2$, $SO_2$, NHC(O)NH, C(O), C(O)O, or
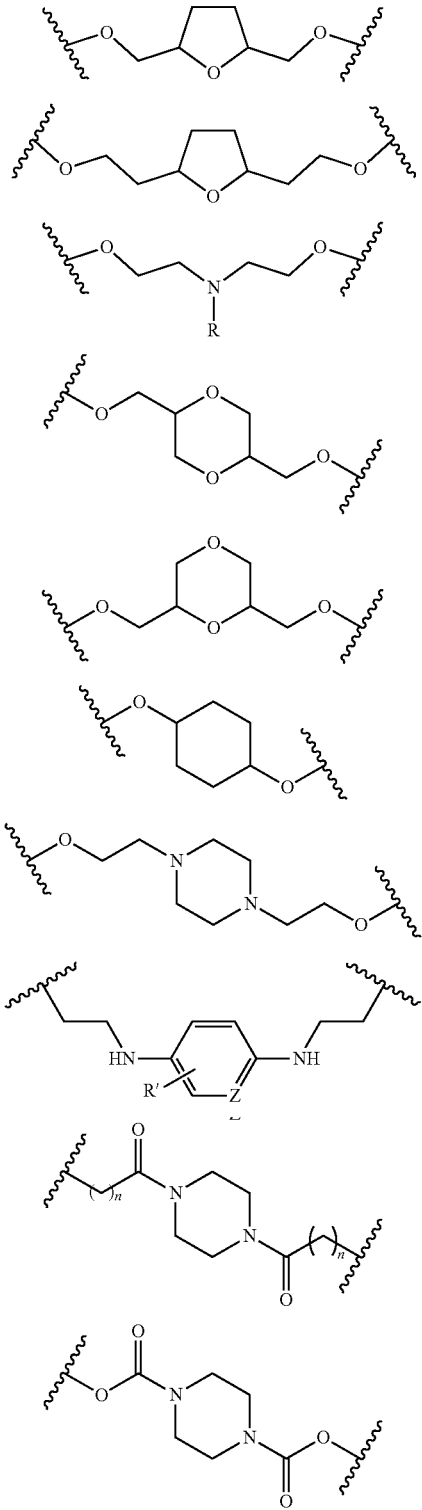
-continued
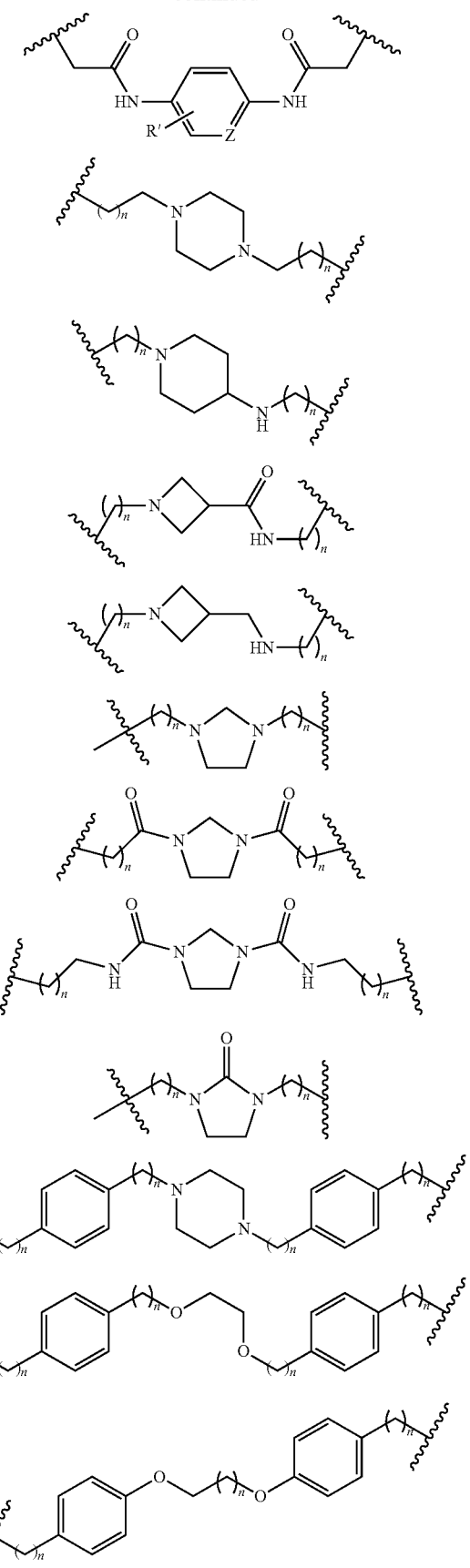

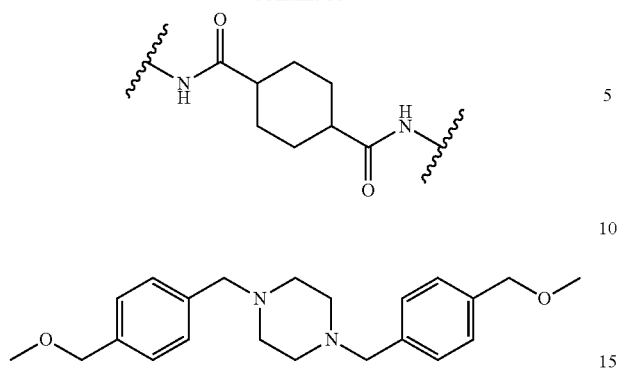
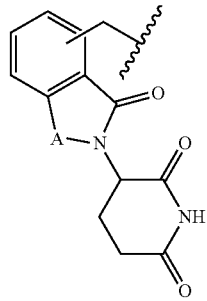

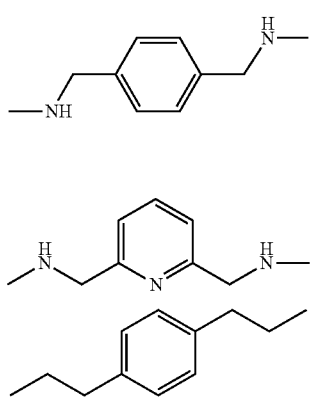
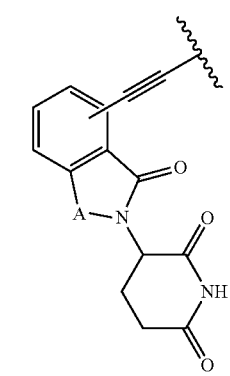

wherein n is 1-6, Z is CH or N; R' is halogen, OH, NHR; and R is aliphatic, aryl, or NO₂.

In further specific examples, the compounds can have formula VI-A through VI-F:

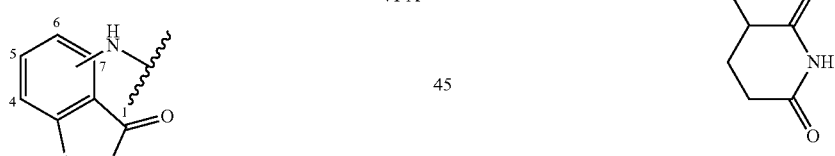

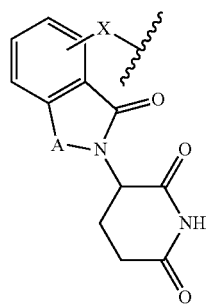

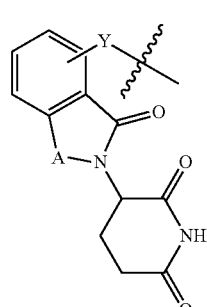

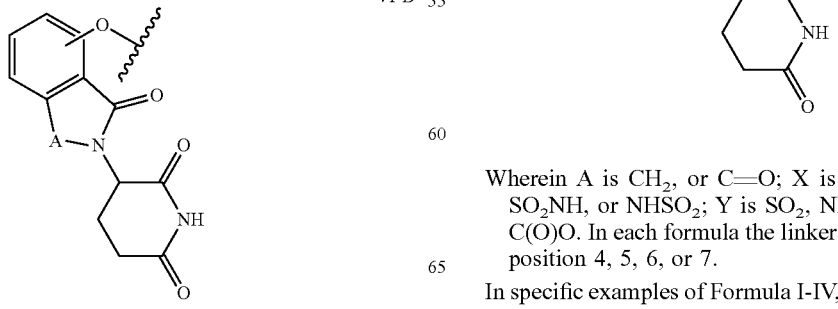

Wherein A is CH₂, or C=O; X is C(O)NH, NHC(O), SO₂NH, or NHSO₂; Y is SO₂, NHC(O)NH, C(O), or C(O)O. In each formula the linker is can be attached at position 4, 5, 6, or 7.

In specific examples of Formula I-IV, $R^{10}R^{11}ZR^{11}R^{10}$ can together result in a $C_{2-16}$ alkyl.

Some specific compounds that are disclosed herein are:
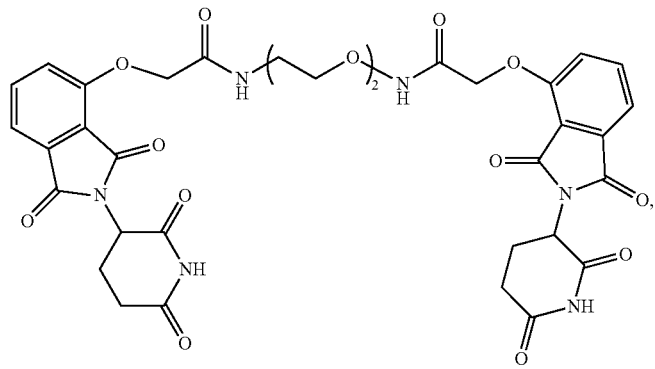
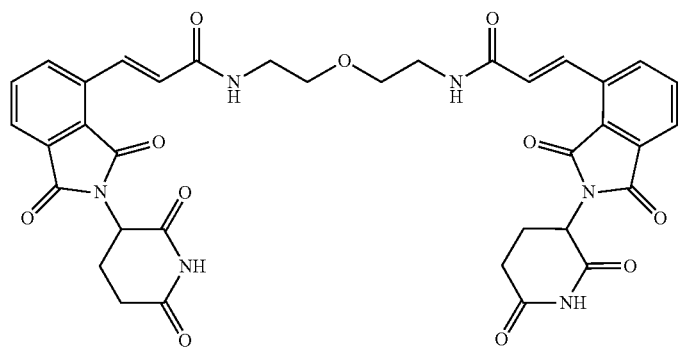
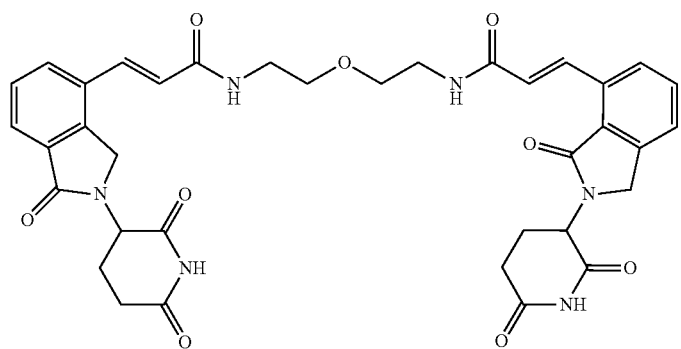
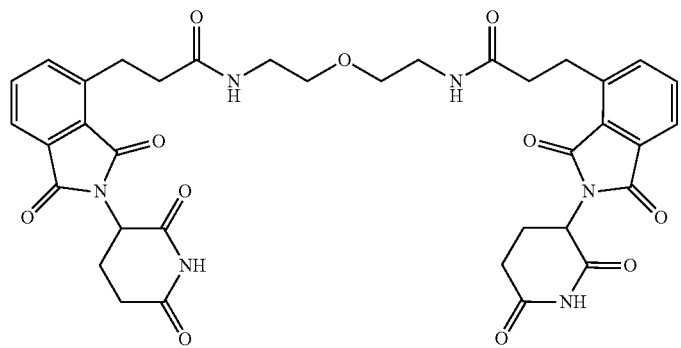

-continued
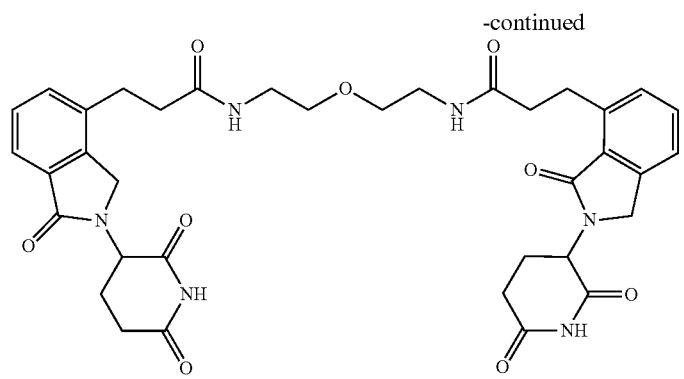
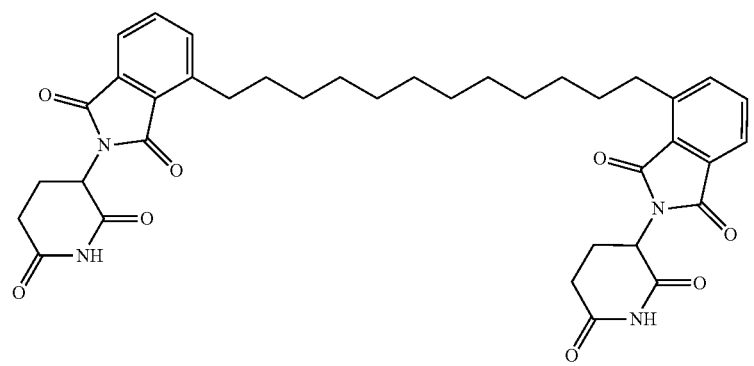
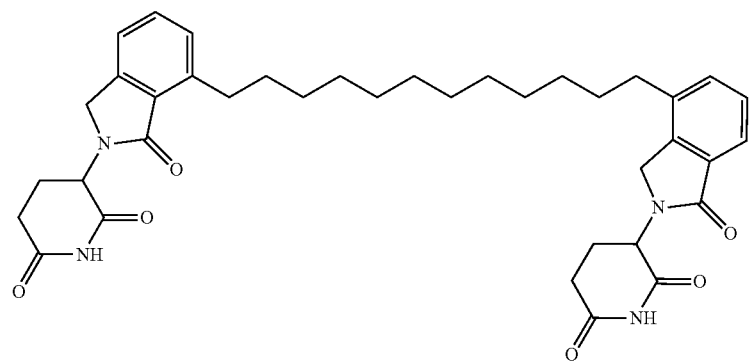
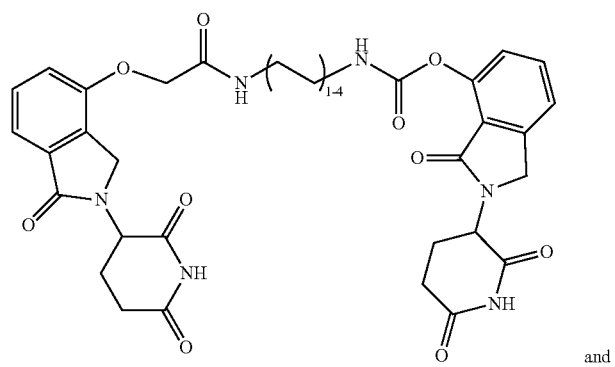
and

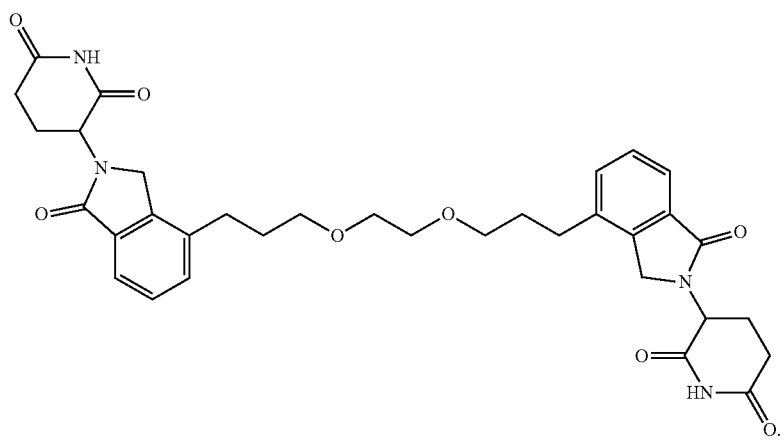
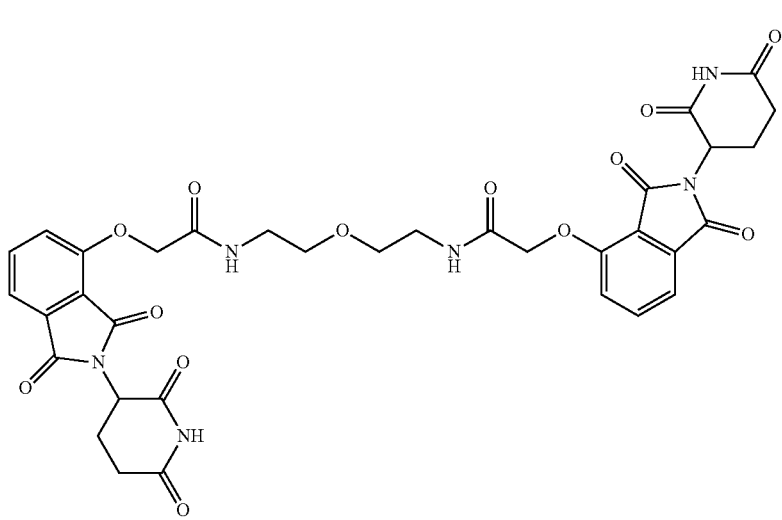
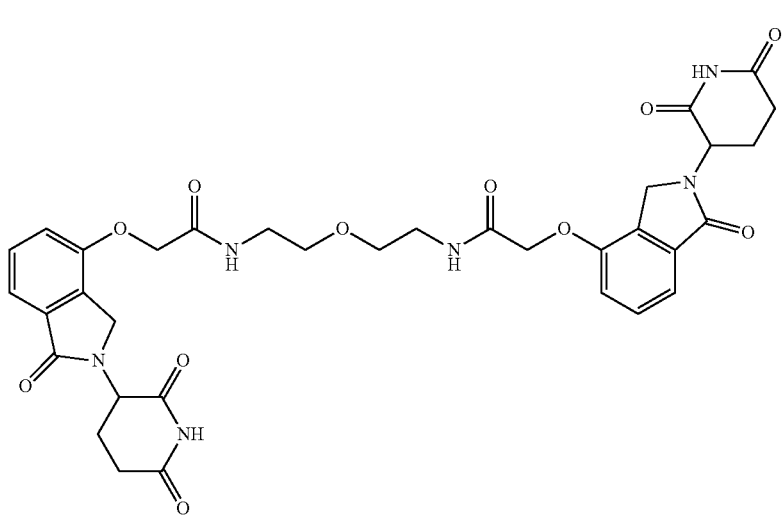

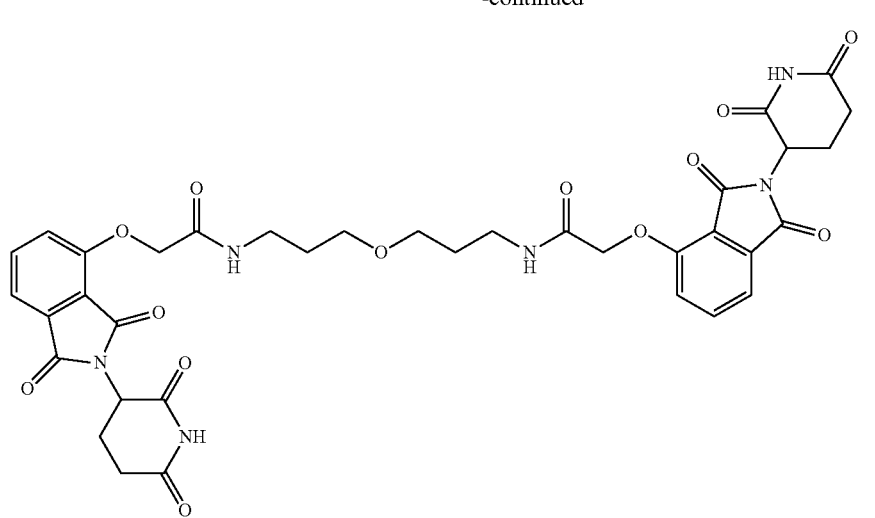
5
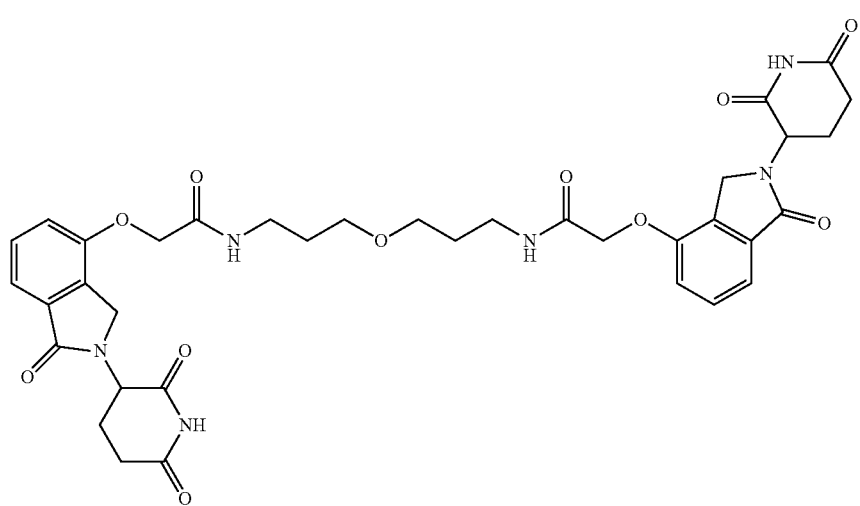
6
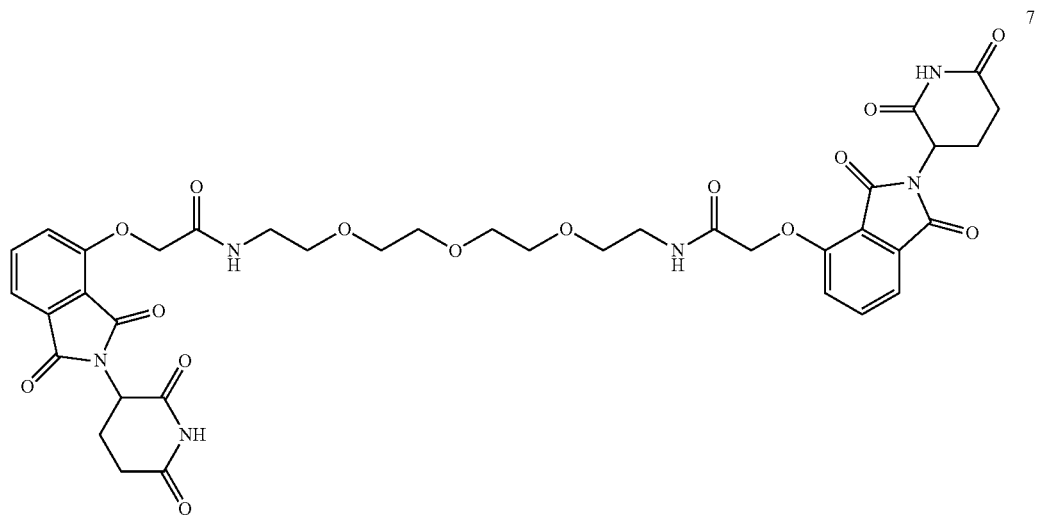
7

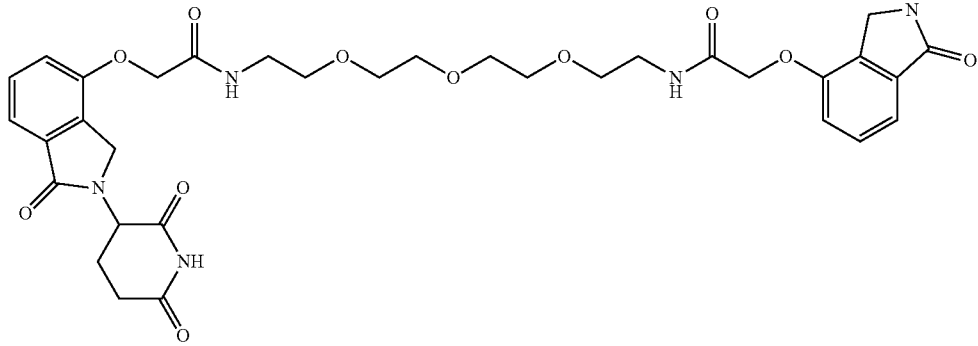

Additional examples are show below in the examples section.

Method

Disclosed herein are methods for treating a disease state or condition in a patient wherein dysregulated protein activity is responsible for said disease state or condition. As described herein, the compounds disclosed comprises an E3 Ubiquitin Ligase binding moiety ("ULM") that is a cereblon E3 Ubiquitin Ligase binding moiety ("CLM"). Cereblon suppressed the expression of lower molecular weight isoforms of Ikaros and aiolos (encoded by gene IKZF1 and IKZF3 respectively) in a temporally-regulated manner during T cell activation. This regulation of IKZF in Crbn$^{-/-}$ T cells after activation indicates that cereblon may be involved in its regulation and that it is a native substrate of the CRBN/Cul4A/Rbx1 E3-ubiquitin ligase complex. This data suggests that cereblon substrates may have a non-canonical outcome. The compounds disclosed herein has significant therapeutic potential in cancers, such as solid tumors and blood-borne tumors; heart disease, such as congestive heart failure; and viral, genetic, inflammatory, allergic, and autoimmune diseases.

Methods of reducing the risk of, preventing, or treating a subject having an autoimmune disease or disorder are provided herein. In specific examples, methods of reducing the risk of developing, preventing, or treating graft versus host disease (GVHD) in a subject are provided. GVHD may be due to a transplantation procedure involving the implantation of immunogenic tissue including but are not limited to, solid organ transplants (such as heart, kidney, and liver), tissue grafts (such as skin, intestine, pancreas, cornea, gonad, bone, and cartilage), and cellular transplants (such as cells from pancreas, brain and nervous tissue, muscle, skin, bone, cartilage, and liver). In such procedures, organ rejection is an obstacle to complete recovery. The individual's immune system recognizes antigens (HLA or minor H antigens) on the implanted tissue as foreign and mounts an immune response against it, which injures and destroys the implanted tissue. The method can include administering to the subject an effective amount of a compound or composition as disclosed herein. The methods can further include administering a second compound or composition, such as, for example, an immunosuppressant.

The autoimmune diseases can include, for example, rheumatoid arthritis, multiple sclerosis, juvenile-onset diabetes, systemic lupus erythematosus, autoimmune uveoretinitis, autoimmune vasculitis, bullous pemphigus, myasthenia gravis, autoimmune thyroiditis or Hashimoto's disease, Sjogren's syndrome, granulomatous orchitis, autoimmune oophoritis, Crohn's disease, sarcoidosis, rheumatic carditis, ankylosing spondylitis, Grave's disease, and autoimmune thrombocytopenic purpura.

In one embodiment, an effective amount of one or more compounds or compositions disclosed herein is administered to a patient at risk of developing or have an autoimmune disease or disorder and who is in need of treatment thereof. The patient can be a human or other mammal, such as a primate (monkey, chimpanzee, ape, etc.), dog, cat, cow, pig, or horse, or other animals at risk of developing or have an autoimmune disease or disorder.

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder.

The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Further provided herein are methods of treating a genetic disease or disorder in a subject, comprising administering to the subject an effective amount of a compound or composition as disclosed herein. The methods can further comprise administering a second compound or composition.

"Genetic disorder" can be caused by and/or based on changes in one or more genes that are inherited from at least one of the parents. Examples include urea cycle disorders, thalassemia, but also the embodiments of diseases or symptoms such as varicosis, vaginitis, depression or Sudden Infant Death Syndrome etc., that are based on or caused by these changes. The genetic disorder can be epigenetic which is defined as an inherited change in phenotype or gene expression which is not caused by changes to the gene sequence but is caused other mechanism/non-genetic factors.

The genetic disorder treating using the compounds disclosed herein can include disorders that manifests itself in symptoms or diseases selected from urea cycle disorders, thalassemia, cystic fibrosis, rheumatoid arthritis, Sjogren's syndrome, uveitis, varicosis, polymyositis, and dermatomyositis, arteriosclerosis, amyotrophic lateral sclerosis, asociality, affective disorders, systemic lupus erythematosus. It rest also in cardiovascular and neurological diseases, type II diabetes, neurodegenerative diseases, Rubinstein-Taybi-Syndrome, Rett syndrome, Friedreich's ataxia, Huntingdon's disease, multiple sclerosis, depression. It might also include mucositis, skin/mucosal itching, degenerative diseases of the eye, eating disorders and obesity, drug induced weight gain, pruritus, alcoholism, grey hair, hair loss, cardiac injury, lack of neuronal growth, osteoporosis, bone and joint diseases, epithelial damage, desmosis, Parkinson's disease, myelodysplastic syndrome, fibrotic lung diseases, hepatic encephalopathies, infections by human papilloma virus (HPV) or autoimmune diseases or also vaginitis or Sudden Infant Death Syndrome. In general, as already stated in the definition of "genetic disorder" the use refers only to diseases/symptoms listed in this paragraph as far as their cause rests in a genetic disorder, especially in an epigenetic disorder.

Genetic disorders in general include the 22q11.2 deletion syndrome, Angelman Syndrome, Canavan disease, celiac disease, Charcot-Marie-Tooth disease, Color blindness, Cri du chat, Down syndrome, Cystic fibrosis, Duchenne muscular dystrophy, Haemophilia, Klinefelter's syndrome, neurofibromatosis, phenylketonuria, Prader-Willi syndrome, sickle cell disease, Tay-Sachs disease, Turner syndrome etc.

In some embodiments, the composition can be used to treat a genetic disorder being selected from or manifests itself in symptoms or diseases selected from urea cycle disorders, thalassemia, cystic fibrosis, rheumatoid arthritis, Sjogren's syndrome, uveitis, polymyositis, and dermatomyositis, arteriosclerosis, amyotrophic lateral sclerosis, asociality, affective disorders, systemic lupus erythematosus, immune response, varicosis, vaginitis, including chronic recurrent yeast vaginitis, depression or Sudden Infant Death Syndrome, preferably selected from depression, varicosis, or Sudden Infant Death Syndrome.

Methods of inducing degradation of a target protein in a cell are also provided. The methods comprise contacting the cell with an effective amount of a compound or composition as disclosed herein.

Methods of inhibiting a cereblon E3 Ubiquitin Ligase binding moiety (CLM) are also provided. The methods comprise contacting the cell with an effective amount of a compound or composition as disclosed herein.

Methods of reducing the risk of, preventing, or treating other disease state or condition in a patient are also provided. In some embodiments of the methods described herein, the disease state or condition can include asthma, multiple sclerosis, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome, Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

The activity of the compounds to reduce the risk of, treat, prevent, or inhibit a disease condition can be determined using molecular dynamic simulation. In particular, molecular dynamic simulations can be performed using the known crystal structures of CRBN in various species. Several libraries are available for screening inhibitors.

The compounds can be assayed using known techniques in the art. For example, the biological assay can include overexpress human CRBN into Crbn-/- mouse T cells to determine the ability for each unique aminoacid to contribute to protein interactions with Myc, Ikaros and to identify new substrates involved in metabolite regulation. The CRBN-Cul4 in vitro Ub assay can be development using recombinant Cell based analysis can be used to assess the expression of Myc and Ikaros will be used for screening purposes in treated cells. Expression of Myc and Ikaros will be visualized using luciferase-based expression assays as described previously. Development of substrate-targeted reduction in luciferase expression using IMiD compounds and constructs. The results show the ability of test chemical "HITS" to block CRBN-Cul4 mediated ubiquitination of target substrates using in vitro ubiquitination assays and luciferase constructs.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Examples

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

All reagents were purchased from commercial suppliers and used without further purification (except where mentioned otherwise). $^1$H NMR spectra were recorded on an Agilent-Varian Mercury 400 MHz spectrometer with DMSO-$d_6$ as the solvent. All coupling constants are measured in Hertz, and the chemical shifts (δH) are quoted in parts per million relative to TMS (δ 0), which was used as the internal standard. High-resolution mass spectroscopy was carried out on an Agilent 6210 LC-MS (ESI-TOF) system. HPLC analysis was performed using a JASCO HPLC system equipped with a PU-2089 Plus quaternary gradient pump and a UV-2075 Plus UV-Vis detector, using an Alltech Kromasil C-18 column (150×4.6 mm, 5 μm) and an Agilent Eclipse XDB-C18 column (150×4.6 mm, 5 μm). The purities of the final compounds used for the biochemical and functional studies were >95% as measured by HPLC. Melting points were recorded on an Optimelt automated melting point system (Stanford Research Systems). Thin-layer chromatography was performed using silica gel 60 F254 plates (Fisher Scientific), with observation under UV when necessary. Anhydrous dimethylformamide was used as purchased from Sigma Aldrich. Burdick and Jackson HPLC-grade solvents were purchased from VWR for HPLC, HPLC-MS and high-resolution mass analysis. Detailed theoretical calculations and synthesis of N-methyl-lenalidomide and N-methyl-dBET1 are provided below.

General method A: A mixture of acid (1.2-1.5 equiv.), HATU (2.0 equiv.), DIPEA (4.0 equiv.) in DMF (0.3-1 M) was stirred at room temperature for 30 min. The amine (1.0 equiv.) was added to the acid mixture and the solution was stirred overnight at room temperature. The mixture was concentrated under reduced pressure. Water (10 mL) was added and extracted with DCM (2×10 mL). The combined organic layers were dried (Na$_2$SO$_4$) and concentrated. The resulting residue was purified by SiO$_2$ column chromatography eluting with MeOH in DCM (0-8% MeOH, gradient elution) to provide the title compound.

General method B: A mixture of amine SG5-046B3 (1 equiv.) and Et$_3$N (3.0 equiv.) in THF (0.5 mL) was cooled to 0° C. The corresponding acid chloride (1.5 equiv.) was added. The mixture was warm to room temperature and stirred until the reaction was completed. Water (10 mL) was added and extracted with EtOAc (2×10 mL). The combined organic layers were dried (Na$_2$SO$_4$) and concentrated. The resulting residue was purified by SiO$_2$ column chromatography eluting with MeOH in DCM (0-10% MeOH, gradient elution) to provide the title compound.

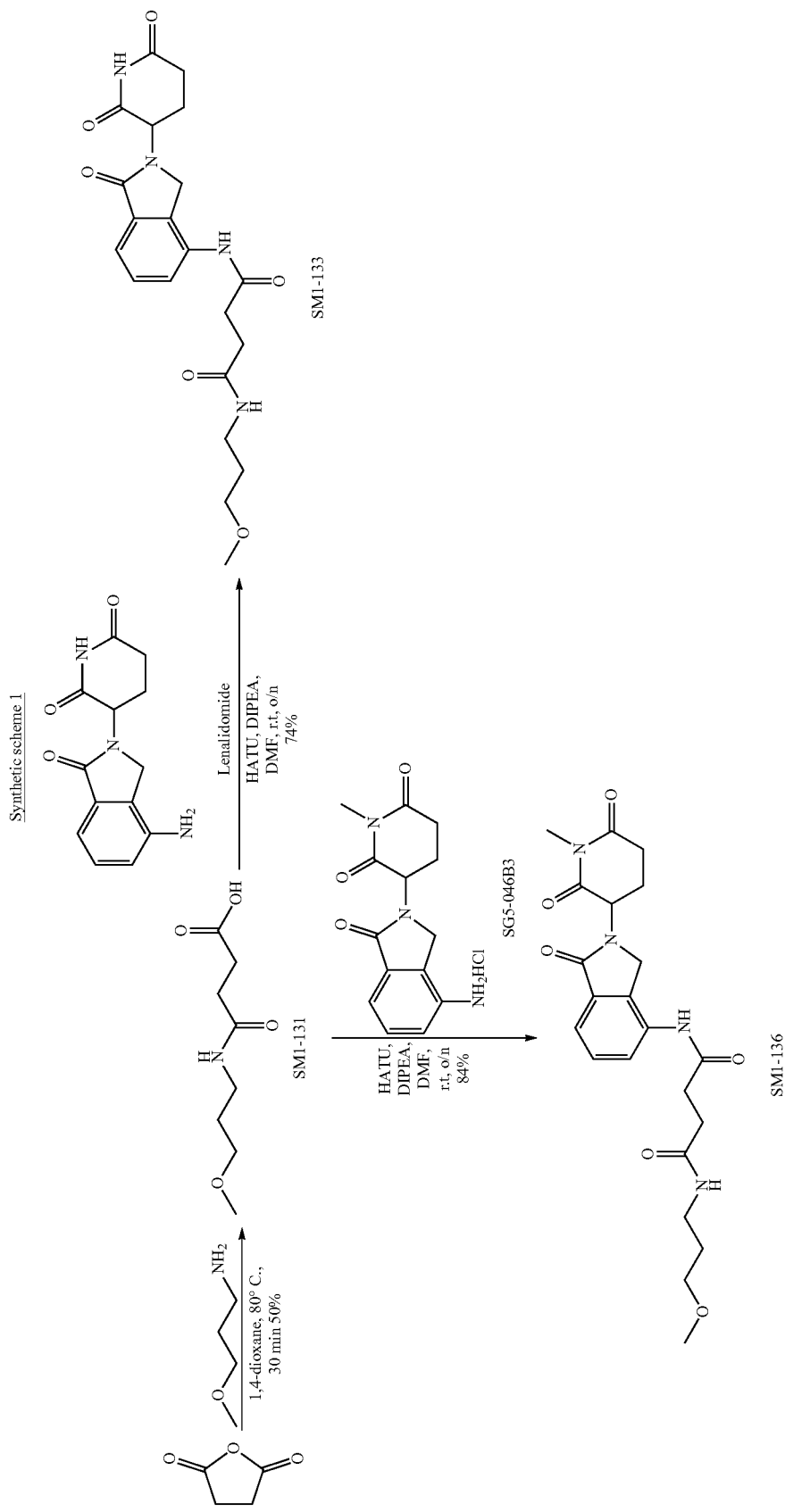

4-[(3-Methoxypropyl)amino]-4-oxobutanoic acid (SM1-131): To succinic anhydride (2.47 g, 24.68 mmol) in dioxane (10 mL) was slowly added 3-methoxypropan-1-amine (2.29 mL, 22.44 mmol) in 10 mL of dioxane (10 mL). The solution obtained was heated to 80° C. and stirred for 30 min, and then cooled to room temperature. The white crystals obtained were filtered, dried, and recrystallized from dioxane to give the title compound as a white solid (2.13 g, 50%). $^1$H NMR (500 MHz, DMSO-d$_6$) δ 12.05 (s, 1H), 7.81 (t, J=5.7 Hz, 1H), 3.30 (t, J=6.4 Hz, 3H), 3.21 (s, 3H), 3.06 (td, J=5.6, 7.0 Hz, 2H), 2.41 (t, J=7.1 Hz, 2H), 2.28 (t, J=6.9 Hz, 2H), 1.62-1.57 (m, 2H). HPLC-MS (ESI$^+$): m/z 190.2 [100%, (M+H)$^+$].

mmol), DIPEA (0.112 mL, 0.646 mmol) in DMF (0.5 mL) using general method A. The title compound was obtained as a white solid (60 mg, 84%). HPLC: 98% [t$_R$=6.9 min, Grad MeOH 5-95% water (with 0.1% TFA), flow: 1.0 mL/min, 20 min]. $^1$H NMR (500 MHz, DMSO-d$_6$) δ 9.86 (s, 1H), 7.87 (t, J=5.4 Hz, 1H), 7.81 (d, J=7.2 Hz, 1H), 7.49 (q, J=7.5 Hz, 2H), 5.22 (dd, J=13.4, 5.0 Hz, 1H), 4.42-4.27 (m, 2H), 3.30 (t, J=6.4 Hz, 2H), 3.18 (d, J=11.1 Hz, 3H), 3.06 (dt, J=12.7, 6.2 Hz, 2H), 3.03-2.95 (m, 3H), 2.77 (d, J=18.7 Hz, 1H), 2.65-2.56 (m, 2H), 2.46-2.23 (m, 4H), 2.08-2.00 (m, 1H), 1.63-1.57 (m, 2H). HPLC-MS (ESI+): m/z 911.4 [35%, (2M+Na)$^+$], 467.1 [50%, (M+Na)$^+$], 445.2 [100%, (M+H)$^+$]. HRMS (ESI$^+$): m/z calcd for C$_{13}$H$_{14}$N$_2$O$_3$ (M+Na)$^+$ 467.1901, found 467.1919.

Synthetic scheme 2

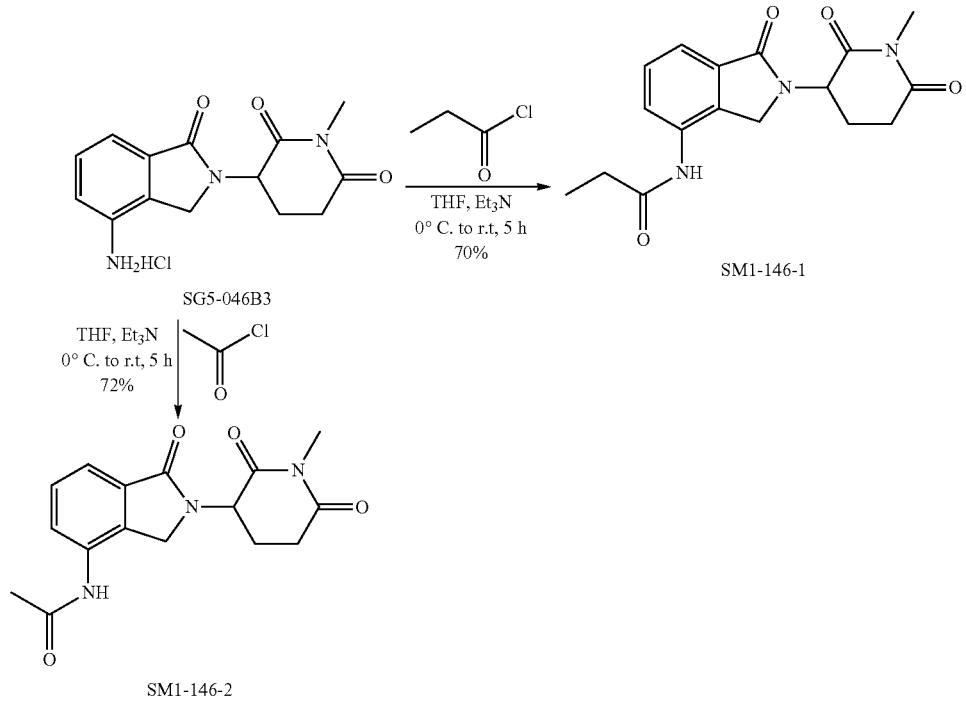

SG5-046B3

SM1-146-1

SM1-146-2

N$^1$-(2-(2,6-Dioxopiperidin-3-yl)-1-oxoisoindolin-4-yl)-N$^4$-(3-methoxypropyl)succinamide (SM1-133): Synthesized from Lenalidomide (100 mg, 0.385 mmol), SM1-131 (87.6 mg, 0.463 mmol), HATU (293.3 mg, 0.771 mmol), DIPEA (0.269 mL, 1.54 mmol) in DMF (1 mL) using general method A. The title compound was isolated as a white solid (123 mg, 74%). HPLC: 99% [t$_R$=6.9 min, Grad MeOH 5-95% water (with 0.1% TFA), flow: 1.0 mL/min, 20 min]. $^1$H NMR (500 MHz, DMSO-d$_6$) δ 11.03 (s, 1H), 9.86 (s, 1H), 8.03-7.75 (m, 2H), 7.61-7.31 (m, 2H), 5.15 (dd, J=13.3, 5.1 Hz, 1H), 4.35 (q, J=17.5 Hz, 2H), 3.30 (t, J=6.4 Hz, 2H), 3.23-3.16 (m, 3H), 3.07 (q, J=6.7 Hz, 2H), 2.92 (ddd, J=17.2, 13.6, 5.4 Hz, 1H), 2.66-2.54 (m, 3H), 2.46-2.23 (m, 3H), 2.10-1.98 (m, 1H), 1.63-1.59 (m, 2H). HPLC-MS (ESI+): m/z 861.4 [20%, (2M+H)$^+$], 431.2 [40%, (M+H)$^+$]. HRMS (ESI+): m/z calcd for C$_{13}$H$_{14}$N$_2$O$_3$ (M+Na)$^+$ 453.1745, found 453.1762.

N$^1$-(3-Methoxypropyl)-N$^4$-(2-(1-methyl-2,6-dioxopiperidin-3-yl)-1-oxoisoindolin-4-yl)succinamide (SM1-136): Synthesized from SG5-046B2 (50 mg, 0.161 mmol), SM1-131 (45.8 mg, 0.242 mmol), HATU (122.8 mg, 0.323

N-(2-(1-Methyl-2,6-dioxopiperidin-3-yl)-1-oxoisoindolin-4-yl)propionamide (SM1-146-1): Synthesized from SG5-046B3 (40 mg, 0.129 mmol), propionyl chloride (0.017 mL, 0.194 mmol), Et$_3$N (0.054 mL, 0.387 mmol) in DMF (0.5 mL) using general method B. The title compound was obtained as a white solid (29 mg, 70%). HPLC: 99% [t$_R$=11.5 min, Grad MeOH 5-95% water (with 0.1% formic acid), flow: 1.0 mL/min, 20 min]. $^1$H NMR (500 MHz, DMSO-d$_6$) δ 9.76 (s, 1H), 7.81 (dd, J=7.3, 1.6 Hz, 1H), 7.55-7.46 (m, 2H), 5.22 (dd, J=13.5, 5.1 Hz, 1H), 4.44-4.29 (m, 2H), 3.02 (s, 4H), 2.77 (m, 1H), 2.42-2.32 (m, 3H), 2.04 (m, 1H), 1.10 (t, J=7.5 Hz, 3H). HPLC-MS (ESI$^+$): m/z 681.3 [100%, (2M+Na)$^+$], 330.2 [70%, (M+H)$^+$]. HRMS (ESI$^+$): m/z calcd for C$_{17}$H$_{19}$N$_3$O$_4$ (M+H)$^+$ 330.1448, found 330.1446.

N-(2-(1-Methyl-2,6-dioxopiperidin-3-yl)-1-oxoisoindolin-4-yl)acetamide (SM1-146-2): Synthesized from SG5-046B3 (40 mg, 0.129 mmol), acetyl chloride (0.014 mL, 0.194 mmol), Et$_3$N (0.054 mL, 0.387 mmol) in DMF (0.5 mL) using general method B. The title compound was obtained as a white solid (30 mg, 72%). HPLC: 98%

[$t_R$=10.5 min, Grad MeOH 5-95% water (with 0.1% formic acid), flow: 1.0 mL/min, 20 min]. $^1$H NMR (500 MHz, DMSO-$d_6$) δ 9.84 (s, 1H), 7.84-7.76 (m, 1H), 7.56-7.43 (m, 2H), 5.22 (dd, J=13.5, 5.1 Hz, 1H), 4.43-4.28 (m, 2H), 3.07-2.89 (m, 4H), 2.76 (m, 1H), 2.36 (qd, J=13.4, 4.5 Hz, 1H), 2.13-1.94 (m, 4H). HPLC-MS (ESI$^+$): m/z 653.3 [100%, (2M+Na)$^+$], 316.2 [70%, (M+H)$^+$]. HRMS (ESI$^+$): m/z calcd for $C_{16}H_{17}N_3O_4$ (M+H)$^+$ 346.1292, found 346.1292.

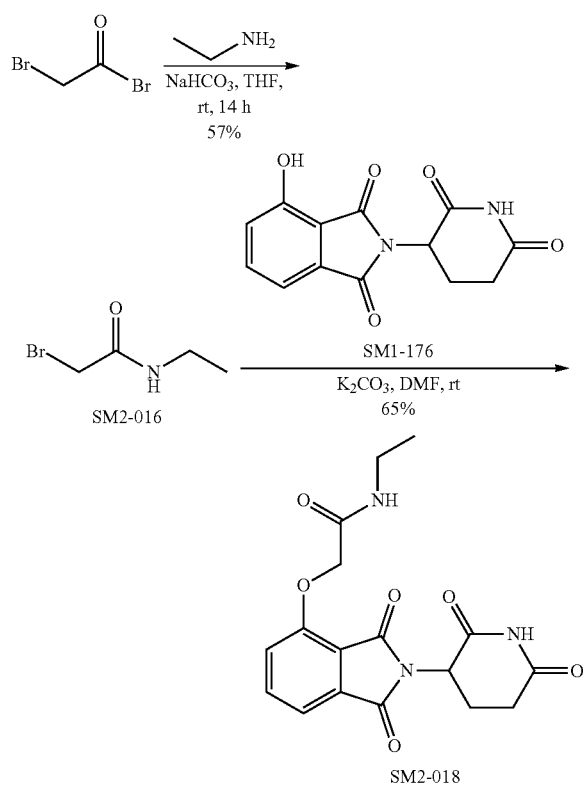

Synthetic scheme 3

2-Bromo-N-ethylacetamide (SM2-016): This compound was prepared using a reported procedure (Shaw, S. J.; et al., Structure-activity relationships of 9-substituted-9-dihydro-erythromycin-based motilin agonists: optimizing for potency and safety. Journal of medicinal chemistry 2009, 52, 6851-9). To a mixture of bromoacetyl bromide (0.645 mL, 7.43 mmol) and sodium bicarbonate (1.25 g, 14.86 mmol) in tetrahydrofuran (50 mL) at −78° C. was added ethylamine (2M in THF, 5.58 mL, 11.15 mmol). The resulting mixture was allowed to warm to room temperature over 14 h and partitioned between EtOAc and NaHCO$_3$. The organic layer was washed with brine, dried (MgSO$_4$), and concentrated to provide the title compound as a yellow solid (0.72 g, 57%). $^1$H NMR (500 MHz, CDCl$_3$) δ 6.46 (s, 1H), 3.88 (s, 2H), 3.34 (qd, J=5.6, 7.3 Hz, 2H), 1.19 (t, J=7.3 Hz, 3H).

2-((2-(2,6-Dioxopiperidin-3-yl)-1,3-dioxoisoindolin-4-yl)oxy)-N-ethylacetamide (SM2-018): The SM1-176 (80.0 mg, 0.292 mmol) was dissolved in DMF (0.5 mL) and potassium carbonate (60.5 mg, 0.438 mmol) was added, followed by SM2-016 (72.7 mg, 0.438 mmol), and the mixture was stirred at room temperature for 3 h. The solvent was removed using BIOTAGE™ V-10 evaporator. The resulting residue was purified by SiO$_2$ chromatography eluting with MeOH in DCM (0-10% MeOH, gradient elution) to provide the title compound as a white solid (68.1 mg, 65%). HPLC: 99% [$t_R$=9.41 min, 35% CH$_3$OH in 0.1% TFA/water, 20 min]. $^1$H NMR (500 MHz, DMSO-$d_6$) δ 11.12 (s, 1H), 7.95 (t, J=5.6 Hz, 1H), 7.82 (dd, J=7.3, 8.5 Hz, 1H), 7.51 (d, J=7.2 Hz, 1H), 7.41 (d, J=8.4 Hz, 1H), 5.13 (dd, J=5.4, 12.8 Hz, 1H), 4.76 (s, 2H), 3.21-3.15 (m, 2H), 2.90 (ddd, J=5.5, 13.8, 16.9 Hz, 1H), 2.65-2.52 (m, 2H), 2.05 (dtd, J=2.1, 5.2, 12.9 Hz, 1H), 1.06 (t, J=7.2 Hz, 3H). $^{13}$C NMR (126 MHz, DMSO-$d_6$) δ 173.24, 170.34, 167.19, 166.96, 165.97, 155.53, 137.42, 133.49, 120.93, 117.30, 116.53, 68.17, 49.27, 33.76, 31.41, 22.46, 15.11. HPLC-MS (ESI$^+$): m/z 360.2 [100%, (M+H)$^+$], 741.2 [70%, (2M+Na)$^+$]. HRMS (ESI$^+$): m/z calcd for $C_{17}H_{17}N_8O_6$ (M+Na)$^+$ 382.1010, found 382.1016.

Synthetic scheme 4

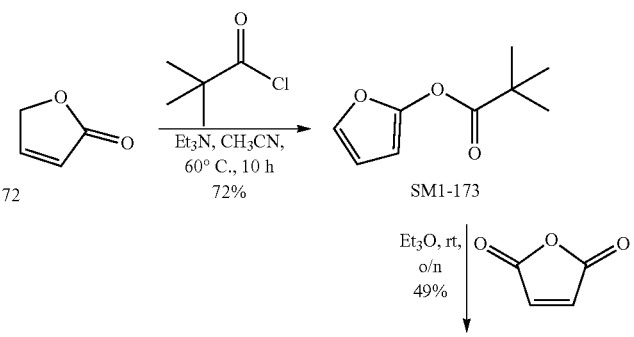

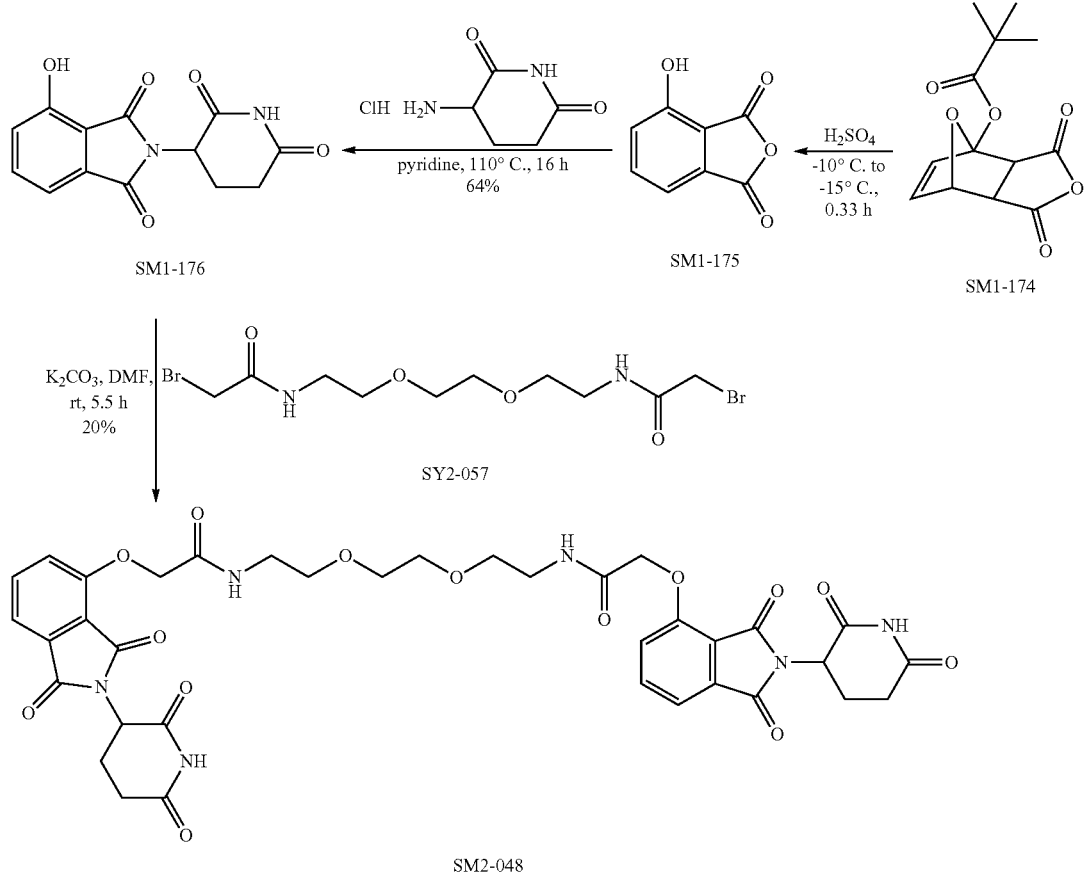

Furan-2(3H)-one and Furan-2(5H)-one (SM1-172): The furanones SM1-172 were prepared using a reported procedure (Cao, R.; et al., A convenient synthesis of 2(5H)-Furanone. *Organic Preparations and Procedures International* 1996, 28, 215-216). To a 250 mL flask equipped with a stirring bar, was added furfural (14.40 g, 149.87 mmol), DCM (30 mL) and sodium sulfate (18.09 g, 127.39 mmol) at room temperature. Then 35% hydrogen peroxide (33 mL, 383.66 mmol) was added dropwise with stirring at 60~70° C. for 2 h. The mixture was refluxed for 10 h, cooled to room temperature and filtered. The aqueous layer was extracted with DCM (2×20 mL), the combined organic layers were dried ($Na_2SO_4$), concentrated to give SM1-172 (6.88 g, 54%) as a red liquid. This was used in the next step without purification.

3-Hydroxyphthalic anhydride (SM1-175): This compound was prepared using a reported procedure (Näsman, J.-A. H. A Versatile Synthetic Route to 3-Hydroxyphthalic Anhydride. *Synthesis* 1985, 1985, 788-789) from SM1-172. $^1$H NMR (500 MHz, DMSO-$d_6$) δ 11.72 (s, 1H), 7.78 (t, J=7.8 Hz, 1H), 7.46 (d, J=7.3 Hz, 1H), 7.34 (d, J=8.4 Hz, 1H).

2-(2,6-Dioxopiperidin-3-yl)-4-hydroxyisoindoline-1,3-dione (SM1-176) (WO2017024317 (A2)): The 3-hydroxyphthalic anhydride (SM1-175) (2.00 g, 12.19 mmol) and 3-aminopiperidine-2,6-dione hydrochloride (2.01 g, 12.19 mmol) were dissolved in pyridine (19 mL) and heated to 110° C. for 16 h. The mixture was concentrated and purified by $SiO_2$ chromatography eluting with 5% MeOH in DCM followed by trituration from MeOH to give the title compound SM1-175 as an off-white solid (2.15 g, 64%). $^1$H NMR (500 MHz, DMSO-$d_6$) δ 11.18 (s, 1H), 11.09 (s, 1H), 7.68-7.62 (m, 1H), 7.32 (d, J=7.1 Hz, 1H), 7.25 (d, J=8.4 Hz, 1H), 5.07 (dd, J=5.4, 12.8 Hz, 1H), 2.88 (ddd, J=5.4, 13.8, 16.9 Hz, 1H), 2.63-2.51 (m, 2H), 2.00-2.03 (m, J=3.2, 10.5 Hz, 1H). HPLC-MS (ESI$^+$): m/z 571.1 [100%, (2M+Na)$^+$], 297.1 [50%, (M+Na)$^+$], 275.2 [30%, (M+H)$^+$]. HRMS (ESI$^-$): m/z calcd. for $C_{13}H_{10}N_2O_5$ (M−H)$^-$ 273.0517, found 273.0516.

N,N'-((Ethane-1,2-diylbis(oxy))bis(ethane-2,1-diyl))bis (2-((2-(2,6-dioxopiperidin-3-yl)-1,3-dioxoisoindolin-4-yl) oxy)acetamide (SM2-048): To a mixture of SM1-176 (73.8 mg, 0.269 mmol) and $K_2CO_3$ (44.3 mg, 0.320 mmol) in DMF (0.5 mL) was added SY2-057 (50.0 mg, 0.128 mmol). The mixture was stirred for 5.5 h at room temperature. The solvent was removed and the resulting residue was purified by $SiO_2$ chromatography eluting with MeOH in DCM (0-10% MeOH, gradient elution) to provide the title compound as an off-white solid (20.0 mg, 20%). HPLC: 99% [$t_R$=5.52 min, $CH_3OH$ in 0.1% TFA/water, 20 min]. $^1$H NMR (500 MHz, DMSO-$d_6$) δ 11.12 (s, 2H), 7.99 (t, J=5.7 Hz, 2H), 7.80 (dd, J=8.5, 7.3 Hz, 2H), 7.49 (d, J=7.2 Hz, 2H), 7.39 (d, J=8.5 Hz, 2H), 5.11 (dd, J=12.8, 5.4 Hz, 2H), 4.78 (s, 4H), 3.52 (s, 4H), 3.45 (t, J=5.7 Hz, 4H), 3.31 (d, J=5.8 Hz, 4H), 2.89 (ddd, J=16.8, 13.8, 5.4 Hz, 2H), 2.64-2.51 (m, 4H), 2.04 (dtd, J=12.9, 5.2, 2.1 Hz, 2H). $^{13}$C NMR (126 MHz, DMSO-$d_6$) δ 173.23, 170.33, 167.36, 167.18, 165.90, 155.42, 137.39, 133.49, 120.80, 117.21, 116.51, 70.05, 69.30, 67.96, 49.27, 38.86, 31.41, 22.46. HPLC-MS (ESI$^+$): m/z 799.3 [100%, (M+Na)$^+$], 777.2

[50%, (M+H)+]. HRMS (ESI+): m/z calcd. for $C_{13}H_{14}N_2O_3$ (M+Na)+ 799.2182, found 799.2178.

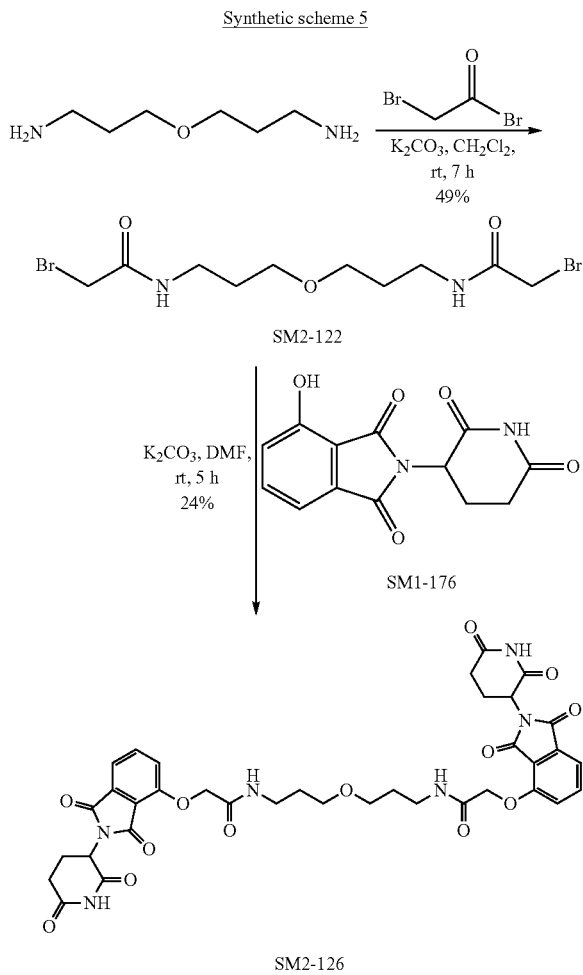

Synthetic scheme 5

N,N'-(Oxybis(propane-3,1-diyl))bis(2-bromoacetamide (SM2-122): The 3,3'-oxybis(propan-1-amine) (0.20 g, 1.51 mmol) was dissolved in DCM (2 mL), $K_2CO_3$ (0.52 g, 3.78 mmol) and bromoacetyl bromide (0.76 g, 3.78 mmol) were added and the mixture was stirred at rt for 7 h. The reaction was quenched with water and the mixture was extracted with DCM (3×20 mL). The combined organic extracts were dried over $MgSO_4$, filtered and the filtrate concentrated. The residue obtained was purified by $SiO_2$ chromatography eluting with MeOH in DCM (0-8% MeOH, gradient elution) to provide the title compound as a white solid (275.0 mg, 49%). $^1$H NMR (500 MHz, $CDCl_3$) δ 7.05 (s, 2H), 3.90 (s, 4H), 3.53 (t, J=5.6 Hz, 4H), 3.44 (q, J=6.0 Hz, 4H), 1.87-1.80 (m, 4H). HPLC-MS (ESI+): m/z 397.0 [100%, (M+Na)+], 375.1 [84%, (M+H)+].

N,N'-(Oxybis(propane-3,1-diyl))bis(2-((2-(2,6-dioxopiperidin-3-yl)-1,3-dioxoisoindolin-4-yl)oxy)acetamide (SM2-126): To a mixture of SM1-176 (77.0 mg, 0.281 mmol) and $K_2CO_3$ (46.2 mg, 0.334 mmol) in DMF (0.5 mL) was added SM2-122 (50.0 mg, 0.134 mmol). The mixture was stirred for 5 h at room temperature. The solvent was removed and the resulting residue was purified by $SiO_2$ chromatography eluting with MeOH in DCM (0-8% MeOH, gradient elution) to provide the title compound as an off-white solid (24.0 mg, 24%). HPLC: 95% [$t_R$=9.63 min, gradient 20-95% MeOH/water (with 0.1% TFA), 20 min]. $^1$H NMR (500 MHz, DMSO-$d_6$) δ 11.11 (s, 2H), 7.95 (t, J=5.7 Hz, 2H), 7.80 (dd, J=7.3, 8.5 Hz, 2H), 7.49 (d, J=7.2 Hz, 2H), 7.38 (d, J=8.5 Hz, 2H), 5.11 (dd, J=5.5, 12.8 Hz, 2H), 4.76 (s, 4H), 3.36 (t, J=6.2 Hz, 4H), 3.20 (q, J=6.7 Hz, 4H), 2.89 (ddd, J=5.5, 13.8, 16.9 Hz, 2H), 2.64-2.51 (m, 4H), 2.03 (dtd, J=2.1, 5.3, 12.9 Hz, 2H), 1.65 (p, J=6.5 Hz, 4H). $^{13}$C NMR (126 MHz, DMSO-$d_6$) δ 173.23, 170.33, 167.19, 165.93, 155.50, 137.39, 133.49, 120.84, 117.26, 116.51, 68.09, 68.05, 55.38, 49.27, 36.20, 31.41, 29.69, 22.46. HPLC-MS (ESI+): m/z 783.3 [100%, (M+Na)+], 761.3 [90%, (M+H)+]. HRMS (ESI+): m/z calcd. for $C_{36}H_{36}N_6O_{13}$ (M+Na)+ 783.2233, found 783.2230.

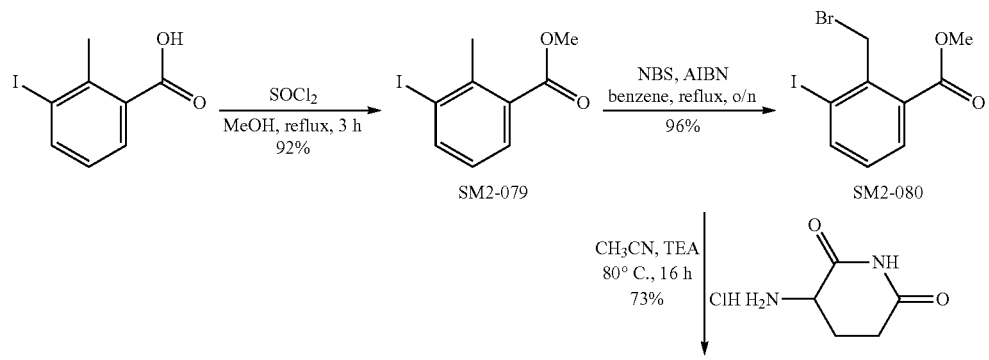

Synthetic scheme 6

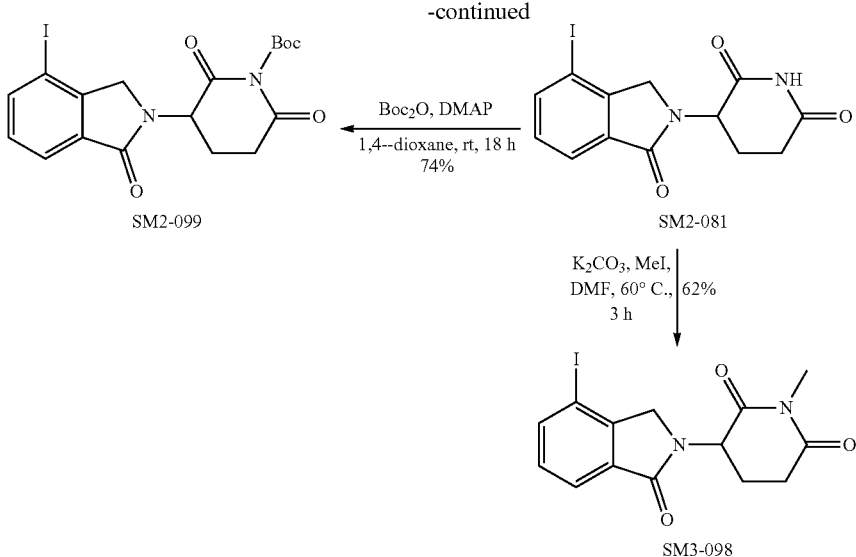

Methyl 3-iodo-2-methylbenzoate (SM2-079) (WO2006117669 (A1)): To a solution of 3-iodo-2-methylbenzoic acid (5.00 g, 19.08 mmol) in MeOH (20 mL) was added dropwise a solution of SOCl$_2$ (4.16 mL, 57.24 mmol) in MeOH (10 mL) at 0° C. The mixture was heated to reflux for 3 h. The mixture was concentrated and the residue obtained was purified using SiO$_2$ chromatography eluting with EtOAc in hexanes (0-15% EtOAc, gradient elution) to provide the title compound 5 as a brown oil (4.00 g, 75%). 1H NMR (500 MHz, CDCl$_3$) δ 8.00 (dd, J=1.3, 7.9 Hz, 1H), 7.76 (dd, J=1.3, 7.7 Hz, 1H), 6.95 (td, J=0.7, 7.8 Hz, 1H), 3.93 (s, 3H), 2.69 (s, 3H). HPLC-MS (ESI+): m/z 276.9 [100%, (M+H)+], 761.3 [72%, (M+Na)+].

Methyl 2-(bromomethyl)-3-iodobenzoate (SM2-080): To a solution of SM2-079 (4.00 g, 14.49 mmol) in benzene (66 mL) (CAUTION) at room temperature were added N-bromosuccinimide (NBS) (3.09 g, 17.39 mmol) and AIBN (237.9 mg, 1.45 mmol). The reaction was refluxed for 6 h, the mixture was cooled to room temperature and the solid obtained was filtered. The filtrate was diluted with EtOAc and washed with sat. NaHCO$_3$ solution, brine, dried (MgSO$_4$) and concentrated. The residue was purified by SiO$_2$ chromatography with EtOAc/hexane (0% to 10% EtOAc, gradient elution) to obtain the title compound[6] (4.95 g, 96%) as a white solid. $^1$H NMR (500 MHz, DMSO-d$_6$) δ 8.15 (dd, J=1.3, 7.9 Hz, 1H), 7.85 (dd, J=1.4, 7.8 Hz, 1H), 7.21 (t, J=7.8 Hz, 1H), 5.03 (s, 2H), 3.88 (s, 3H).

3-(4-Iodo-1-oxoisoindolin-2-yl)piperidine-2,6-dione (SM2-081): A mixture of SM2-080 (3.50 g, 9.86 mmol), 3-aminopiperidine-2,6-dione hydrochloride (2.43 g, 14.79 mmol) and triethylamine (2.27 mL, 16.27 mmol) in CH$_3$CN (20 mL) was stirred at 80° C. for 16 h. The solution was evaporated to remove most of the solvent. EtOAc (20 mL) and water (20 mL) were added and the solid obtained was filtered, washed with water and EtOAc to afford the title compound (WO2018052949 (A1)) as a purple solid (2.68 g, 73%). $^1$H NMR (500 MHz, DMSO-d$_6$) δ 11.00 (s, 1H), 8.04 (dd, J=0.9, 7.8 Hz, 1H), 7.77 (dd, J=0.9, 7.5 Hz, 1H), 7.35 (t, J=7.7 Hz, 1H), 5.15 (dd, J=5.2, 13.3 Hz, 1H), 4.29 (d, J=17.4 Hz, 1H), 4.14 (d, J=17.5 Hz, 1H), 2.91 (ddd, J=5.4, 13.7, 17.3 Hz, 1H), 2.59 (ddd, J=2.3, 4.5, 17.3 Hz, 1H), 2.46 (dd, J=4.6, 13.3 Hz, 1H), 2.02 (dtd, J=2.2, 5.3, 12.7 Hz, 1H). $^{13}$C NMR (126 MHz, DMSO-d$_6$) δ 172.83, 170.88, 167.63, 146.37, 140.49, 133.28, 130.23, 122.90, 91.64, 51.69, 51.11, 31.19, 22.27. HPLC-MS (ESI+): m/z 762.9 [100%, (M+Na)+], 371.0 [50%, (M+H)+]. HRMS (ESI+): m/z calcd for C$_{13}$H$_{11}$IN$_2$O$_3$ (M+H)+ 370.9887, found 370.9891.

tert-Butyl-3-(4-iodo-1-oxoisoindolin-2-yl)-2,6-dioxopiperidine-1-carboxylate (SM2-099): To a stirred suspension of SM2-081 (2.00 g, 5.40 mmol) and di-tert-butyl dicarbonate (1.77 g, 8.10 mmol) in 1,4-dioxane (10.0 mL) was added N,N-dimethylaminopyridine (66.0 mg, 0.54 mmol) at room temperature. The solution was stirred at room temperature for 18 h. Water and EtOAc were added to the mixture, and the aqueous layer was extracted with EtOAc (3×20 mL). The combined organic layers were washed with brine, dried (MgSO$_4$), filtered, concentrated and the residue was triturated from EtOAc/hexane followed by MeOH to afford the title compound as an off-white solid (1.85 g, 74%). $^1$H NMR (500 MHz, DMSO-d$_6$) δ 8.05 (dd, J=0.9, 7.8 Hz, 1H), 7.78 (dd, J=0.9, 7.6 Hz, 1H), 7.35 (t, J=7.6 Hz, 1H), 5.37 (dd, J=5.1, 13.4 Hz, 1H), 4.32 (d, J=17.4 Hz, 1H), 4.17 (d, J=17.4 Hz, 1H), 3.16-3.07 (m, 1H), 2.79 (ddd, J=2.3, 4.5, 17.6 Hz, 1H), 2.59 (td, J=4.6, 13.2 Hz, 1H), 2.08 (dtd, J=2.2, 5.3, 15.1 Hz, 1H), 1.49 (s, 9H). $^{13}$C NMR (126 MHz, CDCl$_3$) δ 168.99, 168.70, 167.49, 148.02, 146.28, 141.14, 133.20, 130.26, 124.03, 90.59, 87.23, 51.85, 51.10, 31.83, 27.56, 22.81. HPLC-MS (ESI+): m/z 963.0 [100%, (2M+Na)+], 493.1 [50%, (M+Na)+]. HRMS (ESI+): m/z calcd. for C$_{18}$H$_{19}$IN$_2$O$_5$ (M+Na)+ 493.0231, found 493.0233.

3-(4-Iodo-1-oxoisoindolin-2-yl)-1-methylpiperidine-2,6-dione (SM3-098): The K$_2$CO$_3$ (448.1 mg, 3.24 mmol) and MeI (0.25 mL, 4.05 mmol) were added to a solution of SM2-081 (1.00 g, 2.70 mmol) in DMF (8.0 mL), and the mixture was stirred at 60° C. for 3 h. Water and EtOAc were added to the mixture. The aqueous layer was extracted with EtOAc (3×20 mL), combined organic layers were washed with brine, dried (Na$_2$SO$_4$), filtered and concentrated. The title compound was obtained by triturating from EtOAc/hexane and MeOH as a white solid (0.65 g, 62%). $^1$H NMR (500 MHz, DMSO-d$_6$) δ 8.04 (dd, J=0.9, 7.8 Hz, 1H), 7.78 (dd, J=0.9, 7.6 Hz, 1H), 7.35 (t, J=7.6 Hz, 1H), 5.22 (dd, J=5.1, 13.5 Hz, 1H), 4.28 (d, J=17.4 Hz, 1H), 4.14 (d, J=17.4 Hz, 1H), 3.03-2.95 (m, 4H), 2.78-2.73 (m, 1H), 2.48-2.41 (m, 1H), 2.00-2.05 (m, 1H). $^{13}$C NMR (126 MHz, CDCl$_3$) δ 171.20, 169.99, 168.97, 146.28, 140.99, 133.52, 130.23, 124.00, 90.57, 52.65, 51.36, 32.16, 27.35, 22.88. HPLC-MS (ESI$^+$): m/z 791.0 [100%, (2M+Na)$^+$], 385.0 [50%, (M+H)$^+$]. HRMS (ESI$^+$): m/z calcd for $C_{14}H_{13}IN_2O_3$ (M+H)$^+$ 385.0044, found 385.0039.

General Method C:

As described by Jervis et al. (Jervis, P. J.; et al., Towards multivalent CD1d ligands: synthesis and biological activity of homodimeric alpha-galactosyl ceramide analogues. *Carbohydrate research* 2012, 356, 152-62) sodium hydride (60 percent w/w in mineral oil, 3 equiv) was added to a solution of appropriate diol (1 equiv) in anhydrous THF (0.2 M) at 0° C. under argon. A catalytic amount of Bu$_4$NI (0.05 equiv) and propargyl bromide (3 or 4 equiv.) was added sequentially. The mixture was stirred at rt overnight, concentrated under reduced pressure. Purification of the residue by SiO$_2$ chromatography afforded the required diyne.

General Method D:

To a solution of the diyne (1.0 equiv) and SM2-099B2 (2.1 equiv) in DMF (0.2 M) were added Pd(PPh$_3$)$_2$Cl$_2$ (0.03 equiv) and CuI (0.03 equiv) under argon. The mixture was degassed and purged with argon for 10 minutes. The triethylamine (¼ of DMF) was added and the reaction was stirred at room temperature overnight. Water (10 mL) was added and extracted with EtOAc (2×10 mL). The combined organic layers were washed with brine and dried (Na$_2$SO$_4$), concentrated. The resulting residue was purified by SiO$_2$ chromatography eluting with EtOAc in hexane (gradient elution) to provide the title compound.

General Method E:

To a mixture of 10% Pd/C (0.2 equiv) in EtOAc (0.1 M) was deoxygenated using argon gas for 15 min., and added appropriate alkyne (1.0 equiv) under argon. The flask was evacuated and purged with argon (three times). Argon gas was evacuated and a balloon of hydrogen was attached to the system. The reaction mixture was stirred at room temperature for 24 h, filtered using a short plug of celite, washed with EtOAc and concentrated under reduced pressure. The resulting residue was purified by SiO$_2$ chromatography eluting with EtOAc in hexane (gradient elution) to provide the title compound.

General Method F:

Boc protected bis-immunomodulatory drugs (1 equiv) was treated with 4N HCl in dioxane (2 mL) and the mixture was stirred at room temperature for 14 h. The solution obtained was concentrated to afford the desired compound.

Synthetic scheme 7

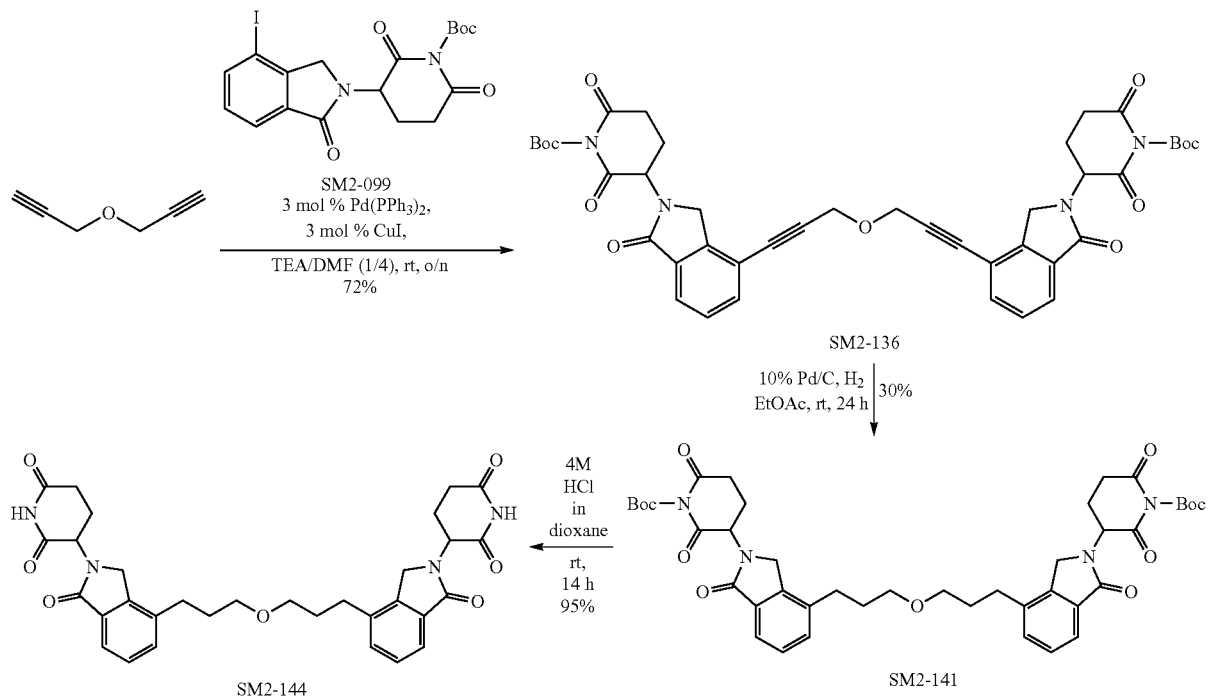

Di-tert-butyl 3,3'-((oxybis(prop-1-yne-3,1-diyl))bis(1-oxoisoindoline-4,2-diyl))bis(2,6-dioxopiperidine-1-carboxylate) (SM2-136): Synthesized from 3-(prop-2-yn-1-yloxy)prop-1-yne (50.0 mg, 0.53 mmol), SM2-099B2 (524.6 mg, 1.12 mmol), Pd(PPh$_3$)$_2$Cl$_2$ (11.2 mg, 15.94 µmol), CuI (3.04 mg, 15.94 µmol), and trimethylamine (0.8 mL) in DMF (3.2 mL), using general method D. The title compound SM2-136 was obtained as an off-white solid (298.0 mg, 72%). $^1$H NMR (500 MHz, DMSO-d$_6$) δ 7.79 (d, J=7.5 Hz, 2H), 7.75 (d, J=7.7 Hz, 2H), 7.57 (t, J=7.5 Hz, 2H), 5.37 (dd, J=4.9, 13.3 Hz, 2H), 4.62 (s, 4H), 4.54 (dd, J=4.9, 17.9 Hz, 2H), 4.39 (d, J=17.8 Hz, 2H), 3.17-3.09 (m, 2H), 2.78 (ddt, J=2.3, 4.5, 17.6 Hz, 2H), 2.61-2.52 (m, 2H), 2.09-2.03 (m, 2H), 1.48 (s, 18H). HPLC-MS (ESI$^+$): m/z 801.3 [100%, (M+Na)$^+$].

Di-tert-butyl 3,3'-((oxybis(propane-3,1-diyl))bis(1-oxoisoindoline-4,2-diyl))bis(2,6-dioxopiperidine-1-carboxylate) (SM2-141): Synthesized from SM2-136 (270.0 mg, 0.346 mmol) and 10% Pd/C (73.8 mg, 0.069 mmol) using general method E and purified by SiO$_2$ chromatography eluting with EtOAc in hexane (20-65% EtOAc, gradient elution). The title compound was obtained as an off-white solid (81.8 mg, 30%). $^1$H NMR (500 MHz, DMSO-d$_6$) δ 7.58 (dd, J=3.5, 5.2 Hz, 2H), 7.46 (d, J=5.2 Hz, 4H), 5.35 (dd, J=5.1, 13.3 Hz, 2H), 4.49 (d, J=17.0 Hz, 2H), 4.33 (d, J=17.0 Hz, 2H), 3.37 (t, J=6.9 Hz, 4H), 3.17-3.09 (m, 2H), 2.82-2.75 (m, 2H), 2.69 (d, J=7.7 Hz, 4H), 2.55-2.52 (m, 1H), 2.55-2.45 (m, 2H), 2.09-2.03 (m, 2H), 1.89-1.81 (m, 4H), 1.47 (s, 18H). HPLC-MS (ESI$^+$): m/z 809.4 [100%, (M+Na)$^+$].

3,3'-((Oxybis(propane-3,1-diyl))bis(1-oxoisoindoline-4,2-diyl))bis(piperidine-2,6-dione) (SM2-144): Synthesized from SM2-141 (60.0 mg, 0.076 mmol) and 4N HCl in dioxane (2.0 mL) using general method F to give the title compound as a white solid (42.4 mg, 95%). HPLC: 99% [t$_R$=12.39 min, gradient 45-85% MeOH/water (with 0.1% formic acid), 20 min]. $^1$H NMR (500 MHz, DMSO-d$_6$) δ 10.92 (s, 2H), 7.53-7.47 (m, 2H), 7.39 (d, J=4.3 Hz, 4H), 5.07 (dd, J=5.0, 13.3 Hz, 2H), 4.39 (d, J=17.1 Hz, 2H), 4.24 (d, J=17.1 Hz, 2H), 3.30 (t, J=6.2 Hz, 4H), 2.89-2.82 (m, 2H), 2.62 (t, J=7.6 Hz, 4H), 2.57-2.48 (m, 2H), 2.35-2.29 (m, 2H), 1.95-1.92 (m, 2H), 1.78 (dt, J=8.2, 13.5 Hz, 4H). $^{13}$C NMR (126 MHz, DMSO-d$_6$) δ 173.34, 171.52, 168.82, 141.11, 137.47, 132.01, 131.97, 128.77, 121.15, 69.65, 52.00, 46.66, 31.66, 29.77, 28.30, 22.99. HPLC-MS (ESI$^+$): m/z 609.3 [100%, (M+Na)$^+$], 587.3 [60%, (M+H)$^+$]. HRMS (ESI$^+$): m/z calcd for $C_{32}H_{34}N_4O_7$ (M+Na)$^+$ 609.2320, found 609.2319.

Synthetic scheme 8
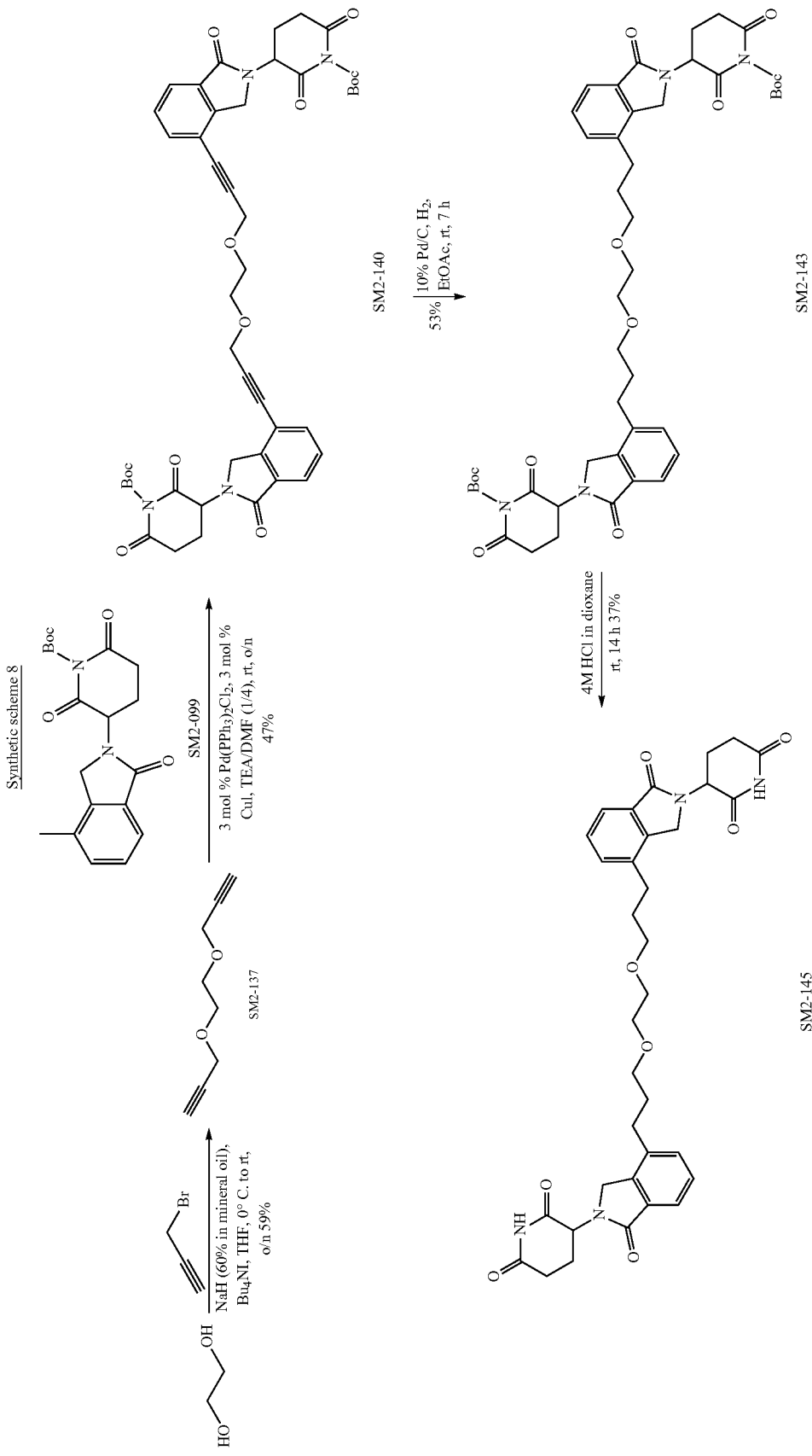

1,2-Bis(prop-2-yn-1-yloxy)ethane (SM2-137): Synthesized from ethylene glycol (1.00 g, 16.11 mmol), propargyl bromide (5.75 g, 48.33 mmol), NaH (60% w/w in mineral oil, 1.16 g, 48.33 mmol) and Bu$_4$NI (297.7 mg, 0.806 mmol) using general method C and purified by SiO$_2$ chromatography eluting with EtOAc in hexane (0-5% EtOAc, gradient elution). The title compound was obtained as a yellow oil (1.32 g, 59%). $^1$H NMR (500 MHz, CDCl$_3$) δ 4.20 (d, J=2.4 Hz, 4H), 3.71 (s, 4H), 2.43 (t, J=2.4 Hz, 2H). $^{13}$C NMR (126 MHz, CDCl$_3$) δ 79.59, 74.76, 68.93, 58.51. HPLC-MS (ESI$^+$): m/z 139.1 [70%, (M+H)$^+$].

Di-tert-butyl 3,3'-(((ethane-1,2-diylbis(oxy))bis(prop-1-yne-3,1-diyl))bis(1-oxoisoindoline-4,2-diyl))bis(2,6-dioxopiperidine-1-carboxylate) (SM2-140): Synthesized from SM2-137 (30.0 mg, 0.217 mmol), SM2-099B2 (214.4 mg, 0.456 mmol), Pd(PPh$_3$)$_2$Cl$_2$ (4.6 mg, 6.51 μmol), CuI (1.24 mg, 6.51 μmol), triethylamine (0.25 mL) and DMF (1.0 mL) using general method D and purified by SiO$_2$ chromatography eluting with EtOAc in hexane (20-60% EtOAc, gradient elution). The title compound was obtained as an off-white solid (84.0 mg, 47%). $^1$H NMR (500 MHz, DMSO-d$_6$) δ 7.79-7.75 (m, 2H), 7.72 (dt, J=1.1, 7.6 Hz, 2H), 7.55 (td, J=1.0, 7.6 Hz, 2H), 5.37 (dd, J=5.1, 13.3 Hz, 2H), 4.52 (dd, J=2.9, 17.6 Hz, 2H), 4.48 (s, 4H), 4.36 (d, J=17.7 Hz, 2H), 3.74 (s, 4H), 3.16-3.09 (m, 2H), 2.80-2.74 (m, 2H), 2.60-2.53 (m, 2H), 2.08-2.05 (m, 2H), 1.47 (s, 18H). $^{13}$C NMR (126 MHz, DMSO-d$_6$) δ 170.06, 168.53, 167.56, 148.44, 144.00, 134.51, 131.82, 128.77, 123.55, 117.50, 91.33, 85.85, 81.34, 68.59, 58.12, 51.62, 47.08, 30.88, 27.04, 21.35. HPLC-MS (ESI$^+$): m/z 845.3 [100%, (M+Na)$^+$]. HRMS (ESI$^+$): m/z calcd. for C$_{44}$H$_{46}$N$_4$O$_{12}$ (M+Na)$^+$ 845.3004, found 845.2998.

Di-tert-butyl 3,3'-(((ethane-1,2-diylbis(oxy))bis(propane-3,1-diyl))bis(1-oxoisoindoline-4,2-diyl))bis(2,6-dioxopiperidine-1-carboxylate) (SM2-143): Synthesized from SM2-140 (84.0 mg, 0.102 mmol) and 10% Pd/C (21.7 mg, 0.0204 mmol) using general method E and purified by SiO$_2$ chromatography eluting with EtOAc in hexane (80%). The title compound was obtained as an off-white solid (45.0 mg, 53%). $^1$H NMR (500 MHz, DMSO-d$_6$) δ 7.57 (dd, J=2.1, 6.5 Hz, 2H), 7.49-7.41 (m, 4H), 5.35 (dd, J=5.0, 13.3 Hz, 2H), 4.48 (d, J=17.0 Hz, 2H), 4.32 (d, J=16.9 Hz, 2H), 3.48 (s, 4H), 3.43-3.36 (m, 4H), 3.18-3.10 (m, 2H), 2.81-2.75 (m, 2H), 2.69 (t, J=7.6 Hz, 4H), 2.54-2.44 (m, 2H), 2.08-2.03 (m, 2H), 1.87-1.81 (m, 4H), 1.47 (s, 18H). $^{13}$C NMR (126 MHz, DMSO-d$_6$) δ 170.10, 168.63, 168.43, 148.48, 140.68, 136.99, 131.68, 131.27, 128.35, 120.74, 85.83, 69.51, 69.37, 51.51, 46.33, 30.89, 29.22, 27.65, 27.04, 21.55. HPLC-MS (ESI$^+$): m/z 853.4 [100%, (M+Na)$^+$]. HRMS (ESI$^+$): m/z calcd. for C$_{44}$H$_{54}$N$_4$O$_{12}$ (M+Na)$^+$ 853.3630, found 853.3635.

3,3'-(((Ethane-1,2-diylbis(oxy))bis(propane-3,1-diyl))bis(1-oxoisoindoline-4,2-diyl))bis(piperidine-2,6-dione) (SM2-145): Synthesized from SM2-143 (40.0 mg, 0.048 mmol) and 4N HCl in dioxane (2.0 mL) using general method F. The preparative HPLC purification using gradient 45-85% MeOH/water (with 0.1% formic acid, 20 min) afforded the pure product as a white solid (11.0 mg, 37%). HPLC: 99% [t$_R$=12.91 min, gradient 45-85% MeOH/water (with 0.1% formic acid), 20 min]. $^1$H NMR (500 MHz, DMSO-d$_6$) δ 10.99 (s, 2H), 7.56 (dd, J=2.6, 6.0 Hz, 2H), 7.49-7.40 (m, 4H), 5.12 (dd, J=4.8, 13.3 Hz, 2H), 4.45 (d, J=17.1 Hz, 2H), 4.29 (d, J=16.9 Hz, 2H), 3.49 (s, 4H), 3.39 (t, J=6.4 Hz, 4H), 2.95-2.88 (m, 2H), 2.68 (t, J=7.6 Hz, 4H), 2.62-2.54 (m, 2H), 2.46-2.33 (m, 2H), 2.03-1.97 (m, 2H), 1.86-1.78 (m, 4H). $^{13}$C NMR (126 MHz, DMSO-d$_6$) δ 173.35, 171.52, 168.80, 141.11, 137.39, 132.01, 128.75, 121.16, 69.99, 69.85, 51.99, 46.64, 31.66, 29.71, 28.15, 22.99. HPLC-MS (ESI$^+$): m/z 653.3 [100%, (M+Na)$^+$], 631.3 [60%, (M+H)$^+$]. HRMS (ESI$^+$): m/z calcd. for C$_{34}$H$_{38}$N$_4$O$_8$ (M+H)$^+$ 631.2762, found 631.2759.

Synthetic Scheme 9
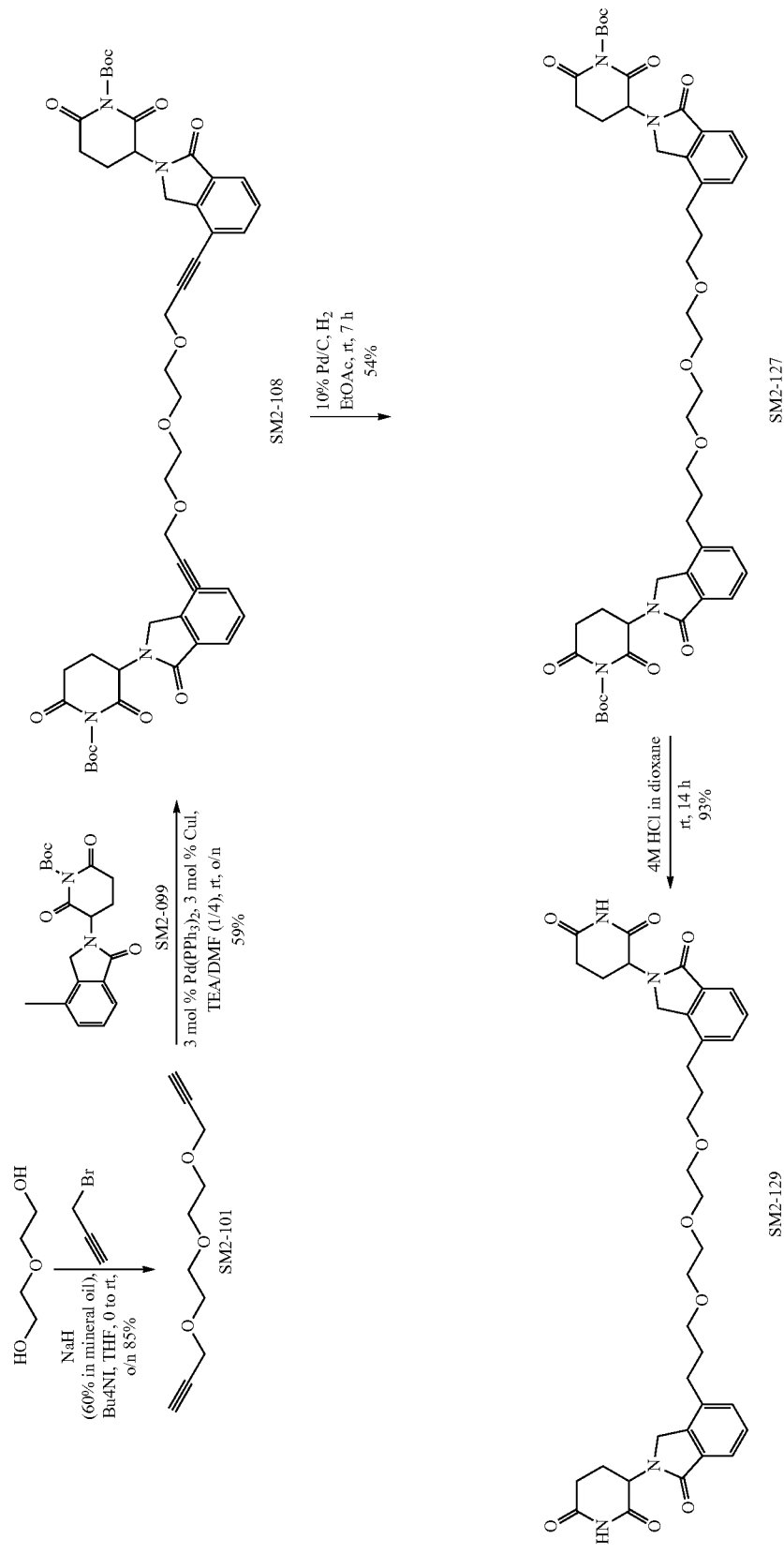

3-(2-(2-(Prop-2-yn-1-yloxy)ethoxy)ethoxy)prop-1-yne (SM2-101): Synthesized from diethylene glycol (5.00 g, 47.12 mmol), propargyl bromide (16.81 g, 141.35 mmol), sodium hydride (60% w/w in mineral oil, 5.65 g, 141.35 mmol) and Bu$_4$NI (870.2 mg, 2.36 mmol) using general method C and purified by SiO$_2$ chromatography eluting with EtOAc in hexane (5% to 15% EtOAc). The title compound was obtained as a pale yellow oil (7.31 g, 85%). $^1$H NMR (500 MHz, CDCl$_3$) δ 4.19 (d, J=2.4 Hz, 4H), 3.72-3.65 (m, 8H), 2.42 (t, J=2.4 Hz, 2H). $^{13}$C NMR (126 MHz, CDCl$_3$) δ 79.64, 74.52, 70.44, 69.11, 58.41.

Di-tert-butyl 3,3'-((((oxybis(ethane-2,1-diyl))bis(oxy))bis(prop-1-yne-3,1-diyl))bis(1-oxoisoindoline-4,2-diyl))bis(2,6-dioxopiperidine-1-carboxylate) (SM2-108): Synthesized from SM2-101 (30.0 mg, 0.165 mmol), SM2-099B2 (170.3 mg, 0.363 mmol), Pd(PPh$_3$)$_2$Cl$_2$ (3.5 mg, 4.95 μmol), CuI (0.941 mg, 4.95 μmol), triethylamine (0.20 mL) in DMF (0.8 mL) using general method D and purified by SiO$_2$ chromatography eluting with EtOAc in hexane (30-80% EtOAc, gradient elution). The title compound was obtained as an off-white solid (83.0 mg, 58%). $^1$H NMR (500 MHz, DMSO-d$_6$) δ 7.76 (dd, J=1.1, 7.5 Hz, 2H), 7.71 (d, J=7.6 Hz, 2H), 7.55 (t, J=7.7 Hz, 2H), 5.37 (dd, J=5.1, 13.3 Hz, 2H), 4.52 (dd, J=2.1, 17.7 Hz, 2H), 4.46 (s, 4H), 4.36 (d, J=17.7 Hz, 2H), 3.68-3.65 (m, 4H), 3.61-3.55 (m, 4H), 3.16-3.09 (m, 2H), 2.81-2.75 (m, 2H), 2.60-2.53 (m, 2H), 2.10-2.04 (m, 2H), 1.47 (s, 18H). HPLC-MS (ESI$^+$): m/z 889.3 [100%, (M+Na)$^+$], HRMS (ESI$^+$): m/z calcd. for C$_{34}$H$_{33}$N$_4$O$_3$ (M+Na)$^+$ 889.3267, found 889.3262.

Di-tert-butyl 3,3'-((((oxybis(ethane-2,1-diyl))bis(oxy))bis(propane-3,1-diyl))bis(1-oxoisoindoline-4,2-diyl))bis(2,6-dioxopiperidine-1-carboxylate) (SM2-127): Synthesized from SM2-108 (70.0 mg, 0.081 mmol) and 10% Pd/C (17.2 mg, 0.01615 mmol) using general method E and purified by SiO$_2$ chromatography eluting with EtOAc in hexane (40%-100% EtOAc, gradient elution). The title compound was obtained as a white solid (38.0 mg, 54%). $^1$H NMR (500 MHz, DMSO-d$_6$) δ 7.57 (dd, J=5.2, 3.4 Hz, 2H), 7.45 (dd, J=4.3, 1.3 Hz, 4H), 5.36 (dd, J=13.4, 5.1 Hz, 2H), 4.48 (dd, J=17.1, 2.1 Hz, 2H), 4.31 (d, J=17.0 Hz, 2H), 3.58-3.51 (m, 4H), 3.48-3.46 (m, 4H), 3.40-3.36 (m, 4H), 3.17-3.10 (m, 2H), 2.79 (ddd, J=17.6, 4.6, 2.3 Hz, 2H), 2.68 (t, J=7.7 Hz, 4H), 2.55-2.51 (m, 2H), 2.08-2.04 (m, 2H), 1.87-1.79 (m, 4H), 1.47 (s, 18H). HPLC-MS (ESI$^+$): m/z 897.4 [100%, (M+Na)$^+$].

3,3'-((((Oxybis(ethane-2,1-diyl))bis(oxy))bis(propane-3,1-diyl))bis(1-oxoisoindoline-4,2-diyl))bis(piperidine-2,6-dione) (SM2-129): Synthesized from SM2-127 (30.0 mg, 0.034 mmol) and 4N HCl in dioxane (2.0 mL) using general method F. The title compound was obtained as a white solid (21.5 mg, 93%). HPLC: 93% [t$_R$=14.81 min, 30% CH$_3$OH in 0.1% TFA/water, 20 min]. $^1$H NMR (500 MHz, DMSO-d$_6$) δ 10.99 (s, 2H), 7.56 (t, J=4.3 Hz, 2H), 7.48-7.39 (m, 4H), 5.13 (dd, J=5.1, 13.3 Hz, 2H), 4.45 (dd, J=2.1, 17.1 Hz, 2H), 4.29 (d, J=17.0 Hz, 2H), 3.56-3.50 (m, 4H), 3.50-3.43 (m, 4H), 3.41-3.34 (m, 4H), 2.92 (ddd, J=5.4, 13.7, 17.3 Hz, 2H), 2.67 (t, J=7.7 Hz, 4H), 2.62-2.52 (m, 2H), 2.43-2.36 (m, 2H), 2.03-1.98 (m 2H), 1.86-1.78 (m, 4H). $^{13}$C NMR (126 MHz, DMSO-d$_6$) δ 173.35, 171.51, 168.81, 141.11, 137.39, 132.00, 128.75, 121.15, 70.30, 69.98, 69.82, 51.99, 46.64, 31.67, 29.71, 28.15, 22.98. HPLC-MS (ESI$^+$): m/z 697.3 [100%, (M+Na)$^+$], 675.4 [50%, (M+H)$^+$], HRMS (ESI$^+$): m/z calcd. for C$_{36}$H$_{42}$N$_4$O$_9$ (M+H)$^+$ 675.3025, found 675.3023.

Synthetic scheme 10

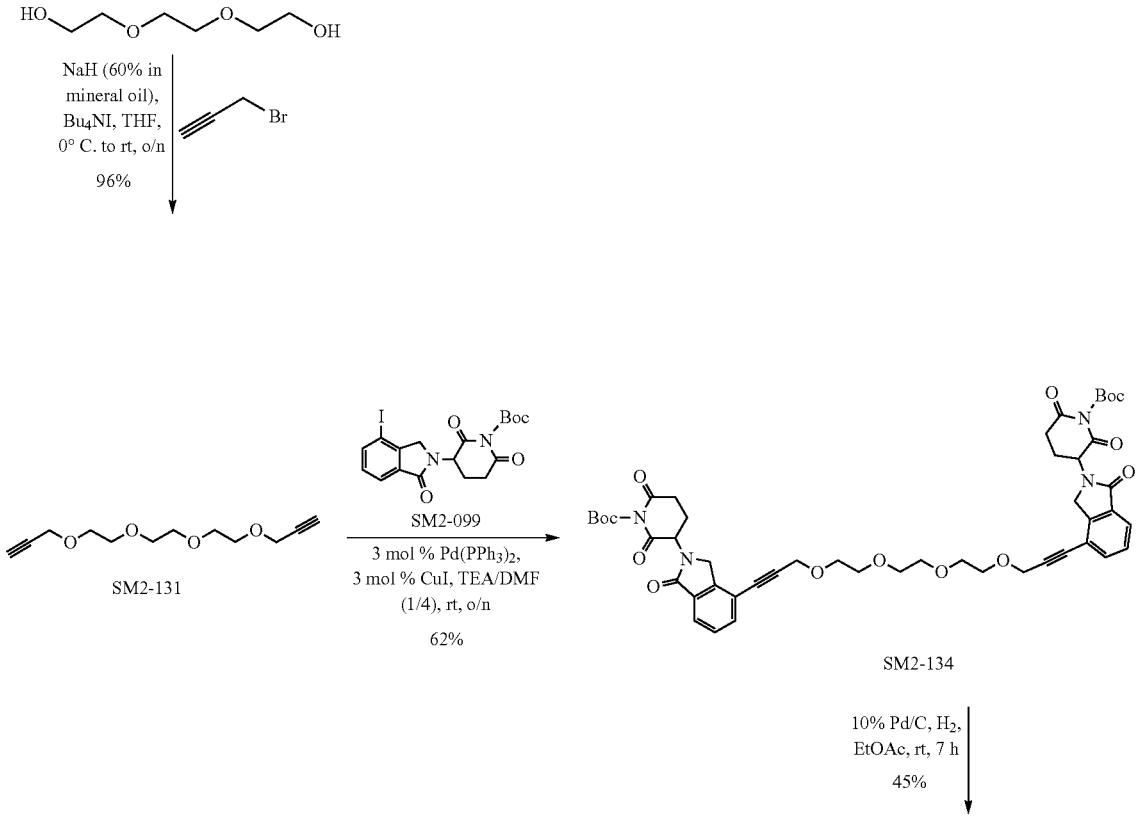

-continued

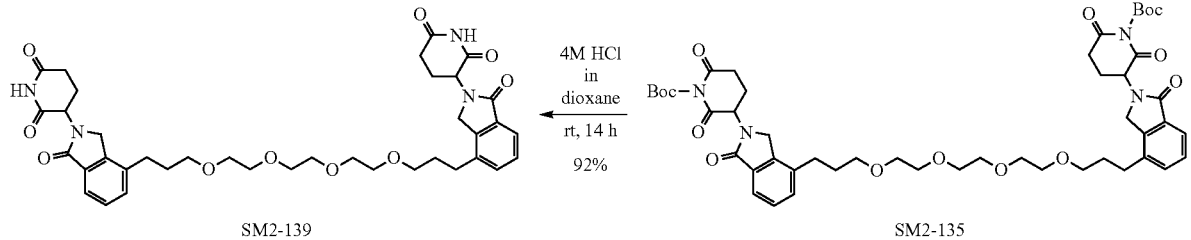

SM2-139 ← 4M HCl in dioxane rt, 14 h 92% ← SM2-135

4,7,10,13-Tetraoxahexadeca-1,15-diyne (SM2-131): Synthesized from triethylene glycol (1.00 g, 6.66 mmol), propargyl bromide (80% wt % solution in toluene, 3.96 g, 26.64 mmol), NaH (60% w/w in mineral oil, 0.799 g, 19.98 mmol) and Bu$_4$NI (123.0 mg, 0.333 mmol) using general method C and purified by SiO$_2$ chromatography eluting with EtOAc in hexane (5%-15% EtOAc, gradient elution). The title compound was obtained as a pale yellow oil (1.45 g, 96%). $^1$H NMR (500 MHz, CDCl$_3$) δ 4.05 (dd, J=1.1, 2.5 Hz, 4H), 3.57-3.52 (m, 8H), 3.51 (d, J=1.1 Hz, 4H), 2.27 (t, J=2.4 Hz, 2H). $^{13}$C NMR (126 MHz, CDCl$_3$) δ 79.68, 74.49, 70.62, 70.43, 69.12, 58.41. HPLC-MS (ESI$^+$): m/z 249.2 [100%, (M+Na)$^+$], 227.2 [40%, (M+H)$^+$].

Di-tert-butyl 3,3'-((4,7,10,13-tetraoxahexadeca-1,15-diyne-1,16-diyl)bis(1-oxoisoindoline-4,2-diyl))bis(2,6-dioxopiperidine-1-carboxylate) (SM2-134): Synthesized from SM2-131 (50.0 mg, 0.221 mmol), SM2-099B2 (228.6 mg, 0.486 mmol), Pd(PPh$_3$)$_2$Cl$_2$ (4.7 mg, 6.66 μmol), CuI (1.26 mg, 6.66 μmol), triethylamine (0.28 mL) in DMF (1.12 mL) using general method D and purified by SiO$_2$ chromatography eluting with EtOAc in hexane (30-80% EtOAc, gradient elution). The title compound was obtained as a white solid (125.0 mg, 62%). $^1$H NMR (500 MHz, DMSO-d$_6$) δ 7.76 (dd, J=1.2, 7.6 Hz, 2H), 7.71 (dd, J=1.0, 7.7 Hz, 2H), 7.55 (t, J=7.6 Hz, 2H), 5.36 (dd, J=5.1, 13.4 Hz, 2H), 4.52 (dd, J=1.7, 17.6 Hz, 2H), 4.45 (s, 4H), 4.36 (d, J=17.7 Hz, 2H), 3.68-3.62 (m, 4H), 3.61-3.56 (m, 4H), 3.54 (s, 4H), 3.16-3.09 (m, 2H), 2.78 (m, 2H), 2.59-2.52 (m, 2H), 2.10-2.04 (m, 2H), 1.48 (s, 18H). HPLC-MS (ESI$^+$): m/z 933.3 [100%, (M+Na)$^+$].

Di-tert-butyl 3,3'-((4,7,10,13-tetraoxahexadecane-1,16-diyl)bis(1-oxoisoindoline-4,2-diyl))bis(2,6-dioxopiperidine-1-carboxylate) (SM2-135): Synthesized from SM2-134 (115.0 mg, 0.126 mmol) and 10% Pd/C (26.9 mg, 0.0252 mmol) using general method E and purified by SiO$_2$ chromatography eluting with EtOAc in hexane (30%-80% EtOAc, gradient elution). The title compound was obtained as a white solid (52.0 mg, 45%). $^1$H NMR (500 MHz, DMSO-d$_6$) δ 7.57 (dd, J=3.4, 5.1 Hz, 2H), 7.48-7.42 (m, 4H), 5.36 (dd, J=5.1, 13.3 Hz, 2H), 4.48 (d, J=17.1 Hz, 2H), 4.32 (d, J=17.0 Hz, 2H), 3.52-3.50 (m, 8H), 3.48-3.43 (m, 4H), 3.37 (td, J=3.2, 6.3 Hz, 4H), 3.18-3.10 (m, 2H), 2.82-2.77 (m, 2H), 2.67 (t, J=7.7 Hz, 4H), 2.55-2.51 (m, 2H), 2.10-2.04 (m, 2H), 1.85-1.78 (m, 4H), 1.47 (s, 18H). HPLC-MS (ESI$^+$): m/z 941.4 [100%, (M+Na)$^+$].

3,3'-((4,7,10,13-Tetraoxahexadecane-1,16-diyl)bis(1-oxoisoindoline-4,2-diyl))bis(piperidine-2,6-dione) (SM2-139): Synthesized from SM2-135 (50.0 mg, 0.054 mmol) and 4N HCl in dioxane (2.0 mL) using general method F to afford the title compound as a white solid (36.0 mg, 92%). HPLC: 96% [t$_R$=10.85 min, gradient 35-85% MeOH/water (with 0.1% TFA), 20 min]. $^1$H NMR (500 MHz, DMSO-d$_6$) δ 10.99 (s, 2H), 7.56 (t, J=4.3 Hz, 2H), 7.44 (d, J=4.2 Hz, 4H), 5.13 (dd, J=5.1, 13.3 Hz, 2H), 4.45 (d, J=17.0 Hz, 2H), 4.29 (d, J=17.1 Hz, 2H), 3.52-3.50 (m, 8H), 3.47-3.45 (m, 4H), 3.37 (t, J=6.5 Hz, 4H), 2.96-2.88 (m, 2H), 2.67 (t, J=7.7 Hz, 4H), 2.63-2.56 (m, 2H), 2.44-2.37 (m, 2H), 2.03-1.98 (m, 2H), 1.85-1.78 (m, 4H). HPLC-MS (ESI$^+$): m/z 741.4 [100%, (M+Na)$^+$], 719.4 [70%, (M+H)$^+$], HRMS (ESI$^+$): m/z calcd. for C$_{38}$H$_{46}$N$_4$O$_{10}$ (M+Na)$^+$ 741.3106, found 741.3101.

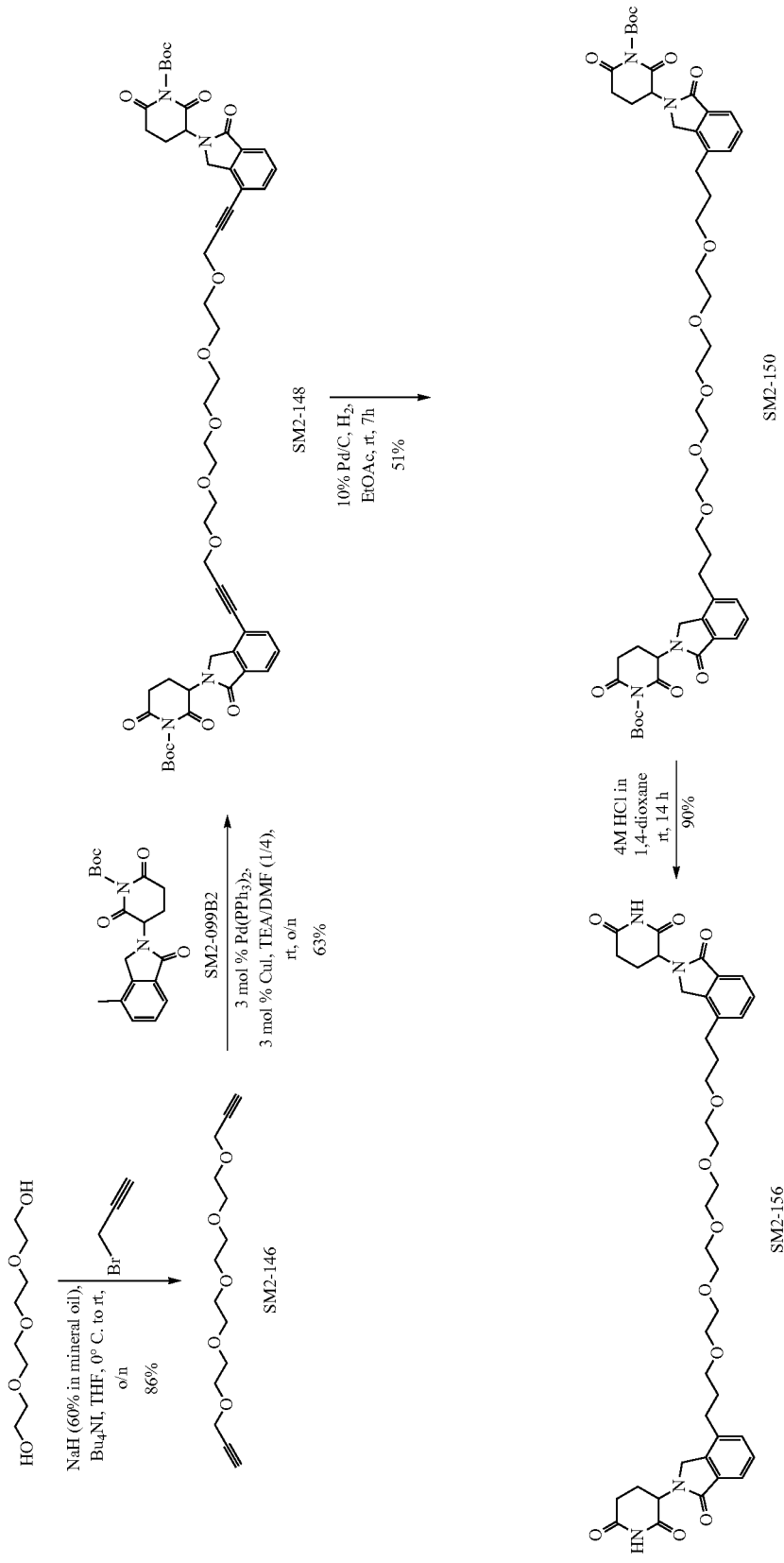

4,7,10,13,16-Pentaoxanonadeca-1,18-diyne (SM2-146): Synthesized from tetraethylene glycol (1.00 g, 5.15 mmol), propargyl bromide (80% wt % solution in toluene, 3.06 g, 20.59 mmol), sodium hydride (60% w/w in mineral oil, 0.618 g, 15.45 mmol) and Bu$_4$NI (95.7 mg, 0.257 mmol) using general method C and purified by SiO$_2$ chromatography eluting with EtOAc in hexane (0%-20% EtOAc, gradient elution). The title compound was obtained as a pale yellow oil (1.24 g, 85%). $^1$H NMR (500 MHz, DMSO-d$_6$) δ 4.14 (d, J=2.4 Hz, 4H), 3.57-3.53 (m, 8H), 3.52 (s, 8H), 3.42 (t, J=2.4 Hz, 2H). $^{13}$C NMR (126 MHz, DMSO-d$_6$) δ 80.80, 77.55, 70.23, 69.96, 68.98, 57.95. HPLC-MS (ESI$^+$): m/z 293.2 [100%, (M+Na)$^+$].

Di-tert-butyl 3,3'-((4,7,10,13,16-pentaoxanonadeca-1,18-diyne-1,19-diyl)bis(1-oxoisoindoline-4,2-diyl))bis(2,6-dioxopiperidine-1-carboxylate) (SM2-148): Synthesized from SM2-146 (60.0 mg, 0.222 mmol), SM2-099B2 (219.2 mg, 0.466 mmol), Pd(PPh$_3$)$_2$Cl$_2$ (4.7 mg, 6.67 μmol), CuI (1.27 mg, 6.67 μmol), trimethylamine (0.28 mL) in DMF (1.12 mL) using general method D and purified by SiO$_2$ chromatography eluting with EtOAc in hexane (30-80% EtOAc gradient elution). The title compound was obtained as a light-yellow solid (133.0 mg, 63%). $^1$H NMR (500 MHz, DMSO-d$_6$) δ 7.77 (d, J=7.5 Hz, 2H), 7.72 (d, J=7.6 Hz, 2H), 7.56 (t, J=7.6 Hz, 2H), 5.37 (dd, J=5.1, 13.4 Hz, 2H), 4.52 (d, J=17.6 Hz, 2H), 4.45 (s, 4H), 4.36 (d, J=17.7 Hz, 2H), 3.65 (dd, J=3.5, 5.9 Hz, 4H), 3.57 (dd, J=3.5, 5.8 Hz, 4H), 3.51 (s, 8H), 3.16-3.09 (m, 2H), 2.81-2.76 (m, 2H), 2.60-2.53 (m, 2H), 2.09-2.04 (m, 2H), 1.48 (s, 18H). HPLC-MS (ESI$^+$): m/z 977.4 [100%, (M+Na)$^+$].

Di-tert-butyl 3,3'-((4,7,10,13,16-pentaoxanonadecane-1,19-diyl)bis(1-oxoisoindoline-4,2-diyl))bis(2,6-dioxopiperidine-1-carboxylate) (SM2-150): Synthesized from SM2-146 (118.0 mg, 0.123 mmol) and 10% Pd/C (26.3 mg, 0.025 mmol) using general method E and purified by SiO$_2$ chromatography eluting with EtOAc in hexane (50%-100% EtOAc, gradient elution). The title compound was obtained as a white solid (69.0 mg, 51%). $^1$H NMR (500 MHz, DMSO-d$_6$) δ 7.58 (dd, J=2.9, 5.7 Hz, 2H), 7.47 (q, J=3.0, 3.9 Hz, 4H), 5.36 (dd, J=5.1, 13.4 Hz, 2H), 4.49 (d, J=17.1 Hz, 2H), 4.33 (d, J=17.1 Hz, 2H), 3.57-3.41 (m, 16H), 3.40-3.35 (m, 4H), 3.18-3.11 (m, 2H), 2.83-2.78 (m, 2H), 2.69 (t, J=7.6 Hz, 4H), 2.56-2.46 (m, 2H), 2.09-2.05 (m, 2H), 1.83 (ddt, J=4.9, 9.5, 13.7 Hz, 4H), 1.48 (s, 18H). HPLC-MS (ESI$^+$): m/z 985.4 [100%, (M+Na)$^+$].

3,3'-((4,7,10,13,16-Pentaoxanonadecane-1,19-diyl)bis(1-oxoisoindoline-4,2-diyl))bis(piperidine-2,6-dione) (SM2-156): Synthesized from SM2-150 (60.0 mg, 0.062 mmol) and 4N HCl in dioxane (2.0 mL) using general method F to afford the title compound as a white solid (39.0 mg, 83%). HPLC: 96% [t$_R$=6.17 min, 55% CH$_3$OH in 0.1% TFA/water, 20 min]. $^1$H NMR (500 MHz, DMSO-d$_6$) δ 10.99 (s, 2H), 7.59-7.54 (m, 2H), 7.45-7.44 (m, 4H), 5.13 (dd, J=5.1, 13.3 Hz, 2H), 4.45 (d, J=17.1 Hz, 2H), 4.30 (d, J=17.1 Hz, 2H), 3.53-3.44 (m, 16H), 3.37 (t, J=6.3 Hz, 4H), 2.96-2.88 (m, 2H), 2.67 (t, J=7.6 Hz, 4H), 2.62-2.54 (m, 2H), 2.46-2.40 (m, 2H), 2.04-1.98 (m, 2H), 1.85-1.80 (m, 4H). $^{13}$C NMR (126 MHz, DMSO-d$_6$) δ 173.35, 171.51, 168.81, 141.12, 137.40, 132.01, 128.75, 121.15, 70.30, 70.27, 70.24, 69.95, 69.81, 52.00, 46.65, 31.67, 29.71, 28.15, 22.99. HPLC-MS (ESI$^+$): m/z 785.3 [100%, (M+Na)$^+$], 763.4 [40%, (M+H)$^+$]. HRMS (ESI$^+$): m/z calcd. for C$_{40}$H$_{50}$N$_4$O$_{11}$ (M+H)$^+$ 763.3549, found 741.3544.

Synthetic scheme 12

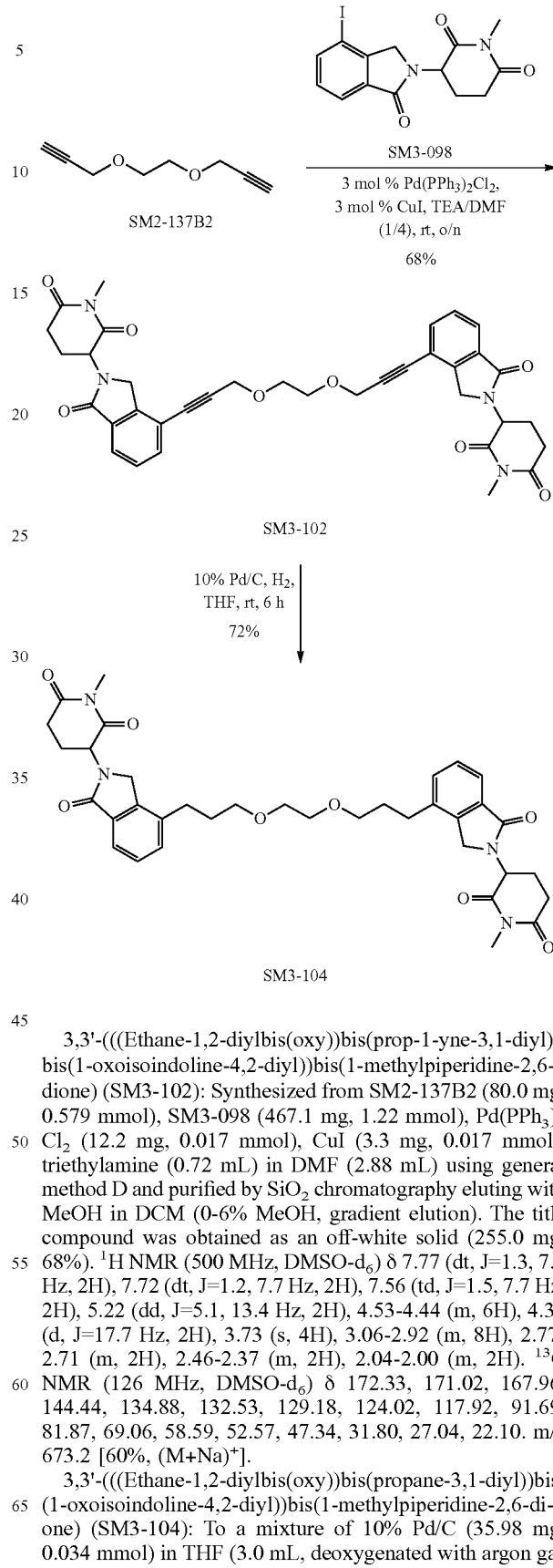

3,3'-(((Ethane-1,2-diylbis(oxy))bis(prop-1-yne-3,1-diyl))bis(1-oxoisoindoline-4,2-diyl))bis(1-methylpiperidine-2,6-dione) (SM3-102): Synthesized from SM2-137B2 (80.0 mg, 0.579 mmol), SM3-098 (467.1 mg, 1.22 mmol), Pd(PPh$_3$)$_2$Cl$_2$ (12.2 mg, 0.017 mmol), CuI (3.3 mg, 0.017 mmol), triethylamine (0.72 mL) in DMF (2.88 mL) using general method D and purified by SiO$_2$ chromatography eluting with MeOH in DCM (0-6% MeOH, gradient elution). The title compound was obtained as an off-white solid (255.0 mg, 68%). $^1$H NMR (500 MHz, DMSO-d$_6$) δ 7.77 (dt, J=1.3, 7.6 Hz, 2H), 7.72 (dt, J=1.2, 7.7 Hz, 2H), 7.56 (td, J=1.5, 7.7 Hz, 2H), 5.22 (dd, J=5.1, 13.4 Hz, 2H), 4.53-4.44 (m, 6H), 4.34 (d, J=17.7 Hz, 2H), 3.73 (s, 4H), 3.06-2.92 (m, 8H), 2.77-2.71 (m, 2H), 2.46-2.37 (m, 2H), 2.04-2.00 (m, 2H). $^{13}$C NMR (126 MHz, DMSO-d$_6$) δ 172.33, 171.02, 167.96, 144.44, 134.88, 132.53, 129.18, 124.02, 117.92, 91.69, 81.87, 69.06, 58.59, 52.57, 47.34, 31.80, 27.04, 22.10. m/z 673.2 [60%, (M+Na)$^+$].

3,3'-(((Ethane-1,2-diylbis(oxy))bis(propane-3,1-diyl))bis(1-oxoisoindoline-4,2-diyl))bis(1-methylpiperidine-2,6-dione) (SM3-104): To a mixture of 10% Pd/C (35.98 mg, 0.034 mmol) in THF (3.0 mL, deoxygenated with argon gas for 15 min) was added SM3-102 (110.0 mg, 0.169 mmol) under argon. The flask was evacuated and purged with argon (three times). Argon gas was evacuated and a balloon of hydrogen was attached to the system. The flask was evacuated and purged with $H_2$ (three times). The reaction mixture was stirred at room temperature for 6 h. The mixture was filtered through a short plug of celite, washed with THF and concentrated. The resulting residue was purified by $SiO_2$ chromatography eluting with MeOH in DCM (0-4% MeOH, gradient elution) to provide the title compound as a white solid (80 mg, 72%). HPLC: 96% [$t_R$=6.17 min, 50% $CH_3OH$ in 0.1% TFA/water, 20 min]. $^1$H NMR (500 MHz, DMSO-$d_6$) δ 7.57 (dd, J=2.8, 5.9 Hz, 2H), 7.49-7.41 (m, 4H), 5.20 (dd, J=5.0, 13.9 Hz, 2H), 4.44 (d, J=17.2 Hz, 2H), 4.28 (d, J=17.1 Hz, 2H), 3.48 (s, 4H), 3.39 (td, J=2.3, 6.3 Hz, 4H), 3.05-2.93 (m, 8H), 2.77-2.71 (m, 2H), 2.68 (t, J=7.7 Hz, 4H), 2.43-2.35 (m, 2H), 2.04-1.97 (m, 2H), 1.87-1.79 (m, 4H). $^{13}$C NMR (126 MHz, DMSO-$d_6$) δ 172.36, 171.14, 168.81, 141.12, 137.37, 132.04, 131.99, 128.77, 121.21, 69.98, 69.83, 52.47, 46.58, 31.81, 29.72, 28.16, 27.02, 22.26. HPLC-MS (ESI$^+$): m/z 681.3 [60%, (M+Na)$^+$]. HRMS (ESI$^+$): m/z calcd. for $C_{36}H_{42}N_4O_3$ (M+Na)$^+$ 681.2895, found 681.2887.

Synthetic scheme 13

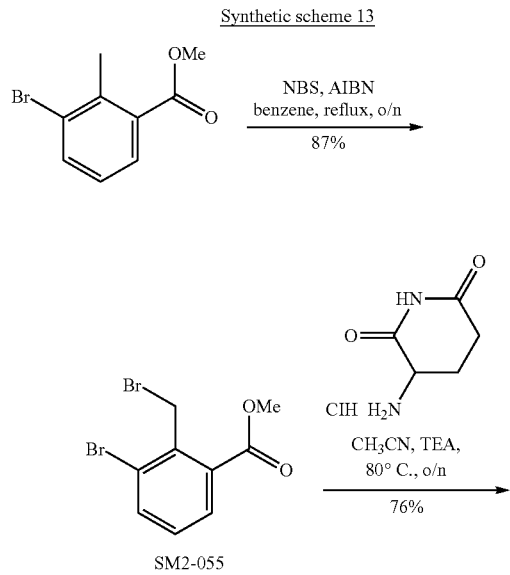

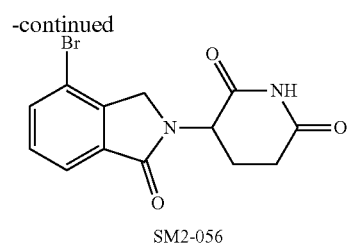

SM2-056

Methyl 3-bromo-2-(bromomethyl)benzoate (SM2-055) (Zhou, B.; et al., Discovery of a Small-Molecule Degrader of Bromodomain and Extra-Terminal (BET) Proteins with Picomolar Cellular Potencies and Capable of Achieving Tumor Regression. *Journal of medicinal chemistry* 2018, 61, 462-481): A solution of methyl 3-bromo-2-methylbenzoate (3.00 g, 13.10 mmol), N-bromosuccinimide (2.80 g, 15.72 mmol) and 2,2'-azobis(isobutyronitrile) (215.1 mg, 1.31 mmol) in benzene (60 mL) (CAUTION) was heated under reflux for 6 h. The reaction mixture was filtered and the solid obtained was washed with diethyl ether. The filtrate was concentrated and the residue was purified by $SiO_2$ chromatography eluting with EtOAc in hexane (0-10% EtOAc, gradient elution) to provide the title compound as a colorless oil (3.51 g, 85%). $^1$H NMR (500 MHz, CDCl$_3$) δ 7.88 (dd, J=1.4, 7.8 Hz, 1H), 7.76 (dd, J=1.3, 8.0 Hz, 1H), 7.23 (t, J=7.9 Hz, 1H), 5.13 (s, 2H), 3.95 (s, 3H).

3-(4-Bromo-1-oxoisoindolin-2-yl)piperidine-2,6-dione (SM2-056) (Zhou, B.; et al., Discovery of a Small-Molecule Degrader of Bromodomain and Extra-Terminal (BET) Proteins with Picomolar Cellular Potencies and Capable of Achieving Tumor Regression. *Journal of medicinal chemistry* 2018, 61, 462-481): The 3-aminopiperidine-2,6-dione hydrochloride (1.96 g, 11.88 mmol) and TEA (1.81 mL, 12.96 mmol) were added to a stirred solution of SM2-055 (3.00 g, 9.74 mmol) in MeCN (20 mL). The solution was stirred at 80° C. for 12 h and then cooled to room temperature and concentrated. EtOAc (30 mL) and $H_2O$ (30 mL) were added to the residue and the solid obtained was filtered to afford the title compound as a purple solid (2.41 g, 76%). $^1$H NMR (500 MHz, DMSO-$d_6$) δ 11.02 (s, 1H), 7.87 (d, J=7.9 Hz, 1H), 7.77 (d, J=7.4 Hz, 1H), 7.51 (t, J=7.7 Hz, 1H), 5.15 (dd, J=5.1, 13.3 Hz, 1H), 4.42 (d, J=17.6 Hz, 1H), 4.26 (d, J=17.6 Hz, 1H), 2.95-2.88 (m, 1H), 2.64-2.55 (m, 1H), 2.47-2.43 (m, 1H), 2.04-1.99 (m, 1H). $^{13}$C NMR (126 MHz, DMSO-$d_6$) δ 172.83, 170.84, 167.20, 142.10, 134.62, 133.92, 130.50, 122.48, 117.31, 51.73, 47.98, 31.18, 22.27. HPLC-MS (ESI$^+$): m/z 669.1 [100%, (M+Na)$^+$], 323.0 [80%, (M+H)$^+$]. HRMS (ESI$^+$): m/z calcd for $C_{13}H_{11}BrN_2O_3$ (M+H)$^+$ 323.0026, found 323.0032.

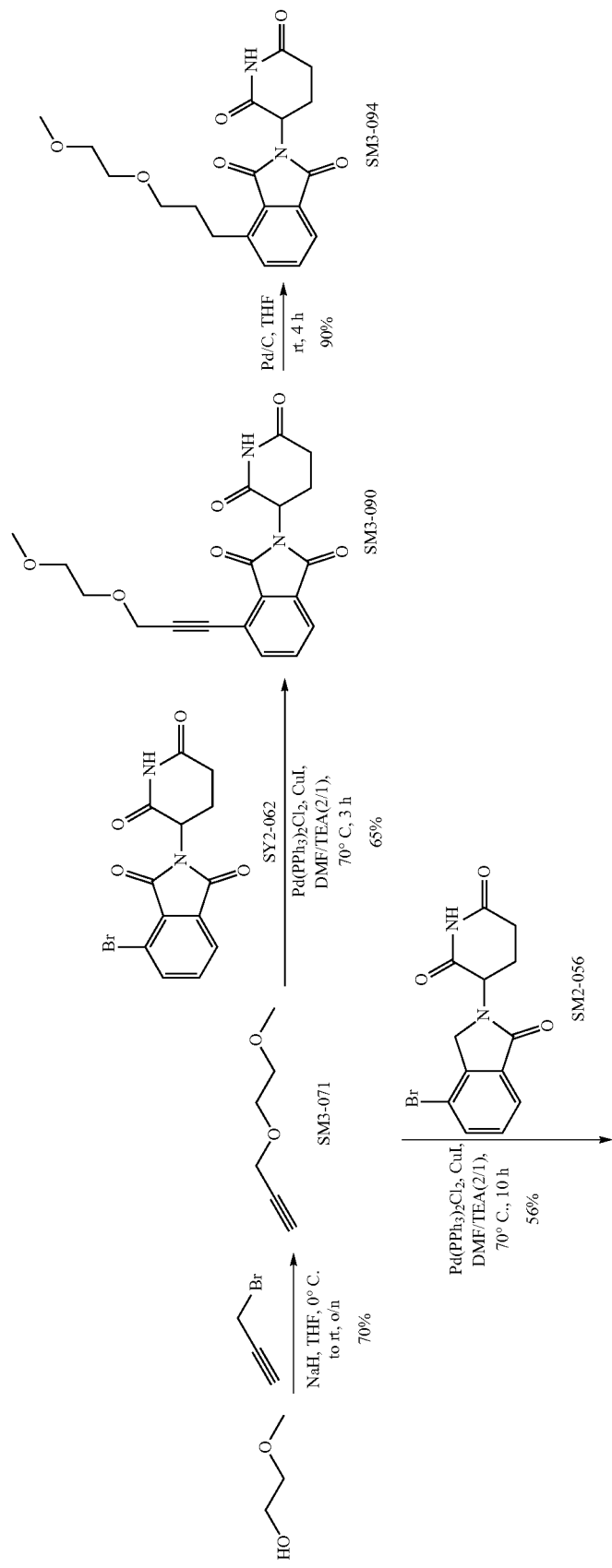
Synthetic scheme 14

-continued
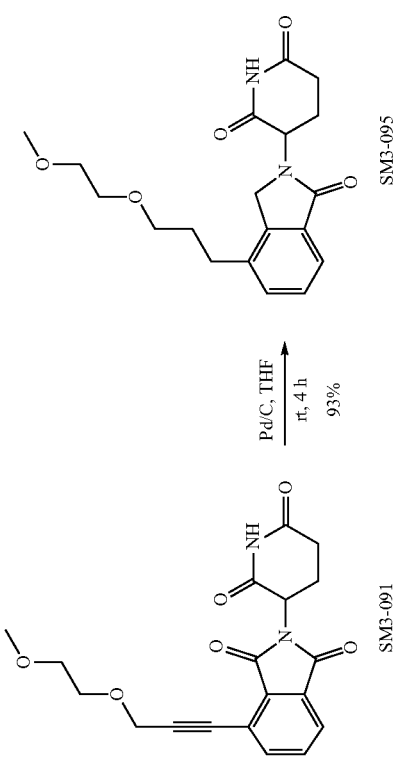

3-(2-Methoxyethoxy)prop-1-yne (SM3-071) (Y., N.; et al., Investigation of catalyst-transfer condensation polymerization for the synthesis of n-type π-conjugated polymer, poly(2-dioxaalkylpyridine-3,6-diyl). *Journal of Polymer Science Part A: Polymer Chemistry* 2012, 50, 3628-3640): To a solution of 2-methoxyethanol (4.00 g, 52.57 mmol) in dry THF (80 mL) was added sodium hydride (60% in oil, 2.52 g, 63.08 mmol), and the reaction mixture was stirred at 0° C. for 1 h under an argon atmosphere. The propargyl bromide (8.98 g, 60.45 mmol) was then added at 0° C. and the mixture was stirred for 17 h at r.t. The reaction was quenched with ice water and extracted with DCM (3×30 mL). The combined organic layers were dried over $MgSO_4$ and concentrated. The residue obtained was purified by $SiO_2$ chromatography eluting with EtOAc in hexane (0-5% EtOAc, gradient elution) to provide the title compound as a colorless oil (4.20 g, 70%). $^1H$ NMR (500 MHz, $CDCl_3$) δ 4.21 (dd, J=0.8, 2.4 Hz, 2H), 3.73-3.67 (m, 2H), 3.60-3.55 (m, 2H), 3.39 (d, J=0.8 Hz, 3H), 2.43 (t, J=2.4 Hz, 1H).

2-(2,6-Dioxopiperidin-3-yl)-4-(3-(2-methoxyethoxy)prop-1-yn-1-yl)isoindoline-1,3-dione (SM3-090): In a 20 mL microwave vial, SY2-062 (400.0 mg, 1.19 mmol) and SM3-071 (270.9 mg, 2.37 mmol) were added to a mixture of CuI (45.2 mg, 0.237 mmol) and $Pd(PPh_3)_2Cl_2$ (83.3 mg, 0.119 mmol) in DMF (6 mL). The mixture was purged and refilled with argon three times. Then triethylamine (3.0 mL) was added. The solution was purged and refilled with argon again. The vial was sealed and the mixture was stirred at 80° C. for 3 h under argon. Water (10 mL) was added and extracted with EtOAc (3×10 mL) and the combined organic layers were washed with brine, dried ($Na_2SO_4$) and concentrated. The resulting residue was purified by $SiO_2$ chromatography eluting with MeOH in DCM (0-4% MeOH, gradient elution) to provide the title compound as a light-yellow solid (285.6 mg, 65%). $^1H$ NMR (500 MHz, DMSO-$d_6$) δ 11.13 (s, 1H), 7.96-7.83 (m, 3H), 5.15 (dd, J=5.4, 12.9 Hz, 1H), 4.49 (s, 2H), 3.76-3.68 (m, 2H), 3.55-3.47 (m, 2H), 3.26 (s, 3H), 2.93-2.85 (m, 1H), 2.69-2.52 (m, 2H), 2.09-2.04 (m, 1H). $^{13}C$ NMR (126 MHz, DMSO-$d_6$) δ 172.75, 169.79, 166.19, 165.60, 138.26, 134.81, 132.07, 130.40, 123.41, 118.49, 93.45, 80.94, 70.98, 68.47, 58.05, 58.03, 49.00, 30.92, 21.90. HPLC-MS (ESI$^+$): m/z 393.1 [100%, (M+Na)$^+$], 763.2 [50%, (2M+Na)$^+$].

3-(4-(3-(2-Methoxyethoxy)prop-1-yn-1-yl)-1-oxoisoindolin-2-yl)piperidine-2,6-dione (SM3-091): Synthesized from SM2-056 (400.0 mg, 1.24 mmol), SM3-071 (282.6 mg, 2.48 mmol), $Pd(PPh_3)_2Cl_2$ (86.9 mg, 0.124 mmol), CuI (47.2 mg, 0.248 mmol), triethylamine (3 mL) in DMF (6 mL) using the method described for synthesis of SM3-090. The reaction time was 10 h and the title compound was obtained as a white solid (247.0 mg, 56%). $^1H$ NMR (500 MHz, DMSO-$d_6$) δ 11.00 (s, 1H), 7.75 (dd, J=7.6, 23.8 Hz, 2H), 7.56 (t, J=7.6 Hz, 1H), 5.15 (dd, J=5.1, 13.3 Hz, 1H), 4.49 (d, J=17.7 Hz, 1H), 4.45 (s, 2H), 4.34 (d, J=17.7 Hz, 1H), 3.69-3.63 (m, 2H), 3.51-3.49 (m, 2H), 3.25 (s, 3H), 2.95-2.88 (m, 1H), 2.62-2.57 (m, 1H), 2.47-2.41 (m, 1H), 2.04-1.99 (m, 1H). $^{13}C$ NMR (126 MHz, DMSO-$d_6$) δ 172.84, 170.94, 167.46, 143.98, 134.34, 132.09, 128.73, 123.48, 117.50, 91.36, 81.30, 71.02, 68.56, 58.08, 58.05, 51.63, 46.91, 31.18, 22.35. HPLC-MS (ESP): m/z 735.3 [100%, (M+Na)$^+$], 357.2 [50%, (M+H)$^+$].

2-(2,6-Dioxopiperidin-3-yl)-4-(3-(2-methoxyethoxy)propyl)isoindoline-1,3-dione (SM3-094): To a mixture of 10% Pd/C (57.5 mg, 0.054 mmol) in THF (4.0 mL, deoxygenated with argon gas for 15 min) was added SM3-090 (100.0 mg, 0.270 mmol) under argon. The flask was evacuated and purged with argon (three times). Argon gas was evacuated and a balloon of hydrogen was attached to the system. The flask was evacuated and purged with $H_2$ (three times). The reaction mixture was stirred at room temperature for 4 h. After the completion of the reaction (monitored by TLC), the mixture was filtered through a short plug of celite, washed with THF and concentrated. The resulting residue was purified by $SiO_2$ chromatography eluting with MeOH in DCM (0-5% MeOH, gradient elution) to provide the title compound as a white solid (91 mg, 90%). HPLC: 96% [$t_R$=5.00 min, 50% $CH_3OH$ in 0.1% TFA/water, 20 min]. $^1H$ NMR (500 MHz, DMSO-$d_6$) δ 11.11 (s, 1H), 7.79-7.74 (m, 2H), 7.70 (d, J=7.6 Hz, 1H), 5.13 (dd, J=5.4, 12.7 Hz, 1H), 3.49-3.47 (m, 2H), 3.45-3.38 (m, 4H), 3.24 (s, 3H), 3.07 (t, J=7.6 Hz, 2H), 2.93-2.85 (m, 1H), 2.66-2.53 (m, 2H), 2.08-2.03 (m, 1H), 1.87-1.82 (m, 2H). $^{13}C$ NMR (126 MHz, DMSO-$d_6$) δ 173.24, 170.36, 168.08, 167.49, 142.48, 136.57, 134.95, 132.32, 128.12, 121.71, 71.74, 70.04, 69.72, 58.56, 49.27, 31.41, 30.53, 27.79, 22.47. HPLC-MS (ESI$^+$): m/z 397.2 [100%, (M+Na)$^+$]. HRMS (ESI$^+$): m/z calcd. for $C_{19}H_{22}N_2O_6$ (M+Na)$^+$ 397.1370, found 397.1366.

3-(4-(3-(2-Methoxyethoxy)propyl)-1-oxoisoindolin-2-yl)piperidine-2,6-dione (SM3-095): Synthesized from SM2-091 (100.0 mg, 0.281 mmol), 10% Pd/C (59.8 mg, 0.056 mmol) in THF (6.0 mL) using the method described for synthesis of SM3-094. The reaction time was 10 h. The title compound was obtained as a white solid (94.0 mg, 93%). %). HPLC: >99% [$t_R$=3.95 min, 50% $CH_3OH$ in 0.1% TFA/water, 20 min]. $^1H$ NMR (500 MHz, DMSO-$d_6$) δ 10.99 (s, 1H), 7.57 (dd, J=3.3, 5.3 Hz, 1H), 7.50-7.42 (m, 2H), 5.13 (dd, J=5.1, 13.3 Hz, 1H), 4.46 (d, J=17.2 Hz, 1H), 4.30 (d, J=17.1 Hz, 1H), 3.50-3.45 (m, 2H), 3.45-3.41 (m, 2H), 3.38 (td, J=2.7, 6.3 Hz, 2H), 3.24 (s, 3H), 2.92 (ddd, J=5.4, 13.7, 17.3 Hz, 1H), 2.69 (t, J=7.7 Hz, 2H), 2.64-2.58 (m, 1H), 2.46-2.37 (m, 1H), 2.04-1.99 (m, 1H), 1.90-1.79 (m, 2H). $^{13}C$ NMR (126 MHz, DMSO-$d_6$) δ 173.36, 171.51, 168.82, 141.17, 137.40, 132.01, 128.77, 121.15, 71.77, 69.78, 69.77, 58.59, 52.00, 46.64, 31.67, 29.76, 28.13, 22.99. HPLC-MS (ESI$^+$): m/z 383.2 [100%, (M+Na)$^+$], 361.2 [60%, (M+H)$^+$]. HRMS (ESI$^+$): m/z calcd. for $C_{19}H_{24}N_2O_5$ (M+Na)$^+$ 383.1577, found 383.1579.

General method G: (Y., K.; Y et al., Polyacrylamide pseudo crown ethers via hydrogen bond-assisted cyclopolymerization. *Journal of Polymer Science Part A: Polymer Chemistry* 2016, 54, 3294-3302):

In a 25 mL round-bottomed flask, acryloyl chloride (2.5 equiv) was added dropwise to the solution of bis-amine (1.0 equiv) and triethylamine (2.5 equiv) or 6N NaOH solution in water (2.5 equiv) in dichloromethane (0.3-0.5 M) at 0° C. under argon. The reaction mixture was stirred at room temperature overnight and the solid obtained was filtered. The filtrate was concentrated and the residue obtained was purified with $SiO_2$ chromatography eluting with MeOH in EtOAc (gradient elution) to effort the title compound as colorless oil.

General Method H: Synthesis of Heck Cross-Coupled Products

In a 5 mL microwave vial, triethylamine (2.5 equiv) was added to a mixture of diacrylamide (1.0 equiv), SM2-056 (2.02 equiv), $Pd(OAc)_2$ (5.0 mol %) and $PPh_3$ (10 mol %) in DMF (0.156 M). The vial was evacuated and purged with argon (three times), sealed and heated to 150° C. for 5 h or 6 h. The solvent was removed using BIOTAGE™ V-10 evaporator. The residue was purified with $SiO_2$ column chromatography eluting with MeOH in DCM (0-10% MeOH, gradient elution) to provide the desired product.

General Method I:

To a mixture of 10% Pd/C (0.2 equiv) in EtOAc/MeOH (v/v=1/1, 0.02 M or 0.004 M, deoxygenated using argon gas for 15 min) was added SM3-003 or SM3-006 or SM3-009 (1 equiv) under argon. The flask was evacuated and purged with argon (three times). Argon gas was evacuated and a balloon of hydrogen was attached to the system. The flask was evacuated and purged with $H_2$ (three times) and the reaction mixture was stirred at room temperature for 5 h. The mixture was filtered through a short plug of celite, washed with EtOAc/MeOH and concentrated under reduced pressure to afford the desired product.

Synthetic scheme 15
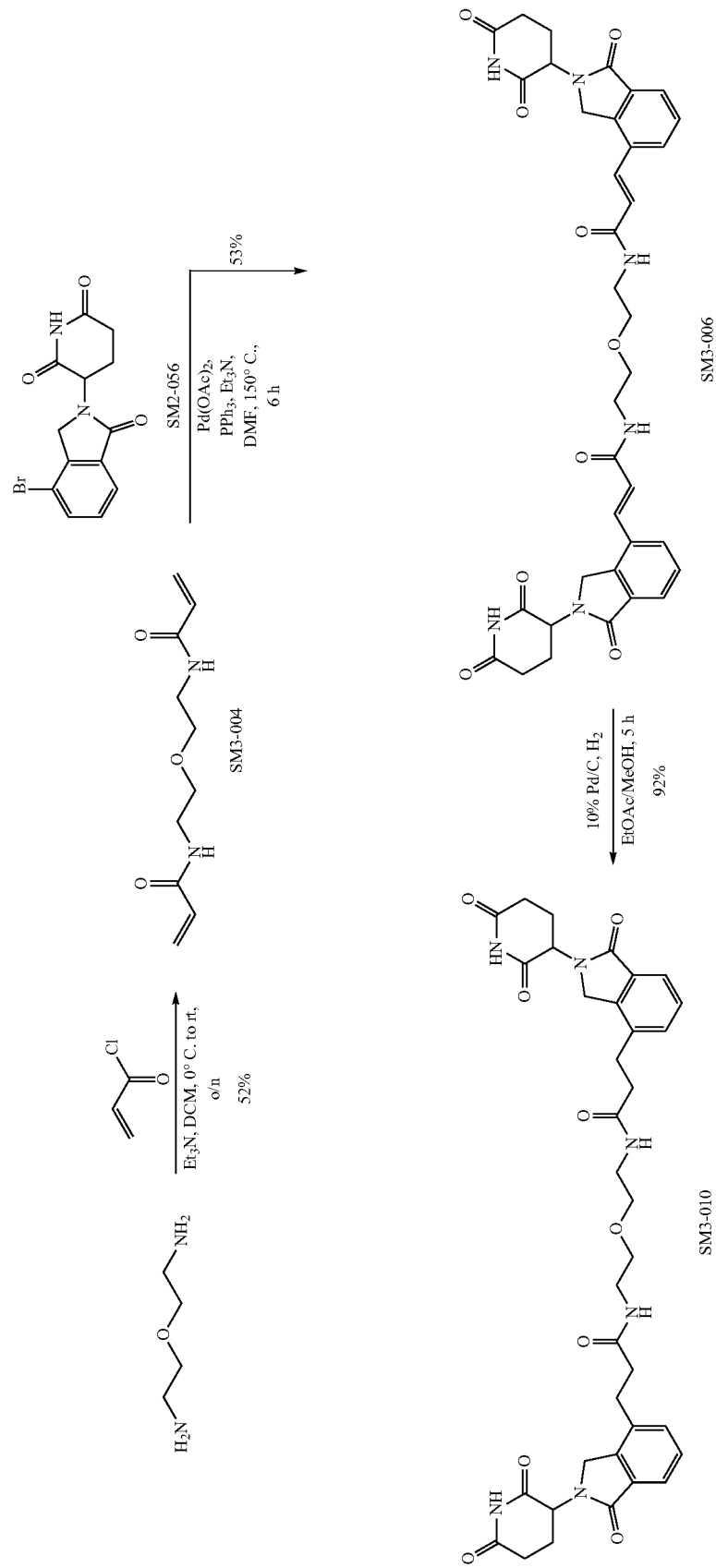

N,N'-(Oxybis(ethane-2,1-diyl))diacrylamide (SM3-004): Synthesized from 2,2'-oxybis(ethan-1-amine) (200.0 mg, 1.92 mmol), acryloyl chloride (0.391 mL, 4.80 mmol), triethylamine (0.669 mL, 4.80 mmol) in DCM (5.0 mL) using general method G and purified by $SiO_2$ chromatography eluting with MeOH in EtOAc (0-20% MeOH, gradient elution). The title compound was obtained as a colorless oil (255.0 mg, 52%). $^1$H NMR (500 MHz, DMSO-$d_6$) δ 8.14 (t, J=5.7 Hz, 2H), 6.25 (dd, J=10.2, 17.1 Hz, 2H), 6.08 (dd, J=2.2, 17.1 Hz, 2H), 5.57 (dd, J=2.2, 10.2 Hz, 2H), 3.45 (t, J=5.8 Hz, 4H), 3.29 (q, J=5.7 Hz, 4H). $^{13}$C NMR (126 MHz, DMSO-$d_6$) δ 165.16, 132.16, 125.55, 69.25, 38.99. HPLC-MS (ESI$^+$): m/z 213.2 [100%, (M+H)$^+$], 235.2 [30%, (M+Na)$^+$].

(2E,2'E)-N,N'-(Oxybis(ethane-2,1-diyl))bis(3-(2-(2,6-dioxopiperidin-3-yl)-1-oxoisoindolin-4-yl)acrylamide) (SM3-006): Synthesized from SM3-004 (60.0 mg, 0.282 mmol), SM2-056 (184.5 mg, 0.571 mmol), Pd(OAc)$_2$ (3.17 mg, 0.014 mmol), PPh$_3$ (7.41 mg, 0.028 mmol), Et$_3$N (0.099 mL, 0.706 mmol) in DMF (1.8 mL) using general method H and purified by $SiO_2$ chromatography eluting with MeOH in DCM (0-25% MeOH, gradient elution). The title compound was obtained as an off-white solid (104.4 mg, 53%). HPLC: 99% [$t_R$=5.73 min, 40% CH$_3$OH in 0.1% TFA/water, 20 min]. $^1$H NMR (500 MHz, DMSO-$d_6$) δ 11.03 (s, 2H), 8.26-8.19 (m, 2H), 7.84-7.76 (m, 2H), 7.72 (dt, J=1.2, 7.6 Hz, 2H), 7.55 (td, J=1.6, 7.6 Hz, 2H), 7.48 (dd, J=1.5, 16.0 Hz, 2H), 6.68 (dd, J=1.9, 15.9 Hz, 2H), 5.18 (dd, J=5.2, 13.3 Hz, 2H), 4.62 (dd, J=3.8, 17.6 Hz, 2H), 4.44 (dd, J=1.7, 17.5 Hz, 2H), 3.52 (t, J=5.7 Hz, 4H), 3.39 (q, J=5.7 Hz, 4H), 2.98-2.91 (m, 2H), 2.66-2.59 (m, 2H), 2.47-2.38 (m, 2H), 2.07-2.01 (m, 2H). $^{13}$C NMR (126 MHz, DMSO-$d_6$) δ 172.86, 170.98, 167.64, 164.74, 140.39, 134.50, 132.39, 130.87, 130.34, 128.80, 125.14, 123.77, 68.87, 51.52, 47.11, 38.73, 31.16, 22.55. HPLC-MS (ESI$^+$): m/z 719.3 [100%, (M+Na)$^+$], 697.2 [90%, (M+H)$^+$]. HRMS (ESI$^+$): m/z calcd. for $C_{36}H_{36}N_6O_9$ (M+Na)$^+$ 719.2436, found 719.2431.

N,N'-(Oxybis(ethane-2,1-diyl))bis(3-(2-(2,6-dioxopiperidin-3-yl)-1-oxoisoindolin-4-yl)propanamide) (SM3-010): Synthesized from SM3-006 (50.0 mg, 0.072 mmol), 10% Pd/C (15.3 mg, 0.0144 mmol) and EtOAc/MeOH (20.0 mL) using general method I. The title compound was obtained as a white solid (46.3 mg, 92%). HPLC: 98% [$t_R$=4.91 min, 40% CH$_3$OH in 0.1% TFA/water, 20 min]. $^1$H NMR (500 MHz, DMSO-$d_6$) δ 10.98 (s, 2H), 7.88 (t, J=5.6 Hz, 2H), 7.56 (dd, J=3.4, 5.2 Hz, 2H), 7.47-7.37 (m, 4H), 5.13 (dd, J=5.2, 13.3 Hz, 2H), 4.48 (d, J=17.1 Hz, 2H), 4.32 (d, J=17.1 Hz, 2H), 3.31 (t, J=5.8 Hz, 4H), 3.16 (q, J=5.8 Hz, 4H), 2.97-2.83 (m, 6H), 2.63-2.58 (m, 2H), 2.47-2.36 (m, 6H), 12.02-1.97 (m, 2H). $^{13}$C NMR (126 MHz, DMSO-$d_6$) δ 172.85, 171.19, 170.98, 168.27, 140.62, 136.52, 131.51, 131.29, 128.24, 120.78, 68.84, 51.53, 46.21, 38.41, 35.12, 31.19, 27.05, 22.54. HPLC-MS (ESI$^+$): m/z 723.3 [100%, (M+Na)$^+$], 701.3 [40%, (M+H)$^+$]. HRMS (ESI$^+$): m/z calcd. for $C_{36}H_{40}N_6O_9$ (M+Na)$^+$ 723.2749, found 723.2748.

Synthetic scheme 16
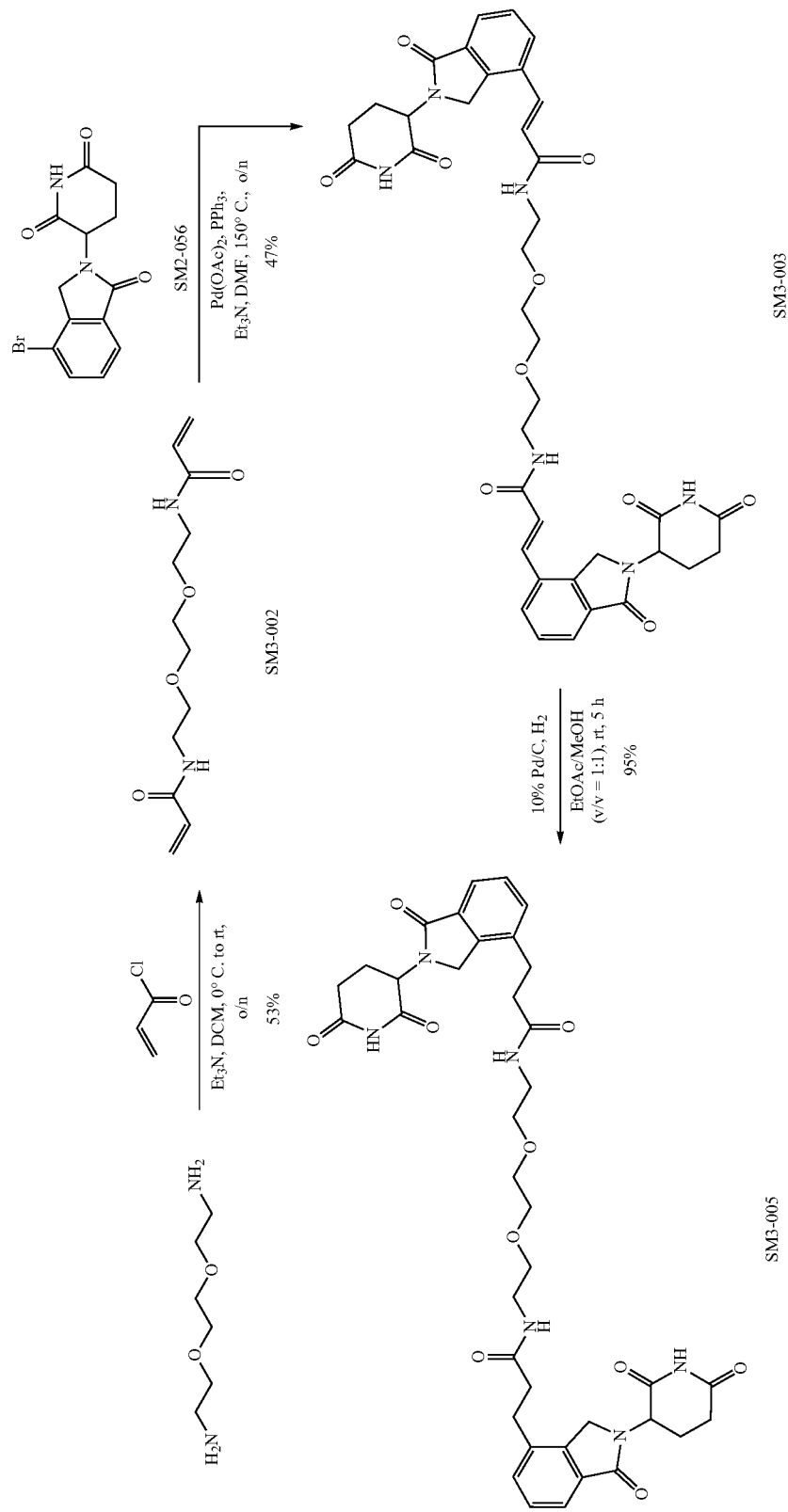

N,N'-((Ethane-1,2-diylbis(oxy))bis(ethane-2,1-diyl))diacrylamide (SM3-002): Synthesized from 2,2'-(ethane-1,2-diylbis(oxy))bis(ethan-1-amine) (500.0 mg, 3.37 mmol), acryloyl chloride (0.685 mL, 8.43 mmol), triethylamine (1.180 mL, 8.43 mmol) and DCM (10.0 mL) using general method G and purified by $SiO_2$ chromatography eluting with MeOH in EtOAc (0-30% MeOH, Gradient elution). The title compound was obtained as a colorless oil (460.0 mg, 53%). $^1$H NMR (500 MHz, DMSO-$d_6$) δ 8.15 (t, J=5.9 Hz, 2H), 6.24 (dd, J=10.1, 17.1 Hz, 2H), 6.07 (dd, J=2.3, 17.1 Hz, 2H), 5.57 (dd, J=2.3, 10.2 Hz, 2H), 3.52 (s, 4H), 3.44 (t, J=5.8 Hz, 4H), 3.28 (q, J=5.8 Hz, 4H). $^{13}$C NMR (126 MHz, CDCl$_3$) δ 165.81, 130.96, 126.60, 70.40, 69.87, 39.42. HPLC-MS (ESI$^+$): m/z 257.2 [100%, (M+H)$^+$], 279.2 [40%, (M+Na)$^+$].

(2E,2'E)-N,N'-((ethane-1,2-diylbis(oxy))bis(ethane-2,1-diyl))bis(3-(2-(2,6-dioxopiperidin-3-yl)-1-oxoisoindolin-4-yl)acrylamide) (SM3-003): Synthesized from SM3-002 (60.0 mg, 0.234 mmol), SM2-056 (152.8 mg, 0.473 mmol), Pd(OAc)$_2$ (2.63 mg, 0.012 mmol), PPh$_3$ (6.14 mg, 0.023 mmol), triethylamine (0.082 mL, 0.585 mmol) in DMF (1.5 mL) using general method H and purified by $SiO_2$ chromatography eluting with MeOH in DCM (0-10% MeOH, gradient elution). The title compound was obtained as a white solid (82.0 mg, 47%). HPLC: 98% [$t_R$=6.96 min, HPLC: 98% [$t_R$=6.96 min, gradient 40-95% MeOH/water (with 0.1% formic acid), 20 min]. $^1$H NMR (500 MHz, DMSO-$d_6$) δ 11.03 (s, 2H), 8.23 (t, J=5.7 Hz, 2H), 7.82 (d, J=7.6 Hz, 2H), 7.74 (dd, J=1.0, 7.6 Hz, 2H), 7.58 (t, J=7.6 Hz, 2H), 7.48 (d, J=16.0 Hz, 2H), 6.68 (d, J=16.0 Hz, 2H), 5.18 (dd, J=5.2, 13.3 Hz, 2H), 4.63 (d, J=17.5 Hz, 2H), 4.44 (d, J=17.4 Hz, 2H), 3.56 (s, 4H), 3.50 (t, J=5.7 Hz, 4H), 3.36 (q, J=5.6 Hz, 4H), 2.99-2.90 (m, 2H), 2.66-2.60 (m, 2H), 2.46-2.38 (m, 2H), 2.08-2.02 (m, 2H). $^{13}$C NMR (126 MHz, DMSO-$d_6$) δ 172.83, 170.95, 167.63, 164.70, 140.37, 134.53, 132.39, 131.00, 130.36, 128.80, 125.16, 123.76, 69.56, 69.15, 51.52, 47.14, 38.81, 31.15, 22.54. HPLC-MS (ESI$^+$): m/z 763.3 [100%, (M+Na)$^+$], 741.3 [70%, (M+H)$^+$]. HRMS (ESI$^+$): m/z calcd. for $C_{38}H_{40}N_6O_{10}$ (M+Na)$^+$ 763.2698, found 763.2704.

N,N'-((Ethane-1,2-diylbis(oxy))bis(ethane-2,1-diyl))bis(3-(2-(2,6-dioxopiperidin-3-yl)-1-oxoisoindolin-4-yl)propanamide) (SM3-005): Synthesized from SM3-003 (60.0 mg, 0.081 mmol), 10% Pd/C (17.2 mg, 0.0162 mmol) and EtOAc/MeOH (5.0 mL) using general method I. The title compound was obtained as a white solid (57.0 mg, 95%). HPLC: 99% [$t_R$=5.80 min, 40% CH$_3$OH in 0.1% TFA/water, 20 min]. $^1$H NMR (500 MHz, DMSO-$d_6$) δ 10.98 (s, 2H), 7.90 (t, J=5.7 Hz, 2H), 7.60-7.52 (m, 2H), 7.48-7.41 (m, 4H), 5.13 (dd, J=5.2, 13.3 Hz, 2H), 4.48 (d, J=17.1 Hz, 2H), 4.32 (d, J=17.1 Hz, 2H), 3.43 (s, 4H), 3.33 (t, J=5.9 Hz, 4H), 3.17 (dd, J=3.4, 5.5 Hz, 4H), 2.96-2.88 (m, 2H), 2.86 (t, J=7.6 Hz, 4H), 2.64-2.58 (m, 2H), 2.44 (t, J=7.5 Hz, 4H), 2.42-2.34 (m, 2H), 2.04-1.97 (m, 2H). $^{13}$C NMR (126 MHz, DMSO-$d_6$) δ 172.84, 171.17, 170.97, 168.27, 140.63, 136.52, 131.51, 131.34, 128.24, 120.78, 69.46, 69.09, 51.52, 46.20, 38.51, 35.13, 31.18, 27.08, 22.54. HPLC-MS (ESI$^+$): m/z 767.3 [100%, (M+Na)$^+$], 745.4 [40%, (M+H)$^+$]. HRMS (ESI$^+$): m/z calcd. for $C_{38}H_{44}N_6O_{10}$ (M+Na)$^+$ 767.3011, found 767.3009.

Synthetic scheme 17
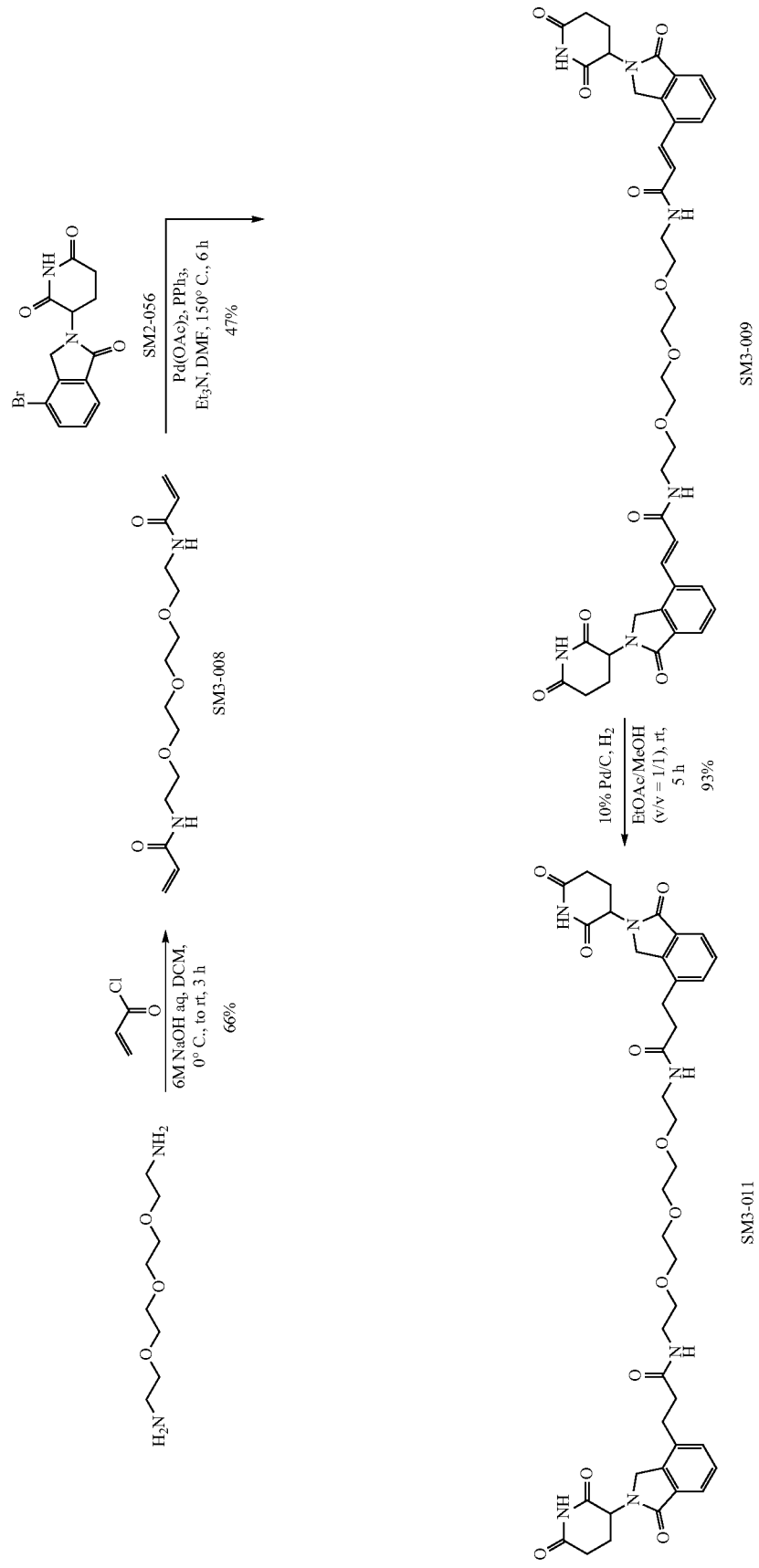

N,N'-(((Oxybis(ethane-2,1-diyl))bis(oxy))bis(ethane-2,1-diyl))diacrylamide (SM3-008): Synthesized from 2,2'-((oxybis(ethane-2,1-diyl))bis(oxy))bis(ethan-1-amine) (150.0 mg, 0.780 mmol), acryloyl chloride (0.159 mL, 1.95 mmol), 6N NaOH solution in water (0.325 mL, 1.95 mmol) in DCM (1.0 mL) using general method G and purified by $SiO_2$ chromatography eluting with MeOH in EtOAc (0-10% MeOH, gradient elution). The title compound was obtained as a colorless oil (156.0 mg, 66%). $^1$H NMR (500 MHz, DMSO-$d_6$) δ 8.14 (d, J=5.9 Hz, 2H), 6.24 (dd, J=10.1, 17.1 Hz, 2H), 6.07 (dd, J=2.3, 17.1 Hz, 2H), 5.57 (dd, J=2.3, 10.2 Hz, 2H), 3.51 (s, 8H), 3.44 (t, J=5.8 Hz, 4H), 3.28 (q, J=5.8 Hz, 4H). $^{13}$C NMR (126 MHz, DMSO-$d_6$) δ 164.62, 131.71, 125.00, 69.69, 69.56, 69.01, 38.59. HPLC-MS (ESI$^+$): m/z 301.2 [100%, (M+H)$^+$], 323.2 [80%, (M+Na)$^+$].

(2E,2'E)-N,N'-(((Oxybis(ethane-2,1-diyl))bis(oxy))bis(ethane-2,1-diyl))bis(3-(2-(2,6-dioxopiperidin-3-yl)-1-oxoisoindolin-4-yl)acrylamide) (SM3-009): Synthesized from SM3-008 (80.0 mg, 0.266 mmol), SM2-056 (173.9 mg, 0.538 mmol), Pd(OAc)$_2$ (2.99 mg, 0.013 mmol), PPh$_3$ (6.99 mg, 0.027 mmol), Et$_3$N (0.093 mL, 0.665 mmol) in DMF (1.7 mL) using general method H and purified by $SiO_2$ chromatography eluting with MeOH in DCM (0-10% MeOH, gradient elution). The title compound was obtained as a white solid (98.0 mg, 47%). HPLC: 98% [$t_R$=6.96 min, HPLC: 98% [$t_R$=11.64 min, gradient 30-95% MeOH/water (with 0.1% TFA), 20 min]. $^1$H NMR (500 MHz, DMSO-$d_6$) δ 11.04 (s, 2H), 8.22 (t, J=5.7 Hz, 2H), 7.82 (d, J=7.6 Hz, 2H), 7.74 (d, J=7.1 Hz, 2H), 7.58 (t, J=7.6 Hz, 2H), 7.49 (d, J=16.0 Hz, 2H), 6.67 (d, J=16.0 Hz, 2H), 5.18 (dd, J=5.1, 13.3 Hz, 2H), 4.63 (d, J=17.5 Hz, 2H), 4.44 (d, J=17.5 Hz, 2H), 3.54 (s, 8H), 3.48 (t, J=5.7 Hz, 4H), 3.35 (q, J=5.7 Hz, 4H), 2.99-2.91 (m, 2H), 2.66-2.60 (m, 2H), 2.47-2.38 (m, 2H), 2.08-2.02 (m, 2H). $^{13}$C NMR (126 MHz, DMSO-$d_6$) δ 172.84, 170.95, 167.63, 164.67, 140.38, 134.50, 132.40, 130.99, 130.37, 128.81, 125.18, 123.76, 69.72, 69.59, 69.13, 51.52, 47.14, 38.82, 31.15, 22.55. HPLC-MS (ESI$^+$): m/z 807.3 [100%, (M+Na)$^+$], 785.4 [30%, (M+H)$^+$]. HRMS (ESI$^+$): m/z calcd for $C_{40}H_{44}N_6O_{11}$ (M+Na)$^+$ 807.2960, found 807.2954.

N,N'-(((Oxybis(ethane-2,1-diyl))bis(oxy))bis(ethane-2,1-diyl))bis(3-(2-(2,6-dioxopiperidin-3-yl)-1-oxoisoindolin-4-yl)propanamide) (SM3-011): Synthesized from SM3-009 (60.0 mg, 0.076 mmol), 10% Pd/C (16.3 mg, 0.0152 mmol) and EtOAc/MeOH (5.0 mL) using general method I. The title compound was obtained as a white solid (56.0 mg, 93%). %). HPLC: 99% [$t_R$=6.69 min, 40% CH$_3$OH in 0.1% formic acid/water, 20 min]. $^1$H NMR (500 MHz, DMSO-$d_6$) δ 10.98 (s, 2H), 7.90 (t, J=5.6 Hz, 2H), 7.56 (dd, J=3.5, 5.2 Hz, 2H), 7.49-7.40 (m, 4H), 5.13 (dd, J=5.2, 13.2 Hz, 2H), 4.48 (d, J=17.1 Hz, 2H), 4.32 (d, J=17.0 Hz, 2H), 3.54-3.38 (m, 8H), 3.34 (t, J=5.9 Hz, 4H), 3.17 (q, 4H), 2.97-2.89 (m, 2H), 2.86 (t, J=7.6 Hz, 4H), 2.64-2.58 (m, 2H), 2.46-2.38 (m, 6H), 2.03-1.98 (m, 2H). $^{13}$C NMR (126 MHz, DMSO-$d_6$) δ 172.86, 171.16, 170.99, 168.27, 140.63, 136.52, 131.51, 131.33, 128.24, 120.77, 69.66, 69.52, 69.10, 51.52, 46.20, 38.52, 35.12, 31.19, 27.08, 22.55. HPLC-MS (ESI$^+$): m/z 811.3 [100%, (M+Na)$^+$], 789.4 [30%, (M+H)$^+$]. HRMS (ESI$^+$): m/z calcd. for $C_{40}H_{48}N_6O_{11}$ (M+Na)$^+$ 811.3273, found 811.3261.

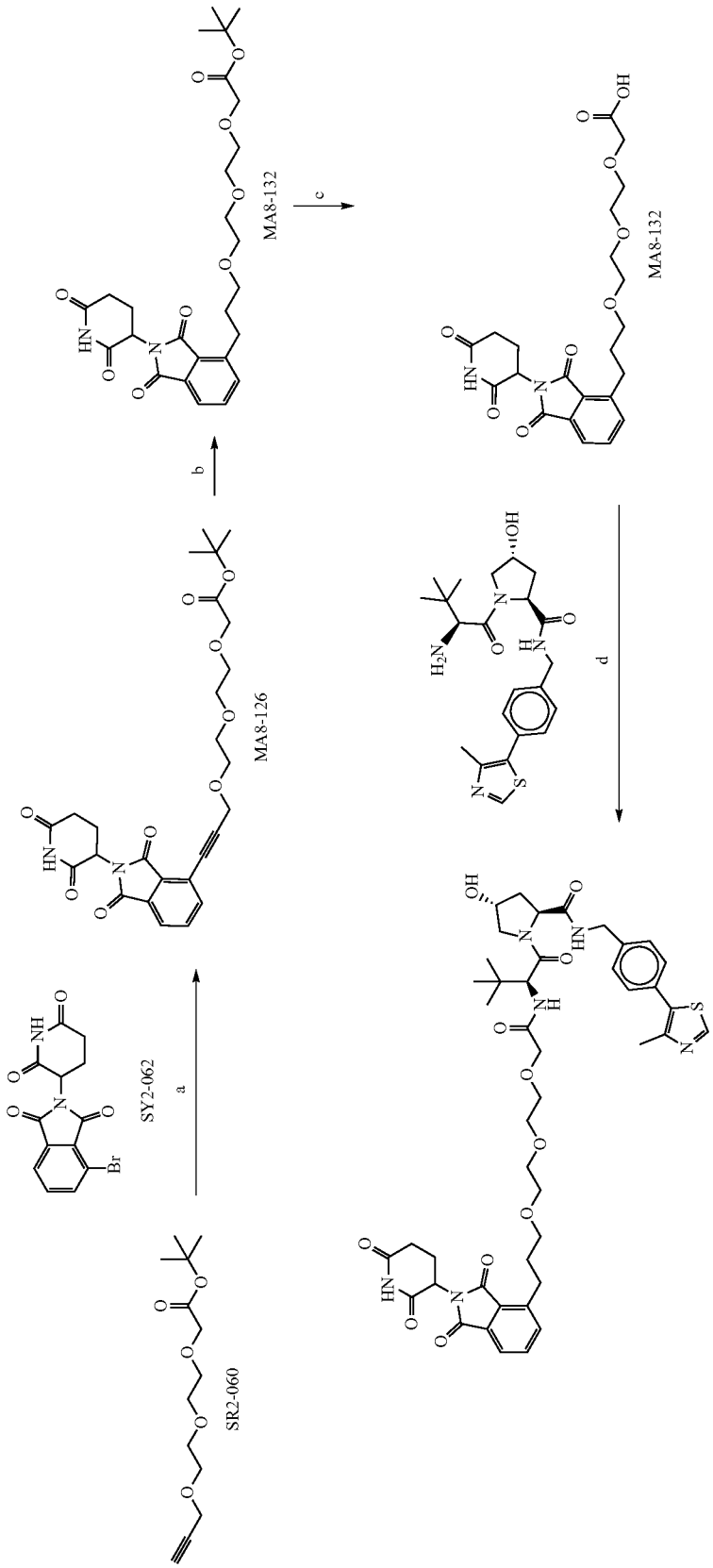

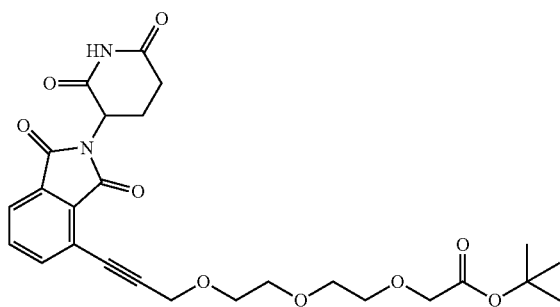 [SMILES: CC(C)(C)OC(=O)COCCOCCOCC#Cc1cccc2c1C(=O)N(C1CCC(=O)NC1=O)C2=O]

tert-Butyl-2-(2-(2-((3-(2-(2,6-dioxopiperidin-3-yl)-1,3-dioxoisoindolin-4-yl)prop-2-yn-1-yl)oxy)ethoxy)ethoxy)acetate (MA8-126): In an oven dried round bottom flask (50 mL), Pd(PPh$_3$)$_4$ (104.1 mg, 0.15 mmol) and CuI (56.4 mg, 0.30 mmol) were dissolved in dry DMF (19 mL) and argon was bubbled through the mixture for ~10 minutes. SY2-062 (500 mg, 1.48 mmol) and SR2-060B2 (574.7 mg, 2.22 mmol) were added under argon followed by the addition of TEA (3.10 mL, 22.2 mmol). The reaction was stirred at 75° C. (oil bath temperature) for 9.5 h at which point the HPLC-MS and TLC showed complete consumption of the starting material. DMF was evaporated under reduced pressure, the crude was diluted with EtOAc (~100 mL) and filtered through a short plug of celite. The solvent was evaporated and the crude mixture was purified using SiO$_2$ chromatography on an Isolera purification system while eluting with a gradient of EtOAc-hexane (0 to 50% EtOAc) to provide MA8-126 as a colorless oil (459 mg, 60%). $^1$H NMR (400 MHz, DMSO-d$_6$): δ 11.13 (s, 1H), 7.97-7.83 (m, 3H), 5.15 (dd, J=12.9, 5.4 Hz, 1H), 4.50 (s, 2H), 3.98 (s, 2H), 3.72 (dd, J=5.5, 4.0 Hz, 2H), 3.62-3.53 (m, 6H), 2.89 (ddd, J=16.9, 13.9, 5.4 Hz, 1H), 2.66-2.55 (m, 2H), 2.12-2.03 (m, 1H), 1.41 (s, 9H). HPLC-MS (ESI+): m/z 537.1 (M+Na)$^+$.

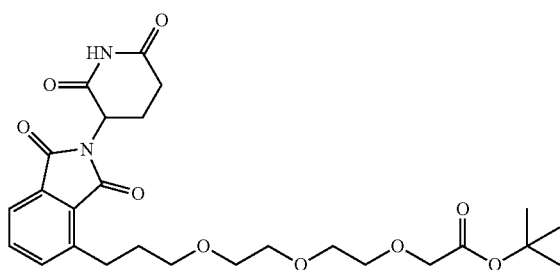 [SMILES: CC(C)(C)OC(=O)COCCOCCOCCCc1cccc2c1C(=O)N(C1CCC(=O)NC1=O)C2=O]

tert-Butyl-2-(2-(2-(3-(2-(2,6-dioxopiperidin-3-yl)-1,3-dioxoisoindolin-4-yl)propoxy)ethoxy)ethoxy)acetate (MA8-132): A two-neck round bottom flask (25 mL) was evacuated and backfilled with argon (twice) followed by the addition of 10% Pd/C (62 mg, 0.058 mmol). EtOAc (~2 mL) was used to wash down the residual Pd/C from the neck of the flask. MeOH (5 mL) was added to the flask and argon was bubbled through the mixture for ~15 minutes. After attaching a septum to the flask, it was evacuated and backfilled with argon (twice). Finally, the argon line was replaced with hydrogen balloon; the flask was evacuated one more time and carefully filled with hydrogen. The MA8-126 (300 mg, 0.58 mmol, dissolved in 5 mL of MeOH) was added to the flask via a syringe and the reaction mixture was stirred under hydrogen atmosphere for 18 h. After the reaction completion (monitored by TLC), the reaction mixture was passed through a short plug of celite and the filtrate was concentrated under reduced pressure. The product was purified using SiO$_2$ column on Biotage Isolera purification system while eluting with a gradient of EtOAc-hexane (0 to 100% EtOAc). The title compound was obtained in a partially pure form as colorless oil (172 mg, 57%) and was used in the next step without further purification. HPLC-MS (ESI+): m/z 541.1 (M+Na)$^+$.

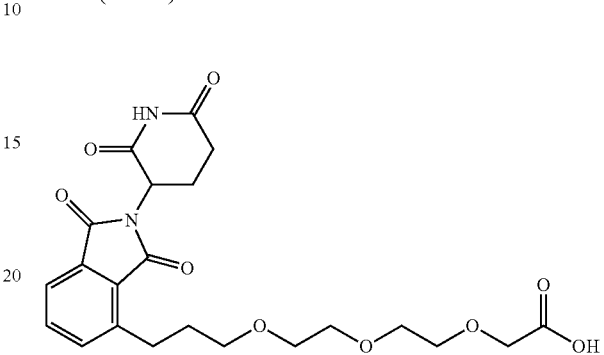

2-(2-(2-(3-(2-(2,6-Dioxopiperidin-3-yl)-1,3-dioxoisoindolin-4 yl)propoxy)ethoxy)ethoxy)acetic acid (MA8-135): In a scintillation vial (20 mL), MA8-132 (166 mg, 0.32 mmol) was dissolved in dry 1,4-dioxane (3 mL). The mixture was cooled to 0° C. and using a syringe, 4 M HCl (in 1,4-dioxane, 3.2 mL) was added dropwise (~over 3 minutes). After ~30 minutes, the ice-water bath was removed and the stirring was continued at room temperature for an additional 4 h. HPLC-MS indicated the completion of the reaction. The volatiles were evaporated under reduced pressure, added DCM (5 mL×2) and the crude mixture evaporated to provide the title compound as a yellow oil (124 mg, 84%). $^1$H NMR (500 MHz, DMSO-d$_6$): δ 12.56 (s, 1H), 11.11 (s, 1H), 7.79-7.72 (m, 2H), 7.70 (dd, J=6.9, 1.9 Hz, 1H), 5.12 (dd, J=12.7, 5.5 Hz, 1H), 4.02 (s, 1H), 4.01 (s, 2H), 3.59-3.54 (m, 2H), 3.55-3.50 (m, 4H), 3.49-3.46 (m, 2H), 3.44-3.40 (m, 2H), 3.07 (dd, J=8.5, 6.8 Hz, 2H), 2.89 (ddd, J=16.8, 13.8, 5.4 Hz, 1H), 2.64-2.54 (m, 1H), 2.09-2.00 (m, 1H), 1.90-1.79 (m, 2H). HPLC-MS (ESI+): m/z 485.2 (M+Na)$^+$, 463.2 (M+H)$^+$.

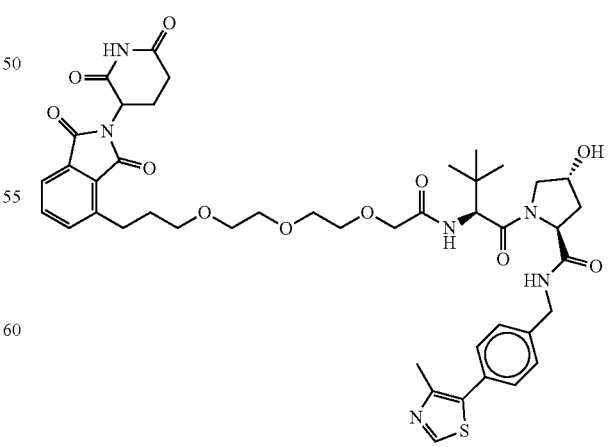

(2S,4R)-1-((2S)-2-(tert-Butyl)-15-(2-(2,6-dioxopiperidin-3-yl)-1,3-dioxoisoindolin-4-yl)-4-oxo-6,9,12-trioxa-3-azapentadecanoyl)-4-hydroxy-N-(4-(4-methylthiazol-5-yl)benzyl)pyrrolidine-2-carboxamide (MA8-150): COMU (66.2 mg, 0.15 mmol) was added to MA8-135 (65 mg, 0.14 mmol) in dry DMF (1 mL) and DIPEA (76 µL, 0.43 mmol), in a 10 mL microwave reaction vial under argon. After ~5 minutes stirring at room temperature, (2S,4R)-1-((S)-2-amino-3,3-dimethylbutanoyl)-4-hydroxy-N-(4-(4-methylthiazol-5-yl)benzyl)pyrrolidine-2-carboxamide (Galdeano, C.; et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. *Journal of medicinal chemistry* 2014, 57, 8657-63) was added to the reaction mixture and stirring was continued for 24 h. The solvent was evaporated under reduced pressure and crude product was directly loaded on to SiO$_2$ column using a Biotage Isolera as purification system. The product was eluted with a gradient of DCM-MeOH (0 to 15% MeOH). The semi-pure material from chromatography was further triturated using EtOAc-hexane to obtain the title compound as a white solid (33 mg, 34%) Mp: 288° C. (dec). HPLC: 99% [t$_R$=15.2 min, gradient MeOH-water (with 0.1% TFA), 5-95% over 20 min]. $^1$H NMR (500 MHz, DMSO-d$_6$): δ 11.11 (s, 1H), 8.96 (s, 1H), 8.59 (t, J=6.1 Hz, 1H), 7.82-7.73 (m, 2H), 7.73-7.63 (m, 1H), 7.47-7.35 (m, 5H), 5.20-5.07 (m, 2H), 4.56 (d, J=9.6 Hz, 1H), 4.48-4.42 (m, 1H), 4.46-4.32 (m, 3H), 4.26-4.20 (m, 1H), 3.96 (s, 2H), 3.70-3.46 (m, 12H), 3.44-3.36 (m, 3H), 3.10-3.00 (m, 2H), 2.88 (ddd, J=16.7, 13.7, 5.4 Hz, 1H), 2.65-2.53 (m, 2H), 2.09-2.00 (m, 2H), 1.90 (ddd, J=13.0, 8.8, 4.5 Hz, 1H), 1.82 (h, J=6.6 Hz, 2H), 0.93 (s, 9H). HPLC-MS (ESI+): m/z 897.3 (M+Na)$^+$, 875.4 (M+H)$^+$, 438.2 (M+2H)$^{2+}$. HRMS (ESI+): m/z calcd. for C$_{44}$H$_{54}$N$_6$O$_{11}$SNa (M+Na)$^+$ 897.3463, found 897.3460.

Synthetic scheme 19
Synthesis of linkers

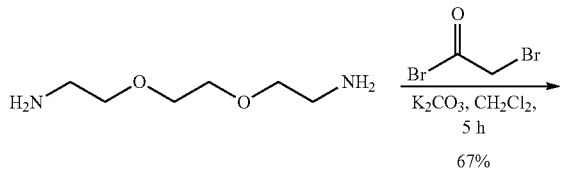

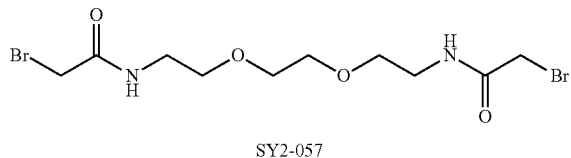

SY2-057

N,N'-((Ethane-1,2-diylbis(oxy))bis(ethane-2,1-diyl))bis(2-bromoacetamide) (SY2-057): 2,2'-(ethylenedioxy)bis(ethylamine) (0.2 g, 1.35 mmol) was dissolved in CH$_2$Cl$_2$ (10 mL). K$_2$CO$_3$ (0.47 g, 3.4 mmol) and bromoacetyl bromide (0.681 g, 3.4 mmol) were added and the mixture was stirred at room temperature for 5 h. The reaction was quenched with water and the mixture extracted with CH$_2$Cl$_2$ (20 mL×3). The combined extracts were dried over Na$_2$SO$_4$ and filtered. The filtrate was concentrated under reduced pressure. The residue was recrystallized from EtOH at −20° C. to afford the titled compound (350 mg, 67%). $^1$H NMR (500 MHz, DMSO-d$_6$) δ 6.89 (br s, 2H), 3.89 (s, 4H), 3.65 (s, 4H), 3.60 (t, J=5 Hz, 4H), 3.51 (q, J=5 Hz, 4H). $^{13}$C NMR (125 MHz, DMSO-d$_6$) δ 165.69, 70.54, 69.58, 40.08, 29.36.

Synthetic scheme 20
Synthesis of linkers

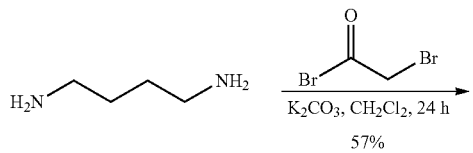

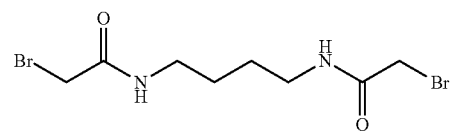

SY2-058

N,N'-(Butane-1,4-diyl)bis(2-bromoacetamide) (SY2-058): The 1,4-diaminobutane (0.2 g, 2.27 mmol) was dissolved in CH$_2$Cl$_2$ (5 mL) and aqueous solution of K$_2$CO$_3$ (0.78 g in 5 mL H$_2$O) was added. The mixture was stirred at 0° C. for 5 min and then bromoacetyl bromide (1.14 g, 5.65 mmol) was added. The mixture was stirred at rt for 24 h. The reaction was quenched with water and the mixture was extracted with CH$_2$Cl$_2$ (20 mL×3). The combined extracts were dried over Na$_2$SO$_4$ and filtered. The filtrate was concentrated under reduced pressure. The residue was dried under vacuum to afford the titled compound as a white solid (0.43 g 57%). $^1$H NMR (500 MHz, DMSO-d$_6$) δ 6.61 (br s, 2H), 3.88 (s, 4H), 3.33 (q, J=3.5 Hz, 4H), 1.60 (pent, J=3.5 Hz, 4H). $^{13}$C NMR (125 MHz, DMSO-d$_6$) δ 165.67, 39.85, 29.41, 26.78.

Synthetic scheme 21
Synthesis of linkers

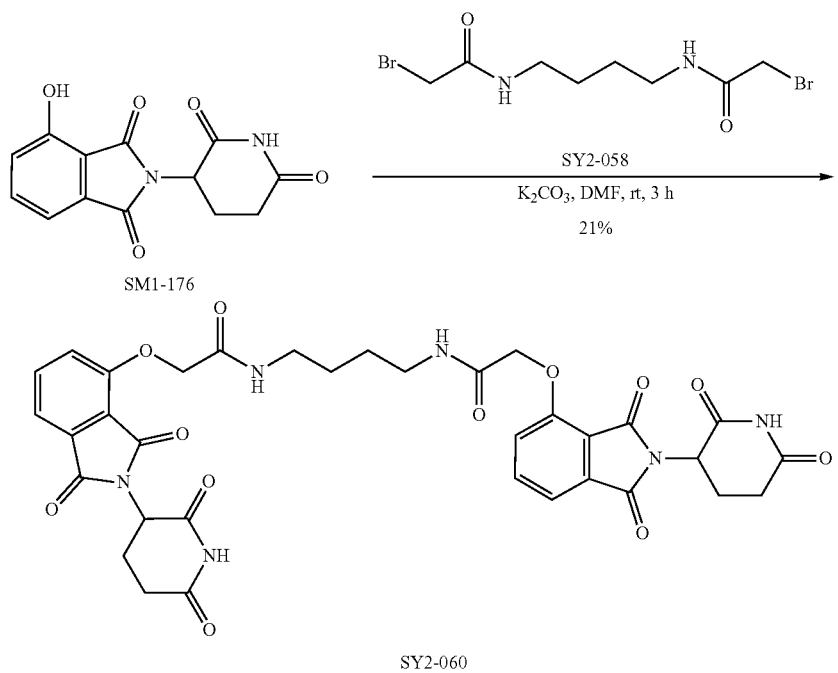

N,N'-(Butane-1,4-diyl)bis(2-((2-(2,6-dioxopiperidin-3-yl)-1,3-dioxoisoindolin-4-yl)oxy)acetamide) (SY2-060): The phenol SM1-176 (0.087 g, 0.317 mmol) was dissolved in 5 mL DMF. $K_2CO_3$ (0.052 g, 0.376 mmol) and SY2-058 (0.050 g, 0.152 mmol) were sequentially added. The mixture was stirred for 3 h at room temperature. The solvent was removed using a BIOTAGE™ V-10 evaporator. The crude product was subjected to $SiO_2$ chromatography (0-10% gradient elution, MeOH/$CH_2Cl_2$) to give a yellow solid. This compound was purified again by preparative HPLC [35-95 gradient elution, MeOH/$H_2O$ (with 0.1% formic acid)] to afford analytically pure compound as a white solid (23 mg, 21%). HPLC: 98.9% [$t_R$=4.87 min, 50% MeOH, 50% water (with 0.1% TFA), 20 min, 254 nm]. $^1$H NMR (500 MHz, DMSO-$d_6$) δ 11.12 (s, 2H), 7.98 (t, J=5.8 Hz, 2H), 7.81 (dd, J=8.5, 7.3 Hz, 2H), 7.49 (d, J=7.2 Hz, 2H), 7.39 (m, 2H), 5.12 (dd, J=12.8, 5.4 Hz, 2H), 4.77 (s, 4H), 3.16 (pent, J=5.3 Hz, 4H), 2.90 (ddd, J=16.8, 13.8, 5.4 Hz, 4H), 2.66-2.52 (m, 4H), 2.04 (ddd, J=10.4, 5.4, 3.0 Hz, 2H), 1.45 (pent, J=3.3 Hz, 4H). $^{13}$C NMR (125 MHz, DMSO-$d_6$) δ 172.76, 169.86, 166.72, 166.69, 165.48, 155.06, 136.93, 133.02, 120.38, 116.79, 116.04, 67.63, 48.80, 38.01, 30.94, 26.40, 21.98. HPLC-MS (ESI+): m/z 739.2 (M+Na)$^+$, 717.3 (M+H)$^+$.

Synthetic scheme 22

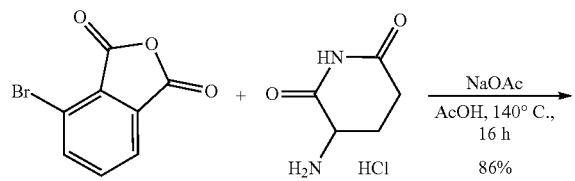

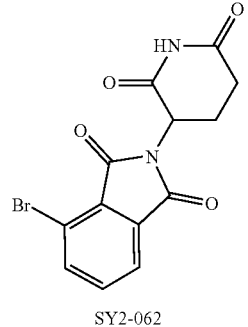

SY2-062

4-Bromo-2-(2,6-dioxopiperidin-3-yl)isoindoline-1,3-dione (SY2-062): 3-Bromophthalic anhydride (4.54 g, 0.02 mol), 3-aminopiperidine-2,6-dione hydrochloride (3.62 g, 0.021 mol) and NaOAc (1.96 g, 0.023 mol) were added to a round bottom flask in acetic acid (30 mL). The mixture was heated at 140° C. for 12 h. The acetic acid was removed under reduced pressure. The residue was purified by $SiO_2$ column chromatography (0-10% gradient elution, MeOH/$CH_2Cl_2$) to provide the title compound as an off white solid (5.6 g, 87%). $^1$H NMR (500 MHz, DMSO-$d_6$) δ11.12 (s, 1H), 8.07 (dd, J=8.1, 0.8 Hz, 1H), 7.94 (dd, J=7.4, 0.8 Hz, 1H), 7.79 (dd, 8.1, 7.4 Hz, 1H), 5.18 (dd, 12.9, 5.5 Hz, 1H), 2.90 (ddd, J=17.2, 14.0, 5.4 Hz, 1H), 2.68-2.48 (m, 4H), 2.08 (ddd, J=9.8, 5.5, 2.7 Hz, 1H). $^{13}$C NMR (125 MHz, DMSO-$d_6$) δ 173.21, 170.18, 166.07, 165.65, 139.66, 136.74, 134.15, 129.2, 123.31, 118.10, 49.63, 31.38, 22.29. HPLC-MS (ESI+): m/z 697.0 (2M+Na)$^+$, 337.1 (M+H)$^+$.

Synthetic scheme 23
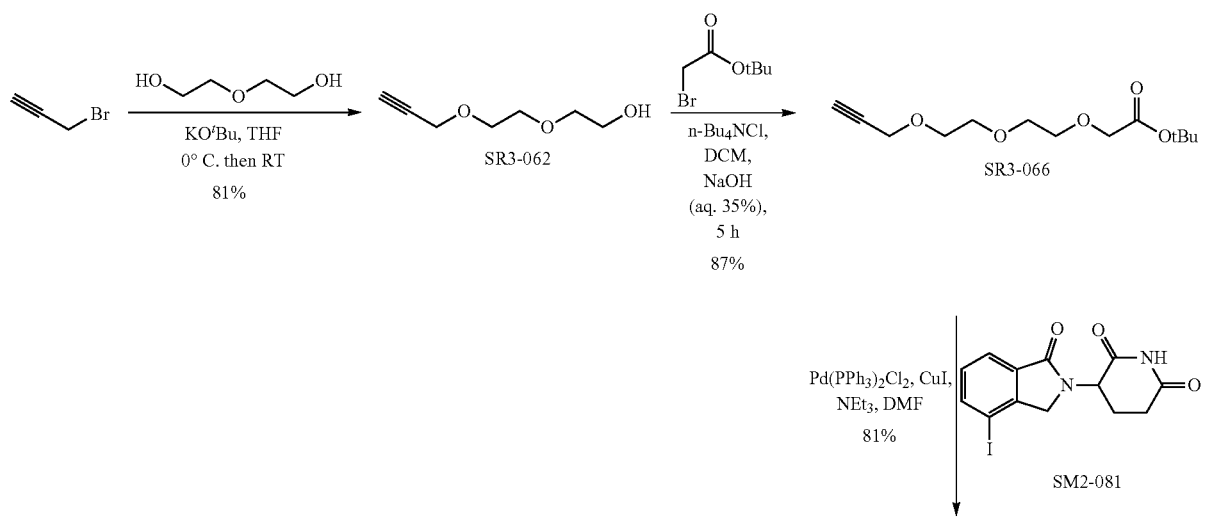
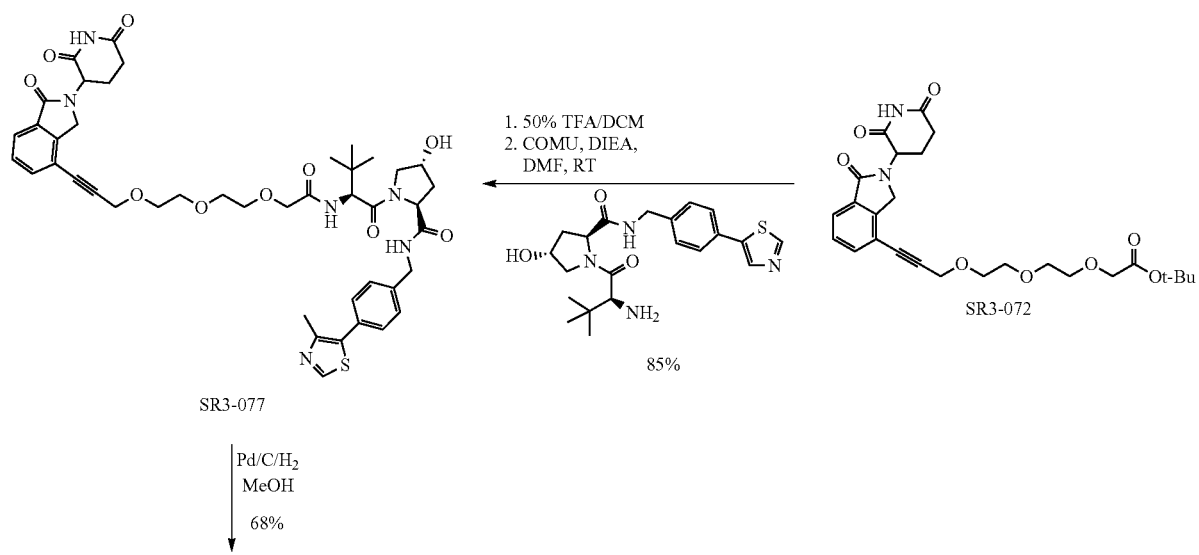

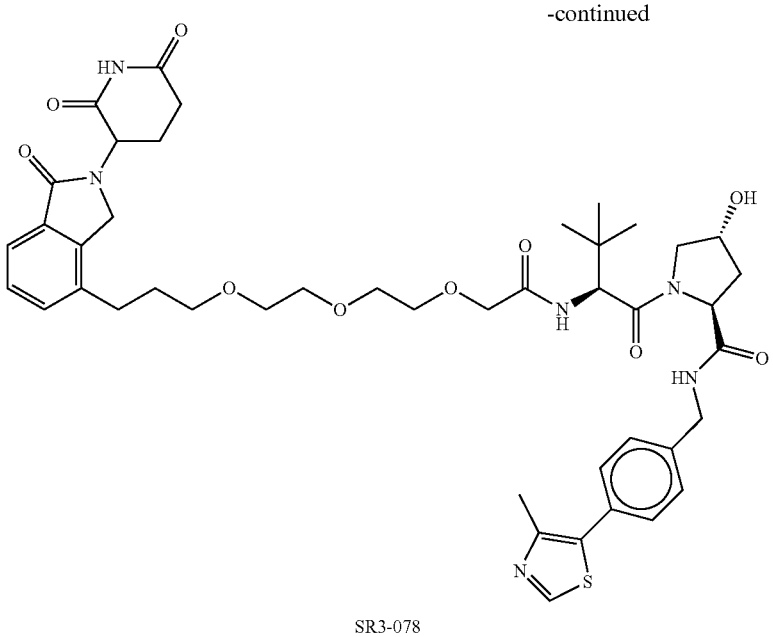

SR3-078

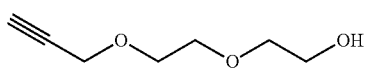

SR3-062

2-(2-(Prop-2-yn-1-yloxy)ethoxy)ethan-1-ol (SR3-062) (Percec, V.; et al., Modular synthesis of amphiphilic Janus glycodendrimers and their self-assembly into glycodendrimersomes and other complex architectures with bioactivity to biomedically relevant lectins. *Journal of the American Chemical Society* 2013, 135, 9055-77): Diethylene glycol (8.00 mL, 84.06 mmol) was added to a suspension of potassium tert-butoxide (5.19 g, 46.23 mmol) in dry THF (40 mL) at 0° C. under argon. The mixture was allowed to warm to room temperature and stirred for 30 min. A solution of propargyl bromide (5.00 g, 46.03 mmol) in dry THF (45 mL) was added to the mixture which was then stirred for 18 h and then filtered through Celite. The solvent was evaporated from the filtrate to provide a residue which was purified by flash column chromatography using EtOAc:hexane (30-100%) as eluent, to afford SR3-062 as a pale-yellow oil (4.90 g, 81%). $^1$H NMR (500 MHz, Chloroform-d) δ 4.21 (d, J=2.4 Hz, 2H), 3.76-3.67 (m, 6H), 3.61 (m, 2H), 2.44 (t, J=2.4 Hz, 1H), 2.24-2.12 (m, 1H). $^{13}$C NMR (126 MHz, CDCl$_3$) δ 79.58, 74.84, 72.62, 70.36, 69.28, 61.89, 58.6. HRMS (ESI+): m/z calcd for C$_7$H$_{13}$O$_3$ (M+H)$^+$ 145.0859, found 145.0864, m/z calcd for C$_7$H$_{12}$O$_3$Na (M+Na)$^+$ 167.0679, found 167.0684. HPLC-MS (ESI+): m/z 145.2 [100%, (M+H)$^+$], 167.2 [100%, (M+Na)$^+$].

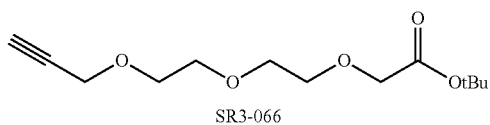 [SMILES: C#CCOCCOCCOCC(=O)OC(C)(C)C]

SR3-066 tert-Butyl 2-(2-(2-(prop-2-yn-1-yloxy)ethoxy)ethoxy)acetate (SR3-066) (Wurz, R. P.; et al., "Click Chemistry Platform" for the Rapid Synthesis of Bispecific Molecules for Inducing Protein Degradation. *Journal of medicinal chemistry* 2018, 61, 453-461). The method, as described by Oberborsch was used to prepare this compound (WO2009124746 A1). To a solution of the alcohol SR3-062 (3.00 g, 20.81 mmol) and n-Bu$_4$NCl (1.908 g, 6.867 mmol) in DCM (102 mL) at 0° C. were added NaOH (102 mL, aq. 35%) and tert-butyl bromoacetate (9.225 mL, 62.427 mmol). The mixture was stirred at room temperature for 5 h and diluted with DCM (25 mL) and water (25 mL). The layers were separated and the organic layer washed with water (2×20 mL), brine (1×20 mL), dried (Na$_2$SO$_4$), and evaporated in vacuo. Purification by flash column chromatography using EtOAc:hexane (5-50%) as eluent afforded SR3-066 (Wurz, R. P.; et al., "Click Chemistry Platform" for the Rapid Synthesis of Bispecific Molecules for Inducing Protein Degradation. *Journal of medicinal chemistry* 2018, 61, 453-461) as a pale-yellow oil (4.724 g, 87%). $^1$H NMR (500 MHz, Chloroform-d) δ 4.23 (d, J=2.4 Hz, 2H), 4.05 (s, 2H), 3.79-3.65 (m, 8H), 2.45 (t, J=2.4 Hz, 1H), 1.50 (s, 9H). $^{13}$C NMR (126 MHz, CDCl$_3$) δ 169.7, 81.5, 79.7, 74.5, 70.7, 70.6, 70.4, 69.1, 69.1, 58.4, 28.1. HRMS (ESI+): m/z calcd for C$_{13}$H$_{23}$O$_5$ (M+H)$^+$ 259.1540, found 259.1547, m/z calcd for C$_{13}$H$_{22}$O$_5$Na (M+Na)$^+$ 281.1359, found 281.1365. HPLC-MS (ESI+): m/z 281.2 [100%, (M+Na)$^+$].

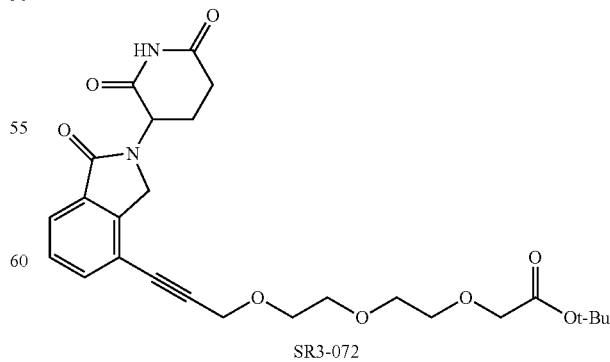

SR3-072 tert-Butyl 2-(2-(2-((3-(2-(2,6-dioxopiperidin-3-yl)-1-oxoisoindolin-4-yl)prop-2-yn-1-yl)oxy)ethoxy)ethoxy)acetate (SR3-072): SM2-081 (0.050 g, 0.135 mmol) and the alkyne SR3-066 (0.042 g, 0.162 mmol) were added into a solution of $PdCl_2(PPh_3)_2$ (0.009 g, 0.014 mmol) and CuI (0.005 g, 0.027 mmol) in DMF (1.75 mL) under Ar. The mixture was heated at 75° C. for 6.5 h. The reaction mixture was cooled and filtered through Celite. The Celite bed was rinsed with EtOAc (20 mL). The filtrate and ethyl acetate wash was concentrated under reduced pressure and purified by flash column chromatography using MeOH:DCM (0-10%) as eluent to afford SR3-072 as an off-white solid (0.055 g, 81%). $^1$H NMR (500 MHz, DMSO-$d_6$) δ 11.00 (s, 1H), 7.77 (dd, J=7.6, 1.1 Hz, 1H), 7.73 (dd, J=7.6, 1.0 Hz, 1H), 7.56 (t, J=7.6 Hz, 1H), 5.15 (dd, J=13.3, 5.1 Hz, 1H), 4.50 (d, J=17.7 Hz, 1H), 4.46 (s, 2H), 4.35 (d, J=17.7 Hz, 1H), 3.98 (s, 2H), 3.68-3.64 (m, 2H), 3.61-3.46 (m, 6H), 2.91 (ddd, J=17.2, 13.6, 5.4 Hz, 1H), 2.65-2.55 (m, 1H), 2.44 (m, 1H), 2.01 (ddd, J=9.5, 5.4, 2.7 Hz, 1H), 1.41 (s, 9H). $^{13}$C NMR (126 MHz, DMSO) δ 172.8, 170.9, 169.3, 167.5, 143.9, 134.4, 132.1, 128.7, 123.5, 117.5, 91.3, 81.3, 80.6, 72.3, 69.8, 69.7, 69.5, 68.8, 68.1, 60.2, 58.1, 51.6, 46.9, 31.2, 27.7, 22.3. HRMS (ESI+): m/z calcd for $C_{26}H_{33}N_2O_8$ (M+H)$^+$ 501.2231, found 501.2240, m/z calcd for $C_{26}H_{32}N_2O_8Na$ (M+Na)$^+$ 523.2051, found 523.2069. HPLC-MS (ESI+): m/z 523.2 [100%, (M+Na)$^+$]. HPLC-MS (ESI−): m/z 499.3 [40%, M−H$^-$].

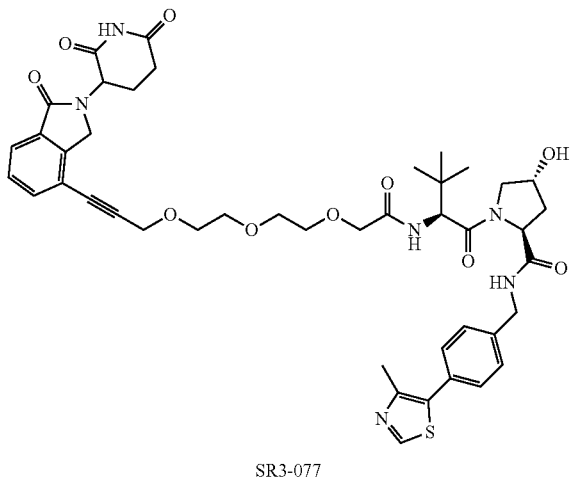 [SMILES: Cc1ncsc1-c1ccc(CNC(=O)[C@@H]2C[C@@H](O)CN2C(=O)[C@@H](NC(=O)COCCOCCOCC#Cc2cccc3c2CN(C2CCC(=O)NC2=O)C3=O)C(C)(C)C)cc1]

SR3-077

(2S,4R)-1-((2S)-2-(tert-Butyl)-15-(2-(2,6-dioxopiperidin-3-yl)-1-oxoisoindolin-4-yl)-4-oxo-6,9,12-trioxa-3-azapentadec-14-ynoyl)-4-hydroxy-N-(4-(4-methylthiazol-5-yl)benzyl)pyrrolidine-2-carboxamide (SR3-077): The tert-butyl ester SR3-072 (0.050 g, 0.099 mmol) was dissolved in 50% TFA in DCM (2.0 mL) and stirred at room temperature for 3 h. The mixture was concentrated under reduced pressure and further dried under high vacuum to afford SR3-075 as a white foam. HPLC-MS (ESI+): m/z 445.2 [50%, (M+H)$^+$], 467.2 [90%, (M+Na)$^+$]. HPLC-MS (ESI−): m/z 443.2 [10%, M−H$^-$]. Without further purification, the carboxylic acid SR3-075 was dissolved in dry DMF (1.5 mL) and (1-Cyano-2-ethoxy-2-oxoethylidenaminooxy)dimethylamino-morpholino-carbenium hexafluorophosphate (COMU) (0.047 g, 0.109 mmol) and DIPEA (0.053 mL, 0.299 mmol) were added. After 3 min stirring at room temperature under argon, the VHL ligand (Galdeano, C.; et al., Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. *Journal of medicinal chemistry* 2014, 57, 8657-63) (2S,4R)-1-((S)-2-amino-3,3-dimethylbutanoyl)-4-hydroxy-N-(4-(thiazol-5-yl)benzyl)pyrrolidine-2-carboxamide (0.051 g, 0.109 mmol) was added to the mixture which was stirred for a further 20 h. The solvent was removed under reduced pressure and the residue purified by flash column chromatography using MeOH:DCM (0-15%) as eluent to afford SR3-077 as a white foam (0.073 g, 85%). HPLC: >99% [$t_R$=6.1 min, 60% MeOH, 40% water (with 0.1% TFA), 20 min]. $^1$H NMR (500 MHz, DMSO-$d_6$) δ 11.00 (s, 1H), 8.97 (s, 1H), 8.59 (t, J=5.8 Hz, 1H), 7.76 (dd, J=7.6, 1.0 Hz, 1H), 7.70 (dd, J=7.7, 1.0 Hz, 1H), 7.55 (t, J=7.6 Hz, 1H), 7.46-7.35 (m, 4H), 5.15 (d, J=3.4 Hz, 1H), 5.13 (m, 1H), 4.57 (d, J=9.7 Hz, 1H), 4.52-4.39 (m, 5H), 4.41-4.30 (m, 2H), 4.25 (dd, J=15.8, 5.6 Hz, 1H), 3.97 (s, 2H), 3.72-3.56 (m, 11H), 2.91 (ddd, J=18.1, 13.6, 5.4 Hz, 1H), 2.66-2.55 (m, 1H), 2.48-2.39 (m, 4H), 2.09-1.96 (m, 2H), 1.90 (ddd, J=13.0, 8.9, 4.5 Hz, 1H), 0.97-0.92 (m, 9H). HRMS (ESI+): m/z calcd for $C_{44}H_{53}N_6O_{10}S$ (M+H)$^+$ 857.3538, found 857.3536, m/z calcd for $C_{44}H_{52}N_6O_{10}SNa$ (M+Na)$^+$ 879.3358, found 879.3369. HPLC-MS (ESI+): m/z 857.4 [60%, (M+H)$^+$], 879.0 [50%, (M+Na)$^+$].

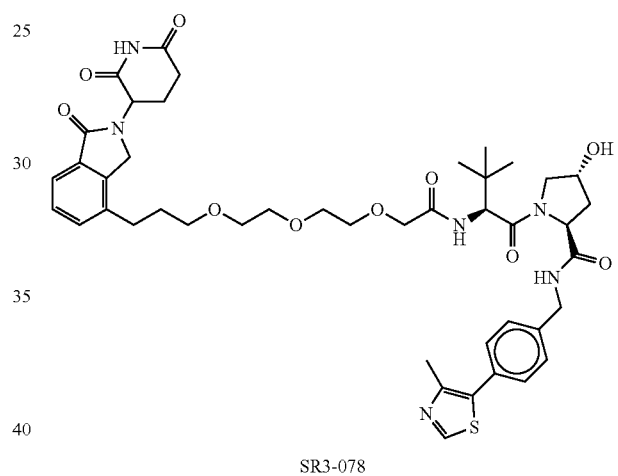

SR3-078

(2S,4R)-1-((2S)-2-(tert-Butyl)-15-(2-(2,6-dioxopiperidin-3-yl)-1-oxoisoindolin-4-yl)-4-oxo-6,9,12-trioxa-3-azapentadecanoyl)-4-hydroxy-N-(4-(4-methylthiazol-5-yl)benzyl)pyrrolidine-2-carboxamide (SR3-078): A 20 mL vial was purged with Ar and charged with Pd/C (10%, 0.003 g). MeOH (1 mL) was added to the vial and purged with $H_2$ (balloon) for 3 min. The alkyne SR3-077 (0.025 g, 0.029 mmol) in MeOH (0.5 mL) was then added to the mixture which was stirred at room temperature for 2.5 h under $H_2$ (balloon). The mixture was filtered through Celite and concentrated under reduced pressure. Purification by flash column chromatography using MeOH:DCM (0-10%) as eluent afforded SR3-078 as a pale yellow oil (17 mg, 68%). HPLC: >98% [$t_R$=7.5 min, 60% MeOH, 40% water (with 0.1% TFA), 20 min]. $^1$H NMR (500 MHz, DMSO-$d_6$) δ 10.92 (s, 1H), 8.90 (s, 1H), 8.52 (t, J=6.1 Hz, 1H), 7.49 (dd, J=5.8, 2.8 Hz, 1H), 7.41-7.29 (m, 7H), 5.08 (m, 1H), 5.05 (d, J=5.1 Hz, 1H), 4.50 (d, J=9.6 Hz, 1H), 4.42-4.29 (m, 3H), 4.29-4.12 (m, 3H), 3.90 (s, 2H), 3.62-3.37 (m, 10H), 3.30 (t, J=6.5 Hz, 2H), 2.91-2.79 (m, 1H), 2.65-2.49 (m, 3H), 2.40-2.25 (m, 4H), 2.07-1.89 (m, 2H), 1.84 (m, 1H), 1.79-1.69 (m, 2H), 0.87 (s, 9H). HRMS (ESI+): m/z calcd for $C_{44}H_{57}N_6O_{10}S$ (M+H)$^+$ 861.3851, found 861.3840, m/z calcd for $C_{44}H_{56}N_6O_{10}SNa$ (M+Na)$^+$ 883.3671, found 883.3683. HPLC-MS (ESI+): m/z 861.0 [70%, (M+H)$^+$], 883.1 [90%, (M+Na)$^+$]. HPLC-MS (ESI−): m/z 859.0 [20%, M−H$^-$].

131
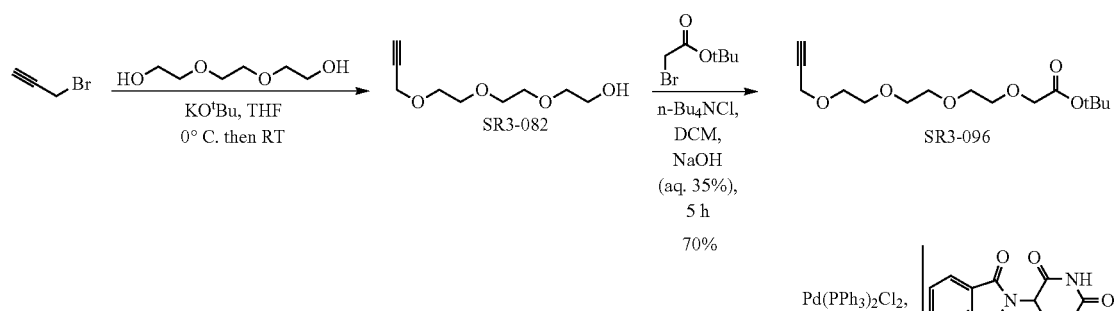
132
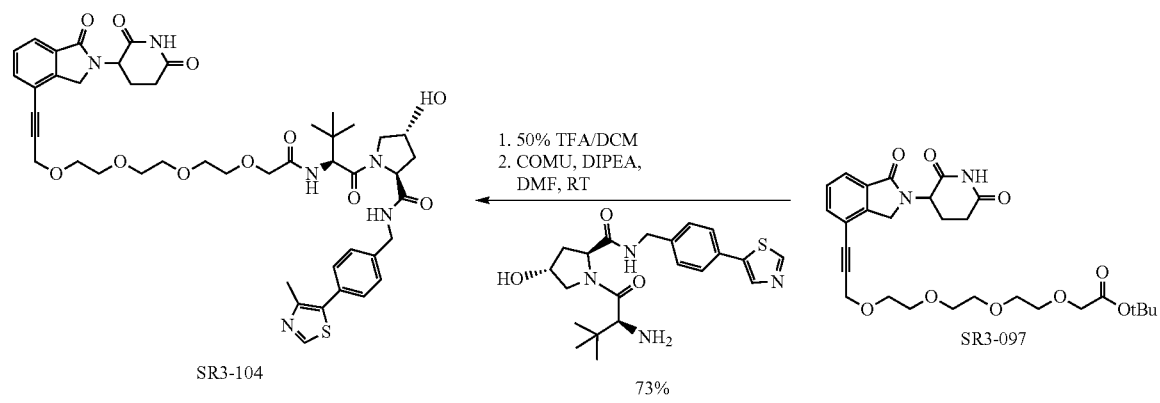
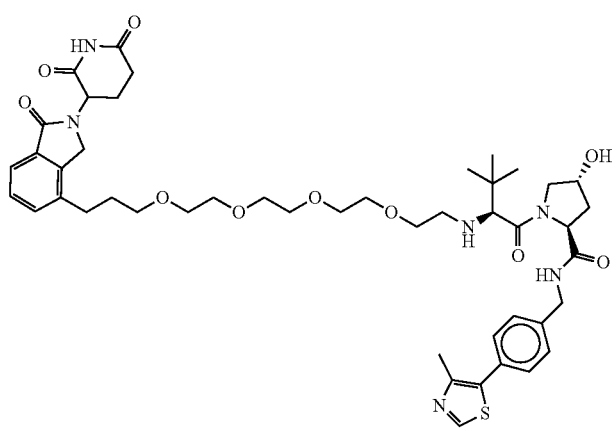

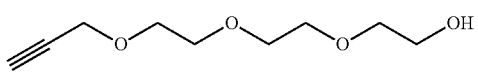

2-(2-(2-(Prop-2-yn-1-yloxy)ethoxy)ethoxy)ethan-1-ol (SR3-082). The alcohol SR3-082 was obtained as a pale-yellow oil (2.49 g, 79%) using triethylene glycol (4.49 mL, 33.62 mmol) by following the same method used to prepare SR3-062. $^1$H NMR (500 MHz, Chloroform-d) δ 4.22 (d, J=2.4 Hz, 2H), 3.77-3.66 (m, 10H), 3.63 (m, 2H), 2.45 (t, J=2.4 Hz, 1H), 2.38 (bs, 1H). $^{13}$C NMR (126 MHz, CDCl$_3$) δ 79.6, 74.6, 72.5, 70.6, 70.4, 70.3, 69.1, 61.7, 58.4. HRMS (ESI+): m/z calcd for C$_9$H$_{17}$O$_4$ (M+H)$^+$ 189.1121, found 189.1126, m/z calcd for C$_9$H$_{16}$O$_4$Na (M+Na)$^+$ 211.0941, found 211.0944. HPLC-MS (ESI+): m/z 189.2 [60%, (M+H)$^+$], 211.2 [70%, (M+Na)$^+$].

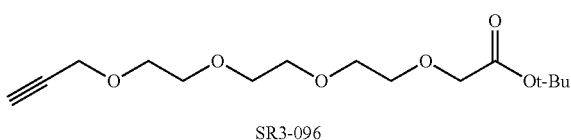 [SMILES: C#CCOCCOCCOCCOCC(=O)OC(C)(C)C]

tert-Butyl 3,6,9,12-tetraoxapentadec-14-ynoate (SR3-096): The tert-butyl ester SR3-096 was obtained as a colorless oil (0.606 g, 70%) by following the same method used to prepare SR3-066. $^1$H NMR (500 MHz, Chloroform-d) δ 4.21 (m, 2H), 4.03 (s, 2H), 3.79-3.60 (m, 12H), 2.44 (t, J=2.5 Hz, 1H), 1.48 (s, 9H). $^{13}$C NMR (126 MHz, CDCl$_3$) δ 169.8, 81.6, 79.8, 74.6, 70.8, 70.7, 70.5, 69.2, 69.2, 58.5, 28.2. HRMS (ESI+): m/z calcd for C$_{15}$H$_{27}$O$_6$ (M+H)$^+$ 303.1802, found 303.1808, m/z calcd for C$_{15}$H$_{26}$O$_6$Na (M+Na)$^+$ 325.1622, found 325.1628. HPLC-MS (ESI+): m/z 325.2 [100%, (M+Na)$^+$].

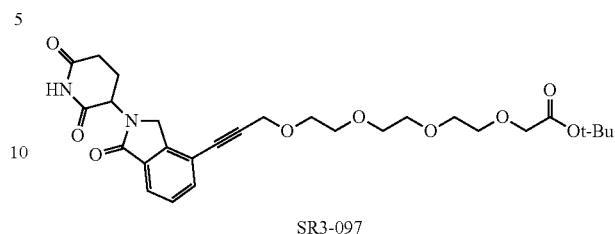

tert-Butyl 15-(2-(2,6-dioxopiperidin-3-yl)-1-oxoisoindolin-4-yl)-3,6,9,12-tetraoxapentadec-14-ynoate (SR3-097): The ester SR3-097 was obtained as an off-white solid (0.134 g, 61%) using triethylene alkyne SR3-096 (0.123 g, 0.405 mmol) and iodo-lenalidomide derivative SM2-081 (0.100 g, 0.270 mmol) by following the method used to prepare SR3-072. $^1$H NMR (500 MHz, DMSO-d$_6$) δ 11.00 (s, 1H), 7.78 (dd, J=7.7, 1.1 Hz, 1H), 7.73 (dd, J=7.7, 1.0 Hz, 1H), 7.57 (t, J=7.6 Hz, 1H), 5.15 (dd, J=13.3, 5.1 Hz, 1H), 4.50 (d, J=17.7 Hz, 1H), 4.47 (s, 2H), 4.35 (d, J=17.7 Hz, 1H), 3.98 (s, 2H), 3.66 (m, 1H), 3.62-3.44 (m, 11H), 2.92 (ddd, J=17.3, 13.7, 5.5 Hz, 1H), 2.68-2.54 (m, 1H), 2.46 (m, 1H), 2.02 (m, 1H), 1.41 (s, 9H). $^{13}$C NMR (126 MHz, DMSO) δ 173.3, 171.4, 167.9, 144.4, 134.9, 132.6, 129.2, 123.9, 117.9, 91.8, 81.8, 81.1, 72.8, 70.3, 70.2, 70.1, 70.0, 69.2, 68.6, 60.7, 58.6, 52.1, 47.4, 31.7, 28.2, 22.8. HRMS (ESI+): m/z calcd for C$_{28}$H$_{37}$N$_2$O$_9$ (M+H)$^+$ 545.2494, found 545.2482, m/z calcd for C$_{28}$H$_{36}$N$_2$O$_9$Na (M+Na)$^+$ 567.2313, found 567.2318. HPLC-MS (ESI+): m/z 567.3 [100%, (M+Na)$^+$]. HPLC-MS (ESI−): m/z 543.3 [100%, M−H$^−$].

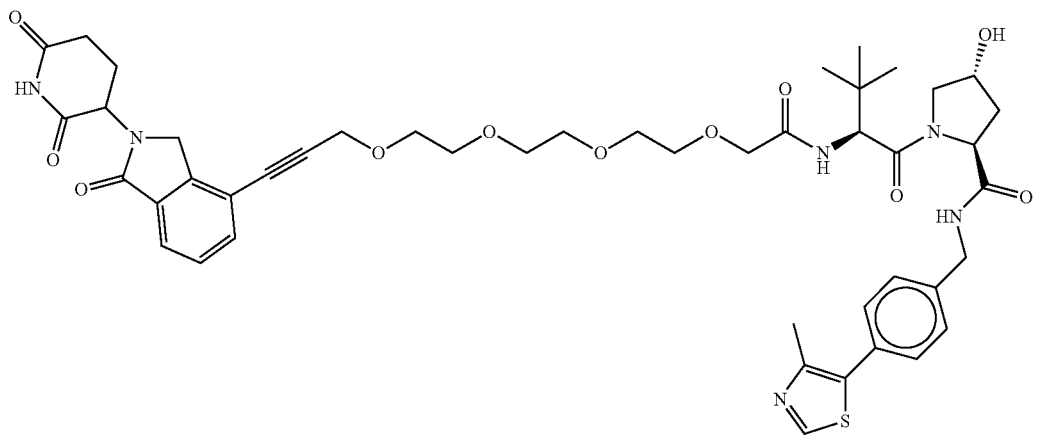

SR3-104

(2S,4R)-1-((2S)-2-(tert-Butyl)-18-(2-(2,6-dioxopiperidin-3-yl)-1-oxoisoindolin-4-yl)-4-oxo-6,9,12,15-tetraoxa-3-azaoctadec-17-ynoyl)-4-hydroxy-N-(4-(4-methylthiazol-5-yl)benzyl)pyrrolidine-2-carboxamide (SR3-104): The alkyne SR3-104 was obtained as a white foam (0.121 g, 73%) using tert-butyl ester SR3-097 (0.100 g, 0.184 mmol) by following the same two step method used to prepare the alkyne SR3-077. Analytical data for intermediate SR3-102: HPLC-MS (ESI+): m/z 489.2 [40%, (M+H)+], 511.2 [100%, (M+Na)+]. HPLC-MS (ESI−): m/z 487.2 [20%, M−H−]. Analytical data for SR3-104: HPLC: >99% [$t_R$=3.0 min, 70% MeOH, 30% water (with 0.1% TFA), 20 min]. $^1$H NMR (500 MHz, DMSO-$d_6$) δ 11.00 (s, 1H), 8.98 (s, 1H), 8.59 (t, J=6.1 Hz, 1H), 7.77 (dd, J=7.6, 1.0 Hz, 1H), 7.71 (dd, J=7.6, 1.0 Hz, 1H), 7.56 (t, J=7.6 Hz, 1H), 7.47-7.34 (m, 4H), 5.20-5.11 (m, 2H), 4.56 (d, J=9.6 Hz, 1H), 4.53-4.40 (m, 4H), 4.40-4.30 (m, 2H), 4.25 (dd, J=15.8, 5.6 Hz, 1H), 3.96 (s, 2H), 3.72-3.50 (m, 16H), 3.16 (d, J=16.3 Hz, 1H), 2.92 (ddd, J=17.2, 13.6, 5.4 Hz, 1H), 2.68-2.55 (m, 1H), 2.44 (s, 3H), 2.09-1.96 (m, 2H), 1.96-1.85 (m, 1H), 0.94 (s, 9H). $^{13}$C NMR (126 MHz, DMSO) δ 173.3, 172.2, 171.4, 169.6, 169.0, 167.9, 151.9, 148.2, 144.4, 139.9, 134.9, 132.5, 131.6, 130.1, 129.1, 127.9, 123.9, 117.9, 91.8, 81.7, 70.9, 70.3, 70.2, 70.1, 70.0, 69.3, 69.2, 66.8, 59.2, 58.5, 57.0, 56.1, 55.4, 54.1, 52.1, 47.4, 42.1, 38.4, 36.2, 31.7, 26.6, 22.8, 16.4. HRMS (ESI+): m/z calcd for $C_{46}H_{57}N_6O_{11}S$ (M+H)+ 901.3801, found 901.3806, m/z calcd for $C_{46}H_{56}N_6O_{11}SNa$ (M+Na)+ 923.3620, found 923.3618. HPLC-MS (ESI+): m/z 901.4 [80%, (M+H)+], 923.4 [90%, (M+Na)+]. HPLC-MS (ESI−): m/z 899.3 [100%, M−H−].

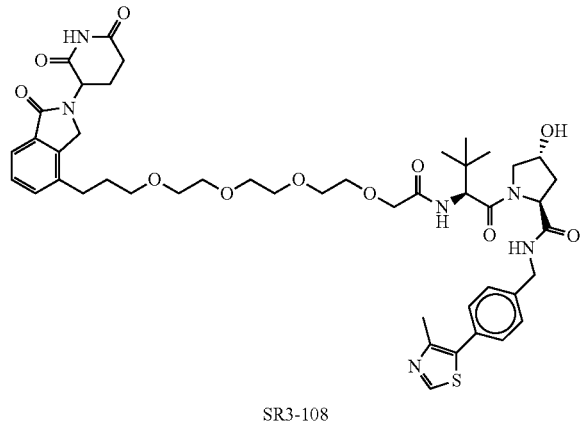

SR3-108

(2S,4R)-1-((2S)-2-(tert-Butyl)-18-(2-(2,6-dioxopiperidin-3-yl)-1-oxoisoindolin-4-yl)-4-oxo-6,9,12,15-tetraoxa-3-azaoctadecanoyl)-4-hydroxy-N-(4-(4-methylthiazol-5-yl)benzyl)pyrrolidine-2-carboxamide (SR3-108): The imide SR3-108 was obtained as a yellow solid (0.076 g, 85%) using alkyne precursor SR3-104 (0.090 g, 0.099 mmol) by following the same method used to prepare SR3-078. HPLC: >97% [$t_R$=3.2 min, 70% MeOH, 30% water (with 0.1% TFA), 20 min]. $^1$H NMR (500 MHz, DMSO-$d_6$) δ 10.99 (s, 1H), 8.98 (s, 1H), 8.59 (t, J=6.0 Hz, 1H), 7.57 (t, J=4.3 Hz, 1H), 7.51-7.34 (m, 7H), 5.15 (d, J=3.8 Hz, 1H), 5.12 (d, J=5.3 Hz, 1H), 4.57 (d, J=9.6 Hz, 1H), 4.50-4.33 (m, 4H), 4.33-4.21 (m, 2H), 3.96 (s, 2H), 3.71-3.41 (m, 14H), 3.41-3.34 (m, 2H), 2.93 (ddd, J=18.0, 13.5, 5.4 Hz, 1H), 2.71-2.58 (m, 3H), 2.44 (s, 3H), 2.42-2.34 (m, 1H), 2.14-1.95 (m, 2H), 1.95-1.87 (m, 1H), 1.87-1.74 (m, 2H), 0.94 (s, 9H). HRMS (ESI+): m/z calcd for $C_{46}H_{61}N_6O_{11}S$ (M+H)+ 905.4114, found 905.4116, m/z calcd for $C_{46}H_{60}N_6O_{11}SNa$ (M+Na)+ 927.3933, found 927.3923. HPLC-MS (ESI+): m/z 905.4 [40%, (M+H)+], 927.4 [100%, (M+Na)+]. HPLC-MS (ESI−): m/z 903.4 [100%, M−H−].

Synthetic scheme 25

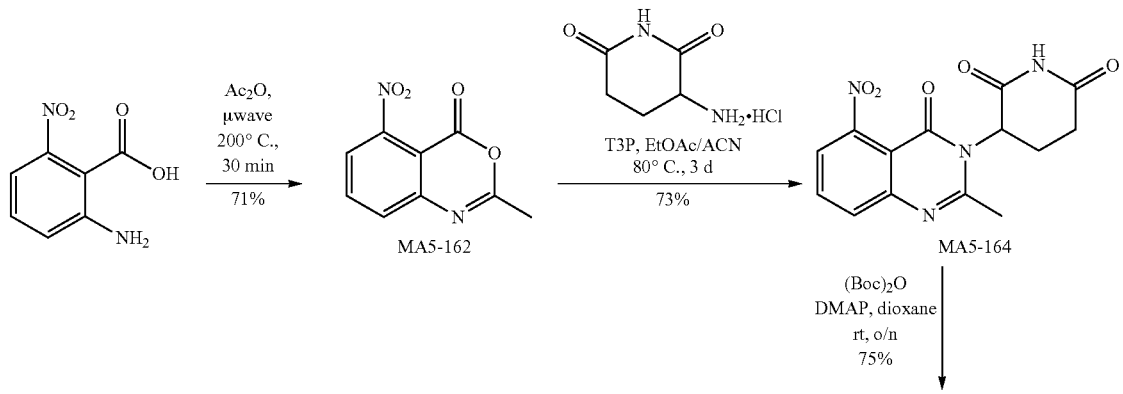

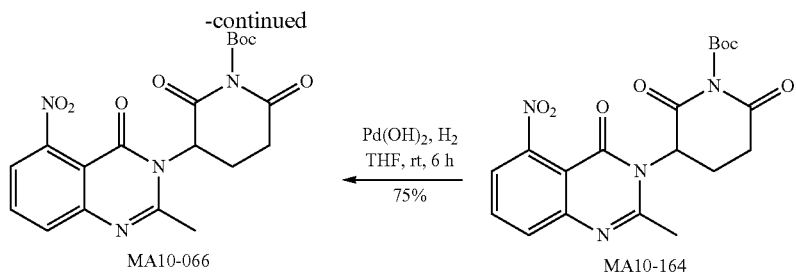

2-Methyl-5-nitro-4H-benzo[d][1,3]oxazin-4-one (MA5-162): In a microwave reaction vial (10 mL), 2-amino-6-nitrobenzoic acid (500 mg, 2.75 mmol) and acetic anhydride (5 mL) were heated in a Biotage Initiator microwave reactor at 200° C. for 30 minutes. After cooling, the excess acetic anhydride was evaporated to provide a dark brown solid (~550 mg) which was dissolved in EtOAc (~5 mL). Upon addition of hexane (~10 mL) and sonication, a light brown solid precipitated. The suspension was kept at 4° C. for 1 h and filtered. The solid obtained was washed with hexane (~20 mL) and air dried to provide the title compound as a beige solid (402 mg, 71%). $^1$H NMR (500 MHz, DMSO-d$_6$): δ 8.06 (t, J=8.0 Hz, 1H), 7.93 (dd, J=8.0, 1.5 Hz, 1H), 7.79 (dd, J=8.0, 1.1 Hz, 1H), 2.42 (s, 3H). HPLC-MS (ESI+): m/z 229.1 (M+Na)$^+$.

3-(2-Methyl-5-nitro-4-oxoquinazolin-3(4H)-yl)piperidine-2,6-dione (MA5-164): The oxazinone MA5-162 (4.30 g, 20.86 mmol) and 3-aminopiperidine-2,6-dione hydrochloride (3.78 g, 22.94 mmol) were dissolved in anhydrous acetonitrile. (23 mL) in a pressure vial followed by the addition of 50% solution of propanephosphonic acid anhydride (T$_3$P solution) in EtOAc (26.55 g) under argon. The vial was sealed and heated at 80° C. for 3 days. After the reaction was complete (as monitored by TLC), the temperature was reduced to 55° C. and water (30 mL) was carefully added (bubbling observed). The reaction was stirred at 55° C. for 30 minutes and at r.t. for 30 minutes. The precipitate was filtered off and washed with a mixture of ACN:water (1:1, 30 mL×2). The precipitate was dried overnight under high vacuum to furnish the title compound as a beige solid (4.83 g, 73%). $^1$H NMR (500 MHz, DMSO-d$_6$): δ 11.06 (s, 1H), 7.98 (t, J=8.0 Hz, 1H), 7.87 (dd, J=8.5, 1.0 Hz, 1H), 7.81 (dd, J=8.0, 1.1 Hz, 1H), 5.34 (dd, J=12.0, 5.5 Hz, 1H), 2.82 (ddd, J=17.8, 13.2, 3.3 Hz, 1H), 2.68 (s, 3H), 2.63-2.53 (m, 2H), 2.24-2.12 (m, 1H); HPLC-MS (ESI+): m/z 317.2 (M+H)$^+$.

tert-Butyl 3-(2-methyl-5-nitro-4-oxoquinazolin-3(4H)-yl)-2,6-dioxopiperidine-1-carboxylate (MA10-064): The glutarimide MA5-164 (2.0 g, 6.32 mmol) was suspended in anhydrous dioxane (25 mL) and (Boc)$_2$O (2.76 g, 12.65 mmol) and DMAP (92.1 mg, 0.76 mmol) were added under argon. After 20 h stirring at r.t., HPLC-MS showed ~30% of unreacted starting material. Additional (Boc)$_2$O (1.38 g, 6.32 mmol) and DMAP (92.1 g, 0.76 mmol) were added and reaction was stirred for 4 hours (TLC now showed only traces of unreacted starting material). The crude reaction mixture was partitioned between EtOAc (150 mL×2) and water (~100 mL). The organic layer was washed with brine (~50 mL) and evaporated. The crude solid obtained was triturated using EtOAc/hexane to provide the title product (1.92 g, 73%) (90% pure by HPLC-MS) which was used for the next step without further purification $^1$H NMR (500 MHz, DMSO-d$_6$): δ 7.92 (dd, J=8.3, 7.7 Hz, 1H), 7.80 (dd, J=8.3, 1.1 Hz, 1H), 7.76 (dd, J=7.7, 1.1 Hz, 1H), 5.53 (dd, J=11.9, 5.6 Hz, 1H), 2.94 (ddd, J=17.2, 14.0, 5.7 Hz, 1H), 2.77-2.68 (m, 1H), 2.61 (s, 3H), 2.58-2.44 (m, 1H), 2.16 (dtd, J=12.8, 5.6, 2.4 Hz, 1H), 1.41 (s, 9H). HPLC-MS (ESI+): m/z 417.2 (M+H)$^+$, 833.3 (2M+H)$^+$.

tert-Butyl 3-(5-amino-2-methyl-4-oxoquinazolin-3 (4H)-yl)-2,6-dioxopiperidine-1-carboxylate (MA10-066): The nitroarene MA10-064 (1.45 g, 3.48 mmol) was dissolved in dry THF (20 mL) and stirred under a hydrogen atmosphere (using standard hydrogenation balloon) in the presence of Pd(OH)$_2$ (20% on carbon, 244.5 mg, 0.35 mmol) for 4 h. Evaporation of the solvent and trituration from EtOAc/hexane furnished pure product MA10-066 as a beige solid (1.01 g, 75%). $^1$H NMR (500 MHz, DMSO-d$_6$): δ 7.99 (dd, J=8.3, 7.6 Hz, 1H), 7.88 (dd, J=8.0, 1.1 Hz, 1H), 7.87 (dd, J=8.0, 1.1 Hz, 2H), 7.83 (dd, J=8.0, 1.1 Hz, 2H), 5.60 (dd, J=11.9, 5.6 Hz, 1H), 3.01 (ddd, J=17.2, 14.0, 5.7 Hz, 1H), 2.79 (ddd, J=17.1, 4.5, 2.4 Hz, 1H), 2.68 (s, 3H), 2.65-2.53 (m, 1H), 2.27-2.18 (m, 1H), 1.48 (s, 9H). HPLC-MS (ESI+): m/z 387.2 (M+H)⁺.

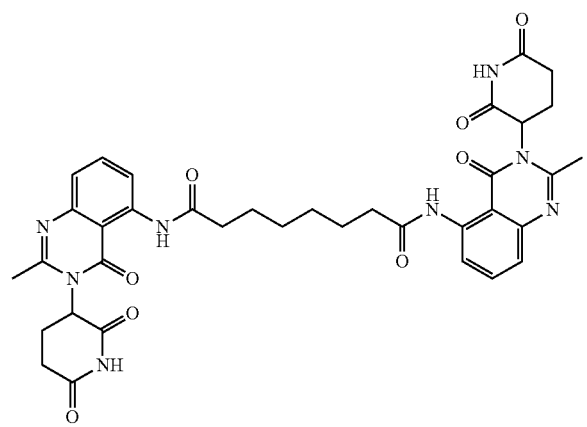

MA10-077

N1,N8-bis(3-(2,6-dioxopiperidin-3-yl)-2-methyl-4-oxo-3,4-dihydroquinazolin-5-yl)octanediamide (MA10-077): In an oven dried reaction vial, aniline MA10-066 was dissolved in dry DCM (0.4 mL) and DIPEA (0.165 mL, 4.0 equiv.) was added at r.t. After 10 minutes stirring at r.t., suberoyl chloride (0.25 M stock in DCM, 0.948 uL, 2.20 equiv.) was added (dropwise, ~50 minutes) and the reaction stirred at r.t. for 4.5 h. The HPLC-MS and TLC analysis showed traces of the starting material left. Evaporation of the volatiles and SiO₂ column chromatography (gradient DCM-MeOH as eluent) resulted in mixed fractions of mono-deboc and bis-deboc products. All of the fractions were combined and after evaporation, treated with a 1:1 mixture of TFA:DCM (6 mL) for 2 h. After the completion of deprotection of the Boc group (as indicated by TLC), the volatiles were evaporated and the crude was directly subjected to SiO₂ column chromatography eluting with DCM/MeOH/TEA albeit no separation was seen. The crude product was thus purified using preparative HPLC eluting with MeOH—H₂O, 0.1% TFA to obtain the title compound MA10-077 as light yellow solid (51 mg, 30%). Note: While ¹H-NMR and ¹³C-NMR showed a single product, the HPLC-MS and HPLC indicated a mixture of diastereomers. HPLC Method 1: 96% [t$_R$=16.3 min, gradient 5-95% MeOH and water (with 0.1% TFA), 20 min], HPLC Method 2: 99% [t$_{R1}$=7.9 min, t$_{R2}$=8.8 min, 60% MeOH, 40% water (with 0.1% TFA), 20 min]. ¹H NMR (500 MHz, DMSO-d₆): δ 11.72 (s, 2H), 11.07 (s, 2H), 8.54 (dd, J=8.2, 2.9 Hz, 2H), 7.75 (td, J=8.2, 2.8 Hz, 2H), 7.26 (dd, J=7.9, 3.0 Hz, 2H), 5.31 (dd, J=11.7, 5.7 Hz, 2H), 2.85 (ddd, J=16.4, 13.5, 5.6 Hz, 2H), 2.76-2.58 (m, 8H), 2.46-2.35 (m, 4H), 2.19 (ddd, J=11.4, 6.5, 4.1 Hz, 2H), 1.70-1.47 (m, 5H), 1.40-1.23 (m, 5H). HPLC-MS (ESI+): m/z 711.3 [(M+H)⁺], 356.2 [(M+2H)²⁺]. HRMS (ESI+): m/z calcd for C₃₆H₃₉N₈O₈ (M+H)⁺ 711.2885, found 711.2875.

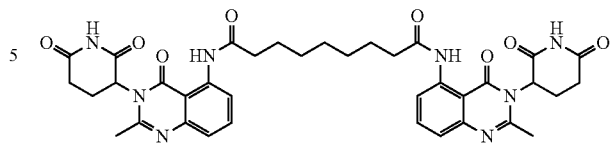

MA10-086

N1,N9-bis(3-(2,6-Dioxopiperidin-3-yl)-2-methyl-4-oxo-3,4-dihydroquinazolin-5-yl)nonanediamide (MA10-086): This compound was obtained by the reaction of azelaoyl chloride (0.25M in DCM, 0.942 mL) and MA10-066 (200 mg, 2.2 equiv.) using the same procedure described for the synthesis of MA10-077. The crude Boc-protected intermediate obtained was directly subjected to deprotection (stirred with 8 mL of 1:1 mixture of TFA:DCM at rt for 3 h). After evaporation of the volatiles, the crude product was purified using SiO₂ column chromatography eluting with gradient DCM-MeOH. The title compound MA10-086 was obtained as a beige solid (31 mg, 18%). HPLC: 97% [t$_R$=16.9 min, gradient 5-95% MeOH and water (with 0.1% TFA), 20 min]. ¹H NMR (500 MHz, DMSO-d₆): δ 11.74 (s, 2H), 11.07 (s, 2H), 8.56 (ddd, J=8.3, 2.4, 1.1 Hz, 2H), 7.76 (td, J=8.1, 2.1 Hz, 3H), 7.27 (ddd, J=8.1, 2.2, 1.1 Hz, 2H), 5.32 (dd, J=11.7, 5.7 Hz, 2H), 2.92-2.81 (m, 2H), 2.74-2.61 (m, 9H), 2.45-2.33 (m, 4H), 2.23-2.15 (m, 2H), 1.69-1.51 (m, 5H), 1.35-1.22 (m, 6H). HPLC-MS (ESI+): m/z 725.3 [(M+Na)⁺], 747.3 [(M+H)⁺], 363.2 [(M+2H)²⁺]. HRMS (ESI+): m/z calcd for C₃₇H₄₀N₈O₈Na (M+Na)⁺ 747.2861, found 747.2850.

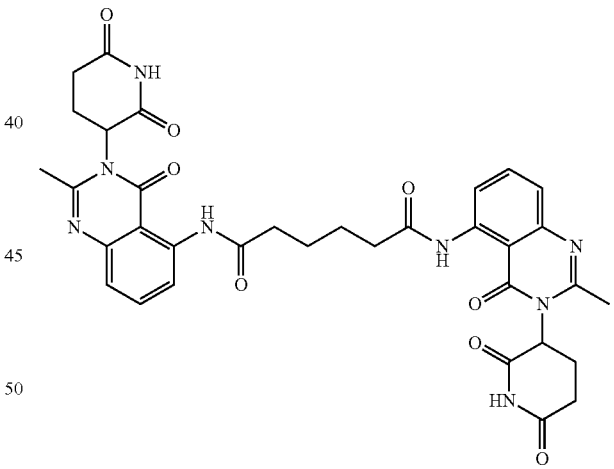

MA10-088

N1,N6-bis(3-(2,6-Dioxopiperidin-3-yl)-2-methyl-4-oxo-3,4-dihydroquinazolin-5-yl)adipamide (MA10-088): This was obtained by the reaction of adipoyl chloride (0.25M in DCM, 0.940 mL) and MA10-066 (200 mg, 2.2 equiv.) using the same procedure described for the synthesis of MA10-077. The crude Boc-protected intermediate was directly subjected to deprotection (stirred with 10 mL of 1:1 mixture of TFA:DCM at r.t. for 3 h). After evaporation of the volatiles, the crude product was purified using prep purification eluting with MeOH—H₂O, 0.1% TFA to provide the title compound MA10-088 as a beige solid (51 mg, 30%). ¹H NMR (500 MHz, DMSO-d₆): δ 11.72 (d, J=2.3 Hz, 2H), 11.07 (s, 2H), 8.55 (q, J=6.7 Hz, 2H), 7.74 (q, J=8.3 Hz, 2H), 7.32-7.20 (m, 2H), 5.32 (dd, J=11.7, 5.6 Hz, 2H), 2.92-2.82 (m, 2H), 2.76-2.58 (m, 9H), 2.47-2.42 (m, 3H), 2.26-2.13 (m, 3H), 1.73-1.49 (m, 5H). Note: diastereomers showing doublets/duplicated peaks. HPLC-MS (ESI+): m/z 683.3 [(M+H)$^+$], 342.3 [(M+2H)$^{2+}$]. HRMS (ESI+): m/z calcd for $C_{34}H_{34}N_8O_8Na$ (M+Na)$^+$ 705.2392, found 705.2390.

2H)$^{2+}$]. HRMS (ESI+): m/z calcd for $C_{38}H_{42}N_8O_8Na$ (M+Na)$^+$ 761.3018, found 761.3013.

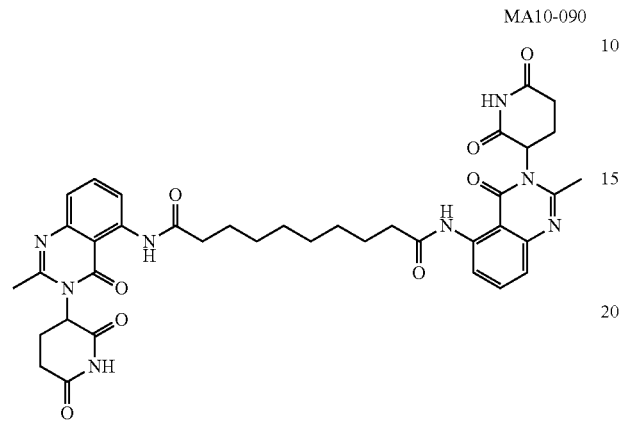

MA10-090

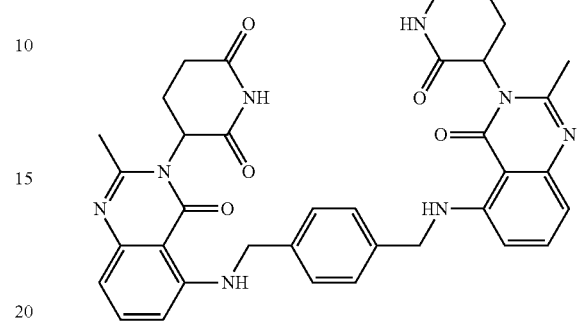

MA10-112

N1,N10-bis(3-(2,6-Dioxopiperidin-3-yl)-2-methyl-4-oxo-3,4-dihydroquinazolin-5-yl)decanediamide (MA10-090): This compound was obtained by the reaction of sebacoyl chloride (0.25M in DCM, 0.937 mL) and MA10-066 (200 mg, 2.2 equiv.) using the same procedure described for the synthesis of MA10-077. The crude Boc-protected intermediate was directly subjected to deprotection (i.e. stirred with 10 mL of 1:1 mixture of TFA:DCM at r.t. for 3 h). After evaporation of the volatiles, the crude product was purified using SiO$_2$ column chromatography eluting with gradient DCM-MeOH. The title compound MA10-090 was obtained as an off-white solid (43 mg, 25%). HPLC: 95% [t$_R$=17.5 min, gradient 5-95% MeOH and water (with 0.1% TFA), 20 min]. $^1$H NMR (500 MHz, DMSO-d$_6$): δ 11.76 (s, 2H), 11.03 (s, 1H), 8.65-8.49 (m, 2H), 7.75 (td, J=8.2, 1.6 Hz, 2H), 7.26 (d, J=8.1 Hz, 2H), 2.85-2.78 (m, 2H), 2.75-2.66 (m, 2H), 2.63 (s, 6H), 2.61-2.57 (m, 2H), 2.41-2.34 (m, 4H), 2.23-2.11 (m, 2H), 1.67-1.55 (m, 4H), 1.33-1.23 (m, 9H). HPLC-MS (ESI+): m/z 739.4 [(M+H)$^+$], 370.2 [(M+

3,3'-(((1,4-Phenylenebis(methylene))bis(azanediyl))bis(2-methyl-4-oxoquinazoline-5,3(4H)-diyl))bis(piperidine-2,6-dione) (MA10-112): To 1,4-bis(bromomethyl)benzene (20 mg, 1 equiv.) and MA10-066 (64.4 mg, 2.2 equiv.) in dry acetonitrile (0.6 mL) was added potassium iodide (5 mg, 0.4 equiv.) under argon. The reaction mixture was heated in a microwave reactor at 80° C. for 2 h followed by heating at 100° C. for 1 additional hour. After failing to purify the desired product using SiO$_2$ column chromatography, the crude product was purified using preparative HPLC (eluent: MeOH, water 0.1% formic acid). The title compound MA10-112 was obtained as an off-white solid (14 mg, 27%). HPLC: 96% [t$_R$=17.3 min, gradient 5-95% MeOH and water (with 0.1% TFA), 20 min]. $^1$H NMR (500 MHz, DMSO-d$_6$): δ 10.97 (s, 2H), 8.75 (dt, J=6.7, 3.2 Hz, 2H), 8.17 (s, 1H), 7.42 (t, J=8.1 Hz, 2H), 7.31 (brs, 4H), 6.65 (d, J=7.8 Hz, 2H), 6.45 (d, J=8.3 Hz, 2H), 5.18 (dd, J=11.5, 5.8 Hz, 2H), 4.41 (d, J=5.8 Hz, 4H), 2.82 (ddd, J=16.2, 13.4, 5.4 Hz, 2H), 2.70-2.57 (m, 4H), 2.56 (s, 6H), 2.20-2.11 (m, 2H). HPLC-MS (ESI+): m/z 675.3 [(M+H)$^+$], 338.2 [(M+2H)$^{2+}$]. HRMS (ESI+): m/z calcd for $C_{36}H_{35}N_8O_6$ (M+H)+ 675.2674, found 675.2658.

Synthetic Scheme 26

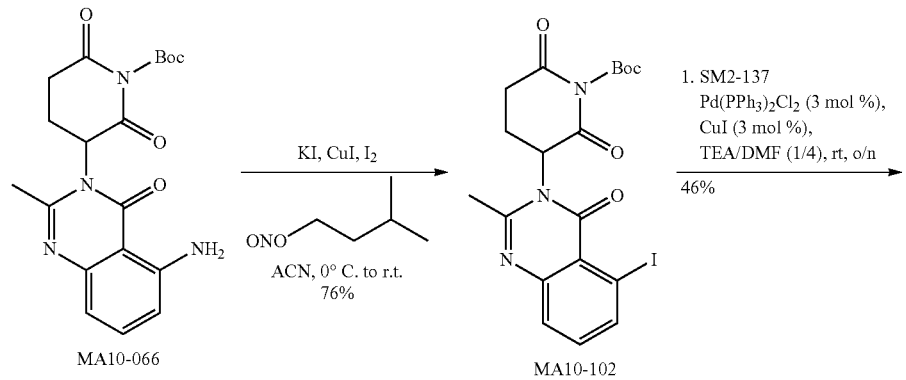

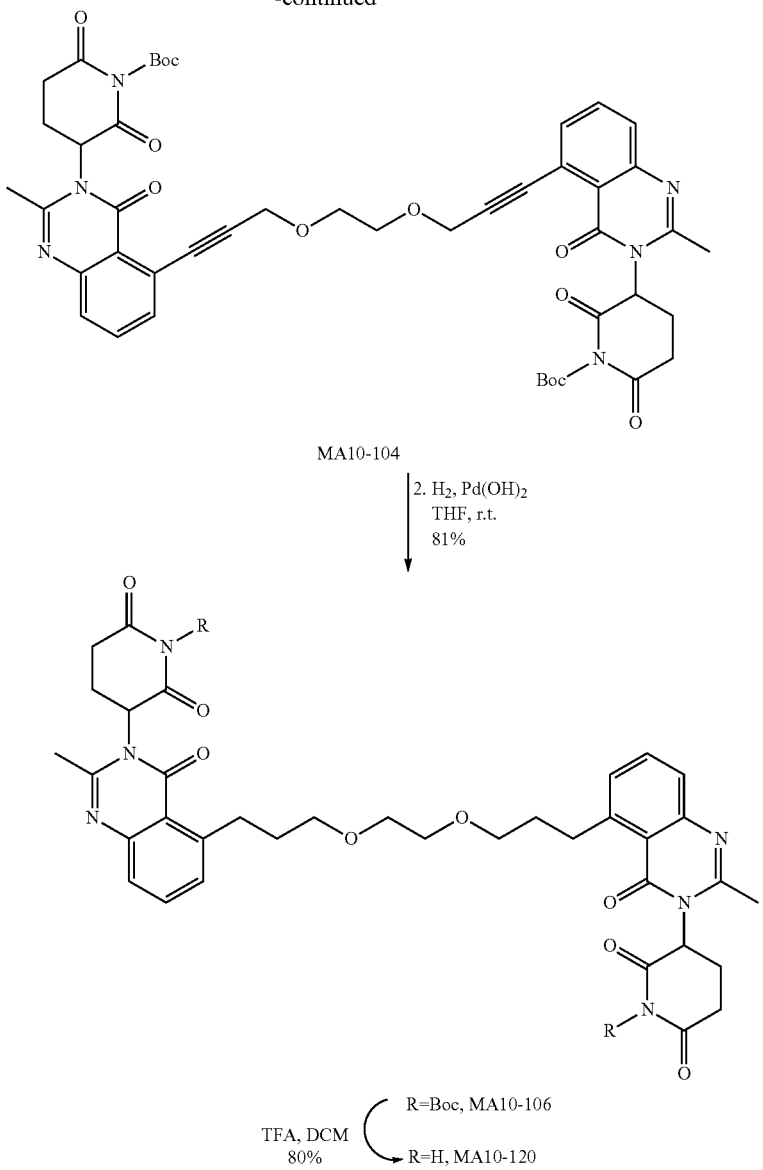

3,3'-(((Ethane-1,2-diylbis(oxy))bis(propane-3,1-diyl))bis(2-methyl-4-oxoquinazoline-5,3(4H)-diyl))bis(piperidine-2,6-dione) (MA10-120): The iodoarene MA10-102 was synthesized from MA10-066 (Scheme 25). The Boc-protected glutarimide MA10-066 (0.129 mmol, 50.00 mg) was dissolved in acetonitrile (1.5 mL), and potassium iodide (26.00 mg, 0.155 mmol), copper(I) iodide (29.6 mg, 0.155 mmol) and iodine (39.4 mg, 0.155 mmol) were added at 0° C. Then isoamylnitrite was added dropwise over 20 min at 0° C. and the reaction stirred for 30 min. at 0° C. and then warmed to r.t. The reaction was complete around 2 h (as monitored by TLC). Saturated NH$_4$Cl (10 ml) was added to the mixture, which was then extracted with EtOAc. The organic layer was dried (Na$_2$SO$_4$) and evaporated. The solid obtained was triturated with DCM to obtain MA10-102 (49 mg, 76%) and used in the next step without further purification. MA10-102 HPLC-MS (ESI+): m/z 498 [(M+H)$^+$]. The bis-alkyne MA10-104 was synthesized via Pd-mediated coupling of MA10-102 and SM2-137 using the procedure used to make the precursor of SM2-143. The bis-alkyne MA10-104 (48 mg, 46%) was obtained as an off-white solid. HPLC-MS (ESI+): m/z 877 [(M+H)$^+$]. Hydrogenation of the bis-alkyne MA10-104 using palladium hydroxide (20% on carbon) under a balloon of hydrogen at r.t. provided the bis-Boc-derivative MA10-106 as an off-white solid (36 mg, 81%). MA10-106 HPLC-MS (ESI+): m/z 885 [(M+H)$^+$]. The bis-Boc-derivative MA10-106 was dissolved in dry DCM (1 mL) and TFA (1 mL) added to the solution. The reaction was stirred at r.t. for 2 h. HPLC-MS confirmed the complete consumption of the starting material. The solvent and TFA was evaporated. The crude mixture was purified using preparative HPLC (eluent: MeOH, water 0.1% formic acid) to provide the title compound MA10-120 as an off-white solid (21 mg, 80%). HPLC: 98% [t$_R$=16.5 min, gradient 5-95% MeOH and water (with 0.1% TFA), 20 min]. $^1$H NMR (500 MHz, DMSO-d$_6$): δ 11.01 (s, 2H), 7.66 (t, J=8.0 Hz, 2H), 7.45 (d, J=8.1 Hz, 2H), 7.25 (d, J=7.5 Hz, 2H), 5.21 (dd, J=11.6, 5.7 Hz, 2H), 3.51-3.46 (m, 5H), 3.42-3.33 (m, 5H), 3.21-3.12 (m, 4H), 2.89-2.79 (m, 2H), 2.68-2.63 (m, 1H), 2.62 (s, 6H), 2.57-2.52 (m, 1H), 2.18-2.11 (m, 2H), 1.78-1.67 (m, 4H). HPLC-MS (ESI+): m/z 685.3 [(M+H)⁺], 343.2 [(M+2H)²⁺]. HRMS (ESI+): m/z calcd for C₃₆H₄₀N₆O₈ (M+Na)⁺ 707.2800, found 707.2785.

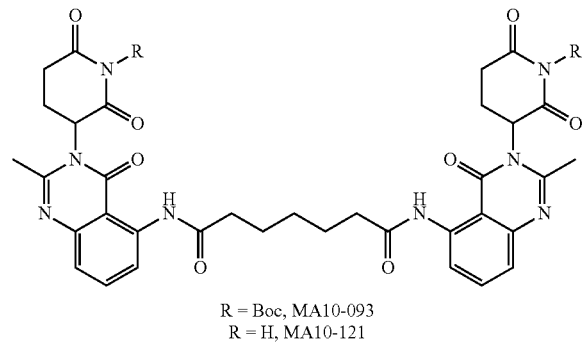

R = Boc, MA10-093
R = H, MA10-121

N1,N7-bis(3-(2,6-Dioxopiperidin-3-yl)-2-methyl-4-oxo-3,4-dihydroquinazolin-5-yl)heptanediamide (MA10-121): The bis-(Boc-glutarimide) MA10-093 was prepared from MA10-066 and pimeloyl chloride similar to the procedure described for MA10-90. The title compound MA10-121 was prepared via deprotection of intermediate MA10-093 (36 mg, 1 equiv.) using TFA:DCM (1:1, 2 mL) in a similar procedure as described for MA10-120. The crude product was triturated using EtOAc and hexane to obtain the title compound as a white powder (15 mg, 31%). ¹H NMR (500 MHz, DMSO-d₆): δ 11.73 (brs, 2H), 11.06 (s, 2H), 8.54 (dd, J=8.3, 4.4 Hz, 2H), 7.75 (td, J=8.2, 3.0 Hz, 2H), 7.27 (dd, J=8.1, 2.2 Hz, 2H), 5.31 (dd, J=11.7, 5.7 Hz, 2H), 2.84 (ddd, J=16.4, 13.7, 5.6 Hz, 2H), 2.74-2.67 (m, 2H), 2.64 (s, 6H), 2.62-2.54 (m, 2H), 2.41 (dd, J=8.1, 6.3 Hz, 4H), 2.18 (ddt, J=11.8, 5.9, 3.3 Hz, 2H), 1.64 (p, J=7.4 Hz, 4H), 1.38 (q, J=7.7, 5.3 Hz, 2H). HPLC-MS (ESI+): m/z 697.3 [(M+H)⁺]. HRMS (ESI+): m/z calcd for C₃₅H₃₆N₈O₈Na+ (M+Na)⁺ 719.2548, found 719.2539.

MA10-126

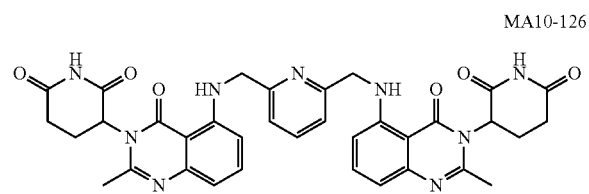 [SMILES: Cc1nc2cccc(NCc3cccc(CNc4cccc5nc(C)n(C6CCC(=O)NC6=O)c(=O)c45)n3)c2c(=O)n1C1CCC(=O)NC1=O]

3,3'-(((Pyridine-2,6-diylbis(methylene))bis(azanediyl))bis(2-methyl-4-oxoquinazoline-5,3(4H)-diyl))bis(piperidine-2,6-dione) (MA10-126): This was prepared by the reaction of 2,6-bis(bromomethyl)pyridine (30 mg, 1 equiv.) and MA10-066 (96.3 mg, 2.2 equiv.) using a procedure described for the synthesis of MA10-112. The product was purified using preparative HPLC (eluent: MeOH, water 0.1% formic acid). The title compound was obtained as an off white solid (3.9 mg, 5%). HPLC: 93% [t_R=15.3 min, gradient 5-95% MeOH and water (with 0.1% TFA), 20 min]. HPLC-MS (ESI+): m/z 676.3 [(M+H)⁺], 338.8 [(M+2H)²⁺].

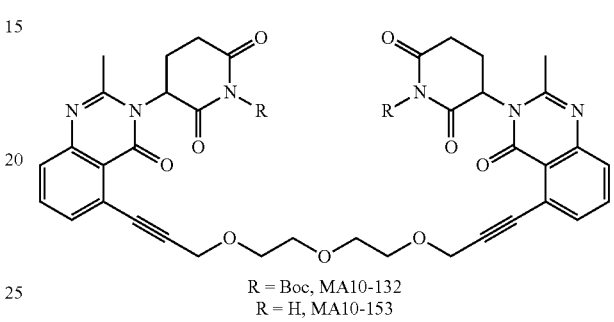

R = Boc, MA10-132
R = H, MA10-153

3,3'-((((Oxybis(ethane-2,1-diyl))bis(oxy))bis(prop-1-yne-3,1-diyl))bis(2-methyl-4-oxoquinazoline-5,3(4H)-diyl))bis(piperidine-2,6-dione) (MA10-153): The dimer MA10-132 was prepared using MA10-102 and SM2-137 similar to the procedure described for SM2-143 precursor. MA10-132 HPLC-MS (ESI+): m/z 921.4 [(M+H)⁺]. The dimer MA10-153 was synthesized via deprotection of the Boc-intermediate MA10-132 (10.33 mg, 0.11 mmol) using TFA:DCM (1:1, 2 mL) in a similar procedure as described for MA10-120. The crude mixture was triturated with DCM and hexane to obtain the title compound MA10-153 as a light yellow solid (6.2 mg, 77%). HPLC: 98% [t_R=14.5 min, gradient 5-95% MeOH and water (with 0.1% TFA), 20 min]. ¹H NMR (500 MHz, DMSO-d₆): δ 11.02 (s, 2H), 7.73 (td, J=7.9, 2.0 Hz, 2H), 7.59-7.54 (m, 4H), 5.23 (dd, J=11.5, 5.6 Hz, 2H), 4.44 (s, 4H), 3.59 (t, J=4.7 Hz, 8H), 2.89-2.78 (m, 2H), 2.69-2.56 (m, 10H), 2.20-2.10 (m, 2H). HPLC-MS (ESI+): m/z 721.4 [(M+H)⁺], 361.3 [(M+2H)²⁺]. HRMS (ESI+): m/z calcd for C₃₈H₃₆N₆O₉NH₄ (M+NH₄)⁺ 738.2882, found 738.2868.

Synthetic scheme 27

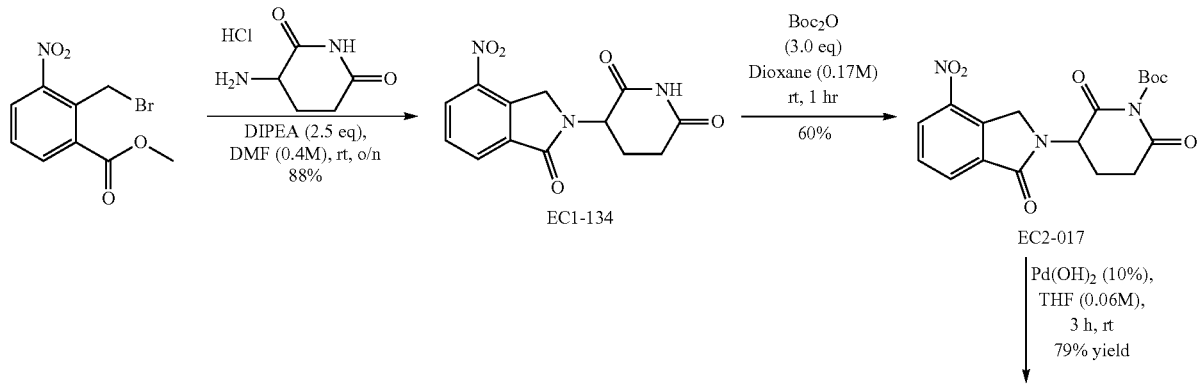

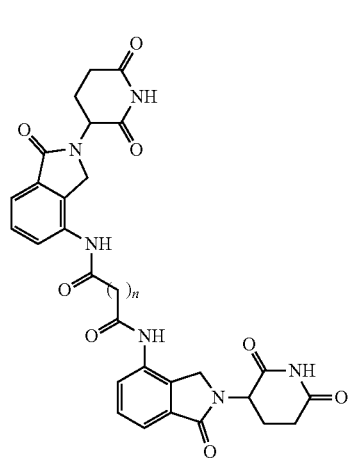 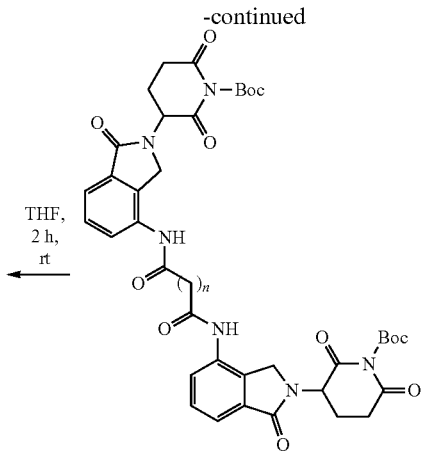 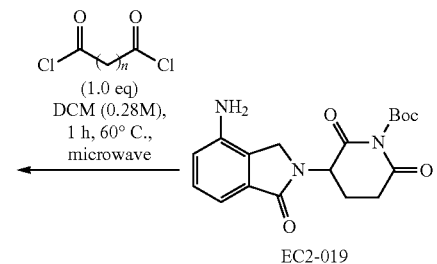

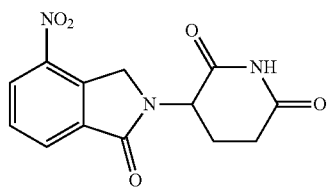

3-(4-Nitro-1-oxoisoindolin-2-yl)piperidine-2,6-dione (EC1-134): Methyl 2-(bromomethyl)-3-nitrobenzoate (4.0 g, 14.6 mmol, 1.0 eq.) was added to a solution of 3-aminopiperidine-2,6-dione.HCl (3.4 g, 20.4 mmol, 1.4 eq.) and DIPEA (6.4 mL, 2.5 eq.) in dry DMF (37 mL) and the solution was stirred under Argon at 50° C.; overnight. The purple suspension that formed was cooled to room temperature and the solvent was removed under reduced pressure. The residue was triturated with MeOH (ca. 20 mL), filtered and washed further with MeOH (3×10 mL) to give 3-(4-nitro-1-oxoisoindolin-2-yl)piperidine-2,6-dione (EC1-134) as a grey solid (3.7 g, 88%) and was used in the next step without further purification. $^1$H NMR (500 MHz, DMSO-$d_6$) δ 11.04 (s, 1H), 8.48 (dd, J=8.2, 1.0 Hz, 1H), 8.20 (dd, J=7.5, 1.0 Hz, 1H), 7.86 (t, J=7.8 Hz, 1H), 5.19 (dd, J=13.3, 5.2 Hz, 1H), 4.92 (d, J=19.2 Hz, 1H), 4.81 (d, J=19.2 Hz, 1H), 2.98-2.86 (m, 1H), 2.67-2.53 (m, 2H), 2.07-1.99 (m, 1H); HPLC-MS (ESI−): m/z 288.2 [100%, (M−H)$^+$], 576.1 [20%, (2M−2H)$^{2+}$]. (See WO2013/126394).

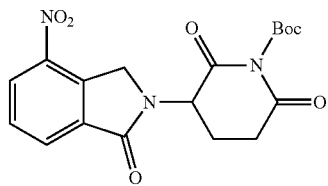

Tert-butyl 3-(4-nitro-1-oxoisoindolin-2-yl)-2,6-dioxopiperidine-1-carboxylate (EC2-017): The glutarimide 3-(4-nitro-1-oxoisoindolin-2-yl)piperidine-2,6-dione EC1-134 (2.0 g, 6.9 mmol, 1.0 eq.) was suspended in dry dioxane (20 mL), DMAP (168 mg, 0.2 eq.) was then added and the mixture was stirred under Argon for 2-3 minutes. A solution of Boc$_2$O (4.5 g, 20.7 mmol, 3.0 eq.) in dry dioxane (20 mL) was added dropwise and the reaction was stirred for 1.5 hours at room temperature. The residue was partitioned between EtOAc (50 mL) and H$_2$O (50 mL) and the two phases were separated. The organic phase was washed with brine (100 mL), dried (MgSO$_4$), filtered and the solvent evaporated under reduced pressure. The crude material was purified by column chromatography (0-100% EtOAc:hexane, 1% Et$_3$N) to give tert-butyl 3-(4-nitro-1-oxoisoindolin-2-yl)-2,6-dioxopiperidine-1-carboxylate (EC2-017) (1.5 g, 56%) as an orange foam. $^1$H NMR (500 MHz, DMSO-$d_6$) δ 8.27 (dd, J=8.2, 0.9 Hz, 1H), 7.99 (dd, J=7.5, 1.0 Hz, 1H), 7.64 (t, J=7.8 Hz, 1H), 5.20 (dd, J=13.4, 5.2 Hz, 1H), 4.73 (d, J=19.2 Hz, 1H), 4.62 (d, J=19.2 Hz, 1H), 2.96-2.87 (m, 1H), 2.63-2.54 (m, 1H), 2.50-2.37 (m, 1H), 1.92-1.82 (m, 1H), 1.27 (s, 9H); HPLC-MS (ESI+): m/z 290.1 [60%, (M−Boc+H)$^+$], 412.2 [60%, (M+Na)$^+$], 801.3 [100%, (2M+Na)$^+$].

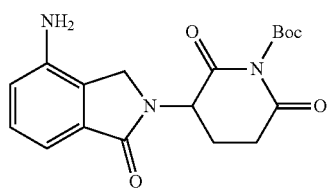

Tert-butyl 3-(4-amino-1-oxoisoindolin-2-yl)-2,6-dioxopiperidine-1-carboxylate (EC2-019): A suspension of Pd(OH)$_2$ (10% on carbon, 253 mg, 0.1 eq.) in dry THF (10 mL) was degassed for 15 minutes, the system was evacuated and refilled with H$_2$ (3 times) and then kept under H$_2$ atmosphere for 5 minutes. A degassed solution of tert-butyl 3-(4-nitro-1-oxoisoindolin-2-yl)-2,6-dioxopiperidine-1-carboxylate (EC2-017) (1.4 g, 3.60 mmol, 1.0 eq.) in dry THF (50 mL) was added slowly to the suspension and the reaction was stirred at room temperature under H$_2$ atmosphere for 3 hours. The suspension was filtered through Celite® (ca. 2 inch) and washed with THF (ca. 50 mL). The solvent evaporated under reduced pressure and the residue was purified by column chromatography (0-100% EtOAc:hexane, 1% Et$_3$N) to give tert-butyl 3-(4-amino-1-oxoisoindolin-2-yl)-2,6-dioxopiperidine-1-carboxylate EC2-019 (1.1 g, 72%) as a yellow solid. $^1$H NMR (500 MHz, DMSO-$d_6$) δ 7.20 (t, J=7.7 Hz, 1H), 6.93 (dd, J=7.5, 0.9 Hz, 1H), 6.81 (dd, J=7.9, 0.9 Hz, 1H), 5.45 (s, 2H), 5.35 (dd, J=13.4, 5.1

Hz, 1H), 4.24 (d, J=16.8 Hz, 1H), 4.11 (d, J=16.8 Hz, 1H), 3.20-3.09 (m, 1H), 2.86-2.77 (m, 1H), 2.44-2.32 (m, 1H), 2.15-2.06 (m, 1H), 1.49 (s, 9H); HPLC-MS (ESI+): m/z 260.2 [100%, (M-Boc+H)⁺], 719.3 [80%, (2M+H)⁺], 741.3 [20%, (2M+Na)⁺].

General Procedure A:

Tert-butyl 3-(4-amino-1-oxoisoindolin-2-yl)-2,6-dioxopiperidine-1-carboxylate EC2-019 (150 mg, 0.42 mmol, 2.1 eq.) was suspended in dry CH₂Cl₂ (1.5 mL), the bis-acyl chloride (0.2 mmol, 1.0 eq.) and DIPEA (70 µL, 0.42 mmol, 2.1 eq.) were added and the suspension was heated in the microwave reactor at 60° C.; for 1 hour. The solvent was removed under reduced pressure and the residue purified by column chromatography (0-100% EtOAc:hexane, 1% Et₃N) to give the corresponding Boc-protected dimer.

(EC2-028)

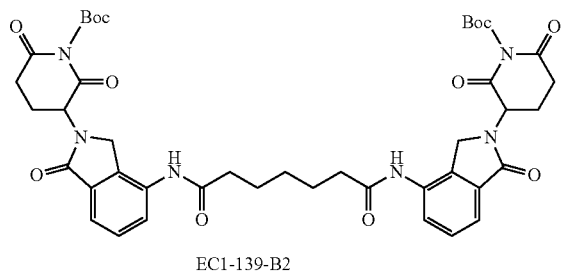

EC1-139-B2

Di-tert-butyl 3,3'-((heptanedioylbis(azanediyl))bis(1-oxoisoindoline-4,2-diyl))bis(2,6-dioxopiperidine-1-carboxylate) (EC1-139): This was obtained as a white solid (101 mg, 60%) from pimeloyl chloride (39 mg, 0.2 mmol, 1.0 eq.), following the General Procedure A. ¹H NMR (500 MHz, DMSO-d₆) δ 9.77 (s, 2H), 7.84 (d, J=7.6 Hz, 2H), 7.54-7.44 (m, 4H), 5.39 (dd, J=13.4, 5.1 Hz, 2H), 4.42 (dd, J=17.4, 4.6 Hz, 2H), 4.36 (d, J=17.4 Hz, 2H), 3.17-3.08 (m, 2H), 2.83-2.75 (m, 2H), 2.49-2.34 (m, 6H), 2.13-2.02 (m, 2H), 1.67 (m, 4H), 1.49 (s, 18H), 1.44-1.35 (m, 2H); HPLC-MS (ESI+): m/z 643.3 [75%, (M-2Boc+H)⁺], 865.3 [100%, (M+Na)⁺].

EC1-143

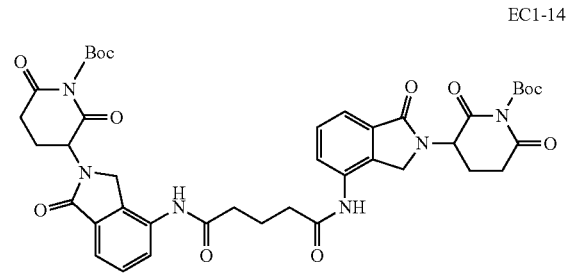

Di-tert-butyl 3,3'-((glutaroyl bis(azanediyl))bis(1-oxoisoindoline-4,2-diyl))bis(2,6-dioxopiperidine-1-carboxylate) (EC1-143): This was obtained as a white solid (113 mg, 69%), from glutaryl chloride (26 µL, 0.2 mmol, 1.0 eq.), following the General Procedure A. ¹H NMR (500 MHz, DMSO-d₆) δ 9.88 (s, 2H), 8.00-7.88 (m, 2H), 7.60-7.52 (m, 4H), 5.44 (ddd, J=13.5, 5.4, 1.4 Hz, 2H), 4.48 (d, J=17.4 Hz, 2H), 4.42 (d, J=17.4 Hz, 2H), 3.16-3.21 (m, 2H), 2.82-2.86 (m, 2H), 2.54-2.42 (m, 4H), 2.18-2.08 (m, 2H), 2.08-1.97 (m, 2H), 1.54 (s, 18H), 1.36-1.26 (m, 2H); HPLC-MS (ESI+): m/z 615.3 [85%, (M-2Boc+H)⁺], 837.4 [100%, (M+Na)⁺].

EC1-142

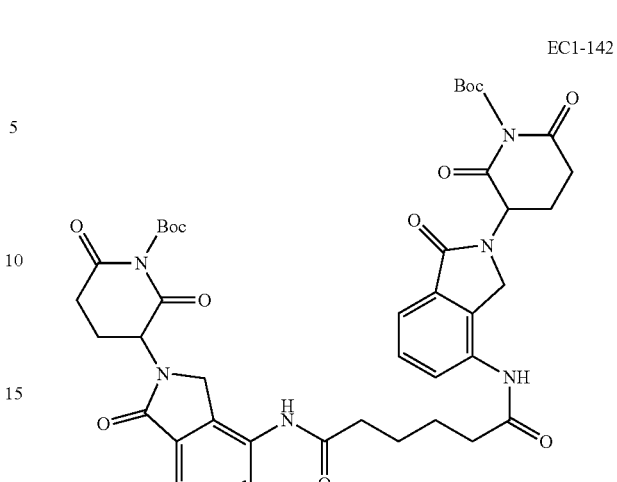

Di-tert-butyl 3,3'-((adipoylbis(azanediyl))bis(1-oxoisoindoline-4,2-diyl))bis(2,6-dioxopiperidine-1-carboxylate) (EC1-142): This was obtained as a white solid (92 mg, 56%), from adipoyl chloride (29 µL, 0.2 mmol, 1.0 eq.), following the General Procedure A. ¹H NMR (500 MHz, DMSO-d₆) δ 9.86 (s, 2H), 7.91 (dd, J=7.4, 1.5 Hz, 2H), 7.61-7.52 (m, 4H), 5.45 (dd, J=13.4, 5.1 Hz, 2H), 4.49 (d, J=17.2 Hz, 2H), 4.42 (d, J=17.2 Hz, 2H), 3.26-3.13 (m, 2H), 2.89-2.78 (m, 2H), 2.54-2.40 (m, 5H), 2.17-2.10 (m, 1H), 1.78-1.71 (m, 3H), 1.54 (s, 18H), 1.38-1.27 (m, 3H); HPLC-MS (ESI+): m/z 629.3 [100%, (M-2Boc+H)⁺], 851.3 [100%, (M+Na)⁺].

EC1-140

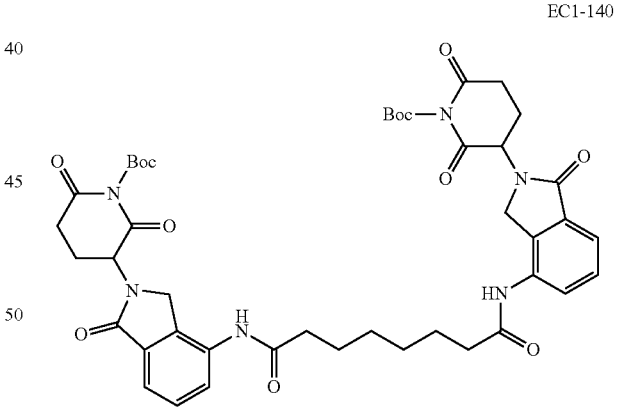

Di-tert-butyl 3,3'-((octanedioyl bis(azanediyl))bis(1-oxoisoindoline-4,2-diyl))bis(2,6-dioxopiperidine-1-carboxylate) (EC1-140): This was obtained as a white solid (108 mg, 63%) from suberoyl chloride (36 µL, 0.2 mmol, 1.0 eq.) following the General Procedure A. ¹H NMR (500 MHz, DMSO-d₆) δ 9.77 (s, 2H), 7.84 (dd, J=7.5, 1.6 Hz, 2H), 7.55-7.45 (m, 4H), 5.39 (dd, J=13.4, 5.1 Hz, 2H), 4.42 (d, J=17.5 Hz, 2H), 4.36 (d, J=17.5 Hz, 2H), 3.18-3.09 (m, 2H), 2.83-2.74 (m, 2H), 2.48-2.41 (m, 2H), 2.41-2.34 (m, 4H), 2.15-2.04 (m, 2H), 1.68-1.58 (m, 4H), 1.49 (s, 18H), 1.41-1.34 (m, 4H); HPLC-MS (ESI+): m/z 657.3 [100%, (M-2Boc+H)⁺], 879.4 [100%, (M+Na)⁺].

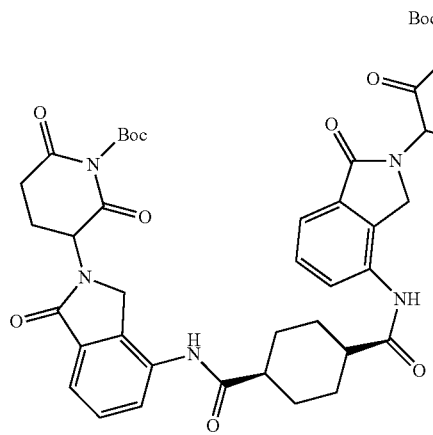

EC1-146

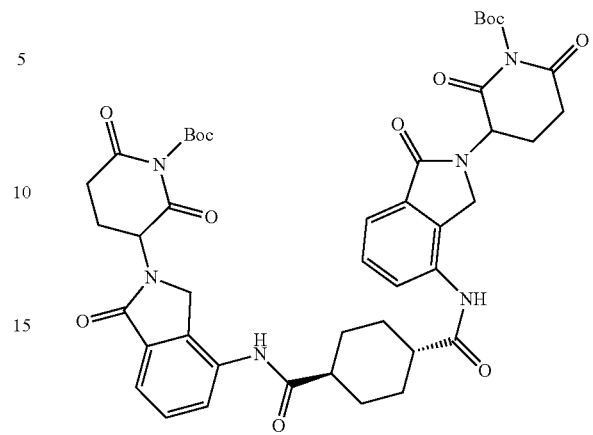

EC1-147

Di-tert-butyl 3,3'-(((cis-cyclohexane-1,4-dicarbonyl)bis(azanediyl))bis(1-oxoisoindoline-4,2-diyl))bis(2,6-dioxopiperidine-1-carboxylate) (EC1-146): This was obtained as a white solid (110 mg, 64%) from cis-cyclohexane-1,4-dicarbonyl dichloride (42 mg, 0.2 mmol, 1.0 eq.) following the General Procedure A. $^1$H NMR (500 MHz, DMSO-$d_6$) δ 9.74 (s, 2H), 7.89 (dd, J=7.4, 1.6 Hz, 2H), 7.61-7.52 (m, 4H), 5.45 (dd, J=12.8, 5.6 Hz, 2H), 4.49 (d, J=17.5 Hz, 2H), 4.42 (d, J=17.5 Hz, 2H), 3.25-3.14 (m, 2H), 2.90-2.80 (m, 2H), 2.72-2.66 (m, 2H), 2.55-2.47 (m, 2H), 2.20-2.01 (m, 2H), 2.11-2.01 (m, 4H), 1.74 (m, 4H), 1.54 (s, 18H); HPLC-MS (ESI+): m/z 655.3 [80%, (M-2Boc+H)$^+$], 877.4 [100%, (M+Na)$^+$].

Di-tert-butyl 3,3'-(((trans-cyclohexane-1,4-dicarbonyl)bis(azanediyl))bis(1-oxoisoindoline-4,2-diyl))bis(2,6-dioxopiperidine-1-carboxylate) (EC1-147): This was obtained as a white solid (30 mg, 50%) from EC2-019 (50 mg, 0.14 mmol, 2.1 eq.), dry CH$_2$Cl$_2$ (0.5 mL), DIPEA (24 μL, 0.14 mmol, 2.1 eq.) and trans-cyclohexane-1,4-dicarbonyl dichloride (15 mg, 0.07 mmol, 1.0 eq.), following General Procedure A. $^1$H NMR (500 MHz, DMSO-$d_6$) δ 9.77 (s, 2H), 7.87 (dd, J=7.2, 1.7 Hz, 2H), 7.55-7.48 (m, 4H), 5.40 (dd, J=13.4, 5.1 Hz, 2H), 4.44 (d, J=17.5 Hz, 2H), 4.38 (d, J=17.5 Hz, 2H), 3.21-3.10 (m, 3H), 2.86-2.77 (m, 2H), 2.49-2.40 (m, 4H), 2.15-2.05 (m, 2H), 2.05-1.92 (m, 4H), 1.56-1.51 (m, 2H), 1.50 (s, 18H), 1.29-1.23 (m, 1H); HPLC-MS (ESI+): m/z 655.3 [100%, (M-2Boc+H)$^+$], 877.4 [40%, (M+Na)$^+$].

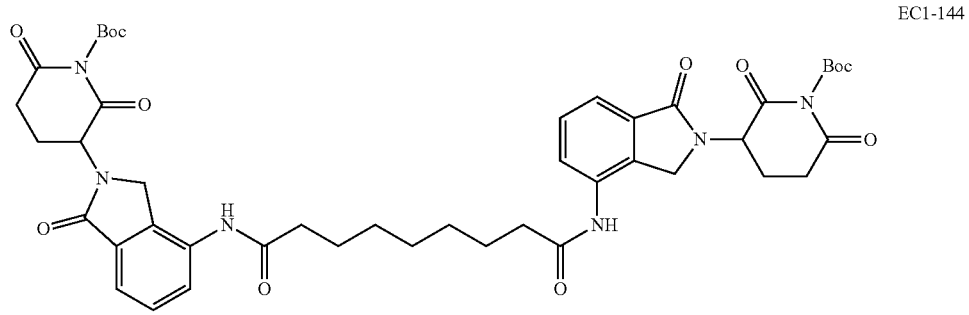 [SMILES: CC(C)(C)OC(=O)N1C(=O)CCC(N2Cc3c(NC(=O)CCCCCCCC(=O)Nc4cccc5c4CN(C4CCC(=O)N(C(=O)OC(C)(C)C)C4=O)C5=O)cccc3C2=O)C1=O]

EC1-144

Di-tert-butyl 3,3'-((nonanedioyl bis(azanediyl))bis(1-oxoisoindoline-4,2-diyl))bis(2,6-dioxopiperidine-1-carboxylate) (EC1-144): This was obtained as a pale yellow solid (26 mg, 43%), from EC2-019 (50 mg, 0.14 mmol, 2.1 eq.), dry $CH_2Cl_2$ (0.5 mL), DIPEA (24 μL, 0.14 mmol, 2.1 eq.) and azelaoyl chloride (14 μL, 0.07 mmol, 1.0 eq.), following a Procedure A. $^1$H NMR (500 MHz, DMSO-$d_6$) δ 9.77 (s, 2H), 7.84 (dd, J=7.3, 1.6 Hz, 2H), 7.55-7.43 (m, 4H), 5.39 (dd, J=13.4, 5.2 Hz, 2H), 4.42 (d, J=17.4 Hz, 2H), 4.35 (d, J=17.4 Hz, 2H), 3.20-3.07 (m, 3H), 2.85-2.75 (m, 2H), 2.48-2.29 (m, 7H), 2.16-2.01 (m, 2H), 1.66-1.57 (m, 4H), 1.49 (s, 18H), 1.39-1.29 (m, 4H); HPLC-MS (ESI+): m/z 671.3 [80%, (M-2Boc+H)$^+$], 893.4 [100%, (M+Na)$^+$].

solid (84 mg, 99%) from EC1-143 (113 mg, 0.14 mmol), following the General Procedure B. Mp=236° C. (dec); HPLC: 98% [$t_R$=6.8 min, Gradient MeOH-water 5%-95% (with 0.1% TFA), 20 min]; $^1$H NMR (500 MHz, DMSO-$d_6$) δ 11.02 (s, 2H), 9.82 (s, 2H), 7.85 (ddd, J=7.1, 3.4, 2.0 Hz, 2H), 7.59-7.44 (m, 4H), 5.14 (ddd, J=13.3, 5.1, 2.5 Hz, 2H), 4.40 (dd, J=17.6, 2.9 Hz, 2H), 4.34 (dd, J=17.6, 1.5 Hz, 2H), 2.95-2.87 (m, 2H), 2.65-2.54 (m, 2H), 2.49-2.42 (m, 4H), 2.38-2.23 (m, 2H), 2.05-1.89 (m, 4H); HPLC-MS (ESI+): m/z 615.2 [100%, (M+H)$^+$]; HRMS (ESI+): m/z calcd for $C_{31}H_{30}N_6O_8$ 615.2125 (M+H)$^+$, found 615.1999.

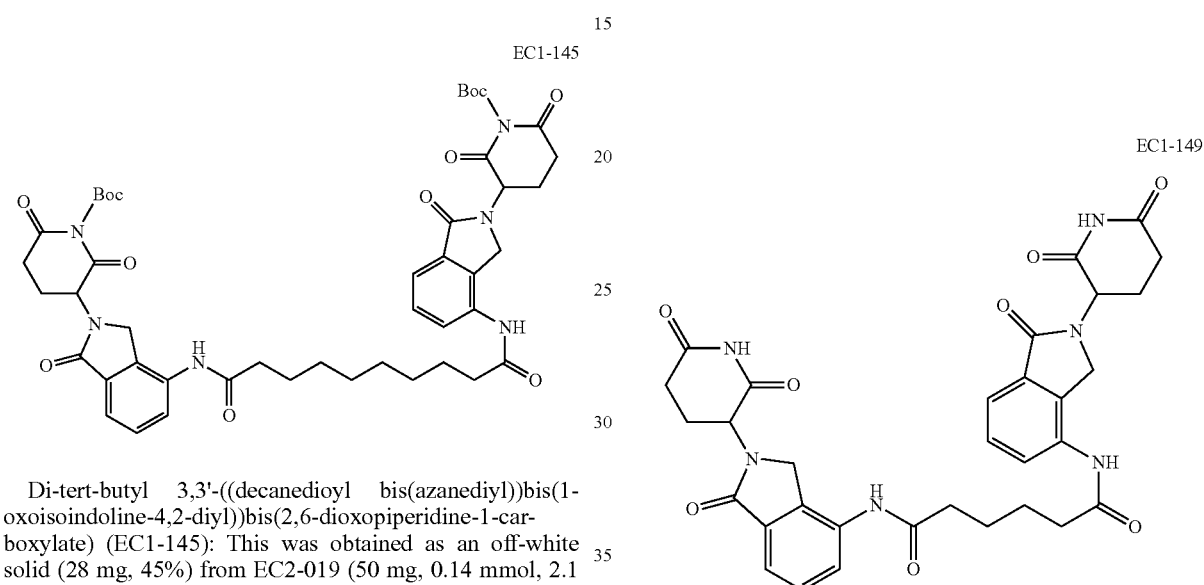

Di-tert-butyl 3,3'-((decanedioyl bis(azanediyl))bis(1-oxoisoindoline-4,2-diyl))bis(2,6-dioxopiperidine-1-carboxylate) (EC1-145): This was obtained as an off-white solid (28 mg, 45%) from EC2-019 (50 mg, 0.14 mmol, 2.1 eq.), dry $CH_2Cl_2$ (0.5 mL), DIPEA (24 μL, 0.14 mmol, 2.1 eq.) and sebacoyl chloride (11 μL, 0.07 mmol, 1.0 eq.), following a General Procedure A. $^1$H NMR (500 MHz, DMSO-$d_6$) δ 9.77 (s, 2H), 7.84 (dd, J=7.3, 1.6 Hz, 2H), 7.56-7.43 (m, 4H), 5.39 (dd, J=13.4, 5.1 Hz, 2H), 4.42 (d, J=17.4 Hz, 2H), 4.35 (d, J=17.4 Hz, 2H), 3.20-3.07 (m, 2H), 2.84-2.75 (m, 2H), 2.48-2.30 (m, 7H), 2.13-2.04 (m, 2H), 1.68-1.56 (m, 4H), 1.49 (s, 18H), 1.36-1.20 (m, 7H); HPLC-MS (ESI+): m/z 685.4 [60%, (M-2Boc+H)$^+$], 907.4 [100%, (M+Na)$^+$].

General Procedure B

The Boc-protected dimer (0.1 mmol) was dissolved in TFA (2 mL) and the solution stirred at room temperature for 2 hours. The TFA was removed under reduced pressure and the residue formed was purified by trituration with MeOH to give the final bis-glutarimide derivative.

$N^1,N^6$-Bis(2-(2,6-dioxopiperidin-3-yl)-1-oxoisoindolin-4-yl)adipamide (EC1-149): This was obtained as a white solid (68 mg, 99%) from EC1-142 (90 mg, 0.11 mmol), following the General Procedure B. Mp=260° C. (dec.); HPLC: 99% [$t_R$=6.8 min, Gradient MeOH-water 5%-95% (with 0.1% TFA), 20 min]; $^1$H NMR (500 MHz, DMSO-$d_6$) δ 11.02 (s, 2H), 9.80 (s, 2H), 7.82 (dd, J=7.4, 2.2 Hz, 2H), 7.54-7.46 (m, 4H), 5.14 (ddd, J=13.3, 5.1, 1.4 Hz, 2H), 4.40 (d, J=17.5 Hz, 2H), 4.34 (dd, J=17.5, 1.6 Hz, 2H), 2.96-2.87 (m, 2H), 2.67-2.54 (m, 2H), 2.46-2.28 (m, 6H), 2.07-1.97 (m, 2H), 1.73-1.63 (m, 4H); HPLC-MS (ESI+): m/z 629.2 [80%, (M+H)$^+$], 651.3 [100%, (M+Na)$^+$]; HRMS (ESI+): m/z calcd for $C_{32}H_{32}N_6O_8$ 651.2174 (M+Na)$^+$, found 651.2159.

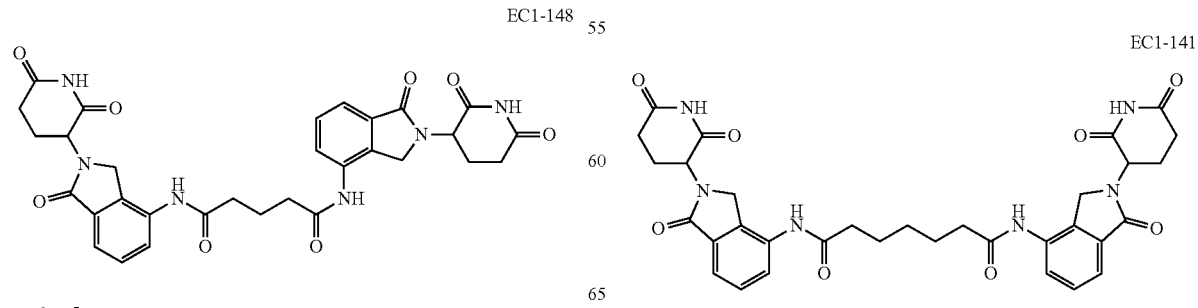

$N^1,N^5$-Bis(2-(2,6-dioxopiperidin-3-yl)-1-oxoisoindolin-4-yl)glutaramide (EC1-148): This was obtained as a white N$^1$,N$^7$-Bis(2-(2,6-dioxopiperidin-3-yl)-1-oxoisoindolin-4-yl)heptanediamide (EC1-141): This was obtained as a white solid (72 mg, 94%) from EC1-139 (100 mg, 0.12 mmol), following the General Procedure B. Mp=260° C. (dec.); HPLC: 96% [$t_R$=6.9 min, Gradient MeOH-water 5%-95% (with 0.1% TFA), 20 min]; $^1$H NMR (500 MHz, DMSO-d$_6$) δ 11.02 (s, 2H), 9.77 (s, 2H), 7.82 (dt, J=7.5, 1.4 Hz, 2H), 7.55-7.43 (m, 4H), 5.14 (dd, J=13.3, 5.2 Hz, 2H), 4.39 (dd, J=17.5, 2.8 Hz, 2H), 4.34 (d, J=17.5 Hz, 2H), 2.97-2.86 (m, 2H), 2.67-2.54 (m, 2H), 2.42-2.29 (m, 6H), 2.05-1.97 (m, 2H), 1.70-1.61 (m, 4H), 1.45-1.35 (m, 2H); HPLC-MS (ESI+): m/z 643.2 [100%, (M+H)$^+$], 665.2 [20%, (M+Na)$^+$]; HRMS (ESI+): m/z calcd for C$_{33}$H$_{34}$N$_6$O$_8$ 665.2330 (M+Na)$^+$, found 665.2329.

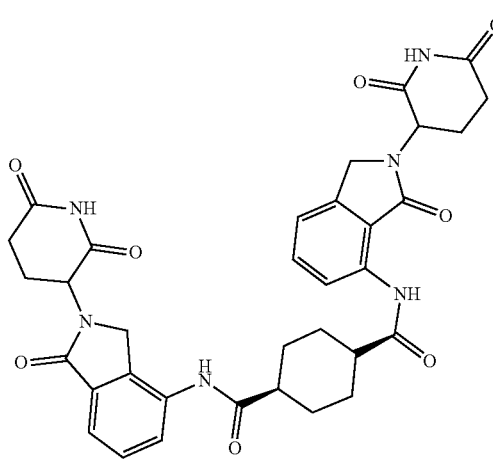

EC1-153

(Cis)-N$^1$-(2-(2,6-dioxopiperidin-3-yl)-1-oxoisoindolin-4-yl)-N$^4$-(2-(2,6-dioxopiperidin-3-yl)-3-oxoisoindolin-4-yl)cyclohexane-1,4-dicarboxamide (EC1-153): This was obtained as a white solid (14 mg, 16%) from EC1-146 (110 mg, 0.13 mmol), after trituration with MeOH (3 times, ca. 6 mL), following General Procedure B. Mp=263° C. (dec.); HPLC: 100% [$t_R$=6.8 min, Gradient MeOH-water 5%-95% (with 0.1% TFA), 20 min]; $^1$H NMR (500 MHz, DMSO-d$_6$) δ 11.02 (s, 2H), 9.68 (s, 2H), 7.80 (dt, J=7.1, 1.6 Hz, 2H), 7.53-7.47 (m, 4H), 5.15 (dd, J=13.3, 5.3 Hz, 2H), 4.40 (d, J=17.4 Hz, 2H), 4.34 (dd, J=17.4, 1.6 Hz, 2H), 2.98-2.86 (m, 2H), 2.67-2.54 (m, 6H), 2.42-2.30 (m, 1H), 2.08-1.91 (m, 6H), 1.68 (d, J=12.4 Hz, 3H); HPLC-MS (ESI+): m/z 655.3 [60%, (M+H)$^+$], 677.3 [60%, (M+Na)$^+$]; HRMS (ESI+): m/z calcd for C$_{34}$H$_{34}$N$_6$O$_8$ 655.2511 (M+Na)$^+$, found 655.2505.

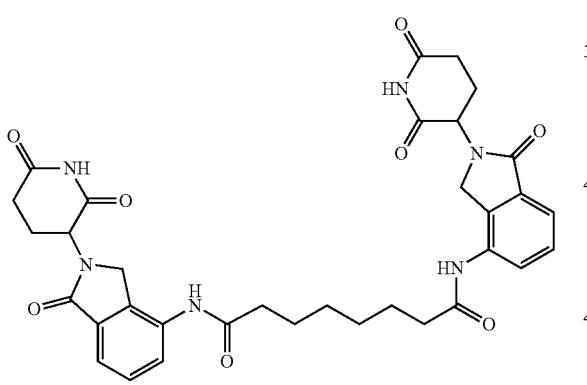

EC1-150

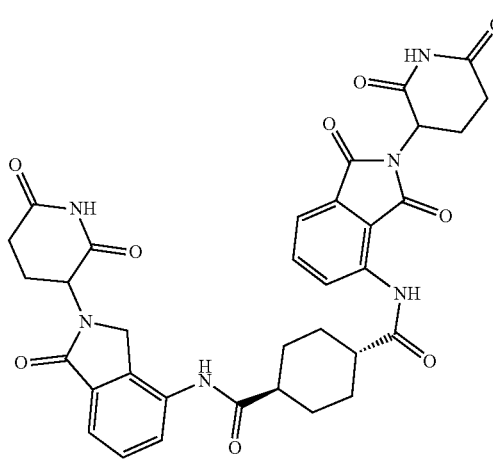

EC1-154

N$^1$,N$^8$-Bis(2-(2,6-dioxopiperidin-3-yl)-1-oxoisoindolin-4-yl)octanediamide (EC1-150): This was obtained as a white solid (78 mg, 99%), from EC1-140 (105 mg, 0.12 mmol), following the General Procedure B. Mp=260° C. (dec.); HPLC: 98% [$t_R$=6.8 min, Gradient MeOH-water 5%-95% (with 0.1% TFA), 20 min]; $^1$H NMR (500 MHz, DMSO-d$_6$) δ 11.02 (s, 2H), 9.77 (s, 2H), 7.82 (dd, J=7.3, 1.6 Hz, 2H), 7.54-7.43 (m, 4H), 5.15 (dd, J=13.3, 5.1 Hz, 2H), 4.39 (d, J=17.6 Hz, 2H), 4.34 (d, J=17.6 Hz, 2H), 2.98-2.85 (m, 2H), 2.67-2.53 (m, 2H), 2.42-2.27 (m, 6H), 2.08-1.98 (m, 2H), 1.71-1.56 (m, 4H), 1.45-1.27 (m, 4H); HPLC-MS (ESI+): m/z 657.3 [100%, (M+H)$^+$], 679.3 [40%, (M+Na)$^+$]; HRMS (ESI+): m/z calcd for C$_{34}$H$_{36}$N$_6$O$_8$ 679.2487 (M+Na)$^+$, found 679.2480.

(Trans)-N$^1$,N$^4$-Bis(2-(2,6-dioxopiperidin-3-yl)-1-oxoisoindolin-4-yl)cyclohexane-1,4-dicarboxamide (EC1-154): This was obtained as a pale yellow solid (21 mg, 91%) from EC1-147 (30 mg, 0.04 mmol), following General Procedure B., Mp=263° C. (dec.); $^1$H NMR (500 MHz, DMSO-d$_6$) δ 11.03 (s, 2H), 9.76 (s, 2H), 7.84 (dd, J=7.2, 1.7 Hz, 2H), 7.59-7.40 (m, 4H), 5.16 (dd, J=13.3, 5.2 Hz, 2H), 4.41 (d, J=17.5 Hz, 2H), 4.35 (d, J=17.5 Hz, 2H), 2.98-2.88 (m, 2H), 2.68-2.56 (m, 2H), 2.48-2.44 (m, 2H), 2.41-2.33 (m, 2H), 2.12-1.90 (m, 5H), 1.59-1.47 (m, 3H), 1.30-1.21 (m, 2H); HPLC-MS (ESI+): m/z 655.2 [40%, (M+H)$^+$]; HRMS (ESI+): m/z calcd for C$_{34}$H$_{34}$N$_6$O$_8$ 655.2509 (M+H)$^+$, found 655.2485.

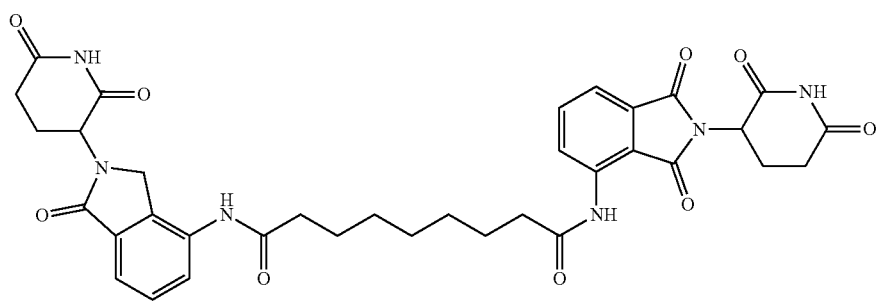

EC1-151

N[1],N[9]-Bis(2-(2,6-dioxopiperidin-3-yl)-1-oxoisoindolin-4-yl)nonanediamide (EC1-151): This was obtained as a yellow solid (20 mg, 99%) from EC1-144 (26 mg, 0.03 mmol), following General Procedure B; Mp=196-198° C.; HPLC: 94% [$t_R$=13.2 min, MeOH 95% and water 5% (with 0.1% TFA), 20 min]; $^1$H NMR (500 MHz, DMSO-$d_6$) δ 11.02 (s, 2H), 9.76 (s, 2H), 7.81 (dd, J=7.3, 1.7 Hz, 2H), 7.56-7.44 (m, 4H), 5.15 (dd, J=13.3, 5.1 Hz, 2H), 4.39 (d, J=17.5 Hz, 2H), 4.33 (d, J=17.5 Hz, 2H), 2.97-2.84 (m, 2H), 2.67-2.56 (m, 2H), 2.44-2.30 (m, 6H), 2.10-1.97 (m, 2H), 1.68-1.56 (m, 4H), 1.40-1.26 (m, 6H); HPLC-MS (ESI+): m/z 693.4 [40%, (M+Na)+]; HRMS (ESI+): m/z calcd for $C_{35}H_{38}N_6O_8$ 693.2643 (M+Na)+, found 693.2640.

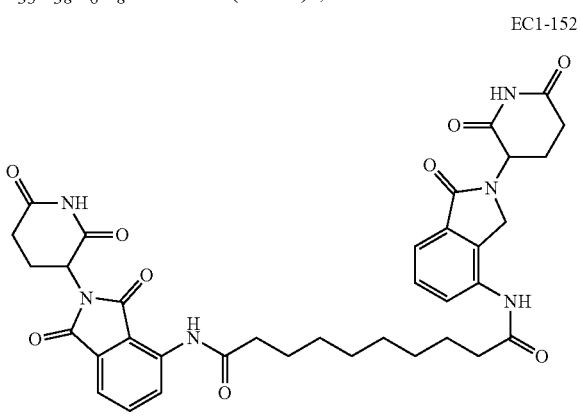

EC1-152

N[1],N[10]-Bis(2-(2,6-dioxopiperidin-3-yl)-1-oxoisoindolin-4-yl)decanediamide (EC1-152): This was obtained as a yellow solid (21 mg, 95%) from EC1-145 (28 mg, 0.03 mmol), following General Procedure B. Mp=227° C. (dec.); HPLC: 89% [$t_R$=13.7 min, MeOH 95% and water 5% (with 0.1% TFA), 20 min]; $^1$H NMR (500 MHz, DMSO-$d_6$) δ 11.02 (s, 2H), 9.76 (s, 2H), 7.81 (dd, J=7.3, 1.7 Hz, 2H), 7.55-7.42 (m, 4H), 5.15 (dd, J=13.3, 5.2 Hz, 2H), 4.39 (d, J=17.5 Hz, 2H), 4.33 (d, J=17.5 Hz, 2H), 2.98-2.88 (m, 2H), 2.68-2.56 (m, 2H), 2.40-2.29 (m, 5H), 2.09-1.98 (m, 2H), 1.67-1.56 (m, 4H), 1.40-1.17 (m, 9H); HPLC-MS (ESI+): m/z 685.4 [100%, (M+H)+]; HRMS (ESI+): m/z calcd for $C_{36}H_{40}N_6O_8$ 707.2800 (M+Na)+, found 707.2799.

Synthetic scheme 28

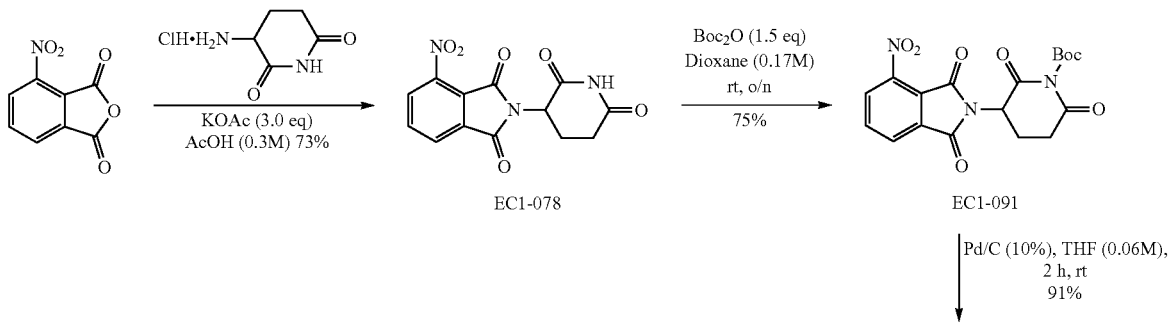

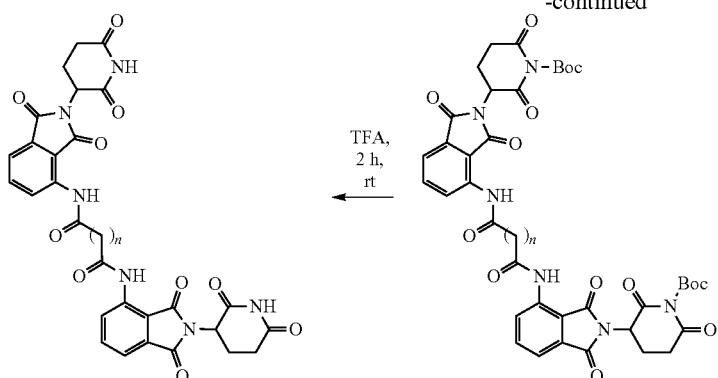
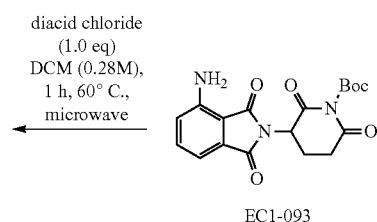

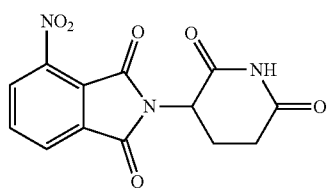

2-(2,6-Dioxopiperidin-3-yl)-4-nitroisoindoline-1,3-dione (EC1-078): 4-Nitroisobenzofuran-1,3-dione (2.0 g, 10 mmol, 1.0 eq.) was added to a mixture of 3-aminopiperidine-2,6-dione.HCl (1.9 g, 11 mmol, 1.1 eq.) and potassium acetate (2.9 g, 30 mmol, 3.0 eq.) in acetic acid (30 mL) and the mixture was stirred at 120° C. overnight. The reaction was cooled to room temperature and the solvent removed under reduced pressure. The amorphous solid that formed was stirred in $H_2O$ (ca. 30 mL) for 1 hour, to give a brown solid which was filtered and dried under high vacuum at 60° C. for 1 hour. The solid was used without further purification (2.4 g, 73%). $^1$H NMR (500 MHz, DMSO-$d_6$) δ 11.18 (s, 1H), 8.36 (dd, J=8.1, 0.9 Hz, 1H), 8.25 (dd, J=7.6, 0.9 Hz, 1H), 8.13 (t, J=7.8 Hz, 1H), 5.21 (dd, J=13.0, 5.4 Hz, 1H), 2.85-2.80 (m, 1H), 2.67-2.58 (m, 1H), 2.58-2.51 (m, 1H), 2.13-2.06 (m, 1H); HPLC-MS (ESI+): m/z 304.2 [100%, (M+H)$^+$]. (See U.S. Pat. No. 9,365,640.)

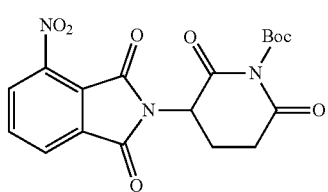

Tert-butyl 3-(4-nitro-1,3-dioxoisoindolin-2-yl)-2,6-dioxopiperidine-1-carboxylate (EC1-091): 2-(2,6-Dioxopiperidin-3-yl)-4-nitroisoindoline-1,3-dione (EC1-078) (2.0 g, 6.6 mmol, 1.0 eq.), di-tert-butyl dicarbonate (2.1 g, 9.8 mmol, 1.5 eq.) and DMAP (78 mg, 0.6 mmol, 0.1 eq.) were stirred in dioxane (12 mL) at room temperature overnight. The mixture was diluted with EtOAc (ca. 30 mL) and washed with $H_2O$ (ca. 30 mL). The organic phase was collected, washed with brine (ca. 30 mL), dried (MgSO$_4$), filtered and the solvent was removed under reduced pressure. The crude mixture was purified by column chromatography (0-100% EtOAc:hexane, 1% Et$_3$N) to give tert-butyl 3-(4-nitro-1,3-dioxoisoindolin-2-yl)-2,6-dioxopiperidine-1-carboxylate (EC1-091) (2.0 g, 75%) as a yellow foam. $^1$H NMR (500 MHz, DMSO-$d_6$) δ 8.38 (dd, J=8.1, 0.9 Hz, 1H), 8.26 (dd, J=7.6, 0.9 Hz, 1H), 8.14 (dd, J=8.1, 7.5 Hz, 1H), 5.50 (dd, J=13.0, 5.3 Hz, 1H), 3.11-3.07 (m, 1H), 2.82-2.78 (m, 1H), 2.66-2.53 (m, 1H), 2.18-2.08 (m, 1H), 1.49 (s, 9H); HPLC-MS (ESI+) and (ESI−): m/z 829.2 [30%, (2M+Na)$^+$], 402.2 [100%, (M−H)$^+$]. (See Man, H.-W., et al., *Bioorg. Med. Chem. Lett.*, 13:3415-3417, 2003.)

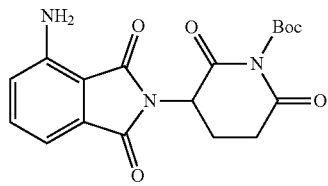

tert-Butyl 3-(4-amino-1,3-dioxoisoindolin-2-yl)-2,6-dioxopiperidine-1-carboxylate (EC1-093): A suspension of palladium (10%) on carbon (531 mg, 0.1 eq.) in dry THF (5 mL) was degassed for 15 minutes, the system evacuated and refilled with $H_2$ (3 times) and then kept under $H_2$ atmosphere for 5 minutes. A degassed solution of tert-butyl 3-(4-nitro-1,3-dioxoisoindolin-2-yl)-2,6-dioxopiperidine-1-carboxylate (EC1-091) (2.0 g, 5.0 mmol, 1.0 eq.) in dry THF (5 mL) was added slowly to the suspension and the reaction was stirred at room temperature under $H_2$ atmosphere for 2 hours. The suspension was filtered through Celite® (ca. 2 inch) and washed with THF (50 mL). The solvent evaporated under reduced pressure to give a dark green solid (1.7 g, 91%) which was used without further purification. $^1$H NMR (500 MHz, DMSO-$d_6$) δ 7.49 (dd, J=8.5, 7.0 Hz, 1H), 7.06-7.00 (m, 2H), 6.56 (s, 2H), 5.33 (dd, J=13.0, 5.4 Hz, 1H), 3.13-3.10 (m, 1H), 2.82-2.79 (m, 1H), 2.65-2.59 (m, 1H), 2.03-2.09 (m, 1H), 1.49 (s, 9H); HPLC-MS (ESI+): m/z 274.2 [100%, (M-Boc+H)$^+$], 769.3 [50%, (2M+Na)$^+$]. (See WO2017/197055.)

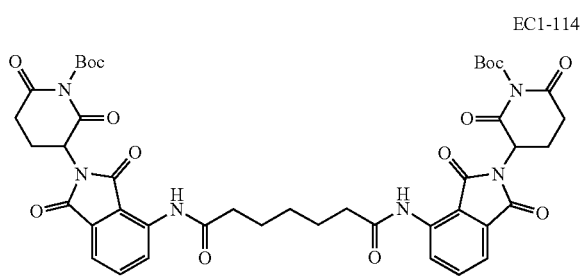

EC1-114

Di-tert-butyl 3,3'-((heptanedioylbis(azanediyl))bis(1,3-dioxoisoindoline-4,2-diyl))bis(2,6-dioxopiperidine-1-carboxylate) (EC1-114): This was obtained as a yellow solid (46 mg, 20%) from EC1-093 (200 mg, 0.54 mmol, 2.1 eq.), dry CH$_2$Cl$_2$ (2.0 mL), DIPEA (92 μL, 0.54 mmol, 2.1 eq.) and pimeloyl chloride (53 mg, 0.26 mmol, 1.0 eq.), following General Procedure A. $^1$H NMR (500 MHz, DMSO-d$_6$) δ 9.72 (brs, 2H), 8.47 (d, J=8.3 Hz, 2H), 7.84 (dd, J=8.3, 7.2 Hz, 2H), 7.63 (d, J=7.2 Hz, 2H), 5.43 (dd, J=13.0, 5.4 Hz, 2H), 3.13-3.10 (m, 2H), 2.84-2.79 (m, 2H), 2.67-2.55 (m, 2H), 2.52-2.43 (m, 2H), 2.12-2.08 (m, 2H), 1.71-1.67 (m, 2H), 1.63-1.51 (m, 2H), 1.49 (s, 18H), 1.46-1.35 (m, 2H), 1.34-1.20 (m, 2H); HPLC-MS (ESI+): m/z 671.3 [40%, (M-2Boc+H)$^+$], 893.3 [100%, (M+Na)$^+$].

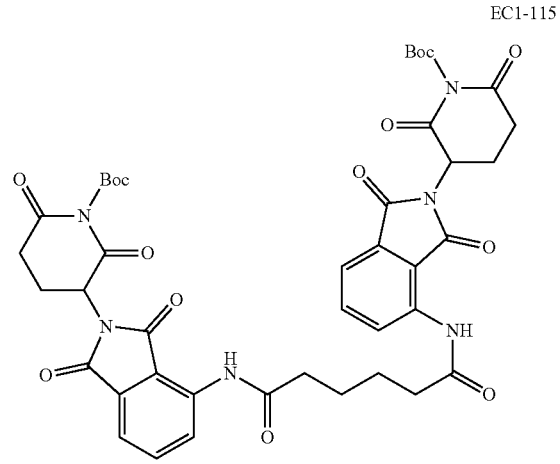 [SMILES: CC(C)(C)OC(=O)N1C(=O)CCC(N2C(=O)c3cccc(NC(=O)CCCCC(=O)Nc4cccc5c4C(=O)N(C4CCC(=O)N(C(=O)OC(C)(C)C)C4=O)C5=O)c3C2=O)C1=O]

EC1-115

Di-tert-butyl 3,3-((adipoylbis(azanediyl))bis(1,3-dioxoisoindoline-4,2-diyl))bis(2,6-dioxopiperidine-1-carboxylate) (EC1-115): This was obtained as a yellow solid (10 mg, 4%), from EC1-093 (200 mg, 0.54 mmol, 2.1 eq.), dry CH$_2$Cl$_2$ (2.0 mL), DIPEA (92 μL, 0.54 mmol, 2.1 eq.) and adipoyl chloride (38 μL, 0.2 mmol, 1.0 eq.), following General Procedure A. $^1$H NMR (500 MHz, DMSO-d$_6$) δ 9.72 (s, 2H), 8.48 (d, J=8.3 Hz, 2H), 7.84 (dd, J=8.3, 7.3 Hz, 2H), 7.63 (dd, J=7.3, 0.8 Hz, 2H), 5.43 (dd, J=13.0, 5.3 Hz, 2H), 3.13-3.09 (m, 2H), 2.85-2.76 (m, 2H), 2.67-2.58 (m, 2H), 2.57-2.52 (m, 2H), 2.16-2.08 (m, 1H), 1.74-1.70 (m, 4H), 1.49 (s, 18H), 1.36-1.04 (m, 3H); HPLC-MS (ESI+): m/z 657.1 [50%, (M-2Boc+H)$^+$], 879.3 [100%, (M+Na)$^+$].

EC1-108

Di-tert-butyl 3,3'-((glutaroyl bis(azanediyl))bis(1,3-dioxoisoindoline-4,2-diyl))bis(2,6-dioxopiperidine-1-carboxylate) (EC1-108): This was obtained as a yellow solid (20 mg, 18%), from EC1-093 (100 mg, 0.27 mmol, 2.1 eq.), dry CH$_2$Cl$_2$ (1.0 mL), DIPEA (46 μL, 0.27 mmol, 2.1 eq.) and glutaryl chloride (17 μL, 0.13 mmol, 1.0 eq.), following General Procedure A. $^1$H NMR (500 MHz, DMSO-d$_6$) δ 9.77 (s, 2H), 8.47 (dd, J=8.3, 0.8 Hz, 2H), 7.85 (dd, J=8.3, 7.3 Hz, 2H), 7.64 (dd, J=7.3, 0.8 Hz, 2H), 5.43 (dd, J=13.0, 5.3 Hz, 2H), 3.12-3.08 (m, 2H), 2.85-2.74 (m, 2H), 2.63-2.55 (m, 4H), 2.14-2.10 (m, 2H), 2.04-1.93 (m, 2H), 1.49 (s, 18H), 1.31-1.21 (m, 2H); HPLC-MS (ESI+): m/z 643.2 [40%, (M-2Boc+H)$^+$], 865.3 [100%, (M+Na)$^+$].

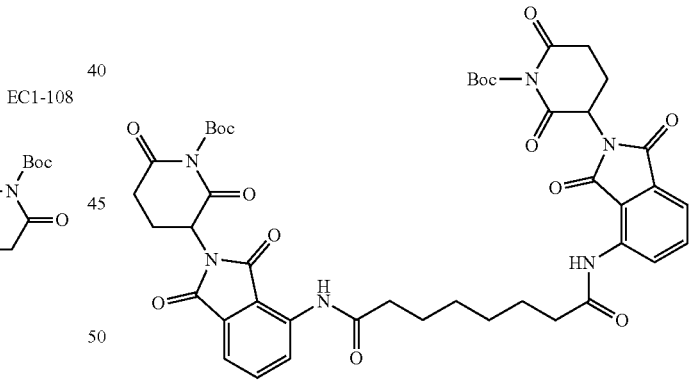

EC1-122

Di-tert-butyl 3,3'-((octanedioyl bis(azanediyl))bis(1,3-dioxoisoindoline-4,2-diyl))bis(2,6-dioxopiperidine-1-carboxylate) (EC1-122): This was obtained as a yellow solid (60 mg, 52%) from EC1-093 (100 mg, 0.27 mmol, 2.1 eq.), dry CH$_2$Cl$_2$ (1.0 mL), DIPEA (46 μL, 0.27 mmol, 2.1 eq.) and suberoyl chloride (26 μL, 0.13 mmol, 1.0 eq.) following General Procedure A. $^1$H NMR (500 MHz, DMSO-d$_6$) δ 9.70 (s, 2H), 8.47 (dd, J=8.4, 0.8 Hz, 2H), 7.84 (dd, J=8.4, 7.3 Hz, 2H), 7.63 (dd, J=7.3, 0.8 Hz, 2H), 5.43 (dd, J=13.8, 5.5 Hz, 2H), 3.11 (ddd, J=17.5, 13.8, 5.5 Hz, 2H), 2.85-2.76 (m, 2H), 2.67-2.57 (m, 2H), 2.50-2.48 (m, 3H), 2.16-2.08 (m, 1H), 1.66-1.62 (m, 4H), 1.49 (s, 18H), 1.43-1.35 (m, 4H), 1.28-1.24 (m, 2H); HPLC-MS (ESI+): m/z 685.3 [60%, (M-2Boc+H)$^+$], 907.3 [100%, (M+Na)$^+$].

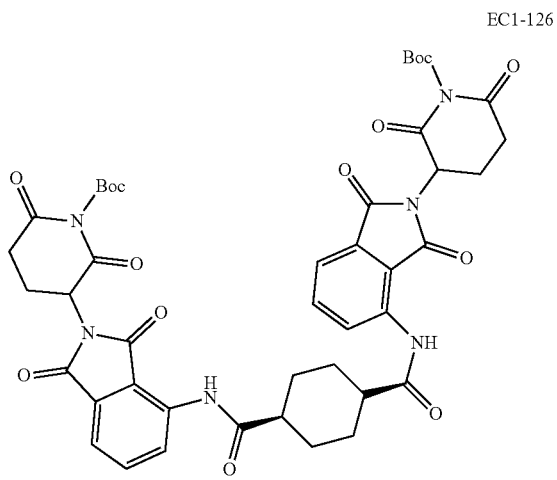

EC1-126

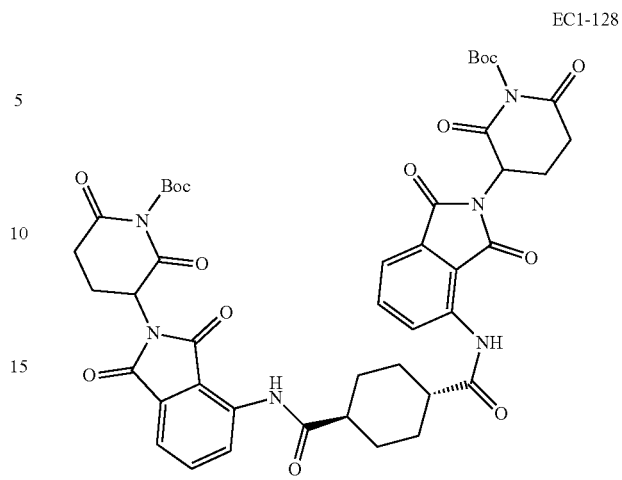

EC1-128

Di-tert-butyl 3,3'-(((cis-cyclohexane-1,4-dicarbonyl)bis(azanediyl))bis(1,3-dioxoisoindoline-4,2-diyl))bis(2,6-dioxopiperidine-1-carboxylate) (EC1-126): This was obtained as a yellow solid (35 mg, 31%) from EC1-093 (100 mg, 0.27 mmol, 2.1 eq.), dry $CH_2Cl_2$ (1.0 mL), DIPEA (46 µL, 0.27 mmol, 2.1 eq.) and cis-cyclohexane-1,4-dicarbonyl dichloride (27 mg, 0.13 mmol, 1.0 eq.) following General Procedure A. $^1$H NMR (500 MHz, DMSO-$d_6$) δ 9.78 (s, 2H), 8.51 (d, J=8.3 Hz, 2H), 7.84 (ddd, J=8.3, 7.4, 4.9 Hz, 2H), 7.63 (dd, J=7.4, 0.7 Hz, 2H), 5.44 (dd, J=13.5, 5.4 Hz, 2H), 3.10 (ddd, J=17.4, 13.5, 5.5 Hz, 2H), 2.85-2.69 (m, 3H), 2.63-2.59 (m, 1H), 2.12-2.09 (m, 1H), 2.05-2.00 (m, 3H), 1.80-1.77 (m, 4H), 1.49 (s, 18H), 1.28-1.21 (m, 2H), 1.05 (t, J=7.2 Hz, 2H); HPLC-MS (ESI−): m/z 881.3 [30%, (M−H)$^+$].

Di-tert-butyl 3,3'-(((trans-cyclohexane-1,4-dicarbonyl)bis(azanediyl))bis(1,3-dioxoisoindoline-4,2-diyl))bis(2,6-dioxopiperidine-1-carboxylate) (EC1-128): This was obtained as a yellow solid (52 mg, 45%) from EC1-093 (100 mg, 0.27 mmol, 2.1 eq.), dry $CH_2Cl_2$ (1.0 mL), DIPEA (46 µL, 0.27 mmol, 2.1 eq.) and trans-cyclohexane-1,4-dicarbonyl dichloride (27 mg, 0.13 mmol, 1.0 eq.), following General Procedure A. $^1$H NMR (500 MHz, DMSO-$d_6$) δ 9.79 (s, 2H), 8.48 (d, J=8.3 Hz, 2H), 7.86 (dd, J=8.4, 7.3 Hz, 2H), 7.65 (dd, J=7.3, 0.8 Hz, 2H), 5.45 (dd, J=13.5, 5.4 Hz, 2H), 3.11 (ddd, J=17.5, 13.5, 5.6 Hz, 2H), 2.86-2.78 (m, 2H), 2.68-2.53 (m, 6H), 2.13-2.08 (m, 4H), 1.57-1.53 (m, 3H), 1.49 (s, 18H), 1.20-1.24 (m, 1H); HPLC-MS (ESI+): m/z 683.3 [20%, (M−2Boc+H)$^+$], 905.4 [40%, (M+Na)$^+$].

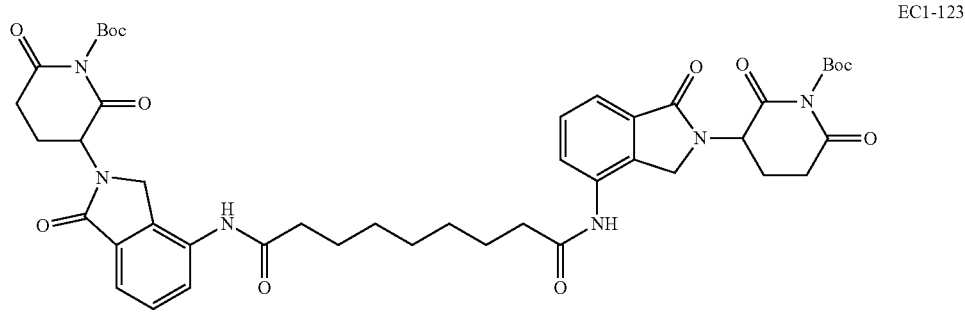 [SMILES: CC(C)(C)OC(=O)N1C(=O)CCC(N2Cc3c(NC(=O)CCCCCCCC(=O)Nc4cccc5c4CN(C4CCC(=O)N(C(=O)OC(C)(C)C)C4=O)C5=O)cccc3C2=O)C1=O]

EC1-123

Di-tert-butyl 3,3'-((nonanedioyl bis(azanediyl))bis(1-oxoisoindoline-4,2-diyl))bis(2,6-dioxopiperidine-1-carboxylate) (EC1-123): This was obtained as a pale yellow solid (59 mg, 51%), from EC1-093 (100 mg, 0.27 mmol, 2.1 eq.), dry CH$_2$Cl$_2$ (1.0 mL), DIPEA (46 μL, 0.27 mmol, 2.1 eq.) and azelaoyl chloride (26 μL, 0.13 mmol, 1.0 eq.), following General Procedure A. $^1$H NMR (500 MHz, DMSO-d$_6$) δ 9.70 (s, 2H), 8.47 (dd, J=8.4, 0.8 Hz, 2H), 7.84 (dd, J=8.4, 7.3 Hz, 2H), 7.63 (dd, J=7.3, 0.8 Hz, 2H), 5.43 (dd, J=13.5, 5.4 Hz, 2H), 3.11 (ddd, J=17.5, 13.5, 5.5 Hz, 2H), 2.83-2.79 (m, 2H), 2.67-2.55 (m, 2H), 2.49-2.46 (m, 4H), 2.16-2.08 (m, 1H), 1.68-1.59 (m, 5H), 1.49 (s, 18H), 1.38-1.34 (m, 6H); HPLC-MS (ESI+): m/z 699.3 [20%, (M-2Boc+H)$^+$], 921.4 [100%, (M+Na)$^+$].

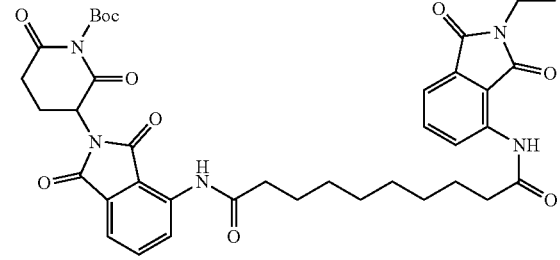

EC1-127

Di-tert-butyl 3,3'-((decanedioyl bis(azanediyl))bis(1,3-dioxoisoindoline-4,2-diyl))bis(2,6-dioxopiperidine-1-carboxylate) (EC1-127): This was obtained as yellow solid (11 mg, 9%) from EC1-093 (100 mg, 0.27 mmol, 2.1 eq.), dry CH$_2$Cl$_2$ (1.0 mL), DIPEA (46 μL, 0.27 mmol, 2.1 eq.) and sebacoyl chloride (21 μL, 0.13 mmol, 1.0 eq.), following General Procedure A. $^1$H NMR (500 MHz, DMSO-d$_6$) δ 9.78 (s, 2H), 8.51 (d, J=8.4 Hz, 2H), 7.85 (dd, J=8.4, 7.3 Hz, 2H), 7.63 (dd, J=7.3, 0.7 Hz, 2H), 5.44 (dd, J=13.5, 5.5 Hz, 2H), 3.10 (ddd, J=17.4, 13.5, 5.5 Hz, 2H), 2.86-2.69 (m, 5H), 2.67-2.54 (m, 3H), 2.15-2.09 (m, 1H), 2.00-1.92 (m, 4H), 1.83-1.78 (m, 5H), 1.49 (s, 18H), 1.29-1.22 (m, 2H), 1.05 (t, J=7.2 Hz, 2H); HPLC-MS (ESI+) and (ESI–): m/z 935.4 [20%, (M+Na)$^+$], 911.3 [20%, (M–H)$^+$].

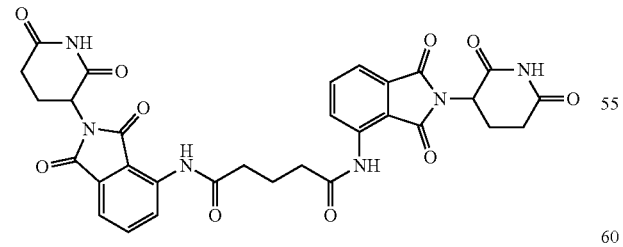

EC1-117

N$^1$,N$^5$-bis(2-(2,6-Dioxopiperidin-3-yl)-1,3-dioxoisoindolin-4-yl)glutaramide (EC1-117): This was obtained as a yellow solid (10 mg, 66%) from EC1-108 (20 mg, 0.024 mmol, 1.0 eq.), following the General Procedure B. HPLC: 98% [t$_R$=14.6 min, Gradient MeOH-water 5%-95% (with 0.1% TFA), 20 min]; $^1$H NMR (500 MHz, DMSO-d$_6$) δ 11.05 (s, 2H), 9.67 (s, 2H), 8.37 (d, J=8.4 Hz, 2H), 7.75 (dd, J=8.4, 7.3 Hz, 2H), 7.53 (d, J=7.3 Hz, 2H), 5.05 (dd, J=13.5, 5.5 Hz, 2H), 2.80 (ddd, J=17.1, 13.5, 5.4 Hz, 2H), 2.56-2.37 (m, 7H), 2.00-1.85 (m, 5H); HPLC-MS (ESI+): m/z 643.2 [100%, (M+H)$^+$], 665.2 [60%, (M+Na)$^+$]; HRMS (ESI+): m/z calcd for C$_{31}$H$_{26}$N$_6$O$_{10}$ 665.1603 (M+Na)$^+$, found 665.1600.

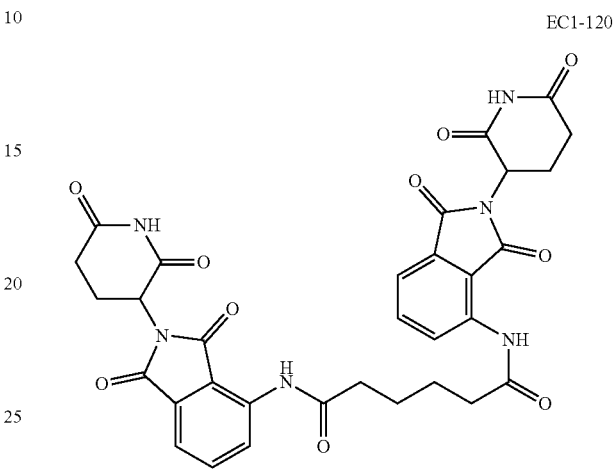

EC1-120

N$^1$,N$^6$-bis(2-(2,6-Dioxopiperidin-3-yl)-1,3-dioxoisoindolin-4-yl)adipamide (EC1-120): This was obtained as a yellow solid (42 mg, 71%) from EC1-115 (8 mg, 0.01 mmol, 1.0 eq.), following the General Procedure B. HPLC: 86% [t$_R$=14.9 min, Gradient MeOH-water 5%-95% (with 0.1% TFA), 20 min; $^1$H NMR (500 MHz, DMSO-d$_6$) δ 11.14 (s, 2H), 9.71 (s, 2H), 8.52-8.44 (m, 2H), 7.83 (dd, J=8.5, 7.3 Hz, 2H), 7.61 (d, J=7.3 Hz, 2H), 5.14 (dd, J=13.5, 5.4 Hz, 2H), 2.90 (ddd, J=17.0, 13.5, 5.4 Hz, 2H), 2.66-2.52 (m, 5H), 2.50-2.46 (m, 1H), 2.10-2.02 (m, 2H), 1.75-1.71 (m, 3H), 1.27-1.05 (m, 3H); HPLC-MS (ESI+): m/z 657.2 [40%, (M+H)$^+$], 679.3 [100%, (M+Na)$^+$]; HRMS (ESI+): m/z calcd for C$_{32}$H$_{28}$N$_6$O$_{10}$ 679.1759 (M+Na)$^+$, found 679.1763.

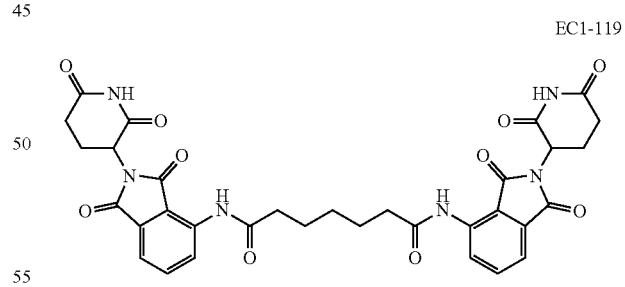

EC1-119

N$^1$,N$^7$-bis(2-(2,6-Dioxopiperidin-3-yl)-1,3-dioxoisoindolin-4-yl)heptanediamide (EC1-119): This was obtained as a yellow solid (28 mg, 82%) from EC1-114 (46 mg, 0.05 mmol, 1.0 eq.), following the General Procedure B. HPLC: 96% [t$_R$=15.5 min, Gradient MeOH-water 5%-95% (with 0.1% TFA), 20 min]; $^1$H NMR (500 MHz, DMSO-d$_6$) δ 11.14 (s, 2H), 9.71 (s, 2H), 8.47 (d, J=8.4 Hz, 2H), 7.83 (dd, J=8.4, 7.2 Hz, 2H), 7.61 (d, J=7.2 Hz, 2H), 5.15 (dd, J=13.5, 5.4 Hz, 2H), 2.90 (ddd, J=16.9, 13.5, 5.4 Hz, 2H), 2.67-2.53 (m, 4H), 2.50-2.45 (m, 4H), 2.12-2.05 (m, 2H), 1.72-1.64 (m, 4H), 1.40-1.50 (m, 2H); HPLC-MS (ESI+): m/z 671.2

[100%, (M+H)⁺], 693.2 [20%, (M+Na)⁺]; HRMS (ESI+): m/z calcd for $C_{33}H_{30}N_6O_{10}$ 693.1916 (M+Na)⁺, found 693.1920.

EC1-130

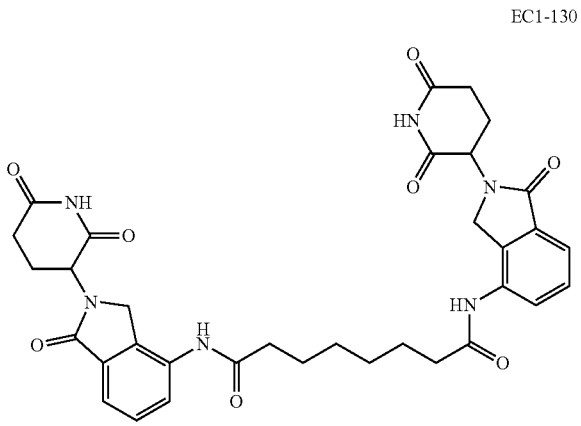 [SMILES: O=C1CCC(N2Cc3c(NC(=O)CCCCCCC(=O)Nc4cccc5c4CN(C4CCC(=O)NC4=O)C5=O)cccc3C2=O)C(=O)N1]

$N^1,N^8$-bis(2-(2,6-dioxopiperidin-3-yl)-1-oxoisoindolin-4-yl)octanediamide (EC1-130): This was obtained as a yellow solid (40 mg, 99%), from EC1-122 (56 mg, 0.06 mmol, 1.0 eq.), following the General Procedure B. HPLC: 100% [$t_R$=16.1 min, Gradient MeOH-water 5%-95% (with 0.1% TFA), 20 min]; ¹H NMR (500 MHz, DMSO-d₆) δ 11.15 (s, 2H), 9.70 (s, 2H), 8.47 (d, J=8.4 Hz, 2H), 7.83 (dd, J=8.4, 7.2 Hz, 2H), 7.61 (d, J=7.2 Hz, 2H), 5.15 (dd, J=13.5, 5.4 Hz, 2H), 2.90 (ddd, J=17.0, 13.5, 5.4 Hz, 2H), 2.66-2.53 (m, 3H), 2.50-2.47 (m, 5H), 2.10-2.05 (m, 2H), 1.70-1.65 (m, 4H), 1.43-1.34 (m, 4H); HPLC-MS (ESI+): m/z 685.3 [100%, (M+H)⁺], 707.2 [80%, (M+Na)⁺]; HRMS (ESI+): m/z calcd for $C_{34}H_{36}N_6O_8$ 679.2487 (M+Na)⁺, found 679.2480.

EC1-133

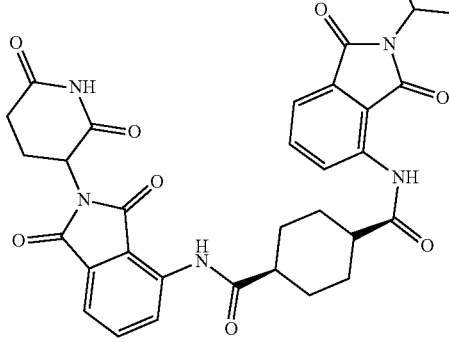

(cis)-$N^1,N^4$-bis(2-(2,6-Dioxopiperidin-3-yl)-1,3-dioxoisoindolin-4-yl)cyclohexane-1,4-dicarboxamide (EC1-133): This was obtained as a yellow solid (20 mg, 99%) from EC1-126 (110 mg, 0.13 mmol, 1.0 eq.), after trituration with MeOH (3 times, ca. 6 mL), following a modified General Procedure B. HPLC: 95% [$t_R$=15.7 min, Gradient MeOH-water 5%-95% (with 0.1% TFA), 20 min]; ¹H NMR (500 MHz, DMSO-d₆) δ 11.15 (s, 1H), 9.78 (s, 1H), 8.51 (d, J=8.1 Hz, 1H), 7.84 (dd, J=8.5, 7.3 Hz, 1H), 7.62 (dd, J=7.3, 0.8 Hz, 1H), 5.15 (dd, J=13.5, 5.4 Hz, 1H), 2.89 (ddd, J=17.0, 13.8, 5.4 Hz, 2H), 2.79-2.73 (m, 2H), 2.66-2.53 (m, 4H), 2.11-2.05 (m, 2H), 2.0-1.91 (m, 3H), 1.81-1.75 (m, 3H), 1.29-1.12 (m, 2H); HPLC-MS (ESI+): m/z 683.2 [40%, (M+H)⁺], 705.3 [30%, (M+Na)⁺]; HRMS (ESI+): m/z calcd for $C_{34}H_{30}N_6O_{10}$ 705.1916 (M+Na)⁺, found 705.1916.

EC1-135

(trans)-$N^1,N^4$-bis(2-(2,6-Dioxopiperidin-3-yl)-1,3-dioxoisoindolin-4-yl)cyclohexane-1,4-dicarboxamide (EC1-135): This was obtained as a pale solid (35 mg, 92%) from EC1-128 (50 mg, 0.06 mmol, 1.0 eq.), following General Procedure B, ¹H NMR (500 MHz, DMSO-d₆) δ 11.16 (s, 2H), 9.78 (s, 2H), 8.48 (d, J=8.3 Hz, 2H), 7.85 (dd, J=8.3, 7.3 Hz, 2H), 7.63 (d, J=7.3 Hz, 2H), 5.16 (dd, J=13.5, 5.5 Hz, 2H), 2.90 (ddd, J=17.1, 13.5, 5.5 Hz, 2H), 2.60-2.50 (m, 6H), 2.20-2.10 (m, 6H), 1.61-1.50 (m, 4H); HPLC-MS (ESI+): m/z 683.2 [40%, (M+H)⁺]; HRMS (ESI+): m/z calcd for $C_{34}H_{30}N_6O_{10}$ 705.1916 (M+Na)⁺, found 705.1913.

EC1-131

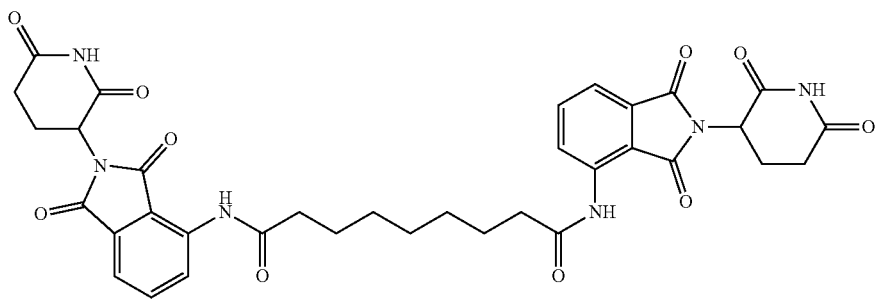

$N^1,N^9$-bis(2-(2,6-Dioxopiperidin-3-yl)-1-oxoisoindolin-4-yl)nonanediamide (EC1-131): This was obtained as a yellow solid (35 mg, 99%) from EC1-123 (49 mg, 0.05 mmol, 1.0 eq.), following General Procedure B. HPLC: 99% [$t_R$=16.7 min, MeOH 95% and water 5% (with 0.1% TFA), 20 min]; $^1$H NMR (500 MHz, DMSO-$d_6$) δ 11.15 (s, 2H), 9.69 (s, 2H), 8.47 (d, J=8.4 Hz, 2H), 7.83 (dd, J=8.4, 7.3 Hz, 2H), 7.61 (d, J=7.3 Hz, 2H), 5.15 (dd, J=13.5, 5.4 Hz, 2H), 2.90 (ddd, J=17.1, 13.5, 5.4 Hz, 2H), 2.66-2.54 (m, 4H), 2.50-2.35 (m, 5H), 2.02-2.15 (m, 2H), 1.69-1.58 (m, 4H), 1.39-1.34 (m, 5H); HPLC-MS (ESI+): m/z 699.3 [20%, (M+H)$^+$], 721.2 [20%, (M+Na)$^+$]; HRMS (ESI+): m/z calcd for $C_{35}H_{34}N_6O_{10}$ 721.2229 (M+Na)$^+$, found 721.2236.

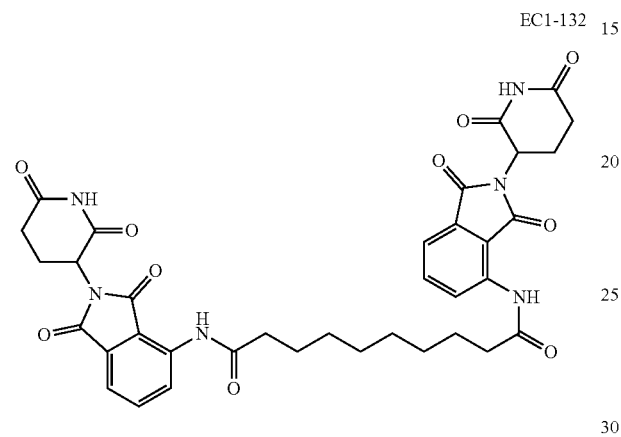

EC1-132

$N^1,N^{10}$-bis(2-(2,6-Dioxopiperidin-3-yl)-1,3-dioxoisoindolin-4-yl)decanediamide (EC1-132): This was obtained as a yellow solid (5 mg, 77%) from EC1-127 (9 mg, 0.01 mmol, 1.0 eq.), following General Procedure B. HPLC: 98% [$t_R$=17.2 min, MeOH 95% and water 5% (with 0.1% TFA), 20 min]; $^1$H NMR (500 MHz, DMSO-$d_6$) δ 11.15 (s, 2H), 9.69 (s, 2H), 8.47 (d, J=8.4 Hz, 2H), 7.83 (dd, J=8.4, 7.4 Hz, 2H), 7.61 (d, J=7.3 Hz, 2H), 5.15 (dd, J=13.5, 5.4 Hz, 2H), 2.90 (ddd, J=17.0, 13.5, 5.4 Hz, 2H), 2.67-2.53 (m, 4H), 2.50-2.48 (m, 4H), 2.12-1.98 (m, 2H), 1.70-1.62 (m, 3H), 1.11-1.35 (m, 9H); HPLC-MS (ESI+): m/z 713.4 [60%, (M+H)$^+$], 735.3 [80%, (M+Na)$^+$]; HRMS (ESI+): m/z calcd for $C_{36}H_{36}N_6O_{10}$ 735.2385 (M+Na)$^+$, found 735.2396.

Synthetic scheme 29

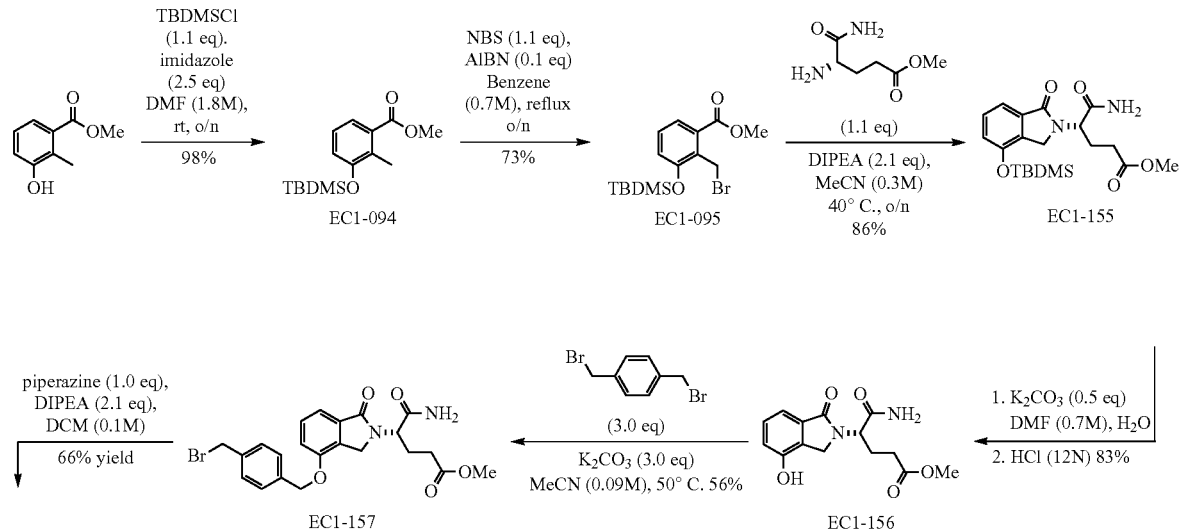

-continued

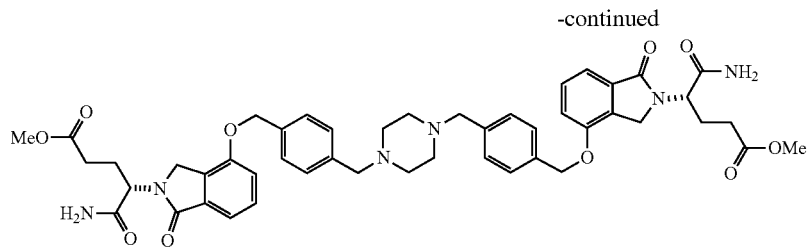

EC1-163

1. KO$^t$Bu (1 eq), THF, 0° C. to rt
2. MsOH (1 eq), DCM, rt
43%

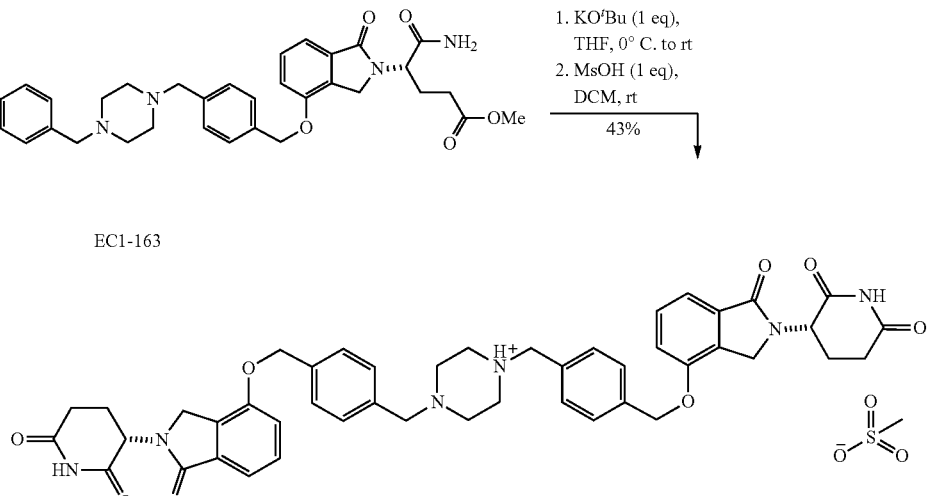

EC1-168

EC1-094

Methyl 3-((tert-butyldimethylsilyl)oxy)-2-methylbenzoate (EC1-094): Tert-butyldimethylsilyl chloride (2.0 g, 13 mmol, 1.1 eq.) was added at 0° C. to a solution of methyl 3-hydroxy-2-methylbenzoate (2.0 g, 12 mmol, 1.0 eq.) and imidazole (2.0 g, 30 mmol, 2.5 eq.) in DMF (7 mL) and the reaction was stirred at room temperature overnight. The mixture was diluted with EtOAc (50 mL) and washed with ice-cold H$_2$O (50 mL). The organic phase was washed with brine (100 mL), dried (MgSO$_4$), filtered and the solvent evaporated under reduced pressure to give methyl 3-((tert-butyldimethylsilyl)oxy)-2-methylbenzoate (EC1-094) as a pale brown liquid (3.3 g, 98%) which was used to the next step without purification. $^1$H NMR (500 MHz, DMSO-d6) δ 7.13 (dd, J=7.8, 1.2 Hz, 1H), 6.98 (t, J=7.9 Hz, 1H), 6.82 (dd, J=8.1, 1.2 Hz, 1H), 3.60 (s, 3H), 2.10 (s, 3H), 0.78 (s, 9H), 0.00 (s, 6H); HPLC-MS (ESI+): m/z 281.3 [100%, (M+H)$^+$], 303.2 [80%, (M+Na)$^+$]. (See WO2018/85247.)

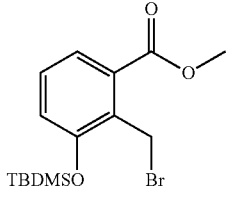

EC1-095

Methyl 2-(bromomethyl)-3-((tert-butyldimethylsilyl)oxy) benzoate (EC1-095): N-Bromosuccinimide (2.3 g, 13 mmol, 1.1 eq.) was added to a solution of methyl 3-((tert-butyldimethylsilyl)oxy)-2-methylbenzoate (EC1-094) (3.3 g, 12 mmol, 1.0 eq.) and 2,2'-azobis(2-methylpropionitrile (194 mg, 1.2 mmol, 0.1 eq.) in benzene (20 mL) and the mixture was refluxed overnight. The suspension was cooled to room temperature, the solvent evaporated under reduced pressure and the residue partitioned between EtOAc (50 mL) and H$_2$O (50 mL). The organic phase was washed with brine (100 mL), dried (MgSO$_4$), filtered and the solvent evaporated under reduced pressure. The residue was purified by column chromatography (0-100% EtOAc:hexane) to give methyl 2-(bromomethyl)-3-((tert-butyldimethylsilyl)oxy) benzoate (EC1-095) as a yellow oil (3.1 g, 73%). $^1$H NMR (500 MHz, DMSO-d$_6$) δ 7.28 (dd, J=7.9, 1.2 Hz, 1H), 7.20 (t, J=8.0 Hz, 1H), 6.98 (dd, J=8.2, 1.2 Hz, 1H), 4.78 (s, 2H), 3.68 (s, 3H), 0.86 (s, 9H), 0.12 (s, 6H); HPLC-MS (ESI+): m/z 381.1 and 383.1 [100%, (M+Na)$^+$], 741.2 and 743.2 [20%, (2M+Na)$^+$]. (See WO2018/85247.)

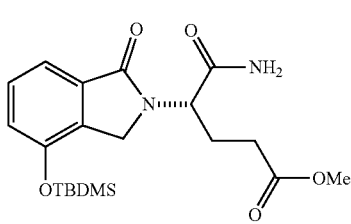

EC1-155

Methyl (S)-5-amino-4-(4-((tert-butyldimethylsilyl)oxy)-1-oxoisoindolin-2-yl)-5-oxopentanoate (EC1-155): Methyl (S)-4,5-diamino-5-oxopentanoate (610 mg, 3.1 mmol, 1.1 eq.) was added to a solution of 2-(bromomethyl)-3-((tert-butyldimethylsilyl)oxy)benzoate (EC1-095) (1.0 g, 2.8 mmol, 1.0 eq.) in acetonitrile (10 mL). DIPEA (1.2 mL, 5.6 mmol, 2.1 eq.) was then added and the suspension stirred at 40° C. overnight. The suspension was cooled to room temperature, the solvent evaporated under reduced pressure and the residue partitioned between EtOAc (20 mL) and 1 M HCl (20 mL). The organic phase was washed with sat. NaHCO$_3$ (20 mL), brine (50 mL), dried (MgSO$_4$), filtered and the solvent evaporated under reduced pressure. The residue was purified by column chromatography (0-10% MeOH:CH$_2$Cl$_2$) to give methyl (S)-5-amino-4-(4-((tert-butyldimethylsilyl)oxy)-1-oxoisoindolin-2-yl)-5-oxopentanoate (EC1-155-B3, EC2-151) as a yellow oil (520 mg, 46%). $^1$H NMR (500 MHz, DMSO-d$_6$) δ 7.35 (s, 1H), 7.16 (t, J=7.7 Hz, 1H), 7.08 (dd, J=7.5, 0.8 Hz, 1H), 6.94 (s, 1H), 6.83 (dd, J=8.0, 0.8 Hz, 1H), 4.49 (dd, J=10.4, 4.9 Hz, 1H), 4.24 (d, J=17.3 Hz, 1H), 4.09 (d, J=17.3 Hz, 1H), 3.24 (s, 3H), 2.07-2.01 (m, 2H), 1.99-1.91 (m, 1H), 1.86-1.76 (m, 1H), 0.75 (s, 9H), 0.01 (s, 3H), 0.00 (s, 3H); HPLC-MS (ESI+): m/z 407.2 [100%, (M+H)$^+$], 835.5 [50%, (2M+H)$^+$]. (See WO2018/85247.)

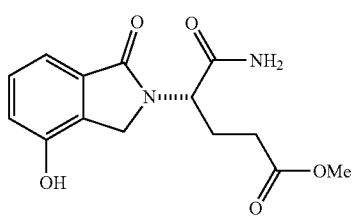

EC1-156

Methyl (S)-5-amino-4-(4-hydroxy-1-oxoisoindolin-2-yl)-5-oxopentanoate (EC1-156): Potassium carbonate (510 mg, 3.7 mmol, 0.5 eq.) was added to a solution of methyl (S)-5-amino-4-(4-((tert-butyldimethylsilyl)oxy)-1-oxoisoindolin-2-yl)-5-oxopentanoate (EC1-155) (3.0 g, 7.4 mmol, 1.0 eq.) in DMF (10 mL) and H$_2$O (1 mL) and the reaction stirred at room temperature for 40 minutes. Hydrochloric acid (12 N, 0.6 mL, 7.4 mmol, 1.0 eq.) and acetonitrile (10 mL) were added, the suspension filtered and the filtrate concentrated under reduced pressure. The residue was dried under high vacuum overnight to give methyl (S)-5-amino-4-(4-hydroxy-1-oxoisoindolin-2-yl)-5-oxopentanoate (EC1-156) (2.1 g, 99%) as a thick orange oil which was used to the next step without purification. $^1$H NMR (500 MHz, DMSO-d$_6$) δ 10.02 (s, 1H), 7.55 (s, 1H), 7.29 (t, J=7.7 Hz, 1H), 7.17 (s, 1H), 7.14 (dd, J=7.5, 0.8 Hz, 1H), 6.97 (dd, J=8.0, 0.9 Hz, 1H), 4.71 (dd, J=10.5, 4.8 Hz, 1H), 4.46 (d, J=17.4 Hz, 1H), 4.30 (d, J=17.4 Hz, 1H), 3.49 (s, 3H), 2.28-2.22 (m, 2H), 2.21-2.13 (m, 1H), 2.09-1.97 (m, 1H); HPLC-MS (ESI+) and (ESI-): m/z 293.2 [100%, (M+H)$^+$], 315.1 [100%, (M+Na)$^+$], 607.2 [80%, (2M+Na)$^+$], 291.1 [100%, (M–H)$^+$]. (See WO2014/39960.)

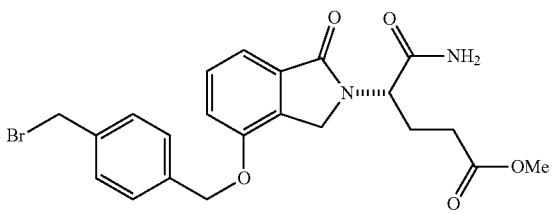

EC1-157

Methyl (S)-5-amino-4-(4-((4-(bromomethyl)benzyl)oxy)-1-oxoisoindolin-2-yl)-5-oxopentanoate (EC1-157): Potassium carbonate (141 mg, 1.02 mmol, 3.0 eq.) was added to a solution of (S)-5-amino-4-(4-hydroxy-1-oxoisoindolin-2-yl)-5-oxopentanoate (EC1-156) (100 mg, 0.34 mmol, 1.0 eq.) in acetonitrile (4 mL) followed by 1,4-bis(bromomethyl)benzene (269 mg, 1.02 mmol, 3.0 eq.) and the reaction stirred at 50° C. for 2 hours. The crude residue was suspended in a 1:1 mixture (MeOH:CH$_2$Cl$_2$, 10 mL), filtered and the filtrate evaporated under reduced pressure. The residue was purified by column chromatography (0-10% MeOH:CH$_2$Cl$_2$) to give methyl (S)-5-amino-4-(4-((4-(bromomethyl)benzyl)oxy)-1-oxoisoindolin-2-yl)-5-oxopentanoate (EC1-157) as a pale yellow oil (90 mg, 56%). $^1$H NMR (500 MHz, DMSO-d$_6$) δ 7.58 (s, 1H), 7.51-7.42 (m, 5H), 7.29 (ddd, J=8.1, 5.5, 0.8 Hz, 2H), 7.20 (s, 1H), 5.26 (s, 2H), 4.76-4.69 (m, 3H), 4.55 (d, J=17.6 Hz, 1H), 4.43 (d, J=17.6 Hz, 1H), 3.51 (s, 3H), 2.30-2.16 (m, 3H), 2.12-2.04 (m, 1H); HPLC-MS (ESI+): m/z 971.2 and 973.2 [50%, (2M+Na)$^+$]. (See US2018/224435.)

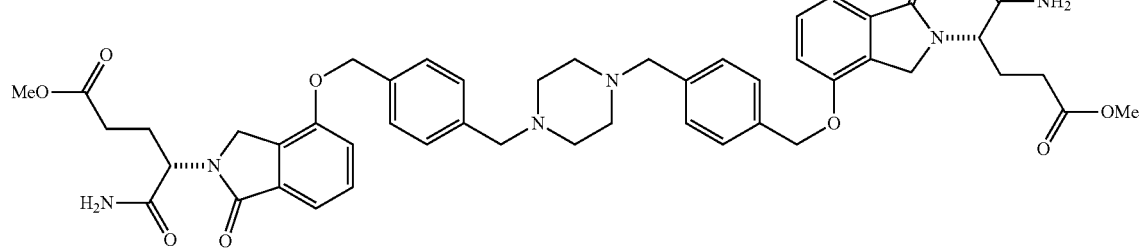

EC1-163

Dimethyl 4,4'-(((((piperazine-1,4-diylbis(methylene))bis(4,1-phenylene))bis(methylene))bis(oxy))bis(1-oxoisoindoline-4,2-diyl))(4S,4'S)-bis(5-amino-5-oxopentanoate) (EC1-163): Piperazine (18 mg, 0.21 mmol, 1.0 eq.) was added to a solution of methyl (S)-5-amino-4-(4-((4-(bromomethyl)benzyl)oxy)-1-oxoisoindolin-2-yl)-5-oxopentanoate (EC1-157) (200 mg, 0.42 mmol, 2.1 eq.) in $CH_2Cl_2$ (1.5 mL) followed by addition of DIPEA (73 µL, 2.1 eq.) and the reaction stirred at room temperature for 5 hours. The solvent was removed under reduced pressure, the residue dissolved in $CH_2Cl_2$ (10 mL) and washed with sat. $NaHCO_3$ (10 mL). The organic phase was washed with brine (10 mL), dried ($MgSO_4$), filtered and the solvent evaporated under reduced pressure. The residue was purified by column chromatography (0-20% $MeOH:CH_2Cl_2$) to give dimethyl 4,4'-(((((piperazine-1,4-diylbis(methylene))bis(4,1-phenylene))bis(methylene))bis(oxy))bis(1-oxoisoindoline-4,2-diyl))(4S,4'S)-bis(5-amino-5-oxopentanoate) (EC1-163) (120 mg, 66%) as a pale yellow solid. $^1H$ NMR (500 MHz, DMSO-$d_6$) δ 7.59 (s, 2H), 7.48-7.41 (m, 6H), 7.35-7.27 (m, 8H), 7.18 (s, 2H), 5.22 (s, 4H), 4.72 (dd, J=10.5, 4.9 Hz, 2H), 4.53 (d, J=17.7 Hz, 2H), 4.40 (d, J=17.7 Hz, 2H), 3.50 (s, 4H), 2.46-2.29 (m, 6H), 2.28-2.22 (m, 3H), 2.23-2.15 (m, 2H), 2.11-2.03 (m, 3H), 1.28-1.22 (m, 2H); HPLC-MS (ESI+): m/z 875.4 [100%, (M+H)$^+$].

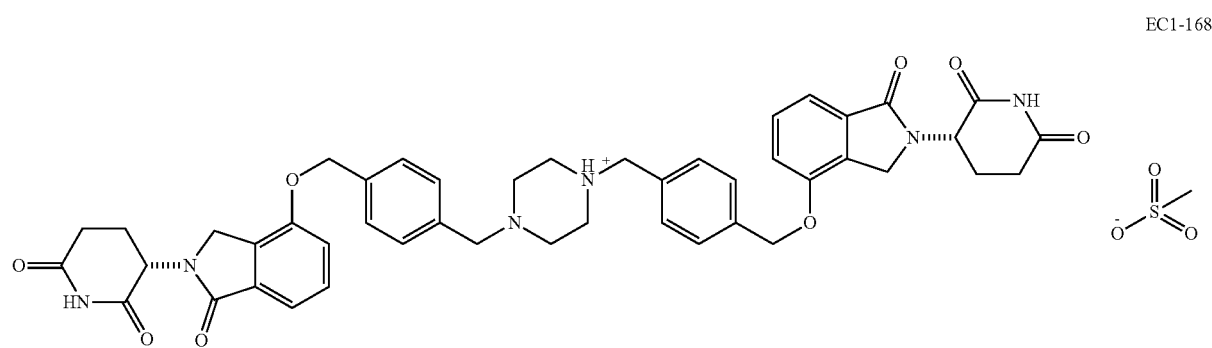

EC1-168

(4-(4-(((2-((S)-2,6-dioxopiperidin-3-yl)-1-oxoisoindolin-4-yl)oxy)methyl)benzyl)-114-piperazin-1-yl)(4-(((2-((S)-2,6-dioxopiperidin-3-yl)-1-oxoisoindolin-4-yl)oxy)methyl)phenyl)methylium methyl sulfonate (EC1-168): A solution of KO$^t$Bu (24 mg, 0.2 mmol, 2.0 eq.) in THF (0.5 mL) was added slowly to a solution of dimethyl 4,4'-(((((piperazine-1,4-diylbis(methylene))bis(4,1-phenylene))bis(methylene))bis(oxy))bis(1-oxoisoindoline-4,2-diyl))(4S,4'S)-bis(5-amino-5-oxopentanoate) (EC1-163) (95 mg, 0.1 mmol, 1.0 eq.) in anhydrous THF (1.0 mL) at 0° C. and stirred for 30 minutes. Hydrochloric acid (0.2 mL of 1.0 M aq. solution) was added slowly at the same temperature and then the mixture was basified with sat. $NaHCO_3$ (10 mL). The residue was extracted with $CH_2Cl_2$ (3×20 mL), dried ($MgSO_4$), filtered and the solvent removed under reduced pressure to give the free base of EC1-168 (35 mg). The free base of EC1-168 (35 mg, 0.04 mmol, 1.0 eq.) was suspended in MeOH (5 mL), methylsulfonic acid (2.9 mg, 0.03 mmol, 1.0 eq.) added and the mixture stirred at room temperature for 30 minutes. Evaporation of the solvent gave the final sulfonate (EC1-168) as a pale yellow solid (39 mg, 43% over two steps); $^1H$ NMR (500 MHz, DMSO-$d_6$) δ 10.97 (s, 2H), 9.45 (s, 1H), 7.67-7.39 (m, 8H), 7.35-7.25 (m, 6H), 5.34-5.19 (m, 4H), 5.12 (dd, J=13.3, 5.1 Hz, 2H), 4.42 (d, J=17.5 Hz, 2H), 4.34 (brs, 2H), 4.26 (d, J=17.5 Hz, 2H), 3.62-3.44 (m, 3H), 3.14-3.01 (m, 2H), 2.97-2.86 (m, 4H), 2.65-2.54 (m, 3H), 2.47-2.36 (m, 4H), 2.30 (s, 3H), 2.04-1.95 (m, 2H); HPLC-MS (ESI+): m/z 811.4 [100%, (M+H)$^+$]; HRMS (ESI+): m/z calcd for $C_{46}H_{46}N_6O_8$ 811.3450 (M+H)$^+$, found 811.3448.

Synthetic scheme 30

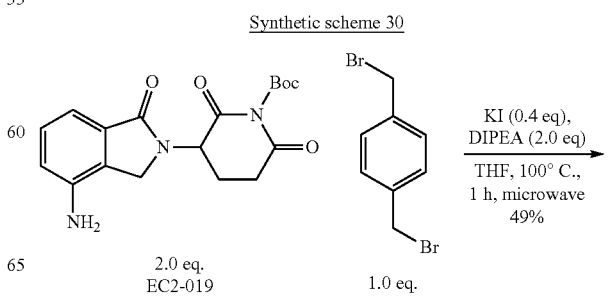

-continued

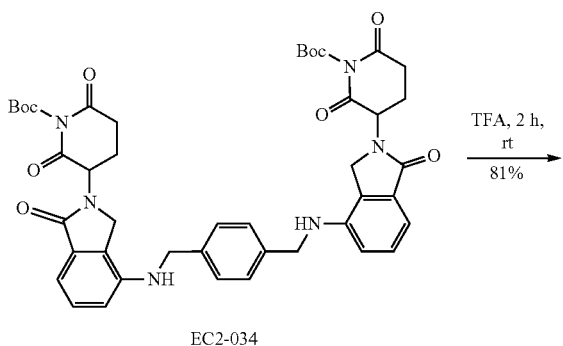

EC2-034

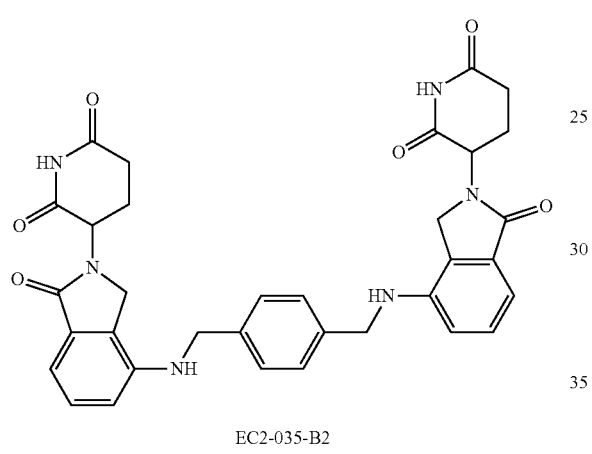

EC2-035-B2

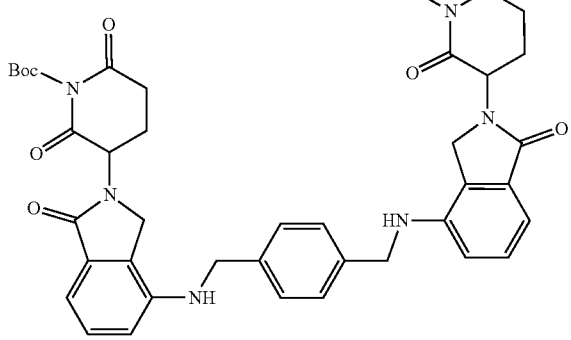

EC2-034

Di-tert-butyl 3,3'-(((1,4-phenylenebis(methylene))bis(azanediyl))bis(1-oxoisoindoline-4,2-diyl))bis(2,6-dioxopiperidine-1-carboxylate) (EC2-034): 1,4-Bis(bromomethyl)benzene (70 mg, 0.26 mmol, 1.0 eq.) was added to a suspension of tert-butyl 3-(4-amino-1-oxoisoindolin-2-yl)-2,6-dioxopiperidine-1-carboxylate (EC2-019) (200 mg, 0.56 mmol, 2.0 eq.). Potassium iodide (40 mg, 0.22 mmol, 0.4 eq.) in THF (1.2 mL) and DIPEA (94 µL, 0.56 mmol, 2.0 eq.) were then added and the suspension was heated in the microwave reactor at 100° C. for 1 hour. The solvent was removed under reduced pressure and the residue was purified by column chromatography (0-100% EtOAc:hexane, 1% Et$_3$N) to give di-tert-butyl 3,3'-(((1,4-phenylenebis(methylene))bis(azanediyl))bis(1-oxoisoindoline-4,2-diyl))bis(2,6-dioxopiperidine-1-carboxylate) (EC2-157, EC2-034-B2) (104 mg, 47%) as a pale yellow solid. $^1$H NMR (500 MHz, DMSO-d$_6$) δ 7.34 (s, 4H), 7.20 (t, J=7.7 Hz, 2H), 6.92 (d, J=7.4 Hz, 2H), 6.65 (d, J=8.1 Hz, 2H), 6.40-6.33 (m, 2H), 5.35 (dd, J=13.4, 5.0 Hz, 2H), 4.40-4.28 (m, 6H), 4.19 (d, J=17.1 Hz, 2H), 3.15 (ddd, J=18.2, 13.5, 5.6 Hz, 2H), 2.86-2.78 (m, 2H), 2.44-2.33 (m, 2H), 2.14-2.07 (m, 2H), 1.49 (s, 18H); HPLC-MS (ESI+): m/z 621.3 [100%, (M-2Boc+H)$^+$], 721.4 [100%, (M-Boc+H)$^+$], 843.3 [100%, (M+Na)$^+$].

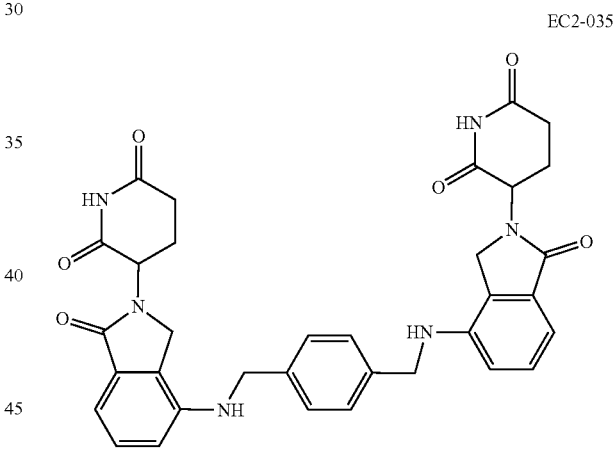

EC2-035

3,3'-(((1,4-Phenylenebis(methylene))bis(azanediyl))bis(1-oxoisoindoline-4,2-diyl))bis(piperidine-2,6-dione) (EC2-035-B2 or EC2-183): The di-tert-butyl 3,3'-(((1,4-phenylenebis(methylene))bis(azanediyl))bis(1-oxoisoindoline-4,2-diyl))bis(2,6-dioxopiperidine-1-carboxylate)(EC2-034) (170 mg, 0.20 mmol) was dissolved in TFA (2 mL) and the solution was stirred at room temperature for 1 hour. The TFA was removed under reduced pressure and the residue was triturated with MeOH (3×5 mL) to give the final dimer (EC2-035) as a pale yellow solid (100 mg, 81%). $^1$H NMR (500 MHz, DMSO-d$_6$) δ 11.08 (s, 2H), 7.40 (s, 4H), 7.26 (t, J=7.8 Hz, 2H), 6.98 (d, J=7.4 Hz, 2H), 6.71 (d, J=8.1 Hz, 2H), 6.40 (s, 2H), 5.18 (dd, J=13.3, 5.1 Hz, 2H), 4.46-4.40 (m, 4H), 4.36 (d, J=17.2 Hz, 2H), 4.24 (d, J=17.2 Hz, 2H), 3.06-2.92 (m, 2H), 2.74-2.65 (m, 2H), 2.47-2.30 (m, 2H), 2.15-2.07 (m, 2H); HPLC-MS (ESI+) and (ESI−): m/z 621.2 [100%, (M+H)$^+$] and 619.0 [10%, (M−H)$^+$]; HRMS (ESI+): m/z calcd for C$_{34}$H$_{32}$N$_6$O$_8$ 643.2276 (M+Na)$^+$, found 643.2254.

Synthetic scheme 31

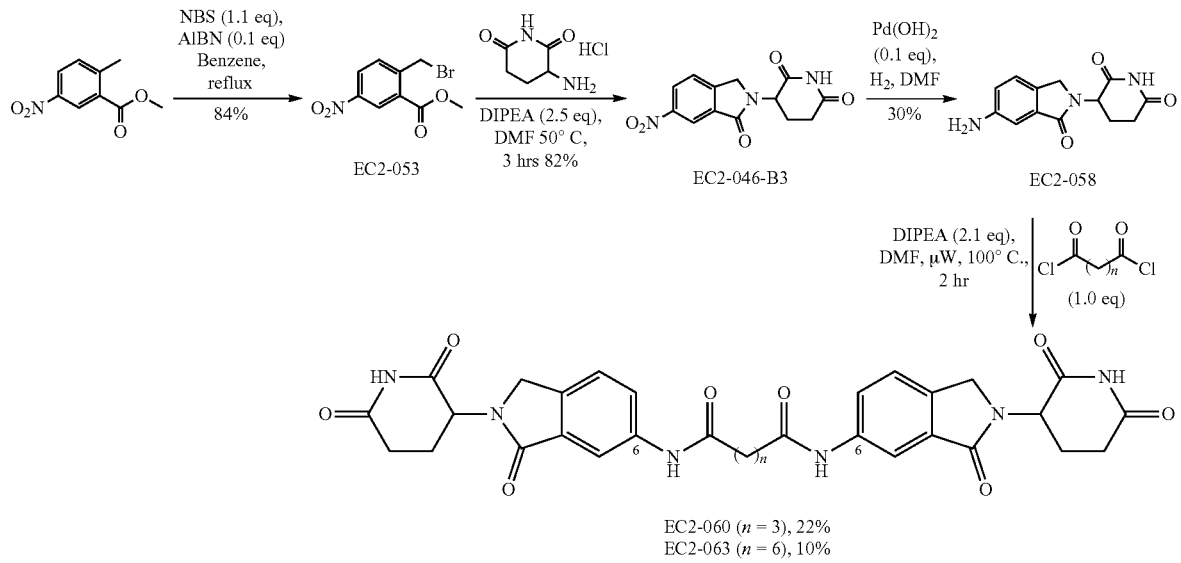

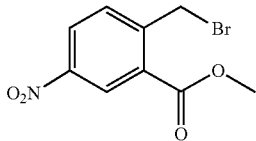

Methyl 2-(bromomethyl)-5-nitrobenzoate (EC2-053): N-Bromosuccinimide (5.0 g, 28 mmol, 1.1 eq.) was added to a solution of methyl 2-methyl-5-nitrobenzoate (5.0 g, 25 mmol, 1.0 eq.) and AIBN (410 mg, 2.5 mmol, 0.1 eq.) in benzene (40 mL) and the mixture refluxed overnight. The suspension was cooled to room temperature, the solvent evaporated under reduced pressure and the residue partitioned between EtOAc (50 mL) and H$_2$O (50 mL). The organic phase was washed with brine (100 mL), dried (MgSO$_4$), filtered and the solvent evaporated under reduced pressure. The residue was purified by column chromatography (0-100% EtOAc:hexane) to give methyl 2-(bromomethyl)-5-nitrobenzoate (EC2-053) as an off-white solid (5.9 g, 84%). $^1$H NMR (500 MHz, DMSO-d$_6$) δ 8.59 (d, J=2.6 Hz, 1H), 8.43 (dd, J=8.5, 2.6 Hz, 1H), 7.91 (d, J=8.5 Hz, 1H), 5.10 (s, 2H), 3.94 (s, 3H); HPLC-MS (ESI+): m/z 296.0 and 298.0 [40%, (M+Na)$^+$]. (See WO2017/197056.)

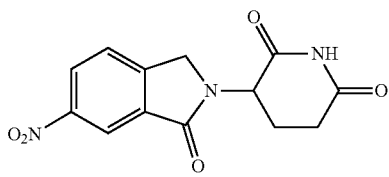

3-(6-Nitro-1-oxoisoindolin-2-yl)piperidine-2,6-dione (EC2-046-B3): 3-Aminopiperidine-2,6-dione.HCl (420 mg, 2.6 mmol, 1.4 eq.) was added to a solution of methyl 2-(bromomethyl)-5-nitrobenzoate EC2-053 (500 mg, 1.8 mmol, 1.0 eq.) in DMF (5 mL), DIPEA (0.8 mL, 4.6 mmol, 2.5 eq.) was then added and the suspension was stirred at 50° C. for 2 hours. The mixture was cooled to room temperature, the solvent evaporated under reduced pressure. The residue was triturated with MeOH (50 mL), filtered and washed further with MeOH (50 mL) to give 3-(6-nitro-1-oxoisoindolin-2-yl)piperidine-2,6-dione (EC2-046) as a purple solid (340 mg, 65%) which was used to the next step without further purification. $^1$H NMR (500 MHz, DMSO-d$_6$) δ 11.04 (s, 1H), 8.51 (dd, J=8.3, 2.2 Hz, 1H), 8.42 (d, J=2.2 Hz, 1H), 7.93 (d, J=8.4 Hz, 1H), 5.18 (dd, J=13.3, 5.2 Hz, 1H), 4.66 (d, J=18.6 Hz, 1H), 4.53 (d, J=18.6 Hz, 1H), 2.99-2.87 (m, 1H), 2.67-2.59 (m, 1H), 2.48-2.36 (m, 1H), 2.10-2.03 (m, 1H); HPLC-MS (ESI+) and (ESI−): m/z 290.0 [100%, (M+H)$^+$], 601.2 [100%, (2M+Na)$^+$], 288.1 [100%, (M−H)$^+$]. (See WO2017/197056.)

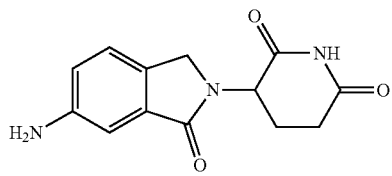

3-(6-Amino-1-oxoisoindolin-2-yl)piperidine-2,6-dione (EC2-058): A suspension of Pd(OH)$_2$ (10% on carbon, 366 mg, 0.1 eq.) in anhydrous DMF (45 mL) was degassed for 15 minutes, the system was evacuated and refilled with H$_2$ (3 times) and then kept under H$_2$ atmosphere for 5 minutes. A degassed solution of 3-(6-nitro-1-oxoisoindolin-2-yl)piperidine-2,6-dione (EC2-046) (1.5 g, 5.2 mmol, 1.0 eq.) in anhydrous DMF (45 mL) was added slowly to the suspension and the reaction stirred overnight at room temperature under H$_2$ atmosphere. The suspension was filtered through Celite® (ca. 2 inch) and washed with EtOAc (ca. 50 mL). The solvent was evaporated under reduced pressure and the residue was purified by column chromatography (0-20% MeOH:CH$_2$Cl$_2$) to give 3-(6-amino-1-oxoisoindolin-2-yl)

piperidine-2,6-dione (EC2-058) (400 mg, 30%) as a purple solid. $^1$H NMR (500 MHz, DMSO-d$_6$) δ 10.94 (s, 1H), 7.22 (d, J=8.1 Hz, 1H), 6.87 (d, J=2.0 Hz, 1H), 6.83 (dd, J=8.1, 2.2 Hz, 1H), 5.33 (s, 2H), 5.04 (dd, J=13.3, 5.1 Hz, 1H), 4.25 (d, J=16.3 Hz, 1H), 4.13 (d, J=16.3 Hz, 1H), 2.66-2.55 (m, 2H), 2.41-2.33 (m, 1H), 2.04-1.93 (m, 1H); HPLC-MS (ESI+) and (ESI−): m/z 260.1 [100%, (M+H)$^+$], 519.2 [100%, (2M+H)$^+$], 258.2 [100%, (M−H)$^+$]. (See WO2017/197056.)

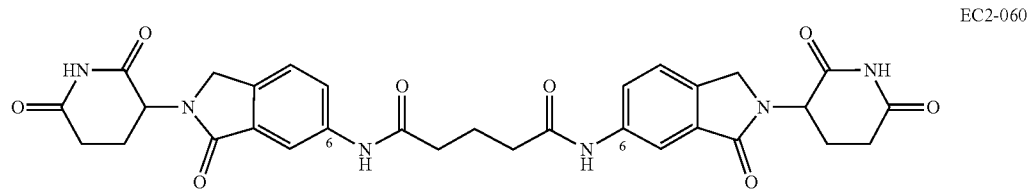 [SMILES: O=C1CCC(N2Cc3ccc(NC(=O)CCCC(=O)Nc4ccc5c(c4)C(=O)N(C4CCC(=O)NC4=O)C5)cc3C2=O)C(=O)N1]

EC2-060

N$^1$,N$^5$-bis(2-(2,6-Dioxopiperidin-3-yl)-3-oxoisoindolin-5-yl)glutaramide (EC2-060): Glutaryl chloride (12 μL, 0.09 mmol, 1.0 eq.) and DIPEA (33 μL, 0.19 mmol, 2.1 eq.) were added to a suspension of 3-(6-amino-1-oxoisoindolin-2-yl) piperidine-2,6-dione (EC2-058) (50 mg, 0.19 mmol, 2.1 eq.) in DMF (0.5 mL) and the mixture was heated in the microwave reactor at 100° C. for 2 hours. Methanol (5 mL) was then added and the precipitate formed was collected by filtration. Trituration with methanol (5×5 mL) gave the final dimer (EC2-060) as an off-white solid (12 mg, 22%). $^1$H NMR (500 MHz, DMSO-d$_6$) δ 10.98 (s, 2H), 10.17 (s, 2H), 8.12 (s, 2H), 7.77-7.67 (m, 2H), 7.53 (d, J=8.2 Hz, 2H), 5.10 (dd, J=13.2, 5.1 Hz, 2H), 4.40 (d, J=17.0 Hz, 2H), 4.28 (d, J=17.0 Hz, 2H), 2.96-2.87 (m, 2H), 2.66-2.57 (m, 2H), 2.47-2.36 (m, 6H), 2.09-1.89 (m, 4H); HPLC-MS (ESI+) and (ESI−): m/z 615.3 [20%, (M+H)$^+$] and 613.4 [40%, (M−H)$^+$]; HRMS (ESI+): m/z calcd for C$_{31}$H$_{30}$N$_6$O$_8$ 615.2198 (M+H)$^+$, found 615.2187.

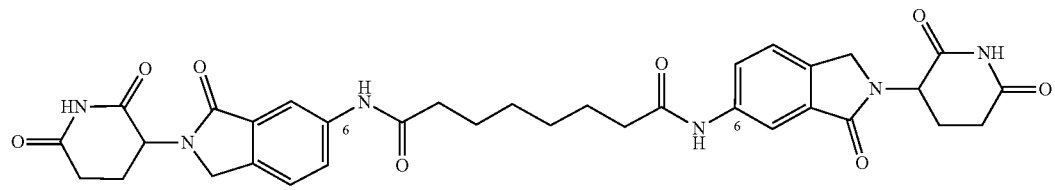

EC2-063

183

N[1],N[8]-bis(2-(2,6-Dioxopiperidin-3-yl)-3-oxoisoindolin-5-yl)octanediamide (EC2-063): Suberoyl chloride (34 µL, 0.19 mmol, 1.0 eq.) and DIPEA (66 µL, 0.39 mmol, 2.0 eq.) were added to a suspension of 3-(6-amino-1-oxoisoindolin-2-yl)piperidine-2,6-dione (EC2-058) (100 mg, 0.39 mmol, 2.1 eq.) in DMF (1.0 mL) and the mixture was heated in the microwave reactor at 100° C.; for 1 hour. The solvent was removed under reduced pressure and the residue purified by column chromatography (0-100% EtOAc:hexane then 0-2% MeOH:CH$_2$Cl$_2$) to give the final dimer (EC2-063) as an off-white solid (12 mg, 10%). $^1$H NMR (500 MHz, DMSO-d$_6$) δ 10.98 (s, 2H), 10.10 (s, 2H), 8.10 (d, J=2.0 Hz, 2H), 7.71 (dd, J=8.2, 2.0 Hz, 2H), 7.52 (d, J=8.2 Hz, 2H), 5.09 (dd, J=13.2, 5.1 Hz, 2H), 4.40 (d, J=17.0 Hz, 2H), 4.27 (d, J=17.0 Hz, 2H), 2.96-2.85 (m, 2H), 2.67-2.56 (m, 2H), 2.44-2.30 (m, 6H), 2.06-1.97 (m, 2H), 1.68-1.57 (m, 4H), 1.41-1.29 (d, J=24.1 Hz, 4H); HRMS (ESI+): m/z calcd for C$_{34}$H$_{36}$N$_6$O$_8$ 657.2667 (M+H)$^+$, found 657.2666.

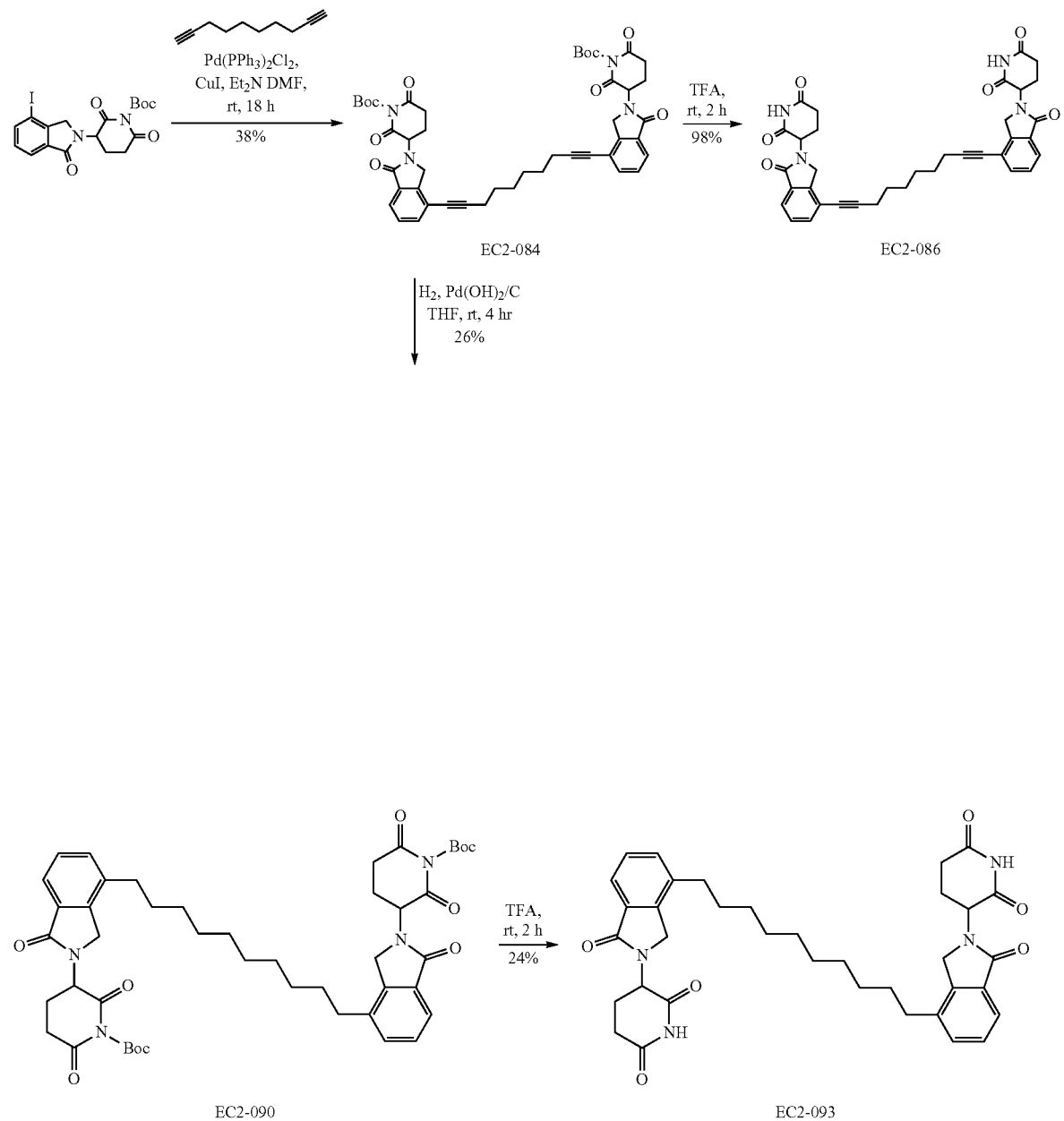

Synthetic scheme 32

EC2-084

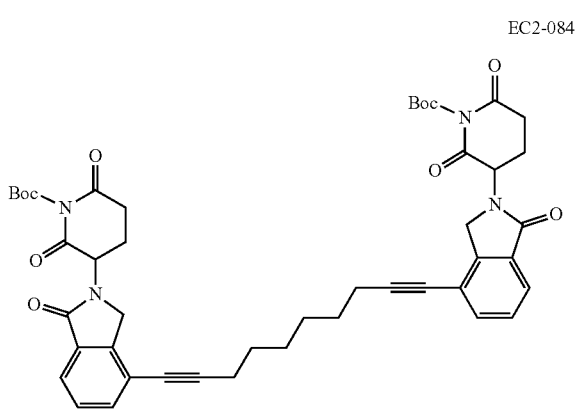 [SMILES: CC(C)(C)OC(=O)N1C(=O)CCC(N2Cc3c(C#CCCCCCCC#Cc4cccc5c4CN(C4CCC(=O)N(C(=O)OC(C)(C)C)C4=O)C5=O)cccc3C2=O)C1=O]

Di-tert-butyl 3,3'-(deca-1,9-diyne-1,10-diylbis(1-oxoisoindoline-4,2-diyl))bis(2,6-dioxopiperidine-1-carboxylate) (EC2-084): Palladium(II)bis(triphenylphosphine) dichloride (4.4 mg, 0.06 mmol) and copper(I) iodide (1 mg, 0.06 mmol) were dissolved in dry DMF (1 mL) and argon bubbled through the mixture for ca. 10 minutes. Tert-butyl 3-(4-iodo-1-oxoisoindolin-2-yl)-2,6-dioxopiperidine-1-carboxylate (100 mg, 0.21 mmol, 2.1 eq.) and deca-1,9-diyne (17 µL, 0.1 mmol, 1.0 eq.) were added followed by the addition of TEA (0.25 mL). The reaction was stirred at 90° C. overnight. The solvent was evaporated under reduced pressure, the crude residue diluted with EtOAc (~10 mL) and filtered through a short plug of Celite®. The solvent was evaporated and the residue was purified by column chromatography (0-100% EtOAc:hexane, 1% Et$_3$N) to give di-tert-butyl 3,3'-(deca-1,9-diyne-1,10-diylbis(1-oxoisoindoline-4,2-diyl))bis(2,6-dioxopiperidine-1-carboxylate) (EC2-084) as a pale yellow solid (31 mg, 38%). $^1$H NMR (500 MHz, DMSO-d$_6$) δ 7.71 (d, J=6.4 Hz, 2H), 7.62 (d, J=7.7 Hz, 2H), 7.51 (td, J=7.6, 1.5 Hz, 2H), 5.36 (dd, J=13.4, 5.2 Hz, 2H), 4.48 (dd, J=17.6, 3.1 Hz, 2H), 4.32 (d, J=17.6 Hz, 2H), 3.19-3.07 (m, 2H), 2.83-2.74 (m, 3H), 2.60-2.53 (m, 2H), 2.12-2.04 (m, 2H), 1.68-1.55 (m, 4H), 1.53-1.50 (m, 2H), 1.48 (s, 18H), 1.32-1.22 (s, 3H), 0.89-0.81 (m, 2H); HPLC-MS (ESI+): m/z 619.3 [100%, (M-2Boc+H)$^+$], 841.4 [100%, (M+Na)$^+$].

Di-tert-butyl 3,3'-(decane-1,10-diylbis(1-oxoisoindoline-4,2-diyl))bis(2,6-dioxopiperidine-1-carboxylate) (EC2-090): A suspension of Pd(OH)$_2$ (10% on carbon, 20 mg, 0.1 eq.) in anhydrous THF (5 mL) was degassed for 15 minutes, the system was evacuated and refilled with H$_2$ (3 times) and then kept under H$_2$ atmosphere for 5 minutes. A degassed solution of di-tert-butyl 3,3'-(deca-1,9-diyne-1,10-diylbis(1-oxoisoindoline-4,2-diyl))bis(2,6-dioxopiperidine-1-carboxylate) (EC2-084) (64 mg, 0.08 mmol, 1.0 eq.) in anhydrous THF (5 mL) was added slowly to the suspension and the reaction was stirred at 50° C. for 3 hours under H$_2$ atmosphere. The suspension was filtered through Celite® (ca. 2 inch) and washed with EtOAc (ca. 10 mL). The solvent was evaporated under reduced pressure and the residue purified by column chromatography (0-100% EtOAc:hexane) to give di-tert-butyl 3,3'-(decane-1,10-diylbis(1-oxoisoindoline-4,2-diyl))bis(2,6-dioxopiperidine-1-carboxylate) (EC2-090) (17 mg, 26%) as an off-white solid. $^1$H NMR (500 MHz, DMSO-d$_6$) δ 7.75-7.69 (m, 2H), 7.65-7.62 (m, 2H), 7.55-7.51 (m, 2H), 5.36 (d, J=13.2, 5.4 Hz, 2H), 4.45 (d, J=17.1 Hz, 2H), 4.31-4.24 (m, 2H), 3.16-3.09 (m, 3H), 2.80-2.70 (m, 6H), 2.28-2.18 (m, 6H), 2.12-2.03 (m, 5H), 2.12-2.04 (m, 5H), 1.28-1.23 (m, 3H); HPLC-MS (ESI+) and (ESI−): m/z 627.4 [100%, (M-2Boc+H)$^+$], 649.3 [50%, (M-2Boc+Na)$^+$], 625.2 [100%, (M-2Boc-H)$^+$].

EC2-086

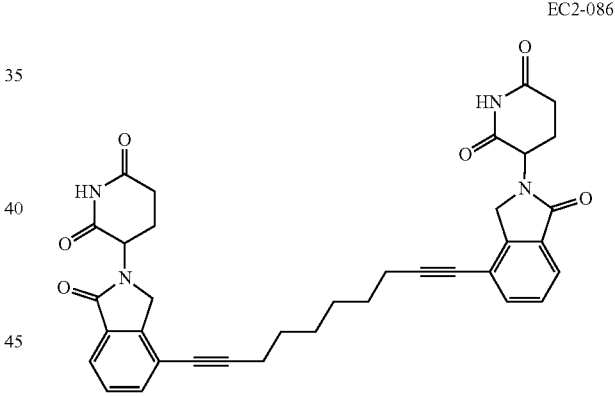

3,3'-(Deca-1,9-diyne-1,10-diylbis(1-oxoisoindoline-4,2-diyl))bis(piperidine-2,6-dione) (EC2-086): The di-tert-butyl 3,3'-(deca-1,9-diyne-1,10-diylbis(1-oxoisoindoline-4,2-diyl))bis(2,6-dioxopiperidine-1-carboxylate) (EC2-084) (30 mg, 0.036 mmol, 1.0 eq.) was dissolved in TFA (2.0 mL) and the solution stirred at room temperature for 1 hour. The solvent was removed under reduced pressure and the residue was triturated with MeOH (2×5 mL) to give the final dimer (EC2-086) as a pale yellow solid (22 mg, 98%). HPLC: 96% [t$_R$=16.6 min, Gradient MeOH-water 5%-95% (with 0.1% TFA)], 20 min; $^1$H NMR (500 MHz, DMSO-d$_6$) δ 10.99 (s, 2H), 7.70 (ddd, J=7.7, 2.6, 1.0 Hz, 2H), 7.62 (ddd, J=7.7, 2.2, 1.0 Hz, 2H), 7.50 (td, J=7.6, 2.3 Hz, 2H), 5.14 (dd, J=13.3, 5.1 Hz, 2H), 4.45 (dd, J=17.6, 3.6 Hz, 2H), 4.31 (d, J=17.6 Hz, 2H), 2.95-2.86 (m, 2H), 2.67-2.55 (m, 2H), 2.48-2.34 (m, 4H), 2.02-(m, 2H), 1.67-1.45 (m, 8H), 1.24 (m, 2H); HPLC-MS (ESI+): m/z 619.2 [50%, (M+H)$^+$]; HRMS (ESI+): m/z calcd for C$_{36}$H$_{34}$N$_4$O$_6$ 641.2371 (M+Na)$^+$, found 641.2361.

EC2-090

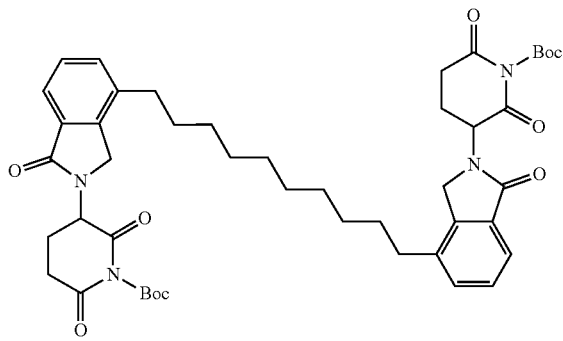

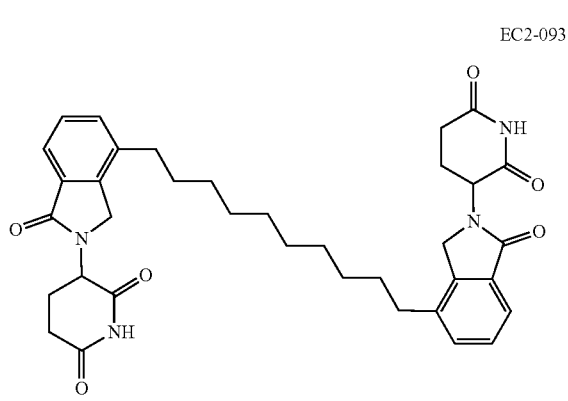 [SMILES: O=C1CCC(N2Cc3c(CCCCCCCCCCc4cccc5c4CN(C4CCC(=O)NC4=O)C5=O)cccc3C2=O)C(=O)N1]

EC2-093

3,3'-(Decane-1,10-diylbis(1-oxoisoindoline-4,2-diyl))bis (piperidine-2,6-dione) (EC2-093): The di-tert-butyl 3,3'-(decane-1,10-diylbis(1-oxoisoindoline-4,2-diyl))bis(2,6-dioxopiperidine-1-carboxylate) (EC2-090) (17 mg, 0.027 mmol, 1.0 eq.) was dissolved in TFA (1.0 mL) and the solution stirred at room temperature for 2 hours. The solvent was removed under reduced pressure and the residue was triturated with MeOH (2×5 mL) and hexane (2×5 mL) to give the final dimer (EC2-093) as a white solid (4 mg, 24%). HPLC: >95% [$t_R$=17.4 min, Gradient MeOH-water 5%-95% (with 0.1% TFA)], 20 min; $^1$H NMR (500 MHz, DMSO-$d_6$) δ 10.98 (s, 2H), 7.56 (dd, J=4.9, 3.7 Hz, 2H), 7.48-7.43 (m, 4H), 5.13 (dd, J=13.3, 5.1 Hz, 2H), 4.46 (d, J=17.1 Hz, 2H), 4.30 (d, J=17.1 Hz, 2H), 2.93 (ddd, J=18.1, 13.7, 5.4 Hz, 2H), 2.67-2.60 (m, 4H), 2.47-2.34 (m, 2H), 2.07-1.96 (m, 2H), 1.59 (s, 4H), 1.38-1.18 (m, 14H); HPLC-MS (ESI+): m/z 649.3 [40%, (M+Na)$^+$]; HRMS (ESI+): m/z calcd for $C_{36}H_{42}N_4O_6$ 649.2997 (M+Na)$^+$, found 649.2985.

Synthetic scheme 33

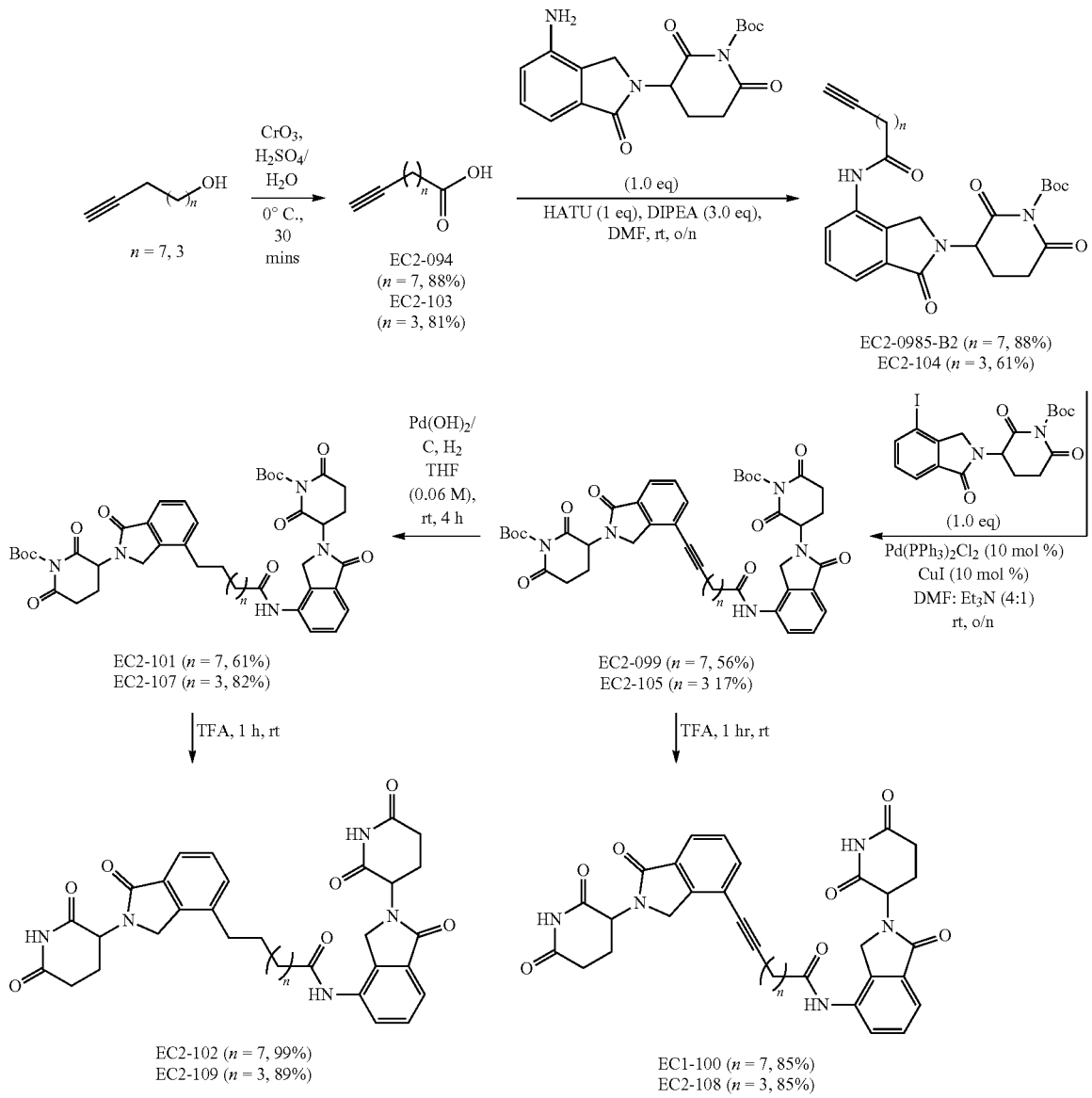

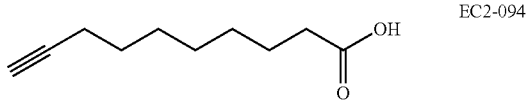

EC2-094

Dec-9-ynoic acid (EC2-094): Jones reagent (2 M, 1.78 mL, 3.56 mmol, 1.1 eq.) was added dropwise to a solution of dec-9-yn-1-ol (500 mg, 3.24 mmol, 1.0 eq.) in acetone (32 mL) at 0° C. and the reaction was left stirring at this temperature for 30 minutes. The ice-bath was removed and the reaction was stirred for 1 hour at room temperature. The solvent was removed under reduced pressure, the residue partitioned between EtOAc (20 mL) and H$_2$O (20 mL), the two phases separated and the organic phase washed with NaHCO$_3$ (3×20 mL). The aqueous phase was collected, acidified by addition of 1 M HCl until pH=1 and the residue re-extracted with EtOAc (3×20 mL). These organic extracts were dried (MgSO$_4$) and the solvent evaporated to give dec-9-ynoic acid (EC2-094) (480 mg, 88%) as a pale yellow oil. $^1$H NMR (500 MHz, CDCl$_3$-d) δ 2.28 (t, J=7.5 Hz, 2H), 2.11 (td, J=7.1, 2.7 Hz, 2H), 1.87 (t, J=2.7 Hz, 1H), 1.57 (p, J=7.6 Hz, 2H), 1.50-1.41 (m, 2H), 1.38-1.20 (m, 6H). (See Morcillo, et al., J. Org. Chem., 76:2277-81, 2011.)

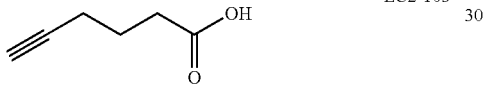

EC2-103

Hex-5-ynoic acid (EC2-103): This was prepared in the same way as EC2-094 from hex-5-yn-1-ol (318 mg, 3.24 mmol, 1.0 eq.) to give hex-5-ynoic acid (EC2-103) (293 mg, 81%) as a pale yellow oil. $^1$H NMR (500 MHz, CDCl$_3$-d) δ 2.45 (t, J=7.4 Hz, 2H), 2.23 (td, J=6.9, 2.7 Hz, 2H), 1.91 (t, J=2.7 Hz, 1H), 1.80 (p, J=7.1 Hz, 2H). (See Earl; V., J. Org. Chem., 49:4786-4800, 1984.)

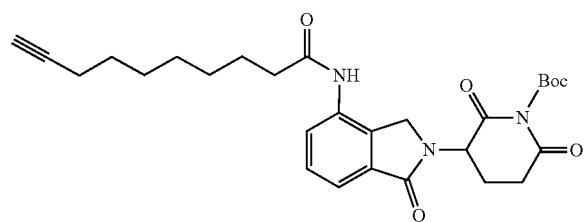

EC2-095

Tert-butyl 3-(4-(dec-9-ynamido)-1-oxoisoindolin-2-yl)-2,6-dioxopiperidine-1-carboxylate (EC2-095): Tert-butyl 3-(4-amino-1-oxoisoindolin-2-yl)-2,6-dioxopiperidine-1-carboxylate (EC2-019) (128 mg, 0.36 mmol, 1.0 eq.) and dec-9-ynoic acid (EC2-094) (90 mg, 0.54 mmol, 1.5 eq.) were dissolved in DMF (3 mL). HATU (140 mg, 0.36 mmol, 1.0 eq.) and DIPEA (192 µL, 1.1 mmol, 3.0 eq.) were then added and the reaction was stirred at room temperature overnight. The mixture was diluted with EtOAc (10 mL), washed with NH$_4$Cl (10 mL), NaHCO$_3$ (2×10 mL), brine (10 mL), dried (MgSO$_4$), filtered and the solvent removed under reduced pressure to give tert-butyl 3-(4-(dec-9-ynamido)-1-oxoisoindolin-2-yl)-2,6-dioxopiperidine-1-carboxylate (EC2-095-B2, EC2-098) (174 mg, 95%) as a white solid which was used to the next step without further purification. $^1$H NMR (500 MHz, DMSO-d$_6$) δ 9.76 (s, 1H), 7.84 (dd, J=7.2, 1.7 Hz, 1H), 7.55-7.47 (m, 2H), 5.39 (dd, J=13.4, 5.1 Hz, 1H), 4.42 (d, J=17.4 Hz, 1H), 4.35 (d, J=17.4 Hz, 1H), 3.14 (ddd, J=18.2, 13.5, 5.4 Hz, 1H), 2.85-2.76 (m, 1H), 2.74-2.72 (m, 1H), 2.39-2.34 (m, 1H), 2.21-2.06 (m, 4H), 1.66-1.58 (m, 2H), 1.49 (s, 9H), 1.47-1.21 (m, 9H); HPLC-MS (ESI+): m/z 410.2 [100%, (M-Boc+H)$^+$].

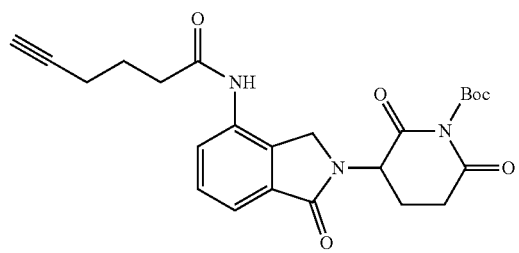

EC2-104

Tert-butyl 3-(4-(hex-5-ynamido)-1-oxoisoindolin-2-yl)-2,6-dioxopiperidine-1-carboxylate (EC2-104): Tert-butyl 3-(4-amino-1-oxoisoindolin-2-yl)-2,6-dioxopiperidine-1-carboxylate (EC2-019) (256 mg, 0.70 mmol, 1.0 eq.) and hex-5-ynoic acid (EC2-103) (123 mg, 1.1 mmol, 1.5 eq.) were dissolved in DMF (6 mL). HATU (280 mg, 0.70 mmol, 1.0 eq.) and DIPEA (384 µL, 1.1 mmol, 3.0 eq.) were then added and the mixture stirred at room temperature overnight. The mixture was diluted with EtOAc (10 mL), washed with NH$_4$Cl (10 mL), NaHCO$_3$ (2×10 mL), brine (10 mL), dried (MgSO$_4$), filtered and the solvent removed under reduced pressure. The residue was triturated with MeOH (10 mL) to give tert-butyl 3-(4-(hex-5-ynamido)-1-oxoisoindolin-2-yl)-2,6-dioxopiperidine-1-carboxylate (EC2-104) (194 mg, 61%) as a white solid which was used to the next step without further purification. $^1$H NMR (500 MHz, DMSO-d$_6$) δ 9.84 (s, 1H), 7.84 (dd, J=7.3, 1.7 Hz, 1H), 7.56-7.47 (m, 2H), 5.39 (dd, J=13.4, 5.1 Hz, 1H), 4.43 (d, J=17.4 Hz, 1H), 4.36 (d, J=17.4 Hz, 1H), 3.20-3.09 (m, 1H), 2.83 (t, J=2.7 Hz, 1H), 2.49-2.46 (m, 1H), 2.25 (td, J=7.0, 2.6 Hz, 2H), 2.14-2.05 (m, 1H), 1.79 (p, J=7.2 Hz, 2H), 1.49 (s, 9H), 1.32-1.20 (m, 2H), 0.90-0.80 (m, 1H); HPLC-MS (ESI+): m/z 354.2 [30%, (M-Boc+H)$^+$], 929.4 [40%, (2M+Na)$^+$].

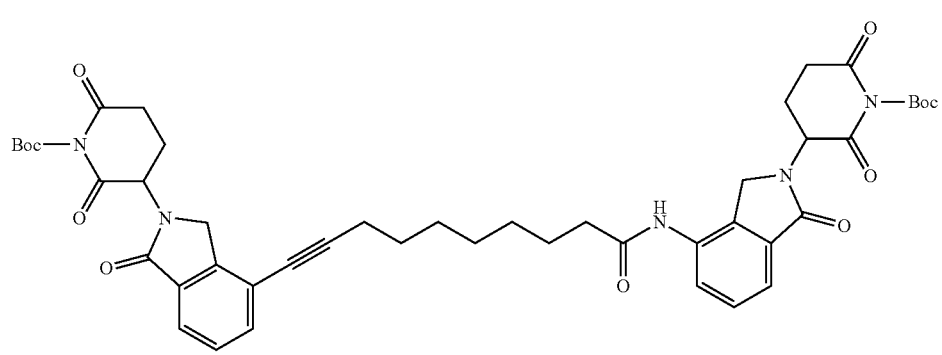

EC2-099

Tert-butyl 3-(4-(10-((2-(1-(tert-butoxycarbonyl)-2,6-dioxopiperidin-3-yl)-1-oxoisoindolin-4-yl)amino)-10-oxodec-1-yn-1-yl)-1-oxoisoindolin-2-yl)-2,6-dioxopiperidine-1-carboxylate (EC2-099): This was prepared in the same way as EC2-084 from tert-butyl 3-(4-iodo-1-oxoisoindolin-2-yl)-2,6-dioxopiperidine-1-carboxylate (38 mg, 0.08 mmol, 1.0 eq.) and tert-butyl 3-(4-(dec-9-ynamido)-1-oxoisoindolin-2-yl)-2,6-dioxopiperidine-1-carboxylate (EC2-095) (50 mg, 0.1 mmol, 1.2 eq.) to provide tert-butyl 3-(4-(10-((2-(1-(tert-butoxycarbonyl)-2,6-dioxopiperidin-3-yl)-1-oxoisoindolin-4-yl)amino)-10-oxodec-1-yn-1-yl)-1-oxoisoindolin-2-yl)-2,6-dioxopiperidine-1-carboxylate (EC2-099) as a pale yellow solid (38 mg, 56%). $^1$H NMR (500 MHz, DMSO-$d_6$) δ 9.76 (s, 1H), 7.83 (d, J=7.2 Hz, 1H), 7.72 (dd, J=7.7, 1.0 Hz, 1H), 7.66-7.60 (m, 2H), 7.57 (dd, J=7.4, 3.1 Hz, 1H), 7.52-7.49 (m, 1H), 5.38 (td, J=13.2, 5.1 Hz, 2H), 4.48 (d, J=17.6 Hz, 1H), 4.44-4.29 (m, 3H), 3.20-3.08 (m, 2H), 2.84-2.74 (m, 2H), 2.64 (q, J=1.9 Hz, 1H), 2.46-2.33 (m, 3H), 2.14-2.04 (m, 2H), 1.56-1.67 (m, 3H), 1.495 (s, 9H), 1.493 (s, 9H), 1.47-1.42 (m, 2H), 1.40-1.22 (m, 6H), 0.90-0.83 (m, 1H); HPLC-MS (ESI+): m/z 652.3 [100%, (M-2Boc+H)$^+$], 774.3 [80%, (M-Boc+Na)$^+$], 874.2 [80%, (M+Na)$^+$].

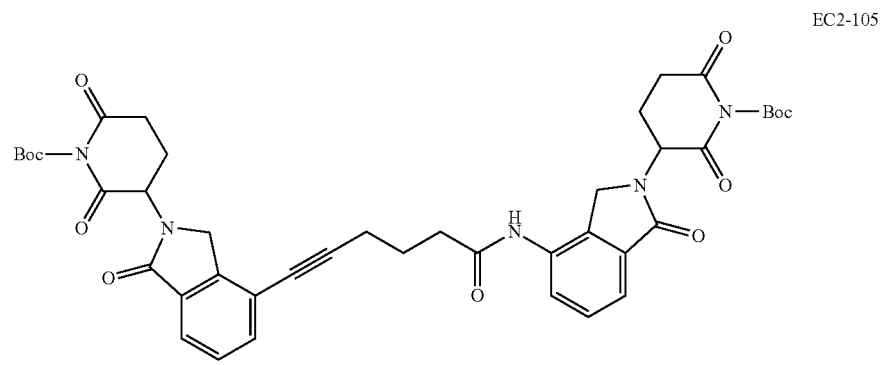 [SMILES: CC(C)(C)OC(=O)N1C(=O)CCC(N2Cc3c(C#CCCCC(=O)Nc4cccc5c4CN(C4CCC(=O)N(C(=O)OC(C)(C)C)C4=O)C5=O)cccc3C2=O)C1=O]

EC2-105

Tert-butyl 3-(4-(6-((2-(1-(tert-butoxycarbonyl)-2,6-dioxopiperidin-3-yl)-1-oxoisoindolin-4-yl)amino)-6-oxohex-1-yn-1-yl)-1-oxoisoindolin-2-yl)-2,6-dioxopiperidine-1-carboxylate (EC2-105): This was prepared in the same way as EC2-084 from tert-butyl 3-(4-iodo-1-oxoisoindolin-2-yl)-2,6-dioxopiperidine-1-carboxylate (72 mg, 0.16 mmol, 1.0 eq.) and tert-butyl 3-(4-(hex-5-ynamido)-1-oxoisoindolin-2-yl)-2,6-dioxopiperidine-1-carboxylate (EC2-104) (83 mg, 0.18 mmol, 1.2 eq.) to provide tert-butyl 3-(4-(6-((2-(1-(tert-butoxycarbonyl)-2,6-dioxopiperidin-3-yl)-1-oxoisoindolin-4-yl)amino)-6-oxohex-1-yn-1-yl)-1-oxoisoindolin-2-yl)-2,6-dioxopiperidine-1-carboxylate (EC2-105) as a white solid (14 mg, 17%). $^1$H NMR (500 MHz, DMSO-$d_6$) δ 9.86 (s, 1H), 7.83 (t, J=7.4 Hz, 1H), 7.74-7.70 (m, 1H), 7.68-7.60 (m, 2H), 7.58-7.51 (m, 2H), 5.36 (td, J=14.1, 5.1 Hz, 2H), 4.53-4.31 (m, 4H), 3.17-3.08 (m, 2H), 2.84-2.71 (m, 2H), 2.65-2.55 (m, 2H), 2.43-2.34 (m, 2H), 2.13-2.00 (m, 2H), 1.98-1.90 (m, 2H), 1.49 (s, 9H), 1.48 (s, 9H), 1.31-1.21 (m, 2H); HPLC-MS (ESI+) and (ESI−): m/z 818.3 [30%, (M+Na)$^+$], 794.4 [50%, (M−H)$^+$].

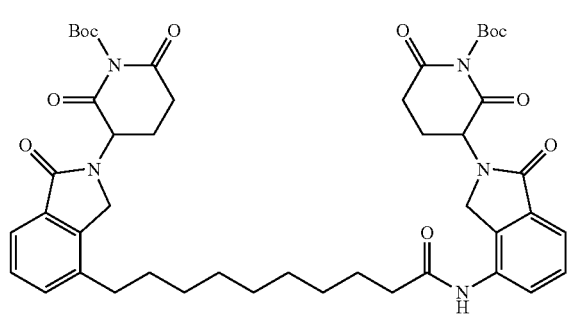

EC2-101

Tert-butyl 3-(4-(10-((2-(1-(tert-butoxycarbonyl)-2,6-dioxopiperidin-3-yl)-1-oxoisoindolin-4-yl)amino)-10-oxodecyl)-1-oxoisoindolin-2-yl)-2,6-dioxopiperidine-1-carboxylate (EC2-101): This was prepared in the same way as EC2-090 from tert-butyl 3-(4-(10-((2-(1-(tert-butoxycarbonyl)-2,6-dioxopiperidin-3-yl)-1-oxoisoindolin-4-yl)amino)-10-oxodec-1-yn-1-yl)-1-oxoisoindolin-2-yl)-2,6-dioxopiperidine-1-carboxylate (EC2-099) (17 mg, 0.02 mmol, 1.0 eq.) to provide tert-butyl 3-(4-(10-((2-(1-(tert-butoxycarbonyl)-2,6-dioxopiperidin-3-yl)-1-oxoisoindolin-4-yl)amino)-10-oxodecyl)-1-oxoisoindolin-2-yl)-2,6-dioxopiperidine-1-carboxylate (EC2-101) (12 mg, 71%) as a white solid which was used to the next step without further purification. $^1$H NMR (500 MHz, DMSO-$d_6$) δ 9.81 (s, 1H), 7.89 (d, J=7.6 Hz, 1H), 7.72-7.60 (m, 2H), 7.59-7.54 (m, 2H), 7.52 (d, J=4.2 Hz, 1H), 5.43 (ddd, J=17.9, 13.3, 5.1 Hz, 2H), 4.55 (d, J=17.0 Hz, 1H), 4.50-4.36 (m, 3H), 3.25-3.15 (m, 2H), 2.91-2.81 (m, 2H), 2.74-2.67 (m, 2H), 2.63-2.59 (m, 2H), 2.51-2.45 (m, 2H), 2.44-2.38 (m, 2H), 2.19-2.10 (m, 2H), 1.70-1.62 (m, 3H), 1.55 (s, 9H), 1.54 (s, 9H), 1.43-1.27 (m, 7H), 0.95-0.88 (m, 2H); HPLC-MS (ESI+): m/z 656.4 [20%, (M−2Boc+H)$^+$], 878.4 [20%, (M+Na)$^+$].

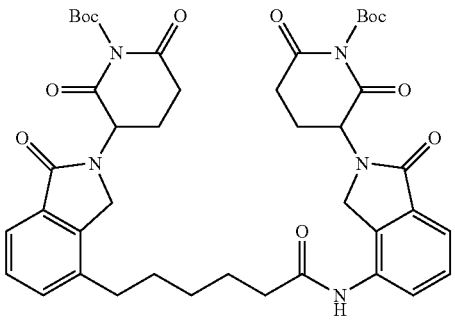

EC2-107

Tert-butyl 3-(4-(6-((2-(1-(tert-butoxycarbonyl)-2,6-dioxopiperidin-3-yl)-1-oxoisoindolin-4-yl)amino)-6-oxohexyl)-1-oxoisoindolin-2-yl)-2,6-dioxopiperidine-1-carboxylate (EC2-107): This was prepared in the same way as EC2-090 from tert-butyl 3-(4-(6-((2-(1-(tert-butoxycarbonyl)-2,6-dioxopiperidin-3-yl)-1-oxoisoindolin-4-yl)amino)-6-oxohex-1-yn-1-yl)-1-oxoisoindolin-2-yl)-2,6-dioxopiperidine-1-carboxylate (EC2-105) (8 mg, 0.02 mmol, 1.0 eq.) to provide tert-butyl 3-(4-(6-((2-(1-(tert-butoxycarbonyl)-2,6-dioxopiperidin-3-yl)-1-oxoisoindolin-4-yl)amino)-6-oxohexyl)-1-oxoisoindolin-2-yl)-2,6-dioxopiperidine-1-carboxylate (EC2-107) (17 mg, 82%) as a white solid which was used to the next step without further purification. $^1$H NMR (500 MHz, DMSO-$d_6$) δ 9.81 (s, 1H), 7.89 (d, J=7.3 Hz, 1H), 7.63 (dd, J=7.1, 1.5 Hz, 1H), 7.59-7.49 (m, 4H), 5.48-5.36 (m, 2H), 4.56 (d, J=17.0 Hz, 1H), 4.49-4.37 (m, 3H), 3.90-3.81 (m, 2H), 3.65-3.15 (m, 2H), 2.90-2.81 (m, 2H), 2.77-2.67 (m, 2H), 2.48-2.40 (m, 2H), 2.18-2.09 (m, 2H), 1.77-1.69 (m, 2H), 1.54 (s, 9H), 1.54 (s, 9H), 1.49-1.41 (m, 2H), 1.37-1.26 (m, 2H); HPLC-MS (ESI+): m/z 600.3 [20%, (M−2Boc+H)$^+$], 822.3 [40%, (M+Na)$^+$].

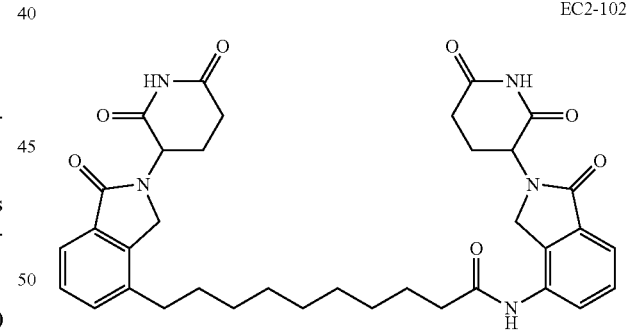

EC2-102

N,10-bis(2-(2,6-Dioxopiperidin-3-yl)-1-oxoisoindolin-4-yl)decanamide (EC2-102): The tert-butyl 3-(4-(10-((2-(1-(tert-butoxycarbonyl)-2,6-dioxopiperidin-3-yl)-1-oxoisoindolin-4-yl)amino)-10-oxodecyl)-1-oxoisoindolin-2-yl)-2,6-dioxopiperidine-1-carboxylate (EC2-101) (12 mg, 0.01 mmol, 1.0 eq.) was dissolved in TFA (2.0 mL) and the solution stirred at room temperature for 1 hour. The solvent was removed under reduced pressure and the residue was triturated with MeOH (2×5 mL) to give the final dimer (EC2-102) as a white solid (9 mg, 99%). HPLC: 98% [$t_R$=19.8 min, Gradient MeOH-water 20%-95% (with 0.1% TFA)], 20 min; $^1$H NMR (500 MHz, DMSO-$d_6$) δ 10.94 (s, 1H), 10.91 (s, 1H), 9.67 (s, 1H), 7.73 (dd, J=7.2, 1.7 Hz, 1H), 7.59-7.53 (m, 2H), 7.51-7.46 (m, 2H), 7.41-7.35 (m, 1H), 5.07 (ddd, J=13.0, 7.3, 5.1 Hz, 2H), 4.38 (d, J=17.1 Hz, 1H), 4.31-4.20 (m, 3H), 2.85 (ddd, J=17.9, 13.0, 5.4 Hz, 2H), 2.61-2.53 (m, 2H), 2.32-2.25 (m, 5H), 1.99-1.90 (m, 2H), 1.58-1.48 (m, 3H), 1.28-1.13 (m, 10H), 0.82-0.75 (m, 2H) HPLC-MS (ESI+) and (ESI−): m/z 656.3 [40%, (M+H)$^+$] and 654.3 [100%, (M−H)$^+$]; HRMS (ESI+): m/z calcd for $C_{36}H_{41}N_5O_7$ 678.2898 (M+Na)$^+$, found 678.2880.

N,6-bis(2-(2,6-Dioxopiperidin-3-yl)-1-oxoisoindolin-4-yl)hexanamide (EC2-109): The tert-butyl 3-(4-(6-((2-(1-(tert-butoxycarbonyl)-2,6-dioxopiperidin-3-yl)-1-oxoisoindolin-4-yl)amino)-6-oxohexyl)-1-oxoisoindolin-2-yl)-2,6-dioxopiperidine-1-carboxylate (EC2-107) (17 mg, 0.02 mmol, 1.0 eq.) was dissolved in TFA (2.0 mL) and the solution stirred at room temperature for 1 hour. The solvent was removed under reduced pressure and the residue was triturated with MeOH (2×5 mL) to give the final dimer (EC2-109) as a white solid (11 mg, 85%). HPLC: 96% [t$_R$=16.3 min, Gradient MeOH-water 20%-95% (with 0.1% TFA)], 20 min; $^1$H NMR (500 MHz, DMSO-d$_6$) δ 11.01 (s, 1H), 10.98 (s, 1H), 9.76 (s, 1H), 7.82-7.78 (m, 1H), 7.57 (dd, J=6.7, 1.9 Hz, 1H), 7.53-7.42 (m, 4H), 5.17-5.09 (m, 2H), 4.47 (d, J=17.2 Hz, 1H), 4.38-4.28 (m, 3H), 2.92 (ddd, J=18.0, 13.7, 5.4 Hz, 2H), 2.70-2.56 (m, 5H), 2.40-2.33 (m, 3H), 2.06-1.97 (m, 1H), 1.71-1.62 (m, 3H), 1.43-1.35 (m, 2H), 1.27-1.21 (m, 2H); HPLC-MS (ESI+): m/z 600.3 [100%, (M+H)$^+$], 622.2 [40%, (M+Na)$^+$]; HRMS (ESI+): m/z calcd for $C_{32}H_{33}N_5O_7$ 600.2453 (M+H)$^+$, found 600.2477.

EC2-109

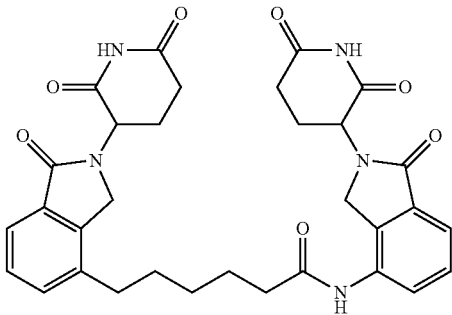

EC2-100

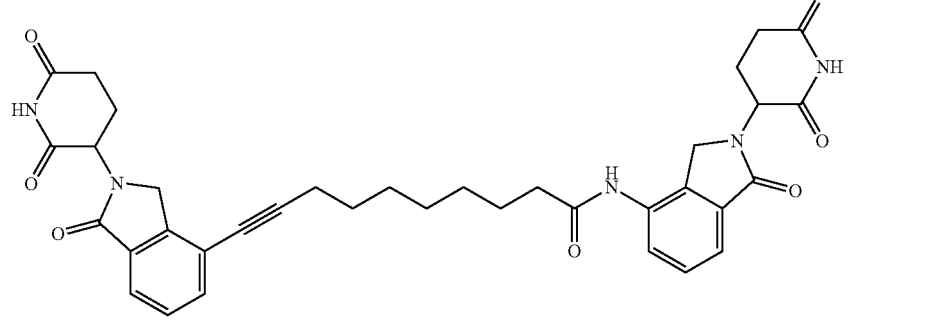

N,10-bis(2-(2,6-Dioxopiperidin-3-yl)-1-oxoisoindolin-4-yl)dec-9-ynamide (EC2-100): The tert-butyl 3-(4-(10-((2-(1-(tert-butoxycarbonyl)-2,6-dioxopiperidin-3-yl)-1-oxoisoindolin-4-yl)amino)-10-oxodec-1-yn-1-yl)-1-oxoisoindolin-2-yl)-2,6-dioxopiperidine-1-carboxylate (EC2-099) (8 mg, 0.009 mmol, 1.0 eq.) was dissolved in TFA (1.0 mL) and the solution was stirred at room temperature for 1 hour. The solvent was removed under reduced pressure and the residue was triturated with MeOH (2×5 mL) to give the final dimer (EC2-100) as a white solid (5 mg, 85%). HPLC: 98% [$t_R$=19.8 min, Gradient MeOH-water 20%-95% (with 0.1% TFA)], 20 min; $^1$H NMR (500 MHz, DMSO-$d_6$) δ 11.02 (s, 1H), 10.99 (s, 1H), 9.74 (s, 1H), 7.81 (dd, J=7.5, 1.7 Hz, 1H), 7.71 (dd, J=7.6, 1.0 Hz, 1H), 7.66-7.60 (m, 2H), 7.54-7.47 (m, 2H), 5.18-5.11 (m, 2H), 4.45 (d, J=17.6 Hz, 1H), 4.39-4.27 (m, 3H), 2.97-2.86 (m, 2H), 2.66-2.56 (m, 2H), 2.39-2.30 (m, 5H), 2.07-1.96 (m, 2H), 1.67-1.55 (m, 3H), 1.51-1.41 (m, 2H), 1.40-1.20 (m, 6H); HPLC-MS (ESI+): m/z 652.4 [20%, (M+H)$^+$], 674.3 [20%, (M+Na)$^+$]; HRMS (ESI+): m/z calcd for $C_{36}H_{37}N_5O_7$ 674.2585 (M+Na)$^+$, found 674.2602.

N,6-bis(2-(2,6-Dioxopiperidin-3-yl)-1-oxoisoindolin-4-yl)hex-5-ynamide (EC2-108): The tert-butyl 3-(4-(6-((2-(1-(tert-butoxycarbonyl)-2,6-dioxopiperidin-3-yl)-1-oxoisoindolin-4-yl)amino)-6-oxohex-1-yn-1-yl)-1-oxoisoindolin-2-yl)-2,6-dioxopiperidine-1-carboxylate (EC2-105) (14 mg, 0.02 mmol, 1.0 eq.) was dissolved in TFA (2.0 mL) and the solution stirred at room temperature for 1 hour. The solvent was removed under reduced pressure and the residue was triturated with MeOH (2×5 mL) to give the final dimer (EC2-108) as a pale yellow solid (10 mg, 93%). HPLC: 97% [$t_R$=15.8 min, Gradient MeOH-water 20%-95% (with 0.1% TFA)], 20 min; $^1$H NMR (500 MHz, DMSO-$d_6$) δ 11.01 (s, 1H), 10.98 (d, J=2.0 Hz, 1H), 9.85 (s, 1H), 7.81 (ddd, J=7.6, 3.2, 1.4 Hz, 1H), 7.71 (dt, J=7.6, 1.3 Hz, 1H), 7.67-7.60 (m, 2H), 7.56 (ddd, J=7.6, 5.1, 3.4 Hz, 1H), 7.53-7.47 (m, 1H), 5.13 (ddd, J=12.8, 7.4, 5.4 Hz, 2H), 4.47 (dd, J=17.8, 3.5 Hz, 1H), 4.40-4.29 (m, 3H), 2.96-2.88 (m, 2H), 2.66-2.54 (m, 4H), 2.46-2.30 (m, 2H), 2.06-1.89 (m, 3H), 1.30-1.23 (m, 2H), 0.90-0.81 (m, 1H); HPLC-MS (ESI+): m/z 596.2 [100%, (M+H)$^+$], 618.2 [30%, (M+Na)$^+$]; HRMS (ESI+): m/z calcd for $C_{32}H_{29}N_5O_7$ 596.2140 (M+H)$^+$, found 596.2118.

EC2-108

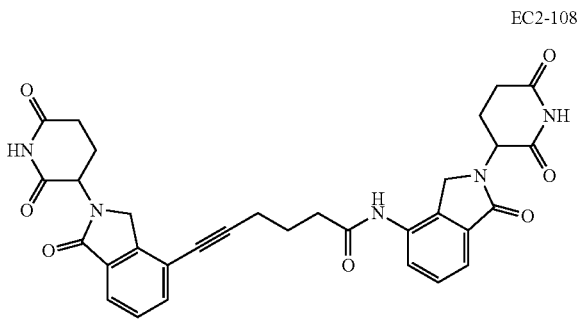 [SMILES: O=C1CCC(N2Cc3c(C#CCCCC(=O)Nc4cccc5c4CN(C4CCC(=O)NC4=O)C5=O)cccc3C2=O)C(=O)N1]

Synthetic scheme 34

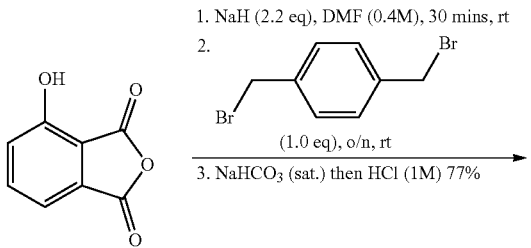

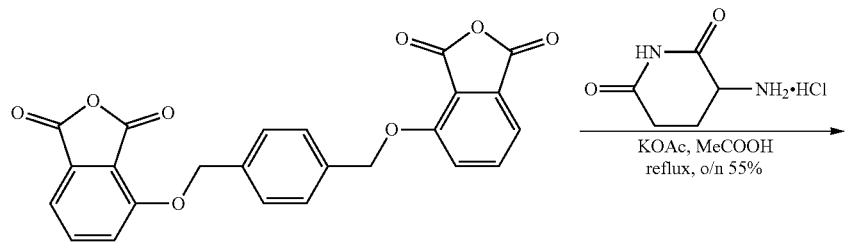

EC2-179

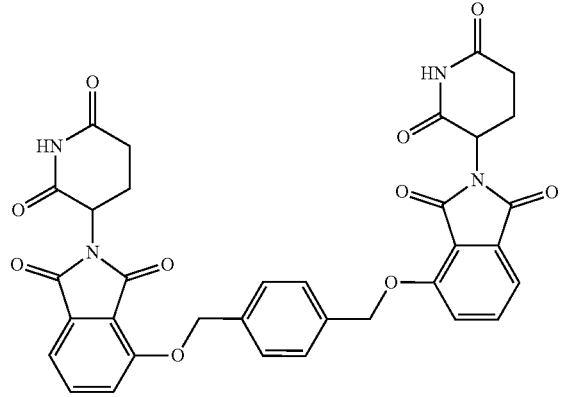

EC2-180

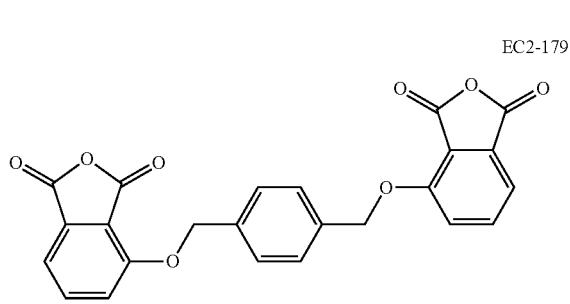 [SMILES: O=C1OC(=O)c2c(OCc3ccc(COc4cccc5c4C(=O)OC5=O)cc3)cccc21]

EC2-179

4,4'-((1,4-Phenylenebis(methylene))bis(oxy))bis(isobenzofuran-1,3-dione) (EC2-179): Sodium hydride (60%, 120 mg, 3.1 mmol, 2.2 eq.) was added to a solution of 4-hydroxyisobenzofuran-1,3-dione (500 mg, 3.1 mmol, 2.2 eq.) in DMF (7 mL) at 0° C. and the mixture stirred at this temperature for 30 minutes. The bis-bromide 1,4-bis(bromomethyl)benzene (377 mg, 1.4 mmol, 1.0 eq.) was then added and the reaction stirred at room temperature overnight. The mixture was diluted with EtOAc (20 mL), washed with H$_2$O (20 mL), sat. NaHCO$_3$ (20 mL), 1 M HCl (20 mL), brine (20 mL), dried (MgSO$_4$) and the solvent was removed under reduced pressure to give 4,4'-((1,4-phenylenebis(methylene))bis(oxy))bis(isobenzofuran-1,3-dione) (EC2-179) (472 mg, 77%) as a white solid which was used to the next step without further purification. $^1$H NMR (500 MHz, DMSO-d$_6$) δ 7.95 (dd, J=8.4, 7.4 Hz, 2H), 7.71 (d, J=8.4 Hz, 2H), 7.61 (d, J=7.4 Hz, 2H), 7.57 (s, 4H), 5.45 (s, 4H).

4,4'-((1,4-Phenylenebis(methylene))bis(oxy))bis(2-(2,6-dioxopiperidin-3-yl)isoindoline-1,3-dione) (EC2-180): The 4,4'-((1,4-phenylenebis(methylene))bis(oxy))bis(isobenzofuran-1,3-dione) (EC2-179) (100 mg, 0.23 mmol, 1.0 eq.) was added to a solution of 3-aminopiperidine-2,6-dione.HCl (83 mg, 0.51 mmol, 2.2 eq.) and potassium acetate (135 mg, 1.38 mmol, 6.0 eq.) in glacial acetic acid (1.0 mL) and the mixture stirred under argon at 120° C. overnight. The purple suspension that formed was cooled to room temperature and the solvent was removed under reduced pressure. The residue was triturated with MeOH (ca. 10 mL), filtered and washed further with MeOH (3×10 mL) to give the final dimer (EC2-180) as a gray solid (82 mg, 55%). $^1$H NMR (500 MHz, DMSO-d$_6$) δ 11.12 (s, 2H), 7.83 (t, J=7.9 Hz, 2H), 7.61 (d, J=8.5 Hz, 2H), 7.56 (s, 4H), 7.48 (d, J=7.2 Hz, 2H), 5.40 (s, 4H), 5.10 (dd, J=12.8, 5.4 Hz, 2H), 2.95-2.81 (m, 2H), 2.66-2.53 (m, 4H), 2.09-1.99 (m, 2H); HRMS (ESI+): m/z calcd for C$_{34}$H$_{26}$N$_4$O$_{10}$ 668.1987 (M+NH$_4$)$^+$, found 668.1976.

Synthetic scheme 35

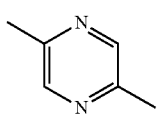

NBS (2.0 eq),
benzoyl peroxide (0.05 eq),
CCl$_4$ (0.1M), reflux, o/n

7%

EC2-180

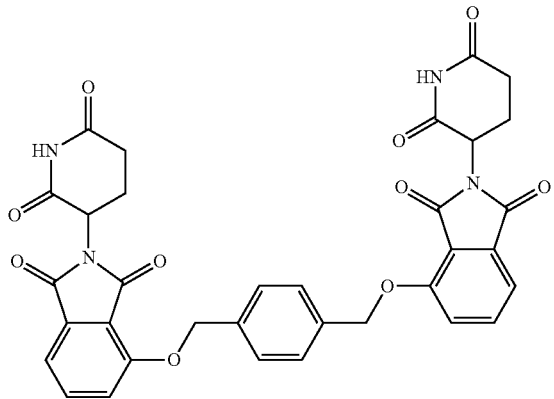

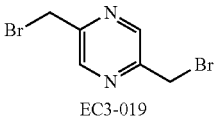

EC3-019

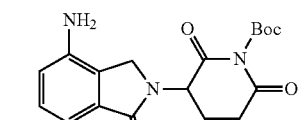

1. DIPEA, KI, THF, 100° C., MW
2. TFA, 1 h
54% over two steps

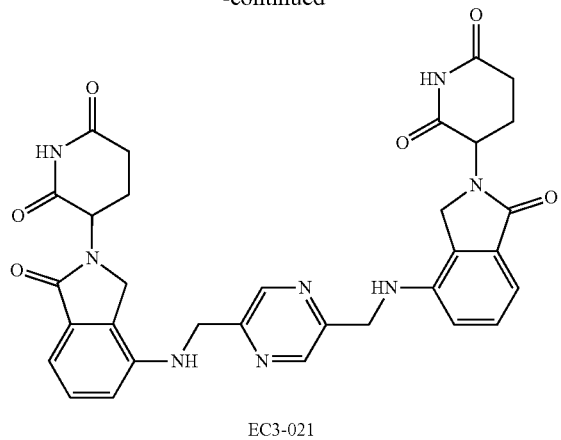

EC3-021

3,3'-(((Pyrazine-2,5-diylbis(methylene))bis(azanediyl))bis(1-oxoisoindoline-4,2-diyl))bis(piperidine-2,6-dione) (EC3-021): The 2,5-bis(bromomethyl)pyrazine (EC3-019) (34 mg, 0.13 mmol, 1.0 eq) was added to a solution of tert-butyl 3-(4-amino-1-oxoisoindolin-2-yl)-2,6-dioxopiperidine-1-carboxylate (EC2-040) (100 mg, 0.28 mmol, 2.1 eq.) in THF (0.6 mL), followed by addition of potassium iodide (19 mg, 0.11 mmol, 0.4 eq.) and DIPEA (47 µL, 0.28 mmol, 2.1 eq.) and the suspension heated in the microwave at 100° C. for 1 hour. The solvent was removed under reduced pressure and the residue purified by column chromatography (0-20% MeOH:CH$_2$Cl$_2$, 1% Et$_3$N) to give a mixture of (mono- and bis-Boc) protected and unprotected dimers (101 mg). The mixture was dissolved in TFA (2.0 mL) and the solution stirred at room temperature for 1 hour. The solvent was removed under reduced pressure and the residue purified by column chromatography (0-20% MeOH:CH$_2$Cl$_2$, 1% Et$_3$N) to give the final dimer (EC3-021) as a pale yellow solid (44 mg, 54%). HPLC: 96% [t$_R$=2.4 min, Gradient MeOH-water 5%-95% (with 0.1% TFA)], 20 min; $^1$H NMR (500 MHz, DMSO-d$_6$) δ 11.01 (s, 2H), 8.62 (s, 2H), 7.22 (t, J=7.7 Hz, 2H), 6.96 (d, J=7.4 Hz, 2H), 6.70 (d, J=8.0 Hz, 2H), 6.45 (t, J=6.0 Hz, 2H), 5.12 (dd, J=13.2, 5.1 Hz, 2H), 4.54 (d, J=5.8 Hz, 4H), 4.32 (d, J=17.0 Hz, 2H), 4.20 (d, J=17.0 Hz, 2H), 2.93 (ddd, J=17.3, 13.5, 5.4 Hz, 2H), 2.69-2.57 (m, 2H), 2.40-2.26 (m, 2H), 2.10-1.98 (m, 2H); HPLC-MS (ESI+) and (ESI-): m/z 623.4 [50%, (M+H)$^+$] and 621.3 [20%, (M−H)$^+$]; HRMS (ESI+): m/z calcd for C$_{32}$H$_{30}$N$_8$O$_6$ 623.2361 (M+H)$^+$, found 623.2357.

EC3-019

2,5-Bis(bromomethyl)pyrazine (EC3-019): 2,5-Dimethylpyrazine (500 mg, 4.6 mmol, 1.0 eq.) and N-bromosuccinimide (1.6 g, 9.2 mmol, 2.0 eq.) were suspended in CCl$_4$ (50 mL) and the mixture was refluxed for 45 minutes. Benzoyl peroxide was then added in three batches (25 mg, 22 mg and 15 mg) after 1 hour, 4 hours and 4 hours stirring respectively. After the complete addition of the peroxide the reaction was refluxed overnight. The mixture was cooled to room temperature, the solid formed filtered and the filtrate evaporated under reduced pressure. The residue was purified by column chromatography (0-100% EtOAc:hexane) to give 2,5-bis(bromomethyl)pyrazine (EC3-019) as a white solid (85 mg, 7%). $^1$H NMR (500 MHz, CDCl$_3$-d) δ 8.60 (s, 2H), 4.49 (s, 4H); HPLC-MS (ESI+): m/z 265.0 and 267.0 [50%, (M+H)$^+$]. (See Guo, et al. *Biorg. Med. Chem.* 1041-1058, 2000.)

Synthetic scheme 36

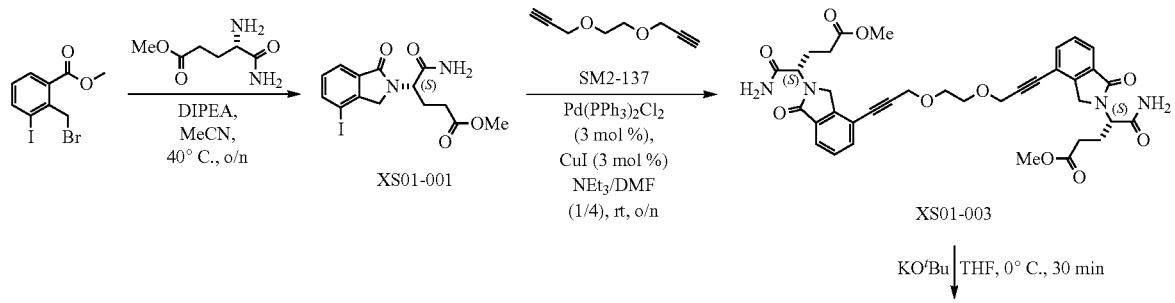

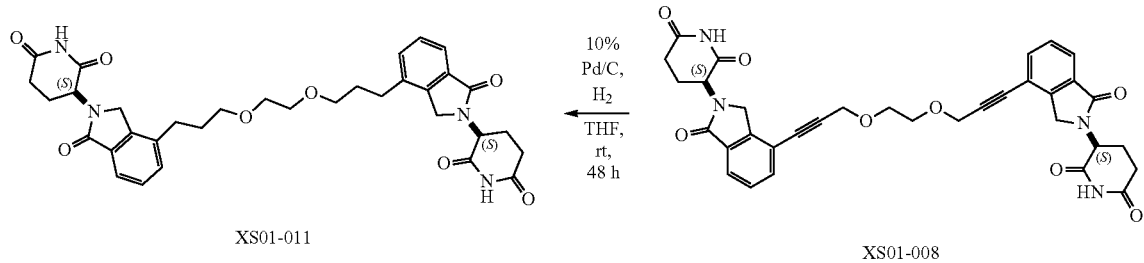

XS01-011 → XS01-008

10% Pd/C, H₂, THF, rt, 48 h

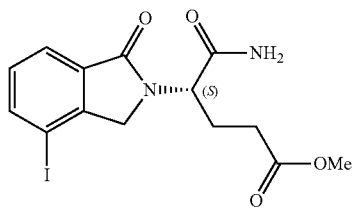

XS01-001

Methyl (S)-5-amino-4-(4-iodo-1-oxoisoindolin-2-yl)-5-oxopentanoate (XS01-001): Methyl 2-(bromomethyl)-3-iodobenzoate (1.00 g, 2.82 mmol) and methyl (S)-4,5-diamino-5-oxopentanoate (609 mg, 3.09 mmol) were suspended in MeCN (30 mL), and DIPEA (765 mg, 5.92 mmol) was added slowly to the mixture. The mixture was then stirred at 40° C. under argon overnight. The solvent was removed by rotary evaporation under vacuum, and H₂O (20 mL) and dichloromethane (20 mL) were added to the residue. The organic phase was separated and washed with brine (3×20 mL), dried with Na₂SO₄, and concentrated under reduced pressure to provide the crude product. Purification of the crude material by silica gel chromatography (0-10% MeOH in dichloromethane) afforded methyl (S)-5-amino-4-(4-iodo-1-oxoisoindolin-2-yl)-5-oxopentanoate (XS01-001) (640 mg, 56%) as a white solid. Mp: 65° C. (dec); HPLC 79% ($t_R$=10.7 min, CH₃OH in 0.1% TFA water 5%~95% in 20 min); ¹H NMR (500 MHz, DMSO-d₆) δ 8.02 (dd, J=7.8, 0.9 Hz, 1H), 7.74 (dd, J=7.5, 0.9 Hz, 1H), 7.63 (s, 1H), 7.24 (s, 1H), 4.77 (dd, J=10.4, 4.9 Hz, 1H), 4.42-4.22 (m, 2H), 3.51 (s, 3H), 2.30 (m, 2H), 2.26-2.17 (m, 1H), 2.16-2.02 (m, 1H). HPLC-MS (ESI+) m/z 403.1 (M+H)⁺.

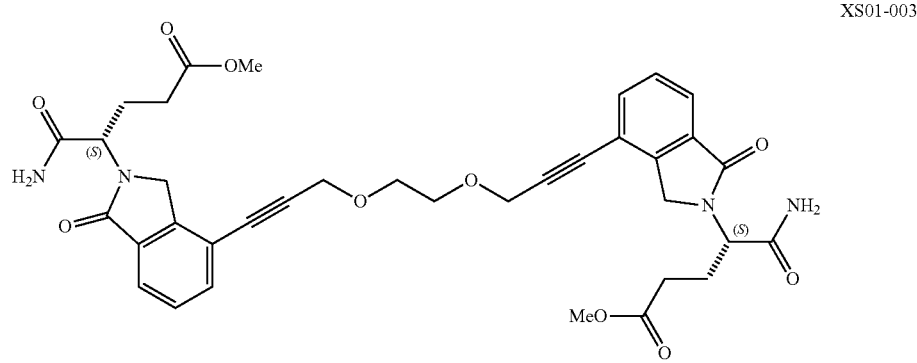

XS01-003

4,4'-(((Ethane-1,2-diylbis(oxy))bis(prop-1-yne-3,1-diyl))bis(1-oxoisoindoline-4,2-diyl))(4S,4'S)-bis(5-amino-5-oxopentanoate) (XS01-003): Methyl (S)-5-amino-4-(4-iodo-1-oxoisoindolin-2-yl)-5-oxopentanoate (XS01-001) (300 mg, 0.75 mmol), 1,2-bis(prop-2-yn-1-yloxy)ethane (47 mg, 0.34 mmol) and bis(triphenylphosphine)palladium(II) dichloride (7.3 mg, 0.01 mmol) were dissolved in a mixture of TEA/DMF1/4 (2.5 mL, 1:4, v/v). The solution was degassed for 10 min, and copper(I) iodide (1.9 mg, 0.01 mmol) was added under argon atmosphere. The tube was sealed and the mixture stirred overnight at room temperature. Water (10 ml) was added and the mixture was extracted with ethyl acetate (3×10 ml). The combined organic phase was washed with $H_2O$ (3×10 mL) and brine (3×10 mL), dried with $Na_2SO_4$, and then concentrated under reduced pressure to provide the crude product. Purification of the crude material by silica gel chromatography (0-10% MeOH in dichloromethane) afforded dimethyl 4,4'-(((ethane-1,2-diylbis(oxy))bis(prop-1-yne-3,1-diyl))bis(1-oxoisoindoline-4,2-diyl))(4S,4'S)-bis(5-amino-5-oxopentanoate) (120 mg, 23%) as a white solid. HPLC 87% ($t_R$=11.4 min, $CH_3OH$ in 0.1% TFA water 5%~95% in 20 min); $^1$H NMR (500 MHz, DMSO-$d_6$) δ 7.71 (m, 1H), 7.62 (s, 1H), 7.53 (t, J=7.6 Hz, 1H), 7.23 (s, 1H), 4.76 (dd, J=10.5, 5.0 Hz, 1H), 4.61 (d, J=17.9 Hz, 1H), 4.52 (s, 2H), 3.76 (s, 1H), 3.49 (s, 2H), 2.29 (m, 1H), 2.25-2.14 (m, 1H), 2.08 (m, 1H). HPLC-MS (ESI+) m/z 709.3 (M+Na)$^+$.

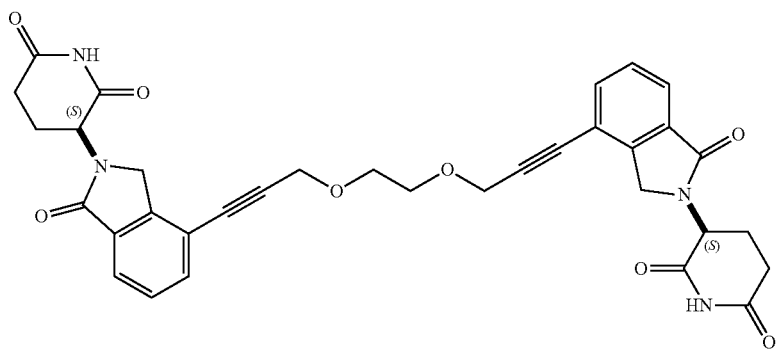

XS01-008

(3S,3'S)-3,3'-(((Ethane-1,2-diylbis(oxy))bis(prop-1-yne-3,1-diyl))bis(1-oxoisoindoline-4,2-diyl))bis(piperidine-2,6-dione) (XS01-008): Potassium tert-butoxide (147 mg, 1.75 mmol) dissolved in THF (2 ml) was slowly added to dimethyl 4,4'-(((ethane-1,2-diylbis(oxy))bis(prop-1-yne-3,1-diyl))bis(1-oxoisoindoline-4,2-diyl))(4S,4'S)-bis(5-amino-5-oxopentanoate) (XS01-003) (300 mg, 0.436 mmol) in THF (2 ml) at 0° C. The mixture was stirred for 30 min. Hydrochloric acid (~1 mL of 1 $M_{aq.}$ solution) was added to quench the reaction. Ammonium hydroxide was added to adjust the pH to 11. The organic solvent was removed by rotary evaporation under vacuum. Methanol (10 mL) was added, and the solid filtered from the solution to provide (3S,3'S)-3,3'-(((ethane-1,2-diylbis(oxy))bis(prop-1-yne-3,1-diyl))bis(1-oxoisoindoline-4,2-diyl))bis(piperidine-2,6-dione) (XS01-008) (172 mg, 63%) as a white solid. Mp: 256° C. (dec); HPLC 81% ($t_R$=10.8 min, $CH_3OH$ in 0.1% TFA water 5%~95% in 20 min); $^1$H NMR (500 MHz, DMSO-$d_6$) δ 11.01 (s, 2H), 7.84-7.60 (m, 4H), 7.55 (t, J=7.7 Hz, 2H), 5.14 (dd, J=13.3, 5.1 Hz, 2H), 4.54-4.42 (m, 6H), 4.35 (d, J=17.8 Hz, 2H), 3.74 (s, 4H), 2.91 (m, 2H), 2.59 (m, 2H), 2.45 (m, 2H), 2.01 (m, 2H). HPLC-MS (ESI+) m/z 623.3 (M+H)$^+$.

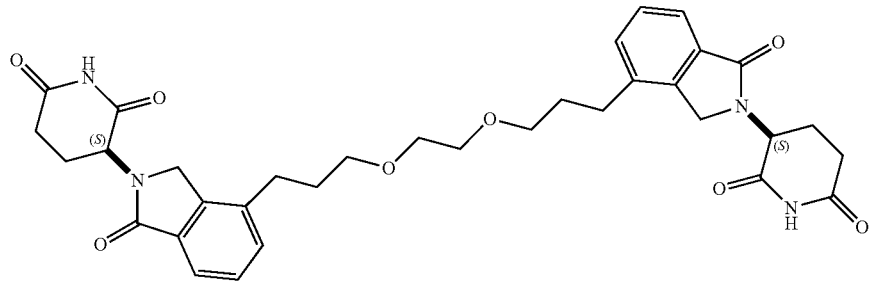

XS01-011

(3S,3'S)-3,3'-(((Ethane-1,2-diylbisbis(oxy))bisbis(propane-3,1-diyl))bisbis(1-oxoisoindoline-4,2-diyl))bisbis(piperidine-2,6-dione) (XS01-011): The bis-alkyne XS01-008 (100 mg, 0.16 mmol) in THF (2 ml) was added to a suspension of palladium on carbon (10 mg 10% Pd/C) in THF (2 ml). The solution was stirred under an atmosphere of hydrogen overnight at room temperature. The mixture was filtered through a bed of celite, which was washed with THF. The solvent from the combined filtrate and washing was removed by rotary evaporation under vacuum to provide (3S,3'S)-3,3'-(((ethane-1,2-diylbis(oxy))bis(propane-3,1-diyl))bis(1-oxoisoindoline-4,2-diyl))bis(piperidine-2,6-dione) (XS01-011) (31 mg, 30%) as a white solid. HPLC 99.9% ($t_R$=7.00 min, CH$_3$OH in 0.1% TFA water 5%~95% in 20 min); Mp: 235° C. (dec); $^1$H NMR (500 MHz, DMSO-d$_6$) δ 10.99 (s, 2H), 7.57 (dd, J=6.0, 2.6 Hz, 2H), 7.49-7.36 (m, 4H), 5.13 (dd, J=13.4, 5.1 Hz, 2H), 4.45 (d, J=17.2 Hz, 2H), 4.30 (d, J=17.1 Hz, 2H), 3.49 (s, 4H), 3.44-3.36 (m, 4H), 2.92 (m, 2H), 2.69 (t, J=7.6 Hz, 4H), 2.63-2.52 (m, 2H), 2.48-2.30 (m, 2H), 2.06-1.90 (m, 2H), 1.91-1.74 (m, 4H); HPLC-MS (ESI$^+$) m/z 631.4 (M+H)$^+$; HRMS (ESI+) m/z calculated for C$_{34}$H$_{39}$N$_4$O$_8$ (M+H)$^+$ 631.2762, found 631.2761.

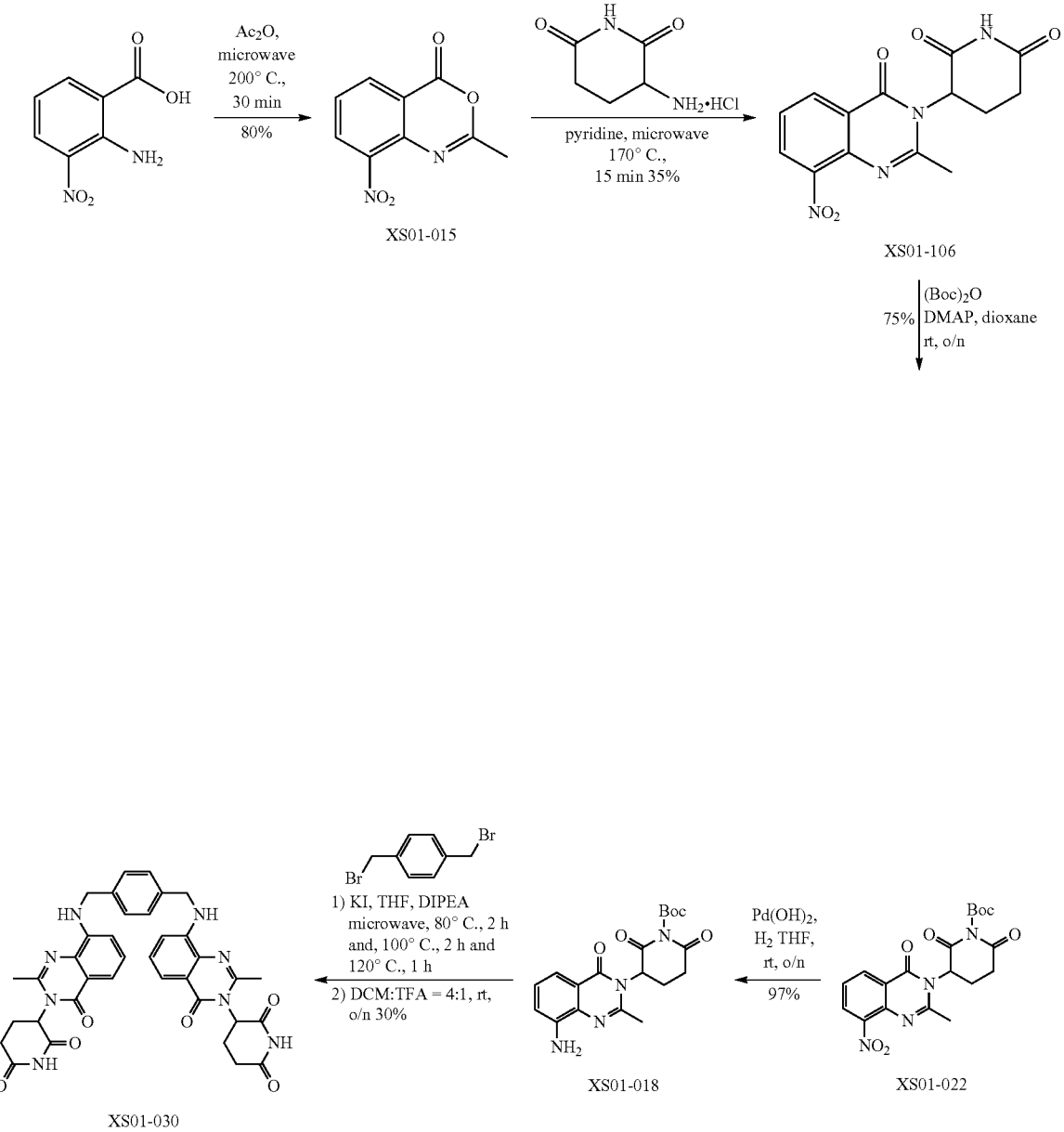

Synthetic scheme 37

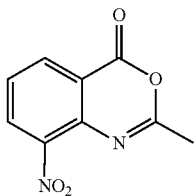

XS01-015

2-Methyl-8-nitro-4H-benzo[d][1,3]oxazin-4-one (XS01-015): 2-Amino-3-nitrobenzoic acid (300 mg, 1.65 mmol) was suspended in acetic anhydride (2 mL), and the reaction mixture was heated at 200° C. for 30 min. in the microwave reactor. The solvent was removed by rotary evaporation under vacuum to provide the crude product. Ethyl acetate (5 mL) was added to the residue, hexane (5 mL) added and the solid filtered to provide 2-methyl-8-nitro-4H-benzo[d][1,3]oxazin-4-one (XS01-015) (270 mg, 80%) as brown solid. $^1$H NMR (500 MHz, DMSO-d$_6$) δ 8.35 (m, 2H), 7.73 (t, J=7.9 Hz, 1H), 2.43 (s, 3H).

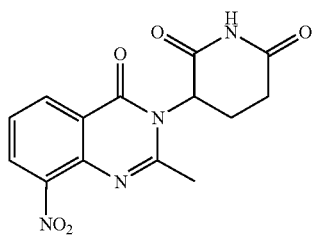

XS01-016

3-(2-Methyl-8-nitro-4-oxoquinazolin-3(4H)-yl)piperidine-2,6-dione (XS01-016): A vial with a suspension of 2-methyl-8-nitro-4H-benzo[d][1,3]oxazin-4-one (XS01-015) (3.30 g, 16.00 mmol) and 3-aminopiperidine-2 6-dione hydrochloride (2.90 g, 17.62 mmol) in pyridine (24 mL) was heated at 170° C. for 15 min in the microwave reactor. The cooled suspension was filtered and washed with pyridine. The filtrate was concentrated by rotary evaporation under vacuum. The resulting mixture was stirred in (1M) HCl (48 mL), ethyl acetate (24 mL) and diethyl ether (24 mL) for 2 h. The suspension was filtered and washed with H$_2$O (24 mL) and ethyl acetate (24 mL) to give a black solid, which was stirred with methanol (20 mL) at room temperature for overnight. The solid was filtered and washed with methanol to provide 3-(2-methyl-8-nitro-4-oxoquinazolin-3(4H)-yl)piperidine-2,6-dione (1.77 g, 35%) as a black solid. HPLC 99.9% (t$_R$=6.95 min, CH$_3$OH in 0.1% TFA water 5%~95% in 20 min); $^1$H NMR (500 MHz, DMSO-d$_6$) δ 11.10 (s, 1H), 8.30 (m, 2H), 7.66 (t, J=7.9 Hz, 1H), 5.35 (dd, J=11.6, 5.7 Hz, 1H), 2.94-2.76 (m, 1H), 2.73-2.56 (m, 5H), 2.22 (m, 1H); HPLC-MS (ESI$^+$) m/z 317.1 (M+H)$^+$.

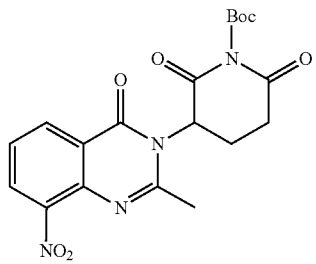

XS01-018

Tert-butyl 3-(2-methyl-8-nitro-4-oxoquinazolin-3(4H)-yl)-2,6-dioxopiperidine-1-carboxylate (XS01-018): 3-(2-Methyl-8-nitro-4-oxoquinazolin-3(4H)-yl)piperidine-2,6-dione (XS01-016) (1.84 g, 5.82 mmol), di-tert-butyl dicarbonate (1.91 g, 8.73 mmol) and DMAP (71 mg, 0.58 mmol) were suspended in dioxane (30 mL), and stirred at room temperature overnight. The solvent was removed by rotary evaporation under vacuum to give the crude residue. The residue was dissolved in ethyl acetate (20 mL), washed with H$_2$O (3×10 mL) and brine (3×10 mL), dried (Na$_2$SO$_4$) and then concentrated under reduced pressure to provide the crude product. The crude product was dissolved in methanol (8 mL), after 30 min solid formed, filtered, and washed carefully with mixture of methanol/hexane (9/1) to provide tert-butyl 3-(2-methyl-8-nitro-4-oxoquinazolin-3(4H)-yl)-2,6-dioxopiperidine-1-carboxylate (XS01-018) (1.82 g, 75%) as black solid. HPLC 87.2% (t$_R$=11.33 min, CH$_3$OH in 0.1% TFA water 5%~95% in 20 min); $^1$H NMR (500 MHz, DMSO-d$_6$) δ 8.46-8.14 (m, 2H), 7.67 (t, J=7.9 Hz, 1H), 5.62 (dd, J=11.8, 5.6 Hz, 1H), 3.10-2.95 (m, 1H), 2.82 (m, 1H), 2.67 (m, 4H), 2.27 (m, 1H), 1.50 (s, 9H); HPLC-MS (ESI$^+$) m/z 417.2 (M+H)$^+$.

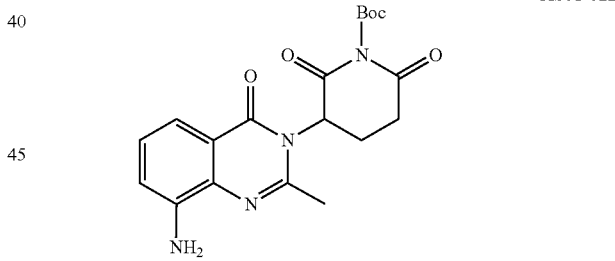

XS01-022

Tert-butyl 3-(8-amino-2-methyl-4-oxoquinazolin-3(4H)-yl)-2,6-dioxopiperidine-1-carboxylate (XS01-022): The tert-butyl 3-(2-methyl-8-nitro-4-oxoquinazolin-3(4H)-yl)-2,6-dioxopiperidine-1-carboxylate (XS01-018): (1.80 g, 4.33 mmol) in THF (50 ml) was added to a suspension of palladium hydroxide (20% on carbon, 210 mg) in THF (50 mL). The solution was stirred under an atmosphere of hydrogen overnight at room temperature. The mixture was filtered through a bed of celite, which was washed with THF. The solvent from the combined filtrate and washing was removed by rotary evaporation under vacuum to provide tert-butyl 3-(8-amino-2-methyl-4-oxoquinazolin-3(4H)-yl)-2,6-dioxopiperidine-1-carboxylate (XS01-022) (1.63 g, 97%) as a white solid. HPLC 91.7% (t$_R$=10.55 min, CH$_3$OH in 0.1% TFA water 5%~95% in 20 min); $^1$H NMR (500 MHz, DMSO-d$_6$) δ 7.26-7.09 (m, 2H), 6.98 (dd, J=7.2, 2.0 Hz, 1H), 5.68 (s, 2H), 5.49 (dd, J=11.7, 5.7 Hz, 1H), 3.04 (m, 1H), 2.78 (m, 1H), 2.64 (s, 3H), 2.20 (m, 1H), 1.80-1.72 (m, 1H), 1.50 (s, 9H); HPLC-MS (ESI⁺) m/z 387.2 (M+H)⁺.

XS01-030

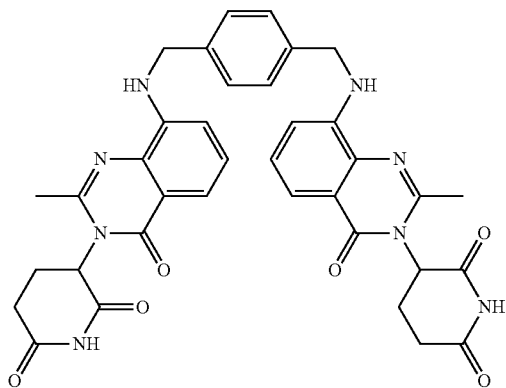

3,3'-(((1,4-Phenylenebis(methylene))bis(azanediyl))bis (2-methyl-4-oxoquinazoline-8,3(4H)-diyl))bis(piperidine-2, 6-dione) (XS01-030): Tert-butyl 3-(8-amino-2-methyl-4-oxoquinazolin-3(4H)-yl)-2,6-dioxopiperidine-1-carboxylate (XS01-022) (100 mg, 0.258 mmol), 1,4-bis(bromomethyl) benzene (33 mg, 0.123 mmol) and potassium iodide (8 mg, 0.05 mmol) were suspended in THF (1 mL), DIPEA (45 µL, 0.25 mmol) was added to the solution. The reaction mixture was heated at 80° C. for 2 h, 100° C. for 2 h and 120° C. for 1 h in the microwave reactor. The reaction was monitored by HPLC-MS. The solvent was removed by rotary evaporation under vacuum, and water (10 mL) and dichloromethane (10 mL) were added to the residue. The organic phase was separated and washed with brine (3×10 mL), dried (Na$_2$SO$_4$) and concentrated under reduced pressure to provide a crude residue. This crude residue was dissolved in a mixture of DCM:TFA=4:1 (2.5 mL), and stirred at room temperature overnight. The solvent was removed by rotary evaporation under vacuum. Dichloromethane (10 mL) was added to the residue and the mixture washed with sat. NaHCO$_3$ solution (3×10 mL), dried (Na$_2$SO$_4$) and concentrated under reduced pressure to provide the crude product. The crude product was dissolved in THF (2 mL), and MeOH (20 mL) was used for trituration to give XS01-030 (25 mg, 30%) as a white solid. Mp: 230° C. (dec); HPLC 98% (t$_R$=7.00 min, CH$_3$OH in 0.1% TFA water 5%~95% in 20 min); ¹H NMR (500 MHz, DMSO-d$_6$) δ 11.01 (s, 2H), 7.31 (s, 4H), 7.22-6.99 (m, 4H), 6.81-6.51 (m, 2H), 5.24 (dd, J=11.4, 5.7 Hz, 2H), 4.46 (d, J=6.3 Hz, 4H), 2.84 (m, 2H), 2.71-2.53 (m, 10H), 2.16 (m, 2H). HPLC-MS (ESI+) m/z 675.4 (M+H)⁺; HRMS (ESI+) m/z calculated for C$_{36}$H$_{35}$N$_8$O$_6$ (M+H)⁺ 675.2674, found 675.2622.

Synthetic scheme 38

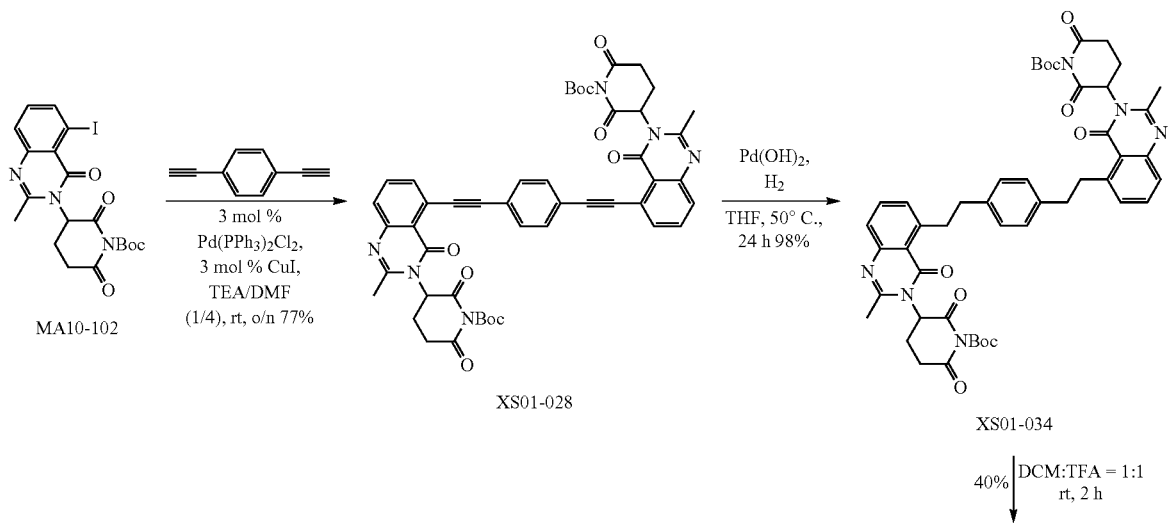

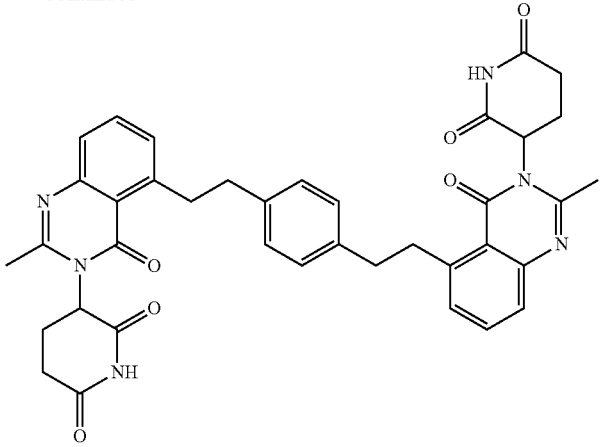

XS01-038

Di-tert-butyl 3,3'-((1,4-phenylenebis(ethyne-2,1-diyl))bis(2-methyl-4-oxoquinazoline-5,3(4H)-diyl))bis(2,6-dioxopiperidine-1-carboxylate) (XS01-028): Tert-butyl 3-(5-iodo-2-methyl-4-oxoquinazolin-3(4H)-yl)-2,6-dioxopiperidine-1-carboxylate (MA10-112) (100 mg, 0.201 mmol), 1,4-diethynylbenzene (11.5 mg, 0.091 mmol) and bis(triphenylphosphine)palladium(II) dichloride (1.9 mg, 0.0027 mmol) were dissolved in a mixture of TEA/DMF (2.5 mL, 1:4, v/v). The solution was degassed for 10 min, and copper(I) iodide (0.52 mg, 0.0027 mmol) was added under argon atmosphere. The tube was sealed and the mixture stirred overnight at room temperature. Water (10 mL) was added and the mixture was extracted with ethyl acetate (3×10 mL). The combined organic phase was washed with H$_2$O (3×10 mL) and brine (3×10 mL), dried with Na$_2$SO$_4$, and then concentrated under reduced pressure to provide the crude product. Dichloromethane and hexane were used for trituration to provide di-tert-butyl 3,3'-((1,4-phenylenebis(ethyne-2,1-diyl))bis(2-methyl-4-oxoquinazoline-5,3(4H)-diyl))bis(2,6-dioxopiperidine-1-carboxylate) (XS01-028) (60 mg, 77%) as a yellow solid. HPLC 83.4% (t$_R$=13.55 min, CH$_3$OH in 0.1% TFA water 5%~95% in 20 min); $^1$H NMR (500 MHz, DMSO-d$_6$) δ 7.83 (t, J=8.0 Hz, 2H), 7.76-7.60 (m, 8H), 5.53 (dd, J=11.7, 5.7 Hz, 2H), 3.05 (m, 2H), 2.85-2.76 (m, 2H), 2.66 (m, 8H), 2.31-2.15 (m, 2H), 1.50 (s, 18H). HPLC-MS (ESI+) m/z 865.4 (M+H)$^+$.

Di-tert-butyl 3,3'-((1,4-phenylenebis(ethane-2,1-diyl))bis(2-methyl-4-oxoquinazoline-5,3(4H)-diyl))bis(2,6-dioxopiperidine-1-carboxylate) (XS01-034): Di-tert-butyl 3,3'-((1,4-phenylenebis(ethyne-2,1-diyl))bis(2-methyl-4-oxoquinazoline-5,3(4H)-diyl))bis(2,6-dioxopiperidine-1-carboxylate) (XS01-028) (60 mg, 0.09 mmol) in THF (3 mL) was added to a suspension of palladium hydroxide (20% on carbon, 10 mg) in THF (2 mL). The solution was stirred under an atmosphere of hydrogen overnight at 50° C. The mixture was filtered through a bed of celite, which was washed with THF. The solvent from the combined filtrate and washing was removed by rotary evaporation under vacuum to provide di-tert-butyl 3,3'-((1,4-phenylenebis(ethane-2,1-diyl))bis(2-methyl-4-oxoquinazoline-5,3(4H)-diyl))bis(2,6-dioxopiperidine-1-carboxylate) (XS01-034) (59 mg, 98%) as a yellow solid. HPLC 86.4% (t$_R$=13.85 min, CH$_3$OH in 0.1% TFA water 5%~95% in 20 min); $^1$H NMR (500 MHz, DMSO-d$_6$) δ 7.75-7.54 (m, 2H), 7.47 (m, 2H), 7.31-7.15 (m, 2H), 7.17-7.00 (s, 4H), 5.50-5.42 (m, 2H), 3.64-3.55 (m, 2H), 3.52-3.42 (m, 4H), 3.17-2.94 (m, 4H), 2.87-2.66 (m, 8H), 2.64 (s, 6H), 2.22 (m, 2H), 1.24 (s, 18H). HPLC-MS (ESI+) m/z 873.4 (M+H)$^+$.

Di-tert-butyl 3,3'-((1,4-phenylenebis(ethane-2,1-diyl))bis(2-methyl-4-oxoquinazoline-5,3(4H)-diyl))bis(2,6-dioxopiperidine-1-carboxylate)

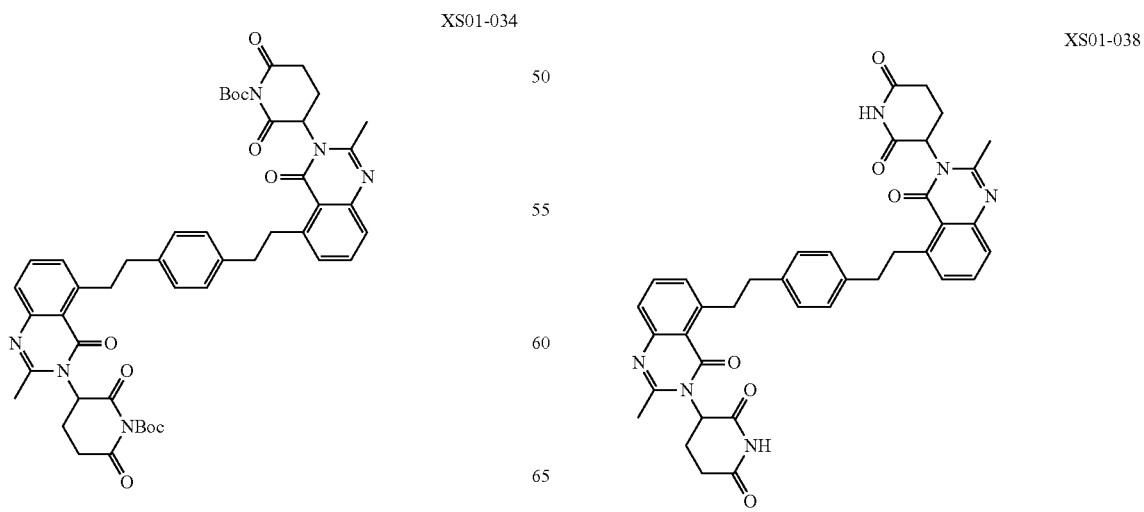

XS01-034

XS01-038

3,3'-((1,4-Phenylenebis(ethane-2,1-diyl))bis(2-methyl-4-oxoquinazoline-5,3(4H)-diyl))bis(piperidine-2,6-dione) (XS01-038): Di-tert-butyl 3,3'-((1,4-phenylenebis(ethane-2,1-diyl))bis(2-methyl-4-oxoquinazoline-5,3(4H)-diyl))bis(2,6-dioxopiperidine-1-carboxylate) (XS01-034) (60 mg, 0.068 mmol) was dissolved in a mixture of DCM:TFA (2 mL, 1:1 v/v), and the solution was stirred for 2 h at room temperature. HPLC and TLC indicated the reaction was complete. The solvent was removed by rotary evaporation under vacuum, dichloromethane (5 mL) was added, and the mixture washed with sat. NaHCO$_3$ solution (3×5 mL) and brine (2×5 mL), dried (Na$_2$SO$_4$) and concentrated under reduced pressure to provide the crude product. The crude product was dissolved in THF (1 mL), and triturated with MeOH to provide 3,3'-((1,4-phenylenebis(ethane-2,1-diyl))bis(2-methyl-4-oxoquinazoline-5,3(4H)-diyl))bis(piperidine-2,6-dione) (XS01-038) (18 mg, 40%) as a white solid. HPLC 95.5% (t$_R$=15.35 min, CH$_3$OH in 0.1% TFA water 5%~95% in 20 min); Mp: 221° C. (dec); $^1$H NMR (500 MHz, DMSO-d$_6$) δ11.05 (s, 2H), 7.65 (t, J=7.8 Hz, 2H), 7.46 (dd, J=8.1, 1.2 Hz, 2H), 7.20 (dd, J=7.5, 1.3 Hz, 2H), 7.09 (s, 4H), 5.23 (dd, J=11.5, 5.8 Hz, 2H), 3.50--3.34 (m, 4H), 2.94-2.78 (m, 2H), 2.78-2.70 (m, 4H), 2.63 (s, 10H), 2.25-2.12 (m, 2H); HPLC-MS (ESI+) m/z 673.4 (M+H)$^+$; HRMS (ESI+) m/z calculated for C$_{38}$H$_{36}$N$_6$NaO$_6$ (M+Na)$^+$ 695.2589, found 695.2581.

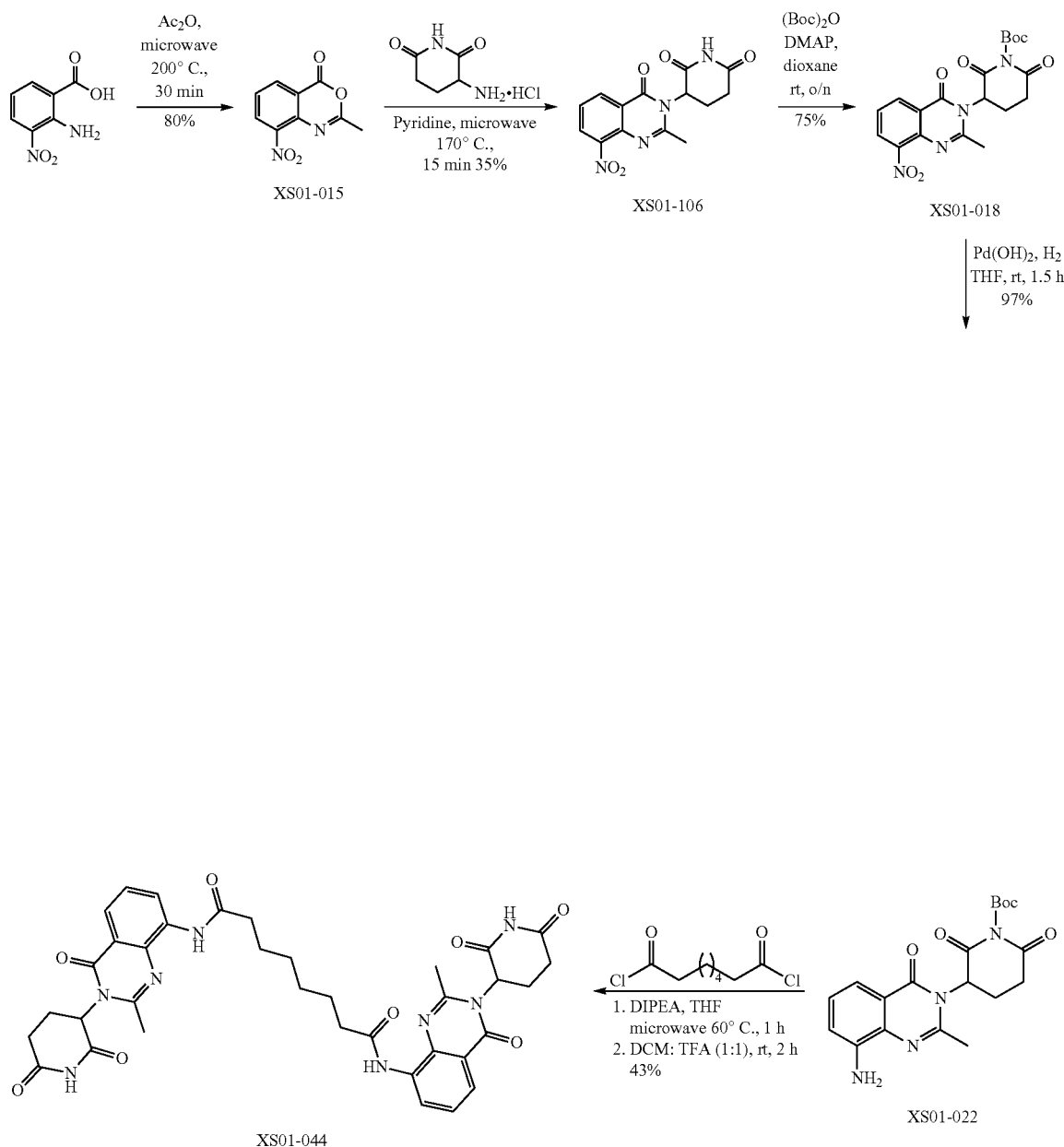

N$^1$,N$^8$-bis(3-(2,6-dioxopiperidin-3-yl)-2-methyl-4-oxo-3,4-dihydroquinazolin-8-yl)octanediamide (XS01-044): Tert-butyl 3-(8-amino-2-methyl-4-oxoquinazolin-3(4H)-yl)-2,6-dioxopiperidine-1-carboxylate (XS01-022) (133 mg, 0.344 mmol) and DIPEA (64 mg, 0.497 mmol) were dissolved in THF (1.8 mL) in a microwave vial. Octanedioyl dichloride (35 mg, 0.164 mmol) was added to the solution. The tube was sealed, and the reaction mixture was heated at 60° C. in a microwave reactor for 1 h. The solvent was removed by rotary evaporation under vacuum, dichloromethane (10 mL) was added. The organic layer washed with water (3×10 mL) and brine (3×10 mL), dried (Na$_2$SO$_4$) and concentrated under reduced pressure to provide the crude product. The crude product was dissolved in a mixture of DCM:TFA (6 mL, 1:1 v/v), and stirred for 2 h at room temperature. The solvent was removed by rotary evaporation under vacuum to provide the crude product which was dissolved in THF (1 mL). Methanol was added to the solution to precipitate solid, which was filtered and dried to provide N$^1$,N$^8$-bis(3-(2,6-dioxopiperidin-3-yl)-2-methyl-4-oxo-3,4-dihydroquinazolin-8-yl)octanediamide (XS01-044) (50 mg, 43%) as a white solid. HPLC 98.4% (t$_R$=12.49 min, CH$_3$OH in 0.1% TFA water 5%~95% in 20 min); Mp: 206° C. (dec); $^1$H NMR (500 MHz, DMSO-d$_6$) δ 11.05 (s, 2H), 9.56 (s, 2H), 8.63 (dd, J=8.0, 1.4 Hz, 2H), 7.68 (m, 2H), 7.44 (t, J=8.0 Hz, 2H), 5.29 (dd, J=11.6, 5.7 Hz, 2H), 2.84 (m, 2H), 2.72 (s, 6H), 2.64-2.52 (m, 8H), 2.18 (m, 2H), 1.74-1.58 (m, 4H), 1.50-1.35 (m, 4H); HPLC-MS (ESI+) m/z 711.3 (M+H)$^+$; HRMS (ESI+) m/z calculated for C$_{36}$H$_{38}$N$_8$NaO$_8$ (M+Na)$^+$ 733.2705, found 733.2700.

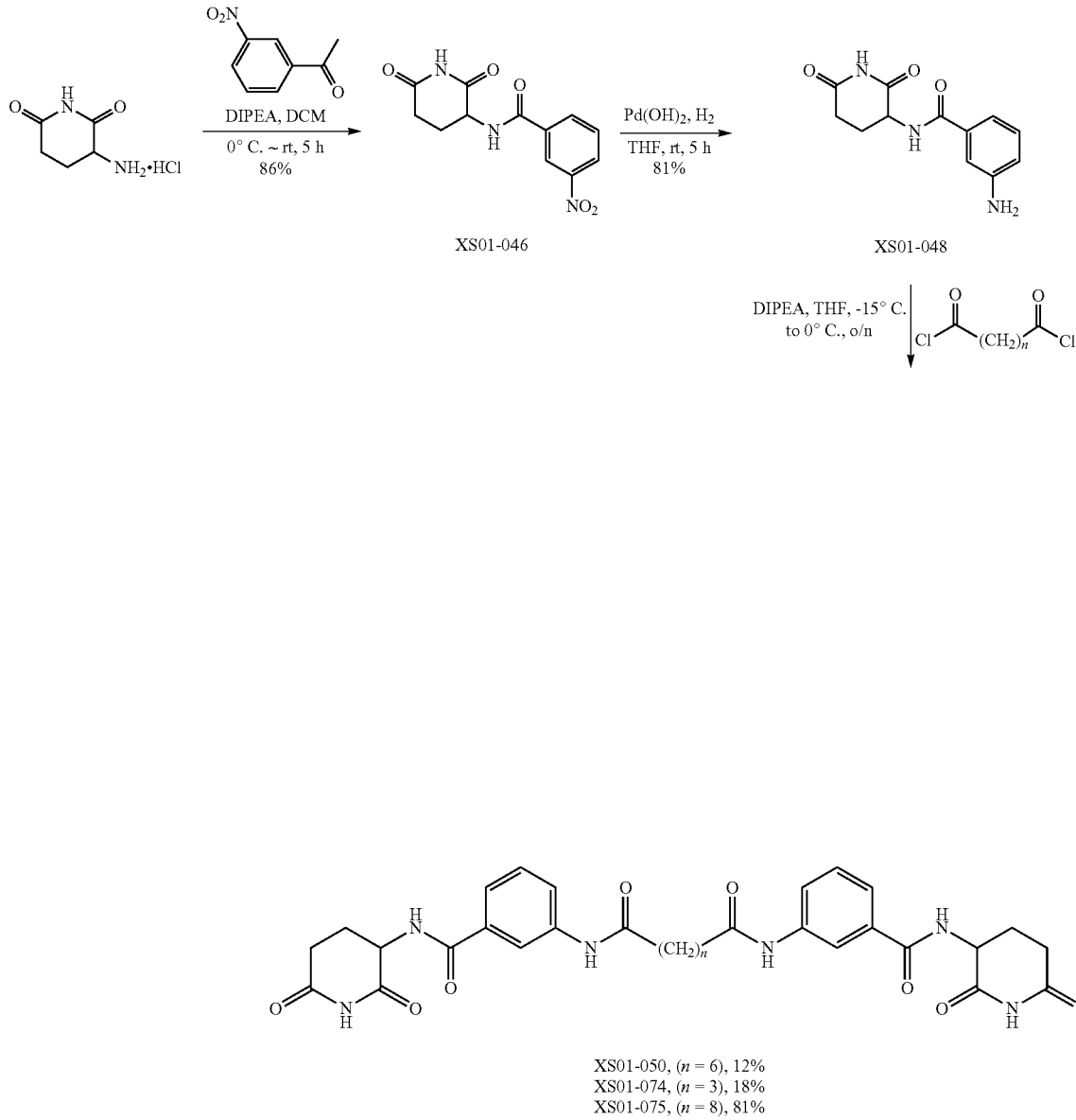

XS01-050, (n = 6), 12%
XS01-074, (n = 3), 18%
XS01-075, (n = 8), 81%

N-(2,6-dioxopiperidin-3-yl)-3-nitrobenzamide (XS01-046): 3-Nitrobenzoyl chloride (270 mg, 1.46 mmol) in dichloromethane (2 mL) was added dropwise at 0° C. to a solution of 3-aminopiperidine-2,6-dione hydrochloride (200 mg, 1.215 mmol) and DIPEA (471 mg, 3.65 mmol) in dichloromethane (8 mL). The reaction mixture was stirred at 0° C. for 5 h. The solvent was removed by rotary evaporation under vacuum, and dichloromethane (10 mL) and H$_2$O (10 mL) added to the residue. The organic phase was separated and washed with sat. NH$_4$Cl (10 mL) and brine (3×20 mL), dried (Na$_2$SO$_4$) and concentrated under reduced pressure to provide N-(2,6-dioxopiperidin-3-yl)-3-nitrobenzamide (XS01-046) (285 mg, 86%) as a white solid. HPLC 100.0% (t$_R$=8.34 min, CH$_3$OH in 0.1% TFA water 5%~95% in 20 min); $^1$H NMR (500 MHz, DMSO-d$_6$) δ 10.92 (s, 1H), 9.20 (d, J=8.3 Hz, 1H), 8.73 (t, J=2.0 Hz, 1H), 8.43 (m, 1H), 8.33 (m, 1H), 7.83 (t, J=8.0 Hz, 1H), 4.85 (m, 1H), 2.83 (m, 1H), 2.61-2.54 (m, 1H), 2.15 m, 1H), 2.02 (m, 1H).

3-Amino-N-(2,6-dioxopiperidin-3-yl)benzamide (XS01-048): The N-(2,6-dioxopiperidin-3-yl)-3-nitrobenzamide (XS01-046) (180 mg, 0.65 mmol) in THF (5 ml) was added to a suspension of palladium hydroxide (20% on carbon, 18 mg) in THF (5 ml). The solution was stirred under an atmosphere of hydrogen overnight at room temperature. The mixture was filtered through a bed of celite, which was washed with THF. The solvent from the combined filtrate and washing was removed by rotary evaporation under vacuum to provide 3-amino-N-(2,6-dioxopiperidin-3-yl)benzamide (XS01-048) (130 mg, 81%) as a white solid. $^1$H NMR (500 MHz, DMSO-d$_6$) δ 10.82 (s, 1H), 8.49 (d, J=8.4 Hz, 1H), 7.14-7.02 (m, 2H), 6.98 (m, 1H), 6.71 (m, 1H), 5.25 (s, 2H), 4.75 (m, 1H), 2.79 (m, 1H), 2.58-2.53 (m, 1H), 2.11 (m, 1H), 1.95 (m, 1H); HPLC-MS (ESI+) m/z 248.2 (M+H)$^+$.

XS01-050

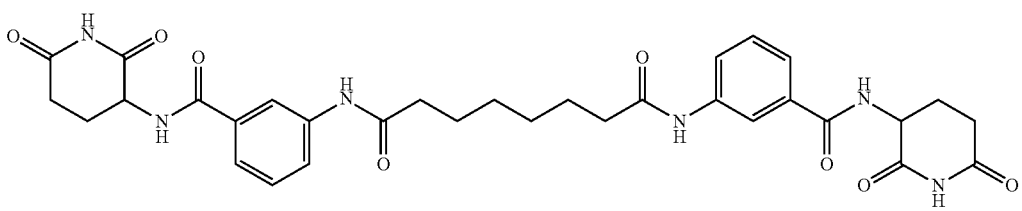

N$^1$,N$^8$-Bis(3-((2,6-dioxopiperidin-3-yl)carbamoyl)phenyl)octanediamide (XS01-050): 3-Amino-N-(2,6-dioxopiperidin-3-yl)benzamide (XS01-048) (100 mg, 0.404 mmol) and DIPEA (75 mg, 0.578 mmol) were dissolved in THF (4 mL). Octanedioyl dichloride (41 mg, 0.193 mmol) in THF (1 mL) was added to the solution, dropwise at −15° C. under argon atmosphere. The reaction mixture was stirred at room temperature overnight. The solvent was removed by rotary evaporation under vacuum, dichloromethane (10 mL) and H$_2$O (10 mL) were added and separated. The aqueous layer was further extracted with dichloromethane (5×10 mL). The solvent was removed from the combined organic layers by rotary evaporation under vacuum to provide the crude product, which was triturated with MeOH (3×5 mL) to give N$^1$,N$^8$-bis(3-((2,6-dioxopiperidin-3-yl)carbamoyl)phenyl)octanediamide (XS01-050) (15 mg, 12%) as a white solid. HPLC 99.9% (t$_R$=6.79 min, CH$_3$OH in 0.1% TFA water 5%~95% in 20 min); Mp: 240° C. (dec); $^1$H NMR (500 MHz, DMSO-d$_6$) δ 10.92 (s, 2H), 10.10 (s, 2H), 8.77 (d, J=8.4 Hz, 2H), 8.12 (t, J=1.9 Hz, 2H), 7.95-7.70 (m, 2H), 7.57 (m, 2H), 7.46 (t, J=7.9 Hz, 2H), 4.85 (m, 2H), 2.86 (m, 2H), 2.66-2.58 (m, 2H), 2.38 (t, J=7.4 Hz, 4H), 2.18 (m, 2H), 2.09-1.93 (m, 2H), 1.78-1.59 (m, 4H), 1.53-1.05 (m, 4H); HRMS (ESI+) m/z calculated for C$_{32}$H$_{36}$N$_6$NaO$_8$ (M+Na)$^+$ 655.2487, found 655.2482.

XS01-074

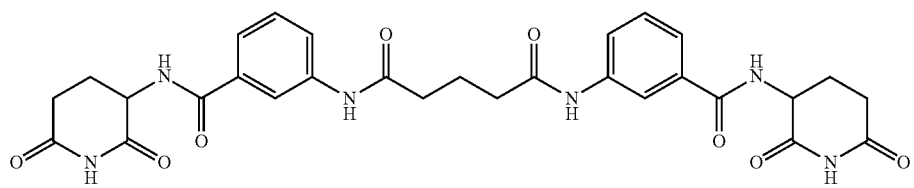

$N^1,N^5$-Bis(3-((2,6-Dioxopiperidin-3-yl)carbamoyl)phenyl)glutaramide (XS01-074): This was prepared in the same way as XS01-050 from 3-amino-N-(2,6-dioxopiperidin-3-yl)benzamide (XS01-048) (100 mg, 0.404 mmol) and glutaroyl dichloride (33 mg, 0.193 mmol) provide $N^1,N^5$-bis (3-((2,6-dioxopiperidin-3-yl)carbamoyl)phenyl)glutaramide (XS01-074) (21 mg, 18%) as a white solid. HPLC 99.7% ($t_R$=12.04 min, CH$_3$OH in 0.1% TFA water 5%~95% in 20 min); Mp: 232° C. (dec); $^1$H NMR (500 MHz, DMSO-d$_6$) δ 10.85 (s, 2H), 10.09 (s, 2H), 8.71 (d, J=8.4 Hz, 2H), 8.09 (t, J=1.9 Hz, 2H), 7.91-7.65 (m, 2H), 7.52 (m, 2H), 7.41 (t, J=7.9 Hz, 2H), 4.79 (m, 2H), 2.81 (m, 2H), 2.59-2.52 (m, 2H), 2.41 (t, J=7.3 Hz, 4H), 2.23-2.04 (m, 2H), 2.03-1.80 (m, 4H); HPLC-MS (ESI+) m/z 613.2 (M+Na)$^+$; HRMS (ESI+) m/z calculated for C$_{29}$H$_{30}$N$_6$NaO$_8$ (M+Na)$^+$ 613.2017, found 613.2014.

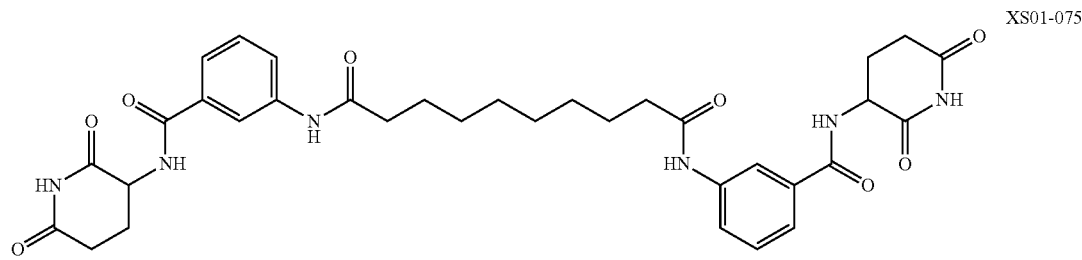 [SMILES: O=C1CCC(NC(=O)c2cccc(NC(=O)CCCCCCCCC(=O)Nc3cccc(C(=O)NC4CCC(=O)NC4=O)c3)c2)C(=O)N1]

XS01-075

$N^1,N^{10}$-Bis(3-((2,6-dioxopiperidin-3-yl)carbamoyl)phenyl)decanediamide (XS01-075): This was prepared in the same way as XS01-050 from 3-amino-N-(2,6-dioxopiperidin-3-yl)benzamide (XS01-048) (100 mg, 0.404 mmol) and decanedioyl dichloride (46 mg, 0.193 mmol) to provide $N^1,N^{10}$-bis(3-((2,6-dioxopiperidin-3-yl)carbamoyl)phenyl)decanediamide (XS01-075) (106 mg, 81%) as a white solid. HPLC 96.9% ($t_R$=13.88 min, CH$_3$OH in 0.1% TFA water 5%~95% in 20 min); Mp: 223° C. (dec); $^1$H NMR (500 MHz, DMSO-d$_6$) δ 10.85 (s, 2H), 10.02 (s, 2H), 8.70 (d, J=8.3 Hz, 2H), 8.06 (t, J=2.0 Hz, 2H), 7.79 (m, 2H), 7.52 (m, 2H), 7.40 (t, J=7.9 Hz, 2H), 4.79 (m, 2H), 2.80 (m, 2H), 2.55 (m, 2H), 2.31 (t, J=7.4 Hz, 4H), 2.19-2.06 (m, 2H), 1.98 (m, 2H), 1.67-1.52 (m, 4H), 1.31 (s, 8H); HPLC-MS (ESI+) m/z 661.4 (M+H)$^+$; HRMS (ESI+) m/z calculated for C$_{34}$H$_{40}$N$_6$NaO$_8$ (M+Na)$^+$ 683.2800, found 683.2797.

Synthetic scheme 41

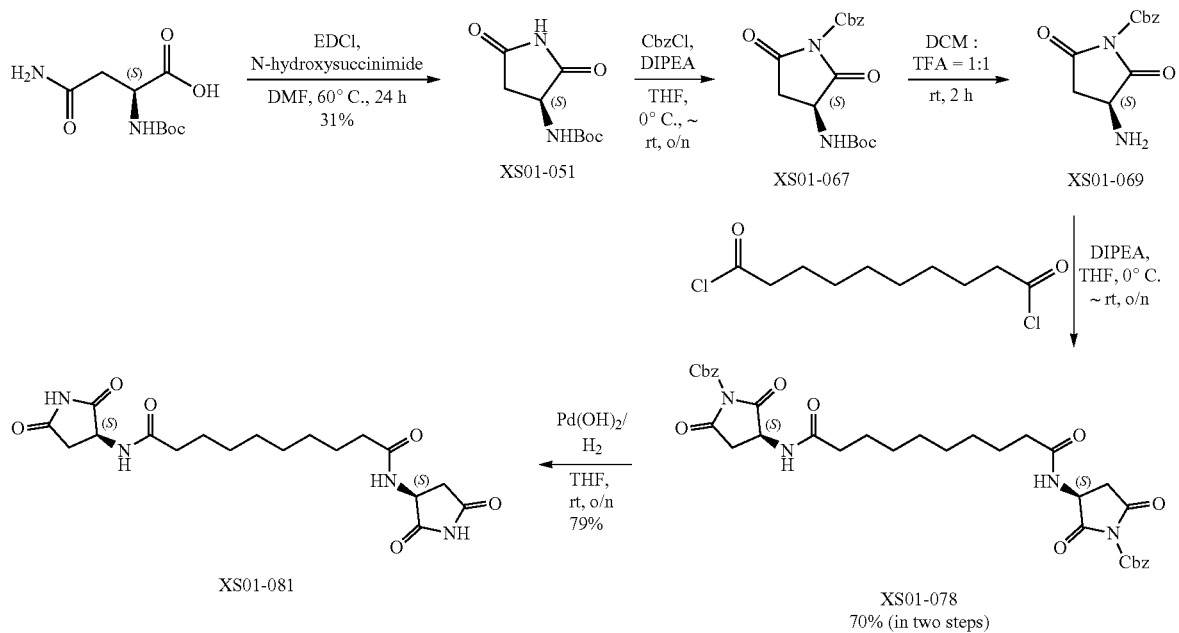

Tert-butyl (S)-(2,5-dioxopyrrolidin-3-yl)carbamate (XS01-051): A mixture of (tert-butoxycarbonyl)-L-asparagine (1.00 g, 4.31 mmol), EDCI (907 mg, 4.74 mmol) and N-hydroxysuccinimide (545 mg, 4.74 mmol) in dimethylformamide (18 mL) was stirred at 60° C. for 24 h. The solution was cooled to room temperature then H$_2$O (20 mL) was added, and extracted with ethyl acetate (2×20 mL). The organic layer was washed with H$_2$O (2×10 mL), sat. NaHCO$_3$ (2×10 mL) and brine (2×10 mL), dried (Na$_2$SO$_4$) and concentrated under reduced pressure to give the crude product. The residue was triturated with methanol/diethyl ether/hexane to provide tert-butyl (S)-(2,5-dioxopyrrolidin-3-yl)carbamate (XS01-051) (282 mg, 31%) as a white solid. $^1$H NMR (500 MHz, DMSO-d$_6$) δ 11.17 (s, 1H), 7.42 (d, J=8.3 Hz, 1H), 4.45-4.17 (m, 1H), 2.94-2.70 (m, 2H), 2.50-2.35 (m, 1H), 1.39 (s, 9H); HPLC-MS (ESI+) m/z 237.1 (M+Na)$^+$. (See Wo2017/161119.)

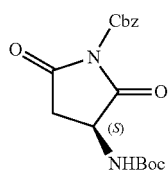

XS01-067

Benzyl (S)-3-((tert-butoxycarbonyl)amino)-2,5-dioxopyrrolidine-1-carboxylate (XS01-067): Benzyl chloroformate (358 mg, 2.10 mmol) in THF (5 mL) was added dropwise at 0° C. to a mixture of tert-butyl (S)-(2,5-dioxopyrrolidin-3-yl)carbamate (XS01-051) (300 mg, 1.40 mmol) and DIPEA (362 mg, 2.80 mmol) in THF (15 mL). The reaction mixture was stirred at room temperature overnight. The solvent was removed by rotary evaporation under vacuum, dichloromethane (20 mL) and sat. NaHCO$_3$ (20 mL) were added to the residue. The organic phase was separated and washed with H$_2$O (10 mL) and brine (3×20 mL), dried (Na$_2$SO$_4$) and concentrated under reduced pressure to provide the crude product. Purification of the crude product by silica gel chromatography (0-10% MeOH in dichloromethane) afforded benzyl (S)-3-((tert-butoxycarbonyl)amino)-2,5-dioxopyrrolidine-1-carboxylate (XS01-067) (141 mg, 29%) as a white solid. HPLC 100.0% (t$_R$=11.51 min, CH$_3$OH in 0.1% TFA water 5%~95% in 20 min); $^1$H NMR (500 MHz, DMSO-d$_6$) δ 7.57-7.44 (m, 2H), 7.44-7.31 (m, 3H), 5.39 (s, 2H), 4.48 (m, 1H), 3.03 (m, 1H), 2.76-2.55 (m, 1H), 1.38 (s, 9H); HPLC-MS (ESI+) m/z 719.3 (2M+Na)$^+$.

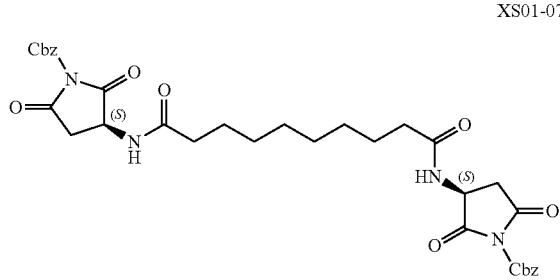

XS01-078

Dibenzyl 3,3'-(decanedioyl bis(azanediyl))(3S,3'S)-bis(2,5-dioxopyrrolidine-1-carboxylate) (XS01-078): Benzyl (S)-3-((tert-butoxycarbonyl)amino)-2,5-dioxopyrrolidine-1-carboxylate (XS01-067) (247 mg, 0.71 mmol) was dissolved in a mixture of dichloromethane:TFA=1:1, the mixture was stirring at room temperature for 2 h. The solvent was removed by rotary evaporation under vacuum to provide the amine XS01-069, which was used without further purification. The amine was suspended in THF (10 mL), and DIPEA (262 mg, 2.03 mmol) was added to the solution. This solution was stirred at 0° C., then decanedioyl dichloride (81 mg, 0.34 mmol) was added. The reaction mixture was stirred at room temperature overnight. The solvent was removed by rotary evaporation under vacuum, dichloromethane (10 mL) and H$_2$O (10 mL) were added. The separated aqueous layer was extracted with dichloromethane (3×10 mL). The combined organic layers were dried (Na$_2$SO$_4$) and concentrated under reduced pressure to give the crude product. Purification of the crude material by silica gel chromatography (0-10% MeOH in dichloromethane) afforded dibenzyl 3,3'-(decanedioyl bis(azanediyl))(3S,3'S)-bis(2,5-dioxopyrrolidine-1-carboxylate) (XS01-078) (157 mg, 70%) as a white solid. HPLC 100.0% (t$_R$=12.04 min, CH$_3$OH in 0.1% TFA water 5%~95% in 20 min); $^1$H NMR (500 MHz, DMSO-d$_6$) δ 8.57 (d, J=7.4 Hz, 2H), 7.53-7.29 (m, 10H), 5.39 (s, 4H), 4.60-4.36 (m, 2H), 3.02 (dd, J=17.8, 9.7 Hz, 2H), 2.69-2.55 (m, 2H), 2.10 (m, 4H), 1.47 (m, 4H), 1.23 (s, 8H); HPLC-MS (ESI+) m/z 685.3 (M+Na)$^+$.

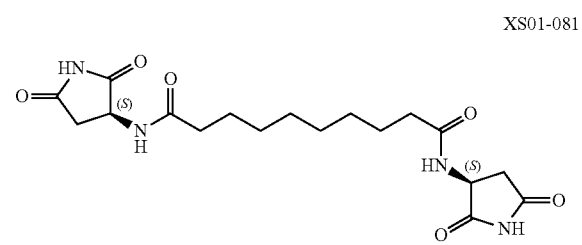

XS01-081

N$^1$,N$^{10}$-Bis((S)-2,5-dioxopyrrolidin-3-yl)decanediamide (XS01-081): Palladium hydroxide (20% on carbon, 20 mg) and THF (15 mL) were charged in a round bottomed flask, and a vacuum applied twice, and finally filled with hydrogen. Dibenzyl 3,3'-(decanedioyl bis(azanediyl))(3S,3'S)-bis(2,5-dioxopyrrolidine-1-carboxylate) (XS01-078) (150 mg, 0.226 mmol) in THF (5 mL) was added to the mixture. The reaction mixture was stirred at room temperature overnight under an atmosphere of hydrogen. The mixture was filtered through a bed of celite, which was washed with THF. The combined filtrates were concentrated under reduced pressure to give the crude product. The crude product was triturated with the mixture of methanol/diethyl ether/hexane/ethyl acetate=1/1/1/1 to get N$^1$,N$^{10}$-bis((S)-2,5-dioxopyrrolidin-3-yl)decanediamide (XS01-081) (71 mg, 79%) as a white solid. Mp: 201° C. (dec); $^1$H NMR (500 MHz, DMSO-d$_6$) δ 11.18 (s, 2H), 8.40 (d, J=7.6 Hz, 2H), 4.36 (m, 2H), 2.85 (dd, J=17.5, 9.3 Hz, 2H), 2.46 (dd, J=17.5, 5.5 Hz, 2H), 2.11-2.02 (m, 4H), 1.47 (t, J=7.2 Hz, 4H), 1.24 (s, 8H); HPLC-MS (ESI+) m/z 395.2 (M+H)$^+$; HRMS (ESI+) m/z calculated for C$_{18}$H$_{26}$N$_4$NaO$_6$ (M+Na)$^+$ 417.1745, found 417.1742.

Synthetic scheme 42

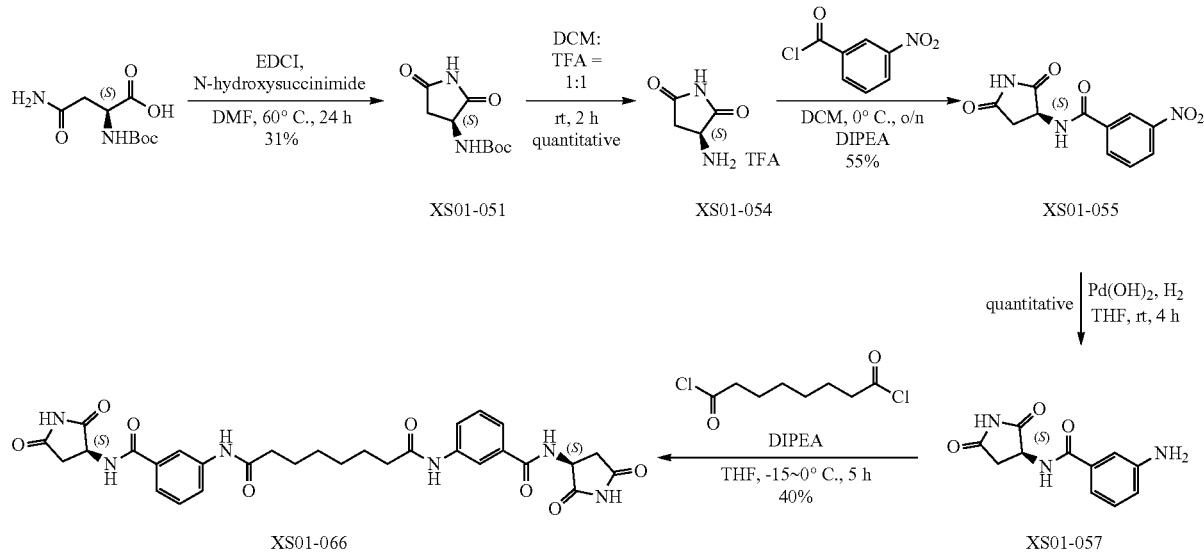

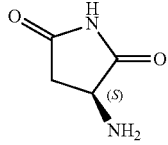

XS01-054

(S)-3-Aminopyrrolidine-2,5-dione (XS01-054): Tert-butyl (S)-(2,5-dioxopyrrolidin-3-yl)carbamate (XS01-051) (280 mg, 1.31 mmol) was dissolved in the mixture of dichloromethane:methanol=1:1, the mixture was stirred at room temperature for 2 h. The solvents were removed by under reduced pressure to get (S)-3-aminopyrrolidine-2,5-dione (XS01-054) (290 mg, 97%) as a yellow gel. $^1$H NMR (500 MHz, DMSO-$d_6$) δ 11.72 (s, 1H), 8.54 (s, 2H), 4.33 (dd, J=9.2, 5.5 Hz, 1H), 2.96 (dd, J=17.7, 9.2 Hz, 1H), 2.69-2.55 (m, 1H); HPLC-MS (ESI+) m/z 115.2 (M+H)$^+$.

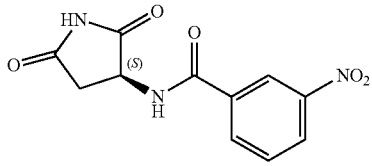

XS01-055

(S)—N-(2,5-dioxopyrrolidin-3-yl)-3-nitrobenzamide (XS02-055): (S)-3-Aminopyrrolidine-2,5-dione (XS01-054) (460 mg, 2.02 mmol) and DIPEA (1042 mg, 8.07 mmol) were stirred in dichloromethane (10 mL), for 30 min at room temperature. 3-Nitrobenzoyl chloride (299 mg, 1.61 mmol) in dichloromethane (3 mL) was added to the solution at 0° C., and the resulting mixture stirred at room temperature overnight. Water (20 mL) and dichloromethane (20 mL) were added and the phases separated. The organic phase was washed with brine (3×10 mL), dried (Na$_2$SO$_4$) and concentrated under reduced pressure to provide the crude product. Purification of the crude material by silica gel chromatography (0-5% MeOH in dichloromethane) afforded (S)—N-(2,5-dioxopyrrolidin-3-yl)-3-nitrobenzamide (245 mg, 58%) as a white solid. HPLC 89.3% ($t_R$=7.87 min, CH$_3$OH in 0.1% TFA water 5%~95% in 20 min); $^1$H NMR (500 MHz, DMSO-$d_6$) δ 11.36 (s, 1H), 9.50 (d, J=7.6 Hz, 1H), 8.68 (t, J=2.0 Hz, 1H), 8.43 (m, 1H), 8.29 (m, 1H), 7.83 (t, J=8.0 Hz, 1H), 4.73 (m, 1H), 2.99 (dd, J=17.6, 9.4 Hz, 1H), 2.83-2.61 (m, 1H); HPLC-MS (ESI+) m/z 264.2 (M+H)$^+$.

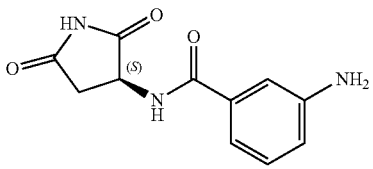

XS01-057

(S)-3-Amino-N-(2,5-dioxopyrrolidin-3-yl)benzamide (XS01-057): (S)—N-(2,5-dioxopyrrolidin-3-yl)-3-nitrobenzamide (XS02-055) (240 mg, 0.91 mmol) in THF (2 mL) was added to a suspension of palladium hydroxide (20% on carbon, 24 mg) in THF (8 ml). The solution was stirred under an atmosphere of hydrogen overnight at room temperature. The mixture was filtered through a bed of celite, which was washed with THF. The solvent from the combined filtrate and washings was removed by rotary evaporation under vacuum to provide (S)-3-amino-N-(2,5-dioxopyrrolidin-3-yl)benzamide (XS01-057) (210 mg, 99%) as a white solid. HPLC 86.6% ($t_R$=2.72 min, CH$_3$OH in 0.1% TFA water 5%~95% in 20 min); $^1$H NMR (500 MHz, DMSO-$d_6$) δ 11.24 (s, 1H), 8.93-8.62 (m, 1H), 7.10 (t, J=7.8 Hz, 1H), 7.01 (t, J=2.0 Hz, 1H), 6.97-6.89 (m, 1H), 6.71 (m, 1H), 5.26 (s, 2H), 4.77-4.47 (m, 1H), 3.04-2.80 (m, 1H), 2.70-2.54 (m, 1H); HPLC-MS (ESI+) m/z 234.1 (M+H)$^+$.

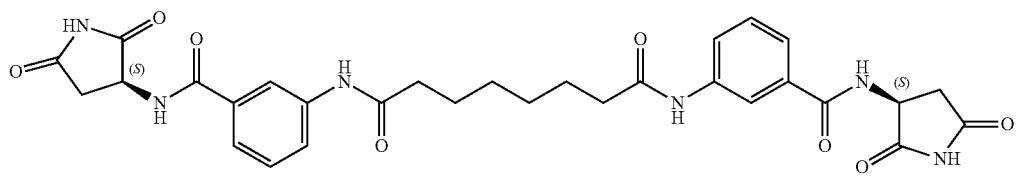

XS01-066

N[1],N[8]-Bis(3-(((S)-2,5-dioxopyrrolidin-3-yl)carbamoyl)phenyl)octanediamide (XS01-066): (S)-3-Amino-N-(2,5-dioxopyrrolidin-3-yl)benzamide (XS01-057) (80 mg, 0.343 mmol) and DIPEA (63 mg, 0.490 mmol) were dissolved in THF (8 mL), octanedioyl dichloride (35 mg, 0.163 mmol) in THF (2 mL) was added to the solution at −15° C., the reaction mixture was stirred at 0° C. for 5 h. The solvent was removed by rotary evaporation under vacuum, and $H_2O$ (10 mL) and dichloromethane (10 mL) were added to the residue. The organic phase was separated and washed with brine (3×10 mL), the aqueous phase was extracted with ethyl acetate (10 mL) and washed with brine (3×10 mL). The combined organic layers were dried ($Na_2SO_4$) and concentrated under reduced pressure to provide the crude product. The crude product was triturated with methanol (3×5 mL), to give N[1],N[8]-bis(3-(((S)-2,5-dioxopyrrolidin-3-yl)carbamoyl)phenyl)octanediamide (XS01-066) (40 mg, 40%) as a white solid. Mp: 218° C. (dec); HPLC 99.9% ($t_R$=6.75 min, $CH_3OH$ in 0.1% TFA water 5%~95% in 20 min); $^1$H NMR (500 MHz, DMSO-$d_6$) δ 11.28 (s, 2H), 10.03 (s, 2H), 9.03 (d, J=7.8 Hz, 2H), 8.08 (t, J=2.0 Hz, 2H), 7.74 (m, 2H), 7.48 (m, 2H), 7.40 (t, J=7.9 Hz, 2H), 4.67 (m, 2H), 2.94 (dd, J=17.5, 9.3 Hz, 2H), 2.69-2.55 (m, 2H), 2.32 (t, J=7.4 Hz, 4H), 1.61 (t, J=7.0 Hz, 4H), 1.35 (d, J=4.1 Hz, 4H); HPLC-MS (ESI+) m/z 605.3 (M+H)$^+$; HRMS (ESI+) m/z calculated for $C_{30}H_{32}N_6NaO_8$ (M+Na)$^+$ 627.2174, found 627.2181.

Synthetic scheme 43

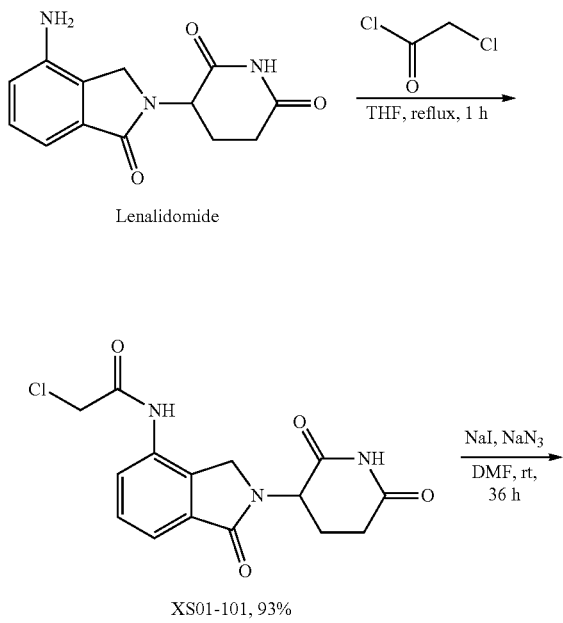

-continued

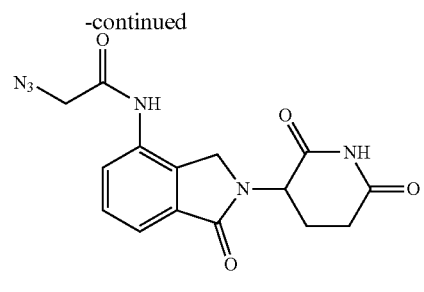

XS01-104, 81%

2-Chloro-N-(2-(2,6-dioxopiperidin-3-yl)-1-oxoisoindolin-4-yl)acetamide (XS01-101): To a solution of 3-(4-amino-1-oxoisoindolin-2-yl)piperidine-2,6-dione (500 mg, 1.93 mmol) in THF (20 mL) was added 2-chloroacetyl chloride (435 mg, 3.86 mmol), the mixture was heated to reflux for 1 h. The solvent was evaporated in vacuo and the resulting solid was slurried in diethyl ether (20 mL) and filtered to give 2-chloro-N-(2-(2,6-dioxopiperidin-3-yl)-1-oxoisoindolin-4-yl)acetamide (XS01-101) (600 mg, 93%) as a white solid. HPLC 98.9% ($t_R$=7.98 min, $CH_3OH$ in 0.1% TFA water 5%~95% in 20 min); $^1$H NMR (500 MHz, DMSO-$d_6$) δ 11.02 (s, 1H), 10.19 (s, 1H), 7.82 (dd, J=7.7, 1.3 Hz, 1H), 7.64-7.42 (m, 2H), 5.16 (dd, J=13.3, 5.1 Hz, 1H), 4.46-4.28 (m, 4H), 2.92 (m, 1H), 2.68-2.57 (m, 1H), 2.43-2.28 (m, 1H), 2.10-1.96 (m, 1H); HPLC-MS (ESI+) m/z 336.1 (M+H)$^+$. (See US2003/96841.)

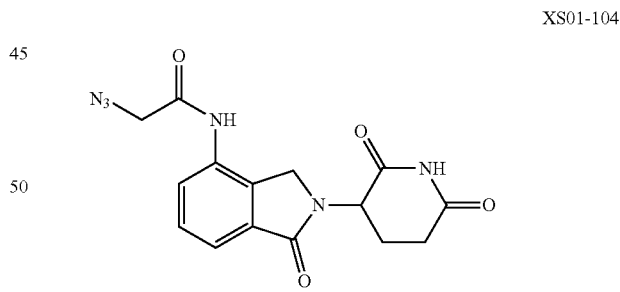

XS01-104

2-Azido-N-(2-(2,6-dioxopiperidin-3-yl)-1-oxoisoindolin-4-yl)acetamide (XS01-104): To a stirred suspension of 2-chloro-N-(2-(2,6-dioxopiperidin-3-yl)-1-oxoisoindolin-4-yl)acetamide (XS01-101) (530 mg, 1.58 mmol) in acetone (50 mL) was added sodium iodide (473 mg, 3.16 mmol) and sodium azide (205 mg, 3.16 mmol), the mixture was heated to reflux for 18 h. The solvent was evaporated in vacuo to provide an off-white solid, which was slurried in a mixture of dichloromethane/$H_2O$=1/1 (10 mL) and filtered to give 2-azido-N-(2-(2,6-dioxopiperidin-3-yl)-1-oxoisoindolin-4-yl)acetamide (XS01-104) (668 mg, 81%) as a white solid. HPLC 94.5% ($t_R$=8.00 min, $CH_3OH$ in 0.1% TFA water 5%~95% in 20 min); ¹H NMR (500 MHz, DMSO-d₆) δ 11.02 (s, 1H), 10.07 (s, 1H), 7.84 (dd, J=7.5, 1.4 Hz, 1H), 7.66-7.33 (m, 2H), 5.16 (dd, J=13.3, 5.1 Hz, 1H), 4.52-4.24 (m, 2H), 4.12 (s, 2H), 2.92 (m, 1H), 2.62 (m, 1H), 2.35 (m, 1H), 2.04 (m, 1H); HPLC-MS (ESI+) m/z 343.0 (M+H)⁺. (See US2003/96841.)

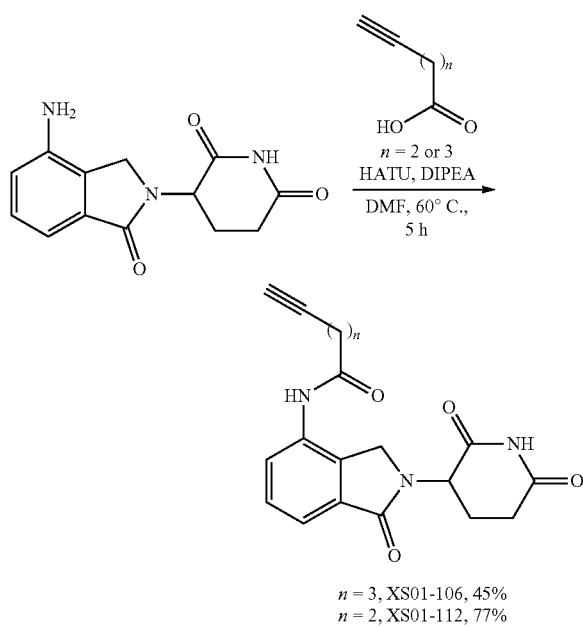

n = 3, XS01-106, 45%
n = 2, XS01-112, 77%

N-(2-(2,6-Dioxopiperidin-3-yl)-1-oxoisoindolin-4-yl)hex-5-ynamide (XS01-106): 3-(4-Amino-1-oxoisoindolin-2-yl)piperidine-2,6-dione (50 mg, 0.19 mmol), hex-5-ynoic acid (24 mg, 0.21 mmol) and DIPEA (75 mg, 0.58 mmol) were dissolved in DMF (1 mL) and stirred for 5 minutes. HATU (73 mg, 0.19 mmol) was added to the solution, and the mixture heated at 60° C. for 5 h. The solvent was removed by rotary evaporation under vacuum to give the crude. Purification of the crude material by silica gel chromatography (0-10% MeOH in dichloromethane) afforded N-(2-(2,6-dioxopiperidin-3-yl)-1-oxoisoindolin-4-yl)hex-5-ynamide (XS01-106) (31 mg, 45%) as a white solid. HPLC 92.4% (t_R=9.02 min, CH₃OH in 0.1% TFA water 5%~95% in 20 min); ¹H NMR (500 MHz, DMSO-d₆) δ 11.01 (s, 1H), 9.82 (s, 1H), 7.82 (dd, J=7.2, 1.8 Hz, 1H), 7.59-7.36 (m, 2H), 5.15 (dd, J=13.4, 5.1 Hz, 1H), 4.62-4.23 (m, 2H), 2.92 (m, 1H), 2.83 (t, J=2.6 Hz, 1H), 2.67-2.54 (m, 1H), 2.47 (d, J=7.5 Hz, 2H), 2.42-2.30 (m, 1H), 2.25 (m, 2H), 2.03 (m, 1H), 1.79 (m, 2H); HPLC-MS (ESI+) m/z 354.2 (M+H)⁺.

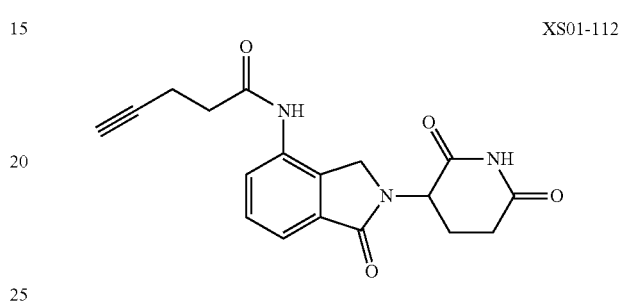

XS01-112

N-(2-(2,6-dioxopiperidin-3-yl)-1-oxoisoindolin-4-yl)pent-4-ynamide (XS01-112): This was prepared in the same way as XS01-106 from 3-(4-amino-1-oxoisoindolin-2-yl)piperidine-2,6-dione (200 mg, 0.77 mmol) and pent-4-ynoic acid (83 mg, 0.85 mmol) to provide N-(2-(2,6-dioxopiperidin-3-yl)-1-oxoisoindolin-4-yl)pent-4-ynamide (XS01-112) (200 mg, 77%) as a white solid. HPLC 94.5% (t_R=8.25 min, CH₃OH in 0.1% TFA water 5%~95% in 20 min); ¹H NMR (500 MHz, DMSO-d₆) δ 11.02 (s, 1H), 9.88 (s, 1H), 7.82 (dd, J=7.3, 1.7 Hz, 1H), 7.63-7.35 (m, 2H), 5.26-4.98 (m, 1H), 4.56-4.19 (m, 2H), 2.93 (m, 1H), 2.83 (t, J=2.6 Hz, 1H), 2.64 (dd, J=3.8, 1.9 Hz, 1H), 2.58 (dd, J=8.4, 6.9 Hz, 2H), 2.49-2.43 (m, 2H), 2.41-2.27 (m, 1H), 2.04 (m, 1H); HPLC-MS (ESI+) m/z 338.2 (M-H)⁻.

Synthetic scheme 44

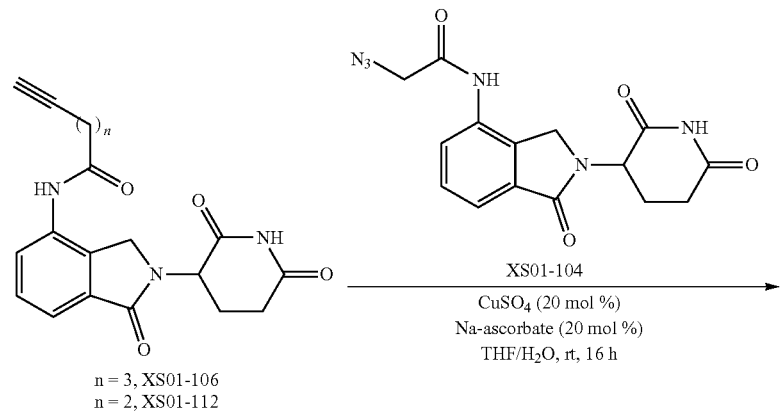

n = 3, XS01-106
n = 2, XS01-112

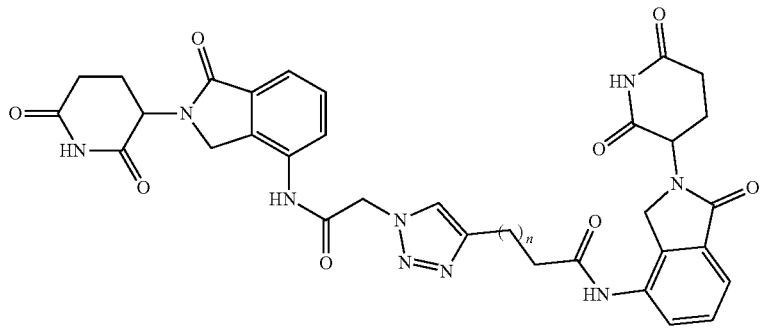

n = 2, XS01-109, 45%
n = 1, XS01-113, 31%

N-(2-(2,6-Dioxopiperidin-3-yl)-1-oxoisoindolin-4-yl)-4-(1-(2-((2-(2,6-dioxopiperidin-3-yl)-1-oxoisoindolin-4-yl)amino)-2-oxoethyl)-1H-1,2,3-triazol-4-yl)butanamide (XS01-109): 2-Azido-N-(2-(2,6-dioxopiperidin-3-yl)-1-oxoisoindolin-4-yl)acetamide (XS01-104) (29 mg, 0.085 mmol), copper(II) sulfate (2.7 mg, 0.017 mmol), sodium ascorbate (3.4 mg, 0.017 mmol) and N-(2-(2,6-dioxopiperidin-3-yl)-1-oxoisoindolin-4-yl)hex-5-ynamide (XS01-106) (30 mg, 0.085 mmol) were added in a microwave tube, THF (1 mL) and 3-4 drops of H$_2$O were added afterwards, the mixture was purged with Argon for 5 min, the tube was sealed, and the reaction mixture was stirred for 16 h at room temperature. The solvent was removed by rotary evaporation under vacuum to provide the crude product. Purification of the crude material by silica gel chromatography (0-10% MeOH in dichloromethane) afforded N-(2-(2,6-dioxopiperidin-3-yl)-1-oxoisoindolin-4-yl)-4-(1-(2-((2-(2,6-dioxopiperidin-3-yl)-1-oxoisoindolin-4-yl)amino)-2-oxoethyl)-1H-1,2,3-triazol-4-yl)butanamide (XS01-109) (30 mg, 52%) as a white solid. HPLC 100.0% ($t_R$=12.09 min, CH$_3$OH in 0.1% TFA water 5%~95% in 20 min); Mp: 231° C. (dec); $^1$H NMR (500 MHz, DMSO-d$_6$) δ 11.02 (d, J=13.9 Hz, 2H), 10.31 (s, 1H), 9.82 (s, 1H), 7.94 (s, 1H), 7.85 (m, 2H), 7.67-7.37 (m, 4H), 5.36 (s, 2H), 5.16 (m, 2H), 4.58-4.25 (m, 4H), 2.92 (m, 2H), 2.73 (t, J=7.6 Hz, 2H), 2.67-2.55 (m, 2H), 2.46 (t, J=7.5 Hz, 2H), 2.41-2.26 (m, 2H), 2.10-1.99 (m, 2H), 1.96 (m, 2H); HPLC-MS (ESI+) m/z 696.3 (M+H)$^+$; HRMS (ESI+) m/z calculated for C$_{34}$H$_{34}$N$_9$O$_8$ (M+H)$^+$ 696.2525, found 696.2509.

N-(2-(2,6-dioxopiperidin-3-yl)-1-oxoisoindolin-4-yl)-3-(1-(2-((2-(2,6-dioxopiperidin-3-yl)-1-oxoisoindolin-4-yl)amino)-2-oxoethyl)-1H-1,2,3-triazol-4-yl)propanamide (XS01-113): This was prepared in the same way as XS01-109 from the azide XS01-104 (66 mg, 0.195 mmol) and N-(2-(2,6-dioxopiperidin-3-yl)-1-oxoisoindolin-4-yl)pent-4-ynamide (XS01-112) (60 mg, 0.177 mmol) to give N-(2-(2,6-dioxopiperidin-3-yl)-1-oxoisoindolin-4-yl)-3-(1-(2-((2-(2,6-dioxopiperidin-3-yl)-1-oxoisoindolin-4-yl)amino)-2-oxoethyl)-1H-1,2,3-triazol-4-yl)propanamide (XS01-113) (37 mg, 31%) as a white solid. HPLC 100.0% ($t_R$=11.72 min, CH$_3$OH in 0.1% TFA water 5%~95% in 20 min); Mp: 221° C. (dec); $^1$H NMR (500 MHz, DMSO-d$_6$) δ 11.02 (d, J=11.7 Hz, 2H), 10.30 (s, 1H), 9.89 (s, 1H), 7.92 (s, 1H), 7.87-7.78 (m, 2H), 7.62-7.41 (m, 4H), 5.35 (s, 2H), 5.22-5.07 (m, 2H), 4.54-4.20 (m, 4H), 3.01 (t, J=7.5 Hz, 2H), 2.91 (m, 2H), 2.77 (t, J=7.5 Hz, 2H), 2.68-2.54 (m, 2H), 2.41-2.26 (m, 2H), 2.14-1.96 (m, 2H); HPLC-MS (ESI+) m/z 682.1 (M+H)$^+$; HRMS (ESI+) m/z calculated for C$_{33}$H$_{32}$N$_9$O$_8$ (M+H)$^+$ 682.2368, found 682.2352.

Synthetic scheme 45

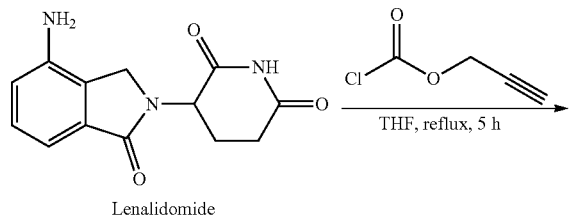

Lenalidomide

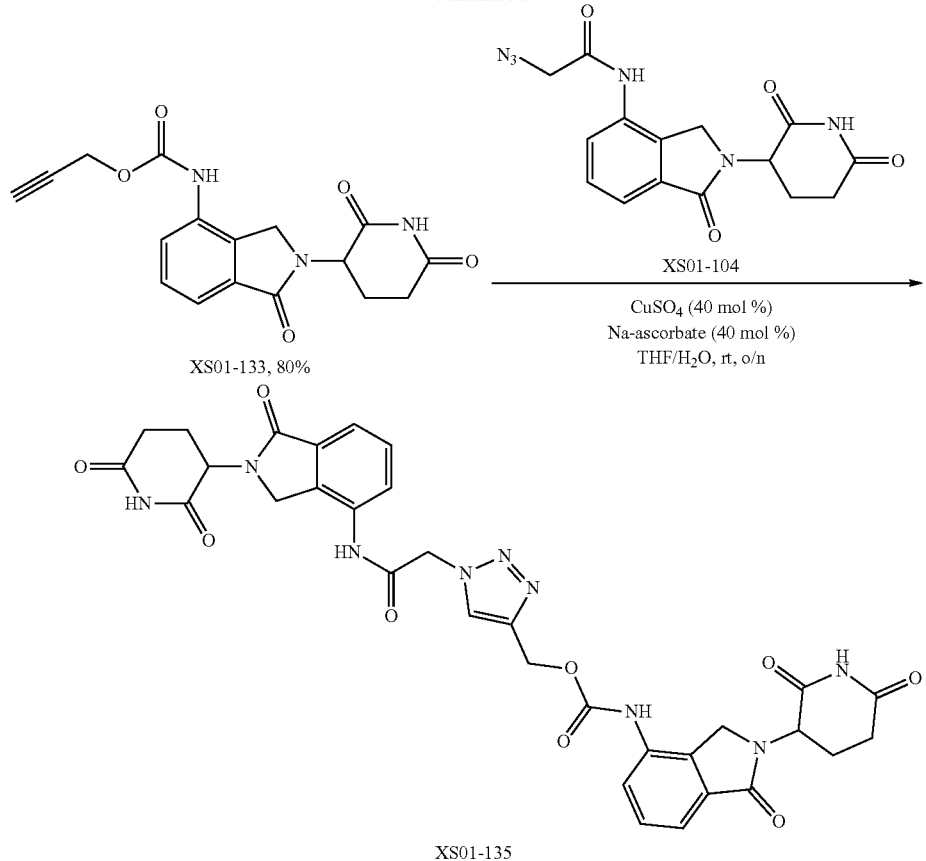

Prop-2-yn-1-yl (2-(2,6-dioxopiperidin-3-yl)-1-oxoisoindolin-4-yl)carbamate (XS01-133): 3-(4-Amino-1-oxoisoindolin-2-yl)piperidine-2,6-dione (200 mg, 0.77 mmol) was suspended in THF (15 mL), propargyl chloroformate (183 mg, 1.54 mmol) added to solution, and the reaction mixture refluxed for 5 h. The solvent was evaporated in vacuo to provide an off-white solid, which was slurried with diethyl ether to give prop-2-yn-1-yl (2-(2,6-dioxopiperidin-3-yl)-1-oxoisoindolin-4-yl)carbamate (XS01-133) (210 mg, 80%) as a white solid. HPLC 93.4% ($t_R$=9.68 min, $CH_3OH$ in 0.1% TFA water 5%~95% in 20 min); $^1H$ NMR (500 MHz, DMSO-$d_6$) δ 11.00 (s, 1H), 9.76 (s, 1H), 7.76 (m, 1H), 7.57-7.35 (m, 2H), 5.13 (dd, J=13.3, 5.1 Hz, 1H), 4.80 (d, J=2.5 Hz, 2H), 4.61-4.20 (m, 2H), 3.59 (s, 1H), 2.92 (m, 1H), 2.66-2.55 (m, 1H), 2.35 (m, 1H), 2.03 (m, 1H); HPLC-MS (ESI+) m/z 342.2 (M+H)+.

XS01-135

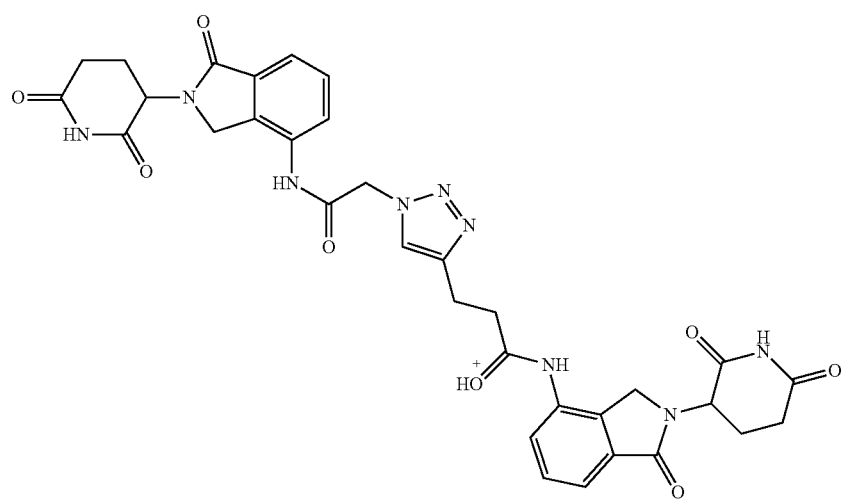

(1-(2-((2-(2,6-Dioxopiperidin-3-yl)-1-oxoisoindolin-4-yl)amino)-2-oxoethyl)-1H-1,2,3-triazol-4-yl)methyl (2-(2,6-dioxopiperidin-3-yl)-1-oxoisoindolin-4-yl)carbamate (XS01-135): This was prepared in the same way as XS01-109 from the azide (XS01-104) (40 mg, 0.117 mmol) and alkyne XS01-133 to give (1-(2-((2-(2,6-dioxopiperidin-3-yl)-1-oxoisoindolin-4-yl)amino)-2-oxoethyl)-1H-1,2,3-triazol-4-yl)methyl (2-(2,6-dioxopiperidin-3-yl)-1-oxoisoindolin-4-yl)carbamate (XS01-135) (35 mg, 43%) as a white solid. HPLC 100.0% ($t_R$=11.72 min, CH$_3$OH in 0.1% TFA water 5%~95% in 20 min); Mp: 220° C. (dec); $^1$H NMR (500 MHz, DMSO-d$_6$) δ 11.05 (s, 1H), 11.01 (s, 1H), 10.37 (s, 1H), 9.73 (s, 1H), 8.26 (s, 1H), 7.86 (dd, J=7.7, 1.2 Hz, 1H), 7.79 (d, J=7.1 Hz, 1H), 7.61-7.44 (m, 4H), 5.43 (s, 2H), 5.26 (s, 2H), 5.15 (m, 2H), 4.56-4.23 (m, 4H), 2.92 (m, 2H), 2.69-2.55 (m, 2H), 2.34 (m, 2H), 2.05 (m, 2H); HRMS (ESI+) m/z calculated for C$_{32}$H$_{30}$N$_9$O$_9$ (M+H)$^+$ 684.2161, found 684.2141.

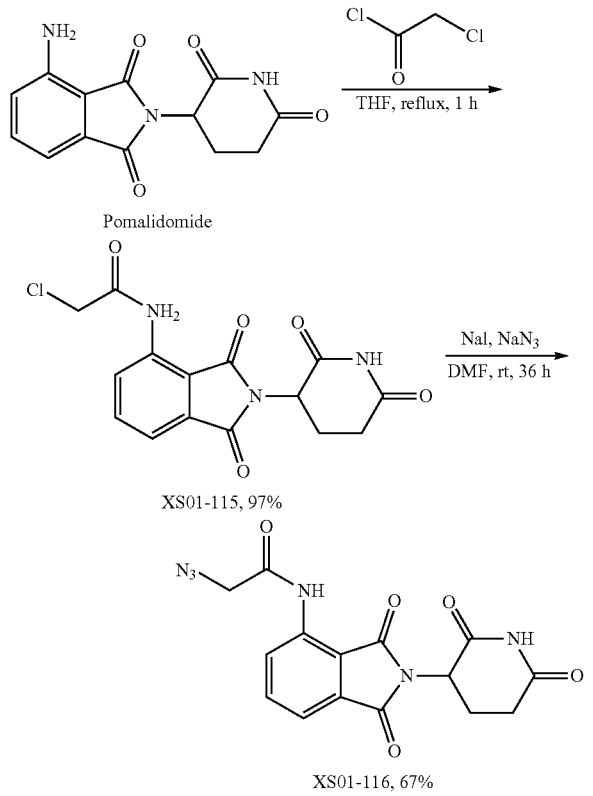

Synthetic scheme 46

Pomalidomide

XS01-115, 97%

XS01-116, 67%

2-Chloro-N-(2-(2,6-dioxopiperidin-3-yl)-1,3-dioxoisoindolin-4-yl)acetamide (XS01-115): To a solution of 4-amino-2-(2,6-dioxopiperidin-3-yl)isoindoline-1,3-dione (500 mg, 1.83 mmol) in THF (30 mL) was added 2-chloroacetyl chloride (413 mg, 3.66 mmol), and the mixture heated to reflux for 1 h. The solvent was evaporated in vacuo and the resulting solid slurried in diethyl ether (20 mL) and filtered to give 2-chloro-N-(2-(2,6-dioxopiperidin-3-yl)-1,3-dioxoisoindolin-4-yl)acetamide (XS01-115) (620 mg, 97%) as a white solid. HPLC 97.7% ($t_R$=9.90 min, CH$_3$OH in 0.1% TFA water 5%~95% in 20 min); $^1$H NMR (500 MHz, DMSO-d$_6$) δ 11.15 (s, 1H), 10.31 (s, 1H), 8.55 (dd, J=8.4, 0.7 Hz, 1H), 7.89 (dd, J=8.5, 7.3 Hz, 1H), 7.69 (dd, J=7.4, 0.7 Hz, 1H), 5.17 (dd, J=12.9, 5.4 Hz, 1H), 4.54 (s, 2H), 2.90 (m, 1H), 2.68-2.59 (m, 1H), 2.59-2.52 (m, 1H), 2.08 (m, 1H); HPLC-MS (ESI+) m/z 350.1 (M+H)$^+$. (See US2003/96841.)

2-Azido-N-(2-(2,6-dioxopiperidin-3-yl)-1,3-dioxoisoindolin-4-yl)acetamide (XS01-116): To a stirred suspension of 2-chloro-N-(2-(2,6-dioxopiperidin-3-yl)-1,3-dioxoisoindolin-4-yl)acetamide (XS01-115) (200 mg, 0.73 mmol) in acetone (50 mL) was added sodium iodide (257 mg, 1.72 mmol) and sodium azide (223 mg, 3.43 mmol), the mixture was heated to reflux for 18 h. The solvent was evaporated in vacuo to provide an off-white solid, which was slurried in a mixture of dichloromethane/H$_2$O=1/1 (10 mL) to give 2-azido-N-(2-(2,6-dioxopiperidin-3-yl)-1,3-dioxoisoindolin-4-yl)acetamide (XS01-116) (410 mg, 67%) as a white solid. HPLC 84.8% ($t_R$=9.76 min, CH$_3$OH in 0.1% TFA water 5%~95% in 20 min); $^1$H NMR (500 MHz, DMSO-d$_6$) δ 11.15 (s, 1H), 10.13 (s, 1H), 8.52 (dd, J=8.4, 0.8 Hz, 1H), 7.88 (dd, J=8.4, 7.3 Hz, 1H), 7.68 (dd, J=7.3, 0.8 Hz, 1H), 5.17 (dd, J=12.9, 5.4 Hz, 1H), 4.34 (s, 2H), 2.90 (m, 1H), 2.62 (m, 1H), 2.54 (dd, J=13.4, 4.4 Hz, 1H), 2.08 (m, 1H); HPLC-MS (ESI+) m/z 357.1 (M+H)$^+$. (See US2003/96841.)

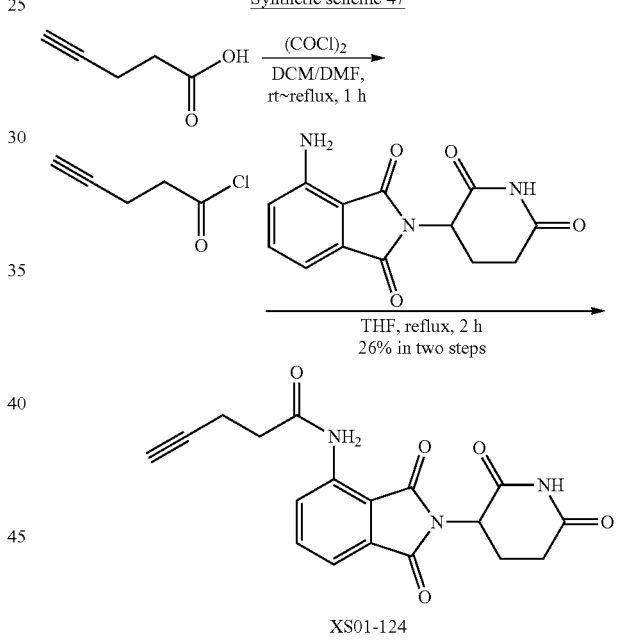

Synthetic scheme 47

XS01-124

N-(2-(2,6-Dioxopiperidin-3-yl)-1,3-dioxoisoindolin-4-yl)pent-4-ynamide (XS01-124): Oxalyl chloride (1.32 g, 10.39 mmol) was added to pent-4-ynoic acid (680 mg, 6.93 mmol) in dichloromethane (5 mL). Dimethyl formamide (1-2 drops) was added to the solution. The reaction mixture was refluxed for 1 h. The solvent was removed under reduced pressure to give the crude acid chloride. Tetrahydrofuran (10 mL) was added to the residue and 4-amino-2-(2,6-dioxopiperidin-3-yl)isoindoline-1,3-dione (180 mg, 0.66 mmol) was added and the reaction mixture refluxed for 2 h. The solvent was removed by rotary evaporation under vacuum to give the crude product. Purification of the crude material by silica gel chromatography (0-10% MeOH in dichloromethane) afforded N-(2-(2,6-dioxopiperidin-3-yl)-1,3-dioxoisoindolin-4-yl)pent-4-ynamide (XS01-124) (60 mg, 26%) as a white solid. HPLC 85.7% ($t_R$=9.81 min, CH$_3$OH in 0.1% TFA water 5%~95% in 20 min); $^1$H NMR (500 MHz, DMSO-$d_6$) δ 11.11 (d, J=33.8 Hz, 1H), 9.79 (s, 1H), 8.46 (dd, J=8.4, 0.8 Hz, 1H), 7.85 (dd, J=8.4, 7.3 Hz, 1H), 7.64 (dd, J=7.3, 0.8 Hz, 1H), 5.21-5.06 (m, 1H), 3.00-2.84 (m, 1H), 2.82 (t, J=2.6 Hz, 1H), 2.70 (t, J=7.2 Hz, 1H), 2.66-2.53 (m, 1H), 2.13-1.97 (m, 1H); HPLC-MS (ESI+) m/z 376.2 (M+Na)+.

Synthetic scheme 48

Prop-2-yn-1-yl (2-(2,6-dioxopiperidin-3-yl)-1,3-dioxoisoindolin-4-yl)carbamate (XS01-134): This was prepared in the same way as XS01-133 from 4-amino-2-(2,6-dioxopiperidin-3-yl)isoindoline-1,3-dione (300 mg, 1.10 mmol) and propargyl chloroformate (325 mg, 2.74 mmol) to give prop-2-yn-1-yl (2-(2,6-dioxopiperidin-3-yl)-1,3-dioxoisoindolin-4-yl)carbamate (XS01-134) (360 mg, 92%) as a white solid. HPLC 83.3% ($t_R$=9.01 min, CH$_3$OH in 0.1% TFA water 5%~95% in 20 min); $^1$H NMR (500 MHz, DMSO-$d_6$) δ 11.15 (s, 1H), 9.27 (s, 1H), 8.22 (d, J=8.3 Hz, 1H), 7.87 (dd, J=8.4, 7.3 Hz, 1H), 7.63 (dd, J=7.3, 0.7 Hz, 1H), 5.15 (dd, J=12.9, 5.4 Hz, 1H), 4.85 (d, J=2.5 Hz, 2H), 3.64 (t, J=2.4 Hz, 1H), 2.90 (m, 1H), 2.68-2.57 (m, 2H), 2.13-1.99 (m, 1H); HPLC-MS (ESI+) m/z 356.2 (M+Na)+.

Synthetic scheme 49

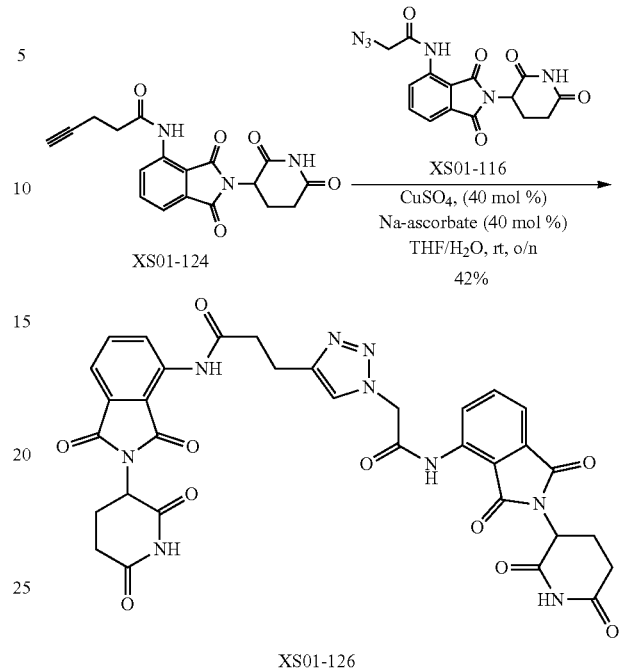

N-(2-(2,6-Dioxopiperidin-3-yl)-1,3-dioxoisoindolin-4-yl)-3-(1-(2-((2-(2,6-dioxopiperidin-3-yl)-1,3-dioxoisoindolin-4-yl)amino)-2-oxoethyl)-1H-1,2,3-triazol-4-yl)propanamide (XS01-126): This was prepared in the same way as XS01-109 from azide XS01-116 (28 mg, 0.079 mmol), copper(II) sulfate (5.0 mg, 0.032 mmol), sodium ascorbate (6.3 mg, 0.032 mmol) and alkyne XS01-124 to give N-(2-(2,6-dioxopiperidin-3-yl)-1,3-dioxoisoindolin-4-yl)-3-(1-(2-((2-(2,6-dioxopiperidin-3-yl)-1,3-dioxoisoindolin-4-yl)amino)-2-oxoethyl)-1H-1,2,3-triazol-4-yl)propanamide (XS01-126) (24 mg, 42%) as a white solid. HPLC 99.8% ($t_R$=13.35 min, CH$_3$OH in 0.1% TFA water 5%~95% in 20 min); Mp: 209° C. (dec); $^1$H NMR (500 MHz, DMSO-$d_6$) δ 11.15 (s, 2H), 10.10 (s, 1H), 9.81 (s, 1H), 8.47 (dd, J=8.5, 0.8 Hz, 1H), 8.38 (d, J=8.3 Hz, 1H), 7.97 (s, 1H), 7.84 (m, 2H), 7.68 (dd, J=7.3, 0.8 Hz, 1H), 7.62 (dd, J=7.3, 0.8 Hz, 1H), 5.50 (s, 2H), 5.15 (m, 2H), 3.03 (t, J=7.4 Hz, 2H), 2.94-2.79 (m, 4H), 2.67-2.53 (m, 4H), 2.07 (dd, J=9.2, 4.3 Hz, 2H); HRMS (ESI+) m/z calculated for C$_{33}$H$_{27}$N$_9$NaO$_{10}$ (M+Na)+ 732.1773, found 732.1761.

Synthetic scheme 50

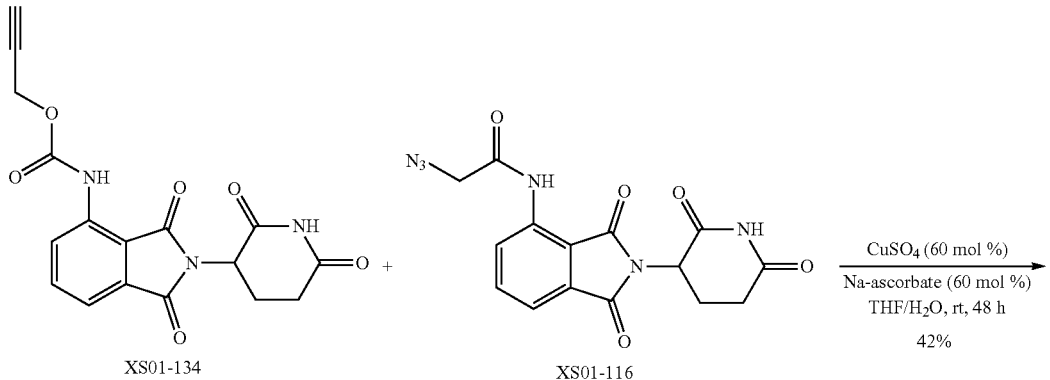

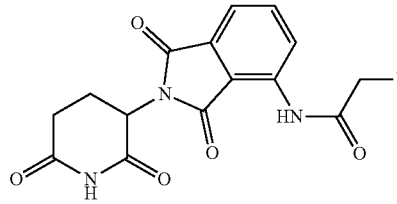

XS01-137

(1-(2-((2-(2,6-Dioxopiperidin-3-yl)-1,3-dioxoisoindolin-4-yl)amino)-2-oxoethyl)-1H-1,2,3-triazol-4-yl)methyl (2-(2,6-dioxopiperidin-3-yl)-1,3-dioxoisoindolin-4-yl)carbamate (XS01-137): This was prepared in the same way as XS01-109 from alkyne XS01-134 (30 mg, 0.084 mmol), copper(II) sulfate (8.1 mg, 0.051 mmol), sodium ascorbate (10.0 mg, 0.051 mmol) and azide XS01-116 to give (1-(2-((2-(2,6-dioxopiperidin-3-yl)-1,3-dioxoisoindolin-4-yl)amino)-2-oxoethyl)-1H-1,2,3-triazol-4-yl)methyl (2-(2,6-dioxopiperidin-3-yl)-1,3-dioxoisoindolin-4-yl)carbamate (XS01-137) (25 mg, 42%) as a white solid. HPLC 100.0% ($t_R$=6.84 min, CH$_3$OH in 0.1% TFA water 5%~95% in 20 min); Mp: 230° C. (dec); $^1$H NMR (500 MHz, DMSO-d$_6$) δ 11.17 (s, 1H), 11.15 (s, 1H), 10.25 (s, 1H), 9.21 (s, 1H), 8.37 (d, J=8.3 Hz, 1H), 8.31-8.21 (m, 2H), 7.86 (m, 2H), 7.69 (d, J=7.2 Hz, 1H), 7.62 (d, J=7.3 Hz, 1H), 5.59 (s, 2H), 5.33 (s, 2H), 5.22-5.07 (m, 2H), 2.98-2.80 (m, 2H), 2.69-2.53 (m, 4H), 2.16-1.95 (m, 2H); HRMS (ESI+) m/z calculated for C$_{32}$H$_{25}$N$_9$NaO$_{11}$ (M+Na)$^+$ 734.1566, found 734.1571.

Synthetic scheme 51

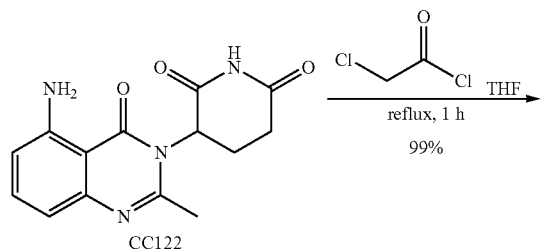

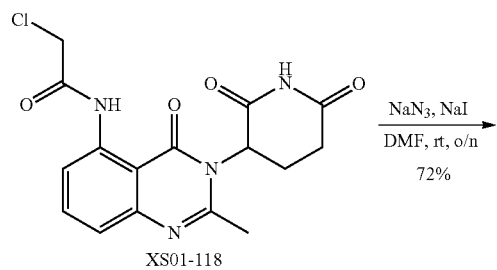

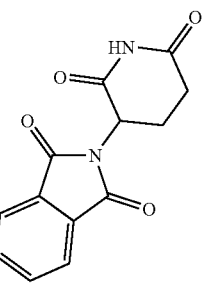

XS01-119

2-Chloro-N-(3-(2,6-dioxopiperidin-3-yl)-2-methyl-4-oxo-3,4-dihydroquinazolin-5-yl)acetamide (XS01-118): To a solution of 3-(5-amino-2-methyl-4-oxoquinazolin-3(4H)-yl)piperidine-2,6-dione (100 mg, 0.35 mmol) in THF (5 mL) was added 2-chloroacetyl chloride (79 mg, 0.70 mmol) and the mixture heated to reflux for 1 h. The solvent was evaporated in vacuo and the resulting solid slurried in diethyl ether (10 mL) and filtered to give 2-chloro-N-(3-(2,6-dioxopiperidin-3-yl)-2-methyl-4-oxo-3,4-dihydroquinazolin-5-yl)acetamide (XS01-118) (125 mg, 99%) as a white solid. HPLC 90.7% ($t_R$=9.86 min, CH$_3$OH in 0.1% TFA water 5%~95% in 20 min); $^1$H NMR (500 MHz, DMSO-d$_6$) δ 12.32 (s, 1H), 11.11 (s, 1H), 8.57 (d, J=8.2 Hz, 1H), 7.82 (t, J=8.2 Hz, 1H), 7.37 (d, J=8.1 Hz, 1H), 5.34 (dd, J=11.8, 5.6 Hz, 1H), 4.48 (d, J=1.8 Hz, 2H), 2.96-2.77 (m, 1H), 2.76-2.56 (m, 5H), 2.28-2.14 (m, 1H); HPLC-MS (ESI+) m/z 363.1 (M+H)$^+$. Ref: CELGENE CORPORATION WO2008/39489, 2008, A2

2-Azido-N-(3-(2,6-dioxopiperidin-3-yl)-2-methyl-4-oxo-3,4-dihydroquinazolin-5-yl)acetamide (XS01-119): To a stirred suspension of 2-chloro-N-(3-(2,6-dioxopiperidin-3-yl)-2-methyl-4-oxo-3,4-dihydroquinazolin-5-yl)acetamide (XS01-118) (120 mg, 0.33 mmol) in acetone (20 mL) was added sodium iodide (50 mg, 0.33 mmol) and sodium azide (43 mg, 0.66 mmol), and the mixture heated to reflux for 18 h. The solvent was evaporated in vacuo to provide an off-white solid, which was slurried in a mixture of dichloromethane/H$_2$O=1/1 (10 mL) and filtered to give 2-azido-N-(3-(2,6-dioxopiperidin-3-yl)-2-methyl-4-oxo-3,4-dihydroquinazolin-5-yl)acetamide (XS01-119) (88 mg, 72%) as a white solid. HPLC 93.3% ($t_R$=9.76 min, CH$_3$OH in 0.1% TFA water 5%~95% in 20 min); $^1$H NMR (500 MHz, DMSO-d$_6$) δ 12.07 (s, 1H), 11.08 (s, 1H), 8.55 (dd, J=8.3, 1.1 Hz, 1H), 7.81 (t, J=8.2 Hz, 1H), 7.35 (dd, J=8.2, 1.1 Hz, 1H), 5.34 (dd, J=11.5, 5.7 Hz, 1H), 4.53-4.06 (m, 2H), 2.87 (m, 1H), 2.76-2.57 (m, 5H), 2.21 (m, 1H); HPLC-MS (ESI+) m/z 392.2 (M+Na)$^+$.

Synthetic scheme 52

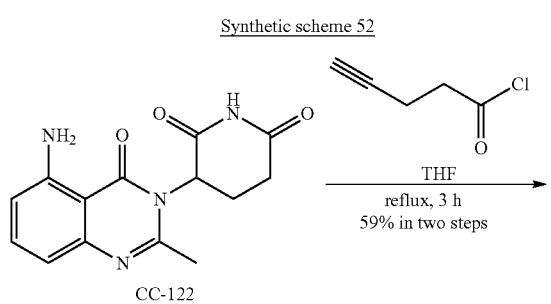

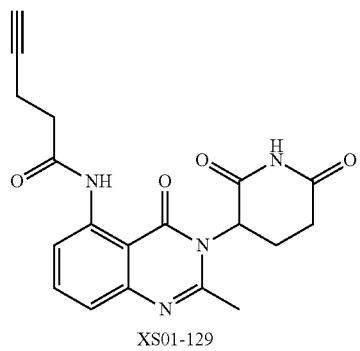

N-(3-(2,6-dioxopiperidin-3-yl)-2-methyl-4-oxo-3,4-dihydroquinazolin-5-yl)pent-4-ynamide (XS01-129): This was prepared in the same way as XS01-124 from pent-4-ynoic acid (600 mg, 6.12 mmol) and 3-(5-amino-2-methyl-4-oxoquinazolin-3(4H)-yl)piperidine-2,6-dione (CC-122) (80 mg, 0.28 mmol) to afford N-(3-(2,6-dioxopiperidin-3-yl)-2-methyl-4-oxo-3,4-dihydroquinazolin-5-yl)pent-4-ynamide (XS01-129) (60 mg, 59%) as a white solid. HPLC 91.6% ($t_R$=7.29 min, CH$_3$OH in 0.1% TFA water 5%~95% in 20 min); $^1$H NMR (500 MHz, DMSO-d$_6$) δ 11.78 (s, 1H), 11.07 (d, J=7.1 Hz, 1H), 8.56 (dd, J=8.3, 1.0 Hz, 1H), 7.79 (t, J=8.2 Hz, 1H), 7.30 (dd, J=8.1, 1.1 Hz, 1H), 5.33 (dd, J=11.7, 5.7 Hz, 1H), 2.87 (m, 1H), 2.78 (t, J=2.6 Hz, 1H), 2.73-2.55 (m, 8H), 2.42-2.34 (m, 1H), 2.21 (m, 1H); HPLC-MS (ESI+) m/z 367.2 (M+Na)$^+$.

Synthetic scheme 53

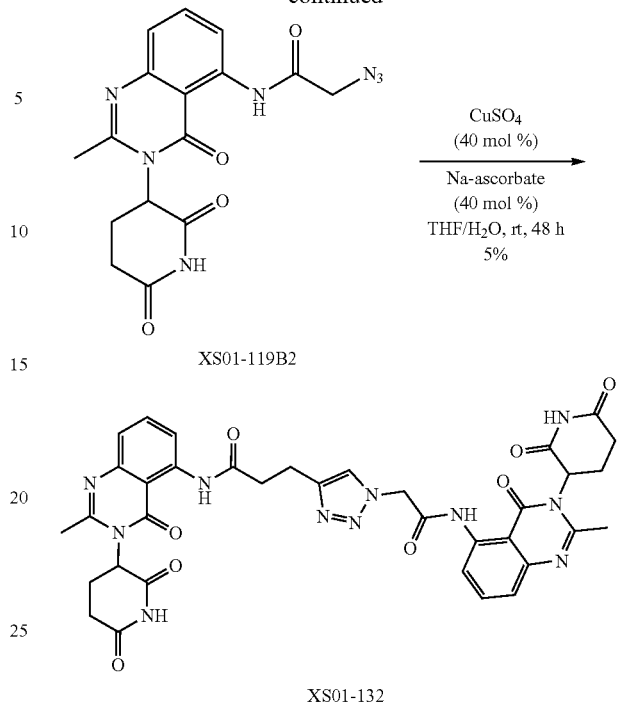

N-(3-(2,6-dioxopiperidin-3-yl)-2-methyl-4-oxo-3,4-dihydroquinazolin-5-yl)-3-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)propanamide (XS01-132): This was prepared in the same way as XS01-109 from alkyne (XS01-129) (46 mg, 0.126 mmol), copper(II) sulfate (14 mg, 0.088 mmol), sodium ascorbate (20.0 mg, 0.10 mmol) and the azide XS01-119 (46 mg, 0.126 mmol) to provide N-(3-(2,6-dioxopiperidin-3-yl)-2-methyl-4-oxo-3,4-dihydroquinazolin-5-yl)-3-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)propanamide (XS01-132) (5 mg, 5%) as a white solid. HPLC 94.7% ($t_R$=13.15 min, CH$_3$OH in 0.1% TFA water 5%~95% in 20 min); Mp: 241° C. (dec); $^1$H NMR (500 MHz, DMSO-d$_6$) δ 11.85-11.75 (m, 2H), 11.09 (d, J=9.7 Hz, 2H), 8.56 (dd, J=8.3, 6.8 Hz, 1H), 8.45 (d, J=8.4 Hz, 1H), 7.94 (d, J=2.2 Hz, 1H), 7.78 (m, 2H), 7.39-7.21 (m, 2H), 5.54-5.37 (m, 2H), 5.33 (m, 2H), 3.00 (t, J=7.3 Hz, 2H), 2.92-2.75 (m, 4H), 2.65 (m, 10H), 2.19 (d, J=12.1 Hz, 2H); HRMS (ESI+) m/z calculated for C$_{35}$H$_{33}$N$_{11}$NaO$_8$ (M+Na)$^+$ 758.2406, found 758.2400.

Prop-2-yn-1-yl (3-(2,6-dioxopiperidin-3-yl)-2-methyl-4-oxo-3,4-dihydroquinazolin-5-yl)carbamate (XS01-139): 3-(5-Amino-2-methyl-4-oxoquinazolin-3(4H)-yl)piperidine-2,6-dione (CC-122)(110 mg, 0.38 mmol) was suspended in THF (5 mL), propargyl chloroformate (137 mg, 1.15 mmol) added to solution, and the reaction mixture refluxed for 48 h. Thin layer chromatography indicated that the reaction was incomplete and additional propargyl chloroformate (137 mg, 1.15 mmol) and DIPEA (50 mg, 0.38 mmol) were added to the solution, and the mixture refluxed overnight. The solvent was evaporated in vacuo to provide an off-white solid, which was slurried in diethyl ether (10 mL) and filtered to give prop-2-yn-1-yl (3-(2,6-dioxopiperidin-3-yl)-2-methyl-4-oxo-3,4-dihydroquinazolin-5-yl)carbamate (XS01-139) (120 mg, 85%) as a white solid. HPLC 90.5% ($t_R$=10.55 min, $CH_3OH$ in 0.1% TFA water 5%~95% in 20 min); $^1H$ NMR (500 MHz, DMSO-$d_6$) δ 11.45 (s, 1H), 11.08 (s, 1H), 8.19 (dd, J=8.3, 1.0 Hz, 1H), 7.81 (t, J=8.2 Hz, 1H), 7.28 (dd, J=8.1, 1.1 Hz, 1H), 5.32 (dd, J=11.8, 5.7 Hz, 1H), 4.91-4.62 (m, 2H), 3.22-3.06 (m, 1H), 2.85 (m, 1H), 2.65 (d, J=4.0 Hz, 5H), 2.21 (dd, J=12.0, 5.8 Hz, 1H); HPLC-MS (ESI+) m/z 369.2 (M+Na)$^+$.

Synthetic scheme 54

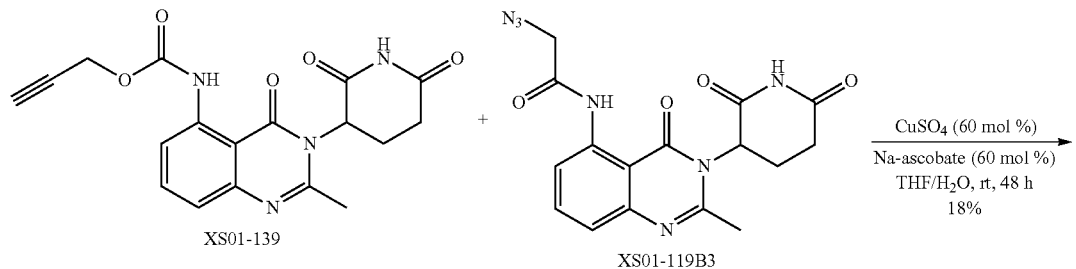

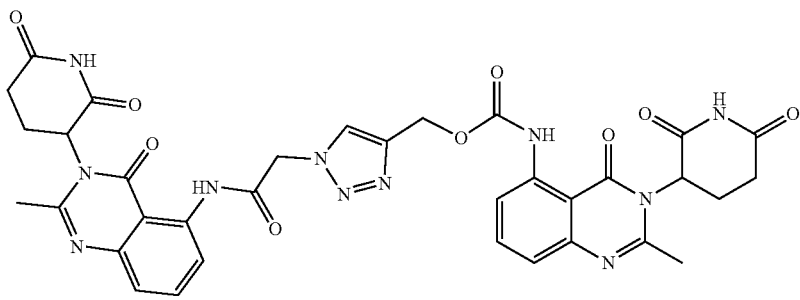

XS01-145

(1-(2-((3-(2,6-Dioxopiperidin-3-yl)-2-methyl-4-oxo-3,4-dihydroquinazolin-5-yl)amino)-2-oxoethyl)-1H-1,2,3-triazol-4-yl)methyl (3-(2,6-dioxopiperidin-3-yl)-2-methyl-4-oxo-3,4-dihydroquinazolin-5-yl)carbamate (XS01-145): This was prepared in the same way as XS01-109 from alkyne XS01-139 (35 mg, 0.095 mmol), copper(II) sulfate (9.0 mg, 0.057 mmol), sodium ascorbate (11.0 mg, 0.057 mmol) and azide XS01-119 (35 mg, 0.095 mmol) to afford (1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)methyl (3-(2,6-dioxopiperidin-3-yl)-2-methyl-4-oxo-3,4-dihydroquinazolin-5-yl)carbamate (XS01-145) (13 mg, 18%) as a white solid. HPLC 99.3% ($t_R$=14.73 min, $CH_3OH$ in 0.1% TFA water 5%~95% in 20 min); Mp: 223° C. (dec); $^1H$ NMR (500 MHz, DMSO-$d_6$) δ 11.87 (d, J=3.4 Hz, 1H), 11.40 (s, 1H), 11.12 (s, 1H), 11.05 (s, 1H), 8.48 (m, 1H), 8.28 (d, J=1.7 Hz, 1H), 8.26-8.21 (m, 1H), 7.94-7.68 (m, 2H), 7.35 (m, 1H), 7.31-7.20 (m, 1H), 5.62-5.44 (m, 2H), 5.42-5.12 (m, 4H), 2.83 (t, J=19.7 Hz, 2H), 2.70-2.56 (m, 10H), 2.14 (d, J=48.8 Hz, 2H); HRMS (ESI+) m/z calculated for $C_{34}H_{31}N_{11}NaO_9$ (M+Na)$^+$ 760.2198, found 760.2206.

Synthetic scheme 55

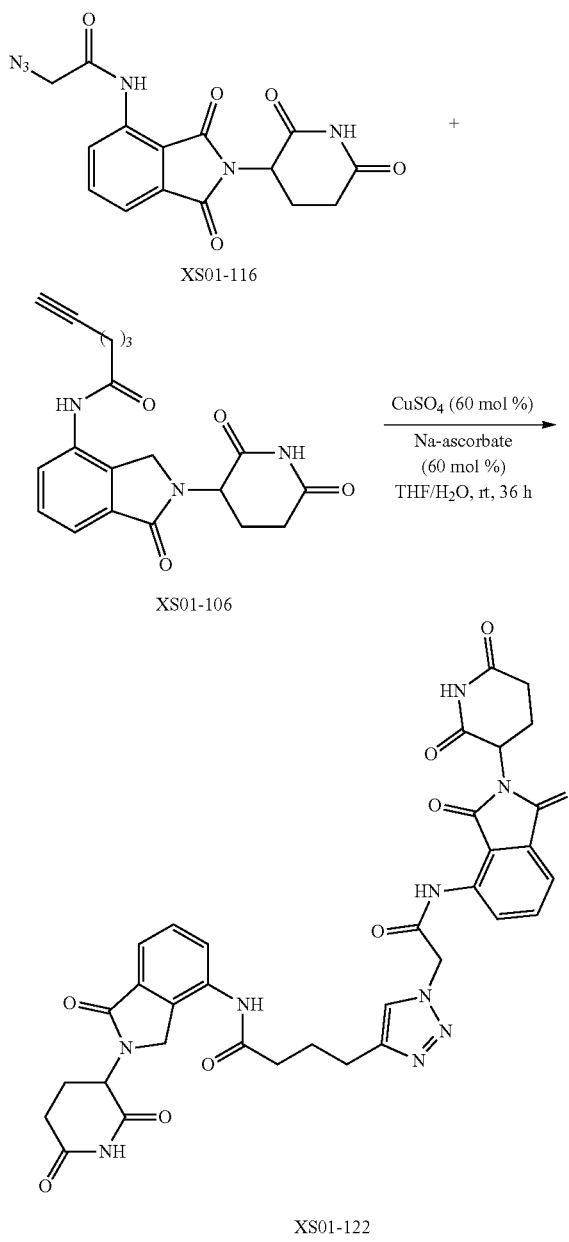

XS01-122

Synthetic scheme 56

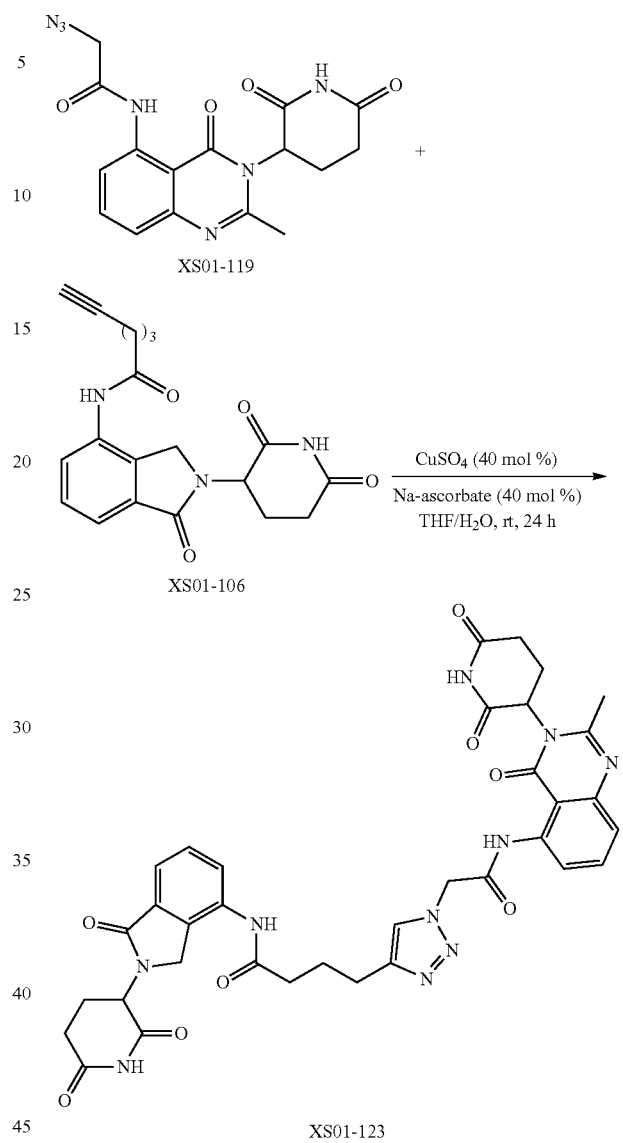

XS01-123

4-(1-(2-((2-(2,6-Dioxopiperidin-3-yl)-1,3-dioxoisoindolin-4-yl)amino)-2-oxoethyl)-1H-1,2,3-triazol-4-yl)-N-(2-(2,6-dioxopiperidin-3-yl)-1-oxoisoindolin-4-yl)butanamide (XS01-122): This was prepared in the same way as XS01-109 from azide XS01-116 (50 mg, 0.14 mmol), and alkyne XS01-106 (50 mg, 0.14 mmol) to orvide 4-(1-(2-((2-(2,6-dioxopiperidin-3-yl)-1,3-dioxoisoindolin-4-yl)amino)-2-oxoethyl)-1H-1,2,3-triazol-4-yl)-N-(2-(2,6-dioxopiperidin-3-yl)-1-oxoisoindolin-4-yl)butanamide (XS01-122) (31 mg, 31%) as a white solid. HPLC 99.4% ($t_R$=13.03 min, $CH_3OH$ in 0.1% TFA water 5%~95% in 20 min); Mp: 237° C. (dec); $^1$H NMR (500 MHz, DMSO-$d_6$) δ 11.15 (s, 1H), 11.00 (s, 1H), 10.11 (s, 1H), 9.81 (s, 1H), 8.41 (d, J=8.4 Hz, 1H), 7.97 (s, 1H), 7.91-7.76 (m, 2H), 7.73-7.63 (m, 1H), 7.60-7.44 (m, 2H), 5.50 (s, 2H), 5.15 (m, 2H), 4.48-4.27 (m, 2H), 3.00-2.79 (m, 2H), 2.74 (t, J=7.6 Hz, 2H), 2.67-2.55 (m, 2H), 2.45 (d, J=7.5 Hz, 2H), 2.40-2.30 (m, 2H), 2.16-1.86 (m, 4H); HRMS (ESI+) m/z calculated for $C_{34}H_{32}N_9NaO_9$ (M+H)$^+$ 710.2318, found 710.2316.

N-(2-(2,6-Dioxopiperidin-3-yl)-1-oxoisoindolin-4-yl)-4-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)butanamide (XS01-123): This was prepared in the same way as XS01-109 from alkyne XS01-106 (38 mg, 0.108 mmol), and azide XS01-119 (40 mg, 0.108 mmol) to provide N-(2-(2,6-dioxopiperidin-3-yl)-1-oxoisoindolin-4-yl)-4-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)butanamide (XS01-123) (30 mg, 38%) as a white solid. HPLC 99.5% ($t_R$=13.17 min, $CH_3OH$ in 0.1% TFA water 5%~95% in 20 min); Mp: 225° C. (dec); $^1$H NMR (500 MHz, DMSO-$d_6$) δ 11.82 (s, 1H), 11.08 (s, 1H), 11.00 (s, 1H), 9.82 (s, 1H), 8.49 (dd, J=8.3, 1.1 Hz, 1H), 7.95 (s, 1H), 7.88-7.74 (m, 2H), 7.55-7.43 (m, 2H), 7.34 (dd, J=8.1, 1.1 Hz, 1H), 5.57-5.37 (m, 2H), 5.33 (dd, J=11.7, 5.6 Hz, 1H), 5.14 (dd, J=13.3, 5.1 Hz, 1H), 4.51-4.28 (m, 2H), 2.98-2.80 (m, 2H), 2.75-2.57 (m, 8H), 2.46 (t, J=7.5 Hz, 2H), 2.42-2.32 (m, 1H), 2.24-2.14 (m, 1H), 2.07-1.89 (m, 3H); HPLC-MS (ESI+) m/z 723.2 (M+H)$^+$; HRMS (ESI+) m/z calculated for $C_{35}H_{35}N_{10}O_8$ (M+H)$^+$ 723.2634, found 723.2629.

Synthetic scheme 57

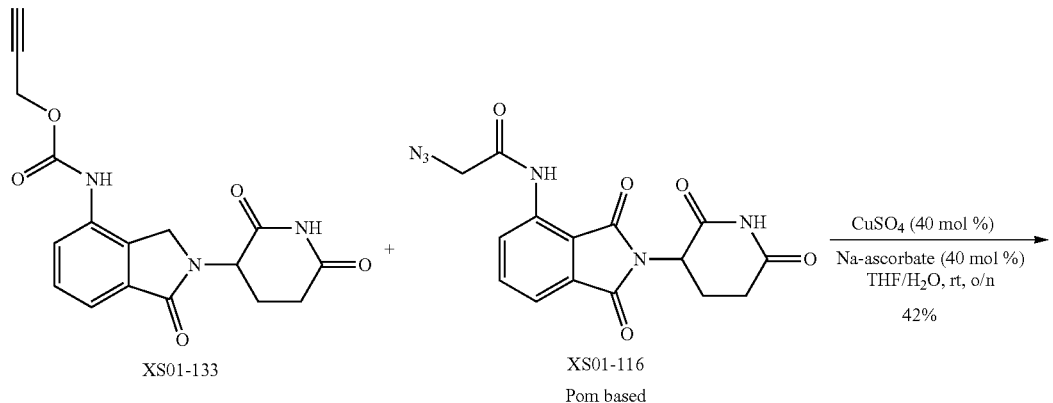

XS01-133 + XS01-116 (Pom based) → (CuSO₄ (40 mol %), Na-ascorbate (40 mol %), THF/H₂O, rt, o/n, 42%)

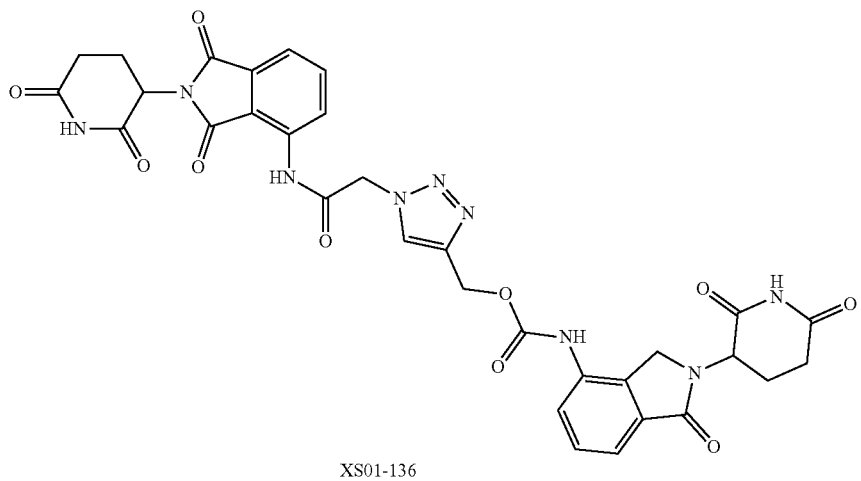

XS01-136

(1-(2-((2-(2,6-Dioxopiperidin-3-yl)-1,3-dioxoisoindolin-4-yl)amino)-2-oxoethyl)-1H-1,2,3-triazol-4-yl)methyl (2-(2,6-dioxopiperidin-3-yl)-1-oxoisoindolin-4-yl)carbamate (XS01-136): This was prepared in the same way as XS01-109 from alkyne XS01-133 (30 mg, 0.087 mmol), and azide XS01-116 (32 mg, 0.087 mmol) to provide (1-(2-((2-(2,6-dioxopiperidin-3-yl)-1,3-dioxoisoindolin-4-yl)amino)-2-oxoethyl)-1H-1,2,3-triazol-4-yl)methyl (2-(2,6-dioxopiperidin-3-yl)-1-oxoisoindolin-4-yl)carbamate (XS01-136) (26 mg, 42%) as a white solid. HPLC 100.0% ($t_R$=6.83 min, CH₃OH in 0.1% TFA water 5%~95% in 20 min); Mp: 218° C. (dec); $^1$H NMR (500 MHz, DMSO-$d_6$) δ 11.23 (s, 1H), 11.07 (s, 1H), 10.32 (s, 1H), 9.79 (s, 1H), 8.42 (dd, J=8.5, 0.8 Hz, 1H), 8.32 (s, 1H), 7.92 (dd, J=8.5, 7.3 Hz, 1H), 7.85 (d, J=7.0 Hz, 1H), 7.75 (dd, J=7.3, 0.8 Hz, 1H), 7.60-7.50 (m, 2H), 5.64 (s, 2H), 5.32 (s, 2H), 5.20 (m, 2H), 4.66-4.23 (m, 2H), 2.96 m, 2H), 2.72-2.60 (m, 3H), 2.40 (m, 1H), 2.21-1.99 (m, 1H); HRMS (ESI+) m/z calculated for $C_{32}H_{27}N_9NaO_{10}$ (M+Na)⁺ 720.1773, found 720.1772.

Synthetic scheme 58

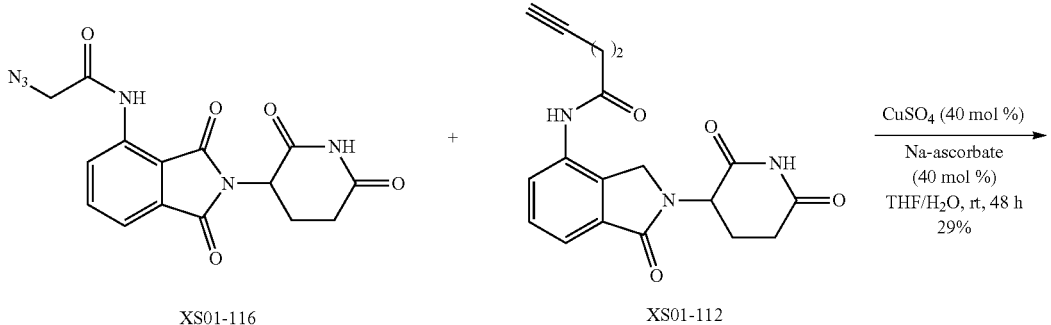

XS01-116 + XS01-112 → (CuSO₄ (40 mol %), Na-ascorbate (40 mol %), THF/H₂O, rt, 48 h, 29%)

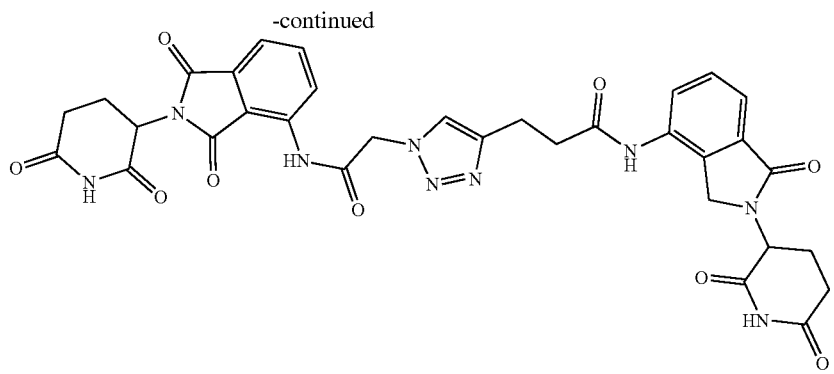

XS01-125

3-(1-(2-((2-(2,6-Dioxopiperidin-3-yl)-1,3-dioxoisoindolin-4-yl)amino)-2-oxoethyl)-1H-1,2,3-triazol-4-yl)-N-(2-(2,6-dioxopiperidin-3-yl)-1-oxoisoindolin-4-yl)propanamide (XS01-125): This was prepared in the same way as XS01-109 from azide XS01-116 (50 mg, 0.14 mmol), alkyne XS01-112 (48 mg, 0.14 mmol), copper(II) sulfate (8.9 mg, 0.056 mmol) and sodium ascorbate (11.1 mg, 0.056 mmol) to provide 3-(1-(2-((2-(2,6-dioxopiperidin-3-yl)-1,3-dioxoisoindolin-4-yl)amino)-2-oxoethyl)-1H-1,2,3-triazol-4-yl)-N-(2-(2,6-dioxopiperidin-3-yl)-1-oxoisoindolin-4-yl)propanamide (XS01-125) (28 mg, 29%) as a white solid. HPLC 98.7% ($t_R$=12.51 min, CH$_3$OH in 0.1% TFA water 5%~95% in 20 min); Mp: 227° C. (dec); $^1$H NMR (500 MHz, DMSO-d$_6$) δ 11.16 (s, 1H), 11.01 (s, 1H), 10.12 (s, 1H), 9.88 (s, 1H), 8.37 (d, J=8.4 Hz, 1H), 7.94 (s, 1H), 7.90-7.75 (m, 2H), 7.68 (dd, J=7.3, 0.8 Hz, 1H), 7.58-7.39 (m, 2H), 5.51 (s, 2H), 5.14 (m, 2H), 4.49-4.21 (m, 2H), 3.01 (t, J=7.5 Hz, 2H), 2.95-2.83 (m, 2H), 2.77 (t, J=7.5 Hz, 2H), 2.66-2.55 (m, 2H), 2.42-2.25 (m, 2H), 2.14-1.96 (m, 2H); HPLC-MS (ESI$^+$) m/z 718.2 (M+Na)$^+$; HRMS (ESI+) m/z calculated for C$_{33}$H$_{30}$N$_9$O$_9$ (M+H)$^+$ 696.2161, found 696.2153.

Synthetic scheme 59

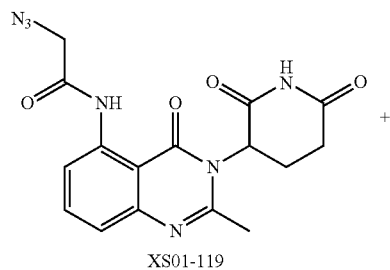

XS01-119

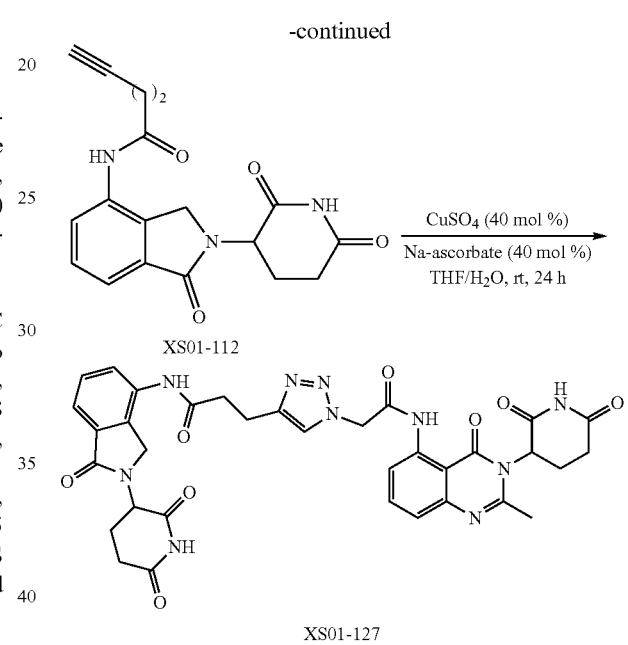

XS01-112

XS01-127

N-(2-(2,6-Dioxopiperidin-3-yl)-1-oxoisoindolin-4-yl)-3-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)propanamide (XS01-127): This was prepared in the same way as XS01-109 from azide XS01-119 (35 mg, 0.094 mmol), alkyne XS01-112 (32 mg, 0.094 mmol), copper(II) sulfate (6.0 mg, 0.038 mmol) and sodium ascorbate (7.5 mg, 0.038 mmol) to provide N-(2-(2,6 dioxopiperidin-3-yl)-1-oxoisoindolin-4-yl)-3-(1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)propanamide (XS01-127) (31 mg, 47%) as a white solid. HPLC 99.3% ($t_R$=12.73 min, CH$_3$OH in 0.1% TFA water 5%~95% in 20 min); Mp: 232° C. (dec); $^1$H NMR (500 MHz, DMSO-d$_6$) δ 11.82 (s, 1H), 11.09 (s, 1H), 11.01 (s, 1H), 9.88 (s, 1H), 8.61-8.34 (m, 1H), 7.92 (s, 1H), 7.84-7.71 (m, 2H), 7.58-7.43 (m, 2H), 7.34 (dd, J=8.2, 1.1 Hz, 1H), 5.56-5.38 (m, 2H), 5.34 (dd, J=11.7, 5.6 Hz, 1H), 5.14 (dd, J=13.3, 5.1 Hz, 1H), 4.52-4.20 (m, 2H), 3.00 (t, J=7.5 Hz, 2H), 2.94-2.81 (m, 2H), 2.76 (t, J=7.6 Hz, 2H), 2.71-2.58 (m, 5H), 2.43-2.27 (m, 2H), 2.25-2.13 (m, 1H), 2.07-1.95 (m, 1H); HPLC-MS (ESI$^+$) m/z 709.4 (M+H)$^+$; HRMS (ESI+) m/z calculated for C$_{34}$H$_{33}$N$_{10}$O$_8$ (M+H)$^+$ 709.2477, found 709.2480.

Synthetic scheme 60
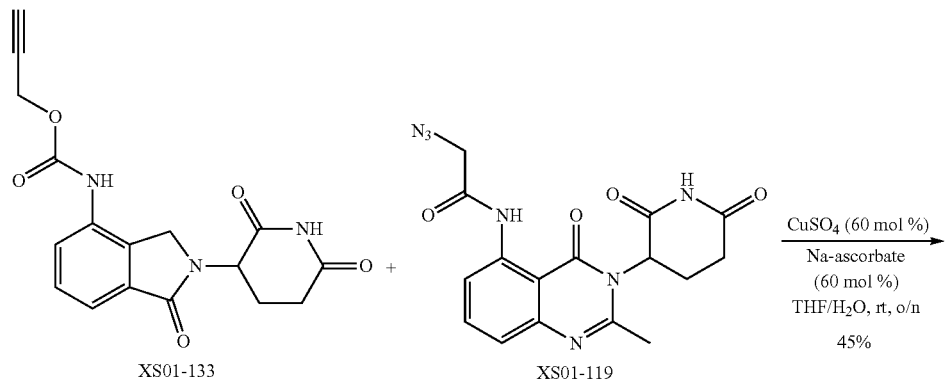
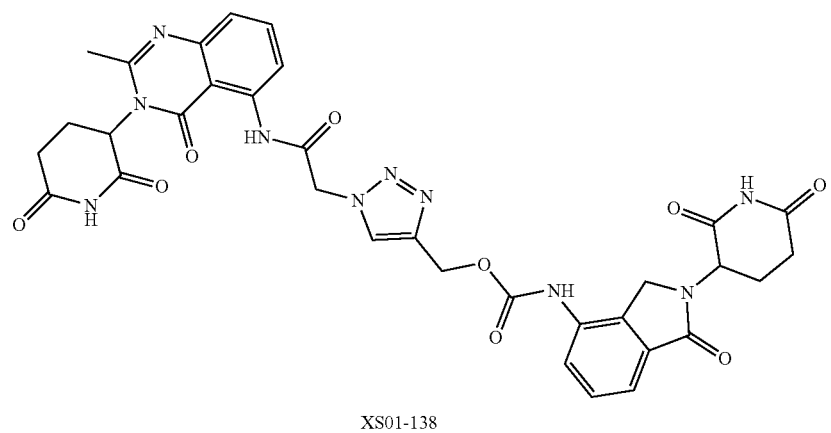

(1-(2-((3-(2,6-Dioxopiperidin-3-yl)-2-methyl-4-oxo-3,4-dihydroquinazolin-5-yl)amino)-2-oxoethyl)-1H-1,2,3-triazol-4-yl)methyl (2-(2,6-dioxopiperidin-3-yl)-1-oxoisoindolin-4-yl)carbamate (XS01-138): This was prepared in the same way as XS01-109 from alkyne XS01-133 (37 mg, 0.108 mmol), azide XS01-119 (40 mg, 0.108 mmol), copper (II) sulfate (10.0 mg, 0.065 mmol) and sodium ascorbate (13 mg, 0.065 mmol) to provide (1-(2-((3-(2,6-dioxopiperidin-3-yl)-2-methyl-4-oxo-3,4-dihydroquinazolin-5-yl)amino)-2-oxoethyl)-1H-1,2,3-triazol-4-yl)methyl (2-(2,6-dioxopiperidin-3-yl)-1-oxoisoindolin-4-yl)carbamate (XS01-138) (35 mg, 45%) as a white solid. HPLC 100.0% ($t_R$=7.00 min, $CH_3OH$ in 0.1% TFA water 5%~95% in 20 min); Mp: 219° C. (dec); $^1$H NMR (500 MHz, DMSO-$d_6$) δ 11.90 (s, 1H), 11.12 (s, 1H), 11.01 (s, 1H), 9.72 (s, 1H), 8.47 (dd, J=8.2, 1.0 Hz, 1H), 8.26 (s, 1H), 7.80 (t, J=8.2 Hz, 2H), 7.58-7.42 (m, 2H), 7.35 (dd, J=8.1, 1.1 Hz, 1H), 5.65-5.46 (m, 2H), 5.35 (dd, J=11.6, 5.7 Hz, 1H), 5.30-5.17 (m, 2H), 5.12 (dd, J=13.3, 5.1 Hz, 1H), 4.55-4.25 (m, 2H), 2.98-2.80 (m, 2H), 2.77-2.53 (m, 6H), 2.41-2.26 (m, 1H), 2.25-2.15 (m, 1H), 2.08-1.94 (m, 1H); HRMS (ESI+) m/z calculated for $C_{33}H_{30}N_{10}NaO_9$ (M+Na)$^+$ 733.2089, found 733.2094.

Synthetic scheme 61

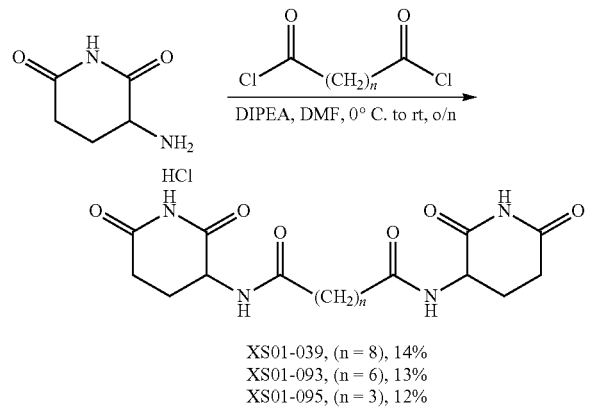

XS01-039, (n = 8), 14%
XS01-093, (n = 6), 13%
XS01-095, (n = 3), 12%

$N^1,N^{10}$-Bis(2,6-dioxopiperidin-3-yl)decanediamide (XS01-039): 3-Aminopiperidine-2,6-dione hydrochloride (100 mg, 0.607 mmol) and DIPEA (214 mg, 1.656 mmol) were dissolved in DMF (5 mL), decanedioyl dichloride (66 mg, 0.276 mmol) was slowly to the solution at 0° C., and the reaction mixture stirred at room temperature overnight. Water (10 mL) was added, and the mixture extracted with ethyl acetate (3×10 mL). The combined organic layers were washed with sat. $NH_4Cl$ (3×5 mL), sat. $NaHCO_3$ (3×5 mL) and brine (3×5 mL), dried ($Na_2SO_4$) and concentrated under reduced pressure to provide the crude product. The crude product was triturated with dichloromethane/hexane to provide $N^1,N^{10}$-bis(2,6-dioxopiperidin-3-yl)decanediamide (XS01-039) (15 mg, 14%) as a white solid. HPLC 98.9% ($t_R$=6.84 min, $CH_3OH$ in 0.1% TFA water 5%~95% in 20 min); Mp: 215° C. (dec); $^1$H NMR (500 MHz, DMSO-$d_6$) δ 10.78 (s, 2H), 8.13 (d, J=8.2 Hz, 2H), 4.75-4.32 (m, 2H), 2.78-2.65 (m, 2H), 2.47 (m, 2H), 2.18-2.04 (m, 4H), 1.91 (m, 4H), 1.56-1.45 (m, 4H), 1.26 (s, 8H); HPLC-MS (ESI$^+$) m/z 445.2 (M+Na)$^+$; HRMS (ESI+) m/z calculated for $C_{20}H_{30}N_4NaO_6$ (M+Na)$^+$ 445.2058, found 445.2059.

$N^1,N^8$-Bis(2,6-dioxopiperidin-3-yl)octanediamide (XS01-093): 3-aminopiperidine-2 6-dione hydrochloride (200 mg, 1.22 mmol) and DIPEA (299 mg, 2.31 mmol) were dissolved in DMF (2 mL), octanedioyl dichloride (122 mg, 0.58 mmol) dissolved in DMF (1 mL) was added to the solution dropwise at 0° C. The reaction mixture was stirred overnight at room temperature. The solvent was removed by rotary evaporation under vacuum to provide a residue which was left under vacuum (1 mm Hg) for 5 h. The crude product was triturated with methanol (3×10 mL) to provide $N^1,N^8$-bis(2,6-dioxopiperidin-3-yl)octanediamide (XS01-093) (30 mg, 13%) as a white solid. Mp: 207° C. (dec); $^1$H NMR (500 MHz, DMSO-$d_6$) δ 10.77 (s, 2H), 8.12 (d, J=8.3 Hz, 2H), 4.53 (m, 2H), 2.80-2.62 (m, 2H), 2.47 (m, 2H), 2.20-2.07 (m, 4H), 1.96-1.83 (m, 4H), 1.51 (t, J=7.2 Hz, 4H), 1.29 (m, 4H); HPLC-MS (ESI+) m/z 395.2 (M+H)$^+$; HRMS (ESI+) m/z calculated for $C_{18}H_{26}N_4NaO_6$ (M+Na)$^+$ 417.1745, found 417.1743.

$N^1,N^5$-Bis(2,6-dioxopiperidin-3-yl)glutaramide (XS01-095): This was prepared in the same way as XS01-093 from 3-aminopiperidine-2 6-dione hydrochloride (200 mg, 1.22 mmol), DIPEA (314 mg, 2.43 mmol), and glutaroyl dichloride (102 mg, 0.61 mmol) to provide $N^1,N^5$-bis(2,6-dioxopiperidin-3-yl)glutaramide (XS01-095) (25 mg, 12%) as a white solid. Mp: 202° C. (dec); $^1$H NMR (500 MHz, DMSO-$d_6$) δ 10.78 (s, 2H), 8.15 (dd, J=8.3, 1.9 Hz, 2H), 4.69-4.34 (m, 2H), 2.80-2.65 (m, 2H), 2.48 (m, 2H), 2.17 (m, 2H), 1.92 (m, 4H), 1.77 (m, 2H), 1.27 (m, 2H); HPLC-MS (ESI+) m/z 353.2 (M+H)$^+$; HRMS (ESI+) m/z calculated for $C_{15}H_{20}N_4NaO_6$ (M+Na)$^+$ 375.1275, found 375.1278.

Synthetic scheme 62

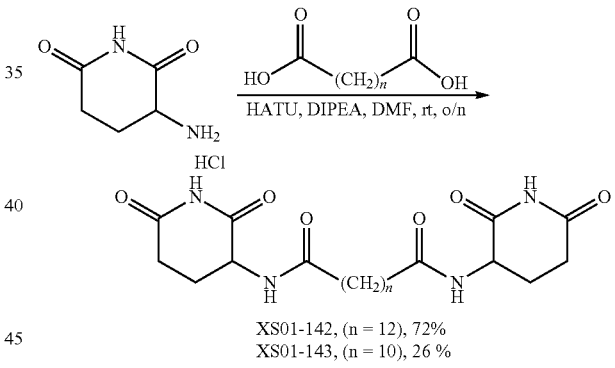

XS01-142, (n = 12), 72%
XS01-143, (n = 10), 26 %

$N^1,N^{14}$-Bis(2,6-dioxopiperidin-3-yl)tetradecanediamide (XS01-142): 3-Aminopiperidine-2,6-dione hydrochloride (200 mg, 1.22 mmol), tetradecanedioic acid (157 mg, 0.607 mmol) and DIPEA (471 mg, 3.65 mmol) in DMF (2 mL), were stirred for 10 min at room temperature. HATU (1-[bis(dimethylamino)methylene]-1H-1,2,3-triazolo[4,5-b]pyridinium 3-oxide hexafluorophosphate) (508 mg, 1.34 mmol) was added and the resulting mixture stirred at room temperature overnight. The solvent was removed by rotary evaporation under vacuum to provide a residue which was left under vacuum (1 mm Hg) overnight. The crude product was triturated with methanol (3×10 mL) to provide $N^1,N^{14}$-bis(2,6-dioxopiperidin-3-yl)tetradecanediamide (XS01-142) (210 mg, 72%) as a white solid. Mp: 236° C. (dec); $^1$H NMR (500 MHz, DMSO-$d_6$) δ10.79 (s, 2H), 8.13 (d, J=8.3 Hz, 2H), 4.53 (m, 2H), 2.78-2.65 (m, 2H), 2.49-2.43 (m, 2H), 2.19-2.05 (m, 4H), 1.90 (m, 4H), 1.50 (m, 4H), 1.25 (s, 16H); HPLC-MS (ESI+) m/z 479.4 (M+H)$^+$; HRMS (ESI+) m/z calculated for $C_{24}H_{38}N_4NaO_6$ (M+Na)$^+$ 501.2684, found 501.2685.

$N^1,N^{12}$-Bis(2,6-dioxopiperidin-3-yl)dodecanediamide (XS01-143): This was prepared in the same way as This was prepared in the same way as from 3-aminopiperidine-2 6-dione hydrochloride (200 mg, 1.22 mmol), dodecanedioic acid (140 mg, 0.607 mmol), DIPEA (471 mg, 3.65 mmol) and HATU (508 mg, 1.34 mmol) to provide $N^1,N^{12}$-bis(2, 6-dioxopiperidin-3-yl)dodecanediamide (XS01-143) (70 mg, 26%) as a white solid. Mp: 225° C. (dec); $^1$H NMR (500 MHz, DMSO-$d_6$) δ 10.78 (s, 2H), 8.12 (d, J=8.4 Hz, 2H), 4.69-4.26 (m, 2H), 2.79-2.62 (m, 2H), 2.49-2.41 (m, 2H), 2.19-2.03 (m, 4H), 1.98-1.78 (m, 4H), 1.59-1.41 (m, 4H), 1.26 (s, 12H); HPLC-MS (ESI+) m/z 473.3 (M+Na)$^+$; HRMS (ESI+) m/z calculated for $C_{22}H_{34}N_4NaO_6$ (M+Na)$^+$ 473.2371, found 473.2375.

Specific Examples

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 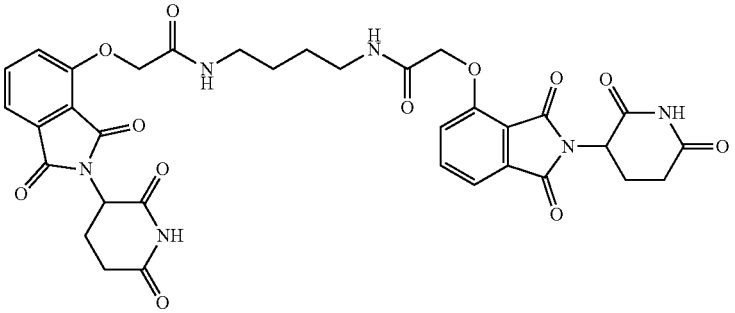 SY2-060 M.W. = 716.66 | Oxyacetamide/ alkyl 12 atom | 10 nM: 103.81% | | (04/20/18 1.52 ± 1.91 |
| 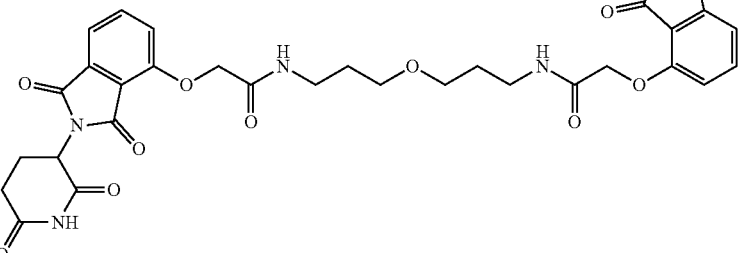 SM2-126 M.W. = 760.7 | Oxyacetamide/ alkylether 15 atom | 10 uM: 13.22% 10 nM: 136.35% | 13.74 ± 0.70 (FI) | 88.94 ± 1.54 |
| 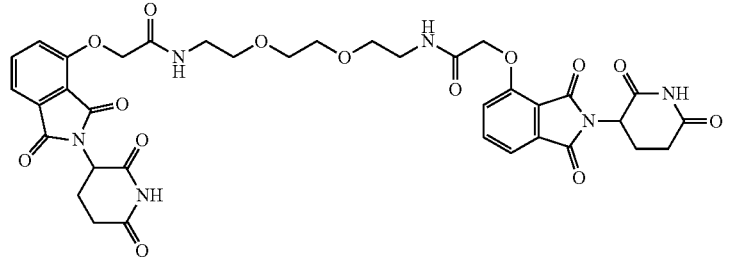 SM2-048 M.W. = 776.71 | Oxyacetamide/ Alkylether 16 atom | (++++) 10 uM: 15.76% 10 nM: 99.51% | 12.3 ± 0.4 ITC 11.34 ± 1.00 (FI) | 68.23 ± 3.33 |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 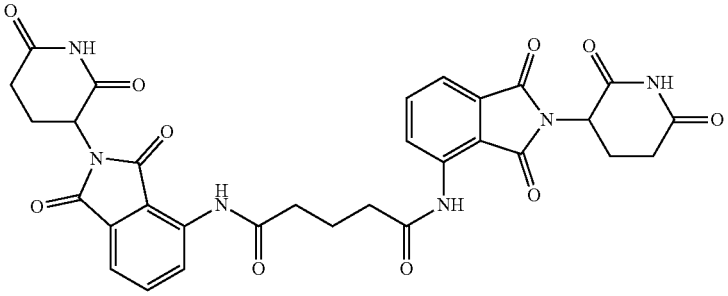 EC1-117 M.W. = 642.58 | Amide/alkyl 7 atom | (+++) 10 uM: 19.82% 10 nM: 114.21% | | 47.9 ± 11% |
| 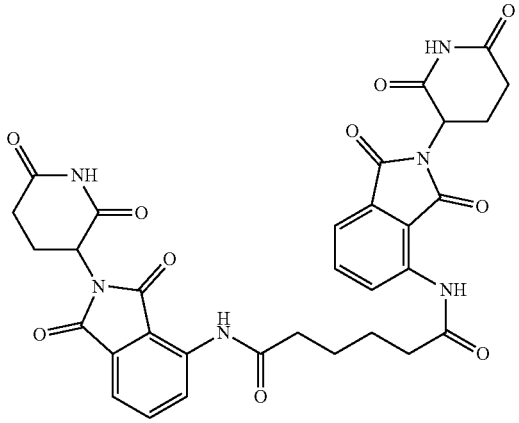 EC1-120 M.W. = 656.61 | Amide/alkyl 8 atom | (+++) 10 uM: 16.79% 10 nM: 95.28% | | 23.2 ± 20% |
| 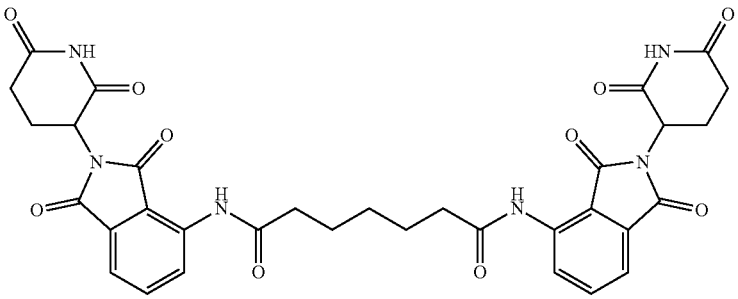 EC1-119 M.W. = 670.64 | Amide/alkyl 9 atom | (++++) 10 uM: 4.91% 10 nM: 30.46% | | 18.0 ± 20% |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| EC1-130 M.W. = 684.66 | Amide/alkyl 10 atom | (+++) 10 uM: 11.65% 10 nM: 44.25% | | n.b. |
| EC1-131 M.W. = 698.69 | Amide/alkyl 11 atom | (+++) 10 uM: 6.19% 10 nM: 29.75% | | n.b. |
| EC1-132 M.W. = 712.72 | Amide/alkyl 12 atom | (++) 10 uM: 33.01% 10 nM: 33.40% | | n.b. |

US 12,233,054 B2
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 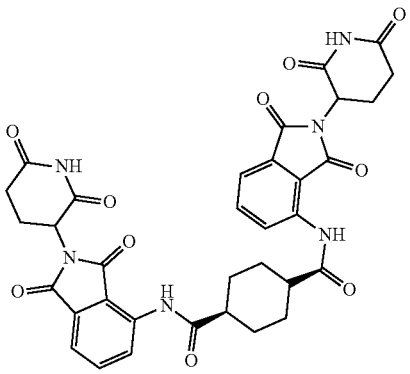 EC1-133 M.W. = 682.65 | Amide/cis-cyclohexyl 8 atom | (+++) 10 uM: 10.35% 10 nM: 119.10% | | n.b. |
| 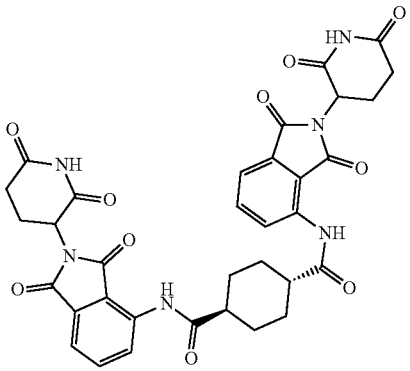 EC1-135 M.W. = 682.65 | Amide/trans-cyclohexyl 8 atom | (++) 10 uM: 36.53% 10 nM: 133.69% | | n.b. |
| 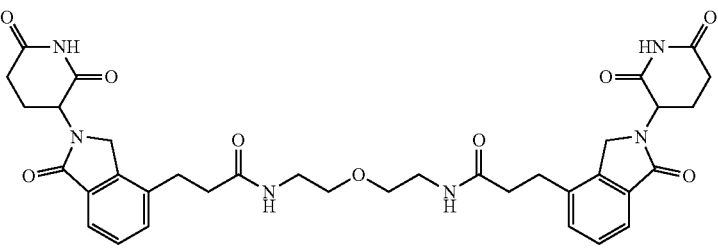 SM3-010 M.W. = 700.75 | Propanamide/ ether 13 atom | 10 uM: 86.88% 10 nM: 118.60% | 14.30 ± 0.52 (FI) | 72.44 ± 0.84 |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 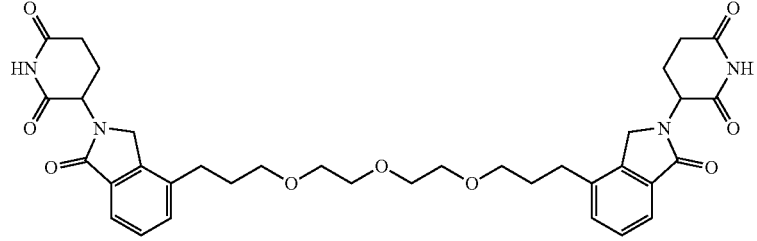 SM2-129 M.W. = 674.8 | Alkyl/PEG 13 atom | 10 uM: 12.45% 10 nM: 53.57% | 11.15 ± 0.58 (FI) | 76.25 ± 1.54 |
| 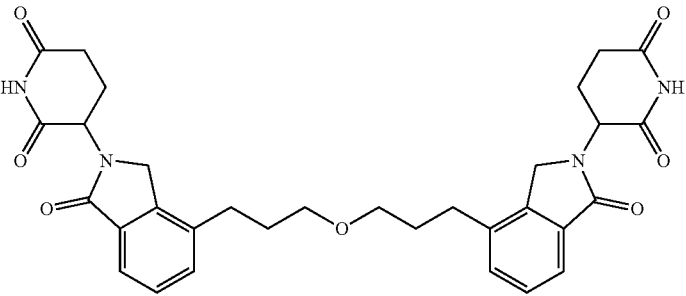 SM2-144 M.W. = 586.64 | Alkyl/ether 7 atom | 10 uM: 3.05% 10 nM: 24.15% | 4.4 ± 1.4 (ITC) 5.88 ± 1.12 (FI) | 73.90 ± 14.92 |
| 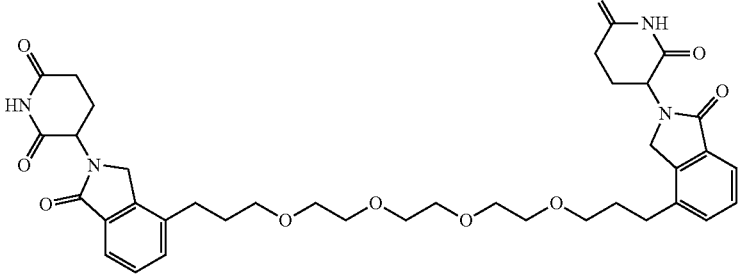 SM2-139 M.W. = 718.80 | Alkyl/PEG 16 atom | 10 uM: 19.44% 10 nM: 44.32% | 9.38 ± 0.59 (FI) | 79.62 ± 3.13 |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 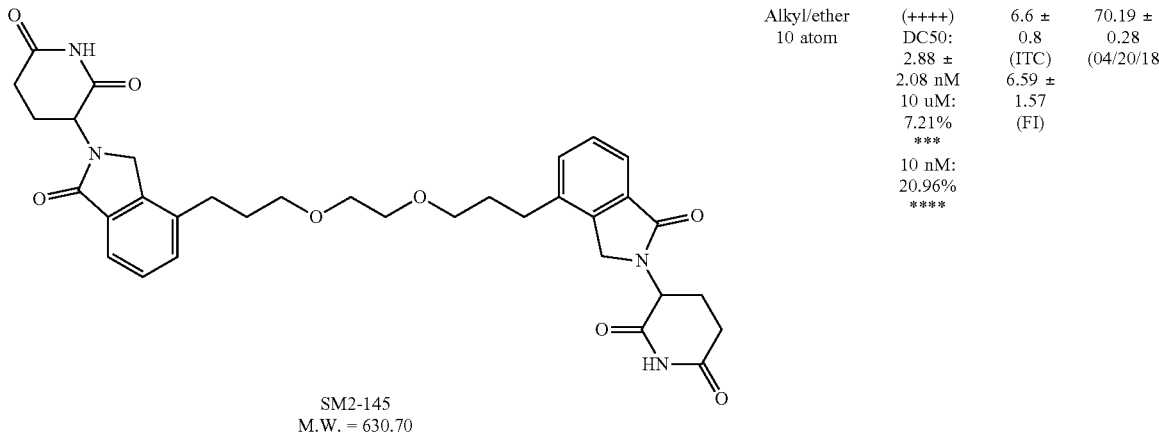<br>SM2-145<br>M.W. = 630.70 | Alkyl/ether<br>10 atom | (++++)<br>DC50:<br>2.88 ±<br>2.08 nM<br>10 uM:<br>7.21%<br>*<br>10 nM:<br>20.96%<br>** | 6.6 ±<br>0.8<br>(ITC)<br>6.59 ±<br>1.57<br>(FI) | 70.19 ±<br>0.28<br>(04/20/18 |
| 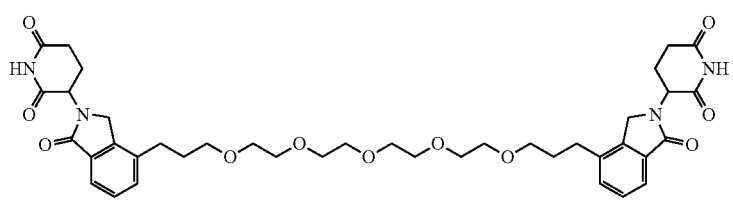<br>SM2-156<br>M.W. = 762.86 | Alkyl/PEG<br>19 atom | 10 uM:<br>33.35%<br>10 nM:<br>56.83% | 11.24 ±<br>0.53<br>(FI) | 79.52 ±<br>2.29 |
| 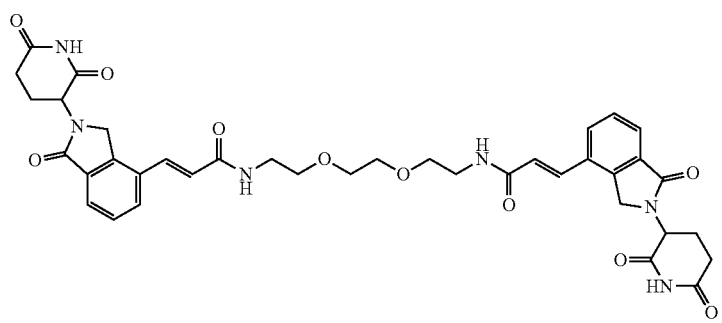<br>SM3-003<br>M.W. = 740.77 | Acrylamide/<br>PEG<br>16 atom | 10 uM:<br>102.08<br>10 nM:<br>124.74% | 14.30 ±<br>0.05<br>(FI) | 72 ±<br>0.80 |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| SM3-005 M.W. = 744.80 | Propanamide/ ether 16 atom | 10 uM: 91.11% 10 nM: 80.59% | 15.02 ± 0.97 (FI) | 72.79 ± 1.38 |
| SM3-006 M.W. = 696.72 | Acrylamide/ ether 13 atom | 10 uM: 85.35% 10 nM: 110.11% | 15.25 ± 1.52 (FI) | 72.94 ± 1.19 (04/20/18 |
| SM3-009 M.W. = 784.82 | Acrylamide/ PEG 19 atom | 10 uM: 59.08% 10 nM: 107.98% | 8.21 ± 1.22 (FI) | 83.88 ± 0.28 |
| SM3-011 M.W. = 788.86 | Propanamide/ PEG 19 atom | 10 uM: 85.43% 10 nM: 102.36% | 14.79 ± 1.08 (FI) | 73.39 ± 0.71 |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 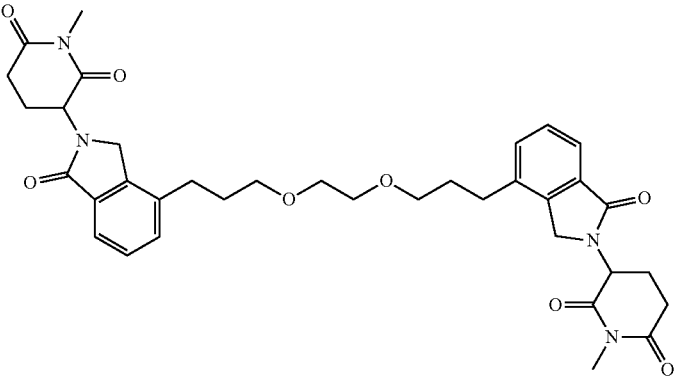  SM3-104  M.W. = 658.75 | Propyl/ether 10 atom | 10 nM: 92.08% | | |
| 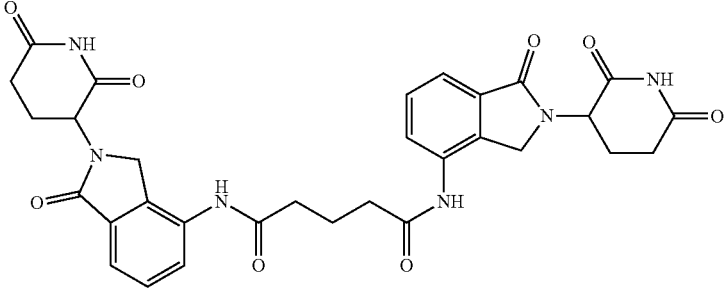  EC1-148  M.W. = 614.62 | Amide/alkyl 7 atom | (++++) 10 uM: 2.97% 10 nM: 73.85% | 23.64 ± 2.55 (FI) | 83.6 ± 4% |
| 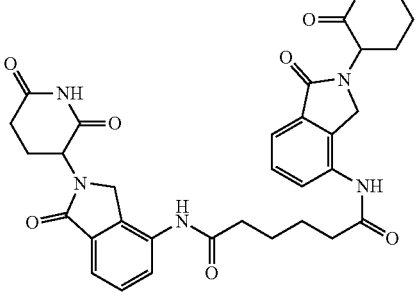  EC1-149  M.W. = 628.64 | Amide/alkyl 8 atom | (++++) 10 uM: 1.74% 10 nM: 76.26% | 22.79 ± 0.55 (FI) | 87.3 ± 2% |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| EC1-141, M.W. = 642.67 | Amide/alkyl 9 atom | (++++) 10 uM: 7.19% 10 nM: 91.18% | 22.15 ± 1.47 (FI) | 71.6 ± 2% |
| EC1-150, M.W. = 656.70 | Amide/alkyl 10 atom | (++++) 10 uM: 6.33% 10 nM: 99.34% | 18.33 ± 1.54 (FI) | 57.2 ± 10% |
| EC1-151, M.W. = 670.72 | Amide/alkyl 11 atom | (++++) 10 uM: 31.99% 10 nM: 137.36% | 14.24 ± 3.16 (FI) | 46.7 ± 9% |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 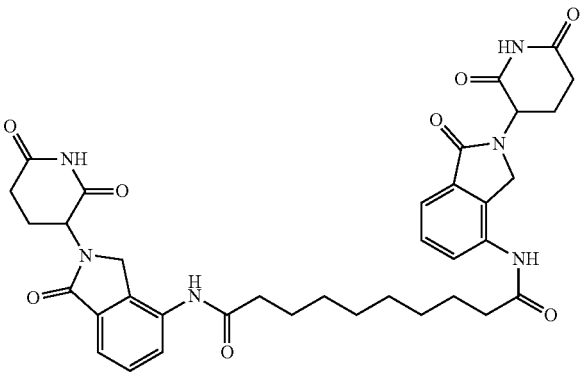 EC1-152 M.W. = 684.75 | Amide/alkyl 12 atom | (+++) 10 uM: 28.18% 10 nM: 133.49% | 15.52 ± 2.26 (FI) | 47.9 ± 2% |
| 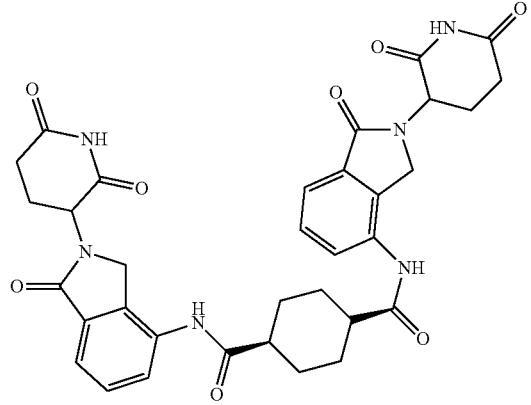 EC1-153 M.W. = 654.68 | Amide/cis-cyclohexyl 8 atom | (+++) 10 uM: 9.54% 10 nM: 118.88% | | 54.1 ± 13% |
| 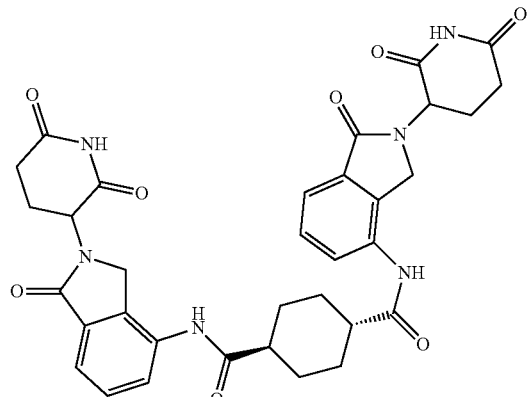 EC1-154 M.W. = 654.68 | Amide/trans-cyclohexyl 8 atom | (++) 10 uM: 44.25% 10 nM: 102.62% | | 18.4 ± 77% |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| XS01-008B2<br>M.W. = 622.63 | Propargyl/ alkylether 10 atom | 10 nM: 11.85% | 2.53 ± 1.53 (FI) | |
| EC1-168.MS<br>M.W. = 907.01 | Benzyl ether/phenyl piperazine 18 atom | 10 uM: 106.53% 10 nM: 31.07% 115.96% | insoluble | |
| EC2-035<br>M.W. = 620.67 | Benzylamine/ phenyl 8 atom | (++) 10 uM: 99.66% 10 nM: 2.32% | | |

-continued

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 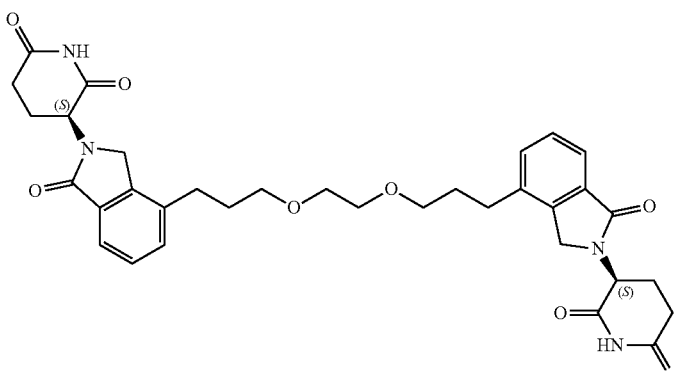<br>XS01-011<br>M.W. = 630.70 | Propyl/ether 10 atom | (++)<br>10 uM: 38.07%<br>10 nM: 3.42% | | |
| 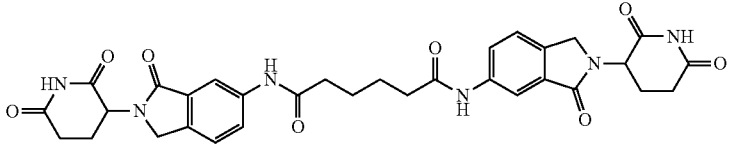<br>EC2-066<br>M.W. = 628.6 | Amide/alkyl 8 atom | 10 uM: 188.89%<br>10 nM: 26.28%<br>36.66%<br>81.12% | | |
| 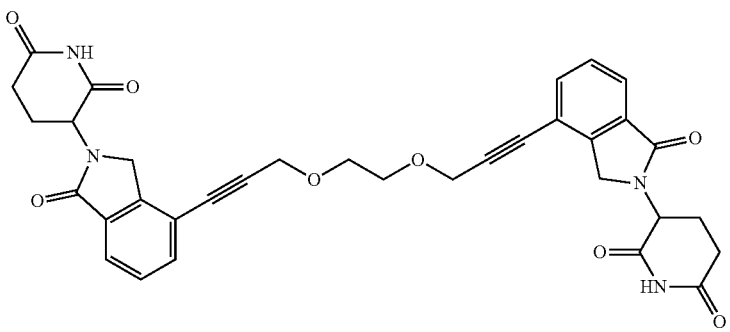<br>SY4-065<br>M.W. = 622.63 | Propargyl/ alkylether 10 atom | (++)<br>10 uM: 135.80%<br>10 nM: 1.75% | n.b. | |
| 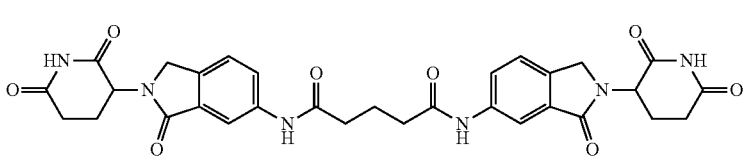<br>EC2-060<br>M.W. = 614.62 | Amide/alkyl 7 atom | No degradation<br>10 uM: 40.28%<br>10 nM: 48.44% | | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 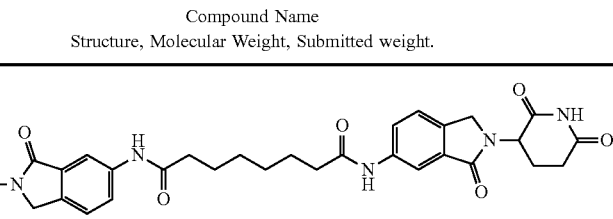 EC2-063 M.W. = 656.70 | Amide/alkyl 10 atom | (++) 10 uM: 13.48% 10 nM: 38.77% | | |
| 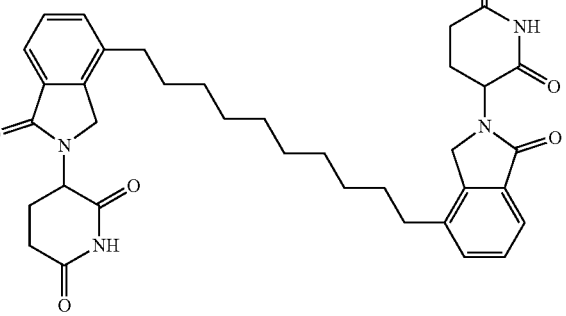 EC2-093 M.W. = 626.7540 | CH$_2$/alkyl 10 atom | 10 uM: 13.34% 10 nM: 2.87% 6.26% | 35.54 ± 47.88 | |
| 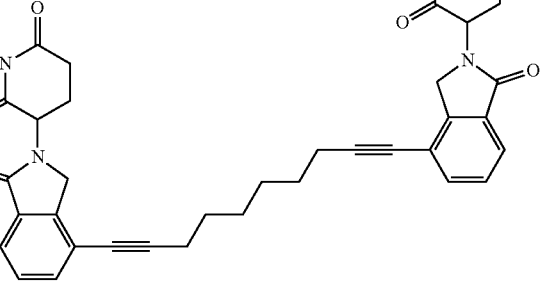 EC2-086 M.W. = 618.6900 | Propargyl/ alkyl 10 atom | 10 uM: 10.33% 10 nM: 7.77% 0.36% | 86.47 ± 25.25 | |
| 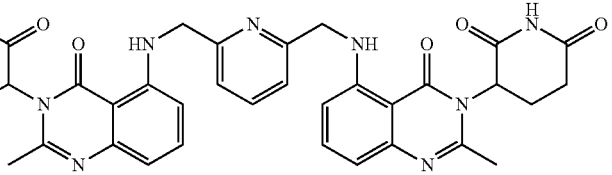 MA10-126 M.W. = 675.71 | Amine/pyridyl 7 atom | (+++) 10 uM: 61.06% 10 nM: 54.22% | | |

-continued

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 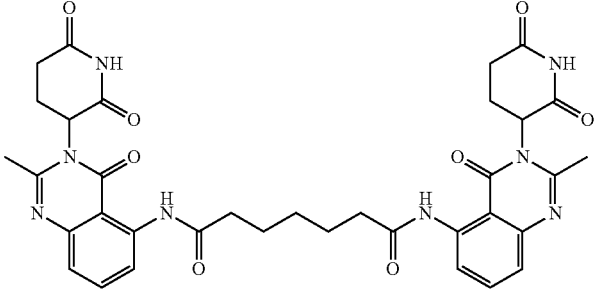<br>MA10-121<br>M.W. = 696.72 | Amide/alkyl<br>9 atom | (+++)<br>10 uM:<br>72.60%<br>10 nM:<br>56.45% | | |
| 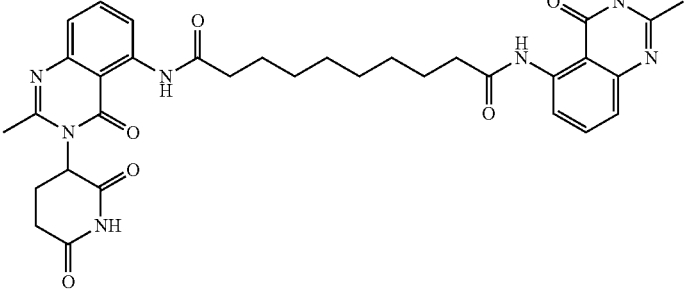<br>MA10-090<br>M.W. = 738.80 | Amide/alkyl<br>12 atom | (+)<br>10 uM:<br>82.18%<br>10 nM:<br>131.74% | | |
| 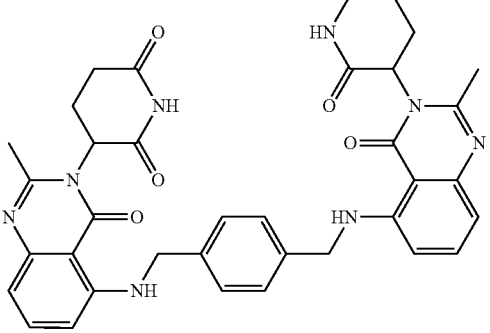<br>MA10-112<br>M.W. = 674.72 | Benzylamine<br>8 atom | (++++)<br>10 uM:<br>21.43%<br>10 nM:<br>5.13% | | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 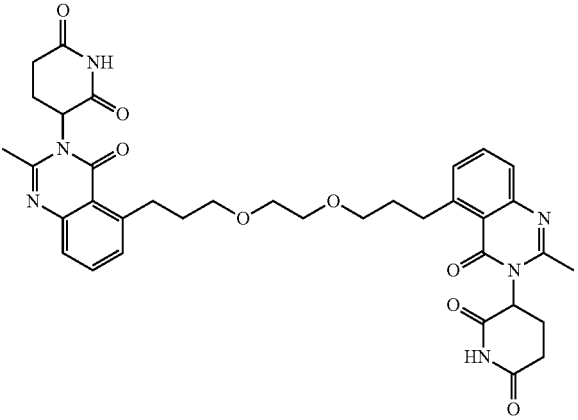 MA10-120 M.W. = 684.75 | Propyl/ether 10 atom | (+++) 10 uM: 82.82% 10 nM: 56.69% | | |
| 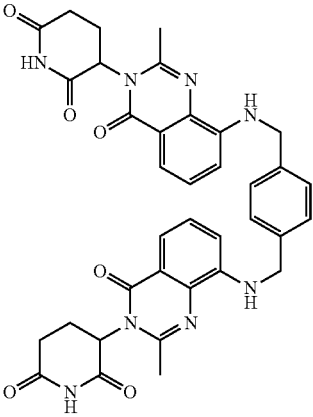 XS01-030 M.W. = 674.72 | Benzylamine/ phenyl 8 atom | (+++) 10 uM: 93.00% 10 nM: 12.14% | | |
| 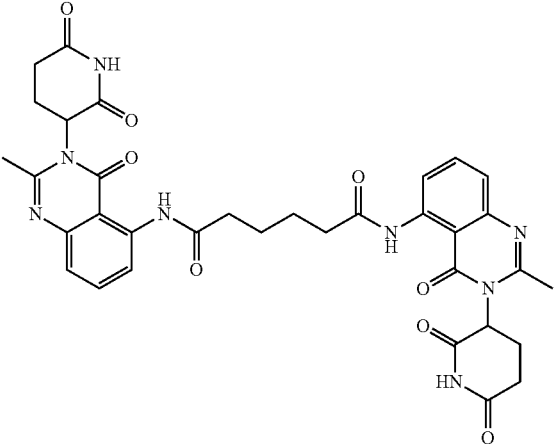 MA10-088 M.W. = 682.69 | Amide/alkyl 8 atom | (+) 10 uM: 58.09% 10 nM: 135.36% | | |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 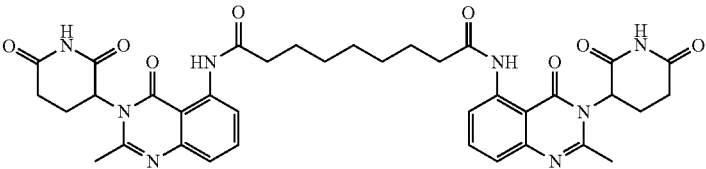 MA10-086 M.W. = 724.78 | Amide/alkyl 11 atom | (+) 10 uM: 71.00% 10 nM: 137.81% | | |
| 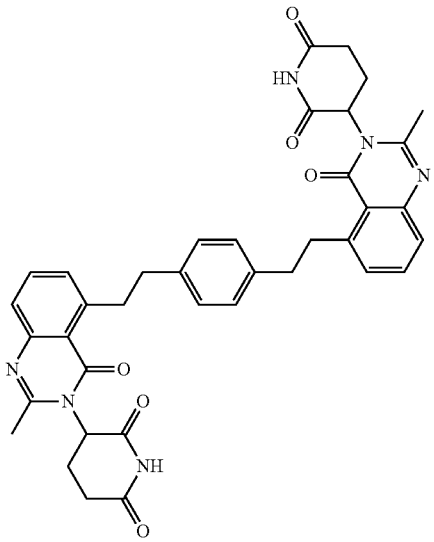 XS01-038 M.W. = 672.74 | Ethyl/ phenyl 8 atom | No degradation 10 uM: 132.65% 10 nM: 29.04% | | |
| 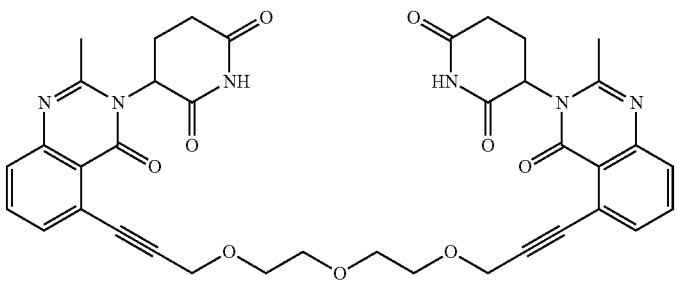 MA10-153 M.W. = 720.74 | Propargyl/ PEG 13 atom | No Degradation 10 uM: 208.22% 10 nM: 14.83% | | |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 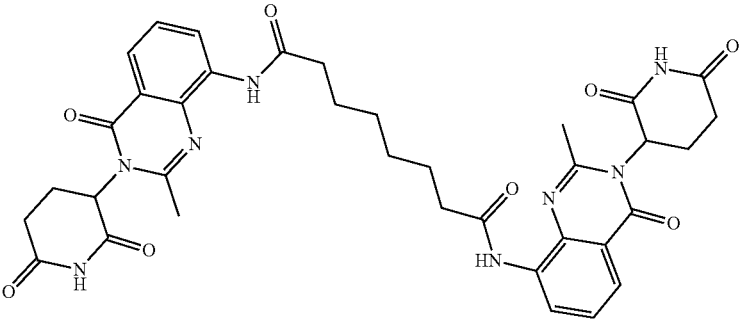<br>XS01-044<br>M.W. = 710.75 | Amide/alkyl 10 atom | No Degradation 10 uM: 48.84% 10 nM: 66.57% | | |
| 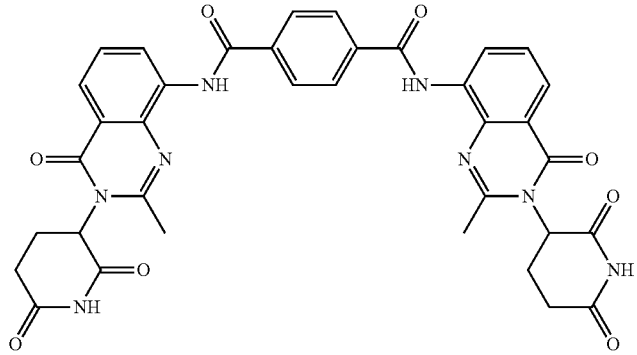<br>XS01-059<br>M.W. = 702.68 | Amide/phenyl 8 atom | No Degradation 10 uM: 355.79% 10 nM: 69.24% | | |
| 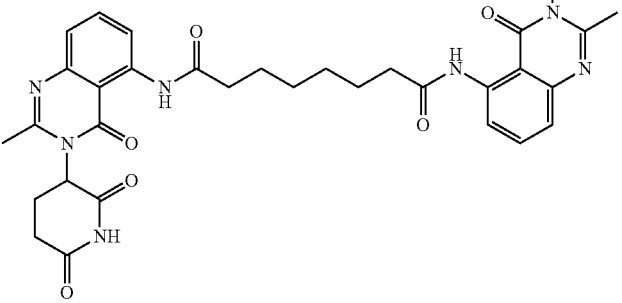<br>MA10-077<br>M.W. = 710.75 | Amide/alkyl 10 atom | 10 uM: 74.32% 10 nM: 139.14% | | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 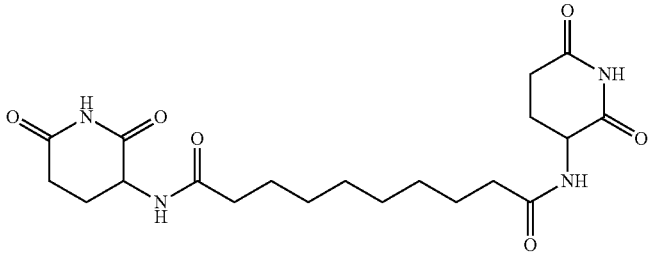 XS01-039 M.W. = 422.48 | Amide/alkyl 12 atom | (++++) 10 uM: 0.98% 10 nM: 61.28% B2-10 uM: 13.06% B2-10 nM: 92.87% | | 161 ±19.34 |
| 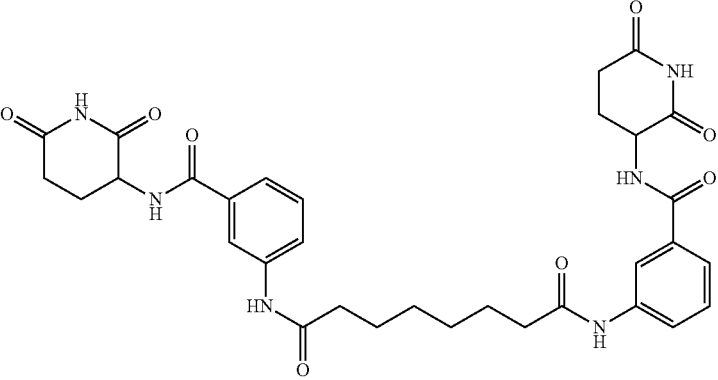 XS01-050 M.W. = 632.67 | Phenylamide/ alkyl 20 atom | (++) 10 uM: 20.04% 10 nM: 167.55% | | |
| 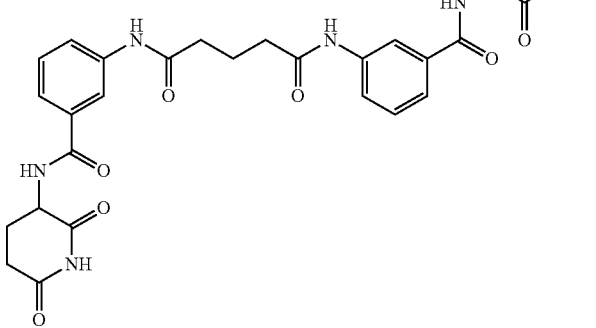 XS01-074 M.W. = 590.59 | Phenylamide/ alkyl 17 atom | (++) 10 uM: 25.88% 10 nM: 88.77% 59.18% | 187.3 ± 16.21 (1/25/19) | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 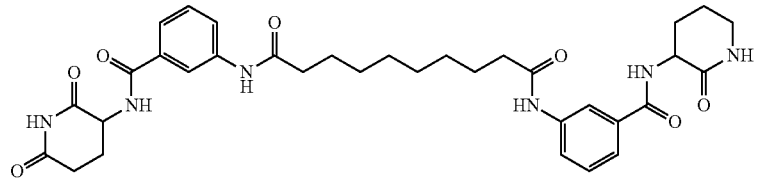<br>XS01-075<br>M.W. = 660.73 | | (++)<br>10 uM:<br>63.41%<br>10 nM:<br>97.99%<br>66.59% | | |
| 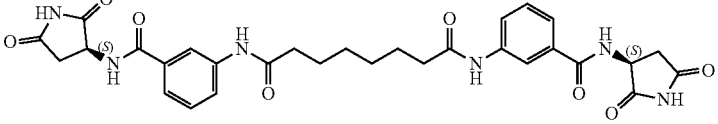<br>XS01-066<br>M.W. = 604.62 | Phenylamide/<br>alkyl<br>20 atom | (++)<br>10 uM:<br>157.27%<br>10 nM:<br>121.78%<br>71.94% | | |
| 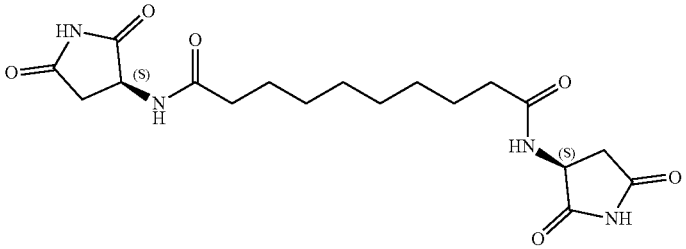<br>XS01-081<br>M.W. = 394.43 | Amide/alkyl<br>12 atom | (+)<br>10 uM:<br>35.01%<br>10 nM:<br>138.50%<br>215.56% | | |
| 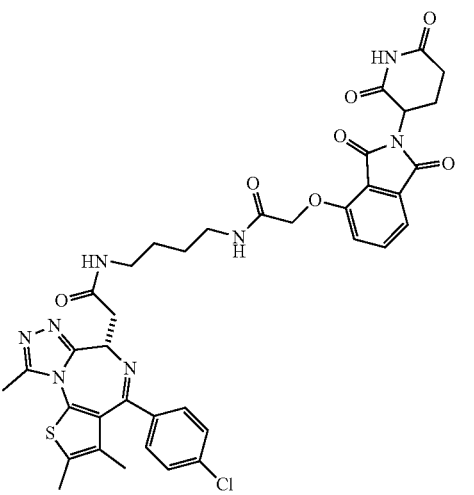<br>SG5-025<br>M.W. = 785.27 | Oxyacetamide/<br>alkyl<br>9 atom | | | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 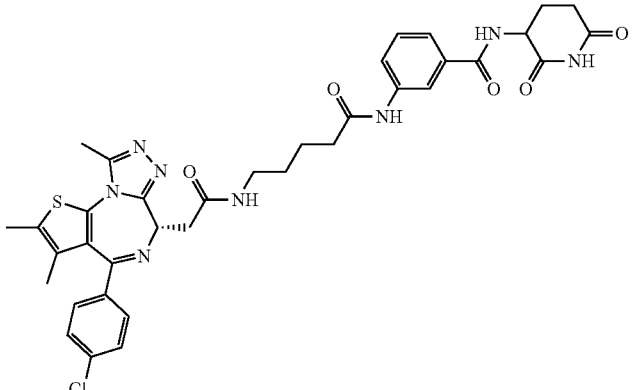<br>EC2-088<br>M.W. = 729.2530 | Amide/alkyl 7 atom | 43.73 ±24.45 (1/25/19) | | |
| 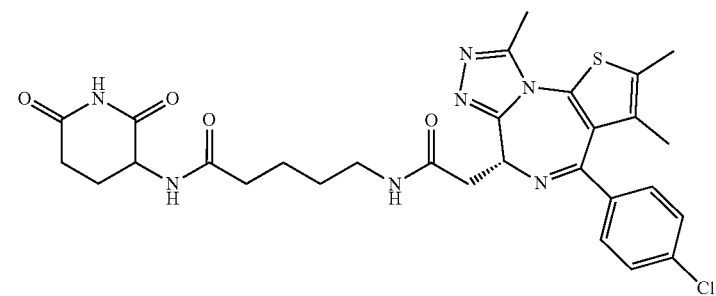<br>EC2-092<br>M.W. = 610.1300 | Amide/alkyl 7 atom | | 225.9 ± 21.57 | |
| 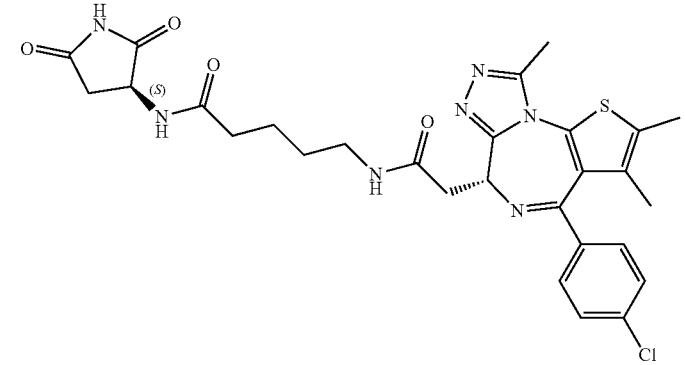<br>XS01-089<br>M.W. = 596.10 | Amide/alkyl 7 atom | | 353 ±108.5 | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 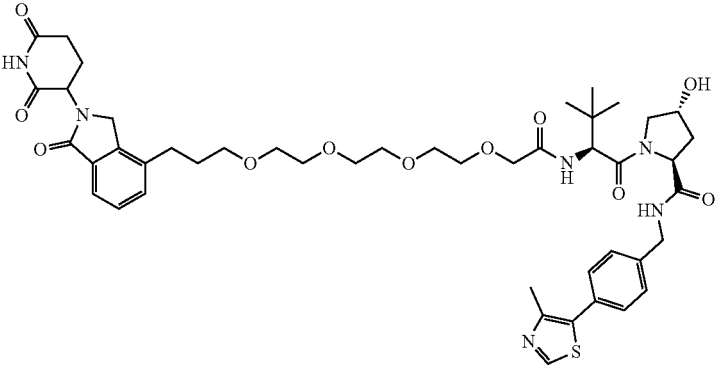 SR3-108 M.W. = 905.1 | Amide-CH$_2$/PEG 7 atom | | 13.56 ± 1.51 (FI) | |
| 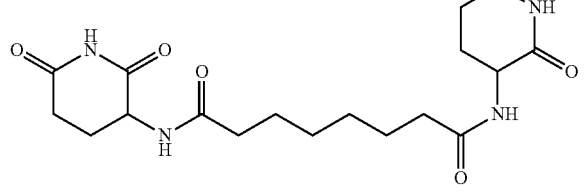 XS01-093 M. W. = 394.4280 | Amide/alkyl 10 atom | 10 uM: 132.53% 10 nM: 116.46% | | |
| 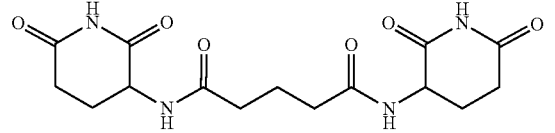 XS01-095 M.W. = 352.3470 | Amide/alkyl 7 atom | 10 uM: 103.59% 10 nM: 84.64% | | |
| 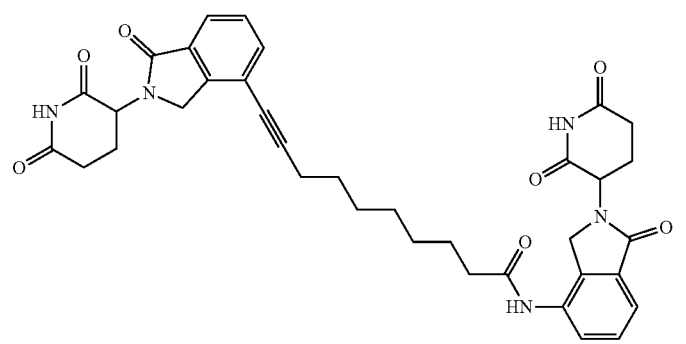 EC2-100 M.W. = 651.72 | Alkynyl/amidic 11 atom | 10 uM: 32.24% 10 nM: 55.52% | | |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 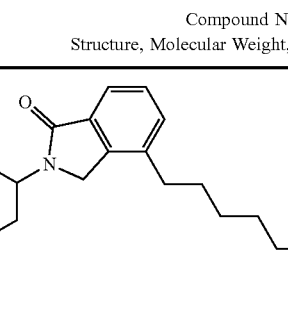 EC2-102 M.W. = 655.75 | Alkyl/amidic 11 atom | 10 uM: 25.22% 10 nM: 58.92% | | |
| 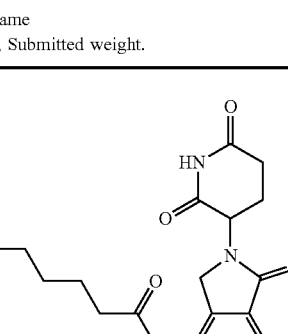 EC2-108 M.W. = 595.61 | Alkynyl/amidic 7 atom | 10 uM: 79.66% 10 nM: 85.63% | | |
| 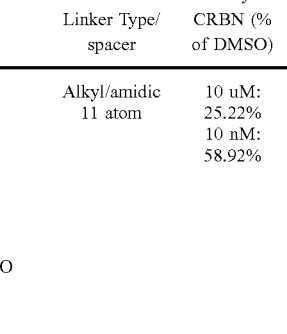 EC2-109 M.W. = 599.64 | Alkyl/amidic 7 atom | 10 uM: 9.84% 10 nM: 97.49% | | |

| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 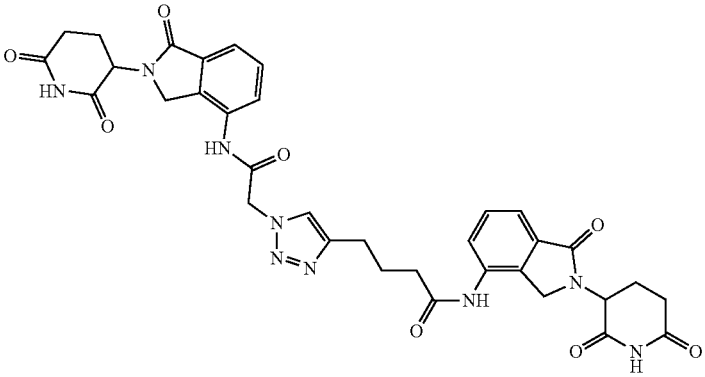 XS01-109 M.W. = 695.6930 | Triazole 11 atoms | 10 uM: 132.25% 10 nM: 212.96% | | |
| 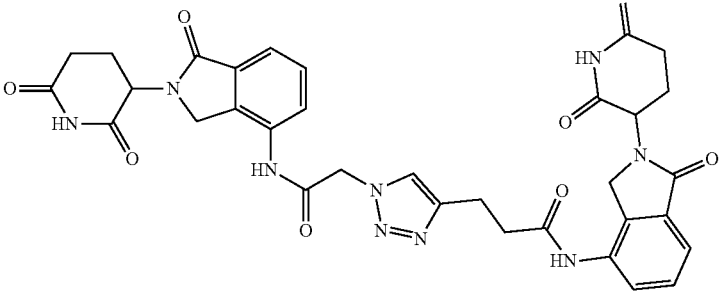 XS01-113 M.W. = 681.6660 | Triazole 10 atoms | 10 uM: 106.50% 10 nM: 225.04% | | |
| 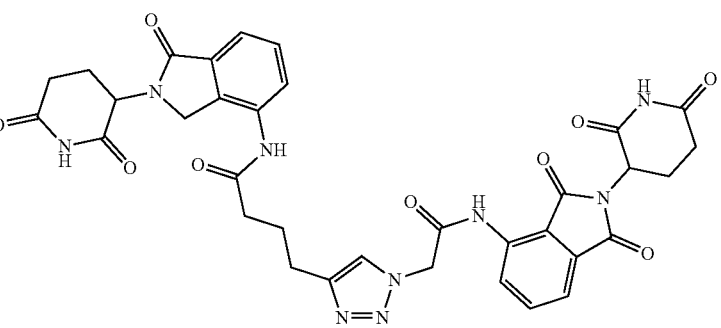 XS01-122 M.W. = 709.6760 | Triazole 11 atoms | 10 uM: 151.45% 10 nM: 255.21% | | |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 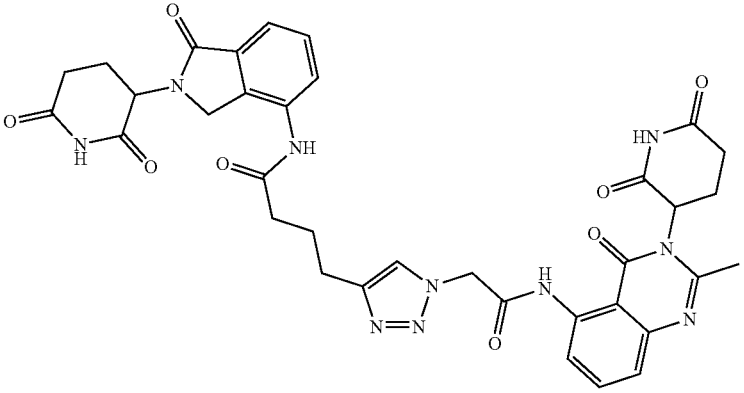 XS01-123 M.W. = 722.7190 | Triazole 11 atoms | 10 uM: 150.73% 10 nM: 242.87% | | |
| 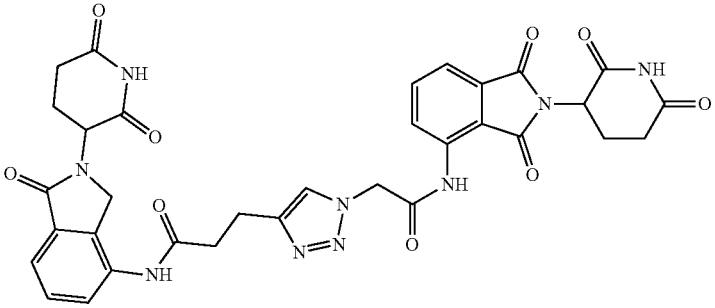 XS01-125 M.W. = 695.6490 | Triazole 10 atoms | 10 uM: 153.23% 10 nM: 195.53% | | |
| 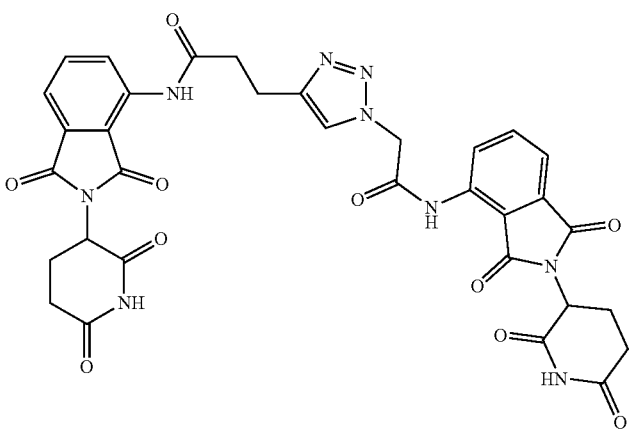 XS01-126 M.W. = 709.6320 | Triazole 10 atoms | 10 uM: 131.39% 10 nM: 206.58% | | |

-continued
| Compound Name Structure, Molecular Weight, Submitted weight. | Exit Vector/ Linker Type/ spacer | CRBN Degradation** (WB)/IC$_{50}$/ DC$_{50}$ Relative Density of CRBN (% of DMSO) | Kd(A) FI/ITC (uM) | % inhibition @ 200 uM from *FI |
|---|---|---|---|---|
| 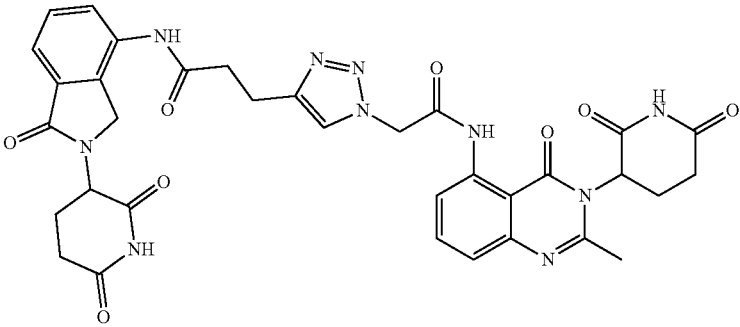<br>XS01-127<br>M.W. = 708.6920 | Triazole 10 atoms | 10 uM: 175.39%<br>10 nM: 228.28% | | |
| 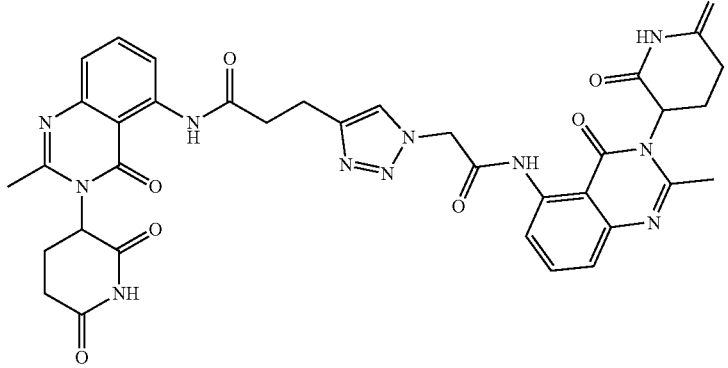<br>XS01-132<br>M.W. = 735.7180 | Triazole 10 atoms | 10 uM: 98.27%<br>10 nM: 199.32% | | |
| 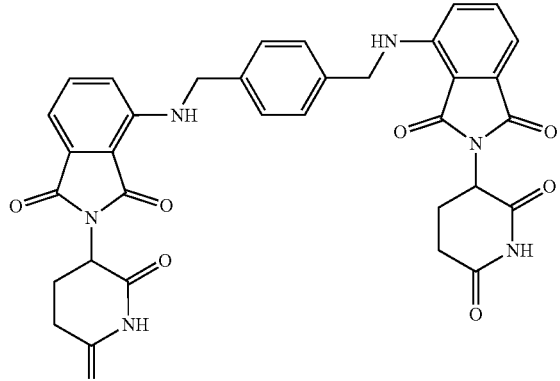<br>EC2-134<br>M.W. = 648.1969 | Benzylamine/ phenyl 8 atoms | 10 uM: 13.82%<br>10 nM: 4.00% | | |

The methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having formula V:

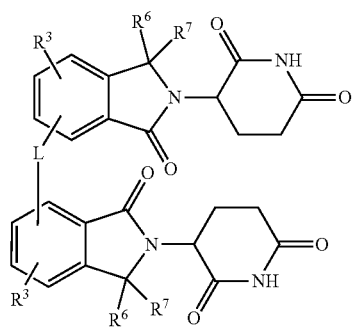

V wherein
$R^3$ is selected from the group consisting of hydrogen, halogen, hydroxyl, azide, alkoxyl, sulfhydryl, imino, amido, phosphonate, phosphinate, carbonyl, carboxyl, cyano, silyl, ether, alkylthio, sulfonyl, sulfonamido, ketone, aldehyde, substituted or unsubstituted amine, substituted or unsubstituted amide, nitro, ester, morpholino, dioxolane, substituted or unsubstituted alkyl, substituted or unsubstituted alkylhalide, substituted or unsubstituted aralkyl, substituted or unsubstituted alkenyl, substituted or unsubstituted alkynyl, substituted or unsubstituted cycloalkyl, substituted or unsubstituted cycloalkyl; substituted or unsubstituted heterocyclyl; substituted or unsubstituted cycloalkenyl, substituted or unsubstituted aryl, substituted or unsubstituted heteroaryl, substituted or unsubstituted arylalkyl, substituted or unsubstituted heteroalkyl, substituted or unsubstituted alkylheteroaryl, and combinations thereof;
$R^6$ and $R^7$ are individually =O, hydrogen, $C_1$-$C_8$ alkyl, or $R^6$ and $R^7$ combine to form =O; and
L is $NH(CO)(CH_2)_nC(O)NH$, wherein n is 3-10.

2. The compound of claim 1, wherein $R^3$ is $SO_2NH_2$, $SO_2NHR'$, or $NHSO_2R'$, wherein R' is $C_1$-$C_6$ alkyl or $C_3$-$C_6$ cycloalkyl optionally substituted with $C_1$-$C_6$ alkyl, $C_1$-$C_6$ alkoxyl, hydroxyl, or halide.

3. The compound of claim 1, wherein $R^3$ is $NHC(O)R$, wherein R is $C_1$-$C_6$ alkyl or $C_3$-$C_6$ cycloalkyl optionally substituted with $C_1$-$C_6$ alkyl, $C_1$-$C_6$ alkoxyl, cycloalkyl, cycloheteroalkyl, hydroxyl, or halide.

4. The compound of claim 1, wherein $R^3$ is $C_1$-$C_6$ alkyl or $C_3$-$C_6$ cycloalkyl.

5. The compound of claim 1, wherein $R^3$ is $C_1$-$C_6$ alkoxyl.

6. The compound of claim 1, wherein $R^3$ is halide.

7. The compound of claim 1, wherein $R^3$ is hydrogen, hydroxyl, substituted or unsubstituted amine, substituted or unsubstituted amide, nitro, ester, morpholino, dioxolane, substituted or unsubstituted $C_1$-$C_6$ alkyl, or combinations thereof.

8. The compound of claim 1, wherein $R^6$ and $R^7$ together form =O.

9. The compound of claim 1, wherein $R^6$ and $R^7$ are both hydrogen.

10. The compound of claim 1, wherein the compound is

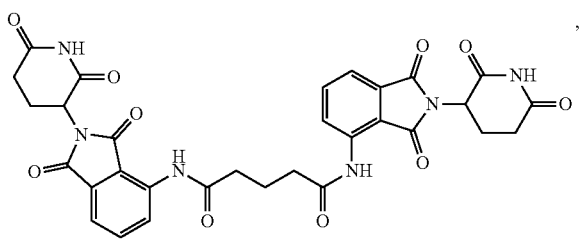

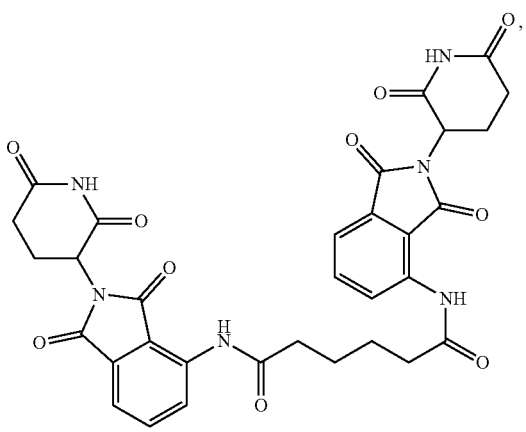

307
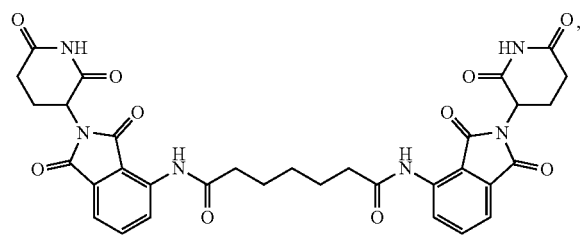
308
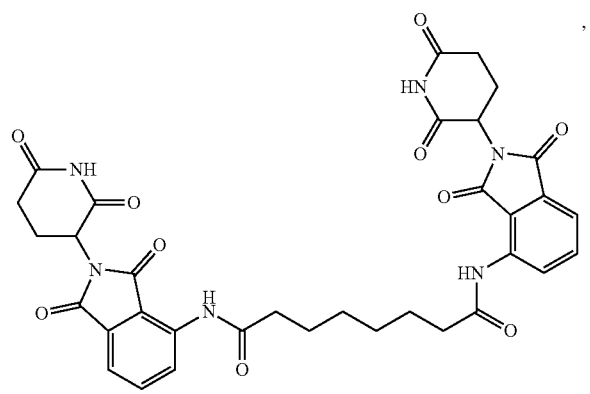
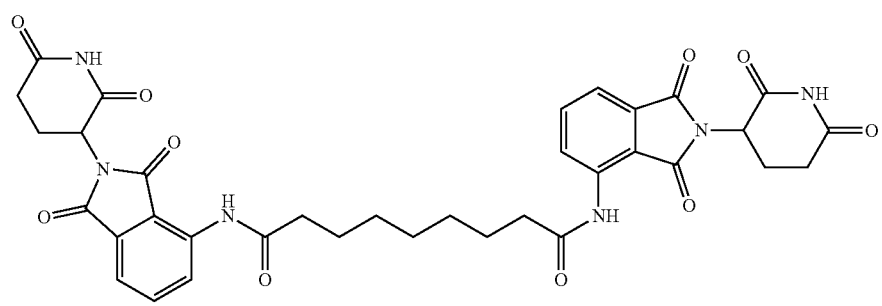
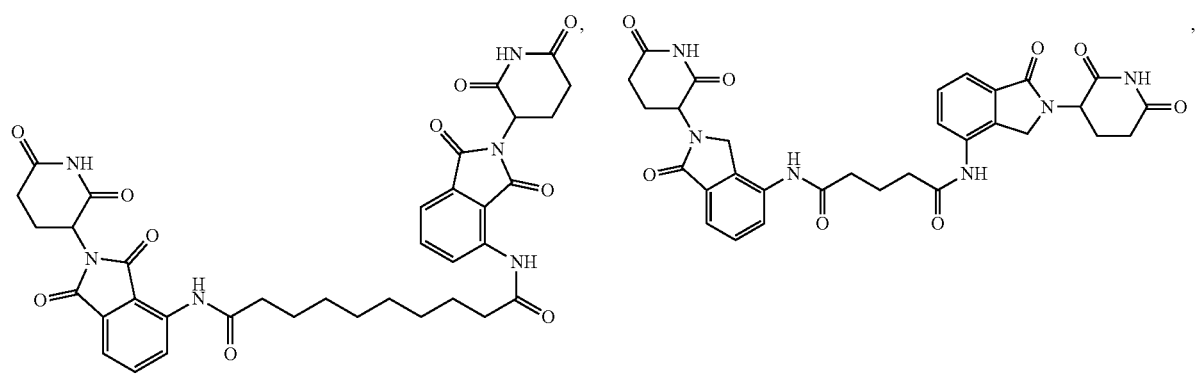

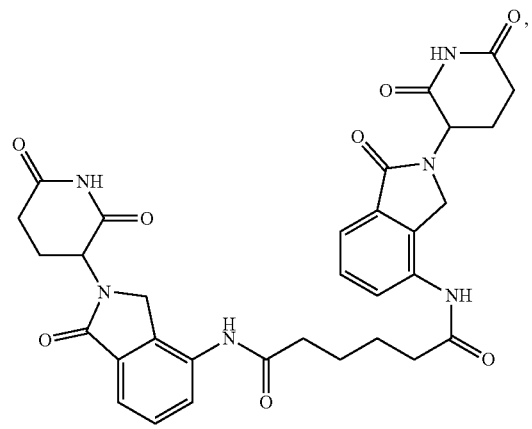
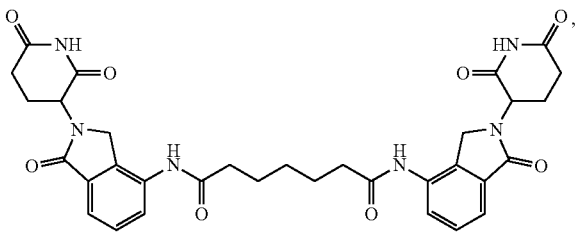
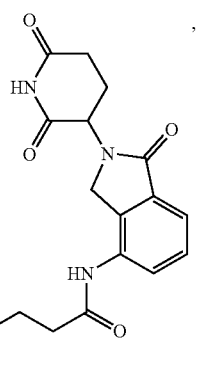
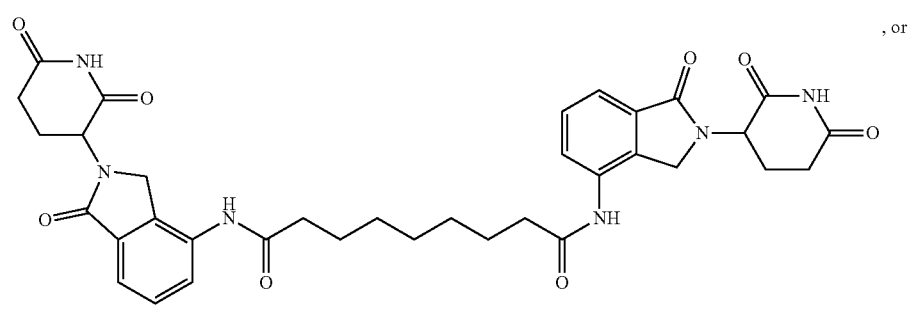
, or
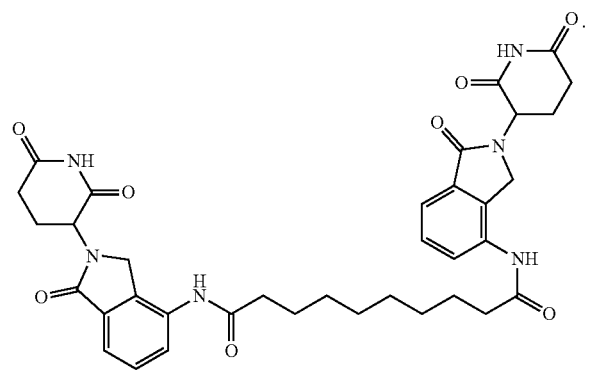

11. A method of treating a subject having an autoimmune disease or disorder, the method comprising administering to the subject an effective amount of a compound according to claim 1.

12. A method of treating cancer in a patient, the method comprising administering to the patient an effective amount of a compound according to claim 1.

13. The method of claim 4, wherein the cancer is multiple myeloma, myelodysplasia syndrome, or lymphoma.

* * * * *